US012760331B2

(12) United States Patent
Liang et al.

(10) Patent No.: US 12,760,331 B2
(45) Date of Patent: Oct. 13, 2026

(54) CAS12 PROTEINS AND USES THEREOF

(71) Applicants: REFORGENE MEDICINE, Guangzhou (CN); ZHEJIANG SYNSORBIO TECHNOLOGY CO., LTD., Shaoxing (CN)

(72) Inventors: Junbin Liang, Guangzhou (CN); Liancheng Huang, Guangzhou (CN); Chongjian Chen, Shaoxing (CN); Yang Sun, Shaoxing (CN); Weiye Pan, Shaoxing (CN); Hui Xu, Guangzhou (CN); Kaiwei Si, Guangzhou (CN); Jinxiu Cai, Guangzhou (CN); Qing Liao, Guangzhou (CN); Desheng Huangfu, Guangzhou (CN)

(73) Assignees: REFORGENE MEDICINE, Guangzhou (CN); ZHEJIANG SYNSORBIO TECHNOLOGY CO., LTD., Shaoxing (CN)

( * ) Notice: Subject to any disclaimer, the term of this patent is extended or adjusted under 35 U.S.C. 154(b) by 0 days.

(21) Appl. No.: 19/303,600

(22) Filed: Aug. 19, 2025

(65) Prior Publication Data

US 2026/0009052 A1 Jan. 8, 2026

Related U.S. Application Data

(63) Continuation-in-part of application No. PCT/CN2024/119862, filed on Sep. 19, 2024.

(30) Foreign Application Priority Data

Aug. 19, 2023 (MA) ........................ 202311214330.6
Apr. 1, 2024 (MA) ........................ 202410388582.2

(51) Int. Cl.
*C12N 9/22* (2006.01)
*C12N 15/10* (2006.01)
*C12N 15/11* (2006.01)
*C12N 15/90* (2006.01)

(52) U.S. Cl.
CPC ........... *C12N 15/907* (2013.01); *C12N 9/226* (2025.05); *C12N 15/1082* (2013.01); *C12N 15/11* (2013.01); *C12N 15/90* (2013.01); *C12N 2310/20* (2017.05)

(58) Field of Classification Search
None
See application file for complete search history.

(56) References Cited

U.S. PATENT DOCUMENTS

| | | | | |
|---|---|---|---|---|
| 10,808,245 B2* | 10/2020 | Chong | .................. | C12N 15/90 |
| 2020/0063126 A1 | 2/2020 | Cheng et al. | | |
| 2021/0163944 A1 | 6/2021 | Zhang et al. | | |
| 2021/0395784 A1 | 12/2021 | Lai et al. | | |
| 2023/0136278 A1 | 5/2023 | Zhang et al. | | |
| 2024/0279630 A1 | 8/2024 | Liang et al. | | |
| 2025/0197827 A1 | 6/2025 | Liang et al. | | |

FOREIGN PATENT DOCUMENTS

| | | | |
|---|---|---|---|
| CN | 113308451 | A | 8/2021 |
| CN | 116716277 | A | 9/2023 |
| CN | 117683749 | A | 3/2024 |
| EP | 4692337 | A1 | 2/2026 |
| WO | 2014093622 | A2 | 6/2014 |
| WO | 2021113522 | A1 | 6/2021 |

OTHER PUBLICATIONS

Swarts et al., 2017, Structural Basis for Guide RNA Processing and Seed-Dependent DNA Targeting by CRISPR-Cas12a. Molecular Cell 66, 221-233 (Year: 2017).*
Zhang et al. Boosting genome editing efficiency in human cells and plants with novel LbCas 12a variants. Genome Biology (2023) 24:102 (Year: 2023).*
International Search Report in PCT/CN2024/119862 mailed on Jan. 16, 2025, 11 pages.
Written Opinion in PCT/CN2024/119862 mailed on Jan. 16, 2025, 9 pages.
Tentative Rules, Iupac-Iub Commission on Biochemical Nomenclature A One-Letter Notation for Amino Acid Sequences, The Journal of Biological Chemistry, 243(13):3557-3559, 1968.
Sergey Shmakov et al., Discovery and Functional Characterization of Diverse Class 2 CRISPR-Cas Systems, Molecular cell, 2015, 37 pages.
David Burstein et al., New CRISPR-Cas Systems from Uncultivated Microbes, Nature, 2017, 17 pages.
Winston X. Yan et al., Functionally Diverse type V CRISPR-Cas Systems, Science, 2019, 5 pages.
Morgan L. Maeder et al., Development of A Gene-Editing Approach to Restore Vision Loss in Leber Congenital Amaurosis Type 10, Nature Medicine, 2019, 24 pages.
Mohammadsharif Tabebordbar et al., Directed Evolution of A Family of AAV Capsid Variants Enabling Potent Muscle-Directed Gene Delivery Across Species, Cell, 2021, 43 pages.
Julian D. Gillmore et al., CRISPR-Cas9 in Vivo Gene Editing for Transthyretin Amyloidosis, The New England Journal of Medicine, 385(6): 493-502, 2021.
Kalina Paunovska et al., Drug Delivery Systems for RNA Therapeutics, Nature Reviews Genetics, 23: 265-280, 2022.
Samagya Banskota et al., Engineered Virus-Like Particles for Efficient in Vivo Delivery of Therapeutic Proteins, Cell, 2022, 33 pages.

(Continued)

*Primary Examiner* — Tiffany Nicole Grooms
(74) *Attorney, Agent, or Firm* — METIS IP LLC

(57) ABSTRACT

Cas12 protein, guide polynucleotide, inactivated Cas12 mutant, fusion protein or conjugate including the Cas12 protein, isolated nucleic acid, CRISPR-Cas12 system, vector system, delivery system, cell, pharmaceutical composition, and kit, and the use thereof are provided.

10 Claims, 27 Drawing Sheets

Specification includes a Sequence Listing.

(56) References Cited

OTHER PUBLICATIONS

Philippe E. Mangeot et al., Genome Editing in Primary Cells and in Vivo Using Viral-Derived Nanoblades Loaded with Cas9-SgRNA Ribonucleoproteins, Nature Communications, 1-15, 2019.
Lee A. Campbell et al., Gesicle-Mediated Delivery of CRISPR/Cas9 Ribonucleoprotein Complex for Inactivating the HIV Provirus, Molecular Therapy, 27(1): 151-163, 2019.
Philippe-Emmanuel Mangeot et al., Protein Transfer Into Human Cells by VSV-G-induced Nanovesicles, Molecular Therapy, 19(9): 1656-1666, 2011.
Hu, Ziying et al., A Compact Cas9 Ortholog from Staphylococcus Auricularis (SauriCas9) Expands the DNA Targeting Scope, PLOS Biology, 18(3): 1-18, 2020.
Huang, X et al., PDB:6LTP_A(Chain A, Cas12i2), GENBANK, 2020, 4 pages.
Huang, Xue et al., Structural Basis for Two Metal-ion Catalysis of DNA Cleavage by Cas12i2, Nature Communications, 1-14, 2020.
Bao, Xinru et al., Characteristics and Application of CRISPR/Cas 12a Genome Editing Technology, China Biotechnology, 43(10): 32-42, 2023.
Fabio, Bigini et al., Unleashing the potential of CRISPR multiplexing: Harnessing Cas12 and Cas13 for precise gene modulation in eye diseases, Vision Research, 213: 1-10, 2023.
The Second Office Action in Chinese Application No. 202480023951.2 mailed on Feb. 14, 2026, 13 pages.

* cited by examiner

| CLUSTER | Protein |
|---|---|
| CLUSTER1 | SEQ ID NO: 31 |
| CLUSTER2 | SEQ ID NO: 28 |
| CLUSTER3 | SEQ ID NO: 24 |
| CLUSTER4 | SEQ ID NO: 32 |
| CLUSTER5 | SEQ ID NO: 29 |
| CLUSTER6 | SEQ ID NO: 30 |
| CLUSTER7 | SEQ ID NO: 38、29、26 |
| CLUSTER8 | SEQ ID NO: 44、33、45 |
| CLUSTER9 | SEQ ID NO: 23、21、20、16、41、40 |
| CLUSTER10 | SEQ ID NO: 42、27、22、25、14、13 |
| CLUSTER11 | SEQ ID NO: 15 |
| CLUSTER12 | SEQ ID NO: 17 |
| CLUSTER13 | SEQ ID NO: 43、18、34、35、36、37 |

FIG. 1B

| | N1 | N2 | N3 | N4 | N5 | N6 | N7 |
|---|---|---|---|---|---|---|---|
| A | 23 | 6 | 27 | 13 | 8 | 2 | 21 |
| T | 22 | 33 | 19 | 23 | 77 | 90 | 35 |
| G | 29 | 40 | 41 | 45 | 11 | 5 | 18 |
| C | 24 | 20 | 10 | 17 | 3 | 1 | 24 |

| | N1 | N2 | N3 | N4 | N5 | N6 | N7 |
|---|---|---|---|---|---|---|---|
| G | 34 | 8 | 13 | 34 | 25 | 29 | 31 |
| T | 25 | 14 | 23 | 24 | 37 | 27 | 25 |
| A | 17 | 67 | 51 | 19 | 15 | 17 | 19 |
| C | 22 | 9 | 10 | 21 | 21 | 24 | 23 |

| | N1 | N2 | N3 | N4 | N5 | N6 | N7 |
|---|---|---|---|---|---|---|---|
| A | 25 | 60 | 51 | 21 | 20 | 20 | 25 |
| G | 23 | 11 | 13 | 28 | 24 | 27 | 24 |
| C | 23 | 13 | 14 | 27 | 25 | 29 | 24 |
| T | 27 | 14 | 20 | 21 | 29 | 22 | 24 |

| | N1 | N2 | N3 | N4 | N5 | N6 | N7 |
|---|---|---|---|---|---|---|---|
| T | 14 | 21 | 4 | 27 | 16 | 32 | 22 |
| A | 0 | 32 | 95 | 60 | 22 | 17 | 24 |
| G | 85 | 26 | NaN | 12 | 33 | 27 | 25 |
| C | NaN | 18 | NaN | NaN | 28 | 23 | 28 |

FIG. 9

| | N1 | N2 | N3 | N4 | N5 | N6 | N7 |
|---|---|---|---|---|---|---|---|
| T | 33 | 33 | 28 | 31 | 61 | 62 | 30 |
| G | 34 | 33 | 32 | 30 | 17 | 14 | 35 |
| C | 21 | 20 | 16 | 21 | 9 | 10 | 19 |
| A | 9 | 13 | 22 | 17 | 11 | 12 | 15 |

| | N1 | N2 | N3 | N4 | N5 | N6 | N7 |
|---|---|---|---|---|---|---|---|
| T | 36 | 18 | 19 | 34 | 30 | 27 | 28 |
| C | 22 | 12 | 11 | 19 | 22 | 24 | 23 |
| G | 28 | 15 | 14 | 26 | 30 | 25 | 25 |
| A | 11 | 53 | 53 | 20 | 16 | 22 | 22 |

| | N1 | N2 | N3 | N4 | N5 | N6 | N7 |
|---|---|---|---|---|---|---|---|
| T | 22 | 0 | 0 | 23 | 23 | 22 | 24 |
| G | 25 | 0 | 0 | 23 | 25 | 27 | 23 |
| C | 24 | 0 | 0 | 24 | 24 | 23 | 25 |
| A | 27 | 98 | 98 | 28 | 26 | 26 | 26 |

| | Mut-02-1-5-426-858-860 | Mut-02-1-426-846-858-860 | Mut-02-426-860 | Wt |
|---|---|---|---|---|
| TTR-sgRNA01 | 25 | 27.3 | 15.1 | 4 |
| TTR-sgRNA02 | 10 | 4.6 | 2 | 1.7 |
| TTR-sgRNA03 | 4.5 | 1.3 | 0.8 | 2.1 |
| TTR-sgRNA04 | 12 | 5.8 | 5.8 | 1.3 |
| TTR-sgRNA05 | 18.9 | 17.7 | 11.8 | 0 |
| TTR-sgRNA06 | 15.7 | 14.5 | 11.3 | 1.2 |
| TTR-sgRNA07 | 10.9 | 10.3 | 6.2 | 0.8 |
| TTR-sgRNA08 | 15.4 | 8.7 | 5.2 | 1.5 |
| TTR-sgRNA09 | 3.7 | 1.5 | 2.6 | 0.4 |
| TTR-sgRNA10 | 15.1 | 13.6 | 9.1 | 2.4 |
| TTR-sgRNA11 | 3 | 12.5 | 5.2 | 0.7 |
| TTR-sgRNA12 | 21.1 | 15.2 | 15.9 | 3.1 |
| TTR-sgRNA13 | 7.5 | 7.9 | 2.3 | 3.2 |
| TTR-sgRNA14 | 14.7 | 16.7 | 6.6 | 0.7 |

| | Mut-02-1-5-426-858-860 | Mut-02-1-426-846-858-860 | Mut-02-426-860 | Wt |
|---|---|---|---|---|
| HBG-sgRNA01 | 7.8 | 12.3 | 5.4 | 0 |
| HBG-sgRNA02 | 9.5 | 8.1 | 5.3 | 0.3 |
| HBG-sgRNA03 | 4.6 | 6.5 | 13.6 | 2.6 |
| HBG-sgRNA04 | 17 | 20.1 | 10 | 0.4 |
| HBG-sgRNA05 | 6.8 | 6.8 | 5.5 | 0 |
| HBG-sgRNA06 | 4.4 | 3.7 | 2.6 | 0.3 |
| HBG-sgRNA07 | 15.7 | 7.7 | 3.8 | 0.9 |
| HBG-sgRNA08 | 14.6 | 14.1 | 8.9 | 0.7 |
| HBG-sgRNA09 | 19.4 | 20.5 | 10.4 | 0.9 |

| Grouping | Editing efficiency(%) |
|---|---|
| Mut-02-426-860 | 28.09 |
| Mut-02-426-860-D651A | 0.87 |
| Mut-02-426-860-E891A | 0.73 |
| Mut-02-426-860-D1082A | 0.56 |
| Mut-02-426-860-D651A-E891A-D1082A | 0.89 |
| Mut-02-1-426-846-858-860 | 34.40 |
| Mut-02-1-426-846-858-860-D651A | 1.14 |
| Mut-02-1-426-846-858-860-E891A | 0.51 |
| Mut-02-1-426-846-858-860-D1082A | 0.35 |
| Mut-02-1-426-846-858-860-D651A-E891A-D1082A | 0.41 |
| Mut-02-1-5-426-858-860 | 33.69 |
| Mut-02-1-5-426-846-858-860-D651A | 1.11 |
| Mut-02-1-5-426-858-860-E891A | 0.54 |
| Mut-02-1-5-426-858-860-D1082A | 0.38 |
| Mut-02-1-5-426-858-860-D651A-E891A-D1082A | 0.45 |
| Cell | 0.35 |
| PEI-Control | 0.35 |

| index | 1 | 2 | 3 | 4 | 5 | 6 | 7 |
|---|---|---|---|---|---|---|---|
| C | 22 | 6 | 6 | 27 | 25 | 26 | 25 |
| A | 28 | 77 | 60 | 23 | 20 | 23 | 25 |
| T | 24 | 10 | 25 | 19 | 29 | 23 | 24 |
| G | 24 | 4 | 7 | 28 | 24 | 26 | 25 |

SEQUENCE LISTING

```
Sequence total quantity: 1006
SEQ ID NO: 1            moltype = AA  length = 888
FEATURE                 Location/Qualifiers
source                  1..888
                        mol_type = protein
                        organism = synthetic construct
SEQUENCE: 1
MKTKDIINTV RSSNIKFKSY DKELETFYNH LQDDYKKFFH LFLDWLCLGY TYINEDNQSV  60
IVEPEEQLKQ LKKYTKGNQK LEANIKAFVN LLTSGQTPAS SCYNSFYANY SAAETSRCNK  120
KLVEKLLESN KKQIEEYIES SKNALLKNIS VDKWLEHKKE LSKFKSISDK KKREKAQAEY  180
WKEHIGQATL NTDRHCGAYL RKELKIKCRH PENASYCKTL CEMIRRQLTA VLEHNKQHAE  240
ELNKTKEQIE KFSQDESFKL ICKIAETYPD DFHHYNFKNA LNHIFYNKKM DSKNKDKIQL  300
IVDALLPSKG LGYKTLFKAF DNWEIFERYQ YRIKNRKYPL KPRLSDVNVP FDNFRFSDGS  360
KFQGKLLNFN FECCYSHYFH DLQFEKIKEG YNLSFFHRLK NGNTKNVILT SNKISGTVKE  420
VSVLKKNNEL HLSVPYNIYH SNQNENLKYY FSFAAPSSEK LDLLPDSFKA IGVDLNIQDP  480
VVVTLGAITK KDSYKIKVRD FGSAKLLETQ TLVPDTNLSN EIKKLNSEIM TIKGILYEIK  540
KISKDDSLEF DIESLGYLGL EIDRSKDHIG ARGVVQNKIK LLKSKIKQYR HKCRNTGNKS  600
VSELIRLIEI VDNFNSMISV YQRLHLKSGE QLLATKRNDN TRKNLKKDLL KKLANKIVKY  660
CLDNQVSLVF LEDLDSEQSS RNSRERNSLI RLFSAKSILD SIETALGKYG ISCLSNIDKK  720
GTSKTDPFTG NIAYRDEKDK RNLYVNVKKK NKLVCYNADH TASLNVFLRG IDHSIIPYSF  780
LWANSKDKDK EKGKRISRFL KDKFGTTKVY FYDLGEDHLT VSTKSLKNKS KYFGKIYYRN  840
NKFITEKQHF EMEEKLKKEI MDGLAVGTQV EKIDITSKNI NTCVNFQE                888

SEQ ID NO: 2            moltype = AA  length = 997
FEATURE                 Location/Qualifiers
source                  1..997
                        mol_type = protein
                        organism = synthetic construct
SEQUENCE: 2
MSETTKSKFP INKQVTNTVS ADILADEKTT SKLTDILNVN SIVKNDLLKL MLTFRGGKCQ  60
LDDVEFDSDK EFDKLYAALG TSLPKEVIKA LAKEFYYGLT GGLTSRAVKN IIYSPKEIKT  120
SVSYKMDVPD QPNKKESKDK DQKKGKTSKK AKKPKKSVVT SEFDILRKSG IFPLKTPQEC  180
SGGMLYSVVK TVQNDLISLE EKTKAYEADK QCWLSKLATA LCKFPHIGRY GDFLASVEGL  240
SGIKSWNANG YIRFIKLWHD NSSRKGIRSF LLEKHTQYGN KSVAFTAEDT CGFGYQPDFF  300
DSLYKNFKDL WLIEDVIGNE DYISFICGRD NTEDDKKNKG GAYHWRKEFI NISSPERYGK  360
KAVLMLSNGV DNDKGNFVPF TLDFSNENWI MTIDNPLTGE KLSFKLSKGT YYNNFSVLPN  420
KPVKVKKDKN VKKDKNVKVE KAKGGYKIRY STRKDDKYMY ISYLKQPCLR YDPKKGCFKI  480
DFINSDKQVE GLDVNVKNLR GMQKYFSTSS NFDKRAKDVL PGFENKEFIA IGADRGTFPT  540
AAFAVARVNK SKDGTFTIKE WLDEEFLSRN ENADEMTRKI KNVTDKITAV KRLTNETVKF  600
KKGEIAEIPP TFTRTFKGKD GTVTATIKWQ TLLEIDAEDY TGQVKKLPYD KDSKFTLLQQ  660
WIPSSVEWDV KRVMHDIKIE KNAIKNAFQN SENKTEYLQQ NNKVDSSTYR KLEMIKGWIS  720
LQKKFCGSGP DVCKKDYDWL NGLRKHIDNQ LSSNIVAVAR KYREKYGLEV VVFLEKLDAF  780
```

```
LSGFDDKHHN STKALWGIGS LNKKLSEKGE KFGILFVPVD PYQTSIMDSE TNLLGYRNWA  840
EDKSDLYVKR NGEIQVVNAD INAAKNIIIR GIFRHKNIVE FSSDEISDDL YRVMPVGKQR  900
KGALFGHTGS DAILLSDKDG DGELFVASKS LNEAQQQATP INKDKKKVYV VFQDGKWIFR  960
HKLDEQLKQY PSLLKAKPQV SKGNKKSVIS RDLQLAH                          997

SEQ ID NO: 3           moltype = AA  length = 903
FEATURE                Location/Qualifiers
source                 1..903
                       mol_type = protein
                       organism = synthetic construct
SEQUENCE: 3
MSCVCNNSIP IDEEIYMALI QRAGVLKTKS DFPKVIKDWH DSLLADYRKF FPIIFSWCPE  60
YGYTTIQDNK PVFVSPEERI ESIRKEAKEH LNEVLAFGKM IGSKGVGGSS SYAIFYKHHK  120
NNENGAYTPS RAKFMKEGIH NRRVELVDAL MLNAIPDKEW IRIAQEVVGY SEDRLKLYWN  180
KFIAKKVVSH DRKLGKIVRE KYLEPKGLVC AQPENSTYCR VLTEIIKRQL HSQIEKSKFH  240
EEELKSIEKT VSEFDSPLLD VICQYAEELN QINSGLSKYV IKNAVKEVIS PPEKQSEIYV  300
QSQVLSQEKY KPLVNATIKE ILSGYEQWKV KSRYENRLKN RKYVLYPKLS ANYKIPIGQN  360
SLGRFKINVS ENGEIVIRLN NMADVVCMPS KYFFNLKSSP VVDKKKQLVG YQISFNHNSR  420
RKEPTEKPDF NGIVKEIGLQ LKDDGRFYIT LPYCMEYSND NFDLIRPLLT SSPTEDQIKK  480
MPSEFNVVGF DLNLSMPLPI TRAIVGKSVK GEINVEYLGQ AKVIESTHLI YDNNRCKVLI  540
AYKRQCDLIK RAIREWKICK GKNIDISEKT YEWLESHTKR WNPSRQPESM QDRFSVSKMR  600
IQILVNKAKS RIAKYNDNSW KTGHGNESEL IRLIDADDAY NSLVSTYNRI HLKSNQFIYA  660
LPSKNNSRSN KKEYCLRRIA AKIARYCHLH NVNICIGENL SFQQDSDNIS KDNSLVRLFS  720
SKSIASYMKL AMEKFGIAFI DSADPSGTSK TDPVTGNIGY RNKFDKRKLH VLRNGNWGWV  780
DSDIAASLNI LIRGINRSIV PYKFFVGKKK QESKRLNHFL NKIFGTTKVF FYEDQFGFAN  840
PSLSKKEGEN LIANQYLYYR EGKFVTQKIH RQIEDDFKKI DFSNTPEVNL IPSGVKLKNF  900
QFE                                                               903

SEQ ID NO: 4           moltype = AA  length = 907
FEATURE                Location/Qualifiers
source                 1..907
                       mol_type = protein
                       organism = synthetic construct
SEQUENCE: 4
MATLDAMPAI HGFDSTSRCY MALIQRAGVL KTKSDFPKVI KDWHDSLLAD YRKFFPIIFS  60
WCPEYGYTTI QDNKPVFVSP EERIESIRKE AKEHLNEVLA FGKMIGSKGV GGSSSYAIFY  120
KHHKNNENGA YTPSRAKFMK EGIHNRRVEL VDALMLNAIP DKEWIRIAQE VVGYSEDRLK  180
LYWNKFIAKK VVSHDRKLGK IVREKYLEPK GLVCAQPENS TYCRVLTEII KRQLHSQIEK  240
SKFHEEELKS IEKTVSEFDS PLLDVICQYA EELNQINSGL SKYVIKNAVK EVISPPEKQS  300
EIYVQSQVLS QEKYKPLVNA TIKEILSGYE QWKVKSRYEN RLKNRKYVLY PKLSANYKIP  360
IGQNSLGRFK INVSENGEIV IRLNNMADVV CMPSKYFFNL KSSPVVDKKK QLVGYQISFN  420
HNSRRKEPTE KPDFNGIVKE IGLQLKDDGR FYITLPYCME YSNDNFDLIR PLLTSSPTED  480
QIKKMPSEFN VVGFDLNLSM PLPITRAIVG KSVKGEINVE YLGQAKVIES THLIYDNNRC  540
KVLIAYKRQC DLIKRAIREW KICKGKNIDI SEKTYEWLES HTKRWNPSRQ PKSMQDRFSV  600
SKMRIQILVN KAKSRIAKYN DNSWKTGHGN ESELIRLIDA DDAYNSLVST YNRIHLKSNQ  660
FIYALPSKNN SRSNKKEYCL RRIAAKIARY CHLHNVNICI GENLSFQQDS DNISKDNSLV  720
RLFSSKSIAS YMKLAMEKFG IAFIDSADPS GTSKTDPVTG NIGYRNKFDK RKLHVLRNGN  780
WGWVDSDIAA SLNILIRGIN RSIVPYKFFV GKKKQESKRL NHFLNKIFGT TKVFFYEDQF  840
GFANPSLSKK EGENLIANQY LYYREGKFVT QKIHRQIEDD FKKIDFSNTS EVNLIPSGVK  900
LKNFQFE                                                           907

SEQ ID NO: 5           moltype = AA  length = 831
FEATURE                Location/Qualifiers
source                 1..831
                       mol_type = protein
                       organism = synthetic construct
SEQUENCE: 5
VVTPESQSDA KKAFADALFA GQEAAYGSFY AKYTPLPFPR KDSALGRLTA ELGTIGDEKY  60
AKALKLNGLD PDEWAGYRNR AIAGEPPDAL WEEIKVKVGV TNKATLASRG VGNLPTLRPD  120
SKSYATALAY MLSSSLSSWE ECAKLHRARR EEIAAKAAVP DSMTEEYALV CQLAQALEEA  180
GSGLTAKMLN GAIREMAKTD SVYMVAITEL ADPKYKPLLA LDKEDRARLM DTWQAERKLS  240
TSLAAPKRPL FDKDYQIPFG MTGRGESFAL RTDDSGRLWV KIGDHEEFSC AASDYFGNLK  300
VEALPSDKGY KITYRKMVKN RRRQRAGYKS SVGGPLIEGE VKQILLQRRM NRRGKESFYV  360
YLPHSIAVKD DRRHLSWFFK RADWKDGKGL EELPDQLIVS GIDLNIDQPV TVTKAIVSKN  420
YTEGEINCPY GGGHLTGKPR SVCPDTPISQ EAKLTHRKMR LLIEVIRESK ACHKAGTPLS  480
SEGSERLKIL YADISKPPCR NNRESIQVVY SSLKKTYRRL KYELMQQGAN DVSGCIRMLQ  540
LDDTHRALTA CFDAFSGKPA LAGRNFGVAR KKTSKGTARL NFREHVSHLY ANAVLRACHG  600
SDVVFIEDLS TSFDGNAHNS LKRLFAPGQL IDAITSLLES HGIAVVTVDP SGTSRRHPIT  660
GDIWYRDSMK KRELVGLIDG ELVSVNDDLA ASINVLTKGL NHSVVPHKFK VDPSGRVNVK  720
EDGGKRLKVF LREKGLSGRL PVGSADAAKS KKAKALTVYP SSSGLLSDRQ VFEVLEQIKH  780
LLAAGCKPRP VELMAGPGET YAAFSLKEVL EWSKSKSSED LRHTGLGDET G           831

SEQ ID NO: 6           moltype = AA  length = 882
FEATURE                Location/Qualifiers
source                 1..882
                       mol_type = protein
                       organism = synthetic construct
SEQUENCE: 6
MEKFPRCSHL KVKQHCGPFV EWYEDLQSDR QKYVSLFFPW IGIGYGERKD EGDDIDFISP  60
```

-continued

```
EQTLERRKAE LGKLEELVVR FVTVMLKGGS SASSCYSLFY EDYKGKDTAK KSTSKVNFIK  120
ALPLLSKKEI EDRVLGDNQL SLINLDEWME LGQSGLSADD IWDKVSQRLV TGERSLGVDV  180
RHTLKIRCQR PRDRGYCVVL MEMVARQLRS CYECYKNHLN ELQELREKTT KQITESRDDL  240
FSLVCDLATV LTEQDSGLSE RTLFSGRKQA LKPQGKPSKI QAIVDELRQP QYSPLLEADD  300
KELRQAYKAW NSQRRLRDRE TRRPYPCRPN WRNDYQVSLG LTGRGGFWMW MDGSDVVVDL  360
QDCGRLTCSP SHYFGDLAIE GQLHQYDIRY RNKLKRRGKK LRKPPAYGEW IEATIKEIGI  420
QRKGGDYYVY LLPVISHDST NFQAAKKFFA AAAPKQEIID ALPDEMKVLA LDLNISNPVC  480
SVKARIGRAL DGPLSVLDYG QGEIVDGPKI LVTDGPRCVA LIELHSDVFF VKDAIREYKR  540
THGVAFNGAG MDDEMLERLS SIPSPSPSVR CQIQAWVAAI GKRLHLLHYG MRREGYKNLG  600
EAIRLLAAMD AYDSMLQSYQ RIHLKKGQSL PRQAKNDHSR AGLRETITRR IAYAIAQEAR  660
DCNVVFVEDL KADFDADNDN NALLRLFAVK TLIRYIQEAL EKIGVGLVLV AKDGTSKTNP  720
MNGDLGWRDR NNKEHLYFEL NGEAVRCHAD LVASLNVLLR GLDHSVCPYS FVTKDTNKKP  780
GRADQKDKGY GKRLKRFFKD RFGSSNLRFV AKPDGEVTAT TRRPKDALIG ERVYYHGGKL  840
VTSEVHYRME NEIKHLLTLK SPAKELSLTE DGIRSYENFT HV                    882

SEQ ID NO: 7            moltype = AA  length = 882
FEATURE                 Location/Qualifiers
source                  1..882
                        mol_type = protein
                        organism = synthetic construct
SEQUENCE: 7
MEKFPRCSHL KVKQHCGPFV EWYEDLQSDR QKYVSLFFPW IGIGYGERKD EGDDIDFISP  60
EQTLERRKAE LGKLEELVVR FVTVMLKGGS SASSCYSLFY EDYKGKDTAK KSTSKVNFIK  120
ALPLLSKKEI EDRVLGDNQL SLINLDEWME LGQSGLSADD IWDKVSQRLV TGERSLGVDV  180
RHTLKIRCQR PRDRGYCVVL MEMVARQLRS CYECYKNHLN ELQELREKTT KQITESRDDL  240
FSLVCDLATV LTEQDSGLSE RTLFSGRKQA LKPQGKPSKI QAIVDELRQP QYSPLLEADD  300
KELRQAYKAW NSQRRLRDRE TRRPYPCRPN WRNDYQVSLG LTGRGGFWMW MDGSDVVVDL  360
QDCGRLTCSP SHYFGDLAIE GQLHQYDIRY RNKLKRRGKK LRKPPAYGEW IEATIKEIGI  420
QRKGGDYYVY LLPVISHDST NFQAAKKFFA AAAPKQEIID ALPDEMKVLA LDLNISNPVC  480
SVKARIGRAL DGPLSVLDYG QGEIVDGPKI LVTDGPRCVA LIELHSDVFF VKDAIREYKR  540
THGVAFNGAG MDDEMLERLS SIPSPSPSVR CQIQAWVAAI GKRLHLLHYG MRREGYKNLG  600
EAIRLLAAMD AYDSMFQSYQ RIHLKKGQSL PRQAKNDHSR AGLRETITRR IAYAIAQEAR  660
DCNVVFVEDL KADFDADNDN NALLRLFAVK TLIRYIQEAL EKIGVGLVLV AKDGTSKTNP  720
MNGDLGWRDR NNKEHLYFEL NGEAVRCHAD LVASLNVLLR GLDHSVCPYS FVTKDTNKKP  780
GRADQKDKGY GKRLKRFFKD RFGSSNLRFV AKPDGEVTAT TRRPKDALIG ERVYYHGGKL  840
VTSEVHYRME NEIKHLLTLK SPAKELSLTE DGIRSYENFT HV                    882

SEQ ID NO: 8            moltype = AA  length = 994
FEATURE                 Location/Qualifiers
source                  1..994
                        mol_type = protein
                        organism = synthetic construct
SEQUENCE: 8
MSETTKSEFP INKQVTNTVS ADILADEKTT SKLTDILNVN SIVKNDLLKL MLTFRGGKCQ  60
LDDVEFDSDK EFDKLYAALG TSLPKEVIKA LAKEFYYGLT GGLTSRAVKN IIYSPKEIKT  120
SVSYKMDVPD QPNKKESKDK DQKKGKTSKK AKKPKKSVVT SEFDILRKSG IFPLKTPQEC  180
SGGMLYSVVK TVQNDLISLE EKTKAYEADK QYWLSKLATC KYPHIGRYGD FLASVEGLSG  240
IKSWNANGYI RFIKLWHDNS SRKGIRSFLL EKHTQYGNKS VAFTAEDTCG FGYQPDFFDS  300
LYKNFKDLWL IEDVIGNEDY ISFICGRDNT EDDKKNKGAY HWRKEFINIS SPERYGKKAV  360
LMLSNGVDND KGNFVPFTLD FSNENWIMTI DNPLTGEKLS FKLSKGTYYN NFSVLPNKPV  420
KVKKDKNVKK DKNVKVEKAK GGYKIRYSTR KDDKYMYISY LKQPCLRYDP KKGCFKIDFI  480
NSDKQVEGLD VNVKNLRGMQ KYFSTSSNFD KRAKDVLPGF ENKEFIAIGA DRGTFPTAAF  540
AVARVNKSKD GTFTIKEWLD EEFLSRNENA DEMTRKIKNV TDKITAVKRL TNETVKFKKG  600
EIAEIPPTFT RTFKGKDGTV TATIKWQTLL EIDAEDYTGQ VKKLPYDKDS KFTLLQQWIP  660
SSVEWDVKRV MHDIKIEKNA IKNAFQNSEN KTEYLQQNNK VDSSTYRKLE MIKGWISLQK  720
KFCGSGPDVC KKDYDWLNGL RKHIDNQLSS NIVAVARKYR EKYGLEVVVF LEKLDAFLSG  780
FDDKHHNSTK ALWGIGSLNK KLSEKGEKFG ILFVPVDPYQ TSIMDSETNL LGYRNWAEDK  840
SDLYVKRNGE IQVVNADINA AKNIIIRGIF RHKNIVEFSS DEISDDLYRV MPVGKQRKGA  900
LFGHTGSDAI LLSDKDGDGE LFVASKSLNE AQQQATPINK DKKKVYVVFQ DGKWIFRHKL  960
DEQLKQYPSL LKAKPQVSKG NKKSVISRDL QLAH                              994

SEQ ID NO: 9            moltype = AA  length = 887
FEATURE                 Location/Qualifiers
source                  1..887
                        mol_type = protein
                        organism = synthetic construct
SEQUENCE: 9
MALIQRAGVL KTKSDFPKVI KDWHDSLLAD YRKFFPIIFS WCPEYGYTTI QDNKPVFVSP  60
EERIESIRKE AKEHLNEVLA FGKMIGSKGV GGSSSYAIFY KHHKNNENGA YTPSRAKFMK  120
EGIHNRRVEL VDALMLNAIP DKEWIRIAQE VVGYSEDRLK LYWNKFIAKK VVSHDRKLGK  180
IVREKYLEPK GLVCAQPENS TYCRVLTEII KRQLHSQIEK SKFHEEELKS IEKTVSEFDS  240
PLLDVICQYA EELNQINSGL SKYVIKNAVK EVISPPEKQS EIYVQSQVLS QEKYKPLVNA  300
TIKEILSGYE QWKVKSRYEN RLKNRKYVLY PKLSANYKIP IGQNSLGRFK INVSENGEIV  360
IRLNNMADVV CMPSKYFFNL KSSPVVDKKK QLVGYQISFN HNSRRKEPTE KPDFNGIVKE  420
IGLQLKKDDGR FYITLPYCME YSNDNFDLIR PLLTSSPTED QIKKMPSEFN VVGFDLNLSM  480
PLPITRAIVG KSVKGEINVE YLGQAKVIES THLIYDNNRC KVLIAYKRQC DLIKRAIREW  540
KICKGKNIDI SEKTYEWLES HTKRWNPSRQ PESMQDRFSV SKMRIQILVN KAKSRIAKYN  600
DNSWKTGHGN ESELIRLIDA DDAYNSLVST YNRIHLKSNQ FIYALPSKNN SRSNKKEYCL  660
RRIAAKIARY CHLHNVNICI GENLSFQQDS DNISKDNSLV RLFSSKSIAN YMKLAMEKFG  720
```

-continued

```
IAFIDSADPS GTSKTDPVTG NIGYRNKFDK RKLHVLRNGN WGWVDSDIAA SLNILIRGIN  780
RSIVPYKFFV GKKKQESKRL NHFLNKIFGT TKVFFYEDQF GFANPSLSKK EGENLIANQY  840
LYYREGKFVT QKIHRQIEDD FKKIDFSNTP EVNLIPSGVK LKNFQFE                887

SEQ ID NO: 10          moltype = AA  length = 824
FEATURE                Location/Qualifiers
source                 1..824
                       mol_type = protein
                       organism = synthetic construct
SEQUENCE: 10
MESIRKEAKE HLNEVLAFGK MIGSKGVGGS SSYAIFYKHH KNNENGAYTP SRAKFMKEGI  60
HNRRVELVDA LMLNAIPDKE WIRIAQEVVG YSEDRLKLYW NKFIAKKVVS HDRKLGKIVR  120
EKYLEPKGLV CAQPENSTYC RVLTEIIKRQ LHSQIEKSKF HEEELKSIEK TVSEFDSPLL  180
DVICQYAEEL NQINSGLSKY VIKNAVKEVI SPPEKQSEIY VQSQVLSQEK YKPLVNATIK  240
EILSGYEQWK VKSRYENRLK NRKYVLYPKL SANYKIPIGQ NSLGRFKINV SENGEIVIRL  300
NNMADVVCMP SKYFFNLKSS PVVDKKKQLV GYQISFNHNS RRKEPTEKPD FNGIVKEIGL  360
QLKDDGRFYI TLPYCMEYSN DNFDLIRPLL TSSPTEDQIK KMPSEFNVVG FDLNLSMPLP  420
ITRAIVGKSV KGEINVEYLG QAKVIESTHL IYDNNRCKVL IAYKRQCDLI KRAIREWKIC  480
KGKNIDISEK TYEWLESHTK RWNPSRQPES MQDRFSVSKM RIQILVNKAK SRIAKYNDNS  540
WKTGHGNESE LIRLIDADDA YNSLVSTYNR IHLKSNQFIY ALPSKNNSRS NKKEYCLRRI  600
AAKIARYCHL HNVNICIGEN LSFQQDSDNI SKDNSLVRLF SSKSIANYMK LAMEKFGIAF  660
IDSADPSGTS KTDPVTGNIG YRNKFDKRKL HVLRNGNWGW VDSDIAASLN ILIRGINRSI  720
VPYKFFVGKK KQESKRLNHF LNKIFGTTKV FFYEDQFGFA NPSLSKKEGE NLIANQYLYY  780
REGKFVTQKI HRQIEDDFKK IDFSNTPEVN LIPSGVKLKN FQFE                   824

SEQ ID NO: 11          moltype = AA  length = 903
FEATURE                Location/Qualifiers
source                 1..903
                       mol_type = protein
                       organism = synthetic construct
SEQUENCE: 11
MNHFTQNLAV TKIDSSVQTL YDDFQEDFRK WYSILCSWAK VPYRVEDDNG NITHVHAKQR  60
AAELSSLYSA QEQLLIERFM RVFLGASKEA SSSYSLFYDK YAPNGAKKTA ALKEFLGEIP  120
TLDDSQVEKK ANTNKNCKRI TVKEWRDFAA QFNKLGIDAI WGKLKEKITS PDRGVGLQVR  180
GFVSERCKHP ENAGYCRQLC QKLTEQVKST VRICELYIQE TADLQSEIGN KTKQPEVKKC  240
FDLLCQLSDE LRDVNSGLSG RVLFQSIKDI QGGKDSDRKN KVCRTVMSDD KYLCLIDSDK  300
KIVQRAFQAW KLSITLKKRQ EKLYPKQRSH QNDVPMPFGL TGLASFDVSP DGSKFTFSEG  360
SVETKPSLYF DGLRFQKNKH SFDMEYRVAY ASRRTKKGRR PKRVGRLRKA TLKQVELFNK  420
GGKFVIKLPH GIELPEHRAK LATFLMCADP KEKGYSKGGL VDEFRALAID VNLSNPLAAC  480
VADVSKHGDG PIQALDYGRA KLCVDPFFLV ANTPVCGQLI KLCKECKAVV QAIKEFKECQ  540
AAGSDFSFET DLFLPAGHSP RHRIQSKVQE LSRVLRDWKF KLQNTNQVAE MIRLLELMDA  600
YQSMISSYQR IHLKAGQTLP PQKKNSTKRA NYRKDISRRL AFVVADYAQS LNVDVVFGED  660
LKADFDRDKN TNSLSRLFAG GMFLQHLENA LAIRGIAFVK CAKNGTSITD PVSGVFGWRD  720
KFNKERLWIE RDGELGWVNS DHAACLNVLL VGLMHSVVPY RVYVKAGRKT TDDVEVFEED  780
HPIGPRKKRF FELCFGENKP KFEVVENRVI LDNAGTYQGF IYAHCLDAMQ SEKQHWAEYD  840
RIKELALAET NPKQFGLTPK KGEGYRNFCQ PDIHEQVEVV GNKRVAATKQ ILESLADEKI  900
EAT                                                                903

SEQ ID NO: 12          moltype = AA  length = 872
FEATURE                Location/Qualifiers
source                 1..872
                       mol_type = protein
                       organism = synthetic construct
SEQUENCE: 12
MAYPPFVRTQ NFKIKNITTN DELLQWYEDL QFDQRKFYNE FFSWTGLGYY VLAENDEIIY  60
TSPEEAAIQR KEKLGDNESC VARYVDLILQ GGKSASSCYN VFYENYKSTG KAKFSEMKCE  120
FLKNLPFQTK KQIQEKISKN KQLSCLTLNE WWGIRDKIKT INKLESNEEK EIETKKVWNT  180
ISSQIADTDQ TIGVEVRELL NIKCRRPNDC QYCKILSDMV GRQLRSFSEV TKNHLKGTDE  240
LKQKLNDSKN DLYNIICEYS DALDALESGL SKYVLFQAIK EAEKPNPESK IQLAVNEIKK  300
GKYESLRQAS RKELMKAWKA LKLKKRLQIR KKYPRFVVGG NDYPINVGLT GKGNFRLSTH  360
NNKILIEINN FGTFECYPSC YFGNFQATPI MRNKCICGYN IKFRNINKSK NSVTYGPWVI  420
GVVKEVGIKR KNGNYYVSMP YTMRPEDTNF KIATYFAKAK PTLDEFEALP NEIICAGYDL  480
NISNPVVQTT GRVVKNGHGP LKALDYGAGH ITKIPTILTP NGLRCHRLIQ LKADVYKTKD  540
AIKEYSGNLK QHQDVSNETK EWLKSSDHNN TRYLIQKKIG SITKRFKTLA FEMRAEGYQN  600
LAECIRLLDA MDARNSLLNS YKRGVQKLPP KRQFDSKRAD FRNYINRRIG YLIAKSASEE  660
NCNIVFLEDL ESDFDRDNNN NSLMRLFTPN TLIKCIEEAL EKKGIGLVTV AKDGTSKTDP  720
ITGSPAHRDR YNKEKLYVER NGQIGWVHAD ESASLNVLLQ GLNHSVCPYK FYVKESTKDY  780
GIRMQRFLKE RYGTTNVSFV EDNGQVEAVP KKRPANRLQN TYVYAHHDGI MVTKDKHLQI  840
ERKIEDSVMQ QIDLPKFSLT DCDERGYRNF SV                                872

SEQ ID NO: 13          moltype = AA  length = 464
FEATURE                Location/Qualifiers
source                 1..464
                       mol_type = protein
                       organism = synthetic construct
SEQUENCE: 13
MPRNSKKKKQ SEVRTLRLDV LPVRFGLHNA ERVKYPAETT DEAKARVGEA CNTVRTYIRK  60
YRLAIRKACA PLLFAQAATE EWSDEKGRAV IGKADAVTEE MSKLTGDKVC IQRNLDRFVK  120
ALIPTLKCEC FQQVANRIYT AITAKDPDIP ISRHLLILDG VRKLPWFMNE PIHLKYCPTY  180
```

```
RSDVIFNGHR VFLRWDKELG YVEFKLIGKK LKQNAKGNSK RGLDASQWYI IKQLQSGAWA  240
PGGAKLQLMK DGDFRLICGY QGFELDRPEL RAKAGRERIE LIPVDKDRID ELSFTEDRER  300
FMVLQLSSGH RASAGIPVDE VTKHEWSALG MLAHVDRLSK QQDRSKKRTS SCGAFHKARE  360
AEQARRDRIT RARENAVANW AHEWSLQVAN RCMAMRCGQL RVFDIPKEVL FFRPFPWSKF  420
RFDLEYKCRE RGIEVSYHES PKDSKGSSDP NAEDSATASV DGQE                  464

SEQ ID NO: 14          moltype = AA  length = 617
FEATURE                Location/Qualifiers
source                 1..617
                       mol_type = protein
                       organism = synthetic construct
SEQUENCE: 14
MSETKEVFEA KKKLEEQEPT AEAVVALGKL LLAAEEEIGL NAASELLPKY LRKRMQLLLS  60
AATGGKAEIE AALEPFVLDW HKKAINSAWK ELREVKLERQ LIQLARTLQE IDGRIGRQKL  120
VSITPKRLLQ QRKLDTLLTV ASGLESAEEA LEKVVSEPRP LRLQVRPIRV GLERPEHPKK  180
IKNETAEEAK ARVGAACEKL RAYLRKYRFS LRQAMNVMYW AQARTEKWNE EKGVPRVGSV  240
EEVKAELRKM TGDPVSIVRN IDRYVRTMLP RINANCLQMA SARMYVAWTS KMPETGIPRN  300
LAVMDAAARM PWFANEPLHF KCFKSLNSDV KFDGHRIFVR FDHDLKWVEL KIINTKHKRT  360
YNEKPPPKGK RNGGKKSLDY MYWYVLKNLQ KGEYSPAGAR LQMKDGKFSF SCCYNSERGR  420
PELNDGKKRP FRKVSYDRVA DASFTEERTS FIKLSLREGH EPSAGIPVDQ VREYPISAEA  480
AIAAIDRLDA QQRKAENRIA ATGSSNKRRK AEQKRRKRIT EHRENVINQY CHDWSRQLAD  540
WCSVMGCGRM MVFDVPDLLF GRSFQWAKLR FHLQSKCRER GIEASFHESP KDSTGDTSRS  600
GDPQAEVSAP CSVGLDE                                                617

SEQ ID NO: 15          moltype = AA  length = 517
FEATURE                Location/Qualifiers
source                 1..517
                       mol_type = protein
                       organism = synthetic construct
SEQUENCE: 15
MEVKVLTKVK QPRKEGRGGG SILAARNDLV LKSDSLNVLF DGDLSHFRGV LSKWRCMIQE  60
MENLVEIVEK AVADFSMKKK VVSEIDDPKH PGEKKKVSTW VPTDYVIVRM KLDDAKQAAT  120
SILGKDVNLC ETKYQEWYRK WQELDVSMGG PHFDRRMFEQ AIKIMGAIRN KKVPDRGNIP  180
RNHLVVAGAA KQPWFGNVPL ECIYASQSNV FRAKFVKEGN IRKVVLMLND KDEDAKLTFV  240
VRGAIVDKNG KPHTIGTKKS DRVFDNYFEG RWIPTNPRAN IDKRGYCHLY VSNYRPRRAF  300
TGLLDANTLE VTFHKINGED IRKPWRPEKE QDRLTGRVFT IHTRIMRGNK RSWPANIAIN  360
DAIAAMRGYS KRMDEKRECW NTRRFGPKRL RRPFQEIIDN ISKAKERTQR QINHRWTNEV  420
IFQATRKGRC RTIRLYGFPD GVKAGLLLDG TVQWPWSEWL RMLIYKAEEA GCFIELVTTQ  480
EDINAMGVAL HEELTRVKHK EEEEEDDDEA EYGPEAA                          517

SEQ ID NO: 16          moltype = AA  length = 844
FEATURE                Location/Qualifiers
source                 1..844
                       mol_type = protein
                       organism = synthetic construct
SEQUENCE: 16
MEFTNVVSKI REGIFHISMS TSPEITNKHR PLAMARSGSL TFSGNTVTFK GETHTVETPL  60
TDERMPVHVT LTNYNGKVYE FPRSPNVDGL FAVKQKNGDF FLRGSNRNRG DKTEKEQGNY  120
LTVKGRVYHH HRGVETSAEL PAWAEAIRTR WKQGWNVLAL TLRWVLWKTE DCGETEQDWE  180
ALIKNKVDHL LNSREGYVQP DALSPESTAI VDRIRRVIVD SSMAHYATRG REAKLSIPIV  240
LRDNSKVPPA FSDLRNFAYQ LGRYEKEEGV KVQMVDEGGE IDILSEWLGI ELKALKRNKA  300
PLKAFKALLK AKGEVWTDGF MGTLFGRIRA HLGMDALEAE ALSTRFTAVL KQRESKSMPF  360
DRGWPRPIRT GEDAWQLVYN LKGKTTLGEL MNNKCSDIQF TQPVSSEISG SPNNKVVTKL  420
KDGTFDVTNE YKPLTPGSVA SQRELRGLSF TKGKKGMEPY KLAVLMHRND VDLNAKVKRV  480
VLSIKTEIEP YVIYKGQPTP SLGAASAFTS PAGRKVTFYQ LNICLEGVKT NEKYDRRGTG  540
ASHLKLGWKV NGDQLTVVTE TRPTGVIVPY SLPLGEVWKT EGILDAGCHS DKPGNAWSRR  600
NNYKMAFYAL NGWPVSPLVI EAQKQELVSR FIEGRLTLDW LKTTSLSLPK QIDTLLNVAK  660
AEGFKLMTGG QRAIVTREGW HMVHQKGLVR RIKELRMAEN GEAYPASNSN PSRSKEPSKP  720
LGKNKELLTL WLRWLEYNDR LRAVERMVRG HLLGRRKAYY YALAHHLCDH TAAIQYTKLN  780
LKDQAEKKTR KKKDKGEKAV VDNSQKYRMW ASLGEFTTIL KQVGIKRGVE VKEIEIALTK  840
VAAA                                                              844

SEQ ID NO: 17          moltype = AA  length = 629
FEATURE                Location/Qualifiers
source                 1..629
                       mol_type = protein
                       organism = synthetic construct
SEQUENCE: 17
MKTKTKTATK TATKTHIDLV LRARLAERGS AGSAVRREAR IVIFGADQQT PHPDSEKIVE  60
DDLRGTHEYY NRLVRAVSPK YKKARGLVVG PEARKQELRE KQISALYQER HDCAKSEEAR  120
INEEILKLKQ ERRESWALVD KERTALRKKN AEKIQDLIGP STITPLIKAE RNRVSVYGKT  180
RQSSDPTIGW GNYTLAEKDF GLATRKAFNL KSIPHFRGED RDGTAPEDFR AYKFWQKDGT  240
LRSDFTQKNH HAHRTPEAIF GGKGKLMTIR PFEESDLAAF NLPAAFWDQI ARHRSEGKPD  300
RWYVILIVRN GTKVPDADWY GVVANFPAGS KQTPSLLDRL RSVDHVTEAR IVRKKQGLRL  360
ETHVNLHVKI AVAAKVARET VEVSWGSFTN KGVGKLLVTY PDGRVDEFSE ANVPALLRCR  420
QHEETSRKLH ESLSKHEKDA RKAFKTLNLD PSIIWDREEF PRSPGSIRHV YRRLFRDEMV  480
EALGGEAARE KRDEIMRLCL KLYRQPGPDG EKNPYGGDPD QAREIVAMRM AEIFPISEDK  540
AAAMAVVFVF MERFNHLADW AHRSGFRYHT SRREFYRTFA AELCQKYNVT YLRPPKAGRK  600
VSGDRSVVAP FVLETILKTA ALKMGRAWE                                   629
```

-continued

```
SEQ ID NO: 18          moltype = AA  length = 437
FEATURE                Location/Qualifiers
source                 1..437
                       mol_type = protein
                       organism = synthetic construct
SEQUENCE: 18
MSISDIFKAN QFKTEIEELK RECNRLQSLL TPEMQDAAQL KREIDKLNFD KYNINNQIND  60
LDKTLDAKYD AIKKLDIVIN NKKSQIIWMD DEILVQEFGL YQPKFEFANS QQYKEKLNNN  120
RKLQKESIKN CTAVTGSTNW TVDGNKSKGN KMVKDMQKLL LRAFNGECDE LIGKVKYNNY  180
DTSLKRITAS KDAISKLGTI MGISITDTYF RLKKEELNLA LEYQLKKQQE KEALAQARAE  240
MREAVKLQKE LDEQRKKIEK EQNHYQNALH SILKQLENAK DNEKEALETK RLELSKELEN  300
IKTSLKDLDY REANQKAGYV YIISNIGAFG ENIYKIGMTR RLDPQERIDE LGDASVPFKF  360
DVHAIIFSDN APALEAKLHK AFDSKKVNMV NQRREFFNVS LDEIKEVIRK NYDKTVEFID  420
VPEAEQFRIS QKMKEQL                                                 437

SEQ ID NO: 19          moltype = AA  length = 425
FEATURE                Location/Qualifiers
source                 1..425
                       mol_type = protein
                       organism = synthetic construct
SEQUENCE: 19
MLEDNEFSKF AFTTHMKKYY KWCRSNISSM VAQAISENVW RAFEKYFYSN GKRLHFKKIG  60
SVTTVAGKGG ASGPREIRFK DGYVLWNGLR LKVKLDESNV YEQQMLEHRI RFCRILKKPD  120
RRKNHYYVQF VLEGRPEIKI RPDTGEALHP VGVGRVGIDI GPQTIAYAAE CGAGLRELAE  180
GVGNIEREKR LLQRKLDRSR RATNPNNYNA DGTIRRGVKL TKNKSNRYLA VQRELAYVYQ  240
RQAAMRKQKH IALANELLAL GDTFFVEDMP WKGLAKKAKK TEISPKTGKY KRKKRFGKSL  300
GNKAPATLIM ILDNKLKSLG LDGVQKIPTT ARASQYNHIT QTYTQKTLSQ RWNTMEDGTK  360
IQRDLYSAFL LQHINEDNKT FNQQTLEEDY PAFQRYHDRV IVQLQNNPHN VASMGIRSAT  420
HKRAE                                                              425

SEQ ID NO: 20          moltype = AA  length = 416
FEATURE                Location/Qualifiers
source                 1..416
                       mol_type = protein
                       organism = synthetic construct
SEQUENCE: 20
MGIIKAAIQS ATSTLADQWL DIIEPDTMDN TTLMCKGVLM SKNKKRGSNT KGSVDYISDG  60
SIIRVYPNMM MLLVDGGQII DYTAEEGYYK VDNSAAPSLF NGDFEGALNE SFERFRFGGV  120
TPSKQEVFFI NLQEIRGIRF GTQQPINYFD NFYNAELFVR AHGSYSIAIT DPILFFKNVV  180
PKGVTRLTID EINEQFLMEF VSGLQSSINQ LSAQGERISY LASKTAELSK VMNQNLDEQW  240
KSLRGIEIVS IALASISYTD DSQQLINMRN KGAMFNDPNL RESFMQTSIA QGIADAGNNP  300
NGAANAFFGM NMGANLTGDY LSQQASRQNQA QTQQAAQKQQ TANTSSAQES SWQCPNCNQE 360
NTGKFCSNCG TPKPTPTANT GMKVRCSKCK SVIEITNAMP KFCPECGQPF LAESLD      416

SEQ ID NO: 21          moltype = AA  length = 416
FEATURE                Location/Qualifiers
source                 1..416
                       mol_type = protein
                       organism = synthetic construct
SEQUENCE: 21
MGIIKAAIQS ATSTLADQWL DIIEPDTMDN TTLMCKGVLM SKNKKRGSNT KGSVDYISDG  60
SMIRVYPNMM MLLVDGGQII DYTAEEGYYK VDNSAAPSLF NGDFEGALNE SFERFRFGGV  120
TPSKQEVFFI NLQEIRGIRF GTQQPINYFD NFYNAELFVR AHGSYSIAIT DPILFFKNVV  180
PKGVTRLTID EINEQFLMEF VSGLQSSINQ LSAQGERISY LASKTAELSK VMNQNLDEQW  240
KALRGIEIVS IALASISYTD DSQQLINMRN KGAMFNDPNL RESFMQTSIA QGIADAGNNP  300
NGAANAFFGM NMGANLTGDY LSQASRQNQA QAQQAAQKQQ TANTSAAQES SWQCPNCNQE  360
NTGKFCSNCG TPKPTPTTNA GMKVRCSKCK SVIEITNAMP KFCPECGQPF LAESLD      416

SEQ ID NO: 22          moltype = AA  length = 1125
FEATURE                Location/Qualifiers
source                 1..1125
                       mol_type = protein
                       organism = synthetic construct
SEQUENCE: 22
MAKRSVTPLT EDRQLWEPLP PDDVRLAFVK YLDRRPGSIR RTIQLQLHNP GWRKTQNLLW  60
ARKHFNNYIF TILETLREDP HQFRDDGAFE CIHEMMVRRE ETRRQGKPPG KYTRVLGEVI  120
AERFRRPARS GPNNQDTNDE TVADNASDRR NHPSRRRPPL RILEARDYPI IHMLRPGAQR  180
RCALILLNFY IQSQKIPQAH EQAPDSQSDE ASQNTASNRE LEHAHDASHS TAAADFSDEE  240
AAEREETLEA EMEALETDSI PTIEMMHQMW AQRWMRYEAA ASTRIPYGQH RGKPFGEALA  300
ARRMRTGRER GRLVRKPGKR RVRWLKERTY ALEQVHTCLR AVQILLHRDT YGNDSAEVLE  360
AEQVRHLWKY ESRTLRRPRA RRVEHYRSRQ SQPLATLGSL SQEELHTFRD ELYEQLDHAH  420
QYAQIAEAVD IFLEHAPPSY PTIDIGLFND SPERREHHSA LNWFPRPVTR GSIRDSDDDI  480
ERRPGPSVDE LLHRAEYDAV TRLLQAESEL GERALQPLTY TRTMRPPAPL PCWALLYKRS  540
CPSHEEREQC ARRLPKRMRQ RYKDTALNST DGYVYTFVLA MVVHHTTHAF TGEQPADYFS  600
PSLSEDEYFY VNFPLTPFHP PQGVSLMMFP LECGEEYQEG LLHDLIERLR AEQHAQYAHQ  660
FTDPDVDPAD RVPVEACLPT QAALGEAKIV TRQNGDDWYE FFLHCAVPID ILVREPPERI  720
LGLHHHQHGY SWALIDAVGT LINAGDLQIP WHVRLRPGSS AYSDNYAFEV ANQIVALAQE  780
QNALICIENT WTNKKATTSA HQNQRAFAHP SRKIYDQVVS KAIEAGLPRP RAVYGISRSR  840
```

-continued

```
CGACGNRINN QRGKETLSAC PACGSLSRSA HIQFPLASLA PTADGSTAAW VLLAQEQEHG  900
ERAAALTDFF YWTLRQAAAD VVPAPDRRQA FIAGLEQVQW QGRQVFRPKS GRNTYTRNNQ  960
QAGTNSAPSY TFRPRRLEAD VVIAGPEAYA PRVQQWIAAY ELVAPDVLIE YVSMLREHAL  1020
DILYGGREDA VADVILLDTP ASERELAAGL AQQRSWFCQD CGQHWQVDEL RFRCTYEPCR  1080
HHDLARYNTA AVVAQIAVHK LLEGSQQERQ HATPGTTGGE HETLA                  1125

SEQ ID NO: 23          moltype = AA  length = 465
FEATURE                Location/Qualifiers
source                 1..465
                       mol_type = protein
                       organism = synthetic construct
SEQUENCE: 23
MEKYNVSISK SELMSKQDFF KLWMRAYDGA EEVEENHWMT RFDNIINNSA KRIPRYKEKI  60
AQIVFKVLEE SYPFFIWGIP NEEQGDFIKT CEKDIKNATK KTISIIIAPC TSLSDFCAKY  120
VRLQLMGGQE WLDMFASNIS HYIPTYYAAN YLQMPKSEEE TLSSFFKGSA ITVDNESVSF  180
ASLFERELQT ACFVYLAKKI MDDEDITEEN FIRRLPLLGT PDAGILFHDI LSSLLPRLFF  240
DVYQLFAQRS AVEAASSGKT LKKMEEEKKA LKAQVSDLNK KLKEKERIIA EKETKIQTLS  300
KKLVTANETS KNIEEVVEKR TEAIAYENKS LMRQNKKLQA YYSDLRSKYD RLKIEMGSSG  360
ADVEEDEREE MREVDVNARY LFLLYDDIGC RQNIKQEFPN AEFTSKVVPL SSHKYDMVVS  420
LTECIDHSNY LAMKKQCKIH GVPFAHSPYS NIDMIKTVIW NVLNG                  465

SEQ ID NO: 24          moltype = AA  length = 1235
FEATURE                Location/Qualifiers
source                 1..1235
                       mol_type = protein
                       organism = synthetic construct
SEQUENCE: 24
MTAKKKQQPR VWEPPARDAL LHAFEQAYAA RPDTVTLTII LKLLTQRDTE ALLHTAQMRV  60
TNMLHDVTVR FFDDLEQIDA GTTAEHLIDA IIELVSDPIQ VDAHHAQAVS QLRASLAVVR  120
TQTIGAMDTT FVSALIAAAA SADTADPSHR GWSVLRAFLE QWYIDHPGDK MISTINHAAQ  180
ATSKRKVKDE HGNLKKDAQG KPMTDVVQTY TPEQVYHIKL ALTLRLALVA RHEAQVITTR  240
AMALVVLALR QCSNTQAFAW VSTTLTQRFT NTRIHAALAL LLVVQQRVHD EACHRIFVTI  300
NQRCAGNQMF AVIEVIVELV SRHIPEADNK PAVADTVRHY LYQLTRSRKQ RRKPHHVTHA  360
NAQVPADETA HADAALFVDE KPHPVRPVLL RIVDALVGSN ENTGILPLRM CLEHWYSSFA  420
EQEREERFSA GDRRLIAIAR DPTRQDEAGD RHTGMSLLLF HWLQYHCVLS TDVLLLVSLS  480
EKAIRRIGDG DTVLSGILSN CYGEVCSRYQ YPLSGELREG VFFNRGGAIL GWCQLVADYV  540
AERDKRRPGT TLPPWKTGKP KNVSRVDFFK GNRVVRIGLA YALWKREDTA YKAAVATEAP  600
VGPDEGKTLG NPYAYTELRR QVAGNRRRRV TILGRGSIGK RGARRMKKWM LPAAERRATL  660
RHLDVLLYPE LVWNDEERVA AAQASHPYWM KRTKRGITAV RPTQFRLYPS TYPKSLKDLS  720
REKQIQLREE LREQERYAPQ FAPFRHALDR FLEAAPPAPP FIAPMVLTDA DMAQLTPEAQ  780
LEWTATFETY KAEFDQNLNW YRDFRPSRGT PTEEYSDEKL YDVETLHNRE LEWSAATLAQ  840
RHPQPIYFKR GMNAELKPRS FALLYHIPQR KGCARYRFTF VCDLVGETAT EREALLTKRR  900
ARGEHTVENF LVNHPDQRVT HPNETTLHYF ATQMGSDHQE RILLEYMDWR RREPERKKPL  960
ISTARIVSHK RTRQRTDWYA HLPVPLPAPT HTATLDTVIG FHEHEGTFFY AVVDLDGRLL  1020
ALGDVDLPNC VRPKRTDGMT NDNFAFETAV RMVWRSMTQQ YFHKFRDNPK RYTAFIGIEN  1080
TGWKQDRVGT KAADNRQNIS LPRQRIIEIV TYKAIRHGLP TPLSVKRISP GRDCGHCDAR  1140
IEHGSGIEKR PVTHCFHCQT LGIEHELEWH KEADNKWSAR CITCGRSWRK EEPQFKCQHC  1200
RTQQYARYNT ALATVHCTVD ILVGRKRNTP DSEQE                             1235

SEQ ID NO: 25          moltype = AA  length = 404
FEATURE                Location/Qualifiers
source                 1..404
                       mol_type = protein
                       organism = synthetic construct
SEQUENCE: 25
VAKKKPEWLM RTVSVPVRFW PSDVGGDGRL VLDDKGEPVP THTRQQMWAA CGEAWKLSTE  60
LANWAGRELL RADVSPPHPG KLPAMPKVYL YGLLTPLLKE RWAGQLASAN CVLRAVERAY  120
RAKRFEVQAR CSAAPAAFRY PYPFRVHNQI WSVHVPADAE MNAGEHPVCT LTLPGIGRVH  180
LPLSRASGHR RALALLRRIA AGDPTVKKGE LTVTRQRDGD RNGGHGTDGG PDRAKRAWTI  240
MLRFSVGTRP AENDGTQTMN LVTDPEALLV CWLVGRKDWV VNDDHVRRRI AAHAARRQRL  300
SQDRKAERRL RRGVGIQARL DLECEKHERF MDTYLHQTAA AVAGYAVRNR VGCVFADLSP  360
SGYVDSFPWF KLRERIGNRL AREGVELVDD KWAGSNETST PEED                   404

SEQ ID NO: 26          moltype = AA  length = 517
FEATURE                Location/Qualifiers
source                 1..517
                       mol_type = protein
                       organism = synthetic construct
SEQUENCE: 26
LEDTSKNVFQ SPLLLSKTAE TYTPIGYEEA VAITFYYAED NRRKPGFLRR TGERITLVAP  60
LNYALYIIDI DGRNSVIIDP NKGSELEITY YKPLISLIEE KIEKLRTAET KEFIDILTEL  120
KQVLQGMASD KAGVEKYSIR ISNILKNRPL IEELKILVRN ASENIYEALR IEEKKIDLQG  180
TKNNIREALI LLSETRKKLV NLLGEINPIH EKWLEEIRTS YAEKIHEIEQ KLEEVKKDVD  240
EKINELKKKQ AEEIKNIREK YIGQIETLER RMNEINTKLG QLKTQYEKAK EYGEDTRMIK  300
KRINDLTKKL SDLNKEKKEL KEKMNSEMEA VRSKYLEYIN AERMRIDKLK KEIEKLNDEL  360
ESIEKQAGDR LDEIRSLINQ LIDKASRAES KLLSIMINTP PHGEGAHYLP VMIITYKSKN  420
KSRRDSFTPA YISVGKLSRT PKISFFEEVR KYLSDIPSIL SDARYADQVE KYNLLKTVNP  480
SRIISLLDRL ADNGIINRKK VQKIAEKIVE QIKMAQA                           517
```

```
SEQ ID NO: 27          moltype = AA  length = 731
FEATURE                Location/Qualifiers
source                 1..731
                       mol_type = protein
                       organism = synthetic construct
SEQUENCE: 27
MAENTNKLPV IGTAYFKDIE GYAAFWKAKD HDWVKTQRKE LPPLIYPVDK THNGVVVKAL  60
YRWLYEYWSM SQLTEEELHR RVQDQANEQM KQLREAVYFS ETYQQPFQVR ALFDFGAYIT  120
LGNADFFVFE HEKYLSEITY PKDYSQYTLG ELRAIASGVS AGSTVPATLS NEISISQAKD  180
SIQAAKNRLE EMKKEAENLQ WERHEELAEL KRQAEEAMAK LRQRKSELLD MLEQKREELE  240
DKIEAMNDQV FFLESQIYCI ECYLGETVNF AKVRSGRNAP DDEPIVLYQK QRFLDEEMGR  300
LASVYELDFS ELNLFEEFLA ASPAALEVFA PNERCVTLVR LSKTSLEYGL HPKWANMLKA  360
YDKFHGKMVG IIIRNGENIY IGWTDDDKVI VTDDLFLDFT PAEEVPSDIP VDETERQMKA  420
RMRKERAQMR VFAKEAVSRV FIFNILQGIV DNSPILPLPK GEKITKESKY VRFSMADRWL  480
ADNRFGSFTD IVSRCNAQFS EGDMLLTTQY LRPENGKHTK NDRGRGYADR THDVSVQNCA  540
IYPLNLIEYD RPKQVTEYQF KMPACGNTPE RWVTSTTDGD GSRLDPKDTR IIRTYTKRDA  600
HYFVSLEKKW SYSGARANFE VFPDEVLNLH YMNSVWLMYA ITNRNLGGWR VGGESVDYAF  660
AIRYLKTALD FIRKREADEK MVLDEVAPGF TDRNPEWPVA LSEWKLEKKA RSFTPVLAKR  720
FVNWAKEREK G                                                       731

SEQ ID NO: 28          moltype = AA  length = 491
FEATURE                Location/Qualifiers
source                 1..491
                       mol_type = protein
                       organism = synthetic construct
SEQUENCE: 28
MLRRSVAVEL EVTKDLNKLF YSVETAYLSI VREVVEYAVA NNVTGANKLQ RLFYNKYRLE  60
YPSLNSQLII QAIRQASEIA RSFLRRKRKG LVDKPYPEVR RVSIRFSEMA WSYEEFVKSV  120
APVRLGLSLP NGRMEVWLRP HKRFWQYWWR VLIGEAELAS TLMIKRRLNR WYAVFIFELK  180
PRVEKPQSII AFDINENTVV VGRIDIETTV GKVVDWNRQY VTPQLYMIRT DFGRLARRYE  240
AIRNKIIEKL KPEFALPSGN YVNVANTREF RKRVKRLREG DRKIGRVRQV ANELTKTPSI  300
IITEELGENP QESMIEDVGK DELRHRIKQT PFKALVRAVE DKALERGSKL FHVSSYRNSR  360
VCPIHFTRLG ETNDWHTLQC PKGHYMHRDY ASVTNMAWKL TPESWIKAFW WNMKKDMNWR  420
EHEGKSNPLI PHPIVHHLHA TLREFMASLE KSPAVLARGN PMNPAGRADE DWARETTRPP  480
GREGGRCRVC G                                                       491

SEQ ID NO: 29          moltype = AA  length = 517
FEATURE                Location/Qualifiers
source                 1..517
                       mol_type = protein
                       organism = synthetic construct
SEQUENCE: 29
LEETSKKAFQ SPLLLSRTAE TYTPIGYEEA IAITFYYAED NRRKPGFLRR TGERITLVAP  60
INYALYIVDI DGRNSIIIDP NKGSELVITY YKPITSLIEE KIYKLRAAES KEFIDILTEL  120
KQVLQGMTND KSGVEKYSIR ISNIVKDRTL IEELKILVRN ASENIYEALR IEEKKIDLLE  180
TKKNIREALI LLSDTRKKLV KLLGEINPIH EKWLEEIRTS YAEKIHEIEQ KLEEVKKEVD  240
ERINELKKKQ AEEIKSIREK YIGQIETLER RINEINAKLE QLKAQYEKAK EYGEDTKMIK  300
KRINDLSKKL SDLIKEKKEL EEKMNSEIEA VRSKYLEYIN AERMRIDKLK KEIEKLNNEL  360
DSIEKQAGDR IDEIRALINQ LIDKASKAEN GIVSIMINTP PHGEGLHYLP VMIITYRSKN  420
KSRRDSFTPA YISTGKLSRT PKISFFEEVR KYLSDIPGIL SDARYADQVE KYNLLKTVNP  480
TRIISLLDRL ADNGIINRKK VQKIAEKIVE QIKMVQA                           517

SEQ ID NO: 30          moltype = AA  length = 664
FEATURE                Location/Qualifiers
source                 1..664
                       mol_type = protein
                       organism = synthetic construct
SEQUENCE: 30
MIDMVKEGIK EDLVKLYDNI SSSSVVEDFY FPIIASNPKF YSTSGLQHYL GTAFLAFRIS  60
QHLSLDDYSS ATAFLSGLLH DANKWGIPQD EIVKRFENTK LFSIFSEFFG EEKTKKIIKD  120
SMEIAKTLER GGSSRNLQKI SEAVRISDYI SGDERSWKIS RVIDILRNSS LINIGYEHIY  180
PIYLGRQRLV TVYLSHLVKD ELIERGMIPL ITSSEGMIFL RRSSVSITYD DVIKRMIPLL  240
SSGFRRSKTK SPDASKLVRA LEDCKMNLSR SYESLSGYDY DDLLEGLEEA KISRIDHINY  300
LLTLIYVLQR PEGKEHREKR EKIFRKISEI LNTNLSSSKL CETLITIRDV LMKSDDDFIR  360
RFEEKILEMI REEMREKEVK PDLLRRKISR YISLPREEDV SEDNITRRCP VCGEEILEAR  420
PLSAFLKELK KIVGKINTVE IFLPGIQGSP DRPGSIEKLG HKTDVCETCF FEIKELMPRL  480
GLADGLWSAV LTYYPNISID LADVISNSIK TIVGLDKSSE SYKIVPDYMS GRILVGISVR  540
GKGLDKKALS NALKVWLIFG GNMFITTNPL TSPPLIDAPI RLEVGDMIFL ECSSKYLEIL  600
KKASAYSSYL SFTSQMRYWL FTSLLRYVSS LETTSSGSDA MFRRSFGYTT GFCTLDVLSS  660
ESIR                                                               664

SEQ ID NO: 31          moltype = AA  length = 1276
FEATURE                Location/Qualifiers
source                 1..1276
                       mol_type = protein
                       organism = synthetic construct
SEQUENCE: 31
MIYNSLLLNS GGGIIPQFQK SAQSKEAAVL AIGIGGTGVR ALSRLKQKVY QQLKSDNEED  60
DSAVKLYKHI QFLAIDSDET DFKQIRGEAK INADTEFISI QDPALNTIIS HNDKKPILDD  120
```

-continued

```
PRLNWMDIDH ITALLAPHGA GGVRQLGRYM IIKKAQRLST LISGKINLAM ENMPNDNVHV  180
YIFAGISGGT GSGCFLDTCY IVRKALKDLG IGGNGKIMGF FFLPDVVTSK REVAANRELV  240
LYNESNGYAA IKELDYLMNL RSAKERFKQV YDEGFVVDTD EPPVDMCHLI SAKKADGTVI  300
TDGFKYCIHV AADYVMSYLA VVDGNNLEAD DTGLTMSGHL ANVTAGVGLL PKDAGVNLNY  360
HILGAANAEI PMTQIATYLT TGFIRRFHEL VGVKTVTVTK DTVNSFAENI GLSVDDLIEY  420
IHRSNNYPNV QIPDADYQTI YEIGSDNPGV YPRVWVQPRD KAIDSLRGVI TYLKNALTSV  480
PDDLDVEKLT ANGGESLQVK IFLELCKISA EEEKGPYFAS AILGQGGYNL INYIEGQIRQ  540
VGEYIQTANK DLYFAQDQAY KAQAEIFKNN GIFANKKKLA KNYKDCVQDW FNYEVEIEEL  600
KGAERILETL RISLRNQLKD GFFSKLINML DNIKDTFKEN GDYLNSLRST QTDAYTIRLV  660
QLTEVRDTLD EAIKKMQPNQ LVTDFINRLL KSPKKWLSND DTQIGQFIST YMQEIFNVEM  720
NKSIQTYLQE KYPDVAGTTE LTELVKSTII SELNDKAQPM FWKNPIFNMG ASFSTGRMSV  780
PAASNVICNA ASSFVENKAD KNYTVRKTGI NDRVFVLRFH SGLPFYAYQG VTKMYESYRS  840
VANAMPGVGA HLYAKTGRGS GIDDSGMHDW RNELPTPMPY SKVPEFTPNG EELEKLYVKA  900
EEEKVIMPVD INAQPVNYKI CYSEKIVKKE FKKEDYLLAS GEFNLQKWDE DKKWLENELN  960
RRITRPEKVI DDFADGAADS PVVQRRIHID YFIHYKYYQK IVLDELESRE YLKKAMKRLD  1020
DIKKELELYI NEVNRYNDII LFGFINCLNA TGKFDINRYR IKSINYKYED KFGVAREEIF  1080
AKINDDSEFS SEPLYRGFLH YCKMNPDEEP RRSIDNMLNE RKSSTLKAGR DTFIAYQFET  1140
NWNKDILADM EIEIKGKLTN EQQEDVKRYY RFMITKVQEL KKQFLLNEWQ LNPEDENRVE  1200
PKKETIRFNE NTNTTQEFSN TWECPECGFR KNIGNFCSGC GKAKPKAEVS ATWECPECGF  1260
RKNIGNFCSG CGRKRD                                                1276

SEQ ID NO: 32          moltype = AA  length = 548
FEATURE                Location/Qualifiers
source                 1..548
                       mol_type = protein
                       organism = synthetic construct
SEQUENCE: 32
MSDINDIKFK TGWLKDPKDN QKFAPKTTTN QVLTGDGERL TDTLATFITN AADDLKNYYL  60
KSETYTQDEV NELISLIPKF KLEVVASLDD LSATDINEAT VYLVSNKSTS GSNVYTEYVY  120
KNNRWEILGE QKLDLSGYVT EEYINNNFED KNVIKQKLDV VTELVNNNLE AANDYTDEVK  180
EQLSNYETKE AASNKLTEAK QFATNEASKI KNDLLNGAGA AYDTLKELGD LIDESVDAVE  240
ALKIIATNKA DKEHTHEFTA KYDITTLTEL QNASTAGKNI KVVRNFERPI PGAYDENDTM  300
LYSWQELLDM DVEYEEFDGF DETGANVWVT KIDKCLTVED GALKSIVTYS PSTHSYTNWS  360
IDALTGVTKL VINEGVTAIG PSGLAAFNVA EIIMPSTLTT IEDDALSHIF EYWDWGDYSV  420
TVHIPKAVNN ISFNAFSYSK VFIKYEGTET EFNTIASVAD FNLNSYEFNY SCNYNLVPAP  480
IYGYIKNKLE DRFIFTAHED DGEIEYVCNS SGWSTRNIQM MKLGDAVFKY DYDNARIILS  540
FPMEGAVG                                                         548

SEQ ID NO: 33          moltype = AA  length = 1138
FEATURE                Location/Qualifiers
source                 1..1138
                       mol_type = protein
                       organism = synthetic construct
SEQUENCE: 33
MTYRVVGCSE CQSLWLLEDT DDESATCPTC GTRHQRHRLR TLAQADDKDG ANQQRSALLA  60
ERADAGDADL DPYWEQATRA SEPIVDDRAY LDGLGIDPNL VEDLTSEDDD TSASEQTTRT  120
PGIGPDVPAP VADRPQLRGP VDDARSPGVS LIEAGGQLGI AGQTYHEVSP RTFEWLADVV  180
SDLVPSTARL VQDLARERYN FDYRDPDAGA GAVATFIHEE LVGRVAQLDT ADAPTAAVEE  240
ARSYLDAIGR YALLWADDVY RVRRGFDGAE QFEHITRTLE TTGTSQGQFN AGVDALRHSL  300
VALHAERAVP RTLTFVLDGE QWTGADRETI KRALTAVDAL AAGFDVRLWM SPGVRQRVRR  360
LTSTALDDDD APTWAERFAF LTDAGQTSRR SPEATASSTS ADEAEEAWAF VEDNRTQTGL  420
LTLLAQLDAD SERSVRALKR DTQIDYADAS IDRYVADLEA AGLVAIDRSH ASNRLSLTAL  480
GIAAQNYVTP TGDVVHRYQS RLVGASYGHP SASHKYSVAP QGTGGDHHPP AERWLADTGD  540
PAEDGYVQFL GDSTGPREIE PPVFHRRMLA GERVSGVNFA DADLIDWTNE RQAPTGDGRV  600
TYASIFDDHA LLITQWGGPA QTMARLCAGL LGNRMLSKAL SVDAVGTQFE QTHGGVKAFE  660
NDLHDVLVRA QQIGWLSEDE LEHYDNWRDR IGAVRSNILS KIGELDELDS GLRRELFRDL  720
QGLLTSATHL YYAAGIDVTI NLRLPRTTEL LANDEALQHF LDFMRFTVTK QAGYEDENGF  780
HSWYRMCIED RKEKLKARAA YDVDEADSTA DLTASWIISG PGATALKDHV QEAIGEESSR  840
LRERVDEGVE DAATLDIPMV EANSHGHIRG LVREIADRKG FYETNRRDLD RLTRCLEAAL  900
ATNDRGPDPF LVADALAALE SRDTARDRLD TLSVQNALAT LPSEAVFPTL PPAARRMLSA  960
LFASDEPLDR QALIEVTSES SYDRHWKTLR AFFLVEETDD GFVAQLEPWW ASTNEERKPF  1020
HEDHPNPVTQ PPGGHIKQHA PPTRPYGVIF EIANETDFFE IPPDRYYEFG QRWDEIEWIL  1080
DELDLERLRP ILKAYCADWP DYTAQSYSDP SGVQIAPQQP DSPSTQATLA TAATINRQ  1138

SEQ ID NO: 34          moltype = AA  length = 408
FEATURE                Location/Qualifiers
source                 1..408
                       mol_type = protein
                       organism = synthetic construct
SEQUENCE: 34
MELTLLLIIA ALLVALLVLT LTRNNRAQSE EMQRALRQQM QENREELNRS IRELRMEMTQ  60
TLNQGLQQLQ DAMHKNMMTT GELQRQKFDA MARQQETLIQ STEKRLDDMR VMVEEKLQKT  120
LNERIGQSFE IVRSQLENVQ KGLGEMKSLA QDVGGLKKVL SNVKMRGTFG EVQLGALLEQ  180
MMSPEQYEAN VKTKKSGTEF VEFAIKLPGN DDANSTVYLP IDAKFPKDVY EQYYDAFEAG  240
DAALMESCGR QLETTIKKMA KDIHDKYVDP PFTTDFAILF LPFESIYAEV IRRTSLVETL  300
QKDYKIVVTG PTTLGAILNS LQMGFRTLAI QKRTGEVWTV LGAVKTEFGK FGGLLEKVQK  360
NLQSAGDQLE EVMGKRTRAI ERKLRQVEEL PHEESRRILP IDDGGEDD              408

SEQ ID NO: 35          moltype = AA  length = 408
```

```
FEATURE                Location/Qualifiers
source                 1..408
                       mol_type = protein
                       organism = synthetic construct
SEQUENCE: 35
MELTLLLIIA ALLVALLALT LTRNNRAQSE EMQRALRQQM QENREELNRS IRELRMEMTQ  60
TLNQGLQQLQ DAMHKNMMTT GELQRQKFDA MARQQETLIQ STEKRLDDMR VMVEEKLQKT  120
LNERIGQSFE IVRSQLENVQ KGLGEMKSLA QDVGGLKKVL SNVKMRGTFG EVQLGALLEQ  180
MMSPEQYEAN VKTKKSGTEF VEFAIKLPGK DDANSTVYLP IDAKFPKDVY EQYYDAFEAG  240
DAALMESCGR QLETTIKKMA KDIHDKYVDP PFTTDFAILF LPFESIYAEV IRRTSLVETL  300
QKDYKIVVTG PTTLGAILNS LQMGFRTLAI QKRTGEVWTV LGAVKTEFGK FGGLLEKVQK  360
NLQSAGDQLE EVMGKRTRAI ERKLRQVEEL PHEESRRILP IDDGGEDD              408

SEQ ID NO: 36          moltype = AA  length = 408
FEATURE                Location/Qualifiers
source                 1..408
                       mol_type = protein
                       organism = synthetic construct
SEQUENCE: 36
MELTLLLIIA ALLVALLVLT LTRNNRAQSE EMQRALRQQM QENREELNRS IRELRMEMTQ  60
TLNQGLQQLQ DAMHKNMMTT GELQRQKFDA MARQQETLLQ STEKRLDDMR VMVEEKLQKT  120
LNERIGQSFE IVRSQLENVQ KGLGEMKSLA QDVGGLKKVL SNVKMRGTFG EVQLGALLEQ  180
MMSPEQYEAN VKTKKSGTEF VEFAIKLPGK DDANSTVYLP IDAKFPKDVY EQYYDAFEAG  240
DAALMESCGR QLETTIKKMA KDIHDKYVDP PFTTDFAILF LPFESIYAEV IRRTSLVETL  300
QKDYKIVVTG PTTLGAILNS LQMGFRTLAI QKRTGEVWTV LGAVKTEFGK FGGLLEKVQK  360
NLQSAGDQLE EVMGKRTRAI ERKLRQVEEL PHEESRRILP IDDGGEDD              408

SEQ ID NO: 37          moltype = AA  length = 408
FEATURE                Location/Qualifiers
source                 1..408
                       mol_type = protein
                       organism = synthetic construct
SEQUENCE: 37
MELTLLLIIA ALLVALLVLT LTRNNRAQSE EMQRALRQQM QENREELNRS IRELRMEMTQ  60
TLNQGLQQLQ DAMHKNMMTT GELQRQKFDA MARQQETLIQ STEKRLDDMR VMVEEKLQKT  120
LNERIGQSFE IVRSQLENVQ KGLGEMKSLA QDVGGLKKVL SNVKMRGTFG EVQLGALLEQ  180
MMSPEQYEAN VKTKKSGTEF VEFAIKLPGN DDANSTVYLP IDAKFPKDVY EQYYDAFEAG  240
DAALMESCGR QLETTIKKMA KDIHDKYVDP PFTTDFAILF LPFESIYAEV IRRTSLVETL  300
QKDYKIVVTG PTTLGAILNS LQMGFRTLAI QKRTGEVWTV LGAVKTEFGN FGGLLEKVQK  360
NLQSAGDQLE EVMGKRTRAI ERKLRQVEEL PHEESRRILP IDDGGEDD              408

SEQ ID NO: 38          moltype = AA  length = 681
FEATURE                Location/Qualifiers
source                 1..681
                       mol_type = protein
                       organism = synthetic construct
SEQUENCE: 38
MGSECIYIFR AYRDGRLSDI LRDLDRCDSA STVLFTISEY RMVRLRYASE QGYMAGRLLT  60
AYISLKGYAP VTRNILYEWV SRMLAVSSRE KAEHNIELLW RDRQIVNLQK NAVEEVIREL  120
SKEGLENLAI NPPKPIQKVL ETLIKCPRCG SQPSYGEKYC KQCGARIPTK AWETTEETHK  180
PITVEIEQKA GTPTIECPHC GKALRQGAKY CTKCGSSIVS PAHKGMKIRE IFRKIQQDVS  240
RKTTPEEPAP ELGREVSPES AEKPTLTTFK EPVKSEEKPS QVEEHVKPTA EKPAAEREPR  300
TPTDVGEKPQ PQQPAPPTRG VTAPEPVPAG VDWEPEDEMV EAFDDMGVPL EAFRREAIRL  360
ALLDVDERVF EREVMRSASK LATSVEGLNR DFRDQLTLSI SQYLRDAVFI IRKEIKRPET  420
PRPTVPEHII SEKPAQPALE PPKHVIQQPK PPEQLEKRAP TVESAKQQPP KMDGIELWTL  480
VREGPKPGHV YLLDLPRSAL PTSIISKMFE GVVNVEEVDY VGPDTPVALT RTTYRANYIS  540
LIKPSPTNPY ANKLYRIVEM RCGSCIITTL ETYFMNRYVF DSRGLKPFKI ILDIEASRKA  600
LEKVMHPQYA ARLAKLGALL PWLAEELASN GLDGVRNRLH GLLSPEDGEE VYQAIKGVLE  660
NDMRYVNKAL AISLGIIDEE E                                           681

SEQ ID NO: 39          moltype = AA  length = 444
FEATURE                Location/Qualifiers
source                 1..444
                       mol_type = protein
                       organism = synthetic construct
SEQUENCE: 39
MATRIKAIKC PHCGSSNHRQ TGEKRFVCNN CGTEFFLDDD DINININHYN HNSDAPLLSM  60
DSDNAKKLKA ALLIFFPVLI LFFFISSLFH TSPISDKAGK DSIRVREEYL LVQTFAKEDT  120
YIVFCISDRN YYADYNNKSK KQPTNGIYYM FRNVRTGEIV KEGLLISDEQ KGDRAFYTFG  180
DNVKLRRFAN TRRWYLIIGN RLVYEVNPKR MTLVDAAPQL MSAQKALSSG FAAIGFINKN  240
EAEGFAIQNN LGKIYYYCPA TNHLYTKVAF DYATALPANE MPGQCRDSTY YLLQNASSEE  300
SENITRIWRV TYKHFNGDPE DRIDRIDDWY LDRLSRYRIS EIKPVSSWFI SFHPTIIYQD  360
RQHILLQYEA TMAPNSPVTL QLRGTDGRVK WTRTLNRELN RTSAEKSSVG YIITTWPYSF  420
IEISNNGKQL TEYTLPEEYQ IKAK                                        444

SEQ ID NO: 40          moltype = AA  length = 507
FEATURE                Location/Qualifiers
source                 1..507
                       mol_type = protein
```

```
                        organism = synthetic construct
SEQUENCE: 40
MSNFCSICGK EFKSSRVGQK ACSECLKSEF SVASKMEEEE VEMYRAKQAA AARRQHARMA  60
KLLDSYKNGT MFNMSGKIMF CVGLFILLFC HLIFFLDGRE LIYWGVEGMD ESGKKAISML  120
LSFACVLLLV FSTRRFKIVM MLGSVVILLL GWYATAIWKS SSDAMTGGGI VEKKQLPEPG  180
NEAVIPITEE ELGVFYELKK NYPRATHYAV FLDNQEPIVR DLVREALTRL LEAEYTRAYT  240
RSNGVLYVVA NAAGVPRNVS PIVDRLGEIV NADVAKGLYL VRFDAEKTNL VCKYSSEVLS  300
SPLNSSFVIA NINELRCLDA MRIRVAARSL RNANVQMLRR EVRDALVRVL GDSWTQDQDT  360
YSALIDSLVT YASAKDREVI NICSDYFMKR YGAKKDVLPG VVDYLIKEVP DQMVQPIIDY  420
WLLNPMSWTV QMRNLSWRVQ PKLLERMEQE VSIKDLSLIL RYLQNNGNED AIPAVKKLLT  480
HSDAIIRFSA QETLRELESK ASEKIEE                                    507

SEQ ID NO: 41           moltype = AA  length = 507
FEATURE                 Location/Qualifiers
source                  1..507
                        mol_type = protein
                        organism = synthetic construct
SEQUENCE: 41
MSNFCSICGK EFKSSRVGQK ACSECLKSEF SAASKMEEEE VEMYRAKQAA AARRQHARMA  60
KLLDSYKNGT MFNMSGKIMF CVGLFILLFC HLIFFLDGRE LIYWGVEGMD ESGKKAISML  120
LSFACVLLLV FSTRRFKIVM MLGSVVILLL GWYATAIWKS SSDAMAGGGI VEKKQLPEPG  180
NEAVIPITEE ELGVFYELKK NYPRATHYAV FLDNQEPIVR DLVREALTRL LEAEYTRAYT  240
RSNGVLYVVA NAAGVPRNVS PIVDRLGEIV NADVAKGLYL VRFDAEKTNL VCKYSSEVLS  300
SPLNSSFVIA NINELRCLDA MRIRVAARSL RNANVQMLRR EVRDALVRVL GDSWTQDQDT  360
YSALIDSLVT YASAKDREVI NICSDYFMKR YGAKKDVLPG VVDYLIKEVP DQMVQPIIDY  420
WLLNPMSWTV QMRNLSWRVQ PKLLERMEQE VSIKDLSLIL RYLQNNGNED AIPAVKKLLT  480
HSDAIIRFSA QETLRELESK ASEKIEE                                    507

SEQ ID NO: 42           moltype = AA  length = 765
FEATURE                 Location/Qualifiers
source                  1..765
                        mol_type = protein
                        organism = synthetic construct
SEQUENCE: 42
MALTIIGKAR FYNFAGFATW HEALTREQAQ KLWQSSICSR QNELGKAYDN VYTNFNAFGF  60
DSGNQERRKR LQKFQDYLEL TDQPWDVRYV DHVAKFMVIS YGQCDDNTKG KENQFLIENW  120
PEYIEYTPFT DFSAVPMSQL RQITMLGCEG ITGGTSLIPQ NAGINLSVAD VRRGISAQEQ  180
ALADLQAKVK AVEEGKTEEL SPLKKQIDEL MAQMNALQEK KKAELSAMKA ELEAKKKEME  240
KQIFILEAEI YSIRCFLGET IQFVKLRSGS NAPLEQPVIL YQKLRFMVED LQKFAIMWPE  300
EKIGKSIEAA LKASDSLMDA FAPSTKCITL IRYSETGKVF RAHEEELNIL DEYELMHGNQ  360
LAILIRNGEN LYIGWADEDK ITLKDNFFLK PTEAKMEAMP EQRPNESDEY YQARLERMQK  420
DMEEANKKAA REGLSRHFLF SILNGVSASD NSILPLPKFS NKAERNQHII FSMADGALVD  480
RRFGSFGNIV KRCNSVVKKG DMILTTMSLR AEGPYWSKPG QYTTWYNDRG RGERNRTHDV  540
HASDCTIYPV NLVEFDKPER KVRYRSTYTI PEEVNGEYRQ VKRTSIHVTD ADAKLSEDVE  600
ILEYFDYIQQ HTFISLQKEG GWWKCDVGPS YANFEVNTDE FINLTYMNSV WLNYVLSCRD  660
LSGWRVGGTT VNYEYALRYL KKALSHIRER EKTEEENIRL AGGAAILADP DWPVALSEWK  720
MDKGVRNMTE YQAKRFVKAM LAGEIDITPK PVAEGDVEMY DAVIV                 765

SEQ ID NO: 43           moltype = AA  length = 516
FEATURE                 Location/Qualifiers
source                  1..516
                        mol_type = protein
                        organism = synthetic construct
SEQUENCE: 43
MVDAAARSPG RLLVFVHIPK TAGTTLRTVL GMNEPGARSR ALGNVFKGGG GISKSLIDRL  60
RKDKGPDLSG VGLIRGHFPL GIREHLPRYL PRGREVACFT FLREPADRTL SHYFAIREHG  120
RGYQLPPLPA EATVEDALER GYIHDNVQTR MLSGLAEPFG EVDQEMLERA KDNLREELVF  180
FGLTERFDES LVLAKRRLGF RSILYKTSGR VNVNRARGDE VPAELREAAQ ACNRYDIELY  240
RYAEQLFETA PERQELEFDA ELAALRAAKA NGDGESTSIS VPASYGGDEQ AWTMLVEARA  300
ELLRLEFERR RHRVPHVAAT VQDEVRESEL KAARTRTKKL EQEVERLKTA QAKTKRLEQQ  360
VERLKAASSR VEELEREVER LNAVASRAEE LEQRLEQQVE HLNAASAKTE KFEQQVERLK  420
AARSRNRKLQ QEVERLKTAV ARTEELEEEV QRLETAAAKA EGLEEEVERL KTAASRAEEL  480
EHELEQQLKL LDAARSRKTK LEQKVERLRD AAAVRE                           516

SEQ ID NO: 44           moltype = AA  length = 1123
FEATURE                 Location/Qualifiers
source                  1..1123
                        mol_type = protein
                        organism = synthetic construct
SEQUENCE: 44
MDKTALEPTR TYHATVDLGE NTEAFLAHHV ATNNAAGELA GALKHMIATL VPAQWVELWE  60
NHAGTPAGVR IASWIAGSWV GTERSDSAPP RTVTHAQAID AVRRRAVELR PGIDAEQFLK  120
DAAILHGTVR DDAVWVDYLD GDPVPAIGWE GLDVRLLGSA SEPVKSNDEI TKPGKGDMVQ  180
SCSRLWGRAV GTGRKADGLL LVERSAALRD AAADPTNRTV ADVAQALTGQ PLDGAGLAAW  240
ANHTNPKSPT KVTAALVGND ASADLSTEVA GKTLRDRIVT GASEVHANWV ARTGEARRAA  300
DGEILAGTWL HGILLRHMAA NLTGGARTNV LSAAASTVAT HRDRLHKQAV ELAALQQSLA  360
NALEQVDPDD LADLDAWARA HLYENEDSPG YLLPRIPRRE GTAKLATVTN KWRNKPKMGV  420
EERVAAAKGA GAGWTVWWDY LARNEHLWNP NTDRLLRVVG GGDGFAGVQP LRRKIAGVQM  480
PTFARPHPQA APAPSYYGGG RLTGRLGADG TLVLQVATPD GLARISARWM STRLREALKV  540
```

-continued

```
GAQVVDGQPT ITRDDPTSRL AAGVDQDTPV NVAADPTSST FTVGYDRENQ RWLLAVAIKH  600
HTPRRYLPGD PLRLMGVQIG MNRHDVTYAV WETVDGVSAP QDVEVADVHA VNARGQATVR  660
RARRVAATGN LFEFARPVRE GSIDLPAGDR ESQVGESAQI AELLDDLPVH DAYIQGELRR  720
VARDAAVDLG AGTPRSQLLQ AAMRVLNRAL DAQGCLARLA GQARGLGEAG PDDLEELESI  780
WPATGGDLGA LWSQRAATIA RYARIVRDDL LTRAHSRRVS VERVVELDEF ARLLRRLETC  840
PTPSRPFEHR TLPFGFAPTI RTMRNRAREA WTDKIASDTV KTALRLGVSV IAVYKDEDST  900
PSQVRPAHIN RRLATEARRA IADQIALVAP LHGIEVKVVS KGVGHRARVV DGREMFAVTP  960
ITLGEFADLA RRDTKGAKGA IASWDNRVVA AANLLAGKEK KRKGRDGRVY EESAQRKAAN  1020
LAVAALTVQA GQFLDRELEP VLGLNDRAFR TWRSSAAASQ TLHLPGLFPD GQVLVPADAQ  1080
YEPGTLRFRS VSSRDIAIAH AVAHRGCTWV LNPKKQKKDD ESE                   1123

SEQ ID NO: 45          moltype = AA  length = 1073
FEATURE                Location/Qualifiers
source                 1..1073
                       mol_type = protein
                       organism = synthetic construct
SEQUENCE: 45
VRPAVRNYNV AAGAHKQERD ERTYIKGAFG SFSREEDNRA STQFLRPAGS QHYSAILASF  60
TDENRDDTFT LAVLLYLNSE GGADKVYCFA NGERSIAADC SRIETVEKLR QQMEWRGFHA  120
TTTYTEYYGW FRRKTGVQFK AMDVFNQTVA VKDIKSLNQF VREHMLEAKP WSEKVDSLLN  180
HFTQLHEAHQ SLLRVQRQFQ LLEPVGEAGE VYRVHAEKLE SVRRLIDATD SFFRQKTVDI  240
LGPSAKEWKD LRHAVGRQRE RLDQDIREVL EECRRLQNEI EQAGGDRLRQ IPLLIKQHES  300
NAATKRTANG HYHGALAAAS IRETVADAEG FARIQAQIPQ LVRDLDQQIE ETDKRKEDLV  360
IERATLNQSI RNDETELESL KQRQGNLPHA LVTVRQTICT DLQLPERELP FVAELVAVKP  420
EEQAWEASAE LALRTFALSL LVPHRHYPLV AGFVDRTRIT DAAGAGQRLV YLRVGDRAKV  480
AAQAALHPQS LIRKLTFRDG HPLLPWVKGE LEDRFDYRCC ETLEEFQEAH GLAMTRHRHL  540
KIRGVRHEKD DRDRVADPRF YVLGWNNSDK KRRLVERIRE HQESRTQLNK RIEGIDAKLA  600
ALRTRHEALR KAGEVADFGE IDYRVHEWEL EALRLEKKQL EENNDAIRLL QGRLADAESR  660
HTGLRASRDD ALLKEAKLTD EISQAEKLVA NAETVLHERQ VSGALQHHAS SFPDLDACFI  720
EQTLTAATLL AEERRFIDAR RAECDRLGRE IEPKKLDLTR AMSRYLREFQ DDRADLEAQA  780
EYLDSFLDLR DHIRKEDLPR HEKRFKAHLN EKVIQEIGIL NGTFQSERSE IITRINQLNA  840
SLRQLEYRPG THMVLEPRAV RDGDIVDFQN ALRECLAGTF EGSPEADEAR FIRIEKPITR  900
LREEQTWREK VTDVRRWFDF AARELENVTN KERSYHEDSA GQSGGEKAKL AFTILVAAIA  960
YQYDIDPDHP TSSRFHFVVV DEMFSKVDDQ YSEYALELFK KFGLQLLIVA PLDAKALVTE  1020
PYVGCYLHAV KDPRTNRSEV FTMSAREFAD TLSAAGQGQK NAMGPAPVKV RSR         1073

SEQ ID NO: 46          moltype = AA  length = 1118
FEATURE                Location/Qualifiers
source                 1..1118
                       mol_type = protein
                       organism = synthetic construct
SEQUENCE: 46
MKTDDEKKDT AIKSYTSWLL PNDRKEKDMV RSFLALDQGS RFFFDLMQAW YGGLTPDIIK  60
SVTKERDLVD LWCAIYWFRP MKKELASHPI DRVDLAKTFQ RYYGGPASDV VQEYLSASIG  120
EDCCWNDCRQ KYQEFCKNLG VDFTPDLKTL VREKLIAVAL NDGSQAAISN LFGNGGKEDR  180
NVKVNICKKI LIALEKAGKS VKYVRDVQSI ILKCANAKDR EDFNRIYADK NGRPGTLLLL  240
LDRKGENTYD AEVLKRYLRK TIKSKNAPLV WNYNQKLFEY IERGIRNLLR RTINYDAWAW  300
GEMWRVGHTP LQTKATRNYH FAQEQLKRHS DIAAASQSSH AIAVALNEFF ESPFFDGENP  360
FTICPHHLGK NLEKLFKAWA DEKNQTDEED AGETAITDYC AEFKDGFDRE PIRNLLRYVY  420
ASLRSKYSAK ELIQAAKYNQ QFERYQRQKA HPVTPDNQGY TWPEAVIKPS KAERKNRENS  480
LDTRIWVSVK LLQKDGTWEK HHIPFYNLRF FEEVYAAASI AEDMPSPTFR NSRFGFKLPK  540
LLNTHAKINK KKDGKKDKK AVNAAKREAR IYLAAKEGRL PAPSVPLDKL SAVIARVNGK  600
FQVTVPVKFK VNKQPKYPLP QLGQIILGYD QNLTANHAWA LFEVVTEDTP GAHFCRNQYL  660
RVLKTGQVRS ITKTKDGQEI DQLSYDGLEY KEYGEWRKQA KKFASQWYIT TKVRKGKETT  720
LLSQPALERF ESIEKYKPAL YRFNKEYARL LLAVIRRKTL NELEEIRPEI FRLVEQGFGI  780
CRFGSLSLSS FEAIRAAKAV IYGYFSTALK HDHNTPITDD ERQAFDPELF GLLNKLETLR  840
QNKGEEKINR AANALIRIAL ENKADFIRGE GDLPTTNKSV KKGQNSRSMD WLARGLFNKI  900
CQLAVMHNII PTAANPHSTS HQDPFEHNKD FDDPQPAMKC RYAEFKIEDI GDSVLERLGT  960
SLRNAKAGQT GAYYYKGAQD FLAHYGLQDI EEELKKCRRG RKANMPCWEL QKRLIQKLGS  1020
KDAVVYIPMR GGRIYLATHS VTTGAKPIIF NGEEVWVSNA DEIAAVNIGL TIIPTSKKDE  1080
EHPDRENDDK AIRKSVRRPR KSGERRSGDK MPATARKT                         1118

SEQ ID NO: 47          moltype = AA  length = 640
FEATURE                Location/Qualifiers
source                 1..640
                       mol_type = protein
                       organism = synthetic construct
SEQUENCE: 47
MDTGIEEYSS IHKDEYDRDP IVDLYRHIYP HREVISAKNF IDAAVLNKLL RLNASRHVHP  60
TVFGKTVISF SPKSSAYGRI TPPSEIVRGR PAGSHGMIWL TMELFDDGKW IEHHLPFHNS  120
RYYEEVYCYQ EGLPVKDEPR SPMFGYRVGN AIADTSKIDN RRRKASKQFL RAQQNITHNV  180
SFDENTAFSV VRNGEDFSIT ISSRIKASNA KSLMTIGDRI MGIDQNQTAA NTYSIWEVVG  240
DGDAGSIQHG NLSLKRIEDG HITSIIRGRG GNFDQLNYGG LSYAKFSEWR SARLGFISSL  300
NAELASKMNW DWCCLYEWNA RYASALRKII YSHKGIDIER VFRREIEDFV EGVLRIGSLS  360
SDALQCLTNA KSLISSYFFL NGKKEPEEQR KFDQGLFDLS AKIDKKRVNK RQQKTKRIMS  420
SIMQIARDRG VSFIVVEGKL STATKDNKSK ANQKAIDWCA RAVVENLEHS CSLVGIKLVA  480
IDPMNTSHLD PFVYVLKTSL GKEARFASVV PAKINARHMK NFKSWSSLLA GNGKIKKTTD  540
AIYVGAFQDF CREYGFVAED ISKMSQSEIQ DKLSSHQFVL VPQRGGRVYM STHPVSSEAK  600
KIVYAGRERW YNNADVVAAV NITLRGCERL SASRKTASTR                       640
```

```
SEQ ID NO: 48          moltype = AA  length = 1018
FEATURE                Location/Qualifiers
source                 1..1018
                       mol_type = protein
                       organism = synthetic construct
SEQUENCE: 48
IFPTQRRNTM SGNVVRSYKS VLRPNIRKRE LLDATFNWFD RAYKKFFDVF VCLYGGVEHD  60
TVHSALLKET TDPDLVCATM WFRVVPKSSC DGISAQEMIR RFGVYAGHEP SAVAMSYLTG  120
NFDDKKNHWI DCREKFVALA RDMVVKPESL SIDIKSMIEH KILPICSQDN WQAWNAISQL  180
FGEGKKENKA EKAQIFVDVV SMLSNNSVQT WEDYKEVISK ATGCRTAGEI NSKFGGRPGI  240
LSVDFSKDDT GSLPKDFIER RIKDLSQKAK EKSAAYELPN RMRLRELIAS VIGPYRLETW  300
SSVAQRACGD IRSKNSNNLL YASERFNRTK EIEEILSAKG DVARAQGQFR SGEFNEFAVE  360
KRHLGNLESL YNIWSKSDMD TGIEEYSSIH KDEYDRDPIV DLYRHIYPHR EVISAKNFID  420
AAVLNKLLRL NASRHVHPTV FGKTVISFSP KSSAYGRITP PSEIVRGRPA GSHGMIWLTM  480
ELFDDGKWIE HHLPFHNSRY YEEVYCYQEG LPVKDEPRSP MFGYRVGNAI ADTSKIDNRR  540
RKASKQFLRA QQNITHNVSF DENTAFSVVR NGEDFSITIS SRIKASNAKS LMTIGDRIMG  600
IDQNQTAANT YSIWEVVGDG DAGSIQHGNL SLKRIEDGHI TSIIRGRGGN FDQLNYGGLS  660
YAKFSEWRSA RLGFISSLNA ELASKMNWDW CCLYEWNARY ASALRKIIYS HKGIDIERVF  720
RREIEDFVEG VLRIGSLSSD ALQCLTNAKS LISSYFFLNG KKEPEEQRKF DQGLFDLSAK  780
IDKKRVNKRQ QKTKRIMSSI MQIARDRGVS FIVVEGKLST ATKDNKSKAN QKAIDWCARA  840
VVENLEHSCS LVGIKLVAID PMNTSHLDPF VYVLKTSLGK EARFASVVPA KINARHMKNF  900
KSWSSLLAGN GKIKKTTDAI YVGAFQDFCR EYGFVAEDIS KMSQSEIQDK LSSHQFVLVP  960
QRGGRVYMST HPVSSEAKKI VYAGRERWYN NADVVAAVNI TLRGCERLSA SRKTASTR    1018

SEQ ID NO: 49          moltype = AA  length = 1035
FEATURE                Location/Qualifiers
source                 1..1035
                       mol_type = protein
                       organism = synthetic construct
SEQUENCE: 49
IFPTQRRNTM SGNVVRSYKS VLRPNIRKRE LLDATFNWFD RAYKKFFDVF VCLYGGVEHD  60
TVHSALLKET TDPDLVCATM WFRVVPKSSC DGISAQEMIR RFGVYAGHEP SAVAMSYLTG  120
NFDDKKNHWI DCREKFVALA RDMVVKPESL SIDIKSMIEH KILPICSQDN WQAWNAISQL  180
FGEGKKENKA EKAQIFVDVV SMLSNNSVQT WEDYKEVISK ATGCRTAGEI NSKFGGRPGI  240
LSVDFSKDDT GSLPKDFIER RIKDLSQKAK EKSAAYELPN RMRLRELIAS VIGPYRLETW  300
SSVAQRACGD IRSKNSNNLL YASERFNRTK EIEEILSAKG DVARAQTNEK AKDILNKIND  360
NLIGQFRSGE FNEFAVEKRH LGNLESLYNI WSKSDMDTGI EEYSSIHKDE YDRDPIVDLY  420
RHIYPHREVI SAKNFIDAAV LNKLLRLNAS RHVHPTVFGK TVISFSPKSS AYGRITPPSE  480
IVRGRPAGSH GMIWLTMELF DDGKWIEHHL PFHNSRYYEE VYCYQEGLPV KDEPRSPMFG  540
YRVGNAIADT SKIDNRRRKA SKQFLRAQQN ITHNVSFDEN TAFSVVRNGE DFSITISSRI  600
KASNAKSLMT IGDRIMGIDQ NQTAANTYSI WEVVGDGDAG SIQHGNLSLK RIEDGHITSI  660
IRGRGGNFDQ LNYGGLSYAK FSEWRSARLG FISSLNAELA SKMNWDWCCL YEWNARYASA  720
LRKIIYSHKG IDIERVFRRE IEDFVEGVLR IGSLSSDALQ CLTNAKSLIS SYFFLNGKKE  780
PEEQRKFDQG LFDLSAKIDK KRVNKRQQKT KRIMSSIMQI ARDRGVSFIV VEGKLSTATK  840
DNKSKANQKA IDWCARAVVE NLEHSCSLVG IKLVAIDPMN TSHLDPFVYV LKTSLGKEAR  900
FASVVPAKIN ARHMKNFKSW SSLLAGNGKI KKTTDAIYVG AFQDFCREYG FVAEDISKMS  960
QSEIQDKLSS HQFVLVPQRG GRVYMSTHPV SSEAKKIVYA GRERWYNNAD VVAAVNITLR  1020
GCERLSASRK TASTR                                                  1035

SEQ ID NO: 50          moltype = AA  length = 1037
FEATURE                Location/Qualifiers
source                 1..1037
                       mol_type = protein
                       organism = synthetic construct
SEQUENCE: 50
IFPTQRRNTM SGNVVRSYKS VLRPNIRKRE LLDATFNWFD RAYKKFFDVF VCLYGGVEHD  60
TVHSALLKET TDPDLVCATM WFRVVPKSSC DGISAQEMIR RFGVYAGHEP SAVAMSYLTG  120
NFDDKKNHWI DCREKFVALA RDMVVKPESL SIDIKSMIEH KILPICSQDN WQAWNAISQL  180
FGEGKKENKA EKAQIFVDVV SMLSNNSVQT WEDYKEVISK ATGCRTAGEI NSKFGGRPGI  240
LSVDFSKDDT GSLPKDFIER RIKDLSQKAK EKSAAYELPN RMRLRELIAS VIGPYRLETW  300
SSVAQRACGD IRSKNSNNLL YASERFNRTK EIEEILSAKG DVARAQKEDI LSAANILNDF  360
RRGEFGQFRS GEFNEFAVEK RHLGNLESLY NIWSKSDMDT GIEEYSSIHK DEYDRDPIVD  420
LYRHIYPHRE VISAKNFIDA AVLNKLLRLN ASRHVHPTVF GKTVISFSPK SSAYGRITPP  480
SEIVRGRPAG SHGMIWLTME LFDDGKWIEH HLPFHNSRYY EEVYCYQEGL PVKDEPRSPM  540
FGYRVGNAIA DTSKIDNRRR KASKQFLRAQ QNITHNVSFD ENTAFSVVRN GEDFSITISS  600
RIKASNAKSL MTIGDRIMGI DQNQTAANTY SIWEVVGDGD AGSIQHGNLS LKRIEDGHIT  660
SIIRGRGGNF DQLNYGGLSY AKFSEWRSAR LGFISSLNAE LASKMNWDWC CLYEWNARYA  720
SALRKIIYSH KGIDIERVFR REIEDFVEGV LRIGSLSSDA LQCLTNAKSL ISSYFFLNGK  780
KEPEEQRKFD QGLFDLSAKI DKKRVNKRQQ KTKRIMSSIM QIARDRGVSF IVVEGKLSTA  840
TKDNKSKANQ KAIDWCARAV VENLEHSCSL VGIKLVAIDP MNTSHLDPFV YVLKTSLGKE  900
ARFASVVPAK INARHMKNFK SWSSLLAGNG KIKKTTDAIY VGAFQDFCRE YGFVAEDISK  960
MSQSEIQDKL SSHQFVLVPQ RGGRVYMSTH PVSSEAKKIV YAGRERWYNN ADVVAAVNIT  1020
LRGCERLSAS RKTASTR                                                1037

SEQ ID NO: 51          moltype = AA  length = 1041
FEATURE                Location/Qualifiers
source                 1..1041
                       mol_type = protein
```

```
                         organism = synthetic construct
SEQUENCE: 51
IFPTQRRNTM SGNVVRSYKS VLRPNIRKRE LLDATFNWFD RAYKKFFDVF VCLYGGVEHD  60
TVHSALLKET TDPDLVCATM WFRVVPKSSC DGISAQEMIR RFGVYAGHEP SAVAMSYLTG  120
NFDDKKNHWI DCREKFVALA RDMVVKPESL SIDIKSMIEH KILPICSQDN WQAWNAISQL  180
FGEGKKENKA EKAQIFVDVV SMLSNNSVQT WEDYKEVISK ATGCRTAGEI NSKFGGRPGI  240
LSVDFSKDDT GSLPKDFIER RIKDLSQKAK EKSAAYELPN RMRLRELIAS VIGPYRLETW  300
SSVAQRACGD IRSKNSNNLL YASERFNRTK EIEEILSAKG DVARAQKDIL LAASILGDFR  360
RGEFNRSVVG QFRSGEFNEF AVEKRHLGNL ESLYNIWSKS DMDTGIEEYS SIHKDEYDRD  420
PIVDLYRHIY PHREVISAKN FIDAAVLNKL LRLNASRHVH PTVFGKTVIS FSPKSSAYGR  480
ITPPSEIVRG RPAGSHGMIW LTMELFDDGK WIEHHLPFHN SRYYEEVYCY QEGLPVKDEP  540
RSPMFGYRVG NAIADTSKID NRRRKASKQF LRAQQNITHN VSFDENTAFS VVRNGEDFSI  600
TISSRIKASN AKSLMTIGDR IMGIDQNQTA ANTYSIWEVV GDGDAGSIQH GNLSLKRIED  660
GHITSIIRGR GGNFDQLNYG GLSYAKFSEW RSARLGFISS LNAELASKMN WDWCCLYEWN  720
ARYASALRKI IYSHKGIDIE RVFRREIEDF VEGVLRIGSL SSDALQCLTN AKSLISSYFF  780
LNGKKEPEEQ RKFDQGLFDL SAKIDKKRVN KRQQKTKRIM SSIMQIARDR GVSFIVVEGK  840
LSTATKDNKS KANQKAIDWC ARAVVENLEH SCSLVGIKLV AIDPMNTSHL DPFVYVLKTS  900
LGKEARFASV VPAKINARHM KNFKSWSSLL AGNGKIKKTT DAIYVGAFQD FCREYGFVAE  960
DISKMSQSEI QDKLSSHQFV LVPQRGGRVY MSTHPVSSEA KKIVYAGRER WYNNADVVAA  1020
VNITLRGCER LSASRKTAST R                                           1041

SEQ ID NO: 52            moltype = AA  length = 1021
FEATURE                  Location/Qualifiers
source                   1..1021
                         mol_type = protein
                         organism = synthetic construct
SEQUENCE: 52
IFPTQRRNTM SGNVVRSYKS VLRPNIRKRE LLDATFNWFD RAYKKFFDVF VCLYGGVEHD  60
TVHSALLKET TDPDLVCATM WFRVVPKSSC DGISAQEMIR RFGVYAGHEP SAVAMSYLTG  120
NFDDKKNHWI DCREKFVALA RDMVVKPESL SIDIKSMIEH KILPICSQDN WQAWNAISQL  180
FGEGKKENKA EKAQIFVDVV SMLSNNSVQT WEDYKEVISK ATGCRTAGEI NSKFGGRPGI  240
LSVDFSKDDT GSLPKDFIER RIKDLSQKAK EKSAAYELPN RMRLRELIAS VIGPYRLETW  300
SSVAQRACGD IRSKNSNNLL YASERFNRTK EIEEILSAKG DVARAQNILG QFRSGEFNEF  360
AVEKRHLGNL ESLYNIWSKS DMDTGIEEYS SIHKDEYDRD PIVDLYRHIY PHREVISAKN  420
FIDAAVLNKL LRLNASRHVH PTVFGKTVIS FSPKSSAYGR ITPPSEIVRG RPAGSHGMIW  480
LTMELFDDGK WIEHHLPFHN SRYYEEVYCY QEGLPVKDEP RSPMFGYRVG NAIADTSKID  540
NRRRKASKQF LRAQQNITHN VSFDENTAFS VVRNGEDFSI TISSRIKASN AKSLMTIGDR  600
IMGIDQNQTA ANTYSIWEVV GDGDAGSIQH GNLSLKRIED GHITSIIRGR GGNFDQLNYG  660
GLSYAKFSEW RSARLGFISS LNAELASKMN WDWCCLYEWN ARYASALRKI IYSHKGIDIE  720
RVFRREIEDF VEGVLRIGSL SSDALQCLTN AKSLISSYFF LNGKKEPEEQ RKFDQGLFDL  780
SAKIDKKRVN KRQQKTKRIM SSIMQIARDR GVSFIVVEGK LSTATKDNKS KANQKAIDWC  840
ARAVVENLEH SCSLVGIKLV AIDPMNTSHL DPFVYVLKTS LGKEARFASV VPAKINARHM  900
KNFKSWSSLL AGNGKIKKTT DAIYVGAFQD FCREYGFVAE DISKMSQSEI QDKLSSHQFV  960
LVPQRGGRVY MSTHPVSSEA KKIVYAGRER WYNNADVVAA VNITLRGCER LSASRKTAST  1020
R                                                                 1021

SEQ ID NO: 53            moltype = AA  length = 933
FEATURE                  Location/Qualifiers
source                   1..933
                         mol_type = protein
                         organism = synthetic construct
SEQUENCE: 53
MSIVAEPESV ADAAEAAPKK KKSDYFTTTR SASLKSTVNP AFEMYEAFQR DFRKNIEILF  60
PWLGIGYGVP DADAKGGIRY VGPEEAVAAR NASLPSAKAV AIVERFVTCL SKNAKTLSSC  120
YSLYYKHYKP TGAKRGESVK KIEKLLESDS FSDLAKSHPG IDWQAAKLVP KDKLWGHLKP  180
QLTDKNREIG REVRQFVTLP CSYPEACDYC KLLWSAVLAF LQSRLEIYQY HMDGTAALKT  240
AFDKGNTPLY AAFVQYTDAV AAMLGNSLSP REILHVIECA KGRKIAERPH LQLAIDELKK  300
PAYALLLAAE TATVKRCFAT RTVAAKLKKR KAYPTKSALD KDQTMNVGSP MFSIPDTSPV  360
SPTKHITVTV TVNGEQVEFP CKHTEYLANL TLEKVSPKKG EAYYKMGFNT NHKARTLGEL  420
KTVSIQKRGG NFYVTLPYTI THPVANFNLA WRFFQAASPK MENLVLPDQV VCASYDLGIN  480
NPVTGCLFKI GRDLQGPIKA RGYGEGYILK LPTYLTSSGS QKNGSAYCQA VVALRNKLGL  540
FHDAMKGLKI HRNTGFPMLE DEVEFLRSAP NMSEKSRQHV AKKNDLRLCV SYWMGFLNAE  600
RKRLNYELRA TGYKDQVGEL IRNIELDDIY YKVRSRYDSL DVSRETPRRY DTSRANRKVN  660
ANRLIASAIA RDCLANGVWI VFVENLASKY AKGSANLLAK LFNASTLLDT IKAALDKIGV  720
ALVRVEKNGT SQHDPVTGAL GYRDDTNHEN LIVSRDGELC SIPCDKSASL CVGLVGVNHS  780
VVPHKFYVPK PDAEAEAEEE EEEDGGSKRL TAFLADAGKT LKDLKNLTAG PGGVVRFTSD  840
PTAKRIAGQS VYPCHATGKL YTAAAKDAIQ DGIRNRCKAG EVPRPAEVIP DGAKTYKAFS  900
TGLVLELAQP SGDQELENIV LPKKRSRSRR VRD                              933

SEQ ID NO: 54            moltype = RNA  length = 36
FEATURE                  Location/Qualifiers
source                   1..36
                         mol_type = other RNA
                         organism = synthetic construct
SEQUENCE: 54
gtgcttttac tcatttctag cgaactgaat aagcac                           36

SEQ ID NO: 55            moltype = RNA  length = 36
FEATURE                  Location/Qualifiers
```

```
source                  1..36
                        mol_type = other RNA
                        organism = synthetic construct
SEQUENCE: 55
gtgcttattc agttcgctag aaatgagtaa aagcac                        36

SEQ ID NO: 56           moltype = RNA  length = 36
FEATURE                 Location/Qualifiers
source                  1..36
                        mol_type = other RNA
                        organism = synthetic construct
SEQUENCE: 56
gtgcttttac tcatttctaa cgaattgaat aagcac                        36

SEQ ID NO: 57           moltype = RNA  length = 36
FEATURE                 Location/Qualifiers
source                  1..36
                        mol_type = other RNA
                        organism = synthetic construct
SEQUENCE: 57
gtgcttattc aattcgttag aaatgagtaa aagcac                        36

SEQ ID NO: 58           moltype = RNA  length = 36
FEATURE                 Location/Qualifiers
source                  1..36
                        mol_type = other RNA
                        organism = synthetic construct
SEQUENCE: 58
gtgcttttac tcatttctag cgaattgaat aagcac                        36

SEQ ID NO: 59           moltype = RNA  length = 36
FEATURE                 Location/Qualifiers
source                  1..36
                        mol_type = other RNA
                        organism = synthetic construct
SEQUENCE: 59
gtgcttattc aattcgctag aaatgagtaa aagcac                        36

SEQ ID NO: 60           moltype = RNA  length = 36
FEATURE                 Location/Qualifiers
source                  1..36
                        mol_type = other RNA
                        organism = synthetic construct
SEQUENCE: 60
gtgcttttac ccgtttctag cgaattggat aagcac                        36

SEQ ID NO: 61           moltype = RNA  length = 36
FEATURE                 Location/Qualifiers
source                  1..36
                        mol_type = other RNA
                        organism = synthetic construct
SEQUENCE: 61
gtgcttatcc aattcgctag aaacgggtaa aagcac                        36

SEQ ID NO: 62           moltype = RNA  length = 36
FEATURE                 Location/Qualifiers
source                  1..36
                        mol_type = other RNA
                        organism = synthetic construct
SEQUENCE: 62
gtgcttttac ttatttctaa cgaattaaat aagcac                        36

SEQ ID NO: 63           moltype = RNA  length = 36
FEATURE                 Location/Qualifiers
source                  1..36
                        mol_type = other RNA
                        organism = synthetic construct
SEQUENCE: 63
gtgcttattt aattcgttag aaataagtaa aagcac                        36

SEQ ID NO: 64           moltype = RNA  length = 36
FEATURE                 Location/Qualifiers
source                  1..36
                        mol_type = other RNA
                        organism = synthetic construct
SEQUENCE: 64
gtgtttttac ccatttctag cgaattggat aagcac                        36

SEQ ID NO: 65           moltype = RNA  length = 36
```

```
FEATURE                Location/Qualifiers
source                 1..36
                       mol_type = other RNA
                       organism = synthetic construct
SEQUENCE: 65
gtgcttatcc aattcgctag aaatgggtaa aaacac                            36

SEQ ID NO: 66          moltype = RNA  length = 36
FEATURE                Location/Qualifiers
source                 1..36
                       mol_type = other RNA
                       organism = synthetic construct
SEQUENCE: 66
gtgcttttac tcatttctaa cgaattgaac aagcac                            36

SEQ ID NO: 67          moltype = RNA  length = 36
FEATURE                Location/Qualifiers
source                 1..36
                       mol_type = other RNA
                       organism = synthetic construct
SEQUENCE: 67
gtgcttgttc aattcgttag aaatgagtaa aagcac                            36

SEQ ID NO: 68          moltype = RNA  length = 36
FEATURE                Location/Qualifiers
source                 1..36
                       mol_type = other RNA
                       organism = synthetic construct
SEQUENCE: 68
gtgcttttac tcatttctaa cgaactgaat aagcac                            36

SEQ ID NO: 69          moltype = RNA  length = 36
FEATURE                Location/Qualifiers
source                 1..36
                       mol_type = other RNA
                       organism = synthetic construct
SEQUENCE: 69
gtgcttattc agttcgttag aaatgagtaa aagcac                            36

SEQ ID NO: 70          moltype = RNA  length = 36
FEATURE                Location/Qualifiers
source                 1..36
                       mol_type = other RNA
                       organism = synthetic construct
SEQUENCE: 70
gtgtttttat tcatttctag cgaactgaat aagcac                            36

SEQ ID NO: 71          moltype = RNA  length = 36
FEATURE                Location/Qualifiers
source                 1..36
                       mol_type = other RNA
                       organism = synthetic construct
SEQUENCE: 71
gtgcttattc agttcgctag aaatgaataa aaacac                            36

SEQ ID NO: 72          moltype = RNA  length = 36
FEATURE                Location/Qualifiers
source                 1..36
                       mol_type = other RNA
                       organism = synthetic construct
SEQUENCE: 72
gtgcttttac tcacttctaa cgaattaaat aagcac                            36

SEQ ID NO: 73          moltype = RNA  length = 36
FEATURE                Location/Qualifiers
source                 1..36
                       mol_type = other RNA
                       organism = synthetic construct
SEQUENCE: 73
gtgcttattt aattcgttag aagtgagtaa aagcac                            36

SEQ ID NO: 74          moltype = RNA  length = 36
FEATURE                Location/Qualifiers
source                 1..36
                       mol_type = other RNA
                       organism = synthetic construct
SEQUENCE: 74
gtgcttttac tcatttctaa cgaatcgaat aagcac                            36
```

```
SEQ ID NO: 75          moltype = RNA  length = 36
FEATURE                Location/Qualifiers
source                 1..36
                       mol_type = other RNA
                       organism = synthetic construct
SEQUENCE: 75
gtgcttattc gattcgttag aaatgagtaa aagcac                      36

SEQ ID NO: 76          moltype = RNA  length = 36
FEATURE                Location/Qualifiers
source                 1..36
                       mol_type = other RNA
                       organism = synthetic construct
SEQUENCE: 76
gtgcttttat ccatttctaa cgaattgaat aagcac                      36

SEQ ID NO: 77          moltype = RNA  length = 36
FEATURE                Location/Qualifiers
source                 1..36
                       mol_type = other RNA
                       organism = synthetic construct
SEQUENCE: 77
gtgcttattc aattcgttag aaatggataa aagcac                      36

SEQ ID NO: 78          moltype = RNA  length = 36
FEATURE                Location/Qualifiers
source                 1..36
                       mol_type = other RNA
                       organism = synthetic construct
SEQUENCE: 78
gttacaatac ctagaggttt taccactaga ttgtac                      36

SEQ ID NO: 79          moltype = RNA  length = 36
FEATURE                Location/Qualifiers
source                 1..36
                       mol_type = other RNA
                       organism = synthetic construct
SEQUENCE: 79
gtacaatcta gtggtaaaac ctctaggtat tgtaac                      36

SEQ ID NO: 80          moltype = RNA  length = 36
FEATURE                Location/Qualifiers
source                 1..36
                       mol_type = other RNA
                       organism = synthetic construct
SEQUENCE: 80
gttacaatac ctagaggtct ttccaatagg ttgtac                      36

SEQ ID NO: 81          moltype = RNA  length = 36
FEATURE                Location/Qualifiers
source                 1..36
                       mol_type = other RNA
                       organism = synthetic construct
SEQUENCE: 81
gtacaaccta ttggaaagac ctctaggtat tgtaac                      36

SEQ ID NO: 82          moltype = RNA  length = 31
FEATURE                Location/Qualifiers
source                 1..31
                       mol_type = other RNA
                       organism = synthetic construct
SEQUENCE: 82
gttgcgaaca catggcatct agcgttgcca t                           31

SEQ ID NO: 83          moltype = RNA  length = 31
FEATURE                Location/Qualifiers
source                 1..31
                       mol_type = other RNA
                       organism = synthetic construct
SEQUENCE: 83
atggcaacgc tagatgccat gtgttcgcaa c                           31

SEQ ID NO: 84          moltype = RNA  length = 31
FEATURE                Location/Qualifiers
source                 1..31
                       mol_type = other RNA
                       organism = synthetic construct
SEQUENCE: 84
gttgcgaaca catggcatct agcgttgcca c                           31
```

```
SEQ ID NO: 85          moltype = RNA  length = 31
FEATURE                Location/Qualifiers
source                 1..31
                       mol_type = other RNA
                       organism = synthetic construct
SEQUENCE: 85
gtggcaacgc tagatgccat gtgttcgcaa c                                  31

SEQ ID NO: 86          moltype = RNA  length = 31
FEATURE                Location/Qualifiers
source                 1..31
                       mol_type = other RNA
                       organism = synthetic construct
SEQUENCE: 86
gttgcgaaca gatggcatct agcgttgcca t                                  31

SEQ ID NO: 87          moltype = RNA  length = 31
FEATURE                Location/Qualifiers
source                 1..31
                       mol_type = other RNA
                       organism = synthetic construct
SEQUENCE: 87
atggcaacgc tagatgccat ctgttcgcaa c                                  31

SEQ ID NO: 88          moltype = RNA  length = 40
FEATURE                Location/Qualifiers
source                 1..40
                       mol_type = other RNA
                       organism = synthetic construct
SEQUENCE: 88
tgttgcgaac acatggcatc tagcgttgcc atgcagcaca                         40

SEQ ID NO: 89          moltype = RNA  length = 40
FEATURE                Location/Qualifiers
source                 1..40
                       mol_type = other RNA
                       organism = synthetic construct
SEQUENCE: 89
tgtgctgcat ggcaacgcta gatgccatgt gttcgcaaca                         40

SEQ ID NO: 90          moltype = RNA  length = 36
FEATURE                Location/Qualifiers
source                 1..36
                       mol_type = other RNA
                       organism = synthetic construct
SEQUENCE: 90
gtgctggcga cctgctacgg cggatcgcca aggcac                             36

SEQ ID NO: 91          moltype = RNA  length = 36
FEATURE                Location/Qualifiers
source                 1..36
                       mol_type = other RNA
                       organism = synthetic construct
SEQUENCE: 91
gtgccttggc gatccgccgt agcaggtcgc cagcac                             36

SEQ ID NO: 92          moltype = RNA  length = 36
FEATURE                Location/Qualifiers
source                 1..36
                       mol_type = other RNA
                       organism = synthetic construct
SEQUENCE: 92
gtgctggcga cctgctacgg tggatcgcca aggcac                             36

SEQ ID NO: 93          moltype = RNA  length = 36
FEATURE                Location/Qualifiers
source                 1..36
                       mol_type = other RNA
                       organism = synthetic construct
SEQUENCE: 93
gtgccttggc gatccaccgt agcaggtcgc cagcac                             36

SEQ ID NO: 94          moltype = RNA  length = 37
FEATURE                Location/Qualifiers
source                 1..37
                       mol_type = other RNA
                       organism = synthetic construct
SEQUENCE: 94
```

agtgctggtt ctcgtcgcta ggggagagtc aaagcac 37

SEQ ID NO: 95 moltype = RNA length = 37
FEATURE Location/Qualifiers
source 1..37
mol_type = other RNA
organism = synthetic construct
SEQUENCE: 95
gtgctttgac tctcccctag cgacgagaac cagcact 37

SEQ ID NO: 96 moltype = RNA length = 37
FEATURE Location/Qualifiers
source 1..37
mol_type = other RNA
organism = synthetic construct
SEQUENCE: 96
ggtacaatct agtggtaaaa cctctaggta ttgtaac 37

SEQ ID NO: 97 moltype = RNA length = 37
FEATURE Location/Qualifiers
source 1..37
mol_type = other RNA
organism = synthetic construct
SEQUENCE: 97
gttacaatac ctagaggttt taccactaga ttgtacc 37

SEQ ID NO: 98 moltype = RNA length = 37
FEATURE Location/Qualifiers
source 1..37
mol_type = other RNA
organism = synthetic construct
SEQUENCE: 98
agtacaacct attggaaaga cctctaggta ttgtaac 37

SEQ ID NO: 99 moltype = RNA length = 37
FEATURE Location/Qualifiers
source 1..37
mol_type = other RNA
organism = synthetic construct
SEQUENCE: 99
gttacaatac ctagaggtct ttccaatagg ttgtact 37

SEQ ID NO: 100 moltype = RNA length = 37
FEATURE Location/Qualifiers
source 1..37
mol_type = other RNA
organism = synthetic construct
SEQUENCE: 100
tgtacaatct agtggtaaaa cctctaggta ttgtaac 37

SEQ ID NO: 101 moltype = RNA length = 37
FEATURE Location/Qualifiers
source 1..37
mol_type = other RNA
organism = synthetic construct
SEQUENCE: 101
gttacaatac ctagaggttt taccactaga ttgtaca 37

SEQ ID NO: 102 moltype = RNA length = 36
FEATURE Location/Qualifiers
source 1..36
mol_type = other RNA
organism = synthetic construct
SEQUENCE: 102
gctgcatggc aacgctagat gccatgtgtt cgcaac 36

SEQ ID NO: 103 moltype = RNA length = 36
FEATURE Location/Qualifiers
source 1..36
mol_type = other RNA
organism = synthetic construct
SEQUENCE: 103
gttgcgaaca catggcatct agcgttgcca tgcagc 36

SEQ ID NO: 104 moltype = RNA length = 36
FEATURE Location/Qualifiers
source 1..36
mol_type = other RNA
organism = synthetic construct

```
SEQUENCE: 104
gctgcgtggc aacgctagat gccatgtgtt cgcaac                    36

SEQ ID NO: 105          moltype = RNA  length = 36
FEATURE                 Location/Qualifiers
source                  1..36
                        mol_type = other RNA
                        organism = synthetic construct
SEQUENCE: 105
gttgcgaaca catggcatct agcgttgcca cgcagc                    36

SEQ ID NO: 106          moltype = RNA  length = 36
FEATURE                 Location/Qualifiers
source                  1..36
                        mol_type = other RNA
                        organism = synthetic construct
SEQUENCE: 106
gctgtatggc aacgctagat gccatctgtt cgcaac                    36

SEQ ID NO: 107          moltype = RNA  length = 36
FEATURE                 Location/Qualifiers
source                  1..36
                        mol_type = other RNA
                        organism = synthetic construct
SEQUENCE: 107
gttgcgaaca gatggcatct agcgttgcca tacagc                    36

SEQ ID NO: 108          moltype = RNA  length = 30
FEATURE                 Location/Qualifiers
source                  1..30
                        mol_type = other RNA
                        organism = synthetic construct
SEQUENCE: 108
tggcaacgct agatgccatg tgttcgcaac                           30

SEQ ID NO: 109          moltype = RNA  length = 30
FEATURE                 Location/Qualifiers
source                  1..30
                        mol_type = other RNA
                        organism = synthetic construct
SEQUENCE: 109
gttgcgaaca catggcatct agcgttgcca                           30

SEQ ID NO: 110          moltype = RNA  length = 30
FEATURE                 Location/Qualifiers
source                  1..30
                        mol_type = other RNA
                        organism = synthetic construct
SEQUENCE: 110
tggcaacgct agatgccatc tgttcgcaac                           30

SEQ ID NO: 111          moltype = RNA  length = 30
FEATURE                 Location/Qualifiers
source                  1..30
                        mol_type = other RNA
                        organism = synthetic construct
SEQUENCE: 111
gttgcgaaca gatggcatct agcgttgcca                           30

SEQ ID NO: 112          moltype = RNA  length = 36
FEATURE                 Location/Qualifiers
source                  1..36
                        mol_type = other RNA
                        organism = synthetic construct
SEQUENCE: 112
gtgctgttcc ttcccgtcag agaaggaaga gggcac                    36

SEQ ID NO: 113          moltype = RNA  length = 36
FEATURE                 Location/Qualifiers
source                  1..36
                        mol_type = other RNA
                        organism = synthetic construct
SEQUENCE: 113
gtgccctctt ccttctctga cgggaaggaa cagcac                    36

SEQ ID NO: 114          moltype = RNA  length = 33
FEATURE                 Location/Qualifiers
source                  1..33
                        mol_type = other RNA
```

```
                         organism = synthetic construct
SEQUENCE: 114
ctgttccttc ccgtcagaga aggaagaggg cac                              33

SEQ ID NO: 115           moltype = RNA  length = 33
FEATURE                  Location/Qualifiers
source                   1..33
                         mol_type = other RNA
                         organism = synthetic construct
SEQUENCE: 115
gtgccctctt ccttctctga cgggaaggaa cag                              33

SEQ ID NO: 116           moltype = RNA  length = 36
FEATURE                  Location/Qualifiers
source                   1..36
                         mol_type = other RNA
                         organism = synthetic construct
SEQUENCE: 116
atagcaattt catctaatgc cgttaggcgt tgagca                           36

SEQ ID NO: 117           moltype = RNA  length = 36
FEATURE                  Location/Qualifiers
source                   1..36
                         mol_type = other RNA
                         organism = synthetic construct
SEQUENCE: 117
tgctcaacgc ctaacggcat tagatgaaat tgctat                           36

SEQ ID NO: 118           moltype = RNA  length = 29
FEATURE                  Location/Qualifiers
source                   1..29
                         mol_type = other RNA
                         organism = synthetic construct
SEQUENCE: 118
ccccaagccc gcatgcgcgt gggctggac                                   29

SEQ ID NO: 119           moltype = RNA  length = 29
FEATURE                  Location/Qualifiers
source                   1..29
                         mol_type = other RNA
                         organism = synthetic construct
SEQUENCE: 119
gtccagccca cgcgcatgcg ggcttgggg                                   29

SEQ ID NO: 120           moltype = RNA  length = 29
FEATURE                  Location/Qualifiers
source                   1..29
                         mol_type = other RNA
                         organism = synthetic construct
SEQUENCE: 120
taaaaggccc acattcgcgt gggctggac                                   29

SEQ ID NO: 121           moltype = RNA  length = 29
FEATURE                  Location/Qualifiers
source                   1..29
                         mol_type = other RNA
                         organism = synthetic construct
SEQUENCE: 121
gtccagccca cgcgaatgtg ggcctttta                                   29

SEQ ID NO: 122           moltype = RNA  length = 29
FEATURE                  Location/Qualifiers
source                   1..29
                         mol_type = other RNA
                         organism = synthetic construct
SEQUENCE: 122
ccccaagccc tcgcgcacgt gggccggac                                   29

SEQ ID NO: 123           moltype = RNA  length = 29
FEATURE                  Location/Qualifiers
source                   1..29
                         mol_type = other RNA
                         organism = synthetic construct
SEQUENCE: 123
gtccggccca cgtgcgcgag ggcttgggg                                   29

SEQ ID NO: 124           moltype = RNA  length = 29
FEATURE                  Location/Qualifiers
source                   1..29
```

```
                        mol_type = other RNA
                        organism = synthetic construct
SEQUENCE: 124
ccccaaaccc tcgcgcacgt gggctggac                                     29

SEQ ID NO: 125          moltype = RNA  length = 29
FEATURE                 Location/Qualifiers
source                  1..29
                        mol_type = other RNA
                        organism = synthetic construct
SEQUENCE: 125
gtccagccca cgtgcgcgag ggtttgggg                                     29

SEQ ID NO: 126          moltype = RNA  length = 30
FEATURE                 Location/Qualifiers
source                  1..30
                        mol_type = other RNA
                        organism = synthetic construct
SEQUENCE: 126
ccccaagccc tcgcgcacgt gggccggact                                    30

SEQ ID NO: 127          moltype = RNA  length = 30
FEATURE                 Location/Qualifiers
source                  1..30
                        mol_type = other RNA
                        organism = synthetic construct
SEQUENCE: 127
agtccggccc acgtgcgcga gggcttgggg                                    30

SEQ ID NO: 128          moltype = RNA  length = 23
FEATURE                 Location/Qualifiers
source                  1..23
                        mol_type = other RNA
                        organism = synthetic construct
SEQUENCE: 128
ccgaccaccc ccgcccgcgt ggg                                           23

SEQ ID NO: 129          moltype = RNA  length = 23
FEATURE                 Location/Qualifiers
source                  1..23
                        mol_type = other RNA
                        organism = synthetic construct
SEQUENCE: 129
cccacgcggg cgggggtggt cgg                                           23

SEQ ID NO: 130          moltype = RNA  length = 23
FEATURE                 Location/Qualifiers
source                  1..23
                        mol_type = other RNA
                        organism = synthetic construct
SEQUENCE: 130
acgaccaccc ccgcccgcgt ggg                                           23

SEQ ID NO: 131          moltype = RNA  length = 23
FEATURE                 Location/Qualifiers
source                  1..23
                        mol_type = other RNA
                        organism = synthetic construct
SEQUENCE: 131
cccacgcggg cgggggtggt cgt                                           23

SEQ ID NO: 132          moltype = RNA  length = 23
FEATURE                 Location/Qualifiers
source                  1..23
                        mol_type = other RNA
                        organism = synthetic construct
SEQUENCE: 132
gcaaacacac tagcccgcgt ggg                                           23

SEQ ID NO: 133          moltype = RNA  length = 23
FEATURE                 Location/Qualifiers
source                  1..23
                        mol_type = other RNA
                        organism = synthetic construct
SEQUENCE: 133
cccacgcggg ctagtgtgtt tgc                                           23

SEQ ID NO: 134          moltype = RNA  length = 23
FEATURE                 Location/Qualifiers
```

```
source                1..23
                      mol_type = other RNA
                      organism = synthetic construct
SEQUENCE: 134
gcgaccaccc ccgcccgcgt ggg                                          23

SEQ ID NO: 135        moltype = RNA  length = 23
FEATURE               Location/Qualifiers
source                1..23
                      mol_type = other RNA
                      organism = synthetic construct
SEQUENCE: 135
cccacgcggg cgggggtggt cgc                                          23

SEQ ID NO: 136        moltype = RNA  length = 29
FEATURE               Location/Qualifiers
source                1..29
                      mol_type = other RNA
                      organism = synthetic construct
SEQUENCE: 136
ccgaccaccc ccgcccgcgt gggcttgac                                    29

SEQ ID NO: 137        moltype = RNA  length = 29
FEATURE               Location/Qualifiers
source                1..29
                      mol_type = other RNA
                      organism = synthetic construct
SEQUENCE: 137
gtcaagccca cgcgggcggg ggtggtcgg                                    29

SEQ ID NO: 138        moltype = RNA  length = 23
FEATURE               Location/Qualifiers
source                1..23
                      mol_type = other RNA
                      organism = synthetic construct
SEQUENCE: 138
caaccaacca ccgaccgcgt ggg                                          23

SEQ ID NO: 139        moltype = RNA  length = 23
FEATURE               Location/Qualifiers
source                1..23
                      mol_type = other RNA
                      organism = synthetic construct
SEQUENCE: 139
cccacgcggt cggtggttgg ttg                                          23

SEQ ID NO: 140        moltype = RNA  length = 23
FEATURE               Location/Qualifiers
source                1..23
                      mol_type = other RNA
                      organism = synthetic construct
SEQUENCE: 140
ccgaccaccc ccgccagcgt ggg                                          23

SEQ ID NO: 141        moltype = RNA  length = 23
FEATURE               Location/Qualifiers
source                1..23
                      mol_type = other RNA
                      organism = synthetic construct
SEQUENCE: 141
cccacgctgg cgggggtggt cgg                                          23

SEQ ID NO: 142        moltype = RNA  length = 37
FEATURE               Location/Qualifiers
source                1..37
                      mol_type = other RNA
                      organism = synthetic construct
SEQUENCE: 142
gttggattca gccataaaat ccagtaggta taaaacc                           37

SEQ ID NO: 143        moltype = RNA  length = 37
FEATURE               Location/Qualifiers
source                1..37
                      mol_type = other RNA
                      organism = synthetic construct
SEQUENCE: 143
ggttttatac ctactggatt ttatggctga atccaac                           37

SEQ ID NO: 144        moltype = RNA  length = 37
```

```
FEATURE                 Location/Qualifiers
source                  1..37
                        mol_type = other RNA
                        organism = synthetic construct
SEQUENCE: 144
gttggattca gccataaaat ccagtaggta taaaact                            37

SEQ ID NO: 145          moltype = RNA  length = 37
FEATURE                 Location/Qualifiers
source                  1..37
                        mol_type = other RNA
                        organism = synthetic construct
SEQUENCE: 145
agttttatac ctactggatt ttatggctga atccaac                            37

SEQ ID NO: 146          moltype = RNA  length = 32
FEATURE                 Location/Qualifiers
source                  1..32
                        mol_type = other RNA
                        organism = synthetic construct
SEQUENCE: 146
gattcagcca taaaatccag taggtataaa ac                                 32

SEQ ID NO: 147          moltype = RNA  length = 32
FEATURE                 Location/Qualifiers
source                  1..32
                        mol_type = other RNA
                        organism = synthetic construct
SEQUENCE: 147
gttttatacc tactggattt tatggctgaa tc                                 32

SEQ ID NO: 148          moltype = RNA  length = 36
FEATURE                 Location/Qualifiers
source                  1..36
                        mol_type = other RNA
                        organism = synthetic construct
SEQUENCE: 148
gttggattca gccataaaat ccagtaggta taaaac                             36

SEQ ID NO: 149          moltype = RNA  length = 36
FEATURE                 Location/Qualifiers
source                  1..36
                        mol_type = other RNA
                        organism = synthetic construct
SEQUENCE: 149
gttttatacc tactggattt tatggctgaa tccaac                             36

SEQ ID NO: 150          moltype = RNA  length = 32
FEATURE                 Location/Qualifiers
source                  1..32
                        mol_type = other RNA
                        organism = synthetic construct
SEQUENCE: 150
gattcagcct tcaaatccag ttgttttcta tt                                 32

SEQ ID NO: 151          moltype = RNA  length = 32
FEATURE                 Location/Qualifiers
source                  1..32
                        mol_type = other RNA
                        organism = synthetic construct
SEQUENCE: 151
aatagaaaac aactggattt gaaggctgaa tc                                 32

SEQ ID NO: 152          moltype = RNA  length = 32
FEATURE                 Location/Qualifiers
source                  1..32
                        mol_type = other RNA
                        organism = synthetic construct
SEQUENCE: 152
gattcagcct acaaatccag taggtgtaaa ac                                 32

SEQ ID NO: 153          moltype = RNA  length = 32
FEATURE                 Location/Qualifiers
source                  1..32
                        mol_type = other RNA
                        organism = synthetic construct
SEQUENCE: 153
gttttacacc tactggattt gtaggctgaa tc                                 32
```

```
SEQ ID NO: 154         moltype = RNA  length = 32
FEATURE                Location/Qualifiers
source                 1..32
                       mol_type = other RNA
                       organism = synthetic construct
SEQUENCE: 154
gattcagtca taaaatccag taggtataaa ac                                    32

SEQ ID NO: 155         moltype = RNA  length = 32
FEATURE                Location/Qualifiers
source                 1..32
                       mol_type = other RNA
                       organism = synthetic construct
SEQUENCE: 155
gttttatacc tactggattt tatgactgaa tc                                    32

SEQ ID NO: 156         moltype = RNA  length = 38
FEATURE                Location/Qualifiers
source                 1..38
                       mol_type = other RNA
                       organism = synthetic construct
SEQUENCE: 156
gttggattca gccataaaat ccagtaggta taaaaccg                              38

SEQ ID NO: 157         moltype = RNA  length = 38
FEATURE                Location/Qualifiers
source                 1..38
                       mol_type = other RNA
                       organism = synthetic construct
SEQUENCE: 157
cggttttata cctactggat tttatggctg aatccaac                              38

SEQ ID NO: 158         moltype = RNA  length = 23
FEATURE                Location/Qualifiers
source                 1..23
                       mol_type = other RNA
                       organism = synthetic construct
SEQUENCE: 158
gttggattca gccataaaat cca                                              23

SEQ ID NO: 159         moltype = RNA  length = 23
FEATURE                Location/Qualifiers
source                 1..23
                       mol_type = other RNA
                       organism = synthetic construct
SEQUENCE: 159
tggattttat ggctgaatcc aac                                              23

SEQ ID NO: 160         moltype = RNA  length = 23
FEATURE                Location/Qualifiers
source                 1..23
                       mol_type = other RNA
                       organism = synthetic construct
SEQUENCE: 160
gttggattca gcctacaaat cca                                              23

SEQ ID NO: 161         moltype = RNA  length = 23
FEATURE                Location/Qualifiers
source                 1..23
                       mol_type = other RNA
                       organism = synthetic construct
SEQUENCE: 161
tggatttgta ggctgaatcc aac                                              23

SEQ ID NO: 162         moltype = RNA  length = 23
FEATURE                Location/Qualifiers
source                 1..23
                       mol_type = other RNA
                       organism = synthetic construct
SEQUENCE: 162
gttggattca gtcataaaat cca                                              23

SEQ ID NO: 163         moltype = RNA  length = 23
FEATURE                Location/Qualifiers
source                 1..23
                       mol_type = other RNA
                       organism = synthetic construct
SEQUENCE: 163
tggattttat gactgaatcc aac                                              23
```

```
SEQ ID NO: 164          moltype = RNA  length = 23
FEATURE                 Location/Qualifiers
source                  1..23
                        mol_type = other RNA
                        organism = synthetic construct
SEQUENCE: 164
tggatttgaa ggttgaatcc aac                                            23

SEQ ID NO: 165          moltype = RNA  length = 23
FEATURE                 Location/Qualifiers
source                  1..23
                        mol_type = other RNA
                        organism = synthetic construct
SEQUENCE: 165
gttggattca accttcaaat cca                                            23

SEQ ID NO: 166          moltype = RNA  length = 23
FEATURE                 Location/Qualifiers
source                  1..23
                        mol_type = other RNA
                        organism = synthetic construct
SEQUENCE: 166
tgggtttgag ggctgaatcc aag                                            23

SEQ ID NO: 167          moltype = RNA  length = 23
FEATURE                 Location/Qualifiers
source                  1..23
                        mol_type = other RNA
                        organism = synthetic construct
SEQUENCE: 167
cttggattca gccctcaaac cca                                            23

SEQ ID NO: 168          moltype = RNA  length = 23
FEATURE                 Location/Qualifiers
source                  1..23
                        mol_type = other RNA
                        organism = synthetic construct
SEQUENCE: 168
tggatttgta gactgaatcc aac                                            23

SEQ ID NO: 169          moltype = RNA  length = 23
FEATURE                 Location/Qualifiers
source                  1..23
                        mol_type = other RNA
                        organism = synthetic construct
SEQUENCE: 169
gttggattca gtctacaaat cca                                            23

SEQ ID NO: 170          moltype = RNA  length = 23
FEATURE                 Location/Qualifiers
source                  1..23
                        mol_type = other RNA
                        organism = synthetic construct
SEQUENCE: 170
tgactttgag ggctgaagcc aac                                            23

SEQ ID NO: 171          moltype = RNA  length = 23
FEATURE                 Location/Qualifiers
source                  1..23
                        mol_type = other RNA
                        organism = synthetic construct
SEQUENCE: 171
gttggcttca gccctcaaag tca                                            23

SEQ ID NO: 172          moltype = RNA  length = 42
FEATURE                 Location/Qualifiers
source                  1..42
                        mol_type = other RNA
                        organism = synthetic construct
SEQUENCE: 172
ggttttatac ctactggatt ttatggctga atccaaccga gc                       42

SEQ ID NO: 173          moltype = RNA  length = 42
FEATURE                 Location/Qualifiers
source                  1..42
                        mol_type = other RNA
                        organism = synthetic construct
SEQUENCE: 173
```

```
gctcggttgg attcagccat aaaatccagt aggtataaaa cc                          42

SEQ ID NO: 174          moltype = RNA  length = 36
FEATURE                 Location/Qualifiers
source                  1..36
                        mol_type = other RNA
                        organism = synthetic construct
SEQUENCE: 174
cttccagagc ctcccgatcg gcttcgtaga tcagac                                 36

SEQ ID NO: 175          moltype = RNA  length = 36
FEATURE                 Location/Qualifiers
source                  1..36
                        mol_type = other RNA
                        organism = synthetic construct
SEQUENCE: 175
gtctgatcta cgaagccgat cgggaggctc tggaag                                 36

SEQ ID NO: 176          moltype = RNA  length = 36
FEATURE                 Location/Qualifiers
source                  1..36
                        mol_type = other RNA
                        organism = synthetic construct
SEQUENCE: 176
tctccagagc ctcccgatcg gcttcgtaga tcagac                                 36

SEQ ID NO: 177          moltype = RNA  length = 36
FEATURE                 Location/Qualifiers
source                  1..36
                        mol_type = other RNA
                        organism = synthetic construct
SEQUENCE: 177
gtctgatcta cgaagccgat cgggaggctc tggaga                                 36

SEQ ID NO: 178          moltype = RNA  length = 36
FEATURE                 Location/Qualifiers
source                  1..36
                        mol_type = other RNA
                        organism = synthetic construct
SEQUENCE: 178
cttccagagc cttccgatcg gcttcgtaga tcagac                                 36

SEQ ID NO: 179          moltype = RNA  length = 36
FEATURE                 Location/Qualifiers
source                  1..36
                        mol_type = other RNA
                        organism = synthetic construct
SEQUENCE: 179
gtctgatcta cgaagccgat cggaaggctc tggaag                                 36

SEQ ID NO: 180          moltype = RNA  length = 36
FEATURE                 Location/Qualifiers
source                  1..36
                        mol_type = other RNA
                        organism = synthetic construct
SEQUENCE: 180
cttccagagc ctcccgatcg gcttcatagg tcggac                                 36

SEQ ID NO: 181          moltype = RNA  length = 36
FEATURE                 Location/Qualifiers
source                  1..36
                        mol_type = other RNA
                        organism = synthetic construct
SEQUENCE: 181
gtccgaccta tgaagccgat cgggaggctc tggaag                                 36

SEQ ID NO: 182          moltype = RNA  length = 36
FEATURE                 Location/Qualifiers
source                  1..36
                        mol_type = other RNA
                        organism = synthetic construct
SEQUENCE: 182
cttccagagc cccctgatcg gcttcgtaga tcagac                                 36

SEQ ID NO: 183          moltype = RNA  length = 36
FEATURE                 Location/Qualifiers
source                  1..36
                        mol_type = other RNA
                        organism = synthetic construct
```

```
SEQUENCE: 183
gtctgatcta cgaagccgat cagggggctc tggaag                          36

SEQ ID NO: 184         moltype = RNA  length = 36
FEATURE                Location/Qualifiers
source                 1..36
                       mol_type = other RNA
                       organism = synthetic construct
SEQUENCE: 184
cttccaaagc ctcccgatcg gcttcgtaga tcagac                          36

SEQ ID NO: 185         moltype = RNA  length = 36
FEATURE                Location/Qualifiers
source                 1..36
                       mol_type = other RNA
                       organism = synthetic construct
SEQUENCE: 185
gtctgatcta cgaagccgat cgggaggctt tggaag                          36

SEQ ID NO: 186         moltype = RNA  length = 36
FEATURE                Location/Qualifiers
source                 1..36
                       mol_type = other RNA
                       organism = synthetic construct
SEQUENCE: 186
cttccagagc ctcctgttcg gcttcgtaga tcagaa                          36

SEQ ID NO: 187         moltype = RNA  length = 36
FEATURE                Location/Qualifiers
source                 1..36
                       mol_type = other RNA
                       organism = synthetic construct
SEQUENCE: 187
ttctgatcta cgaagccgaa caggaggctc tggaag                          36

SEQ ID NO: 188         moltype = RNA  length = 36
FEATURE                Location/Qualifiers
source                 1..36
                       mol_type = other RNA
                       organism = synthetic construct
SEQUENCE: 188
cttccagagc ctcctgatcg gcttcgtagg tcagac                          36

SEQ ID NO: 189         moltype = RNA  length = 36
FEATURE                Location/Qualifiers
source                 1..36
                       mol_type = other RNA
                       organism = synthetic construct
SEQUENCE: 189
gtctgaccta cgaagccgat caggaggctc tggaag                          36

SEQ ID NO: 190         moltype = RNA  length = 36
FEATURE                Location/Qualifiers
source                 1..36
                       mol_type = other RNA
                       organism = synthetic construct
SEQUENCE: 190
cttccagagc cttctgatcg gttcggtgct gggact                          36

SEQ ID NO: 191         moltype = RNA  length = 36
FEATURE                Location/Qualifiers
source                 1..36
                       mol_type = other RNA
                       organism = synthetic construct
SEQUENCE: 191
agtcccagca ccgaaccgat cagaaggctc tggaag                          36

SEQ ID NO: 192         moltype = RNA  length = 34
FEATURE                Location/Qualifiers
source                 1..34
                       mol_type = other RNA
                       organism = synthetic construct
SEQUENCE: 192
tccagagcct cccgatcggc ttcgtagatc agac                            34

SEQ ID NO: 193         moltype = RNA  length = 34
FEATURE                Location/Qualifiers
source                 1..34
                       mol_type = other RNA
```

```
                        organism = synthetic construct
SEQUENCE: 193
gtctgatcta cgaagccgat cgggaggctc tgga                              34

SEQ ID NO: 194          moltype = RNA  length = 34
FEATURE                 Location/Qualifiers
source                  1..34
                        mol_type = other RNA
                        organism = synthetic construct
SEQUENCE: 194
tccagagcct tccgatcggc ttcgtagatc agac                              34

SEQ ID NO: 195          moltype = RNA  length = 34
FEATURE                 Location/Qualifiers
source                  1..34
                        mol_type = other RNA
                        organism = synthetic construct
SEQUENCE: 195
gtctgatcta cgaagccgat cggaaggctc tgga                              34

SEQ ID NO: 196          moltype = RNA  length = 34
FEATURE                 Location/Qualifiers
source                  1..34
                        mol_type = other RNA
                        organism = synthetic construct
SEQUENCE: 196
tccagagcct cccgatcggc ttcataggtc ggac                              34

SEQ ID NO: 197          moltype = RNA  length = 34
FEATURE                 Location/Qualifiers
source                  1..34
                        mol_type = other RNA
                        organism = synthetic construct
SEQUENCE: 197
gtccgaccta tgaagccgat cgggaggctc tgga                              34

SEQ ID NO: 198          moltype = RNA  length = 34
FEATURE                 Location/Qualifiers
source                  1..34
                        mol_type = other RNA
                        organism = synthetic construct
SEQUENCE: 198
tccagagccc cctgatcggc ttcgtagatc agac                              34

SEQ ID NO: 199          moltype = RNA  length = 34
FEATURE                 Location/Qualifiers
source                  1..34
                        mol_type = other RNA
                        organism = synthetic construct
SEQUENCE: 199
gtctgatcta cgaagccgat cagggggctc tgga                              34

SEQ ID NO: 200          moltype = RNA  length = 34
FEATURE                 Location/Qualifiers
source                  1..34
                        mol_type = other RNA
                        organism = synthetic construct
SEQUENCE: 200
tccaaagcct cccgatcggc ttcgtagatc agac                              34

SEQ ID NO: 201          moltype = RNA  length = 34
FEATURE                 Location/Qualifiers
source                  1..34
                        mol_type = other RNA
                        organism = synthetic construct
SEQUENCE: 201
gtctgatcta cgaagccgat cgggaggctt tgga                              34

SEQ ID NO: 202          moltype = RNA  length = 34
FEATURE                 Location/Qualifiers
source                  1..34
                        mol_type = other RNA
                        organism = synthetic construct
SEQUENCE: 202
tccagagcct cctgttcggc ttcgtagatc agaa                              34

SEQ ID NO: 203          moltype = RNA  length = 34
FEATURE                 Location/Qualifiers
source                  1..34
```

```
                        mol_type = other RNA
                        organism = synthetic construct
SEQUENCE: 203
ttctgatcta cgaagccgaa caggaggctc tgga                              34

SEQ ID NO: 204          moltype = RNA  length = 34
FEATURE                 Location/Qualifiers
source                  1..34
                        mol_type = other RNA
                        organism = synthetic construct
SEQUENCE: 204
tccagagcct cctgatcggc ttcgtaggtc agac                              34

SEQ ID NO: 205          moltype = RNA  length = 34
FEATURE                 Location/Qualifiers
source                  1..34
                        mol_type = other RNA
                        organism = synthetic construct
SEQUENCE: 205
gtctgaccta cgaagccgat caggaggctc tgga                              34

SEQ ID NO: 206          moltype = RNA  length = 30
FEATURE                 Location/Qualifiers
source                  1..30
                        mol_type = other RNA
                        organism = synthetic construct
SEQUENCE: 206
atttaaatag aaccatagtg gaatgtaaat                                   30

SEQ ID NO: 207          moltype = RNA  length = 30
FEATURE                 Location/Qualifiers
source                  1..30
                        mol_type = other RNA
                        organism = synthetic construct
SEQUENCE: 207
atttacattc cactatggtt ctatttaaat                                   30

SEQ ID NO: 208          moltype = RNA  length = 32
FEATURE                 Location/Qualifiers
source                  1..32
                        mol_type = other RNA
                        organism = synthetic construct
SEQUENCE: 208
ctttgcctcc gcgcacacac acggattgca ac                                32

SEQ ID NO: 209          moltype = RNA  length = 32
FEATURE                 Location/Qualifiers
source                  1..32
                        mol_type = other RNA
                        organism = synthetic construct
SEQUENCE: 209
gttgcaatcc gtgtgtgtgc gcggaggcaa ag                                32

SEQ ID NO: 210          moltype = RNA  length = 32
FEATURE                 Location/Qualifiers
source                  1..32
                        mol_type = other RNA
                        organism = synthetic construct
SEQUENCE: 210
gtctgcctcc gcgcacacac acggattgca ac                                32

SEQ ID NO: 211          moltype = RNA  length = 32
FEATURE                 Location/Qualifiers
source                  1..32
                        mol_type = other RNA
                        organism = synthetic construct
SEQUENCE: 211
gttgcaatcc gtgtgtgtgc gcggaggcag ac                                32

SEQ ID NO: 212          moltype = RNA  length = 17
FEATURE                 Location/Qualifiers
source                  1..17
                        mol_type = other RNA
                        organism = synthetic construct
SEQUENCE: 212
gaacatcctg aaccaca                                                 17

SEQ ID NO: 213          moltype = RNA  length = 17
FEATURE                 Location/Qualifiers
```

```
source                  1..17
                        mol_type = other RNA
                        organism = synthetic construct
SEQUENCE: 213
tgtggttcag gatgttc                                                17

SEQ ID NO: 214          moltype = RNA  length = 23
FEATURE                 Location/Qualifiers
source                  1..23
                        mol_type = other RNA
                        organism = synthetic construct
SEQUENCE: 214
attaatttac atcattctca aac                                         23

SEQ ID NO: 215          moltype = RNA  length = 23
FEATURE                 Location/Qualifiers
source                  1..23
                        mol_type = other RNA
                        organism = synthetic construct
SEQUENCE: 215
gtttgagaat gatgtaaatt aat                                         23

SEQ ID NO: 216          moltype = RNA  length = 23
FEATURE                 Location/Qualifiers
source                  1..23
                        mol_type = other RNA
                        organism = synthetic construct
SEQUENCE: 216
ttcatattct atcattctca aac                                         23

SEQ ID NO: 217          moltype = RNA  length = 23
FEATURE                 Location/Qualifiers
source                  1..23
                        mol_type = other RNA
                        organism = synthetic construct
SEQUENCE: 217
gtttgagaat gatagaatat gaa                                         23

SEQ ID NO: 218          moltype = RNA  length = 32
FEATURE                 Location/Qualifiers
source                  1..32
                        mol_type = other RNA
                        organism = synthetic construct
SEQUENCE: 218
gtctcacctt acacaggtga gtggattgaa at                               32

SEQ ID NO: 219          moltype = RNA  length = 32
FEATURE                 Location/Qualifiers
source                  1..32
                        mol_type = other RNA
                        organism = synthetic construct
SEQUENCE: 219
atttcaatcc actcacctgt gtaaggtgag ac                               32

SEQ ID NO: 220          moltype = RNA  length = 32
FEATURE                 Location/Qualifiers
source                  1..32
                        mol_type = other RNA
                        organism = synthetic construct
SEQUENCE: 220
gtctcacctt acataggtga gtggattgaa at                               32

SEQ ID NO: 221          moltype = RNA  length = 32
FEATURE                 Location/Qualifiers
source                  1..32
                        mol_type = other RNA
                        organism = synthetic construct
SEQUENCE: 221
atttcaatcc actcacctat gtaaggtgag ac                               32

SEQ ID NO: 222          moltype = RNA  length = 26
FEATURE                 Location/Qualifiers
source                  1..26
                        mol_type = other RNA
                        organism = synthetic construct
SEQUENCE: 222
tccacggcgt tcagcagcta gacatt                                      26

SEQ ID NO: 223          moltype = RNA  length = 26
```

```
FEATURE                Location/Qualifiers
source                 1..26
                       mol_type = other RNA
                       organism = synthetic construct
SEQUENCE: 223
aatgtctagc tgctgaacgc cgtgga                                    26

SEQ ID NO: 224         moltype = RNA  length = 26
FEATURE                Location/Qualifiers
source                 1..26
                       mol_type = other RNA
                       organism = synthetic construct
SEQUENCE: 224
tccacggcgt ttagcagcta gacatt                                    26

SEQ ID NO: 225         moltype = RNA  length = 26
FEATURE                Location/Qualifiers
source                 1..26
                       mol_type = other RNA
                       organism = synthetic construct
SEQUENCE: 225
aatgtctagc tgctaaacgc cgtgga                                    26

SEQ ID NO: 226         moltype = RNA  length = 36
FEATURE                Location/Qualifiers
source                 1..36
                       mol_type = other RNA
                       organism = synthetic construct
SEQUENCE: 226
gtttgagaat gatgtaaatt aatatggttc ttaatc                         36

SEQ ID NO: 227         moltype = RNA  length = 36
FEATURE                Location/Qualifiers
source                 1..36
                       mol_type = other RNA
                       organism = synthetic construct
SEQUENCE: 227
gattaagaac catattaatt tacatcattc tcaaac                         36

SEQ ID NO: 228         moltype = RNA  length = 36
FEATURE                Location/Qualifiers
source                 1..36
                       mol_type = other RNA
                       organism = synthetic construct
SEQUENCE: 228
gtttgagaat gatgtaaatc aatatggttc ttaatc                         36

SEQ ID NO: 229         moltype = RNA  length = 36
FEATURE                Location/Qualifiers
source                 1..36
                       mol_type = other RNA
                       organism = synthetic construct
SEQUENCE: 229
gattaagaac catattgatt tacatcattc tcaaac                         36

SEQ ID NO: 230         moltype = RNA  length = 36
FEATURE                Location/Qualifiers
source                 1..36
                       mol_type = other RNA
                       organism = synthetic construct
SEQUENCE: 230
gtttgagaat gatgtaattc aatatggtta cttaac                         36

SEQ ID NO: 231         moltype = RNA  length = 36
FEATURE                Location/Qualifiers
source                 1..36
                       mol_type = other RNA
                       organism = synthetic construct
SEQUENCE: 231
gttaagtaac catattgaat tacatcattc tcaaac                         36

SEQ ID NO: 232         moltype = RNA  length = 38
FEATURE                Location/Qualifiers
source                 1..38
                       mol_type = other RNA
                       organism = synthetic construct
SEQUENCE: 232
agttacaatg gcctctgccg tgtagcggca agtggagg                       38
```

```
SEQ ID NO: 233          moltype = RNA  length = 38
FEATURE                 Location/Qualifiers
source                  1..38
                        mol_type = other RNA
                        organism = synthetic construct
SEQUENCE: 233
cctccacttg ccgctacacg gcagaggcca ttgtaact                          38

SEQ ID NO: 234          moltype = RNA  length = 38
FEATURE                 Location/Qualifiers
source                  1..38
                        mol_type = other RNA
                        organism = synthetic construct
SEQUENCE: 234
ggttacaatg gcctctgccg tgtagcggca agtggagg                          38

SEQ ID NO: 235          moltype = RNA  length = 38
FEATURE                 Location/Qualifiers
source                  1..38
                        mol_type = other RNA
                        organism = synthetic construct
SEQUENCE: 235
cctccacttg ccgctacacg gcagaggcca ttgtaacc                          38

SEQ ID NO: 236          moltype = RNA  length = 38
FEATURE                 Location/Qualifiers
source                  1..38
                        mol_type = other RNA
                        organism = synthetic construct
SEQUENCE: 236
cgttacaatg gcctctgccg tgtagcggca agtggagg                          38

SEQ ID NO: 237          moltype = RNA  length = 38
FEATURE                 Location/Qualifiers
source                  1..38
                        mol_type = other RNA
                        organism = synthetic construct
SEQUENCE: 237
cctccacttg ccgctacacg gcagaggcca ttgtaacg                          38

SEQ ID NO: 238          moltype = RNA  length = 38
FEATURE                 Location/Qualifiers
source                  1..38
                        mol_type = other RNA
                        organism = synthetic construct
SEQUENCE: 238
agttacaatg gcctctgccg tgtagcggca agtggagc                          38

SEQ ID NO: 239          moltype = RNA  length = 38
FEATURE                 Location/Qualifiers
source                  1..38
                        mol_type = other RNA
                        organism = synthetic construct
SEQUENCE: 239
gctccacttg ccgctacacg gcagaggcca ttgtaact                          38

SEQ ID NO: 240          moltype = RNA  length = 39
FEATURE                 Location/Qualifiers
source                  1..39
                        mol_type = other RNA
                        organism = synthetic construct
SEQUENCE: 240
gttacaatgg cctctgccgt gtagcggcaa gtggaggag                         39

SEQ ID NO: 241          moltype = RNA  length = 39
FEATURE                 Location/Qualifiers
source                  1..39
                        mol_type = other RNA
                        organism = synthetic construct
SEQUENCE: 241
ctcctccact tgccgctaca cggcagaggc cattgtaac                         39

SEQ ID NO: 242          moltype = RNA  length = 36
FEATURE                 Location/Qualifiers
source                  1..36
                        mol_type = other RNA
                        organism = synthetic construct
SEQUENCE: 242
gtctaatact ttatattaat ttctactatt gtagat                            36
```

```
SEQ ID NO: 243          moltype = RNA  length = 36
FEATURE                 Location/Qualifiers
source                  1..36
                        mol_type = other RNA
                        organism = synthetic construct
SEQUENCE: 243
atctacaata gtagaaatta atataaagta ttagac                            36

SEQ ID NO: 244          moltype = RNA  length = 35
FEATURE                 Location/Qualifiers
source                  1..35
                        mol_type = other RNA
                        organism = synthetic construct
SEQUENCE: 244
tctaatactt tatattaatt tctactattg tagat                             35

SEQ ID NO: 245          moltype = RNA  length = 35
FEATURE                 Location/Qualifiers
source                  1..35
                        mol_type = other RNA
                        organism = synthetic construct
SEQUENCE: 245
atctacaata gtagaaatta atataaagta ttaga                             35

SEQ ID NO: 246          moltype = RNA  length = 37
FEATURE                 Location/Qualifiers
source                  1..37
                        mol_type = other RNA
                        organism = synthetic construct
SEQUENCE: 246
gttgcaatgg tcaacagagc gtcgtggcaa gtggagg                           37

SEQ ID NO: 247          moltype = RNA  length = 37
FEATURE                 Location/Qualifiers
source                  1..37
                        mol_type = other RNA
                        organism = synthetic construct
SEQUENCE: 247
cctccacttg ccacgacgct ctgttgacca ttgcaac                           37

SEQ ID NO: 248          moltype = RNA  length = 37
FEATURE                 Location/Qualifiers
source                  1..37
                        mol_type = other RNA
                        organism = synthetic construct
SEQUENCE: 248
gttgcaatgg gcaccgtggc atcgcggcaa gtggagg                           37

SEQ ID NO: 249          moltype = RNA  length = 37
FEATURE                 Location/Qualifiers
source                  1..37
                        mol_type = other RNA
                        organism = synthetic construct
SEQUENCE: 249
cctccacttg ccgcgatgcc acggtgccca ttgcaac                           37

SEQ ID NO: 250          moltype = RNA  length = 37
FEATURE                 Location/Qualifiers
source                  1..37
                        mol_type = other RNA
                        organism = synthetic construct
SEQUENCE: 250
cctgccgaac acatccgatc ggatctcctg ttcgacc                           37

SEQ ID NO: 251          moltype = RNA  length = 37
FEATURE                 Location/Qualifiers
source                  1..37
                        mol_type = other RNA
                        organism = synthetic construct
SEQUENCE: 251
ggtcgaacag gagatccgat cggatgtgtt cggcagg                           37

SEQ ID NO: 252          moltype = RNA  length = 37
FEATURE                 Location/Qualifiers
source                  1..37
                        mol_type = other RNA
                        organism = synthetic construct
SEQUENCE: 252
```

```
cctgccgaac acatccgatc ggatctcctg ttcgacg                          37

SEQ ID NO: 253          moltype = RNA  length = 37
FEATURE                 Location/Qualifiers
source                  1..37
                        mol_type = other RNA
                        organism = synthetic construct
SEQUENCE: 253
cgtcgaacag gagatccgat cggatgtgtt cggcagg                          37

SEQ ID NO: 254          moltype = RNA  length = 37
FEATURE                 Location/Qualifiers
source                  1..37
                        mol_type = other RNA
                        organism = synthetic construct
SEQUENCE: 254
cctgccgaac acatccgatc ggatctcctg ttcgaca                          37

SEQ ID NO: 255          moltype = RNA  length = 37
FEATURE                 Location/Qualifiers
source                  1..37
                        mol_type = other RNA
                        organism = synthetic construct
SEQUENCE: 255
tgtcgaacag gagatccgat cggatgtgtt cggcagg                          37

SEQ ID NO: 256          moltype = RNA  length = 36
FEATURE                 Location/Qualifiers
source                  1..36
                        mol_type = other RNA
                        organism = synthetic construct
SEQUENCE: 256
cctgccgaac acatccgatc ggatctcctg ttcgac                           36

SEQ ID NO: 257          moltype = RNA  length = 36
FEATURE                 Location/Qualifiers
source                  1..36
                        mol_type = other RNA
                        organism = synthetic construct
SEQUENCE: 257
gtcgaacagg agatccgatc ggatgtgttc ggcagg                           36

SEQ ID NO: 258          moltype = RNA  length = 37
FEATURE                 Location/Qualifiers
source                  1..37
                        mol_type = other RNA
                        organism = synthetic construct
SEQUENCE: 258
atccaaagca cctcaatccc cgcgagggga ttacgac                          37

SEQ ID NO: 259          moltype = RNA  length = 37
FEATURE                 Location/Qualifiers
source                  1..37
                        mol_type = other RNA
                        organism = synthetic construct
SEQUENCE: 259
gtcgtaatcc cctcgcgggg attgaggtgc tttggat                          37

SEQ ID NO: 260          moltype = RNA  length = 24
FEATURE                 Location/Qualifiers
source                  1..24
                        mol_type = other RNA
                        organism = synthetic construct
SEQUENCE: 260
ggtaataacg atcagaattg gaag                                        24

SEQ ID NO: 261          moltype = RNA  length = 24
FEATURE                 Location/Qualifiers
source                  1..24
                        mol_type = other RNA
                        organism = synthetic construct
SEQUENCE: 261
cttccaattc tgatcgttat tacc                                        24

SEQ ID NO: 262          moltype = RNA  length = 24
FEATURE                 Location/Qualifiers
source                  1..24
                        mol_type = other RNA
                        organism = synthetic construct
```

```
SEQUENCE: 262
ggtagtaacg atcagaattt gaaa                                  24

SEQ ID NO: 263          moltype = RNA  length = 24
FEATURE                 Location/Qualifiers
source                  1..24
                        mol_type = other RNA
                        organism = synthetic construct
SEQUENCE: 263
tttcaaattc tgatcgttac tacc                                  24

SEQ ID NO: 264          moltype = RNA  length = 24
FEATURE                 Location/Qualifiers
source                  1..24
                        mol_type = other RNA
                        organism = synthetic construct
SEQUENCE: 264
ctttcagttc ttcctagttg ttac                                  24

SEQ ID NO: 265          moltype = RNA  length = 24
FEATURE                 Location/Qualifiers
source                  1..24
                        mol_type = other RNA
                        organism = synthetic construct
SEQUENCE: 265
gtaacaacta ggaagaactg aaag                                  24

SEQ ID NO: 266          moltype = RNA  length = 24
FEATURE                 Location/Qualifiers
source                  1..24
                        mol_type = other RNA
                        organism = synthetic construct
SEQUENCE: 266
cttccaattc tgatcgttgt tacc                                  24

SEQ ID NO: 267          moltype = RNA  length = 24
FEATURE                 Location/Qualifiers
source                  1..24
                        mol_type = other RNA
                        organism = synthetic construct
SEQUENCE: 267
ggtaacaacg atcagaattg gaag                                  24

SEQ ID NO: 268          moltype = RNA  length = 23
FEATURE                 Location/Qualifiers
source                  1..23
                        mol_type = other RNA
                        organism = synthetic construct
SEQUENCE: 268
atctgcaaca gcagaaattt tac                                   23

SEQ ID NO: 269          moltype = RNA  length = 23
FEATURE                 Location/Qualifiers
source                  1..23
                        mol_type = other RNA
                        organism = synthetic construct
SEQUENCE: 269
gtaaaatttc tgctgttgca gat                                   23

SEQ ID NO: 270          moltype = RNA  length = 23
FEATURE                 Location/Qualifiers
source                  1..23
                        mol_type = other RNA
                        organism = synthetic construct
SEQUENCE: 270
acctgcgata gcaggaattg gat                                   23

SEQ ID NO: 271          moltype = RNA  length = 23
FEATURE                 Location/Qualifiers
source                  1..23
                        mol_type = other RNA
                        organism = synthetic construct
SEQUENCE: 271
atccaattcc tgctatcgca ggt                                   23

SEQ ID NO: 272          moltype = RNA  length = 23
FEATURE                 Location/Qualifiers
source                  1..23
                        mol_type = other RNA
```

```
                        organism = synthetic construct
SEQUENCE: 272
atctgcaaca gcagaaattt gat                                          23

SEQ ID NO: 273          moltype = RNA  length = 23
FEATURE                 Location/Qualifiers
source                  1..23
                        mol_type = other RNA
                        organism = synthetic construct
SEQUENCE: 273
atcaaatttc tgctgttgca gat                                          23

SEQ ID NO: 274          moltype = RNA  length = 23
FEATURE                 Location/Qualifiers
source                  1..23
                        mol_type = other RNA
                        organism = synthetic construct
SEQUENCE: 274
atctgcaaca gcagaaattt gga                                          23

SEQ ID NO: 275          moltype = RNA  length = 23
FEATURE                 Location/Qualifiers
source                  1..23
                        mol_type = other RNA
                        organism = synthetic construct
SEQUENCE: 275
tccaaatttc tgctgttgca gat                                          23

SEQ ID NO: 276          moltype = RNA  length = 23
FEATURE                 Location/Qualifiers
source                  1..23
                        mol_type = other RNA
                        organism = synthetic construct
SEQUENCE: 276
atctgcaaca gcagaaattt cgc                                          23

SEQ ID NO: 277          moltype = RNA  length = 23
FEATURE                 Location/Qualifiers
source                  1..23
                        mol_type = other RNA
                        organism = synthetic construct
SEQUENCE: 277
gcgaaatttc tgctgttgca gat                                          23

SEQ ID NO: 278          moltype = RNA  length = 23
FEATURE                 Location/Qualifiers
source                  1..23
                        mol_type = other RNA
                        organism = synthetic construct
SEQUENCE: 278
atctgcaaca gcagaaattt aca                                          23

SEQ ID NO: 279          moltype = RNA  length = 23
FEATURE                 Location/Qualifiers
source                  1..23
                        mol_type = other RNA
                        organism = synthetic construct
SEQUENCE: 279
tgtaaatttc tgctgttgca gat                                          23

SEQ ID NO: 280          moltype = RNA  length = 23
FEATURE                 Location/Qualifiers
source                  1..23
                        mol_type = other RNA
                        organism = synthetic construct
SEQUENCE: 280
atctgcgata gcagaaattt cgc                                          23

SEQ ID NO: 281          moltype = RNA  length = 23
FEATURE                 Location/Qualifiers
source                  1..23
                        mol_type = other RNA
                        organism = synthetic construct
SEQUENCE: 281
gcgaaatttc tgctatcgca gat                                          23

SEQ ID NO: 282          moltype = RNA  length = 23
FEATURE                 Location/Qualifiers
source                  1..23
```

```
                        mol_type = other RNA
                        organism = synthetic construct
SEQUENCE: 282
atctgcaaca gcagaaattt tta                                              23

SEQ ID NO: 283          moltype = RNA  length = 23
FEATURE                 Location/Qualifiers
source                  1..23
                        mol_type = other RNA
                        organism = synthetic construct
SEQUENCE: 283
taaaaatttc tgctgttgca gat                                              23

SEQ ID NO: 284          moltype = RNA  length = 23
FEATURE                 Location/Qualifiers
source                  1..23
                        mol_type = other RNA
                        organism = synthetic construct
SEQUENCE: 284
atcttcaaca gcagaaattt ggc                                              23

SEQ ID NO: 285          moltype = RNA  length = 23
FEATURE                 Location/Qualifiers
source                  1..23
                        mol_type = other RNA
                        organism = synthetic construct
SEQUENCE: 285
gccaaatttc tgctgttgaa gat                                              23

SEQ ID NO: 286          moltype = RNA  length = 23
FEATURE                 Location/Qualifiers
source                  1..23
                        mol_type = other RNA
                        organism = synthetic construct
SEQUENCE: 286
atctgcaaca gcagaaattg gca                                              23

SEQ ID NO: 287          moltype = RNA  length = 23
FEATURE                 Location/Qualifiers
source                  1..23
                        mol_type = other RNA
                        organism = synthetic construct
SEQUENCE: 287
tgccaatttc tgctgttgca gat                                              23

SEQ ID NO: 288          moltype = RNA  length = 23
FEATURE                 Location/Qualifiers
source                  1..23
                        mol_type = other RNA
                        organism = synthetic construct
SEQUENCE: 288
atctgcaaca gcagaaattt gag                                              23

SEQ ID NO: 289          moltype = RNA  length = 23
FEATURE                 Location/Qualifiers
source                  1..23
                        mol_type = other RNA
                        organism = synthetic construct
SEQUENCE: 289
ctcaaatttc tgctgttgca gat                                              23

SEQ ID NO: 290          moltype = RNA  length = 20
FEATURE                 Location/Qualifiers
source                  1..20
                        mol_type = other RNA
                        organism = synthetic construct
SEQUENCE: 290
atctgcaaca gcagaaattt                                                  20

SEQ ID NO: 291          moltype = RNA  length = 20
FEATURE                 Location/Qualifiers
source                  1..20
                        mol_type = other RNA
                        organism = synthetic construct
SEQUENCE: 291
aaatttctgc tgttgcagat                                                  20

SEQ ID NO: 292          moltype = RNA  length = 19
FEATURE                 Location/Qualifiers
```

```
source                1..19
                      mol_type = other RNA
                      organism = synthetic construct
SEQUENCE: 292
atctgcaaca gcagaaatt                                          19

SEQ ID NO: 293        moltype = RNA  length = 19
FEATURE               Location/Qualifiers
source                1..19
                      mol_type = other RNA
                      organism = synthetic construct
SEQUENCE: 293
aatttctgct gttgcagat                                          19

SEQ ID NO: 294        moltype = RNA  length = 25
FEATURE               Location/Qualifiers
source                1..25
                      mol_type = other RNA
                      organism = synthetic construct
SEQUENCE: 294
ctttcaatat tctattgaaa tcaac                                   25

SEQ ID NO: 295        moltype = RNA  length = 25
FEATURE               Location/Qualifiers
source                1..25
                      mol_type = other RNA
                      organism = synthetic construct
SEQUENCE: 295
gttgatttca atagaatatt gaaag                                   25

SEQ ID NO: 296        moltype = RNA  length = 25
FEATURE               Location/Qualifiers
source                1..25
                      mol_type = other RNA
                      organism = synthetic construct
SEQUENCE: 296
ctttcaatat tctactgaaa tcaac                                   25

SEQ ID NO: 297        moltype = RNA  length = 25
FEATURE               Location/Qualifiers
source                1..25
                      mol_type = other RNA
                      organism = synthetic construct
SEQUENCE: 297
gttgatttca gtagaatatt gaaag                                   25

SEQ ID NO: 298        moltype = RNA  length = 25
FEATURE               Location/Qualifiers
source                1..25
                      mol_type = other RNA
                      organism = synthetic construct
SEQUENCE: 298
ctttcgatat tcctctggaa tcatt                                   25

SEQ ID NO: 299        moltype = RNA  length = 25
FEATURE               Location/Qualifiers
source                1..25
                      mol_type = other RNA
                      organism = synthetic construct
SEQUENCE: 299
aatgattcca gaggaatatc gaaag                                   25

SEQ ID NO: 300        moltype = RNA  length = 25
FEATURE               Location/Qualifiers
source                1..25
                      mol_type = other RNA
                      organism = synthetic construct
SEQUENCE: 300
ctttcaatat tctattgaaa ttggc                                   25

SEQ ID NO: 301        moltype = RNA  length = 25
FEATURE               Location/Qualifiers
source                1..25
                      mol_type = other RNA
                      organism = synthetic construct
SEQUENCE: 301
gccaatttca atagaatatt gaaag                                   25

SEQ ID NO: 302        moltype = RNA  length = 25
```

```
FEATURE                Location/Qualifiers
source                 1..25
                       mol_type = other RNA
                       organism = synthetic construct
SEQUENCE: 302
ctttcaatat tccattgaaa tcaac                                    25

SEQ ID NO: 303         moltype = RNA  length = 25
FEATURE                Location/Qualifiers
source                 1..25
                       mol_type = other RNA
                       organism = synthetic construct
SEQUENCE: 303
gttgatttca atggaatatt gaaag                                    25

SEQ ID NO: 304         moltype = RNA  length = 25
FEATURE                Location/Qualifiers
source                 1..25
                       mol_type = other RNA
                       organism = synthetic construct
SEQUENCE: 304
ctttcaatat tctattgaaa atcaa                                    25

SEQ ID NO: 305         moltype = RNA  length = 25
FEATURE                Location/Qualifiers
source                 1..25
                       mol_type = other RNA
                       organism = synthetic construct
SEQUENCE: 305
ttgattttca atagaatatt gaaag                                    25

SEQ ID NO: 306         moltype = RNA  length = 25
FEATURE                Location/Qualifiers
source                 1..25
                       mol_type = other RNA
                       organism = synthetic construct
SEQUENCE: 306
gcttcaattc ttctgtttta gattc                                    25

SEQ ID NO: 307         moltype = RNA  length = 25
FEATURE                Location/Qualifiers
source                 1..25
                       mol_type = other RNA
                       organism = synthetic construct
SEQUENCE: 307
gaatctaaaa cagaagaatt gaagc                                    25

SEQ ID NO: 308         moltype = RNA  length = 23
FEATURE                Location/Qualifiers
source                 1..23
                       mol_type = other RNA
                       organism = synthetic construct
SEQUENCE: 308
tgatttcaga ggaatattga aac                                      23

SEQ ID NO: 309         moltype = RNA  length = 23
FEATURE                Location/Qualifiers
source                 1..23
                       mol_type = other RNA
                       organism = synthetic construct
SEQUENCE: 309
gtttcaatat tcctctgaaa tca                                      23

SEQ ID NO: 310         moltype = RNA  length = 24
FEATURE                Location/Qualifiers
source                 1..24
                       mol_type = other RNA
                       organism = synthetic construct
SEQUENCE: 310
ctttcagtct tatagaattg cttc                                     24

SEQ ID NO: 311         moltype = RNA  length = 24
FEATURE                Location/Qualifiers
source                 1..24
                       mol_type = other RNA
                       organism = synthetic construct
SEQUENCE: 311
gaagcaattc tataagactg aaag                                     24
```

```
SEQ ID NO: 312         moltype = RNA  length = 24
FEATURE                Location/Qualifiers
source                 1..24
                       mol_type = other RNA
                       organism = synthetic construct
SEQUENCE: 312
ctttcagttt tatagaattg cttc                                        24

SEQ ID NO: 313         moltype = RNA  length = 24
FEATURE                Location/Qualifiers
source                 1..24
                       mol_type = other RNA
                       organism = synthetic construct
SEQUENCE: 313
gaagcaattc tataaaactg aaag                                        24

SEQ ID NO: 314         moltype = RNA  length = 24
FEATURE                Location/Qualifiers
source                 1..24
                       mol_type = other RNA
                       organism = synthetic construct
SEQUENCE: 314
ttttggtttt tatagaattg cttc                                        24

SEQ ID NO: 315         moltype = RNA  length = 24
FEATURE                Location/Qualifiers
source                 1..24
                       mol_type = other RNA
                       organism = synthetic construct
SEQUENCE: 315
gaagcaattc tataaaaacc aaaa                                        24

SEQ ID NO: 316         moltype = RNA  length = 24
FEATURE                Location/Qualifiers
source                 1..24
                       mol_type = other RNA
                       organism = synthetic construct
SEQUENCE: 316
ctttcattct tatagaattg cttc                                        24

SEQ ID NO: 317         moltype = RNA  length = 24
FEATURE                Location/Qualifiers
source                 1..24
                       mol_type = other RNA
                       organism = synthetic construct
SEQUENCE: 317
gaagcaattc tataagaatg aaag                                        24

SEQ ID NO: 318         moltype = RNA  length = 24
FEATURE                Location/Qualifiers
source                 1..24
                       mol_type = other RNA
                       organism = synthetic construct
SEQUENCE: 318
ttttcagtct tatagaattg cttc                                        24

SEQ ID NO: 319         moltype = RNA  length = 24
FEATURE                Location/Qualifiers
source                 1..24
                       mol_type = other RNA
                       organism = synthetic construct
SEQUENCE: 319
gaagcaattc tataagactg aaaa                                        24

SEQ ID NO: 320         moltype = RNA  length = 24
FEATURE                Location/Qualifiers
source                 1..24
                       mol_type = other RNA
                       organism = synthetic construct
SEQUENCE: 320
gtaacaactg aaagaaacta aaac                                        24

SEQ ID NO: 321         moltype = RNA  length = 24
FEATURE                Location/Qualifiers
source                 1..24
                       mol_type = other RNA
                       organism = synthetic construct
SEQUENCE: 321
gttttagttt ctttcagttg ttac                                        24
```

```
SEQ ID NO: 322          moltype = RNA  length = 24
FEATURE                Location/Qualifiers
source                 1..24
                       mol_type = other RNA
                       organism = synthetic construct
SEQUENCE: 322
ctttcaattc tctatttgag atgc                                          24

SEQ ID NO: 323          moltype = RNA  length = 24
FEATURE                Location/Qualifiers
source                 1..24
                       mol_type = other RNA
                       organism = synthetic construct
SEQUENCE: 323
gcatctcaaa tagagaattg aaag                                          24

SEQ ID NO: 324          moltype = RNA  length = 32
FEATURE                Location/Qualifiers
source                 1..32
                       mol_type = other RNA
                       organism = synthetic construct
SEQUENCE: 324
gtcgcacctc tcgtaggtgc gtggattgaa at                                 32

SEQ ID NO: 325          moltype = RNA  length = 32
FEATURE                Location/Qualifiers
source                 1..32
                       mol_type = other RNA
                       organism = synthetic construct
SEQUENCE: 325
atttcaatcc acgcacctac gagaggtgcg ac                                 32

SEQ ID NO: 326          moltype = RNA  length = 24
FEATURE                Location/Qualifiers
source                 1..24
                       mol_type = other RNA
                       organism = synthetic construct
SEQUENCE: 326
ccatcagtat caaagtaata ccaa                                          24

SEQ ID NO: 327          moltype = RNA  length = 24
FEATURE                Location/Qualifiers
source                 1..24
                       mol_type = other RNA
                       organism = synthetic construct
SEQUENCE: 327
ttggtattac tttgatactg atgg                                          24

SEQ ID NO: 328          moltype = RNA  length = 25
FEATURE                Location/Qualifiers
source                 1..25
                       mol_type = other RNA
                       organism = synthetic construct
SEQUENCE: 328
ggtactgcat ctcatgctga aggtg                                         25

SEQ ID NO: 329          moltype = RNA  length = 25
FEATURE                Location/Qualifiers
source                 1..25
                       mol_type = other RNA
                       organism = synthetic construct
SEQUENCE: 329
caccttcagc atgagatgca gtacc                                         25

SEQ ID NO: 330          moltype = RNA  length = 25
FEATURE                Location/Qualifiers
source                 1..25
                       mol_type = other RNA
                       organism = synthetic construct
SEQUENCE: 330
ggaaactctg cacatgctga aggcg                                         25

SEQ ID NO: 331          moltype = RNA  length = 25
FEATURE                Location/Qualifiers
source                 1..25
                       mol_type = other RNA
                       organism = synthetic construct
SEQUENCE: 331
```

cgccttcagc atgtgcagag tttcc 25

SEQ ID NO: 332 moltype = RNA length = 25
FEATURE Location/Qualifiers
source 1..25
mol_type = other RNA
organism = synthetic construct
SEQUENCE: 332
ggtagtgcat ctcatgctga aggtg 25

SEQ ID NO: 333 moltype = RNA length = 25
FEATURE Location/Qualifiers
source 1..25
mol_type = other RNA
organism = synthetic construct
SEQUENCE: 333
caccttcagc atgagatgca ctacc 25

SEQ ID NO: 334 moltype = RNA length = 25
FEATURE Location/Qualifiers
source 1..25
mol_type = other RNA
organism = synthetic construct
SEQUENCE: 334
ggatacgcat ctcatgcaga gggtg 25

SEQ ID NO: 335 moltype = RNA length = 25
FEATURE Location/Qualifiers
source 1..25
mol_type = other RNA
organism = synthetic construct
SEQUENCE: 335
caccctctgc atgagatgcg tatcc 25

SEQ ID NO: 336 moltype = RNA length = 25
FEATURE Location/Qualifiers
source 1..25
mol_type = other RNA
organism = synthetic construct
SEQUENCE: 336
aatactcatg cacatgctga aggtg 25

SEQ ID NO: 337 moltype = RNA length = 25
FEATURE Location/Qualifiers
source 1..25
mol_type = other RNA
organism = synthetic construct
SEQUENCE: 337
caccttcagc atgtgcatga gtatt 25

SEQ ID NO: 338 moltype = RNA length = 25
FEATURE Location/Qualifiers
source 1..25
mol_type = other RNA
organism = synthetic construct
SEQUENCE: 338
ggaaattact ctcatgcgga aggtg 25

SEQ ID NO: 339 moltype = RNA length = 25
FEATURE Location/Qualifiers
source 1..25
mol_type = other RNA
organism = synthetic construct
SEQUENCE: 339
caccttccgc atgagagtaa tttcc 25

SEQ ID NO: 340 moltype = RNA length = 25
FEATURE Location/Qualifiers
source 1..25
mol_type = other RNA
organism = synthetic construct
SEQUENCE: 340
aaacacgcat ctcatgcaga aggtg 25

SEQ ID NO: 341 moltype = RNA length = 25
FEATURE Location/Qualifiers
source 1..25
mol_type = other RNA
organism = synthetic construct

```
SEQUENCE: 341
caccttctgc atgagatgcg tgttt                                         25

SEQ ID NO: 342          moltype = RNA  length = 25
FEATURE                 Location/Qualifiers
source                  1..25
                        mol_type = other RNA
                        organism = synthetic construct
SEQUENCE: 342
gctaatcacg cacatgcaga aggtg                                         25

SEQ ID NO: 343          moltype = RNA  length = 25
FEATURE                 Location/Qualifiers
source                  1..25
                        mol_type = other RNA
                        organism = synthetic construct
SEQUENCE: 343
caccttctgc atgtgcgtga ttagc                                         25

SEQ ID NO: 344          moltype = RNA  length = 25
FEATURE                 Location/Qualifiers
source                  1..25
                        mol_type = other RNA
                        organism = synthetic construct
SEQUENCE: 344
ggtaaagcat cacacgcaga aggcg                                         25

SEQ ID NO: 345          moltype = RNA  length = 25
FEATURE                 Location/Qualifiers
source                  1..25
                        mol_type = other RNA
                        organism = synthetic construct
SEQUENCE: 345
cgccttctgc gtgtgatgct ttacc                                         25

SEQ ID NO: 346          moltype = RNA  length = 25
FEATURE                 Location/Qualifiers
source                  1..25
                        mol_type = other RNA
                        organism = synthetic construct
SEQUENCE: 346
ggaagttttt ctcatactca aggta                                         25

SEQ ID NO: 347          moltype = RNA  length = 25
FEATURE                 Location/Qualifiers
source                  1..25
                        mol_type = other RNA
                        organism = synthetic construct
SEQUENCE: 347
taccttgagt atgagaaaaa cttcc                                         25

SEQ ID NO: 348          moltype = RNA  length = 25
FEATURE                 Location/Qualifiers
source                  1..25
                        mol_type = other RNA
                        organism = synthetic construct
SEQUENCE: 348
ggtaatgcat ctcatgctga aggtg                                         25

SEQ ID NO: 349          moltype = RNA  length = 25
FEATURE                 Location/Qualifiers
source                  1..25
                        mol_type = other RNA
                        organism = synthetic construct
SEQUENCE: 349
caccttcagc atgagatgca ttacc                                         25

SEQ ID NO: 350          moltype = RNA  length = 30
FEATURE                 Location/Qualifiers
source                  1..30
                        mol_type = other RNA
                        organism = synthetic construct
SEQUENCE: 350
gtttcagacg gacccttggg cggttgaagc                                    30

SEQ ID NO: 351          moltype = RNA  length = 30
FEATURE                 Location/Qualifiers
source                  1..30
                        mol_type = other RNA
```

```
                          organism = synthetic construct
SEQUENCE: 351
gcttcaaccg cccaagggtc cgtctgaaac                                     30

SEQ ID NO: 352            moltype = RNA  length = 30
FEATURE                   Location/Qualifiers
source                    1..30
                          mol_type = other RNA
                          organism = synthetic construct
SEQUENCE: 352
tttcagacgg atcccttggg cggttgaagc                                     30

SEQ ID NO: 353            moltype = RNA  length = 30
FEATURE                   Location/Qualifiers
source                    1..30
                          mol_type = other RNA
                          organism = synthetic construct
SEQUENCE: 353
gcttcaaccg cccaagggat ccgtctgaaa                                     30

SEQ ID NO: 354            moltype = RNA  length = 30
FEATURE                   Location/Qualifiers
source                    1..30
                          mol_type = other RNA
                          organism = synthetic construct
SEQUENCE: 354
gtttcagacg gcctctggag tggccgaagc                                     30

SEQ ID NO: 355            moltype = RNA  length = 30
FEATURE                   Location/Qualifiers
source                    1..30
                          mol_type = other RNA
                          organism = synthetic construct
SEQUENCE: 355
gcttcggcca ctccagaggc cgtctgaaac                                     30

SEQ ID NO: 356            moltype = RNA  length = 35
FEATURE                   Location/Qualifiers
source                    1..35
                          mol_type = other RNA
                          organism = synthetic construct
SEQUENCE: 356
gtttcaaccg cacgaggatc cgtctgaaac catgg                               35

SEQ ID NO: 357            moltype = RNA  length = 35
FEATURE                   Location/Qualifiers
source                    1..35
                          mol_type = other RNA
                          organism = synthetic construct
SEQUENCE: 357
ccatggtttc agacggatcc tcgtgcggtt gaaac                               35

SEQ ID NO: 358            moltype = RNA  length = 35
FEATURE                   Location/Qualifiers
source                    1..35
                          mol_type = other RNA
                          organism = synthetic construct
SEQUENCE: 358
gtttcaaccg cacgaggatc cgtctgaaac atgga                               35

SEQ ID NO: 359            moltype = RNA  length = 35
FEATURE                   Location/Qualifiers
source                    1..35
                          mol_type = other RNA
                          organism = synthetic construct
SEQUENCE: 359
tccatgtttc agacggatcc tcgtgcggtt gaaac                               35

SEQ ID NO: 360            moltype = RNA  length = 28
FEATURE                   Location/Qualifiers
source                    1..28
                          mol_type = other RNA
                          organism = synthetic construct
SEQUENCE: 360
acccagacct cgacgccgac tgccacgc                                       28

SEQ ID NO: 361            moltype = RNA  length = 28
FEATURE                   Location/Qualifiers
source                    1..28
```

```
                        mol_type = other RNA
                        organism = synthetic construct
SEQUENCE: 361
gcgtggcagt cggcgtcgag gtctgggt                                        28

SEQ ID NO: 362          moltype = RNA  length = 24
FEATURE                 Location/Qualifiers
source                  1..24
                        mol_type = other RNA
                        organism = synthetic construct
SEQUENCE: 362
gtcgccgaac tcgtcgtcac cgcc                                            24

SEQ ID NO: 363          moltype = RNA  length = 24
FEATURE                 Location/Qualifiers
source                  1..24
                        mol_type = other RNA
                        organism = synthetic construct
SEQUENCE: 363
ggcggtgacg acgagttcgg cgac                                            24

SEQ ID NO: 364          moltype = RNA  length = 30
FEATURE                 Location/Qualifiers
source                  1..30
                        mol_type = other RNA
                        organism = synthetic construct
SEQUENCE: 364
catttcaatt ccataaggta caattaatac                                      30

SEQ ID NO: 365          moltype = RNA  length = 30
FEATURE                 Location/Qualifiers
source                  1..30
                        mol_type = other RNA
                        organism = synthetic construct
SEQUENCE: 365
gtattaattg taccttatgg aattgaaatg                                      30

SEQ ID NO: 366          moltype = RNA  length = 29
FEATURE                 Location/Qualifiers
source                  1..29
                        mol_type = other RNA
                        organism = synthetic construct
SEQUENCE: 366
gtattaattg taccttatgg aattgaaat                                       29

SEQ ID NO: 367          moltype = RNA  length = 29
FEATURE                 Location/Qualifiers
source                  1..29
                        mol_type = other RNA
                        organism = synthetic construct
SEQUENCE: 367
atttcaattc cataaggtac aattaatac                                       29

SEQ ID NO: 368          moltype = RNA  length = 29
FEATURE                 Location/Qualifiers
source                  1..29
                        mol_type = other RNA
                        organism = synthetic construct
SEQUENCE: 368
gtattaattg taccttatgg aattaggac                                       29

SEQ ID NO: 369          moltype = RNA  length = 29
FEATURE                 Location/Qualifiers
source                  1..29
                        mol_type = other RNA
                        organism = synthetic construct
SEQUENCE: 369
gtcctaattc cataaggtac aattaatac                                       29

SEQ ID NO: 370          moltype = RNA  length = 29
FEATURE                 Location/Qualifiers
source                  1..29
                        mol_type = other RNA
                        organism = synthetic construct
SEQUENCE: 370
gtattaatta taccttatgg aattgaaat                                       29

SEQ ID NO: 371          moltype = RNA  length = 29
FEATURE                 Location/Qualifiers
```

```
source                  1..29
                        mol_type = other RNA
                        organism = synthetic construct
SEQUENCE: 371
atttcaattc cataaggtat aattaatac                                    29

SEQ ID NO: 372          moltype = RNA  length = 54
FEATURE                 Location/Qualifiers
source                  1..54
                        mol_type = other RNA
                        organism = synthetic construct
SEQUENCE: 372
tttttctttg tcggggtagc gggattcgaa cccacgaccc cctgctccca aagc        54

SEQ ID NO: 373          moltype = RNA  length = 54
FEATURE                 Location/Qualifiers
source                  1..54
                        mol_type = other RNA
                        organism = synthetic construct
SEQUENCE: 373
gctttgggag caggggggtcg tgggttcgaa tcccgctacc ccgacaaaga aaaa       54

SEQ ID NO: 374          moltype = RNA  length = 54
FEATURE                 Location/Qualifiers
source                  1..54
                        mol_type = other RNA
                        organism = synthetic construct
SEQUENCE: 374
tttttctttg tcggggtagc gggattcgaa cccacgaccc ccagctccca aagc        54

SEQ ID NO: 375          moltype = RNA  length = 54
FEATURE                 Location/Qualifiers
source                  1..54
                        mol_type = other RNA
                        organism = synthetic construct
SEQUENCE: 375
gctttgggag ctgggggtcg tgggttcgaa tcccgctacc ccgacaaaga aaaa        54

SEQ ID NO: 376          moltype = RNA  length = 31
FEATURE                 Location/Qualifiers
source                  1..31
                        mol_type = other RNA
                        organism = synthetic construct
SEQUENCE: 376
tatttcaatt ccataaggta caattaatac t                                 31

SEQ ID NO: 377          moltype = RNA  length = 31
FEATURE                 Location/Qualifiers
source                  1..31
                        mol_type = other RNA
                        organism = synthetic construct
SEQUENCE: 377
agtattaatt gtaccttatg gaattgaaat a                                 31

SEQ ID NO: 378          moltype = RNA  length = 31
FEATURE                 Location/Qualifiers
source                  1..31
                        mol_type = other RNA
                        organism = synthetic construct
SEQUENCE: 378
agtcctaatt ccataaggta caattaatac t                                 31

SEQ ID NO: 379          moltype = RNA  length = 31
FEATURE                 Location/Qualifiers
source                  1..31
                        mol_type = other RNA
                        organism = synthetic construct
SEQUENCE: 379
agtattaatt gtaccttatg gaattaggac t                                 31

SEQ ID NO: 380          moltype = RNA  length = 29
FEATURE                 Location/Qualifiers
source                  1..29
                        mol_type = other RNA
                        organism = synthetic construct
SEQUENCE: 380
gtattaattg taccttgtgg aattgaaat                                    29

SEQ ID NO: 381          moltype = RNA  length = 29
```

```
FEATURE                Location/Qualifiers
source                 1..29
                       mol_type = other RNA
                       organism = synthetic construct
SEQUENCE: 381
atttcaattc cacaaggtac aattaatac                                    29

SEQ ID NO: 382         moltype = RNA  length = 29
FEATURE                Location/Qualifiers
source                 1..29
                       mol_type = other RNA
                       organism = synthetic construct
SEQUENCE: 382
gtattaattg tacttatgga attgaaatt                                    29

SEQ ID NO: 383         moltype = RNA  length = 29
FEATURE                Location/Qualifiers
source                 1..29
                       mol_type = other RNA
                       organism = synthetic construct
SEQUENCE: 383
aatttcaatt ccataagtac aattaatac                                    29

SEQ ID NO: 384         moltype = RNA  length = 30
FEATURE                Location/Qualifiers
source                 1..30
                       mol_type = other RNA
                       organism = synthetic construct
SEQUENCE: 384
tgtattaatt gtaccttatg gaattgaaat                                   30

SEQ ID NO: 385         moltype = RNA  length = 30
FEATURE                Location/Qualifiers
source                 1..30
                       mol_type = other RNA
                       organism = synthetic construct
SEQUENCE: 385
atttcaattc cataaggtac aattaataca                                   30

SEQ ID NO: 386         moltype = RNA  length = 30
FEATURE                Location/Qualifiers
source                 1..30
                       mol_type = other RNA
                       organism = synthetic construct
SEQUENCE: 386
ggtattaatt gtaccttatg gaattaggac                                   30

SEQ ID NO: 387         moltype = RNA  length = 30
FEATURE                Location/Qualifiers
source                 1..30
                       mol_type = other RNA
                       organism = synthetic construct
SEQUENCE: 387
gtcctaattc cataaggtac aattaatacc                                   30

SEQ ID NO: 388         moltype = RNA  length = 30
FEATURE                Location/Qualifiers
source                 1..30
                       mol_type = other RNA
                       organism = synthetic construct
SEQUENCE: 388
ggtattaatt gtaccttatg gaattgaaat                                   30

SEQ ID NO: 389         moltype = RNA  length = 30
FEATURE                Location/Qualifiers
source                 1..30
                       mol_type = other RNA
                       organism = synthetic construct
SEQUENCE: 389
atttcaattc cataaggtac aattaatacc                                   30

SEQ ID NO: 390         moltype = RNA  length = 30
FEATURE                Location/Qualifiers
source                 1..30
                       mol_type = other RNA
                       organism = synthetic construct
SEQUENCE: 390
agtattaatt gtaccttatg gaattgaaat                                   30
```

```
SEQ ID NO: 391          moltype = RNA  length = 30
FEATURE                Location/Qualifiers
source                 1..30
                       mol_type = other RNA
                       organism = synthetic construct
SEQUENCE: 391
atttcaattc cataaggtac aattaatact                                    30

SEQ ID NO: 392          moltype = RNA  length = 29
FEATURE                Location/Qualifiers
source                 1..29
                       mol_type = other RNA
                       organism = synthetic construct
SEQUENCE: 392
gtattaattg taccttatgg atttgaaat                                     29

SEQ ID NO: 393          moltype = RNA  length = 29
FEATURE                Location/Qualifiers
source                 1..29
                       mol_type = other RNA
                       organism = synthetic construct
SEQUENCE: 393
atttcaaatc cataaggtac aattaatac                                     29

SEQ ID NO: 394          moltype = RNA  length = 29
FEATURE                Location/Qualifiers
source                 1..29
                       mol_type = other RNA
                       organism = synthetic construct
SEQUENCE: 394
gtattaattg tatcttatgg aattgaaat                                     29

SEQ ID NO: 395          moltype = RNA  length = 29
FEATURE                Location/Qualifiers
source                 1..29
                       mol_type = other RNA
                       organism = synthetic construct
SEQUENCE: 395
atttcaattc cataagatac aattaatac                                     29

SEQ ID NO: 396          moltype = RNA  length = 33
FEATURE                Location/Qualifiers
source                 1..33
                       mol_type = other RNA
                       organism = synthetic construct
SEQUENCE: 396
aaagtattaa ttgtacctta tggaattgaa ata                                33

SEQ ID NO: 397          moltype = RNA  length = 33
FEATURE                Location/Qualifiers
source                 1..33
                       mol_type = other RNA
                       organism = synthetic construct
SEQUENCE: 397
tatttcaatt ccataaggta caattaatac ttt                                33

SEQ ID NO: 398          moltype = RNA  length = 24
FEATURE                Location/Qualifiers
source                 1..24
                       mol_type = other RNA
                       organism = synthetic construct
SEQUENCE: 398
attcccaata tattgtgaat ttga                                          24

SEQ ID NO: 399          moltype = RNA  length = 24
FEATURE                Location/Qualifiers
source                 1..24
                       mol_type = other RNA
                       organism = synthetic construct
SEQUENCE: 399
tcaaattcac aatatattgg gaat                                          24

SEQ ID NO: 400          moltype = RNA  length = 30
FEATURE                Location/Qualifiers
source                 1..30
                       mol_type = other RNA
                       organism = synthetic construct
SEQUENCE: 400
gtttcaagcc cttataggta ttcaccaaac                                    30
```

```
SEQ ID NO: 401          moltype = RNA  length = 30
FEATURE                 Location/Qualifiers
source                  1..30
                        mol_type = other RNA
                        organism = synthetic construct
SEQUENCE: 401
gtttggtgaa tacctataag ggcttgaaac                                    30

SEQ ID NO: 402          moltype = RNA  length = 30
FEATURE                 Location/Qualifiers
source                  1..30
                        mol_type = other RNA
                        organism = synthetic construct
SEQUENCE: 402
tctcaaagcc cttataggta ttcatcaaac                                    30

SEQ ID NO: 403          moltype = RNA  length = 30
FEATURE                 Location/Qualifiers
source                  1..30
                        mol_type = other RNA
                        organism = synthetic construct
SEQUENCE: 403
gtttgatgaa tacctataag ggctttgaga                                    30

SEQ ID NO: 404          moltype = RNA  length = 30
FEATURE                 Location/Qualifiers
source                  1..30
                        mol_type = other RNA
                        organism = synthetic construct
SEQUENCE: 404
gtttcaagcc cttataggca ttcaccaaac                                    30

SEQ ID NO: 405          moltype = RNA  length = 30
FEATURE                 Location/Qualifiers
source                  1..30
                        mol_type = other RNA
                        organism = synthetic construct
SEQUENCE: 405
gtttggtgaa tgcctataag ggcttgaaac                                    30

SEQ ID NO: 406          moltype = RNA  length = 25
FEATURE                 Location/Qualifiers
source                  1..25
                        mol_type = other RNA
                        organism = synthetic construct
SEQUENCE: 406
gtttcccatg aaatgggtgt tgaaa                                         25

SEQ ID NO: 407          moltype = RNA  length = 25
FEATURE                 Location/Qualifiers
source                  1..25
                        mol_type = other RNA
                        organism = synthetic construct
SEQUENCE: 407
tttcaacacc catttcatgg gaaac                                         25

SEQ ID NO: 408          moltype = RNA  length = 47
FEATURE                 Location/Qualifiers
source                  1..47
                        mol_type = other RNA
                        organism = synthetic construct
SEQUENCE: 408
gttgttgctt atagtacaaa ggtattaaaa ttcaagcaaa tcacaac                 47

SEQ ID NO: 409          moltype = RNA  length = 47
FEATURE                 Location/Qualifiers
source                  1..47
                        mol_type = other RNA
                        organism = synthetic construct
SEQUENCE: 409
gttgtgattt gcttgaattt taataccttt gtactataag caacaac                 47

SEQ ID NO: 410          moltype = RNA  length = 17
FEATURE                 Location/Qualifiers
source                  1..17
                        mol_type = other RNA
                        organism = synthetic construct
SEQUENCE: 410
```

```
cggcgactca gtcgccg                                                17

SEQ ID NO: 411          moltype = RNA  length = 17
FEATURE                 Location/Qualifiers
source                  1..17
                        mol_type = other RNA
                        organism = synthetic construct
SEQUENCE: 411
cggcgactga gtcgccg                                                17

SEQ ID NO: 412          moltype = RNA  length = 20
FEATURE                 Location/Qualifiers
source                  1..20
                        mol_type = other RNA
                        organism = synthetic construct
SEQUENCE: 412
aaacatcata cttattcaac                                             20

SEQ ID NO: 413          moltype = RNA  length = 20
FEATURE                 Location/Qualifiers
source                  1..20
                        mol_type = other RNA
                        organism = synthetic construct
SEQUENCE: 413
gttgaataag tatgatgttt                                             20

SEQ ID NO: 414          moltype = RNA  length = 36
FEATURE                 Location/Qualifiers
source                  1..36
                        mol_type = other RNA
                        organism = synthetic construct
SEQUENCE: 414
gtgcaacttg ctgatgtttg tagtaccgaa tggcgg                           36

SEQ ID NO: 415          moltype = RNA  length = 36
FEATURE                 Location/Qualifiers
source                  1..36
                        mol_type = other RNA
                        organism = synthetic construct
SEQUENCE: 415
ccgccattcg gtactacaaa catcagcaag ttgcac                           36

SEQ ID NO: 416          moltype = RNA  length = 36
FEATURE                 Location/Qualifiers
source                  1..36
                        mol_type = other RNA
                        organism = synthetic construct
SEQUENCE: 416
gtgcaacttg ctgatgtttg tagtaccgaa tggcga                           36

SEQ ID NO: 417          moltype = RNA  length = 36
FEATURE                 Location/Qualifiers
source                  1..36
                        mol_type = other RNA
                        organism = synthetic construct
SEQUENCE: 417
tcgccattcg gtactacaaa catcagcaag ttgcac                           36

SEQ ID NO: 418          moltype = RNA  length = 26
FEATURE                 Location/Qualifiers
source                  1..26
                        mol_type = other RNA
                        organism = synthetic construct
SEQUENCE: 418
agtaagaatt tgcattggta ccaaac                                      26

SEQ ID NO: 419          moltype = RNA  length = 26
FEATURE                 Location/Qualifiers
source                  1..26
                        mol_type = other RNA
                        organism = synthetic construct
SEQUENCE: 419
gtttggtacc aatgcaaatt cttact                                      26

SEQ ID NO: 420          moltype = RNA  length = 26
FEATURE                 Location/Qualifiers
source                  1..26
                        mol_type = other RNA
                        organism = synthetic construct
```

```
SEQUENCE: 420
agtaagaatt ggcacgggta ccaaac                                          26

SEQ ID NO: 421          moltype = RNA  length = 26
FEATURE                 Location/Qualifiers
source                  1..26
                        mol_type = other RNA
                        organism = synthetic construct
SEQUENCE: 421
gtttggtacc cgtgccaatt cttact                                          26

SEQ ID NO: 422          moltype = RNA  length = 26
FEATURE                 Location/Qualifiers
source                  1..26
                        mol_type = other RNA
                        organism = synthetic construct
SEQUENCE: 422
agtaagaatt tacacggata ccaaac                                          26

SEQ ID NO: 423          moltype = RNA  length = 26
FEATURE                 Location/Qualifiers
source                  1..26
                        mol_type = other RNA
                        organism = synthetic construct
SEQUENCE: 423
gtttggtatc cgtgtaaatt cttact                                          26

SEQ ID NO: 424          moltype = RNA  length = 26
FEATURE                 Location/Qualifiers
source                  1..26
                        mol_type = other RNA
                        organism = synthetic construct
SEQUENCE: 424
agtaagaatt gtcacggggt accaaa                                          26

SEQ ID NO: 425          moltype = RNA  length = 26
FEATURE                 Location/Qualifiers
source                  1..26
                        mol_type = other RNA
                        organism = synthetic construct
SEQUENCE: 425
tttggtaccc cgtgacaatt cttact                                          26

SEQ ID NO: 426          moltype = RNA  length = 26
FEATURE                 Location/Qualifiers
source                  1..26
                        mol_type = other RNA
                        organism = synthetic construct
SEQUENCE: 426
agcaagaatt tacatgagtt ccaaac                                          26

SEQ ID NO: 427          moltype = RNA  length = 26
FEATURE                 Location/Qualifiers
source                  1..26
                        mol_type = other RNA
                        organism = synthetic construct
SEQUENCE: 427
gtttggaact catgtaaatt cttgct                                          26

SEQ ID NO: 428          moltype = RNA  length = 26
FEATURE                 Location/Qualifiers
source                  1..26
                        mol_type = other RNA
                        organism = synthetic construct
SEQUENCE: 428
agcaagaatt gtcacgggtg ccaaac                                          26

SEQ ID NO: 429          moltype = RNA  length = 26
FEATURE                 Location/Qualifiers
source                  1..26
                        mol_type = other RNA
                        organism = synthetic construct
SEQUENCE: 429
gtttggcacc cgtgacaatt cttgct                                          26

SEQ ID NO: 430          moltype = RNA  length = 26
FEATURE                 Location/Qualifiers
source                  1..26
                        mol_type = other RNA
```

```
                         organism = synthetic construct
SEQUENCE: 430
agtaagaatt tacacgggta ccaaac                                          26

SEQ ID NO: 431           moltype = RNA  length = 26
FEATURE                  Location/Qualifiers
source                   1..26
                         mol_type = other RNA
                         organism = synthetic construct
SEQUENCE: 431
gtttggtacc cgtgtaaatt cttact                                          26

SEQ ID NO: 432           moltype = RNA  length = 26
FEATURE                  Location/Qualifiers
source                   1..26
                         mol_type = other RNA
                         organism = synthetic construct
SEQUENCE: 432
agtaaggatt tacacgggta ccaaac                                          26

SEQ ID NO: 433           moltype = RNA  length = 26
FEATURE                  Location/Qualifiers
source                   1..26
                         mol_type = other RNA
                         organism = synthetic construct
SEQUENCE: 433
gtttggtacc cgtgtaaatc cttact                                          26

SEQ ID NO: 434           moltype = RNA  length = 26
FEATURE                  Location/Qualifiers
source                   1..26
                         mol_type = other RNA
                         organism = synthetic construct
SEQUENCE: 434
agtaagaatt tacatgggta ccaaac                                          26

SEQ ID NO: 435           moltype = RNA  length = 26
FEATURE                  Location/Qualifiers
source                   1..26
                         mol_type = other RNA
                         organism = synthetic construct
SEQUENCE: 435
gtttggtacc catgtaaatt cttact                                          26

SEQ ID NO: 436           moltype = RNA  length = 26
FEATURE                  Location/Qualifiers
source                   1..26
                         mol_type = other RNA
                         organism = synthetic construct
SEQUENCE: 436
agtaagaatt gtcacggggc gccaaa                                          26

SEQ ID NO: 437           moltype = RNA  length = 26
FEATURE                  Location/Qualifiers
source                   1..26
                         mol_type = other RNA
                         organism = synthetic construct
SEQUENCE: 437
tttggcgccc cgtgacaatt cttact                                          26

SEQ ID NO: 438           moltype = RNA  length = 24
FEATURE                  Location/Qualifiers
source                   1..24
                         mol_type = other RNA
                         organism = synthetic construct
SEQUENCE: 438
ttgagtagta agaatttaca tggg                                            24

SEQ ID NO: 439           moltype = RNA  length = 24
FEATURE                  Location/Qualifiers
source                   1..24
                         mol_type = other RNA
                         organism = synthetic construct
SEQUENCE: 439
cccatgtaaa ttcttactac tcaa                                            24

SEQ ID NO: 440           moltype = RNA  length = 24
FEATURE                  Location/Qualifiers
source                   1..24
```

```
                        mol_type = other RNA
                        organism = synthetic construct
SEQUENCE: 440
ttgagtagta agaattgtca tggg                                            24

SEQ ID NO: 441          moltype = RNA  length = 24
FEATURE                 Location/Qualifiers
source                  1..24
                        mol_type = other RNA
                        organism = synthetic construct
SEQUENCE: 441
cccatgacaa ttcttactac tcaa                                            24

SEQ ID NO: 442          moltype = RNA  length = 24
FEATURE                 Location/Qualifiers
source                  1..24
                        mol_type = other RNA
                        organism = synthetic construct
SEQUENCE: 442
ttgagcagta agaatttaca cggg                                            24

SEQ ID NO: 443          moltype = RNA  length = 24
FEATURE                 Location/Qualifiers
source                  1..24
                        mol_type = other RNA
                        organism = synthetic construct
SEQUENCE: 443
cccgtgtaaa ttcttactgc tcaa                                            24

SEQ ID NO: 444          moltype = RNA  length = 24
FEATURE                 Location/Qualifiers
source                  1..24
                        mol_type = other RNA
                        organism = synthetic construct
SEQUENCE: 444
ttgagtagta aaaattgtta cggg                                            24

SEQ ID NO: 445          moltype = RNA  length = 24
FEATURE                 Location/Qualifiers
source                  1..24
                        mol_type = other RNA
                        organism = synthetic construct
SEQUENCE: 445
cccgtaacaa tttttactac tcaa                                            24

SEQ ID NO: 446          moltype = RNA  length = 24
FEATURE                 Location/Qualifiers
source                  1..24
                        mol_type = other RNA
                        organism = synthetic construct
SEQUENCE: 446
ttgagtagta agaatataca cgag                                            24

SEQ ID NO: 447          moltype = RNA  length = 24
FEATURE                 Location/Qualifiers
source                  1..24
                        mol_type = other RNA
                        organism = synthetic construct
SEQUENCE: 447
ctcgtgtata ttcttactac tcaa                                            24

SEQ ID NO: 448          moltype = RNA  length = 24
FEATURE                 Location/Qualifiers
source                  1..24
                        mol_type = other RNA
                        organism = synthetic construct
SEQUENCE: 448
gttattgagt agtaagaatt taca                                            24

SEQ ID NO: 449          moltype = RNA  length = 24
FEATURE                 Location/Qualifiers
source                  1..24
                        mol_type = other RNA
                        organism = synthetic construct
SEQUENCE: 449
tgtaaattct tactactcaa taac                                            24

SEQ ID NO: 450          moltype = RNA  length = 24
FEATURE                 Location/Qualifiers
```

```
source                  1..24
                        mol_type = other RNA
                        organism = synthetic construct
SEQUENCE: 450
gttgctgagt agcaagaaat taca                                              24

SEQ ID NO: 451          moltype = RNA  length = 24
FEATURE                 Location/Qualifiers
source                  1..24
                        mol_type = other RNA
                        organism = synthetic construct
SEQUENCE: 451
tgtaatttct tgctactcag caac                                              24

SEQ ID NO: 452          moltype = RNA  length = 24
FEATURE                 Location/Qualifiers
source                  1..24
                        mol_type = other RNA
                        organism = synthetic construct
SEQUENCE: 452
gtttttgagc aataagaatt tgca                                              24

SEQ ID NO: 453          moltype = RNA  length = 24
FEATURE                 Location/Qualifiers
source                  1..24
                        mol_type = other RNA
                        organism = synthetic construct
SEQUENCE: 453
tgcaaattct tattgctcaa aaac                                              24

SEQ ID NO: 454          moltype = RNA  length = 24
FEATURE                 Location/Qualifiers
source                  1..24
                        mol_type = other RNA
                        organism = synthetic construct
SEQUENCE: 454
gttgaagagc cgcaagaatt cgca                                              24

SEQ ID NO: 455          moltype = RNA  length = 24
FEATURE                 Location/Qualifiers
source                  1..24
                        mol_type = other RNA
                        organism = synthetic construct
SEQUENCE: 455
tgcgaattct tgcggctctt caac                                              24

SEQ ID NO: 456          moltype = RNA  length = 23
FEATURE                 Location/Qualifiers
source                  1..23
                        mol_type = other RNA
                        organism = synthetic construct
SEQUENCE: 456
cttgaggcgc tcgacctcct gtt                                               23

SEQ ID NO: 457          moltype = RNA  length = 23
FEATURE                 Location/Qualifiers
source                  1..23
                        mol_type = other RNA
                        organism = synthetic construct
SEQUENCE: 457
aacaggaggt cgagcgcctc aag                                               23

SEQ ID NO: 458          moltype = RNA  length = 23
FEATURE                 Location/Qualifiers
source                  1..23
                        mol_type = other RNA
                        organism = synthetic construct
SEQUENCE: 458
cttgagccgc tcgacctgct gct                                               23

SEQ ID NO: 459          moltype = RNA  length = 23
FEATURE                 Location/Qualifiers
source                  1..23
                        mol_type = other RNA
                        organism = synthetic construct
SEQUENCE: 459
agcagcaggt cgagcggctc aag                                               23

SEQ ID NO: 460          moltype = RNA  length = 23
```

```
FEATURE                Location/Qualifiers
source                 1..23
                       mol_type = other RNA
                       organism = synthetic construct
SEQUENCE: 460
gttgaggcgc tcgacttccc gct                                          23

SEQ ID NO: 461         moltype = RNA  length = 23
FEATURE                Location/Qualifiers
source                 1..23
                       mol_type = other RNA
                       organism = synthetic construct
SEQUENCE: 461
agcgggaagt cgagcgcctc aac                                          23

SEQ ID NO: 462         moltype = RNA  length = 23
FEATURE                Location/Qualifiers
source                 1..23
                       mol_type = other RNA
                       organism = synthetic construct
SEQUENCE: 462
gttgaggtgc tcgacctgct gct                                          23

SEQ ID NO: 463         moltype = RNA  length = 23
FEATURE                Location/Qualifiers
source                 1..23
                       mol_type = other RNA
                       organism = synthetic construct
SEQUENCE: 463
agcagcaggt cgagcacctc aac                                          23

SEQ ID NO: 464         moltype = RNA  length = 23
FEATURE                Location/Qualifiers
source                 1..23
                       mol_type = other RNA
                       organism = synthetic construct
SEQUENCE: 464
cttgaggcgc tcgacctgct gct                                          23

SEQ ID NO: 465         moltype = RNA  length = 23
FEATURE                Location/Qualifiers
source                 1..23
                       mol_type = other RNA
                       organism = synthetic construct
SEQUENCE: 465
agcagcaggt cgagcgcctc aag                                          23

SEQ ID NO: 466         moltype = RNA  length = 23
FEATURE                Location/Qualifiers
source                 1..23
                       mol_type = other RNA
                       organism = synthetic construct
SEQUENCE: 466
cttgaggcgc tcgacctcct gct                                          23

SEQ ID NO: 467         moltype = RNA  length = 23
FEATURE                Location/Qualifiers
source                 1..23
                       mol_type = other RNA
                       organism = synthetic construct
SEQUENCE: 467
agcaggaggt cgagcgcctc aag                                          23

SEQ ID NO: 468         moltype = RNA  length = 23
FEATURE                Location/Qualifiers
source                 1..23
                       mol_type = other RNA
                       organism = synthetic construct
SEQUENCE: 468
ctccaagcgc tggacctcct cct                                          23

SEQ ID NO: 469         moltype = RNA  length = 23
FEATURE                Location/Qualifiers
source                 1..23
                       mol_type = other RNA
                       organism = synthetic construct
SEQUENCE: 469
aggaggaggt ccagcgcttg gag                                          23
```

```
SEQ ID NO: 470         moltype = RNA  length = 23
FEATURE                Location/Qualifiers
source                 1..23
                       mol_type = other RNA
                       organism = synthetic construct
SEQUENCE: 470
cttgaggcgc tcgacctcct cct                                             23

SEQ ID NO: 471         moltype = RNA  length = 23
FEATURE                Location/Qualifiers
source                 1..23
                       mol_type = other RNA
                       organism = synthetic construct
SEQUENCE: 471
aggaggaggt cgagcgcctc aag                                             23

SEQ ID NO: 472         moltype = RNA  length = 23
FEATURE                Location/Qualifiers
source                 1..23
                       mol_type = other RNA
                       organism = synthetic construct
SEQUENCE: 472
gtcgagaagc ttgagctgct gct                                             23

SEQ ID NO: 473         moltype = RNA  length = 23
FEATURE                Location/Qualifiers
source                 1..23
                       mol_type = other RNA
                       organism = synthetic construct
SEQUENCE: 473
agcagcagct caagcttctc gac                                             23

SEQ ID NO: 474         moltype = RNA  length = 23
FEATURE                Location/Qualifiers
source                 1..23
                       mol_type = other RNA
                       organism = synthetic construct
SEQUENCE: 474
cctgagccgc tccaccttct gct                                             23

SEQ ID NO: 475         moltype = RNA  length = 23
FEATURE                Location/Qualifiers
source                 1..23
                       mol_type = other RNA
                       organism = synthetic construct
SEQUENCE: 475
agcagaaggt ggagcggctc agg                                             23

SEQ ID NO: 476         moltype = RNA  length = 29
FEATURE                Location/Qualifiers
source                 1..29
                       mol_type = other RNA
                       organism = synthetic construct
SEQUENCE: 476
cgtcccgccc acgcacgcga gggaacggc                                       29

SEQ ID NO: 477         moltype = RNA  length = 29
FEATURE                Location/Qualifiers
source                 1..29
                       mol_type = other RNA
                       organism = synthetic construct
SEQUENCE: 477
gccgttccct cgcgtgcgtg ggcgggacg                                       29

SEQ ID NO: 478         moltype = RNA  length = 29
FEATURE                Location/Qualifiers
source                 1..29
                       mol_type = other RNA
                       organism = synthetic construct
SEQUENCE: 478
tgttccgccc acgcacgcga gggaacggc                                       29

SEQ ID NO: 479         moltype = RNA  length = 29
FEATURE                Location/Qualifiers
source                 1..29
                       mol_type = other RNA
                       organism = synthetic construct
SEQUENCE: 479
gccgttccct cgcgtgcgtg ggcggaaca                                       29
```

```
SEQ ID NO: 480          moltype = RNA  length = 29
FEATURE                 Location/Qualifiers
source                  1..29
                        mol_type = other RNA
                        organism = synthetic construct
SEQUENCE: 480
cgttccgccc acgcacgcga gggaacggc                                    29

SEQ ID NO: 481          moltype = RNA  length = 29
FEATURE                 Location/Qualifiers
source                  1..29
                        mol_type = other RNA
                        organism = synthetic construct
SEQUENCE: 481
gccgttccct cgcgtgcgtg ggcggaacg                                    29

SEQ ID NO: 482          moltype = RNA  length = 29
FEATURE                 Location/Qualifiers
source                  1..29
                        mol_type = other RNA
                        organism = synthetic construct
SEQUENCE: 482
ggtctctccc acgcactcga gggaacgtc                                    29

SEQ ID NO: 483          moltype = RNA  length = 29
FEATURE                 Location/Qualifiers
source                  1..29
                        mol_type = other RNA
                        organism = synthetic construct
SEQUENCE: 483
gacgttccct cgagtgcgtg ggagagacc                                    29

SEQ ID NO: 484          moltype = RNA  length = 28
FEATURE                 Location/Qualifiers
source                  1..28
                        mol_type = other RNA
                        organism = synthetic construct
SEQUENCE: 484
gtcccgccca cgcacgcgag ggaacggc                                     28

SEQ ID NO: 485          moltype = RNA  length = 28
FEATURE                 Location/Qualifiers
source                  1..28
                        mol_type = other RNA
                        organism = synthetic construct
SEQUENCE: 485
gccgttccct cgcgtgcgtg ggcgggac                                     28

SEQ ID NO: 486          moltype = RNA  length = 28
FEATURE                 Location/Qualifiers
source                  1..28
                        mol_type = other RNA
                        organism = synthetic construct
SEQUENCE: 486
gttccgccca cgcacgcgag ggaacggc                                     28

SEQ ID NO: 487          moltype = RNA  length = 28
FEATURE                 Location/Qualifiers
source                  1..28
                        mol_type = other RNA
                        organism = synthetic construct
SEQUENCE: 487
gccgttccct cgcgtgcgtg ggcggaac                                     28

SEQ ID NO: 488          moltype = RNA  length = 28
FEATURE                 Location/Qualifiers
source                  1..28
                        mol_type = other RNA
                        organism = synthetic construct
SEQUENCE: 488
gtctctccca cgcacgcgag ggaacggc                                     28

SEQ ID NO: 489          moltype = RNA  length = 28
FEATURE                 Location/Qualifiers
source                  1..28
                        mol_type = other RNA
                        organism = synthetic construct
SEQUENCE: 489
```

gccgttccct cgcgtgcgtg ggagagac 28

SEQ ID NO: 490 moltype = RNA length = 28
FEATURE Location/Qualifiers
source 1..28
mol_type = other RNA
organism = synthetic construct
SEQUENCE: 490
gtcccgccca cgcacacgag ggaacggc 28

SEQ ID NO: 491 moltype = RNA length = 28
FEATURE Location/Qualifiers
source 1..28
mol_type = other RNA
organism = synthetic construct
SEQUENCE: 491
gccgttccct cgtgtgcgtg ggcgggac 28

SEQ ID NO: 492 moltype = RNA length = 28
FEATURE Location/Qualifiers
source 1..28
mol_type = other RNA
organism = synthetic construct
SEQUENCE: 492
gcctcgccca cgcgtcctag gggacatc 28

SEQ ID NO: 493 moltype = RNA length = 28
FEATURE Location/Qualifiers
source 1..28
mol_type = other RNA
organism = synthetic construct
SEQUENCE: 493
gatgtcccct aggacgcgtg ggcgaggc 28

SEQ ID NO: 494 moltype = RNA length = 24
FEATURE Location/Qualifiers
source 1..24
mol_type = other RNA
organism = synthetic construct
SEQUENCE: 494
gccgttccct cgcgtgcgtg ggcg 24

SEQ ID NO: 495 moltype = RNA length = 24
FEATURE Location/Qualifiers
source 1..24
mol_type = other RNA
organism = synthetic construct
SEQUENCE: 495
cgcccacgca cgcgagggaa cggc 24

SEQ ID NO: 496 moltype = RNA length = 24
FEATURE Location/Qualifiers
source 1..24
mol_type = other RNA
organism = synthetic construct
SEQUENCE: 496
gccgttccct cgcgtgcgtg ggag 24

SEQ ID NO: 497 moltype = RNA length = 24
FEATURE Location/Qualifiers
source 1..24
mol_type = other RNA
organism = synthetic construct
SEQUENCE: 497
ctcccacgca cgcgagggaa cggc 24

SEQ ID NO: 498 moltype = RNA length = 28
FEATURE Location/Qualifiers
source 1..28
mol_type = other RNA
organism = synthetic construct
SEQUENCE: 498
gtctcgccca cgcacacgag ggacggc 28

SEQ ID NO: 499 moltype = RNA length = 28
FEATURE Location/Qualifiers
source 1..28
mol_type = other RNA
organism = synthetic construct

```
SEQUENCE: 499
gccgtcccct cgtgtgcgtg ggcgagac                                    28

SEQ ID NO: 500         moltype = RNA  length = 28
FEATURE                Location/Qualifiers
source                 1..28
                       mol_type = other RNA
                       organism = synthetic construct
SEQUENCE: 500
gtctcgctca cgcacgcgag ggaacggc                                    28

SEQ ID NO: 501         moltype = RNA  length = 28
FEATURE                Location/Qualifiers
source                 1..28
                       mol_type = other RNA
                       organism = synthetic construct
SEQUENCE: 501
gccgttccct cgcgtgcgtg agcgagac                                    28

SEQ ID NO: 502         moltype = RNA  length = 28
FEATURE                Location/Qualifiers
source                 1..28
                       mol_type = other RNA
                       organism = synthetic construct
SEQUENCE: 502
gtctcgccca cgcacacgag ggggcgtc                                    28

SEQ ID NO: 503         moltype = RNA  length = 28
FEATURE                Location/Qualifiers
source                 1..28
                       mol_type = other RNA
                       organism = synthetic construct
SEQUENCE: 503
gacgcccccct cgtgtgcgtg ggcgagac                                   28

SEQ ID NO: 504         moltype = RNA  length = 28
FEATURE                Location/Qualifiers
source                 1..28
                       mol_type = other RNA
                       organism = synthetic construct
SEQUENCE: 504
gtcccgccca cgcacacgca cacgaggg                                    28

SEQ ID NO: 505         moltype = RNA  length = 28
FEATURE                Location/Qualifiers
source                 1..28
                       mol_type = other RNA
                       organism = synthetic construct
SEQUENCE: 505
ccctcgtgtg cgtgtgcgtg ggcgggac                                    28

SEQ ID NO: 506         moltype = RNA  length = 28
FEATURE                Location/Qualifiers
source                 1..28
                       mol_type = other RNA
                       organism = synthetic construct
SEQUENCE: 506
cccacgcaca cgcacacgag gggacggc                                    28

SEQ ID NO: 507         moltype = RNA  length = 28
FEATURE                Location/Qualifiers
source                 1..28
                       mol_type = other RNA
                       organism = synthetic construct
SEQUENCE: 507
gccgtcccct cgtgtgcgtg tgcgtggg                                    28

SEQ ID NO: 508         moltype = RNA  length = 25
FEATURE                Location/Qualifiers
source                 1..25
                       mol_type = other RNA
                       organism = synthetic construct
SEQUENCE: 508
ccgcccacgc acgcgaggga acggc                                       25

SEQ ID NO: 509         moltype = RNA  length = 25
FEATURE                Location/Qualifiers
source                 1..25
                       mol_type = other RNA
```

```
                        organism = synthetic construct
SEQUENCE: 509
gccgttccct cgcgtgcgtg ggcgg                                   25

SEQ ID NO: 510          moltype = RNA  length = 37
FEATURE                 Location/Qualifiers
source                  1..37
                        mol_type = other RNA
                        organism = synthetic construct
SEQUENCE: 510
gtcatccccc gcgagcgagc gggggccgca ttgaagc                      37

SEQ ID NO: 511          moltype = RNA  length = 37
FEATURE                 Location/Qualifiers
source                  1..37
                        mol_type = other RNA
                        organism = synthetic construct
SEQUENCE: 511
gcttcaatgc ggcccccgct cgctcgcggg ggatgac                      37

SEQ ID NO: 512          moltype = RNA  length = 37
FEATURE                 Location/Qualifiers
source                  1..37
                        mol_type = other RNA
                        organism = synthetic construct
SEQUENCE: 512
gtcatccccc gcgagcgagc gggggccgca ttgaagg                      37

SEQ ID NO: 513          moltype = RNA  length = 37
FEATURE                 Location/Qualifiers
source                  1..37
                        mol_type = other RNA
                        organism = synthetic construct
SEQUENCE: 513
ccttcaatgc ggcccccgct cgctcgcggg ggatgac                      37

SEQ ID NO: 514          moltype = RNA  length = 36
FEATURE                 Location/Qualifiers
source                  1..36
                        mol_type = other RNA
                        organism = synthetic construct
SEQUENCE: 514
gttgcaatcc caaggtaatg cgtctcccat tgacgc                       36

SEQ ID NO: 515          moltype = RNA  length = 36
FEATURE                 Location/Qualifiers
source                  1..36
                        mol_type = other RNA
                        organism = synthetic construct
SEQUENCE: 515
gcgtcaatgg gagacgcatt accttgggat tgcaac                       36

SEQ ID NO: 516          moltype = RNA  length = 36
FEATURE                 Location/Qualifiers
source                  1..36
                        mol_type = other RNA
                        organism = synthetic construct
SEQUENCE: 516
gaattgatcc cgttgtaatg cgtctcccat tgacgc                       36

SEQ ID NO: 517          moltype = RNA  length = 36
FEATURE                 Location/Qualifiers
source                  1..36
                        mol_type = other RNA
                        organism = synthetic construct
SEQUENCE: 517
gcgtcaatgg gagacgcatt acaacgggat caattc                       36

SEQ ID NO: 518          moltype = RNA  length = 36
FEATURE                 Location/Qualifiers
source                  1..36
                        mol_type = other RNA
                        organism = synthetic construct
SEQUENCE: 518
gcgtcaatgg gagacgcatt actttaggat tgcaac                       36

SEQ ID NO: 519          moltype = RNA  length = 36
FEATURE                 Location/Qualifiers
source                  1..36
```

```
                        mol_type = other RNA
                        organism = synthetic construct
SEQUENCE: 519
gttgcaatcc taaagtaatg cgtctcccat tgacgc                              36

SEQ ID NO: 520          moltype = RNA  length = 36
FEATURE                 Location/Qualifiers
source                  1..36
                        mol_type = other RNA
                        organism = synthetic construct
SEQUENCE: 520
gcgtcaatgg gagacgcatt actttgggat tgcaac                              36

SEQ ID NO: 521          moltype = RNA  length = 36
FEATURE                 Location/Qualifiers
source                  1..36
                        mol_type = other RNA
                        organism = synthetic construct
SEQUENCE: 521
gttgcaatcc caaagtaatg cgtctcccat tgacgc                              36

SEQ ID NO: 522          moltype = RNA  length = 36
FEATURE                 Location/Qualifiers
source                  1..36
                        mol_type = other RNA
                        organism = synthetic construct
SEQUENCE: 522
gcgtcaatgg gagacgcatt actttaggat tgcatc                              36

SEQ ID NO: 523          moltype = RNA  length = 36
FEATURE                 Location/Qualifiers
source                  1..36
                        mol_type = other RNA
                        organism = synthetic construct
SEQUENCE: 523
gatgcaatcc taaagtaatg cgtctcccat tgacgc                              36

SEQ ID NO: 524          moltype = RNA  length = 36
FEATURE                 Location/Qualifiers
source                  1..36
                        mol_type = other RNA
                        organism = synthetic construct
SEQUENCE: 524
gcgtcaatgg gagacgcatt aactttggga ttgcaa                              36

SEQ ID NO: 525          moltype = RNA  length = 36
FEATURE                 Location/Qualifiers
source                  1..36
                        mol_type = other RNA
                        organism = synthetic construct
SEQUENCE: 525
ttgcaatccc aaagttaatg cgtctcccat tgacgc                              36

SEQ ID NO: 526          moltype = RNA  length = 36
FEATURE                 Location/Qualifiers
source                  1..36
                        mol_type = other RNA
                        organism = synthetic construct
SEQUENCE: 526
gcgtcaatgg gagacgcatt actttggaat tgcaac                              36

SEQ ID NO: 527          moltype = RNA  length = 36
FEATURE                 Location/Qualifiers
source                  1..36
                        mol_type = other RNA
                        organism = synthetic construct
SEQUENCE: 527
gttgcaattc caaagtaatg cgtctcccat tgacgc                              36

SEQ ID NO: 528          moltype = RNA  length = 23
FEATURE                 Location/Qualifiers
source                  1..23
                        mol_type = other RNA
                        organism = synthetic construct
SEQUENCE: 528
ggcgtcaatg ggagacgcat tac                                            23

SEQ ID NO: 529          moltype = RNA  length = 23
FEATURE                 Location/Qualifiers
```

```
source                  1..23
                        mol_type = other RNA
                        organism = synthetic construct
SEQUENCE: 529
gtaatgcgtc tcccattgac gcc                                             23

SEQ ID NO: 530          moltype = RNA  length = 23
FEATURE                 Location/Qualifiers
source                  1..23
                        mol_type = other RNA
                        organism = synthetic construct
SEQUENCE: 530
agcgtcaatg ggagacgcat tac                                             23

SEQ ID NO: 531          moltype = RNA  length = 23
FEATURE                 Location/Qualifiers
source                  1..23
                        mol_type = other RNA
                        organism = synthetic construct
SEQUENCE: 531
gtaatgcgtc tcccattgac gct                                             23

SEQ ID NO: 532          moltype = RNA  length = 23
FEATURE                 Location/Qualifiers
source                  1..23
                        mol_type = other RNA
                        organism = synthetic construct
SEQUENCE: 532
ggcgtcaatg ggagacgcat taa                                             23

SEQ ID NO: 533          moltype = RNA  length = 23
FEATURE                 Location/Qualifiers
source                  1..23
                        mol_type = other RNA
                        organism = synthetic construct
SEQUENCE: 533
ttaatgcgtc tcccattgac gcc                                             23

SEQ ID NO: 534          moltype = RNA  length = 36
FEATURE                 Location/Qualifiers
source                  1..36
                        mol_type = other RNA
                        organism = synthetic construct
SEQUENCE: 534
atcgcaacat ctcagaaacc cgtcctaagt tgacgg                               36

SEQ ID NO: 535          moltype = RNA  length = 36
FEATURE                 Location/Qualifiers
source                  1..36
                        mol_type = other RNA
                        organism = synthetic construct
SEQUENCE: 535
ccgtcaactt aggacgggtt tctgagatgt tgcgat                               36

SEQ ID NO: 536          moltype = RNA  length = 36
FEATURE                 Location/Qualifiers
source                  1..36
                        mol_type = other RNA
                        organism = synthetic construct
SEQUENCE: 536
ctcgcaacat ctcagaaacc cgtcctaagt tgacgg                               36

SEQ ID NO: 537          moltype = RNA  length = 36
FEATURE                 Location/Qualifiers
source                  1..36
                        mol_type = other RNA
                        organism = synthetic construct
SEQUENCE: 537
ccgtcaactt aggacgggtt tctgagatgt tgcgag                               36

SEQ ID NO: 538          moltype = RNA  length = 36
FEATURE                 Location/Qualifiers
source                  1..36
                        mol_type = other RNA
                        organism = synthetic construct
SEQUENCE: 538
ctcgcaacat ctcagaaagc cgtcctaagt tgacgg                               36

SEQ ID NO: 539          moltype = RNA  length = 36
```

```
FEATURE                Location/Qualifiers
source                 1..36
                       mol_type = other RNA
                       organism = synthetic construct
SEQUENCE: 539
ccgtcaactt aggacggctt tctgagatgt tgcgag                          36

SEQ ID NO: 540         moltype = RNA  length = 36
FEATURE                Location/Qualifiers
source                 1..36
                       mol_type = other RNA
                       organism = synthetic construct
SEQUENCE: 540
atcgcaacat cttagaaacc cgtcctaagt tgacgg                          36

SEQ ID NO: 541         moltype = RNA  length = 36
FEATURE                Location/Qualifiers
source                 1..36
                       mol_type = other RNA
                       organism = synthetic construct
SEQUENCE: 541
ccgtcaactt aggacgggtt tctaagatgt tgcgat                          36

SEQ ID NO: 542         moltype = RNA  length = 36
FEATURE                Location/Qualifiers
source                 1..36
                       mol_type = other RNA
                       organism = synthetic construct
SEQUENCE: 542
ctcgaaccat ctcagaaatc cgtcctaagc tgagga                          36

SEQ ID NO: 543         moltype = RNA  length = 36
FEATURE                Location/Qualifiers
source                 1..36
                       mol_type = other RNA
                       organism = synthetic construct
SEQUENCE: 543
tcctcagctt aggacggatt tctgagatgg ttcgag                          36

SEQ ID NO: 544         moltype = RNA  length = 35
FEATURE                Location/Qualifiers
source                 1..35
                       mol_type = other RNA
                       organism = synthetic construct
SEQUENCE: 544
tcgcaacatc tcagaaaccc gtcctaagtt gacgg                           35

SEQ ID NO: 545         moltype = RNA  length = 35
FEATURE                Location/Qualifiers
source                 1..35
                       mol_type = other RNA
                       organism = synthetic construct
SEQUENCE: 545
ccgtcaactt aggacgggtt tctgagatgt tgcga                           35

SEQ ID NO: 546         moltype = RNA  length = 35
FEATURE                Location/Qualifiers
source                 1..35
                       mol_type = other RNA
                       organism = synthetic construct
SEQUENCE: 546
tcgcaacatc tcagaaagcc gtcctaagtt gacgg                           35

SEQ ID NO: 547         moltype = RNA  length = 35
FEATURE                Location/Qualifiers
source                 1..35
                       mol_type = other RNA
                       organism = synthetic construct
SEQUENCE: 547
ccgtcaactt aggacggctt tctgagatgt tgcga                           35

SEQ ID NO: 548         moltype = RNA  length = 35
FEATURE                Location/Qualifiers
source                 1..35
                       mol_type = other RNA
                       organism = synthetic construct
SEQUENCE: 548
tcgcaacatc ttagaaaccc gtcctaagtt gacgg                           35
```

```
SEQ ID NO: 549          moltype = RNA  length = 35
FEATURE                Location/Qualifiers
source                 1..35
                       mol_type = other RNA
                       organism = synthetic construct
SEQUENCE: 549
ccgtcaactt aggacgggtt tctaagatgt tgcga                            35

SEQ ID NO: 550          moltype = RNA  length = 35
FEATURE                Location/Qualifiers
source                 1..35
                       mol_type = other RNA
                       organism = synthetic construct
SEQUENCE: 550
tcgaaccatc tcagaaatcc gtcctaagct gagga                            35

SEQ ID NO: 551          moltype = RNA  length = 35
FEATURE                Location/Qualifiers
source                 1..35
                       mol_type = other RNA
                       organism = synthetic construct
SEQUENCE: 551
tcctcagctt aggacggatt tctgagatgg ttcga                            35

SEQ ID NO: 552          moltype = RNA  length = 36
FEATURE                Location/Qualifiers
source                 1..36
                       mol_type = other RNA
                       organism = synthetic construct
SEQUENCE: 552
gtgcattgac cgctccctga cggaaccagc cagcac                           36

SEQ ID NO: 553          moltype = RNA  length = 36
FEATURE                Location/Qualifiers
source                 1..36
                       mol_type = other RNA
                       organism = synthetic construct
SEQUENCE: 553
gtgctggctg gttccgtcag ggagcggtca atgcac                           36

SEQ ID NO: 554          moltype = RNA  length = 36
FEATURE                Location/Qualifiers
source                 1..36
                       mol_type = other RNA
                       organism = synthetic construct
SEQUENCE: 554
gtgccttggc cgacccctga cggaaccggc cagcac                           36

SEQ ID NO: 555          moltype = RNA  length = 36
FEATURE                Location/Qualifiers
source                 1..36
                       mol_type = other RNA
                       organism = synthetic construct
SEQUENCE: 555
gtgctggccg gttccgtcag ggtcggccaa aggcac                           36

SEQ ID NO: 556          moltype = RNA  length = 36
FEATURE                Location/Qualifiers
source                 1..36
                       mol_type = other RNA
                       organism = synthetic construct
SEQUENCE: 556
gtgctttagt tggcccctga cggaaccgac cagcac                           36

SEQ ID NO: 557          moltype = RNA  length = 36
FEATURE                Location/Qualifiers
source                 1..36
                       mol_type = other RNA
                       organism = synthetic construct
SEQUENCE: 557
gtgctggtcg gttccgtcag ggccaacta aagcac                            36

SEQ ID NO: 558          moltype = RNA  length = 36
FEATURE                Location/Qualifiers
source                 1..36
                       mol_type = other RNA
                       organism = synthetic construct
SEQUENCE: 558
gtgccttgat cgacccctga cggaaccgac cagcac                           36
```

```
SEQ ID NO: 559          moltype = RNA  length = 36
FEATURE                 Location/Qualifiers
source                  1..36
                        mol_type = other RNA
                        organism = synthetic construct
SEQUENCE: 559
gtgctggtcg gttccgtcag gggtcgatca aggcac                          36

SEQ ID NO: 560          moltype = RNA  length = 36
FEATURE                 Location/Qualifiers
source                  1..36
                        mol_type = other RNA
                        organism = synthetic construct
SEQUENCE: 560
gtgccttgac cggcccctga cggaaccggt cagcac                          36

SEQ ID NO: 561          moltype = RNA  length = 36
FEATURE                 Location/Qualifiers
source                  1..36
                        mol_type = other RNA
                        organism = synthetic construct
SEQUENCE: 561
gtgctgaccg gttccgtcag gggccggtca aggcac                          36

SEQ ID NO: 562          moltype = RNA  length = 36
FEATURE                 Location/Qualifiers
source                  1..36
                        mol_type = other RNA
                        organism = synthetic construct
SEQUENCE: 562
gcgccttgac tgacccctga cggaaccggc cagcac                          36

SEQ ID NO: 563          moltype = RNA  length = 36
FEATURE                 Location/Qualifiers
source                  1..36
                        mol_type = other RNA
                        organism = synthetic construct
SEQUENCE: 563
gtgctggccg gttccgtcag gggtcagtca aggcgc                          36

SEQ ID NO: 564          moltype = RNA  length = 36
FEATURE                 Location/Qualifiers
source                  1..36
                        mol_type = other RNA
                        organism = synthetic construct
SEQUENCE: 564
gcgccttgac cgacccctga cggaacctgc cagcac                          36

SEQ ID NO: 565          moltype = RNA  length = 36
FEATURE                 Location/Qualifiers
source                  1..36
                        mol_type = other RNA
                        organism = synthetic construct
SEQUENCE: 565
gtgctggcag gttccgtcag gggtcggtca aggcgc                          36

SEQ ID NO: 566          moltype = RNA  length = 36
FEATURE                 Location/Qualifiers
source                  1..36
                        mol_type = other RNA
                        organism = synthetic construct
SEQUENCE: 566
gtgccttgac cgccccctaa tggaaccggt cagcac                          36

SEQ ID NO: 567          moltype = RNA  length = 36
FEATURE                 Location/Qualifiers
source                  1..36
                        mol_type = other RNA
                        organism = synthetic construct
SEQUENCE: 567
gtgctgaccg gttccattag gggcggtca aggcac                           36

SEQ ID NO: 568          moltype = RNA  length = 36
FEATURE                 Location/Qualifiers
source                  1..36
                        mol_type = other RNA
                        organism = synthetic construct
SEQUENCE: 568
```

gtgccttgac cgccccctaa tggaaccggc cagcac 36

SEQ ID NO: 569 moltype = RNA length = 36
FEATURE Location/Qualifiers
source 1..36
mol_type = other RNA
organism = synthetic construct
SEQUENCE: 569
gtgctggccg gttccattag ggggcggtca aggcac 36

SEQ ID NO: 570 moltype = RNA length = 36
FEATURE Location/Qualifiers
source 1..36
mol_type = other RNA
organism = synthetic construct
SEQUENCE: 570
gtgccttgac tgacccctaa cggaaccagc cagcac 36

SEQ ID NO: 571 moltype = RNA length = 36
FEATURE Location/Qualifiers
source 1..36
mol_type = other RNA
organism = synthetic construct
SEQUENCE: 571
gtgctggctg gttccgttag gggtcagtca aggcac 36

SEQ ID NO: 572 moltype = RNA length = 36
FEATURE Location/Qualifiers
source 1..36
mol_type = other RNA
organism = synthetic construct
SEQUENCE: 572
gtgccttgac tgaccactga cggaaccagc cagcac 36

SEQ ID NO: 573 moltype = RNA length = 36
FEATURE Location/Qualifiers
source 1..36
mol_type = other RNA
organism = synthetic construct
SEQUENCE: 573
gtgctggctg gttccgtcag tggtcagtca aggcac 36

SEQ ID NO: 574 moltype = RNA length = 36
FEATURE Location/Qualifiers
source 1..36
mol_type = other RNA
organism = synthetic construct
SEQUENCE: 574
gtgccttgac tgacccctga cggaaccagc cagcac 36

SEQ ID NO: 575 moltype = RNA length = 36
FEATURE Location/Qualifiers
source 1..36
mol_type = other RNA
organism = synthetic construct
SEQUENCE: 575
gtgctggctg gttccgtcag gggtcagtca aggcac 36

SEQ ID NO: 576 moltype = RNA length = 36
FEATURE Location/Qualifiers
source 1..36
mol_type = other RNA
organism = synthetic construct
SEQUENCE: 576
gtgccttggc cgacccctta cggaaccggc cagcac 36

SEQ ID NO: 577 moltype = RNA length = 36
FEATURE Location/Qualifiers
source 1..36
mol_type = other RNA
organism = synthetic construct
SEQUENCE: 577
gtgctggccg gttccgtaag gggtcggcca aggcac 36

SEQ ID NO: 578 moltype = RNA length = 53
FEATURE Location/Qualifiers
source 1..53
mol_type = other RNA
organism = synthetic construct

```
SEQUENCE: 578
gaagccctct gggacaatga aggcggtgcc agccccggca agggcggcaa ggc         53

SEQ ID NO: 579         moltype = RNA  length = 53
FEATURE                Location/Qualifiers
source                 1..53
                       mol_type = other RNA
                       organism = synthetic construct
SEQUENCE: 579
gccttgccgc ccttgccggg gctggcaccg ccttcattgt cccagagggc ttc         53

SEQ ID NO: 580         moltype = RNA  length = 23
FEATURE                Location/Qualifiers
source                 1..23
                       mol_type = other RNA
                       organism = synthetic construct
SEQUENCE: 580
tggccgccgg gcatgccgat cat                                          23

SEQ ID NO: 581         moltype = RNA  length = 23
FEATURE                Location/Qualifiers
source                 1..23
                       mol_type = other RNA
                       organism = synthetic construct
SEQUENCE: 581
atgatcggca tgcccggcgg cca                                          23

SEQ ID NO: 582         moltype = RNA  length = 23
FEATURE                Location/Qualifiers
source                 1..23
                       mol_type = other RNA
                       organism = synthetic construct
SEQUENCE: 582
tggcccccgg gcatgccgat cat                                          23

SEQ ID NO: 583         moltype = RNA  length = 23
FEATURE                Location/Qualifiers
source                 1..23
                       mol_type = other RNA
                       organism = synthetic construct
SEQUENCE: 583
atgatcggca tgcccggggg cca                                          23

SEQ ID NO: 584         moltype = RNA  length = 124
FEATURE                Location/Qualifiers
source                 1..124
                       mol_type = other RNA
                       organism = synthetic construct
SEQUENCE: 584
ttctctcccg gccagccttg gctctcagct caggccgatc cagctcgaat ccctgatagc  60
cacagatgag ccggaaatcc ccgtccttca tcaactggag ctttgcgccg cccggagccc  120
acgc                                                               124

SEQ ID NO: 585         moltype = RNA  length = 124
FEATURE                Location/Qualifiers
source                 1..124
                       mol_type = other RNA
                       organism = synthetic construct
SEQUENCE: 585
tggctatgtc gagttcaagc tgattgggaa aaaactcaag caaaacgcaa aggggaatag  60
caagcgcggc cttgatgcat cgcaatggta catcatcaag caactgcaat cgggtgcgtg  120
ggct                                                               124

SEQ ID NO: 586         moltype = RNA  length = 79
FEATURE                Location/Qualifiers
source                 1..79
                       mol_type = other RNA
                       organism = synthetic construct
SEQUENCE: 586
aacacatcga cattgctgcg ccccctgacc gtggcatgca acgcaccatt ctcgccgctc  60
tgcacattga tgctggctg                                               79

SEQ ID NO: 587         moltype = RNA  length = 132
FEATURE                Location/Qualifiers
source                 1..132
                       mol_type = other RNA
                       organism = synthetic construct
SEQUENCE: 587
aacgtagcag ccgcgggtga ggatgtgaag gtgcggccag ccggacttgt ggagttccag  60
```

```
gaacgccatg tattcgagtc gaggatagtt gcggcggagc cttcgcagca aggccgtcca  120
gcgcccgcgc at                                                      132

SEQ ID NO: 588          moltype = RNA  length = 121
FEATURE                 Location/Qualifiers
source                  1..121
                        mol_type = other RNA
                        organism = synthetic construct
SEQUENCE: 588
ccgcgtccga ctctccaagg cccgcgccca ggccgccgct ggcaagccag agcgcatcat  60
cacgctcact acacgccccc gcccaggtct tagcatcccc tgtgccgtgc gctggatgcg  120
c                                                                  121

SEQ ID NO: 589          moltype = RNA  length = 133
FEATURE                 Location/Qualifiers
source                  1..133
                        mol_type = other RNA
                        organism = synthetic construct
SEQUENCE: 589
gcgatccggg agaaggagca ggtcttcgcg cagacgtgga accgatcgac gctcgacagc  60
ctgcgcgaca cgctctccga cggggtgctg gagggcgaga acaaggaaga gctcacggcc  120
cgcgtgcgcg agg                                                     133

SEQ ID NO: 590          moltype = RNA  length = 124
FEATURE                 Location/Qualifiers
source                  1..124
                        mol_type = other RNA
                        organism = synthetic construct
SEQUENCE: 590
tcctcgcccc atatgtccca agaccaaatg cgcagcttgc aggcgcgcgt gtcaatctcg  60
acgcggcccg gactgctgtt cggcttgata ccaggacagt cgatcctggc cgagaagtcc  120
ggcc                                                               124

SEQ ID NO: 591          moltype = RNA  length = 124
FEATURE                 Location/Qualifiers
source                  1..124
                        mol_type = other RNA
                        organism = synthetic construct
SEQUENCE: 591
cgaaagagca tggctaaaaa accaccgacc attcgaacca cacttcagca cattctggat  60
aacgtgctca tcgccaaaac cagagcagag ggcgacggcg tgattacgct ggtccggccg  120
gact                                                               124

SEQ ID NO: 592          moltype = RNA  length = 128
FEATURE                 Location/Qualifiers
source                  1..128
                        mol_type = other RNA
                        organism = synthetic construct
SEQUENCE: 592
gcgccccgat ctgcggcgtt tcgtcgacgc gcgtcagagc atggtgcacc tgtacggctt  60
gcagacctat gccgacatca tgagcgaatt cgcatccggt gagcgctacg taaatcgggt  120
gtggtcgg                                                           128

SEQ ID NO: 593          moltype = RNA  length = 126
FEATURE                 Location/Qualifiers
source                  1..126
                        mol_type = other RNA
                        organism = synthetic construct
SEQUENCE: 593
ggacgacgcg gccctgatcg cgggcggagg cgagaaaggt ctcgaggttc tgctgcacga  60
cgcggtagag aacggtgtcc tcgggcttgc gccgctggta cccgagcgca ccggcggggt  120
ggtcgg                                                             126

SEQ ID NO: 594          moltype = RNA  length = 128
FEATURE                 Location/Qualifiers
source                  1..128
                        mol_type = other RNA
                        organism = synthetic construct
SEQUENCE: 594
ggagtgacca aagtgttgtt tgccgcggac cgcaaccgtg actgggcatt ccggaattgc  60
tcgacggcct taccgagata ggtctcggcc tccccgtcgt aaccatcggc agaagccgac  120
cacacccg                                                           128

SEQ ID NO: 595          moltype = RNA  length = 126
FEATURE                 Location/Qualifiers
source                  1..126
                        mol_type = other RNA
                        organism = synthetic construct
SEQUENCE: 595
```

```
aatgatgttc ttacctacag gttttagcct gaactgtgca taaaaactgg caacaccata  60
catgtcgcta agttttaagt ttgtttcctt ttcaagcttc aggaacgcat cacgcggtat  120
aaaacc                                                             126

SEQ ID NO: 596         moltype = RNA  length = 126
FEATURE                Location/Qualifiers
source                 1..126
                       mol_type = other RNA
                       organism = synthetic construct
SEQUENCE: 596
agcggaggct tacaacaatc gaggcaacac actacatgct cttcagcaat atcaggcggc  60
cctggatagc tatgacaagg ccatccatct caagccggag tttgcggatg cctattccaa  120
ccgagc                                                             126

SEQ ID NO: 597         moltype = RNA  length = 126
FEATURE                Location/Qualifiers
source                 1..126
                       mol_type = other RNA
                       organism = synthetic construct
SEQUENCE: 597
atgagggcaa acaggatgaa gccggcgaac acaacatcga gcttgtcgaa gcgggagaag  60
atgcggcggt agcctttgag ccgacggaag aggcgttcga tttcatttct gcggcggtat  120
aaaacc                                                             126

SEQ ID NO: 598         moltype = RNA  length = 129
FEATURE                Location/Qualifiers
source                 1..129
                       mol_type = other RNA
                       organism = synthetic construct
SEQUENCE: 598
caaggttacc aacgcctttc agccaccggg gcgctcctgc cggctgcgct tcgtccgtct  60
ttccccgaaa ttgccgtcga ttgtggcgat ctccccgaga ggcttgctct gcgggggttg  120
gagtcagcc                                                          129

SEQ ID NO: 599         moltype = RNA  length = 68
FEATURE                Location/Qualifiers
source                 1..68
                       mol_type = other RNA
                       organism = synthetic construct
SEQUENCE: 599
cagaacaccg ttccagccgc gcccagaacc acggcgcgga tttcgcggtt gcggccgatt  60
tcctccag                                                           68

SEQ ID NO: 600         moltype = RNA  length = 125
FEATURE                Location/Qualifiers
source                 1..125
                       mol_type = other RNA
                       organism = synthetic construct
SEQUENCE: 600
cgcatgatct catcgcgctt ctcgcgggca gcctctcccc ccagcgcctc gaccatctcg  60
tctcggaaca gtcgccgata cacgtggcgg atcgatccgg gactccgggg gaactcctcc  120
cgatc                                                              125

SEQ ID NO: 601         moltype = RNA  length = 125
FEATURE                Location/Qualifiers
source                 1..125
                       mol_type = other RNA
                       organism = synthetic construct
SEQUENCE: 601
tcgctgccgt cagcacgagg agacgagcag gaagctccac gagtccctct ccaagcatga  60
gaaggatgct cggaaggcct tcaagacgct gaacctcgac ccctcgatca tctgggatcg  120
ggagg                                                              125

SEQ ID NO: 602         moltype = RNA  length = 139
FEATURE                Location/Qualifiers
source                 1..139
                       mol_type = other RNA
                       organism = synthetic construct
SEQUENCE: 602
ctcccgatcg gcttcgtaga tcagacctga cgcagaaatg gccggtagct cggtgtccga  60
ctccccatag cctcctgaat ggcttcgtaa ttcagactgg atctatcgcc actgggcctc  120
ccgattggct tcgtagatc                                               139

SEQ ID NO: 603         moltype = RNA  length = 125
FEATURE                Location/Qualifiers
source                 1..125
                       mol_type = other RNA
                       organism = synthetic construct
SEQUENCE: 603
```

```
actcatgatt aaagataaaa gttctacagt aacacttgca aaataatatt ataaaaagga  60
gagtgaaact ctccttaaaa tttaagtaat tatatttccg ttattatctg tgaaagttct  120
attta                                                             125

SEQ ID NO: 604         moltype = RNA  length = 124
FEATURE                Location/Qualifiers
source                 1..124
                       mol_type = other RNA
                       organism = synthetic construct
SEQUENCE: 604
ttatttaaag gtcttaaaga ttttaactca gcttgtaaat cataaatatc tttaaaaaaa  60
acgctcattt cctactcctt ttatttacta taattattta tatcatatca tataatattt  120
aaat                                                              124

SEQ ID NO: 605         moltype = RNA  length = 124
FEATURE                Location/Qualifiers
source                 1..124
                       mol_type = other RNA
                       organism = synthetic construct
SEQUENCE: 605
tatttaaagg tcttaaagat tttaactcag cttgtaaatc ataaatatct ttaaaaaaaa  60
cgctcatttc ctactccttt tatttactat aattatttat atcatatcat ataatattta  120
aata                                                              124

SEQ ID NO: 606         moltype = RNA  length = 132
FEATURE                Location/Qualifiers
source                 1..132
                       mol_type = other RNA
                       organism = synthetic construct
SEQUENCE: 606
acgcttggca tagcagagag caccgtagag tcgcagatgc gcattgcgct gcgcacgttg  60
cgtcgcagct tcgccgtgta acagcccatg tcgcaagacg gacaataacc ccgaccacac  120
acattgattg ca                                                     132

SEQ ID NO: 607         moltype = RNA  length = 132
FEATURE                Location/Qualifiers
source                 1..132
                       mol_type = other RNA
                       organism = synthetic construct
SEQUENCE: 607
tcaggctctc tattcattgt tgatgttgtc tgcctgtggc agaacaggcg gcgcaaggat  60
tgttatcggt gcggcgcagt gattgtgata atgtcctctt tggtgttgtg ttgtgtgcaa  120
tcaatgtgtg tg                                                     132

SEQ ID NO: 608         moltype = RNA  length = 123
FEATURE                Location/Qualifiers
source                 1..123
                       mol_type = other RNA
                       organism = synthetic construct
SEQUENCE: 608
gttgcgagca tgggaatccg cagtgcgacc cataagcgcg cagaataaga gtatagcatt  60
cgcactgcaa tcaatcggtc gattgtccgt ccgaggctgt cgttaatgac atcataggat  120
gtt                                                               123

SEQ ID NO: 609         moltype = RNA  length = 126
FEATURE                Location/Qualifiers
source                 1..126
                       mol_type = other RNA
                       organism = synthetic construct
SEQUENCE: 609
cgataattcc gcggcaccat cgctatttaa cggcgatttt gaaggtgcac taaatgaaag  60
cttcgagcgt ttccgttttg gtggagtgac gccaagtaag caagaagtgt tctttattaa  120
tttaca                                                            126

SEQ ID NO: 610         moltype = RNA  length = 126
FEATURE                Location/Qualifiers
source                 1..126
                       mol_type = other RNA
                       organism = synthetic construct
SEQUENCE: 610
atcggtaatc gcgatggagt agctaccatg agcgcgcacg aataattccg cattgtaaaa  60
attatcgaaa tagttgatcg gttgctgcgt accaaaacga atgccgcgaa tttcttgtaa  120
attaat                                                            126

SEQ ID NO: 611         moltype = RNA  length = 132
FEATURE                Location/Qualifiers
source                 1..132
                       mol_type = other RNA
                       organism = synthetic construct
```

```
SEQUENCE: 611
accaactcgg cattcacgaa ctccacggca ccaaaatcgt aaaactagca gaataaccca  60
accaacctcc ctaaagcccc tgcgaaaagg tcgcgcagaa gcttggggag gttggtttac  120
atcattctca aa                                                       132

SEQ ID NO: 612          moltype = RNA  length = 124
FEATURE                 Location/Qualifiers
source                  1..124
                        mol_type = other RNA
                        organism = synthetic construct
SEQUENCE: 612
agtattgcgc ggatataatt ttgtagatcc ttgatataat gcattttcaa tcgtatatcg  60
ttcttgatac aaaatatgaa gtgcccgata cacatcttcc aattgataag tagattgatg  120
taaa                                                                124

SEQ ID NO: 613          moltype = RNA  length = 124
FEATURE                 Location/Qualifiers
source                  1..124
                        mol_type = other RNA
                        organism = synthetic construct
SEQUENCE: 613
gacgtttggc tgctactgct tggttcgctc ccttgccacc acctgcagaa aagatttctt  60
ttgtatgcat cgtttcacca atttgtggca tatgacttaa gcgaatcgta cggtctaaat  120
taat                                                                124

SEQ ID NO: 614          moltype = RNA  length = 14
FEATURE                 Location/Qualifiers
source                  1..14
                        mol_type = other RNA
                        organism = synthetic construct
SEQUENCE: 614
tcttaaaata gcac                                                     14

SEQ ID NO: 615          moltype = RNA  length = 126
FEATURE                 Location/Qualifiers
source                  1..126
                        mol_type = other RNA
                        organism = synthetic construct
SEQUENCE: 615
cgataattcc gcggcaccat cgctatttaa cggcgatttt gaaggcgcac tgaatgaaag  60
tttcgagcgt ttccgttttg gtggagtgac accaagtaag caagaagtgt tctttattaa  120
tttaca                                                              126

SEQ ID NO: 616          moltype = RNA  length = 126
FEATURE                 Location/Qualifiers
source                  1..126
                        mol_type = other RNA
                        organism = synthetic construct
SEQUENCE: 616
atcggtaatc gcgatggagt agctaccatg agcacgcacg aataattccg cattgtaaaa  60
attatcgaaa tagttgatcg gttgctgcgt accaaaacga atgcctcgta tttcttgtaa  120
attaat                                                              126

SEQ ID NO: 617          moltype = RNA  length = 124
FEATURE                 Location/Qualifiers
source                  1..124
                        mol_type = other RNA
                        organism = synthetic construct
SEQUENCE: 617
gacgtttggc tgctactgct tggttcgctc ccttgccacc acctgcagaa aagatttcct  60
ttgtatgcat cgtttcacca atttgtggca tatgacttaa gcgaatcgta cggtctaaat  120
taat                                                                124

SEQ ID NO: 618          moltype = RNA  length = 134
FEATURE                 Location/Qualifiers
source                  1..134
                        mol_type = other RNA
                        organism = synthetic construct
SEQUENCE: 618
aaacaacgat taaagcaagc aaggataaat taaccattgc ttcttataat attgaaaact  60
tctcagcaaa taaagcgtcc acaagtgatg aaaaagttca acgcattgcc caatcgtttg  120
tgaatgattt aaat                                                     134

SEQ ID NO: 619          moltype = RNA  length = 132
FEATURE                 Location/Qualifiers
source                  1..132
                        mol_type = other RNA
                        organism = synthetic construct
SEQUENCE: 619
```

```
cgcaggatac gctgtctgca gcgattgtcg gcagtagtat cggttctacg aacgcccaga  60
gccatcggcg ggtggcgtgc cagaggcgcc aatgcggtct ggctggggct ggcgcgtagt  120
ggcaagtgga gg                                                      132

SEQ ID NO: 620         moltype = RNA  length = 132
FEATURE                Location/Qualifiers
source                 1..132
                       mol_type = other RNA
                       organism = synthetic construct
SEQUENCE: 620
actcggcgct gctggtgctg cgcgtgctgg aaacgctggg tgaggggtga ggggtgagag  60
gcactggcga atagtggcga ccccgactgg gctcgaacca gtaaccttca gctcccctcc  120
acttgccact ac                                                      132

SEQ ID NO: 621         moltype = RNA  length = 125
FEATURE                Location/Qualifiers
source                 1..125
                       mol_type = other RNA
                       organism = synthetic construct
SEQUENCE: 621
ccgagttgcg gcttgttagc ccctcgcaca gcgcgtgcca gtcgcgctcg ccggcccaga  60
tgcgccgcgt ggcatcggca atctgccagc cgtttgcctc aagacgtggg aggcgctcct  120
ccact                                                              125

SEQ ID NO: 622         moltype = RNA  length = 124
FEATURE                Location/Qualifiers
source                 1..124
                       mol_type = other RNA
                       organism = synthetic construct
SEQUENCE: 622
cgggatagga cccgtggaat tttgtgcttg ccggagctct gaagaagtcg cagttaggcg  60
agagcaagaa ctcgagaagc ttatctgctc cttctctctt gatcttatcc ttgaaaattt  120
ctac                                                               124

SEQ ID NO: 623         moltype = RNA  length = 124
FEATURE                Location/Qualifiers
source                 1..124
                       mol_type = other RNA
                       organism = synthetic construct
SEQUENCE: 623
ataaggcttt attaaaacaa aacactatta tataagaaaa aaaggagaaa acattatgac  60
aaacaataac attaacaaca acacaatcga tagagaagcg gtacaggccc gtttcgtaga  120
aatt                                                               124

SEQ ID NO: 624         moltype = RNA  length = 124
FEATURE                Location/Qualifiers
source                 1..124
                       mol_type = other RNA
                       organism = synthetic construct
SEQUENCE: 624
agaaaaaaca acatgccgaa ttacgattac atcgacagac aaaagttagg gataggcaag  60
gcggacagaa atgcgtttgc cgttcccgag tacgcagacg gttggaacgg cgcgatagaa  120
atta                                                               124

SEQ ID NO: 625         moltype = RNA  length = 131
FEATURE                Location/Qualifiers
source                 1..131
                       mol_type = other RNA
                       organism = synthetic construct
SEQUENCE: 625
cgcgagcgca agggccgcgt gaaatgtcca gggcctgtgg ccggacagcg tggaagcagt  60
cggatcgata tctcgtcgct ttgggacaac caggccgagc agatgtgatt gcgaaagcgt  120
cgtggcaagt g                                                       131

SEQ ID NO: 626         moltype = RNA  length = 131
FEATURE                Location/Qualifiers
source                 1..131
                       mol_type = other RNA
                       organism = synthetic construct
SEQUENCE: 626
cagagctgct acccgtgagg tagatggcag cacctgtagt atatgtcaac agctcgttgc  60
tggcaaccag acaagtcctg attatagaat agggattcga acccccgaca cccctcactt  120
gccacgacgc t                                                       131

SEQ ID NO: 627         moltype = RNA  length = 130
FEATURE                Location/Qualifiers
source                 1..130
                       mol_type = other RNA
                       organism = synthetic construct
```

```
SEQUENCE: 627
gcgaggatcc acggcaagtt ggtcgacaag ctggacctgt cccgcgtcgg cgacatgaag  60
ggcgacacgc tccgccgcga aatccgcgtg gtcatcgaac acctctgcga cgccgacgac  120
gcgctgttga                                                         130

SEQ ID NO: 628         moltype = RNA  length = 125
FEATURE                Location/Qualifiers
source                 1..125
                       mol_type = other RNA
                       organism = synthetic construct
SEQUENCE: 628
cgcgggcggc cttcagatcc ttcttggtga aattcccgac cggcaggggc gtacacaggg  60
acagcacctc ccggaagctc cgcccgaact cgaccagttc cttcgacggc ttgccgttcg  120
gcagg                                                              125

SEQ ID NO: 629         moltype = RNA  length = 125
FEATURE                Location/Qualifiers
source                 1..125
                       mol_type = other RNA
                       organism = synthetic construct
SEQUENCE: 629
ccgtgctggc ggagttggcc gggctggcgg agccccccgg ccgtcctgcc ggggggctgc  60
tgacggtcgg cgggttcgtg cggcggttca tggagcacgc gaaggtgtac taccgcctgc  120
cgaac                                                              125

SEQ ID NO: 630         moltype = RNA  length = 126
FEATURE                Location/Qualifiers
source                 1..126
                       mol_type = other RNA
                       organism = synthetic construct
SEQUENCE: 630
catgtcccgg agttgtcgtc gcaagtcttt gatgtccgtt cgctcccatt tctcagtcct  60
cttctggggt tgaggtttca ttcgatccgg cccatttgtc atccaccagc tcgacccccct  120
cgcggg                                                             126

SEQ ID NO: 631         moltype = RNA  length = 124
FEATURE                Location/Qualifiers
source                 1..124
                       mol_type = other RNA
                       organism = synthetic construct
SEQUENCE: 631
ttttaagcga tgcaagatac gctgatcaag tcgagaagta taacctattg aaaacagtta  60
atccctcgag gataatcagc ctactcgaca gactagccga taacggaata attaatagga  120
agaa                                                               124

SEQ ID NO: 632         moltype = RNA  length = 124
FEATURE                Location/Qualifiers
source                 1..124
                       mol_type = other RNA
                       organism = synthetic construct
SEQUENCE: 632
tccaagtagc gagccaaggg ttccggaaag gtaggcaatt ggtactccgt aaaccgggtt  60
atcaacgagt agtattgttg ttaaaacagc tgttaatgaa ggtatgaatc ccgggacaac  120
gatc                                                               124

SEQ ID NO: 633         moltype = RNA  length = 139
FEATURE                Location/Qualifiers
source                 1..139
                       mol_type = other RNA
                       organism = synthetic construct
SEQUENCE: 633
acaaaaagta ataatccagg catatctacg acaccgccta gcactttcag ttcttcctag  60
ttgttacgca gaatcatagg aaacattgaa tggcttgaac acctagcaga acaatctttc  120
agttcttcct agttgttac                                               139

SEQ ID NO: 634         moltype = RNA  length = 135
FEATURE                Location/Qualifiers
source                 1..135
                       mol_type = other RNA
                       organism = synthetic construct
SEQUENCE: 634
gaagctgggc tacaccatca agcagggcgg caagcgtgtc tccgataaga ccctaaagga  60
agctcaggac gacggtacag gacagttcat gctgggcctg tagcaaaaca cctacaaatt  120
tctgctgttg cagat                                                   135

SEQ ID NO: 635         moltype = RNA  length = 134
FEATURE                Location/Qualifiers
source                 1..134
                       mol_type = other RNA
```

```
                         organism = synthetic construct
SEQUENCE: 635
aagctgggct acaccatcaa gcagggcggc aagcgtgtct ccgataagac cctaaaggaa  60
gctcaggacg acggtacagg acagttcatg ctgggcctgt agcaaaacac ctacaaattt  120
ctgctgttgc agat                                                    134

SEQ ID NO: 636           moltype = RNA  length = 134
FEATURE                  Location/Qualifiers
source                   1..134
                         mol_type = other RNA
                         organism = synthetic construct
SEQUENCE: 636
tgagtggtca ttccccgaga agggtctcga aagattgctc ctaatcccta caagatgtgc  60
attttgtggg gcaaaggagc gggggccatc gggtttccac gtaatatcct ttaatatctg  120
caacagcaga aatt                                                    134

SEQ ID NO: 637           moltype = RNA  length = 124
FEATURE                  Location/Qualifiers
source                   1..124
                         mol_type = other RNA
                         organism = synthetic construct
SEQUENCE: 637
caagtggcta atgaactaac aaagacacca tcaatcataa tcactgagga acttggtgag  60
aacccgcagg agtcgatgat tgaggatgtt gggaaggacg agttgaggca ccgcataaaa  120
caga                                                               124

SEQ ID NO: 638           moltype = RNA  length = 124
FEATURE                  Location/Qualifiers
source                   1..124
                         mol_type = other RNA
                         organism = synthetic construct
SEQUENCE: 638
cgttgcgaat aatgttacgg gtgcgaataa actccagagg ttattctaca ataagtatag  60
gctggagtac ccaagcctta actcacaatt aatcatccaa gcaatcaggc aggcatctga  120
aatc                                                               124

SEQ ID NO: 639           moltype = RNA  length = 124
FEATURE                  Location/Qualifiers
source                   1..124
                         mol_type = other RNA
                         organism = synthetic construct
SEQUENCE: 639
cttgtgaagt gtattgggca taccctactg tttctgtatg atgatacgtg gaatagtttg  60
gatccgcgct ccaaagcctt atcctccaca gccctcacca acgccttgaa tggtgtctgt  120
ttta                                                               124

SEQ ID NO: 640           moltype = RNA  length = 124
FEATURE                  Location/Qualifiers
source                   1..124
                         mol_type = other RNA
                         organism = synthetic construct
SEQUENCE: 640
acttttctgc ttggaggatt tgtcgccgga ataccgatca ttgtttacga tgaacctata  60
aacgctttat tcgagggaat atcggcaatt acaacgaccg gattatctag tttgaatcag  120
aatt                                                               124

SEQ ID NO: 641           moltype = RNA  length = 124
FEATURE                  Location/Qualifiers
source                   1..124
                         mol_type = other RNA
                         organism = synthetic construct
SEQUENCE: 641
atattatagg ccgccgatcc tggtgatact aggaacgata cagtaaggag cgctattcca  60
agccctccta tccattggta atatgatctg agaaaatgta ctccaggggt tagagaattc  120
tgat                                                               124

SEQ ID NO: 642           moltype = RNA  length = 124
FEATURE                  Location/Qualifiers
source                   1..124
                         mol_type = other RNA
                         organism = synthetic construct
SEQUENCE: 642
actcatagta acccctgacc acttactcgt agacggggat actcttgaat ggaaacaagc  60
ctttgaattt aagaaagggg ataaagtact ttcaatacaa aaaataccgg gacacaacaa  120
cgat                                                               124

SEQ ID NO: 643           moltype = RNA  length = 129
FEATURE                  Location/Qualifiers
source                   1..129
```

```
                        mol_type = other RNA
                        organism = synthetic construct
SEQUENCE: 643
aaaagatctt cagaaaaata agtgagattc tcaatacaaa tctttcctcc tcaaagctct  60
gcgaaactct catcacgatc agagatgttc tcatgaagag tgatgatgat ttcatcagaa  120
gatttgaag                                                          129

SEQ ID NO: 644          moltype = RNA  length = 124
FEATURE                 Location/Qualifiers
source                  1..124
                        mol_type = other RNA
                        organism = synthetic construct
SEQUENCE: 644
agtttataag cttcttaaca actattgtta ttgggatagt aaaaatatga tagacatggt  60
taaagaaggc atcaaagagg atcttgtgaa gctatatgac aacatatcct catcatcagt  120
tgtt                                                               124

SEQ ID NO: 645          moltype = RNA  length = 125
FEATURE                 Location/Qualifiers
source                  1..125
                        mol_type = other RNA
                        organism = synthetic construct
SEQUENCE: 645
ctgatcgatg ctcctataag gcttgaggtt ggcgatatga tatttctaga atgttcatct  60
aaatatcttg agatccttaa gaaggcatcg gcatacagct catatctatc gttcacatct  120
caaat                                                              125

SEQ ID NO: 646          moltype = RNA  length = 124
FEATURE                 Location/Qualifiers
source                  1..124
                        mol_type = other RNA
                        organism = synthetic construct
SEQUENCE: 646
gagagagatg ctgagagatt ctgaaagcta agaaggcagt cccaagataa tgttgaagac  60
ctgaagtcga gtagaacttc gggtttgagg ctatgatagg aaaatagaag tcctcaacaa  120
ctga                                                               124

SEQ ID NO: 647          moltype = RNA  length = 64
FEATURE                 Location/Qualifiers
source                  1..64
                        mol_type = other RNA
                        organism = synthetic construct
SEQUENCE: 647
ggtacaaaaa ccagttgtgt atccaaagct tcttctaaac atggcatcag agcctgatga  60
tgtt                                                               64

SEQ ID NO: 648          moltype = RNA  length = 127
FEATURE                 Location/Qualifiers
source                  1..127
                        mol_type = other RNA
                        organism = synthetic construct
SEQUENCE: 648
cttgttttat acaatgagag caatggctat gcagctatca aagagcttga ttatttaatg  60
aatcttagaa gtgcaaaaga gagatttaag caagtttatg acgagggatt tgtagttgat  120
actgatg                                                            127

SEQ ID NO: 649          moltype = RNA  length = 124
FEATURE                 Location/Qualifiers
source                  1..124
                        mol_type = other RNA
                        organism = synthetic construct
SEQUENCE: 649
tgttaccttt atactaatac cccttgtatg agctgcatct gtatataaag tataacgccc  60
accattaaca tttaccttat ttacaggctc ttttgaatta ccataataaa acttagtatt  120
actt                                                               124

SEQ ID NO: 650          moltype = RNA  length = 126
FEATURE                 Location/Qualifiers
source                  1..126
                        mol_type = other RNA
                        organism = synthetic construct
SEQUENCE: 650
cagaacctat ttataaaata tcaattaatt ctgatttaga tgtagataag ctacctaagg  60
ctagagtatt tgagcctgaa gaattcaata aaggttggaa aactgtaaat aactcttggt  120
attact                                                             126

SEQ ID NO: 651          moltype = RNA  length = 123
FEATURE                 Location/Qualifiers
source                  1..123
```

```
                        mol_type = other RNA
                        organism = synthetic construct
SEQUENCE: 651
tcaacaataa taatattatt aatgtcagta acaaatgcac cagcatagct tatattgcta  60
ctaccaccaa ctaatacttt aggcttttca ataaatttgc gtgcgtaaag aataccacct  120
tca                                                                123

SEQ ID NO: 652          moltype = RNA  length = 123
FEATURE                 Location/Qualifiers
source                  1..123
                        mol_type = other RNA
                        organism = synthetic construct
SEQUENCE: 652
aagctatgct ggtgcatttg ttactgacat taataatatt attattgttg atgctaatgg  60
ctacatactg atagagggtt aatgaataga ggtatgtttt aaatgacaca actaaatgca  120
tta                                                                123

SEQ ID NO: 653          moltype = RNA  length = 130
FEATURE                 Location/Qualifiers
source                  1..130
                        mol_type = other RNA
                        organism = synthetic construct
SEQUENCE: 653
aactgctgat gaccctgacc aaaagattcg ttctaatggt tatgtagttc aagttggggc  60
atatggtaag agttctatta tgacaggtgc aaaatctcaa aatgtaggta agaagtctca  120
tactgaaggt                                                         130

SEQ ID NO: 654          moltype = RNA  length = 127
FEATURE                 Location/Qualifiers
source                  1..127
                        mol_type = other RNA
                        organism = synthetic construct
SEQUENCE: 654
tctcggtatc gacgagtttc gtgactttta gcttctgcac gcggtagcta atacgctggc  60
agtagtggcg gcttgctgct gatcgttcgt agaatgtggc gtcgatagca gcatgttcag  120
acggatc                                                            127

SEQ ID NO: 655          moltype = RNA  length = 127
FEATURE                 Location/Qualifiers
source                  1..127
                        mol_type = other RNA
                        organism = synthetic construct
SEQUENCE: 655
ggagatcggc ctcagcgcgg ccgatctccc ttcgccgtcc acgttgtgta aagcgttcga  60
ccggatcgag atgagcgtct gtcgagtgct actgcgccag tcggcgcagt tgcacgatcc  120
gtctgaa                                                            127

SEQ ID NO: 656          moltype = RNA  length = 127
FEATURE                 Location/Qualifiers
source                  1..127
                        mol_type = other RNA
                        organism = synthetic construct
SEQUENCE: 656
accggtcgat cgcgacgagg cctgcggcct ccagatccgc cacgtagcga tcgatactgg  60
cgtcggcgta gtcgatctgg gtatctcgct tcagcgcccg cactgagcgc tcgctgtcgg  120
cgtcgag                                                            127

SEQ ID NO: 657          moltype = RNA  length = 126
FEATURE                 Location/Qualifiers
source                  1..126
                        mol_type = other RNA
                        organism = synthetic construct
SEQUENCE: 657
acgcagcctc ctggaggcca tatcaaacag cacgcaccgc caacacgacc ctacggcgtt  60
attttcgaga tcgccaacga gaccgatttc ttcgagatcc cgcccgatcg ctactacgag  120
ttcggc                                                             126

SEQ ID NO: 658          moltype = RNA  length = 66
FEATURE                 Location/Qualifiers
source                  1..66
                        mol_type = other RNA
                        organism = synthetic construct
SEQUENCE: 658
atgctgtcgg cgctgttcgc gagcgatgag ccactcgatc gacaggcgct catcgaagtc  60
acgagc                                                             66

SEQ ID NO: 659          moltype = RNA  length = 125
FEATURE                 Location/Qualifiers
source                  1..125
```

```
                        mol_type = other RNA
                        organism = synthetic construct
SEQUENCE: 659
tttcctaata caagaatcac tagtaatcag ctcaaaagaa agcctaaagc atgaatagga  60
tgcaaattgt ttgatatata gaaaaatcgc taacttatac taaagataaa agtatcctta  120
tggaa                                                              125

SEQ ID NO: 660          moltype = RNA  length = 130
FEATURE                 Location/Qualifiers
source                  1..130
                        mol_type = other RNA
                        organism = synthetic construct
SEQUENCE: 660
aaaacgcgga agaagcctaa actcctggtt attatagtga tataatgaat cgttacgata  60
ttggcctcca aaccagaaac caatgtccat caccgtccca ttatttagag atttgatttc  120
atttccataa                                                         130

SEQ ID NO: 661          moltype = RNA  length = 127
FEATURE                 Location/Qualifiers
source                  1..127
                        mol_type = other RNA
                        organism = synthetic construct
SEQUENCE: 661
aaaatgactt agcatatttg gatagtcgta tgagcgtttt gattcaagaa atgttctcat  60
ctgatttgtg cgctgttgtg atgacgaagg atcctgtaga actagaagaa gtctttggaa  120
ttgaaat                                                            127

SEQ ID NO: 662          moltype = RNA  length = 129
FEATURE                 Location/Qualifiers
source                  1..129
                        mol_type = other RNA
                        organism = synthetic construct
SEQUENCE: 662
aaagagaata atgattacgg gagctgccgg ttcaattggg cgtgaaatgg tgaggcagat  60
agccggattg aatccatata aattaatttt ggttgatcag gcagaatcac ctttgcataa  120
tgtacaatt                                                          129

SEQ ID NO: 663          moltype = RNA  length = 118
FEATURE                 Location/Qualifiers
source                  1..118
                        mol_type = other RNA
                        organism = synthetic construct
SEQUENCE: 663
aaatttattg atatgtatgc cggacgcctg cggaatcaag tctcttttat gttgagtgcc  60
tgcaacttct atatgcctat ctttgaggag gcccttgatg cgtataattt accattgg    118

SEQ ID NO: 664          moltype = RNA  length = 126
FEATURE                 Location/Qualifiers
source                  1..126
                        mol_type = other RNA
                        organism = synthetic construct
SEQUENCE: 664
aaaaatagaa tctttcaaag ccaatgctaa ctctaaggct tgatcgagat aaaacaaagc  60
ttcctttctt tttccttcaa caacacgcac ccatcccata ttcgaaagag aatacattaa  120
tacttt                                                             126

SEQ ID NO: 665          moltype = RNA  length = 126
FEATURE                 Location/Qualifiers
source                  1..126
                        mol_type = other RNA
                        organism = synthetic construct
SEQUENCE: 665
aaacatagtg gcaagcccca tgcccatacc attaatggcc gaggaagtcg taccgagtgt  60
aggacacata ccaagcagga gcacaaatgt cggattctct ttaacaatcc cattcattaa  120
tacttt                                                             126

SEQ ID NO: 666          moltype = RNA  length = 126
FEATURE                 Location/Qualifiers
source                  1..126
                        mol_type = other RNA
                        organism = synthetic construct
SEQUENCE: 666
aaagaagctg acgcctacaa atccctcttt gaaaaaatgg gtattgaaaa cattgtctat  60
aacatagcaa tgtgctccaa aaaccattat tgcaaatatg aatctcaacg atgttaaagt  120
attaat                                                             126

SEQ ID NO: 667          moltype = RNA  length = 126
FEATURE                 Location/Qualifiers
source                  1..126
```

```
                        mol_type = other RNA
                        organism = synthetic construct
SEQUENCE: 667
aagcatactt cttgattcat actaactata ctttccatat atttgcagta ttcaacacac  60
acatcacatc tttaatgatg aaaataaaaa aacgataaga caatacgaaa ttatgattaa  120
tacttt                                                             126

SEQ ID NO: 668          moltype = RNA  length = 102
FEATURE                 Location/Qualifiers
source                  1..102
                        mol_type = other RNA
                        organism = synthetic construct
SEQUENCE: 668
aaggaaattt attgttttga cgatttacaa attaattgtc cgaaggaacc attcttcggg  60
acaataagtc acaaataccc ggaacatagt tgtctatgtc tc                     102

SEQ ID NO: 669          moltype = RNA  length = 126
FEATURE                 Location/Qualifiers
source                  1..126
                        mol_type = other RNA
                        organism = synthetic construct
SEQUENCE: 669
caaggggtta actttgcttt atttccaata tatctacgac tctccaaatc aaacatctta  60
taccccaaaa gagtgacatc tatatcagtt cgattataga cttcttgtaa tgacaatttc  120
aattcc                                                             126

SEQ ID NO: 670          moltype = RNA  length = 126
FEATURE                 Location/Qualifiers
source                  1..126
                        mol_type = other RNA
                        organism = synthetic construct
SEQUENCE: 670
cagataattg tgttttccga taccttcatt gtctgccgac atattgaata ggatttccgc  60
cccttgtaaa gctagcgatg agctgggagg aatcgtggac catagatctt cacaaatttc  120
aattcc                                                             126

SEQ ID NO: 671          moltype = RNA  length = 126
FEATURE                 Location/Qualifiers
source                  1..126
                        mol_type = other RNA
                        organism = synthetic construct
SEQUENCE: 671
cagctattat ccctgcaaca attcaaaaat atgtaacgac caattatccc gatgctaaaa  60
tcctgaaaat agagagggat aaaaaagatt atgaagtaaa actgtccaac cgtacggaat  120
tgaaat                                                             126

SEQ ID NO: 672          moltype = RNA  length = 126
FEATURE                 Location/Qualifiers
source                  1..126
                        mol_type = other RNA
                        organism = synthetic construct
SEQUENCE: 672
cccaaatcat cttaccaaga gaaccataat cattcttcaa ggcgtctaca tgattaccac  60
cagccgcagc tattacttcg tccttagata ctggcaatct tcttggatta ttaccggaat  120
tgaaat                                                             126

SEQ ID NO: 673          moltype = RNA  length = 113
FEATURE                 Location/Qualifiers
source                  1..113
                        mol_type = other RNA
                        organism = synthetic construct
SEQUENCE: 673
cgtaaaccgg cagacacaca tgtaaattcg cgggtaaaca cgttgacgga tagatgcttc  60
caaaagcgca tagcagcacc aatgttccaa ccatgcgtat catattccgc cat         113

SEQ ID NO: 674          moltype = RNA  length = 126
FEATURE                 Location/Qualifiers
source                  1..126
                        mol_type = other RNA
                        organism = synthetic construct
SEQUENCE: 674
ctttagaaat aatgtgtcga tcaagaataa tataaaaaac ataggttagc gacataggta  60
ctaaacatct atatatcaac atgtcataga gcgtttccgt tactttacca ttgataattc  120
acaata                                                             126

SEQ ID NO: 675          moltype = RNA  length = 125
FEATURE                 Location/Qualifiers
source                  1..125
                        mol_type = other RNA
```

```
                          organism = synthetic construct
SEQUENCE: 675
cctaaaccaa tacagaaggt ccttgaaaca ctgataaaat gccctagatg cggaagccaa  60
ccaagctatg gagaaaaata ctgcaaacaa tgcggagcaa gaatcccaac aaaagcatgg  120
gaaac                                                              125

SEQ ID NO: 676          moltype = RNA  length = 129
FEATURE                 Location/Qualifiers
source                  1..129
                        mol_type = other RNA
                        organism = synthetic construct
SEQUENCE: 676
cctctaccga ggttgccagt ttagatgctg agcgcataac ctccctctca aaaaccctct  60
catccacatc caacaacgcc agcctaatag cctctctcct gaaggcttca agaggaacac  120
ccatatcat                                                          129

SEQ ID NO: 677          moltype = RNA  length = 129
FEATURE                 Location/Qualifiers
source                  1..129
                        mol_type = other RNA
                        organism = synthetic construct
SEQUENCE: 677
ggcgaaaaac cgcagccgca gcagccagct ccgcctacaa gggggtaac ggctcctgag  60
cctgttcctg caggggttga ttgggagcct gatgaagaca tggttgaggc ttttgatgat  120
atgggtgtt                                                          129

SEQ ID NO: 678          moltype = RNA  length = 126
FEATURE                 Location/Qualifiers
source                  1..126
                        mol_type = other RNA
                        organism = synthetic construct
SEQUENCE: 678
acgagtaaga aacgaacacg aggcctacgg attgcatttt gcggaagttt ggttgcaact  60
gcccgactac gacaactacg aactgcaagc caccgtcgta cttgacagtt tgctcactga  120
gtcgcc                                                             126

SEQ ID NO: 679          moltype = RNA  length = 125
FEATURE                 Location/Qualifiers
source                  1..125
                        mol_type = other RNA
                        organism = synthetic construct
SEQUENCE: 679
cctctgcagc tgagattgtt acaggtgcga tacaagacca agacagaggt atggtggtgg  60
gaagacgttc ctttggtaag ggacttgtac agcgcccggt tgagtttcag gatggaagta  120
tgatg                                                              125

SEQ ID NO: 680          moltype = RNA  length = 124
FEATURE                 Location/Qualifiers
source                  1..124
                        mol_type = other RNA
                        organism = synthetic construct
SEQUENCE: 680
cgacgtacaa tatcttctct tgacatcttc acccctgcga tagcggtatc gtttaccata  60
acaatacggt cgccggcaag tatccccacc ttctcagaag gtccgttggt aaccggttga  120
ataa                                                               124

SEQ ID NO: 681          moltype = RNA  length = 129
FEATURE                 Location/Qualifiers
source                  1..129
                        mol_type = other RNA
                        organism = synthetic construct
SEQUENCE: 681
aacacattgt ctgaacttct tctaattcct gttctgttgt aataaacaaa gttggttcat  60
ttgttctgat tttaatccat ccaaaatcac tataaatttc actacaagag aaataacaag  120
catcagcaa                                                          129

SEQ ID NO: 682          moltype = RNA  length = 129
FEATURE                 Location/Qualifiers
source                  1..129
                        mol_type = other RNA
                        organism = synthetic construct
SEQUENCE: 682
gaagtaggag ttcctttata tggaccttta attaacacag taactagagg cgcaagatta  60
aagaaattct atctgcggtc cgcagcttct ggagtcggca aatcaagaac aatgattgct  120
gatgcttgt                                                          129

SEQ ID NO: 683          moltype = RNA  length = 129
FEATURE                 Location/Qualifiers
source                  1..129
```

```
                        mol_type = other RNA
                        organism = synthetic construct
SEQUENCE: 683
ttacggattt ccacaacgtc gtctgttaca agacggtgac cgcgctttac aagttccaaa  60
gcagcctcag atttaccgat gccgctctca ccagtaatca atacaccttc accgtaaaca  120
tcaacaagt                                                          129

SEQ ID NO: 684          moltype = RNA  length = 125
FEATURE                 Location/Qualifiers
source                  1..125
                        mol_type = other RNA
                        organism = synthetic construct
SEQUENCE: 684
caccttatcc atggcaattt gctcttcgga aagcgggccg agcggtttac cttgttcaga  60
aggagaacgg cgagcagcaa aggagaacag accggcggaa tcagcaggag cccctttgct  120
gatgt                                                              125

SEQ ID NO: 685          moltype = RNA  length = 125
FEATURE                 Location/Qualifiers
source                  1..125
                        mol_type = other RNA
                        organism = synthetic construct
SEQUENCE: 685
gaatgtgcct acgctgcgaa taaggcggtg ggtgaggttt tgcctgtacc ccggactcag  60
ggtgaccgag gcggaaagaa gtatctggtg gaactgtggc ccaccaagca gcaatacatc  120
agcaa                                                              125

SEQ ID NO: 686          moltype = RNA  length = 124
FEATURE                 Location/Qualifiers
source                  1..124
                        mol_type = other RNA
                        organism = synthetic construct
SEQUENCE: 686
tcctgaaaaa gacgatgcgt atcgtagatg gcatcatagg gagagtactg tgcattctgt  60
cgcaaatcat catcctcaaa ttcagcattg atgatgcgac cttggtaaat tctgttgatg  120
tttg                                                               124

SEQ ID NO: 687          moltype = RNA  length = 137
FEATURE                 Location/Qualifiers
source                  1..137
                        mol_type = other RNA
                        organism = synthetic construct
SEQUENCE: 687
agcttcattc cgtggaagtg ccccaaaaag gttgcacggc atagtcggat ttggttcccg  60
tgcaattctt gctactcacc agccggcgtg ccccaccgga tactcaggct ccatatttgg  120
tgcccgtgca aattctt                                                 137

SEQ ID NO: 688          moltype = RNA  length = 137
FEATURE                 Location/Qualifiers
source                  1..137
                        mol_type = other RNA
                        organism = synthetic construct
SEQUENCE: 688
gtcgttttca tagtataatt ggcgcgggca ctcacagaat agtgctggat aaaagagtgg  60
cgccttcctc cttcttcgaa aaataagaga tacggggttt gcgttgttga gtagcaagaa  120
tttgcacggg caccaaa                                                 137

SEQ ID NO: 689          moltype = RNA  length = 124
FEATURE                 Location/Qualifiers
source                  1..124
                        mol_type = other RNA
                        organism = synthetic construct
SEQUENCE: 689
tgaaaaaatt atttgtggtt gtcaacacag atacccaacg ggccattcgc gcttttgtga  60
gcgagtcccg agcggatgat tacgctgacg atctatacga aaaaacgaac caggataccc  120
gtgt                                                               124

SEQ ID NO: 690          moltype = RNA  length = 127
FEATURE                 Location/Qualifiers
source                  1..127
                        mol_type = other RNA
                        organism = synthetic construct
SEQUENCE: 690
cgcgcgggag gcctggacgg acaagatcgc ctcggacacc gtcaagacgg ccctgcggct  60
cggggtgagc gtcatcgcgg tgtacaagga cgaggactcc accccctcgc aggtgcgtcc  120
cgcccac                                                            127

SEQ ID NO: 691          moltype = RNA  length = 127
FEATURE                 Location/Qualifiers
```

```
source                  1..127
                        mol_type = other RNA
                        organism = synthetic construct
SEQUENCE: 691
cccggtggcc gacgcccttg ctgacgacct tgacctcgat gccgtgcagc ggcgccacca  60
gggcgatctg gtcggcgatc gcacggcgcg cctcggtggc cagacgccgg ttgatgtggg  120
cgggacg                                                            127

SEQ ID NO: 692          moltype = RNA  length = 125
FEATURE                 Location/Qualifiers
source                  1..125
                        mol_type = other RNA
                        organism = synthetic construct
SEQUENCE: 692
cgggaccttc agcaccgcgg cggtcacccg ccgctcctgg gcaagggcga gggctgcgag  60
cccgccgccg aagctgacgc cgtggatgtc gatgcggcgc aggtcagggt acagggcgtg  120
ggcgg                                                              125

SEQ ID NO: 693          moltype = RNA  length = 125
FEATURE                 Location/Qualifiers
source                  1..125
                        mol_type = other RNA
                        organism = synthetic construct
SEQUENCE: 693
agcgtccagc cggacgtgcc cgacgtcgtg gccgagcacg tcctgcacgg catcgcctcg  60
cgcgagacgt acatcatcgg cgggtgcgtc caaggcgtgt gggccgcggt ctcagccgcc  120
cacgc                                                              125

SEQ ID NO: 694          moltype = RNA  length = 66
FEATURE                 Location/Qualifiers
source                  1..66
                        mol_type = other RNA
                        organism = synthetic construct
SEQUENCE: 694
aggtacatgg ccacgtggta gatcgcctgg atgtccgtct tggtcgggtc ggacgtgtag  60
tagatc                                                            66

SEQ ID NO: 695          moltype = RNA  length = 131
FEATURE                 Location/Qualifiers
source                  1..131
                        mol_type = other RNA
                        organism = synthetic construct
SEQUENCE: 695
catggtgaaa ctggcagact cccactgaac cattgggaac aggatacccg tgctggccga  60
gctttgccag gatagcaggc gccagcaact ggccttttgc tgtaggtata ccgtccttca  120
atgcggcccc c                                                       131

SEQ ID NO: 696          moltype = AA  length = 1139
FEATURE                 Location/Qualifiers
source                  1..1139
                        mol_type = protein
                        organism = synthetic construct
SEQUENCE: 696
IFVVLSVNQF RCNPNAFRQA SMKTDDEKKD TAIKSYTSWL LPNDRKEKDM VRSFLALDQG  60
SRFFFDLMQA WYGGLTPDII KSVTKERDLV DLWCAIYWFR PMKKELASHP IDRVDLAKTF  120
QRYYGGPASD VVQEYLSASI GEDCCWNDCR QKYQEFCKNL GVDFTPDLKT LVREKLIAVA  180
LNDGSQAAIS NLFGNGGKED RNVKVNICKK ILIALEKAGK SVKYVRDVQS IILKCANAKD  240
REDFNRIYAD KNGRPGTLLL LLDRKGENTY DAEVLKRYLR KTIKSKNAPL VWNYNQKLFE  300
YIERGIRNLL RRTINYDAWA WGEMWRVGHT PLQTKATRNY HFAQEQLKRH SDIAAASQSS  360
HAIAVALNEF FESPFFDGEN PFTICPHHLG KNLEKLFKAW ADEKNQTDEE DAGETAITDY  420
CAEFKDGFDR EPIRNLLRYV YASLRSKYSA KELIQAAKYN QQFERYQRQK AHPVTPDNQG  480
YTWPEAVIKP SKAERKNREN SLDTRIWVSV KLLQKDGTWE KHHIPFYNLR FFEEVYAAAS  540
IAEDMPSPTF RNSRFGFKLP KLLNTHAKIN KKKKDGKKDK KAVNAAKREA RIYLAAKEGR  600
LPAPSVPLDK LSAVIARVNG KFQVTVPVKF KVNKQPKYPL PQLGQIILGY DQNLTANHAW  660
ALFEVVTEDT PGAHFCRNQY LRVLKTGQVR SITKTKDGQE IDQLSYDGLE YKEYGEWRKQ  720
AKKFASQWYI TTKVRKGKET TLLSQPALER FESIEKYKPA LYRFNKEYAR LLLAVIRRKT  780
LNELEEIRPE IFRLVEQGFG ICRFGSLSLS SFEAIRAAKA VIYGYFSTAL KHDHNTPITD  840
DERQAFDPEL FGLLNKLETL RQNKGEEKIN RAANALIRIA LENKADFIRG EGDLPTTNKS  900
VKKGQNSRSM DWLARGLFNK ICQLAVMHNI IPTAANPHST SHQDPFEHNK DFDDPQPAMK  960
CRYAEFKIED IGDSVLERLG TSLRNAKAGQ TGAYYYKGAQ DFLAHYGLQD IEEELKKCRR  1020
GRKANMPCWE LQKRLIQKLG SKDAVVYIPM RGGRIYLATH SVTTGAKPII FNGEEVWVSN  1080
ADEIAAVNIG LTIIPTSKKD EEHPDRENDD KAIRKSVRRP RKSGERRSGD KMPATARKT   1139

SEQ ID NO: 697          moltype = DNA  length = 9375
FEATURE                 Location/Qualifiers
source                  1..9375
                        mol_type = other DNA
                        organism = synthetic construct
SEQUENCE: 697
```

gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggag tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900
gtttaaactt aagcttaccg gtgccaccat gccggcagct aagaaaaaga aactggatgg 960
cagcgtcgac atcttcgtgg tgctgagcgt gaatcagttc agatgcaacc ccaacgcctt 1020
cagacaagcc tccatgaaaa ccgacgacga gaagaaggac accgccatca agagctacac 1080
aagctggctg ctgcccaacg acagaaagga gaaggacatg gtgcggagct tcctggccct 1140
ggaccaaggc agcagattct ttttcgacct gatgcaagcc tggtacggcg gcctcacccc 1200
cgacatcatc aagagcgtga ccaaggagcg ggacctggtg gacctgtggt gcgccatcta 1260
ctggttcaga cccatgaaga aggagctggc ctcccacccc atcgacagag tggacctggc 1320
caagaccttt cagagatact acggcggccc cgcctccgac gtggtgcaag agtacctgag 1380
cgcctccatc ggcgaggact gctgctggaa cgactgcaga cagaagtacc aagagttctg 1440
caagaacctc ggggtggact tcacccccga cctcaagacc ctggtgagag agaagctgat 1500
cgccgtggcc ctgaacgacg gcagccaagc cgccatcagc aacctgttcg gcaacggcgg 1560
caaggaggac agaaacgtga aggtgaacat ctgcaagaag atcctgattg ctctggagaa 1620
ggccggcaaa tccgtgaagt acgtgcggga cgtgcagagc atcatcctga agtgcgccaa 1680
cgccaaggac agagaggact tcaacagaat ctacgccgac aagaacggca gacccggcac 1740
cctgctcctg ctcctggaca gaaagggcga gaacacctac gacgccgagg tgctgaagag 1800
atacctgaga aagaccatca agagcaagaa cgccccccctg gtgtggaact acaatcagaa 1860
gctgttcgag tacatcgaga gaggcatccg gaatctgctg agaagaacca tcaactacga 1920
cgcctgggcc tggggcgaga tgtggagagt gggccacacc cccctgcaga ccaaggccac 1980
aagaaactac cacttcgccc aagagcagct gaagagacac agcgacatcg ccgccgcttc 2040
ccaaagcagc cacgccatcg ccgtcgctct gaacgagttc ttcgagagcc ccttcttcga 2100
cggcgagaac cccttcacca tctgccccca ccacctgggc aagaacctgg aaaagctgtt 2160
caaggcctgg gccgacgaaa aaatcagac cgacgaggag gacgccggcg aaaccgccat 2220
caccgactac tgcgccgagt tcaaggacgg cttcgacaga gagcccatta gaaacctgct 2280
gagatacgtg tacgcttccc tgagaagcaa gtacagcgcc aaggagctga tccaagccgc 2340
caagtacaat cagcagttcg agagatatca gagacagaag gcccaccccg tgacccccga 2400
caaccaaggc tacacctggc ccgaggccgt gatcaagcct agcaaggccg agagaaagaa 2460
cagagagaac agcctggaca caagaatctg ggtgagcgtg aagctgctgc aaaaggacgg 2520
cacctgggag aagcaccaca tccccttcta caacctgaga ttcttcgaag aggtgtacgc 2580
cgctgcctcc atcgccgagg acatgcctag ccccaccttc agaaacagca gattcggctt 2640
caagctgccc aagctgctga acacccacgc caagatcaac aagaaaaaga aggacggcaa 2700
gaaggacaag aaggccgtga acgccgccaa gagagaggct agaatctacc tcgctgccaa 2760
ggagggcaga ctgcccgccc cctccgtgcc cctggacaag ctgagcgccg tgatcgctag 2820
agtgaacggc aagttccaag tgaccgtgcc cgtgaagttc aaggtgaaca agcagcccaa 2880
gtacccccctg cctcagctgg ggcagatcat cctgggctac gatcagaacc tgaccgccaa 2940
ccacgcctgg gccctgttcg aggtggtgac cgaggacacc cccggcgccc acttctgcag 3000
aaatcagtac ctgagagtgc tcaagaccgg ccaagtgaga agcatcacca agaccaagga 3060
cggccaagag atcgatcagc tgagctacga cggcctggag tacaaggagt acggcgagtg 3120
gagaaagcaa gccaagaagt tcgcctccca atggtacatc accaccaagg tgagaaaggg 3180
caaggaaacc accctgctga gccaacccgc cctggagaga ttcgagagca tcgagaagta 3240
caagcccgcc ctgtacagat tcaacaagga atacgcccgg ctgctcctgg ccgtcatcag 3300
aagaaagacc ctgaacgagc tggaggagat cagacccgag atcttcagac tggtggagca 3360
aggcttcggc atctgcagat tcggcagcct gagcctgagc agcttcgagg ccatcagagc 3420
cgccaaggcc gtgatctacg gctacttcag caccgccctg aagcacgacc acaacacccc 3480
catcacagat gacgagagac aagccttcga ccccgagctg ttcggcctgc tgaacaagct 3540
ggaaaccctg agacagaaca agggcgagga gaagatcaac agagccgcta acgccctgat 3600
cagaatcgcc ctggagaaca aggccgactt catcagaggc gagggcgacc tgcccaccac 3660
caacaagagc gtcaagaagg ggcagaacag cagaagcatg gactggctgg ctagaggcct 3720
gttcaacaag atctgtcagc tggccgtgat gcacaacatc attcccaccg ccgccaaccc 3780
ccacagcaca agccaccaag accccttcga gcacaacaag gacttcgacg accctcagcc 3840
cgccatgaag tgcagatacg ctgagttcaa gatcgaggac atcggcgaca gcgtgctgga 3900
gagactgggc acctccctga gaaatgccaa ggccgggcag accggcgcct actattacaa 3960
gggcgcccaa gacttcctgg cccactacgg cctgcaagac atcgaggaag agctgaagaa 4020
gtgcagaaga ggcagaaagg ccaacatgcc ctgctgggag ctgcagaaga gactgattca 4080
gaagctgggc agcaaggacg ccgtggtgta catccccatg agaggcggcc ggatctacct 4140
ggctacacac agcgtgacca ccggcgccaa gcccatcatc ttcaacggcg aagaggtgtg 4200
ggtgagcaac gccgacgaga tcgccgccgt gaacatcggc ctgaccatca tccccacaag 4260
caagaaggac gaggagcacc ccgacagaga gaacgacgac aaggccatca gaaagagcgt 4320
cagacggcct agaaagagcg gcgagagaag aagcggcgac aagatgcccg ccaccgctag 4380
aaagaccaca ggcggcggcc ccggcggcgg cgccgccgcc ggcagcggca gccctaagaa 4440
aaaacgaaaa gttggcagcg gaagcaaaag gccggcggcc acgaaaaagg ccggccaggc 4500
aaaaaagaaa aagctcgagt acccatacga tgttccagat tacgcttgag aattcccctt 4560
gagcatctga cttctggcta ataaaggaaa tttattttca ttgcaatagt gtgttggaat 4620
tttttgtgtc tctcaggtac caaaaacggc tcggagatca tcattgcggc gtcaatggga 4680
gacgcattac ggtgtttcgt cctttccaca agatatataa agccaagaaa tcgaaatact 4740

-continued

```
ttcaagttac ggtaagcata tgatagtcca ttttaaaaca taattttaaa actgcaaact  4800
acccaagaaa ttattacttt ctacgtcacg tattttgtac taatatcttt gtgtttacag  4860
tcaaattaat tccaattatc tctctaacag ccttgtatcg tatatgcaaa tatgaaggaa  4920
tcatgggaaa taggccctct agagggcccg tttaaacccg ctgatcagcc tcgactgtgc  4980
cttctagttg ccagccatct gttgtttgcc cctcccccgt gccttccttg accctggaag  5040
gtgccactcc cactgtcctt tcctaataaa atgaggaaat tgcatcgcat tgtctgagta  5100
ggtgtcattc tattctgggg ggtggggtgg ggcaggacag caagggggag gattgggaag  5160
acaatagcag gcatgctggg gatgcggtgg gctctatggc ttctgaggcg gaaagaacca  5220
gctggggctc taggggggtat ccccacgcgc cctgtagcgg cgcattaagc gcggcgggtg  5280
tggtggttac gcgcagcgtg accgctacac ttgccagcgc cctagcgccc gctcctttcg  5340
ctttcttccc ttcctttctc gccacgttcg ccggctttcc ccgtcaagct ctaaatcggg  5400
ggctcccttt agggttccga tttagtgctt tacggcacct cgaccccaaa aaacttgatt  5460
agggtgatgg ttcacgtagt gggccatcgc cctgatagac ggtttttcgc cctttgacgt  5520
tggagtccac gttctttaat agtggactct tgttccaaac tggaacaaca ctcaacccta  5580
tctcggtcta ttcttttgat ttataaggga ttttgccgat ttcggcctat tggttaaaaa  5640
atgagctgat ttaacaaaaa tttaacgcga attaattctg tggaatgtgt gtcagttagg  5700
gtgtggaaag tccccaggct ccccagcagg cagaagtatg caaagcatgc atctcaatta  5760
gtcagcaacc aggtgtggaa agtccccagg ctccccagca ggcagaagta tgcaaagcat  5820
gcatctcaat tagtcagcaa ccatagtccc gcccctaact ccgcccatcc cgcccctaac  5880
tccgcccagt tccgcccatt ctccgcccca tggctgacta attttttta tttatgcaga  5940
ggccgaggcc gcctctgcct ctgagctatt ccagaagtag tgaggaggct tttttggagg  6000
cctaggcttt tgcaaaaagc tcccgggagc ttgtatatcc attttcggat ctgatcaaga  6060
gacaggatga ggatcgtttc gcatgattga acaagatgga ttgcacgcag gttctccggc  6120
cgcttgggtg gagaggctat tcggctatga ctgggcacaa cagacaatcg gctgctctga  6180
tgccgccgtg ttccggctgt cagcgcaggg gcgcccggtt ctttttgtca agaccgacct  6240
gtccggtgcc ctgaatgaac tgcaggacga ggcagcgcgg ctatcgtggc tggccacgac  6300
gggcgttcct tgcgcagctg tgctcgacgt tgtcactgaa gcgggaaggg actggctgct  6360
attgggcgaa gtgccggggc aggatctcct gtcatctcac cttgctcctg ccgagaaagt  6420
atccatcatg gctgatgcaa tgcggcggct gcatacgctt gatccggcta cctgcccatt  6480
cgaccaccaa gcgaaacatc gcatcgagcg agcacgtact cggatggaag ccggtcttgt  6540
cgatcaggat gatctggacg aagagcatca ggggctcgcg ccagccgaac tgttcgccag  6600
gctcaaggcg cgcatgcccg acggcgagga tctcgtcgtg acccatggcg atgcctgctt  6660
gccgaatatc atggtggaaa atggccgctt ttctggattc atcgactgtg gccggctggg  6720
tgtggcggac cgctatcagg acatagcgtt ggctacccgt gatattgctg aagagcttgg  6780
cggcgaatgg gctgaccgct tcctcgtgct ttacggtatc gccgctcccg attcgcagcg  6840
catcgccttc tatcgccttc ttgacgagtt cttctgagcg ggactctggg gttcgaaatg  6900
accgaccaag cgacgcccaa cctgccatca cgagatttcg attccaccgc cgccttctat  6960
gaaaggttgg gcttcggaat cgttttccgg gacgccggct ggatgatcct ccagcgcggg  7020
gatctcatgc tggagttctt cgcccacccc aacttgttta ttgcagctta taatggttac  7080
aaataaagca atagcatcac aaatttcaca aataaagcat ttttttcact gcattctagt  7140
tgtggtttgt ccaaactcat caatgtatct tatcatgtct gtataccgtc gacctctagc  7200
tagagcttgg cgtaatcatg gtcatagctg tttcctgtgt gaaattgtta tccgctcaca  7260
attccacaca acatacgagc cggaagcata aagtgtaaag cctggggtgc ctaatgagtg  7320
agctaactca cattaattgc gttgcgctca ctgcccgctt tccagtcggg aaacctgtcg  7380
tgccagctgc attaatgaat cggccaacgc gcggggagag gcggtttgcg tattgggcgc  7440
tcttccgctt cctcgctcac tgactcgctg cgctcggtcg ttcggctgcg gcgagcggta  7500
tcagctcact caaaggcggt aatacggtta tccacagaat caggggataa cgcaggaaag  7560
aacatgtgag caaaaggcca gcaaaaggcc aggaaccgta aaaaggccgc gttgctggcg  7620
tttttccata ggctccgccc ccctgacgag catcacaaaa atcgacgctc aagtcagagg  7680
tggcgaaacc cgacaggact ataaagatac caggcgtttc cccctggaag ctccctcgtg  7740
cgctctcctg ttccgaccct gccgcttacc ggatacctgt ccgcctttct cccttcggga  7800
agcgtggcgc tttctcatag ctcacgctgt aggtatctca gttcggtgta ggtcgttcgc  7860
tccaagctgg gctgtgtgca cgaacccccc gttcagcccg accgctgcgc cttatccggt  7920
aactatcgtc ttgagtccaa cccggtaaga cacgacttat cgccactggc agcagccact  7980
ggtaacagga ttagcagagc gaggtatgta ggcggtgcta cagagttctt gaagtggtgg  8040
cctaactacg gctacactag aagaacagta tttggtatct gcgctctgct gaagccagtt  8100
accttcggaa aaagagttgg tagctcttga tccggcaaac aaaccaccgc tggtagcggt  8160
ttttttgttt gcaagcagca gattacgcgc agaaaaaaag gatctcaaga agatcctttg  8220
atcttttcta cggggtctga cgctcagtgg aacgaaaact cacgttaagg gattttggtc  8280
atgagattat caaaaaggat cttcacctag atccttttaa attaaaaatg aagttttaaa  8340
tcaatctaaa gtatatatga gtaaacttgg tctgacagtt accaatgctt aatcagtgag  8400
gcacctatct cagcgatctg tctatttcgt tcatccatag ttgcctgact ccccgtcgtg  8460
tagataacta cgatacggga gggcttacca tctggcccca gtgctgcaat gataccgcga  8520
gacccacgct caccggctcc agatttatca gcaataaacc agccagccgg aagggccgag  8580
cgcagaagtg gtcctgcaac tttatccgcc tccatccagt ctattaattg ttgccgggaa  8640
gctagagtaa gtagttcgcc agttaatagt ttgcgcaacg ttgttgccat tgctacaggc  8700
atcgtggtgt cacgctcgtc gtttggtatg gcttcattca gctccggttc ccaacgatca  8760
aggcgagtta catgatcccc catgttgtgc aaaaaagcgg ttagctcctt cggtcctccg  8820
atcgttgtca gaagtaagtt ggccgcagtg ttatcactca tggttatggc agcactgcat  8880
aattctctta ctgtcatgcc atccgtaaga tgcttttctg tgactggtga gtactcaacc  8940
aagtcattct gagaatagtg tatgcggcga ccgagttgct cttgcccggc gtcaatacgg  9000
gataataccg cgccacatag cagaacttta aaagtgctca tcattggaaa acgttcttcg  9060
gggcgaaaac tctcaaggat cttaccgctg ttgagatcca gttcgatgta acccactcgt  9120
gcacccaact gatcttcagc atcttttact ttcaccagcg tttctgggtg agcaaaaaca  9180
ggaaggcaaa atgccgcaaa aaagggaata agggcgacac ggaaatgttg aatactcata  9240
ctcttccttt ttcaatatta ttgaagcatt tatcagggtt attgtctcat gagcggatac  9300
atatttgaat gtatttagaa aaataaacaa ataggggttc cgcgcacatt tccccgaaaa  9360
gtgccacctg acgtc                                                   9375
```

```
SEQ ID NO: 698          moltype = DNA  length = 8956
FEATURE                 Location/Qualifiers
source                  1..8956
                        mol_type = other DNA
                        organism = synthetic construct
SEQUENCE: 698
tggcgaatgg gacgcgccct gtagcggcgc attaagcgcg gcgggtgtgg tggttacgcg  60
cagcgtgacc gctacacttg ccagcgccct agcgcccgct cctttcgctt tcttcccttc  120
ctttctcgcc acgttcgccg gctttccccg tcaagctcta aatcgggggc tccctttagg  180
gttccgattt agtgctttac ggcacctcga ccccaaaaaa cttgattagg gtgatggttc  240
acgtagtggg ccatcgccct gatagacggt ttttcgccct ttgacgttgg agtccacgtt  300
ctttaatagt ggactcttgt tccaaactgg aacaacactc aaccctatct cggtctattc  360
ttttgattta taagggattt tgccgatttc ggcctattgg ttaaaaaatg agctgattta  420
acaaaaattt aacgcgaatt ttaacaaaat attaacgttt acaatttcag gtggcacttt  480
tcggggaaat gtgcgcggaa cccctatttg tttatttttc taaatacatt caaatatgta  540
tccgctcatg aattaattct tagaaaaact catcgagcat caaatgaaac tgcaatttat  600
tcatatcagg attatcaata ccatattttt gaaaaagccg tttctgtaat gaaggagaaa  660
actcaccgag gcagttccat aggatggcaa gatcctggta tcggtctgcg attccgactc  720
gtccaacatc aatacaacct attaatttcc cctcgtcaaa aataaggtta tcaagtgaga  780
aatcaccatg agtgacgact gaatccggtg agaatggcaa aagtttatgc atttctttcc  840
agacttgttc aacaggccag ccattacgct cgtcatcaaa atcactcgca tcaaccaaac  900
cgttattcat tcgtgattgc gcctgagcga gacgaaatac gcgatcgctg ttaaaaggac  960
aattacaaac aggaatcgaa tgcaaccggc gcaggaacac tgccagcgca tcaacaatat  1020
tttcacctga atcaggatat tcttctaata cctggaatgc tgttttcccg gggatcgcag  1080
tggtgagtaa ccatgcatca tcaggagtac ggataaaatg cttgatggtc ggaagaggca  1140
taaattccgt cagccagttt agtctgacca tctcatctgt aacatcattg gcaacgctac  1200
ctttgccatg tttcagaaac aactctggcg catcgggctt cccatacaat cgatagattg  1260
tcgcacctga ttgcccgaca ttatcgcgag cccatttata cccatataaa tcagcatcca  1320
tgttggaatt taatcgcggc ctagagcaag acgtttcccg ttgaatatgg ctcataacac  1380
cccttgtatt actgtttatg taagcagaca gttttattgt tcatgaccaa aatcccttaa  1440
cgtgagtttt cgttccactg agcgtcagac cccgtagaaa agatcaaagg atcttcttga  1500
gatccttttt ttctgcgcgt aatctgctgc ttgcaaacaa aaaaaccacc gctaccagcg  1560
gtggtttgtt tgccggatca agagctacca actctttttc cgaaggtaac tggcttcagc  1620
agagcgcaga taccaaatac tgtccttcta gtgtagccgt agttaggcca ccacttcaag  1680
aactctgtag caccgcctac atacctcgct ctgctaatcc tgttaccagt ggctgctgcc  1740
agtggcgata agtcgtgtct taccgggttg gactcaagac gatagttacc ggataaggcg  1800
cagcggtcgg gctgaacggg gggttcgtgc acacagccca gcttggagcg aacgacctac  1860
accgaactga gatacctaca gcgtgagcta tgagaaagcg ccacgcttcc cgaagggaga  1920
aaggcggaca ggtatccggt aagcggcagg gtcggaacag gagagcgcac gagggagctt  1980
ccagggggaa acgcctggta tctttatagt cctgtcgggt ttcgccacct ctgacttgag  2040
cgtcgatttt tgtgatgctc gtcagggggg cggagcctat ggaaaaacgc cagcaacgcg  2100
gcctttttac ggttcctggc cttttgctgg ccttttgctc acatgttctt tcctgcgtta  2160
tcccctgatt ctgtggataa ccgtattacc gcctttgagt gagctgatac cgctcgccgc  2220
agccgaacga ccgagcgcag cgagtcagtg agcgaggaag cggaagagcg cctgatgcgg  2280
tattttctcc ttacgcatct gtgcggtatt tcacaccgca tatatggtgc actctcagta  2340
caatctgctc tgatgccgca tagttaagcc agtatacact ccgctatcgc tacgtgactg  2400
ggtcatggct gcgccccgac acccgccaac acccgctgac gcgccctgac gggcttgtct  2460
gctcccggca tccgcttaca gacaagctgt gaccgtctcc gggagctgca tgtgtcagag  2520
gttttcaccg tcatcaccga aacgcgcgag gcagctgcgg taaagctcat cagcgtggtc  2580
gtgaagcgat tcacagatgt ctgcctgttc atccgcgtcc agctcgttga gtttctccag  2640
aagcgttaat gtctggcttc tgataaagcg ggccatgtta agggcggttt tttcctgttt  2700
ggtcactgat gcctccgtgt aagggggatt tctgttcatg ggggtaatga taccgatgaa  2760
acgagagagg atgctcacga tacgggttac tgatgatgaa catgcccggt tactggaacg  2820
ttgtgagggt aaacaactgg cggtatggat gcggcgggac cagagaaaaa tcactcaggg  2880
tcaatgccag cgcttcgtta atacagatgt aggtgttcca cagggtagcc agcagcatcc  2940
tgcgatgcag atccggaaca taatggtgca gggcgctgac ttccgcgttt ccagacttta  3000
cgaaacacgg aaaccgaaga ccattcatgt tgttgctcag gtcgcagacg ttttgcagca  3060
gcagtcgctt cacgttcgct cgcgtatcgg tgattcattc tgctaaccag taaggcaacc  3120
ccgccagcct agccgggtcc tcaacgacag gagcacgatc atgcgcaccc gtggggccgc  3180
catgccggcg ataatggcct gcttctcgcc gaaacgtttg gtggcgggac cagtgacgaa  3240
ggcttgagcg agggcgtgca agattccgaa taccgcaagc gacaggccga tcatcgtcgc  3300
gctccagcga aagcggtcct cgccgaaaat gacccagagc gctgccggca cctgtcctac  3360
gagttgcatg ataaagaaga cagtcataag tgcggcgacg atagtcatgc cccgcgccca  3420
ccggaaggag ctgactgggt tgaaggctct caagggcatc ggtcgagatc ccggtgccta  3480
atgagtgagc taacttacat taattgcgtt gcgctcactg cccgctttcc agtcgggaaa  3540
cctgtcgtgc cagctgcatt aatgaatcgg ccaacgcgcg gggagaggcg gtttgcgtat  3600
tgggcgccag ggtggttttt cttttcacca gtgagacggg caacagctga ttgcccttca  3660
ccgcctggcc ctgagagagt tgcagcaagc ggtccacgct ggtttgcccc agcaggcgaa  3720
aatcctgttt gatggtggtt aacggcggga tataacatga gctgtcttcg gtatcgtcgt  3780
atcccactac cgagatatcc gcaccaacgc gcagcccgga ctcggtaatg gcgcgcattg  3840
cgcccagcgc catctgatcg ttggcaacca gcatcgcagt gggaacgatg ccctcattca  3900
gcatttgcat ggtttgttga aaaccggaca tggcactcca gtcgccttcc cgttccgcta  3960
tcggctgaat ttgattgcga gtgagatatt tatgccagcc agccagacgc agacgcgccg  4020
agacagaact taatgggccc gctaacagcg cgatttgctg gtgacccaat gcgaccagat  4080
gctccacgcc cagtcgcgta ccgtcttcat gggagaaaat aatactgttg atgggtgtct  4140
ggtcagagac atcaagaaat aacgccggaa cattagtgca ggcagcttcc acagcaatgg  4200
catcctggtc atccagcgga tagttaatga tcagcccact gacgcgttgc gcgagaagat  4260
tgtgcaccgc cgctttacag gcttcgacgc cgcttcgttc taccatcgac accaccacgc  4320
tggcacccag ttgatcggcg cgagatttaa tcgccgcgac aatttgcgac ggcgcgtgca  4380
```

```
gggccagact ggaggtggca acgccaatca gcaacgactg tttgcccgcc agttgttgtg  4440
ccacgcggtt gggaatgtaa ttcagctccg ccatcgccgc ttccactttt tcccgcgttt  4500
tcgcagaaac gtggctggcc tggttcacca cgcgggaaac ggtctgataa gagacaccgg  4560
catactctgc gacatcgtat aacgttactg gtttcacatt caccaccctg aattgactct  4620
cttccgggcg ctatcatgcc ataccgcgaa aggttttgcg ccattcgatg gtgtccggga  4680
tctcgacgct ctcccttatg cgactcctgc attaggaagc agcccagtag taggttgagg  4740
ccgttgagca ccgccgccgc aaggaatggt gcatgcaagg agatggcgcc caacagtccc  4800
ccggccacgg ggcctgccac catacccacg ccgaaacaag cgctcatgag cccgaagtgg  4860
cgagcccgat cttccccatc ggtgatgtcg gcgatatagg cgccagcaac cgcacctgtg  4920
gcgccggtga tgccggccac gatgcgtccg gcgtagagga tcgagatctc gatcccgcga  4980
aattaatacg actcactata ggggaattgt gagcggataa caattcccct ctagaaataa  5040
ttttgtttaa ctttaagaag gagatatacc atgggcagca gccatcatca tcatcatcac  5100
agcagcggcc tggtgccgcg cggcagccat atggctagca tgactggtgg acagcaaatg  5160
ggtcgcggat ccatgccggc agctaagaaa aagaaactgg atggcagcgt cgacatcttc  5220
gtggtgctga gcgtgaatca gttcagatgc aaccccaacg ccttcagaca agcctccatg  5280
aaaaccgacg acgagaagaa ggacaccgcc atcaagagct acacaagctg gctgctgccc  5340
aacgacagaa aggagaagga catggtgcgg agcttcctgg ccctggacca aggcagcaga  5400
ttctttttcg acctgatgca agcctggtac ggcggcctca cccccgacat catcaagagc  5460
gtgaccaagg agcgggacct ggtggacctg tggtgcgcca tctactggtt cagacccatg  5520
aagaaggagc tggcctccca ccccatcgac agagtggacc tggccaagac ctttcagaga  5580
tactacggcg gccccgcctc cgacgtggtg caagagtacc tgagcgcctc catcggcgag  5640
gactgctgct ggaacgactg cagacagaag taccaagagt tctgcaagaa cctcggggtg  5700
gacttcaccc ccgacctcaa gaccctggtg agagagaagc tgatcgccgt ggccctgaac  5760
gacggcagcc aagccgccat cagcaacctg ttcggcaacg gcggcaagga ggacagaaac  5820
gtgaaggtga acatctgcaa gaagatcctg attgctctgg agaaggccgg caaatccgtg  5880
aagtacgtgc gggacgtgca gagcatcatc ctgaagtgcg ccaacgccaa ggacagagag  5940
gacttcaaca gaatctacgc cgacaagaac ggcagacccg gcaccctgct cctgctcctg  6000
gacagaaagg gcgagaacac ctacgacgcc gaggtgctga agagatacct gagaaagacc  6060
atcaagagca agaacgcccc cctggtgtgg aactacaatc agaagctgtt cgagtacatc  6120
gagagaggca tccggaatct gctgagaaga accatcaact acgacgcctg ggcctggggc  6180
gagatgtgga gagtgggcca caccccctg cagaccaagg ccacaagaaa ctaccacttc  6240
gcccaagagc agctgaagag acacagcgac atcgccgccg cttcccaaag cagccacgcc  6300
atcgccgtcg ctctgaacga gttcttcgag agcccttct tcgacggcga gaaccccttc  6360
accatctgcc cccaccacct gggcaagaac ctggaaaagc tgttcaaggc ctgggccgac  6420
gaaaaaaatc agaccgacga ggaggacgcc ggcgaaaccg ccatcaccga ctactgcgcc  6480
gagttcaagg acggcttcga cagagagccc attagaaacc tgctgagata cgtgtacgct  6540
tccctgagaa gcaagtacag cgccaaggag ctgatccaag ccgccaagta caatcagcag  6600
ttcgagagat atcagagaca gaaggcccac cccgtgaccc ccgacaacca aggctacacc  6660
tggcccgagg ccgtgatcaa gcctagcaag gccgagagaa agaacagaga gaacagcctg  6720
gacacaagaa tctgggtgag cgtgaagctg ctgcaaaagg acggcacctg ggagaagcac  6780
cacatcccct tctacaacct gagattcttc gaagaggtgt acgccgctgc ctccatcgcc  6840
gaggacatgc ctagccccac cttcagaaac agcagattcg gcttcaagct gcccaagctg  6900
ctgaacaccc acgccaagat caacaagaaa aagaaggacg gcaagaagga caagaaggcc  6960
gtgaacgccg ccaagagaga ggctagaatc tacctcgctg ccaaggaggg cagactgccc  7020
gcccctccg tgcccctgga caagctgagc gccgtgatcg ctagagtgaa cggcaagttc  7080
caagtgaccg tgcccgtgaa gttcaaggtg aacaagcagc ccaagtaccc cctgcctcag  7140
ctggggcaga tcatcctggg ctacgatcag aacctgaccg ccaaccacgc ctgggccctg  7200
ttcgaggtgg tgaccgagga cacccccggc gcccacttct gcagaaatca gtacctgaga  7260
gtgctcaaga ccggccaagt gagaagcatc accaagacca aggacggcca agagatcgat  7320
cagctgagct acgacggcct ggagtacaag gagtacggcg agtggagaaa gcaagccaag  7380
aagttcgcct cccaatggta catcaccacc aaggtgagaa agggcaagga aaccaccctg  7440
ctgagccaac ccgccctgga gagattcgag agcatcgaga agtacaagcc cgccctgtac  7500
agattcaaca aggaatacgc ccggctgctc ctggccgtca tcagaagaaa gaccctgaac  7560
gagctggagg agatcagacc cgagatcttc agactggtgg agcaaggctt cggcatctgc  7620
agattcggca gcctgagcct gagcagcttc gaggccatca gagccgccaa ggccgtgatc  7680
tacggctact tcagcaccgc cctgaagcac gaccacaaca cccccatcac agatgacgag  7740
agacaagcct tcgaccccga gctgttcggc ctgctgaaca agctggaaac cctgagacag  7800
aacaagggcg aggagaagat caacagagcc gctaacgccc tgatcagaat cgccctggag  7860
aacaaggccg acttcatcag aggcgagggc gacctgccca ccaccaacaa gagcgtcaag  7920
aaggggcaga acagcagaag catggactgg ctggctagag gcctgttcaa caagatctgt  7980
cagctggccg tgatgcacaa catcattccc accgccgcca acccccacag cacaagccac  8040
caagacccct tcgagcacaa caaggacttc gacgaccctc agcccgccat gaagtgcaga  8100
tacgctgagt tcaagatcga ggacatcggc gacagcgtgc tggagagact gggcacctcc  8160
ctgagaaatg ccaaggccgg gcagaccggc gcctactatt acaagggcgc ccaagacttc  8220
ctggcccact acggcctgca agacatcgag gaagagctga agaagtgcag aagaggcaga  8280
aaggccaaca tgccctgctg ggagctgcag aagagactga ttcagaagct gggcagcaag  8340
gacgccgtgg tgtacatccc catgagaggc ggccggatct acctggctac acacagcgtg  8400
accaccggcg ccaagcccat catcttcaac ggcgaagagg tgtgggtgag caacgccgac  8460
gagatcgccg ccgtgaacat cggcctgacc atcatcccca caagcaagaa ggacgaggag  8520
caccccgaca gagagaacga cgacaaggcc atcagaaaga gcgtcagacg gcctagaaag  8580
agcggcgaga gaagaagcgg cgacaagatg cccgccaccg ctagaaagac cacaggcggc  8640
ggccccggcg gcggcgccgc cgccggcagc ggcagcccta agaaaaaacg aaaagttggc  8700
agcggaagca aaaggccggc ggccacgaaa aaggccggcc aggcaaaaaa gaaaaagctc  8760
gagtacccat acgatgttcc agattacgct tgactcgagc accaccacca ccaccactga  8820
gatccggctg ctaacaaagc ccgaaaggaa gctgagttgg ctgctgccac cgctgagcaa  8880
taactagcat aaccccttgg ggcctctaaa cgggtcttga ggggtttttt gctgaaagga  8940
ggaactatat ccggat                                                 8956
```

SEQ ID NO: 699 moltype = DNA length = 51

```
FEATURE                Location/Qualifiers
source                 1..51
                       mol_type = other DNA
                       organism = synthetic construct
SEQUENCE: 699
tggacagcaa atgggtcgcg gatccatgcc ggcagctaag aaaaagaaac t           51

SEQ ID NO: 700         moltype = DNA  length = 55
FEATURE                Location/Qualifiers
source                 1..55
                       mol_type = other DNA
                       organism = synthetic construct
SEQUENCE: 700
tctcagtggt ggtggtggtg gtgctcgagt caagcgtaat ctggaacatc gtatg       55

SEQ ID NO: 701         moltype = DNA  length = 273
FEATURE                Location/Qualifiers
source                 1..273
                       mol_type = other DNA
                       organism = synthetic construct
SEQUENCE: 701
ggagttcaga cgtgtgctct tccgatctca gcacaaaagg aaactcaccc taactgtaaa  60
gtaattgtgt gttttgagac tataaatatg catgcgagaa aagccttgtt tgccaccatg  120
gaacggctcg gagatcatca ttgcgnnnnn nngtgagcaa gggcgaggag ctgttcaccg  180
gggtggtgcc catcctggtc gagctggacg gcgacgtaaa cggccacaag ttcagcgtgt  240
ccggcagatc ggaagagcac acgtctgaac tcc                               273

SEQ ID NO: 702         moltype = RNA  length = 46
FEATURE                Location/Qualifiers
source                 1..46
                       mol_type = other RNA
                       organism = synthetic construct
SEQUENCE: 702
gtaatgcgtc tcccattgac gcgtgagcaa gggcgaggag ctgttc                 46

SEQ ID NO: 703         moltype = RNA  length = 48
FEATURE                Location/Qualifiers
source                 1..48
                       mol_type = other RNA
                       organism = synthetic construct
SEQUENCE: 703
gtaatgcgtc tcccattgac gccgcaatga tgatctccga gccgttcc               48

SEQ ID NO: 704         moltype = RNA  length = 22
FEATURE                Location/Qualifiers
source                 1..22
                       mol_type = other RNA
                       organism = synthetic construct
SEQUENCE: 704
gtaatgcgtc tcccattgac gc                                           22

SEQ ID NO: 705         moltype = DNA  length = 59
FEATURE                Location/Qualifiers
source                 1..59
                       mol_type = other DNA
                       organism = synthetic construct
SEQUENCE: 705
gttgacatgc tggattgaga cttcctacac tctttcccta cacgacgctc ttccgatct   59

SEQ ID NO: 706         moltype = DNA  length = 58
FEATURE                Location/Qualifiers
source                 1..58
                       mol_type = other DNA
                       organism = synthetic construct
SEQUENCE: 706
gatcggaaga gcgtcgtgta gggaaagagt gtaggaagtc tcaatccagc atgtcaac    58

SEQ ID NO: 707         moltype = DNA  length = 19
FEATURE                Location/Qualifiers
source                 1..19
                       mol_type = other DNA
                       organism = synthetic construct
SEQUENCE: 707
ggagttcaga cgtgtgctc                                               19

SEQ ID NO: 708         moltype = DNA  length = 24
FEATURE                Location/Qualifiers
source                 1..24
                       mol_type = other DNA
```

organism = synthetic construct
SEQUENCE: 708
gttgacatgc tggattgaga cttc 24

SEQ ID NO: 709 moltype = DNA length = 58
FEATURE Location/Qualifiers
source 1..58
mol_type = other DNA
organism = synthetic construct
SEQUENCE: 709
aatgatacgg cgaccaccga gatctacact atagcctaca ctctttccct acacgacg 58

SEQ ID NO: 710 moltype = DNA length = 57
FEATURE Location/Qualifiers
source 1..57
mol_type = other DNA
organism = synthetic construct
SEQUENCE: 710
caagcagaag acggcatacg agatcgagta atgtgactgg agttcagacg tgtgctc 57

SEQ ID NO: 711 moltype = DNA length = 8057
FEATURE Location/Qualifiers
source 1..8057
mol_type = other DNA
organism = synthetic construct
SEQUENCE: 711
tgtagtctta tgcaatactc ttgtagtctt gcaacatggt aacgatgagt tagcaacatg 60
ccttacaagg agagaaaaag caccgtgcat gccgattggt ggaagtaagg tggtacgatc 120
gtgccttatt aggaaggcaa cagacgggtc tgacatggat tggacgaacc actgaattgc 180
cgcattgcag agatattgta tttaagtgcc tagctcgata cataaacggg tctctctggt 240
tagaccagat ctgagcctgg gagctctctg gctaactagg gaacccactg cttaagcctc 300
aataaagctt gccttgagtg cttcaagtag tgtgtgcccg tctgttgtgt gactctggta 360
actagagatc cctcagaccc ttttagtcag tgtggaaaat ctctagcagt ggcgcccgaa 420
cagggacttg aaagcgaaag ggaaaccaga ggagctctct cgacgcagga ctcggcttgc 480
tgaagcgcgc acggcaagag gcgaggggcg gcgactggtg agtacgccaa aaattttgac 540
tagcggaggc tagaaggaga gagatgggtg cgagagcgtc agtattaagc gggggagaat 600
tagatcgcga tgggaaaaaa ttcggttaag gccaggggga aagaaaaaat ataaattaaa 660
acatatagta tgggcaagca gggagctaga acgattcgca gttaatcctg gcctgttaga 720
aacatcagaa ggctgtagac aaatactggg acagctacaa ccatcccttc agacaggatc 780
agaagaactt agatcattat ataatacagt agcaaccctc tattgtgtgc atcaaaggat 840
agagataaaa gacaccaagg aagctttaga caagatagag gaagagcaaa acaaaagtaa 900
gaccaccgca cagcaagcgg ccactgatct tcagacctgg aggaggagat atgagggaca 960
attggagaag tgaattatat aaatataaag tagtaaaaat tgaaccatta ggagtagcac 1020
ccaccaaggc aaagagaaga gtggtgcaga gagaaaaaag agcagtggga ataggagctt 1080
tgttccttgg gttcttggga gcagcaggaa gcactatggg cgcagcgtca atgacgctga 1140
cggtacaggc cagacaatta ttgtctggta tagtgcagca gcagaacaat ttgctgaggg 1200
ctattgaggc gcaacagcat ctgttgcaac tcacagtctg gggcatcaag cagctccagg 1260
caagaatcct ggctgtggaa agatacctaa aggatcaaca gctcctgggg atttggggtt 1320
gctctggaaa actcatttgc accactgctg tgccttggaa tgctagttgg agtaataaat 1380
ctctggaaca gatttggaat cacacgacct ggatggagtg ggacagagaa attaacaatt 1440
acacaagctt aatacactcc ttaattgaag aatcgcaaaa ccagcaagaa aagaatgaac 1500
aagaattatt ggaattagat aaatgggcaa gtttgtggaa ttggtttaac ataacaaatt 1560
ggctgtggta tataaaatta ttcataatga tagtaggagg cttggtaggt ttaagaatag 1620
tttttgctgt actttctata gtgaatagag ttaggcaggg atattcacca ttatcgtttc 1680
agacccacct cccaaccccg aggggacccg acaggcccga aggaatagaa gaagaaggtg 1740
gagagagaga cagagacaga tccattcgat tagtgaacgg atctcgacgg tatcggttaa 1800
cttttaaaag aaaagggggg attggggggt acagtgcagg ggaaagaata gtagacataa 1860
tagcaacaga catacaaact aaagaattac aaaaacaaat tacaaaattc aaaattttat 1920
cgatactagt attatgccca gtacatgacc ttatgggact ttcctacttg gcagtacatc 1980
tacgtattag tcatcgctat taccatggtg atgcggtttt ggcagtacat caatgggcgt 2040
ggatagcggt ttgactcacg gggatttcca agtctccacc ccattgacgt caatgggagt 2100
ttgttttggc accaaaatca acgggacttt ccaaaatgtc gtaacaactc cgccccattg 2160
acgcaaatgg gcggtaggcg tgtacggtgg gaggtttata taagcagagc tcgtttagtg 2220
aaccgtcaga tcgcctggag acgccatcca cgctgttttg acctccatag aagattctag 2280
agctagcgaa ttgggatccc tagagatccg acgccgccat ctctaggccc gcgccggccc 2340
cctcgcacag acttgtggga gaagctcggc tactcccctg ccccggttaa tttgcatata 2400
atatttccta gtaactatag aggcttaatg tgcgataaaa gacagataat ctgttctttt 2460
taatactagc tacattttac atgataggct tggatttcta taagagatac aaatactaaa 2520
ttattatttt aaaaaacagc acaaaaggaa actcacccta actgtaaagt aattgtgtgt 2580
tttgagacta taaatatgca tgcgagaaaa gccttgtttg ccaccatgga acggctcgga 2640
gatatccagc gtacggctct catcaactcc actggggaag aagtggccat gcgcaagctg 2700
gtgcgctcag tgactgtggt tgaggacgac gaggatgagg atggagatga cctgctccat 2760
caccaccacg gctcccactg cagcagctcg ggggaccccg ctgagtacaa cctgcgctcg 2820
cgcaccgtgc tgtgcgggac ctgcgggcag cctgccgaca aggcatctgc cagcggctca 2880
ggagcccagg tgggcggacc catctcctct ggctcttctg cctccagtgt cacggtcact 2940
cgcagctacc gcagtgtggg gggcagtggg ggtggcagct tcggggacaa tctggtcacc 3000
cgctcctacc tcctgggcaa ctccagcccc cgaacccaga gcccccagaa ctgcagcatc 3060
atgtaatctg tctagaagaa ttcctcgagg cggccgctaa atagttgaat ttaaatagat 3120
ctccagcaca gtggtaaata gttgattcga acaaggatct gcgatcgctc cggtgcccgt 3180

-continued

```
cagtgggcag agcgcacatc gcccacagtc cccgagaagt tggggggagg ggtcggcaat  3240
tgaacgggtg cctagagaag gtggcgcggg gtaaactggg aaagtgatgt cgtgtactgg  3300
ctccgccttt ttcccgaggg tgggggagaa ccgtatataa gtgcagtagt cgccgtgaac  3360
gttctttttc gcaacgggtt tgccgccaga acacagctga agcttcgagg ggctcgcatc  3420
tctccttcac gcgcccgccg ccctacctga ggccgccatc cacgccggtt gagtcgcgtt  3480
ctgccgcctc ccgcctgtgg tgcctcctga actgcgtccg ccgtctaggt aagtttaaag  3540
ctcaggtcga gaccgggcct ttgtccggcg ctcccttgga gcctacctag actcagccgg  3600
ctctccacgc tttgcctgac cctgcttgct caactctacg tctttgtttc gttttctgtt  3660
ctgcgccgtt acagatccaa gctgtgaccg gcgcctacgc ccatgggcat ggccaagcct  3720
ttgtctcaag aagaatccac cctcattgaa agagcaacgg ctacaatcaa cagcatcccc  3780
atctctgaag actacagcgt cgccagcgca gctctctcta gcgacggccg catcttcact  3840
ggtgtcaatg tatatcattt tactggggga ccttgtgcag aactcgtggt gctgggcact  3900
gctgctgctg cggcagctgg caacctgact tgtatcgtcg cgatcggaaa tgagaacagg  3960
ggcatcttga gcccctgcgg acggtgccga caggtgcttc tcgatctgca tcctgggatc  4020
aaagccatag tgaaggacag tgatggacag ccgacggcag ttgggattcg tgaattgctg  4080
ccctctggtt atgtgtggga gggctaagca caattcgagc tcgcgtcgac aatcaacctc  4140
tggattacaa aatttgtgaa agattgactg gtattcttaa ctatgttgct ccttttacgc  4200
tatgtggata cgctgcttta atgcctttgt atcatgctat tgcttcccgt atggctttca  4260
ttttctcctc cttgtataaa tcctggttgc tgtctcttta tgaggagttg tggcccgttg  4320
tcaggcaacg tggcgtggtg tgcactgtgt ttgctgacgc aacccccact ggttggggca  4380
ttgccaccac ctgtcagctc ctttccggga ctttcgcttt ccccctccct attgccacgg  4440
cggaactcat cgccgcctgc cttgcccgct gctggacagg ggctcggctg ttgggcactg  4500
acaattccgt ggtgttgtcg gggaaatcat cgtcctttcc ttggctgctc gcctgtgttg  4560
ccacctggat tctgcgcggg acgtccttct gctacgtccc ttcggccctc aatccagcgg  4620
accttccttc ccgcggcctg ctgccggctc tgcggcctct tccgcgtctt cgccttcgcc  4680
ctcagacgag tcggatctcc ctttgggccg cctccccgcc tggtaccttt aagaccaatg  4740
acttacaagg cagctgtaga tcttagccac tttttaaaag aaaagggggg actggaaggg  4800
ctaattcact cccaacgaag ataagatctg ctttttgctt gtactgggtc tctctggtta  4860
gaccagatct gagcctggga gctctctggc taactaggga acccactgct taagcctcaa  4920
taaagcttgc cttgagtgct tcaagtagtg tgtgcccgtc tgttgtgtga ctctggtaac  4980
tagagatccc tcagaccctt ttagtcagtg tggaaaatct ctagcagtag tagttcatgt  5040
catcttatta ttcagtattt ataacttgca aagaaatgaa tatcagagag tgagaggaac  5100
ttgtttattg cagcttataa tggttacaaa taaagcaata gcatcacaaa tttcacaaat  5160
aaagcatttt tttcactgca ttctagttgt ggtttgtcca aactcatcaa tgtatcttat  5220
catgtctggc tctagctatc ccgcccctaa ctccgcccat cccgccccta actccgccca  5280
gttccgccca ttctccgccc catggctgac taattttttt tatttatgca gaggccgagg  5340
ccgcctcggc ctctgagcta ttccagaagt agtgaggagg cttttttgga ggcctagact  5400
tttgcagaga ccaaattcgt aatcatgtca tagctgtttc ctgtgtgaaa ttgttatccg  5460
ctcacaattc cacacaacat acgagccgga agcataaagt gtaaagcctg gggtgcctaa  5520
tgagtgagct aactcacatt aattgcgttg cgctcactgc ccgctttcca gtcgggaaac  5580
ctgtcgtgcc agctgcatta atgaatcggc caacgcgcgg ggagaggcgg tttgcgtatt  5640
gggcgctctt ccgcttcctc gctcactgac tcgctgcgct cggtcgttcg gctgcggcga  5700
gcggtatcag ctcactcaaa ggcggtaata cggttatcca cagaatcagg ggataacgca  5760
ggaaagaaca tgtgagcaaa aggccagcaa aaggccagga accgtaaaaa ggccgcgttg  5820
ctggcgtttt tccataggct ccgcccccct gacgagcatc acaaaaatcg acgctcaagt  5880
cagaggtggc gaaacccgac aggactataa agataccagg cgtttccccc tggaagctcc  5940
ctcgtgcgct ctcctgttcc gaccctgccg cttaccggat acctgtccgc ctttctccct  6000
tcgggaagcg tggcgctttc tcatagctca cgctgtaggt atctcagttc ggtgtaggtc  6060
gttcgctcca agctgggctg tgtgcacgaa ccccccgttc agcccgaccg ctgcgcctta  6120
tccggtaact atcgtcttga gtccaacccg gtaagacacg acttatcgcc actggcagca  6180
gccactggta acaggattag cagagcgagg tatgtaggcg gtgctacaga gttcttgaag  6240
tggtggccta actacggcta cactagaaga acagtatttg gtatctgcgc tctgctgaag  6300
ccagttacct tcggaaaaag agttggtagc tcttgatccg gcaaacaaac caccgctggt  6360
agcggtggtt tttttgtttg caagcagcag attacgcgca gaaaaaaagg atctcaagaa  6420
gatcctttga tcttttctac ggggtctgac gctcagtgga acgaaaactc acgttaaggg  6480
attttggtca tgagattatc aaaaaggatc ttcacctaga tccttttaaa ttaaaaatga  6540
agttttaaat caatctaaag tatatatgag taaacttggt ctgacagtta ccaatgctta  6600
atcagtgagg cacctatctc agcgatctgt ctatttcgtt catccatagt tgcctgactc  6660
cccgtcgtgt agataactac gatacgggag ggcttaccat ctggccccag tgctgcaatg  6720
ataccgcgag acccacgctc accggctcca gatttatcag caataaacca gccagccgga  6780
agggccgagc gcagaagtgg tcctgcaact ttatccgcct ccatccagtc tattaattgt  6840
tgccgggaag ctagagtaag tagttcgcca gttaatagtt tgcgcaacgt tgttgccatt  6900
gctacaggca tcgtggtgtc acgctcgtcg tttggtatgg cttcattcag ctccggttcc  6960
caacgatcaa ggcgagttac atgatccccc atgttgtgca aaaaagcggt tagctccttc  7020
ggtcctccga tcgttgtcag aagtaagttg gccgcagtgt tatcactcat ggttatggca  7080
gcactgcata attctcttac tgtcatgcca tccgtaagat gcttttctgt gactggtgag  7140
tactcaacca agtcattctg agaatagtgt atgcggcgac cgagttgctc ttgcccggcg  7200
tcaatacggg ataataccgc gccacatagc agaactttaa aagtgctcat cattggaaaa  7260
cgttcttcgg ggcgaaaact ctcaaggatc ttaccgctgt tgagatccag ttcgatgtaa  7320
cccactcgtg cacccaactg atcttcagca tcttttactt tcaccagcgt ttctgggtga  7380
gcaaaaacag gaaggcaaaa tgccgcaaaa aagggaataa gggcgacacg gaaatgttga  7440
atactcatac tcttcctttt tcaatattat tgaagcattt atcagggtta ttgtctcatg  7500
agcggataca tatttgaatg tatttagaaa aataaacaaa taggggttcc gcgcacattt  7560
ccccgaaaag tgccacctga cgtctaagaa accattatta tcatgacatt aacctataaa  7620
aataggcgta tcacgaggcc ctttcgtctc gcgcgtttcg gtgatgacgg tgaaaacctc  7680
tgacacatgc agctcccgga gacggtcaca gcttgtctgt aagcggatgc cgggagcaga  7740
caagcccgtc agggcgcgtc agcgggtgtt ggcgggtgtc ggggctggct taactatgcg  7800
gcatcagagc agattgtact gagagtgcac catatgcggt gtgaaatacc gcacagatgc  7860
gtaaggagaa aataccgcat caggcgccat tcgccattca ggctgcgcaa ctgttgggaa  7920
```

```
gggcgatcgg tgcgggcctc ttcgctatta cgccagctgg cgaaaggggg atgtgctgca  7980
aggcgattaa gttgggtaac gccagggttt tcccagtcac gacgttgtaa aacgacggcc  8040
agtgccaagc tgacgcg                                                 8057

SEQ ID NO: 712          moltype = DNA  length = 8131
FEATURE                 Location/Qualifiers
source                  1..8131
                        mol_type = other DNA
                        organism = synthetic construct
SEQUENCE: 712
acgcgtgtag tcttatgcaa tactcttgta gtcttgcaac atggtaacga tgagttagca  60
acatgcctta caaggagaga aaaagcaccg tgcatgccga ttggtggaag taaggtggta  120
cgatcgtgcc ttattaggaa ggcaacagac gggtctgaca tggattggac gaaccactga  180
attgccgcat tgcagagata ttgtatttaa gtgcctagct cgatacaata aacgggtctc  240
tctggttaga ccagatctga gcctgggagc tctctggcta actagggaac ccactgctta  300
agcctcaata aagcttgcct tgagtgcttc aagtagtgtg tgcccgtctg ttgtgtgact  360
ctggtaacta gagatccctc agaccctttt agtcagtgtg gaaaatctct agcagtggcg  420
cccgaacagg gacctgaaag cgaaagggaa accagagctc tctcgacgca ggactcggct  480
tgctgaagcg cgcacggcaa gaggcgaggg gcggcgactg gtgagtacgc caaaaatttt  540
gactagcgga ggctagaagg agagagatgg gtgcgagagc gtcagtatta agcgggggag  600
aattagatcg cgatgggaaa aaattcggtt aaggccaggg ggaaagaaaa aatataaatt  660
aaaacatata gtatgggcaa gcagggagct agaacgattc gcagttaatc ctggcctgtt  720
agaaacatca gaaggctgta gacaaatact gggacagcta caaccatccc ttcagacagg  780
atcagaagaa cttagatcat tatataatac agtagcaacc ctctattgtg tgcatcaaag  840
gatagagata aaagacacca aggaagcttt agacaagata gaggaagagc aaaacaaaag  900
taagaccacc gcacagcaag cggccactga tcttcagacc tggaggagga gatatgaggg  960
acaattggag aagtgaatta tataaatata aagtagtaaa aattgaacca ttaggagtag  1020
cacccaccaa ggcaaagaga agagtggtgc agagagaaaa aagagcagtg ggaataggag  1080
ctttgttcct tgggttcttg ggagcagcag gaagcactat gggcgcagcc tcaatgacgc  1140
tgacggtaca ggccagacaa ttattgtctg gtatagtgca gcagcagaac aatttgctga  1200
gggctattga ggcgcaacag catctgttgc aactcacagt ctggggcatc aagcagctcc  1260
aggcaagaat cctggctgtg gaaagatacc taaaggatca acagctcctg gggatttggg  1320
gttgctctgg aaaactcatt tgcaccactg ctgtgccttg gaatgctagt tggagtaata  1380
aatctctgga acagattgga atcacacgac ctggatggag tgggacagag aaattaacaa  1440
ttacacaagc ttaatacact ccttaattga agaatcgcaa aaccagcaag aaaagaatga  1500
acaagaatta ttggaattag ataaatgggc aagtttgtgg aattggttta acataacaaa  1560
ttggctgtgg tatataaaat tattcataat gatagtagga ggcttggtag gtttaagaat  1620
agtttttgct gtactttcta tagtgaatag agttaggcag ggatattcac cattatcgtt  1680
tcagacccac ctcccaaccc cgaggggacc cgacaggccc gaaggaatag aagaagaagg  1740
tggagagaga gacagagaca gatccattcg attagtgaac ggatctcgac ggtatcggtt  1800
aacttttaaa agaaaagggg ggattggggg gtacagtgca ggggaaagaa tagtagacat  1860
aatagcaaca gacatacaaa ctaaagaatt acaaaaacaa attacaaaat tcaaaatttt  1920
atcgatacta gtattatgcc cagtacatga ccttatggga ctttcctact tggcagtaca  1980
tctacgtatt agtcatcgct attaccatgg tgatgcggtt ttggcagtac atcaatgggc  2040
gtggatagcg gtttgactca cggggatttc caagtctcca ccccattgac gtcaatggga  2100
gtttgttttg gcaccaaaat caacgggact ttccaaaatg tcgtaacaac tccgccccat  2160
tgacgcaaat gggcggtagg cgtgtacggt gggaggttta tataagcaga gctcgtttag  2220
tgaaccgtca gatcgcctgg agacgccatc cacgctgttt tgacctccat agaagattct  2280
agagcgagaa aagccttgtt tgccaccatg gaacggctcg gagatcatca ttgcgtcgcg  2340
aggtgagcaa gggcgaggag ctgttcaccg gggtggtgcc catcctggtc gagctggacg  2400
gcgacgtaaa cggccacaag ttcagcgtgt ccggcgaggg cgagggcgat gccacctacg  2460
gcaagctgac cctgaagttc atctgcacca ccggcaagct gcccgtgccc tggcccaccc  2520
tcgtgaccac cctgacctac ggcgtgcagt gcttcagccg ctaccccgac cacatgaagc  2580
agcacgactt cttcaagtcc gccatgcccg aaggctacgt ccaggagcgc accatcttct  2640
tcaaggacga cggcaactac aagacccgcg ccgaggtgaa gttcgagggc gacaccctgg  2700
tgaaccgcat cgagctgaag ggcatcgact tcaaggagga cggcaacatc ctggggcaca  2760
agctggagta caactacaac agccacaacg tctatatcat ggccgacaag cagaagaacg  2820
gcatcaaggt gaacttcaag atccgccaca acatcgagga cggcagcgtg cagctcgccg  2880
accactacca gcagaacacc cccatcggcg acggccccgt gctgctgccc gacaaccact  2940
acctgagcac ccagtccaag ctgagcaaag accccaacga gaagcgcgat cacatggtcc  3000
tgctggagtt cgtgaccgcc gccgggatca ctctcggcat ggacgagctg tacaagtaag  3060
cggccgcgaa ggatctgcga tcgctccggt gcccgtcagt gggcagagcg cacatcgccc  3120
acagtccccg agaagttggg gggaggggtc ggcaattgaa cgggtgccta gagaaggtgg  3180
cgcggggtaa actgggaaag tgatgtcgtg tactggctcc gcctttttcc cgagggtggg  3240
ggagaaccgt atataagtgc agtagtcgcc gtgaacgttc tttttcgcaa cgggtttgcc  3300
gccagaacac agctgaagct tcgaggggct cgcatctctc cttcacgcgc ccgccgccct  3360
acctgaggcc gccatccacg ccggttgagt cgcgttctgc cgcctcccgc ctgtggtgcc  3420
tcctgaactg cgtccgccgt ctaggtaagt ttaaagctca ggtcgagacc gggcctttgt  3480
ccggcgctcc cttggagcct acctagactc agccggctct ccacgctttg cctgaccctg  3540
cttgctcaac tctacgtctt tgtttcgttt tctgttctgc gccgttacag atccaagctg  3600
tgaccggcgc ctacgctaga tgaccgagta caagcccacg gtgcgcctcg ccacccgcga  3660
cgacgtcccc agggccgtac gcaccctcgc cgccgcgttc gccgactacc ccgccacgcg  3720
ccacaccgtc gatccggacc gccacatcga gcgggtcacc gagctgcaag aactcttcct  3780
cacgcgcgtc gggctcgaca tcggcaaggt gtgggtcgcg gacgacggcg ccgcggtggc  3840
ggtctggacc acgccggaga gcgtcgaagc gggggcggtg ttcgccgaga tcggcccgcg  3900
catggccgag ttgagcggtt cccggctggc cgcgcagcaa cagatggaag gcctcctggc  3960
gccgcaccgg cccaaggagc ccgcgtggtt cctggccacc gtcggcgtct cgcccgacca  4020
ccagggcaag ggtctgggca gcgccgtcgt gctccccgga gtggaggcgg ccgagcgcgc  4080
cggggtgccc gccttcctgg agacctccgc gccccgcaac ctccccttct acgagcggct  4140
```

```
cggcttcacc gtcaccgccg acgtcgaggt gcccgaagga ccgcgcacct ggtgcatgac  4200
ccgcaagccc ggtgcctgag tcgacaatca acctctggat tacaaaattt gtgaaagatt  4260
gactggtatt cttaactatg ttgctccttt tacgctatgt ggatacgctg ctttaatgcc  4320
tttgtatcat gctattgctt cccgtatggc tttcattttc tcctccttgt ataaatcctg  4380
gttgctgtct ctttatgagg agttgtggcc cgttgtcagg caacgtggcg tggtgtgcac  4440
tgtgtttgct gacgcaaccc ccactggttg gggcattgcc accacctgtc agctcctttc  4500
cgggactttc gctttccccc tccctattgc cacggcggaa ctcatcgccg cctgccttgc  4560
ccgctgctgg acaggggctc ggctgttggg cactgacaat tccgtggtgt tgtcggggaa  4620
atcatcgtcc tttccttggc tgctcgcctg tgttgccacc tggattctgc gcgggacgtc  4680
cttctgctac gtcccttcgg ccctcaatcc agcggacctt ccttcccgcg gcctgctgcc  4740
ggctctgcgg cctcttccgc gtcttcgcct tcgccctcag acgagtcgga tctccctttg  4800
ggccgcctcc ccgcctggta cctttaagac caatgactta caaggcagct gtagatctta  4860
gccacttttt aaaagaaaag gggggactgg aagggctaat tcactcccaa cgaaaataag  4920
atctgctttt tgcttgtact gggtctctct ggttagacca gatctgagcc tgggagctct  4980
ctggctaact agggaaccca ctgcttaagc ctcaataaag cttgccttga gtgcttcaag  5040
tagtgtgtgc ccgtctgttg tgtgactctg gtaactagag atccctcaga cccttttagt  5100
cagtgtggaa aatctctagc agtagtagtt catgtcatct tattattcag tatttataac  5160
ttgcaaagaa atgaatatca gagagtgaga ggaacttgtt tattgcagct tataatggtt  5220
acaaataaag caatagcatc acaaatttca caaataaagc atttttttca ctgcattcta  5280
gttgtggttt gtccaaactc atcaatgtat cttatcatgt ctggctctag ctatcccgcc  5340
cctaactccg cccagttccg cccattctcc gccccatggc tgactaattt tttttattta  5400
tgcagaggcc gaggccgcct cggcctctga gctattccag aagtagtgag gaggcttttt  5460
tggaggccta gacttttgca gagacggccc aaattcgtaa tcatggtcat agctgtttcc  5520
tgtgtgaaat tgttatccgc tcacaattcc acacaacata cgagccggaa gcataaagtg  5580
taaagcctgg ggtgcctaat gagtgagcta actcacatta attgcgttgc gctcactgcc  5640
cgctttccag tcgggaaacc tgtcgtgcca gctgcattaa tgaatcggcc aacgcgcggg  5700
gagaggcggt ttgcgtattg ggcgctcttc cgcttcctcg ctcactgact cgctgcgctc  5760
ggtcgttcgg ctgcggcgag cggtatcagc tcactcaaag gcggtaatac ggttatccac  5820
agaatcaggg gataacgcag gaaagaacat gtgagcaaaa ggccagcaaa aggccaggaa  5880
ccgtaaaaag gccgcgttgc tggcgttttt ccataggctc cgcccccctg acgagcatca  5940
caaaaatcga cgctcaagtc agaggtggcg aaacccgaca ggactataaa gataccaggc  6000
gtttccccct ggaagctccc tcgtgcgctc tcctgttccg accctgccgc ttaccggata  6060
cctgtccgcc tttctccctt cgggaagcgt ggcgctttct catagctcac gctgtaggta  6120
tctcagttcg gtgtaggtcg ttcgctccaa gctgggctgt gtgcacgaac cccccgttca  6180
gcccgaccgc tgcgccttat ccggtaacta tcgtcttgag tccaacccgg taagacacga  6240
cttatcgcca ctggcagcag ccactggtaa caggattagc agagcgaggt atgtaggcgg  6300
tgctacagag ttcttgaagt ggtggcctaa ctacggctac actagaagga cagtatttgg  6360
tatctgcgct ctgctgaagc cagttacctt cggaaaaaga gttggtagct cttgatccgg  6420
caaacaaacc accgctggta gcggtggttt ttttgtttgc aagcagcaga ttacgcgcag  6480
aaaaaaagga tctcaagaag atcctttgat cttttctacg gggtctgacg ctcagtggaa  6540
cgaaaactca cgttaaggga ttttggtcat gagattatca aaaaggatct tcacctagat  6600
ccttttaaat taaaaatgaa gttttaaatc aatctaaagt atatatgagt aaacttggtc  6660
tgacagttac caatgcttaa tcagtgaggc acctatctca gcgatctgtc tatttcgttc  6720
atccatagtt gcctgactcc ccgtcgtgta gataactacg atacgggagg gcttaccatc  6780
tggccccagt gctgcaatga taccgcgaga cccacgctca ccggctccag atttatcagc  6840
aataaaccag ccagccggaa gggccgagcg cagaagtggt cctgcaactt tatccgcctc  6900
catccagtct attaattgtt gccgggaagc tagagtaagt agttcgccag ttaatagttt  6960
gcgcaacgtt gttgccattg ctacaggcat cgtggtgtca cgctcgtcgt ttggtatggc  7020
ttcattcagc tccggttccc aacgatcaag gcgagttaca tgatccccca tgttgtgcaa  7080
aaaagcggtt agctccttcg gtcctccgat cgttgtcaga agtaagttgg ccgcagtgtt  7140
atcactcatg gttatggcag cactgcataa ttctcttact gtcatgccat ccgtaagatg  7200
cttttctgtg actggtgagt actcaaccaa gtcattctga gaatagtgta tgcggcgacc  7260
gagttgctct tgcccggcgt caatacggga taataccgcg ccacatagca gaactttaaa  7320
agtgctcatc attggaaaac gttcttcggg gcgaaaactc tcaaggatct taccgctgtt  7380
gagatccagt tcgatgtaac ccactcgtgc acccaactga tcttcagcat cttttacttt  7440
caccagcgtt tctgggtgag caaaaacagg aaggcaaaat gccgcaaaaa agggaataag  7500
ggcgacacgg aaatgttgaa tactcatact cttccttttt caatattatt gaagcattta  7560
tcagggttat tgtctcatga gcggatacat atttgaatgt atttagaaaa ataaacaaat  7620
aggggttccg cgcacatttc cccgaaaagt gccacctgac gtctaagaaa ccattattat  7680
catgacatta acctataaaa ataggcgtat cacgaggccc tttcgtctcg cgcgtttcgg  7740
tgatgacggt gaaaacctct gacacatgca gctcccggag acggtcacag cttgtctgta  7800
agcggatgcc gggagcagac aagcccgtca gggcgcgtca gcgggtgttg gcgggtgtcg  7860
gggctggctt aactatgcgg catcagagca gattgtactg agagtgcacc atatgcggtg  7920
tgaaataccg cacagatgcg taaggagaaa ataccgcatc aggcgccatt cgccattcag  7980
gctgcgcaac tgttgggaag ggcgatcggt gcgggcctct tcgctattac gccagctggc  8040
gaaaggggga tgtgctgcaa ggcgattaag ttgggtaacg ccagggtttt cccagtcacg  8100
acgttgtaaa acgacggcca gtgccaagct g                                8131
```

```
SEQ ID NO: 713          moltype = DNA  length = 8231
FEATURE                 Location/Qualifiers
source                  1..8231
                        mol_type = other DNA
                        organism = synthetic construct
SEQUENCE: 713
tgtagtctta tgcaatactc ttgtagtctt gcaacatggt aacgatgagt tagcaacatg  60
ccttacaagg agagaaaaag caccgtgcat gccgattggt ggaagtaagg tggtacgatc  120
gtgccttatt aggaaggcaa cagacgggtc tgacatggat tggacgaacc actgaattgc  180
cgcattgcag agatattgta tttaagtgcc tagctcgata cataaacggg tctctctggt  240
tagaccagat ctgagcctgg gagctctctg gctaactagg gaacccactg cttaagcctc  300
```

```
aataaagctt gccttgagtg cttcaagtag tgtgtgcccg tctgttgtgt gactctggta  360
actagagatc cctcagaccc ttttagtcag tgtggaaaat ctctagcagt ggcgcccgaa  420
cagggacttg aaagcgaaag ggaaaccaga ggagctctct cgacgcagga ctcggcttgc  480
tgaagcgcgc acggcaagag gcgaggggcg gcgactggtg agtacgccaa aaattttgac  540
tagcggaggc tagaaggaga gagatgggtg cgagagcgtc agtattaagc gggggagaat  600
tagatcgcga tgggaaaaaa ttcggttaag gccaggggga aagaaaaaat ataaattaaa  660
acatatagta tgggcaagca gggagctaga acgattcgca gttaatcctg gcctgttaga  720
aacatcagaa ggctgtagac aaatactggg acagctacaa ccatcccttc agacaggatc  780
agaagaactt agatcattat ataatacagt agcaaccctc tattgtgtgc atcaaaggat  840
agagataaaa gacaccaagg aagctttaga caagatagag gaagagcaaa acaaaagtaa  900
gaccaccgca cagcaagcgg ccactgatct tcagacctgg aggaggagat atgagggaca  960
attggagaag tgaattatat aaatataaag tagtaaaaat tgaaccatta ggagtagcac  1020
ccaccaaggc aaagagaaga gtggtgcaga gagaaaaaag agcagtggga ataggagctt  1080
tgttccttgg gttcttggga gcagcaggaa gcactatggg cgcagcgtca atgacgctga  1140
cggtacaggc cagacaatta ttgtctggta tagtgcagca gcagaacaat ttgctgaggg  1200
ctattgaggc gcaacagcat ctgttgcaac tcacagtctg gggcatcaag cagctccagg  1260
caagaatcct ggctgtggaa agatacctaa aggatcaaca gctcctgggg atttggggtt  1320
gctctggaaa actcatttgc accactgctg tgccttggaa tgctagttgg agtaataaat  1380
ctctggaaca gatttggaat cacacgacct ggatggagtg ggacagagaa attaacaatt  1440
acacaagctt aatacactcc ttaattgaag aatcgcaaaa ccagcaagaa aagaatgaac  1500
aagaattatt ggaattagat aaatgggcaa gtttgtggaa ttggtttaac ataacaaatt  1560
ggctgtggta tataaaatta ttcataatga tagtaggagg cttggtaggt ttaagaatag  1620
tttttgctgt actttctata gtgaatagag ttaggcaggg atattcacca ttatcgtttc  1680
agacccacct cccaaccccg aggggacccg acaggcccga aggaatagaa gaagaaggtg  1740
gagagagaga cagagacaga tccattcgat tagtgaacgg atctcgacgg tatcggttaa  1800
cttttaaaag aaaagggggg attggggggt acagtgcagg ggaaagaata gtagacataa  1860
tagcaacaga catacaaact aaagaattac aaaaacaaat tacaaaattc aaaattttat  1920
cgatactagt attatgccca gtacatgacc ttatgggact ttcctacttg gcagtacatc  1980
tacgtattag tcatcgctat taccatggtg atgcggtttt ggcagtacat caatgggcgt  2040
ggatagcggt ttgactcacg gggatttcca agtctccacc ccattgacgt caatgggagt  2100
ttgttttggc accaaaatca acgggacttt ccaaaatgtc gtaacaactc cgccccattg  2160
acgcaaatgg gcggtaggcg tgtacggtgg gaggtttata taagcagagc tcgtttagtg  2220
aaccgtcaga tcgcctggag acgccatcca cgctgttttg acctccatag aagattctag  2280
agctagcgaa ttgggatccc tagagatccg acgccgccat ctctaggccc gcgccggccc  2340
cctcgcacag acttgtggga gaagctcggc tactcccctg ccccggttaa tttgcatata  2400
atatttccta gtaactatag aggcttaatg tgcgataaaa gacagataat ctgttctttt  2460
taatactagc tacattttac atgataggct tggatttcta taagagatac aaatactaaa  2520
ttattatttt aaaaaacagc acaaaaggaa actcacccta actgtaaagt aattgtgtgt  2580
tttgagacta taaatatgca tgcgagaaaa gccttgtttg ccaccatgga acggctcgga  2640
gatcatcatt gcgnnnnnnn accgagtaca agcccacggt gcgcctcgcc acccgcgacg  2700
acgtccccag ggccgtacgc accctcgccg ccgcgttcgc cgactacccc gccacgcgcc  2760
acaccgtcga tccggaccgc cacatcgagc gggtcaccga gctgcaagaa ctcttcctca  2820
cgcgcgtcgg gctcgacatc ggcaaggtgt gggtcgcgga cgacggcgcc gcggtggcgg  2880
tctggaccac gccggagagc gtcgaagcgg gggcggtgtt cgccgagatc ggcccgcgca  2940
tggccgagtt gagcggttcc cggctggccg cgcagcaaca gatggaaggc ctcctggcgc  3000
cgcaccggcc caaggagccc gcgtggttcc tggccaccgt cggcgtctcg cccgaccacc  3060
agggcaaggg tctgggcagc gccgtcgtgc tccccggagt ggaggcggcc gagcgcgccg  3120
gggtgcccgc cttcctggag acctccgcgc cccgcaacct ccccttctac gagcggctcg  3180
gcttcaccgt caccgccgac gtcgaggtgc ccgaaggacc gcgcacctgg tgcatgaccc  3240
gcaagcccgg tgcctgactc gaggcggccg ctaaatagtt gaatttaaat agatctccag  3300
cacagtggta aatagttgat tcgaacaagg atctgcgatc gctccggtgc ccgtcagtgg  3360
gcagagcgca catcgcccac agtccccgag aagttggggg gaggggtcgg caattgaacg  3420
ggtgcctaga gaaggtggcg cggggtaaac tgggaaagtg atgtcgtgta ctggctccgc  3480
ctttttcccg agggtggggg agaaccgtat ataagtgcag tagtcgccgt gaacgttctt  3540
tttcgcaacg ggtttgccgc cagaacacag ctgaagcttc gaggggctcg catctctcct  3600
tcacgcgccc gccgccctac ctgaggccgc catccacgcc ggttgagtcg cgttctgccg  3660
cctcccgcct gtggtgcctc ctgaactgcg tccgccgtct aggtaagttt aaagctcagg  3720
tcgagaccgg gcctttgtcc ggcgctccct tggagcctac ctagactcag ccggctctcc  3780
acgctttgcc tgaccctgct tgctcaactc tacgtctttg tttcgttttc tgttctgcgc  3840
cgttacagat ccaagctgtg accggcgcct acgcccatgg gcatggccaa gcctttgtct  3900
caagaagaat ccaccctcat tgaaagagca acggctacaa tcaacagcat ccccatctct  3960
gaagactaca gcgtcgccag cgcagctctc tctagcgacg gccgcatctt cactggtgtc  4020
aatgtatatc attttactgg gggaccttgt gcagaactcg tggtgctggg cactgctgct  4080
gctgcggcag ctggcaacct gacttgtatc gtcgcgatcg gaaatgagaa caggggcatc  4140
ttgagcccct gcggacggtg ccgacaggtg cttctcgatc tgcatcctgg gatcaaagcc  4200
atagtgaagg acagtgatgg acagccgacg gcagttggga ttcgtgaatt gctgccctct  4260
ggttatgtgt gggagggcta agcacaattc gagctcgcgt cgacaatcaa cctctggatt  4320
acaaaatttg tgaaagattg actggtattc ttaactatgt tgctcctttt acgctatgtg  4380
gatacgctgc tttaatgcct ttgtatcatg ctattgcttc ccgtatggct ttcattttct  4440
cctccttgta taaatcctgg ttgctgtctc tttatgagga gttgtggccc gttgtcaggc  4500
aacgtggcgt ggtgtgcact gtgtttgctg acgcaacccc cactggttgg ggcattgcca  4560
ccacctgtca gctcctttcc gggactttcg ctttccccct ccctattgcc acggcggaac  4620
tcatcgccgc ctgccttgcc cgctgctgga caggggctcg gctgttgggc actgacaatt  4680
ccgtggtgtt gtcggggaaa tcatcgtcct ttccttggct gctcgcctgt gttgccacct  4740
ggattctgcg cgggacgtcc ttctgctacg tcccttcggc cctcaatcca gcggaccttc  4800
cttcccgcgg cctgctgccg gctctgcggc ctcttccgcg tcttcgcctt cgccctcaga  4860
cgagtcggat ctccctttgg gccgcctccc cgcctggtac ctttaagacc aatgacttac  4920
aaggcagctg tagatcttag ccactttta aaagaaaagg ggggactgga agggctaatt  4980
cactcccaac gaagataaga tctgcttttt gcttgtactg ggtctctctg gttagaccag  5040
```

```
atctgagcct gggagctctc tggctaacta gggaacccac tgcttaagcc tcaataaagc  5100
ttgccttgag tgcttcaagt agtgtgtgcc cgtctgttgt gtgactctgg taactagaga  5160
tccctcagac ccttttagtc agtgtggaaa atctctagca gtagtagttc atgtcatctt  5220
attattcagt atttataact tgcaaagaaa tgaatatcag agagtgagag gaacttgttt  5280
attgcagctt ataatggtta caaataaagc aatagcatca caaatttcac aaataaagca  5340
tttttttcac tgcattctag ttgtggtttg tccaaactca tcaatgtatc ttatcatgtc  5400
tggctctagc tatcccgccc ctaactccgc ccatcccgcc cctaactccg cccagttccg  5460
cccattctcc gccccatggc tgactaattt tttttattta tgcagaggcc gaggccgcct  5520
cggcctctga gctattccag aagtagtgag gaggcttttt tggaggccta gacttttgca  5580
gagaccaaat tcgtaatcat gtcatagctg tttcctgtgt gaaattgtta tccgctcaca  5640
attccacaca acatacgagc cggaagcata aagtgtaaag cctggggtgc ctaatgagtg  5700
agctaactca cattaattgc gttgcgctca ctgcccgctt tccagtcggg aaacctgtcg  5760
tgccagctgc attaatgaat cggccaacgc gcggggagag gcggtttgcg tattgggcgc  5820
tcttccgctt cctcgctcac tgactcgctg cgctcggtcg ttcggctgcg gcgagcggta  5880
tcagctcact caaaggcggt aatacggtta tccacagaat caggggataa cgcaggaaag  5940
aacatgtgag caaaaggcca gcaaaaggcc aggaaccgta aaaaggccgc gttgctggcg  6000
tttttccata ggctccgccc ccctgacgag catcacaaaa atcgacgctc aagtcagagg  6060
tggcgaaacc cgacaggact ataaagatac caggcgtttc cccctggaag ctccctcgtg  6120
cgctctcctg ttccgaccct gccgcttacc ggatacctgt ccgcctttct cccttcggga  6180
agcgtggcgc tttctcatag ctcacgctgt aggtatctca gttcggtgta ggtcgttcgc  6240
tccaagctgg gctgtgtgca cgaacccccc gttcagcccg accgctgcgc cttatccggt  6300
aactatcgtc ttgagtccaa cccggtaaga cacgacttat cgccactggc agcagccact  6360
ggtaacagga ttagcagagc gaggtatgta ggcggtgcta cagagttctt gaagtggtgg  6420
cctaactacg gctacactag aagaacagta tttggtatct gcgctctgct gaagccagtt  6480
accttcggaa aaagagttgg tagctcttga tccggcaaac aaaccaccgc tggtagcggt  6540
ggtttttttg tttgcaagca gcagattacg cgcagaaaaa aaggatctca agaagatcct  6600
ttgatctttt ctacggggtc tgacgctcag tggaacgaaa actcacgtta agggattttg  6660
gtcatgagat tatcaaaaag gatcttcacc tagatccttt taaattaaaa atgaagtttt  6720
aaatcaatct aaagtatata tgagtaaact tggtctgaca gttaccaatg cttaatcagt  6780
gaggcaccta tctcagcgat ctgtctattt cgttcatcca tagttgcctg actccccgtc  6840
gtgtagataa ctacgatacg ggagggctta ccatctggcc ccagtgctgc aatgataccg  6900
cgagacccac gctcaccggc tccagattta tcagcaataa accagccagc cggaagggcc  6960
gagcgcagaa gtggtcctgc aactttatcc gcctccatcc agtctattaa ttgttgccgg  7020
gaagctagag taagtagttc gccagttaat agtttgcgca acgttgttgc cattgctaca  7080
ggcatcgtgg tgtcacgctc gtcgtttggt atggcttcat tcagctccgg ttcccaacga  7140
tcaaggcgag ttacatgatc ccccatgttg tgcaaaaaag cggttagctc cttcggtcct  7200
ccgatcgttg tcagaagtaa gttggccgca gtgttatcac tcatggttat ggcagcactg  7260
cataattctc ttactgtcat gccatccgta agatgctttt ctgtgactgg tgagtactca  7320
accaagtcat tctgagaata gtgtatgcgg cgaccgagtt gctcttgccc ggcgtcaata  7380
cgggataata ccgcgccaca tagcagaact ttaaaagtgc tcatcattgg aaaacgttct  7440
tcggggcgaa aactctcaag gatcttaccg ctgttgagat ccagttcgat gtaacccact  7500
cgtgcaccca actgatcttc agcatctttt actttcacca gcgtttctgg gtgagcaaaa  7560
acaggaaggc aaaatgccgc aaaaaaggga ataagggcga cacggaaatg ttgaatactc  7620
atactcttcc tttttcaata ttattgaagc atttatcagg gttattgtct catgagcgga  7680
tacatatttg aatgtattta gaaaaataaa caaatagggg ttccgcgcac atttccccga  7740
aaagtgccac ctgacgtcta agaaaccatt attatcatga cattaaccta taaaaatagg  7800
cgtatcacga ggccctttcg tctcgcgcgt ttcggtgatg acggtgaaaa cctctgacac  7860
atgcagctcc cggagacggt cacagcttgt ctgtaagcgg atgccgggag cagacaagcc  7920
cgtcagggcg cgtcagcggg tgttggcggg tgtcggggct ggcttaacta tgcggcatca  7980
gagcagattg tactgagagt gcaccatatg cggtgtgaaa taccgcacag atgcgtaagg  8040
agaaaatacc gcatcaggcg ccattcgcca ttcaggctgc gcaactgttg ggaagggcga  8100
tcggtgcggg cctcttcgct attacgccag ctggcgaaag ggggatgtgc tgcaaggcga  8160
ttaagttggg taacgccagg gttttcccag tcacgacgtt gtaaaacgac ggccagtgcc  8220
aagctgacgc g                                                       8231
```

```
SEQ ID NO: 714          moltype = DNA  length = 68
FEATURE                 Location/Qualifiers
source                  1..68
                        mol_type = other DNA
                        organism = synthetic construct
SEQUENCE: 714
tgtttgccac catggaacgg ctcggagatc atcattgcgn nnnnnnaccg agtacaagcc  60
cacggtgc                                                           68
```

```
SEQ ID NO: 715          moltype = DNA  length = 52
FEATURE                 Location/Qualifiers
source                  1..52
                        mol_type = other DNA
                        organism = synthetic construct
SEQUENCE: 715
taaattcaac tatttagcgg ccgcctcgag tcaggcaccg ggcttgcggg tc          52
```

```
SEQ ID NO: 716          moltype = DNA  length = 2322
FEATURE                 Location/Qualifiers
source                  1..2322
                        mol_type = other DNA
                        organism = synthetic construct
SEQUENCE: 716
atcataagat gatcttcttg agatcgtttt ggtctgcgcg taatctcttg ctctgaaaac  60
```

```
gaaaaaaccg ccttgcaggg cggtttttcg aaggttctct gagctaccaa ctctttgaac  120
cgaggtaact ggcttggagg agcgcagtca ccaaaacttg tcctttcagt ttagccttaa  180
ccggcgcatg acttcaagac taactcctct aaatcaatta ccagtggctg ctgccagtgg  240
tgcttttgca tgtctttccg ggttggactc aagacgatag ttaccggata aggcgcagcg  300
gtcggactga acggggggtt cgtgcataca gtccagcttg gagcgaactg cctacccgga  360
actgagtgtc aggcgtggaa tgagacaaac gcggccataa cagcggaatg acaccggtaa  420
accgaaaggc aggaacagga gagcgcacga gggagccgcc agggggaaac gcctggtatc  480
tttatagtcc tgtcgggttt cgccaccact gatttgagcg tcagatttcg tgatgcttgt  540
caggggggcg gagcctatgg aaaaacggct ttgccgcggc cctctcactt ccctgttaag  600
tatcttcctg gcatcttcca ggaaatctcc gccccgttcg taagccattt ccgctcgccg  660
cagtcgaacg accgagcgta gcgagtcagt gagcgaggaa gcggaatata tcctgtatca  720
catattctgc tgacgcaccg gtgcagcctt ttttctcctg ccacatgaag cacttcactg  780
acaccctcat cagtgccaac atagtaagcc agtatacact ccgctagcgc tgatgtccgg  840
cggtgctttt gccgttacgc accaccccgt cagtagctga acaggaggga cagctgatag  900
aaacagaagc cactggagca cctcaaaaac accatcatac actaaatcag taagttggca  960
gcatcacccg acgcactttg cgccgaataa atacctgtga cggaagatca cttcgcagaa  1020
taaataaatc ctggtgtccc tgttgatacc gggaagccct gggccaactt ttggcgaaaa  1080
tgagacgttg atcggcacgt aagaggttcc aactttcacc ataatgaaat aagatcacta  1140
ccgggcgtat tttttgagtt atcgagattt tcaggagcta aggaagctaa aatggagaaa  1200
aaaatcactg gatataccac cgttgatata tcccaatggc atcgtaaaga acattttgag  1260
gcatttcagt cagttgctca atgtacctat aaccagaccg ttcagctgga tattacggcc  1320
tttttaaaga ccgtaaagaa aaataagcac aagttttatc cggcctttat tcacattctt  1380
gcccgcctga tgaatgctca tccggaattc cgtatggcaa tgaaagacgg tgagctggtg  1440
atatgggata gtgttcaccc ttgttacacc gttttccatg agcaaactga aacgttttca  1500
tcgctctgga gtgaatacca cgacgatttc cggcagtttc tacacatata ttcgcaagat  1560
gtggcgtgtt acggtgaaaa cctggcctat ttccctaaag ggtttattga gaatatgttt  1620
ttcgtctcag ccaatccctg ggtgagtttc accagttttg atttaaacgt ggccaatatg  1680
gacaacttct tcgcccccgt tttcaccatg ggcaaatatt atacgcaagg cgacaaggtg  1740
ctgatgccgc tggcgattca ggttcatcat gccgtttgtg atggcttcca tgtcggcaga  1800
atgcttaatg aattacaaca gtactgcgat gagtggcagg gcggggcgta atttggtaca  1860
tctcaaataa aacgaaaggc tcagtcgaaa gactgggcct ttcgttttat ctgttgtttg  1920
tcggtgaacg ctctcgttaa ctagctatac tgatttcgtc agactcacag tcaaacatgc  1980
cggtcagttg gcctggtgat ggcgggatcg ttgtatattt cttgacacct tttcggcacc  2040
gccctaaaat tctgcgtcct cataatatat gaggcgattt attacgtgtt tacgaagcaa  2100
aagctaaaac caggagctat ttaatgccgg cagctaagaa aaagaaactg gatggcagcg  2160
tcgacagtct tcgtttcaaa cgaatggcca ccatgtagaa gactgaattc ggtaccttga  2220
cagctagctc agtcctaggt ataatactag tgtttaaacc gtacgtcgac gctagcataa  2280
ccccttgggg cctctaaacg ggtcttgagg ggttttttgg at                    2322

SEQ ID NO: 717          moltype = DNA  length = 223
FEATURE                 Location/Qualifiers
source                  1..223
                        mol_type = other DNA
                        organism = synthetic construct
SEQUENCE: 717
tcgagtaccc atacgatgtt ccagattacg cttgagaatt cggtaccttg acagctagct  60
cagtcctagg tataatacta gtgtaatgcg tctcccattg acgccgcaat gatgatctcc  120
gagccgttcg gccggcatgg tcccagcctc ctcgctggcg ccggctgggc aacatgcttc  180
ggcatggcga atgggaccgt acgtcgacgc tagcataacc cct                   223

SEQ ID NO: 718          moltype = DNA  length = 36
FEATURE                 Location/Qualifiers
source                  1..36
                        mol_type = other DNA
                        organism = synthetic construct
SEQUENCE: 718
atttaatgcc ggcagctaag aaaaagaaac tggatg                           36

SEQ ID NO: 719          moltype = DNA  length = 5969
FEATURE                 Location/Qualifiers
source                  1..5969
                        mol_type = other DNA
                        organism = synthetic construct
SEQUENCE: 719
atcataagat gatcttcttg agatcgtttt ggtctgcgcg taatctcttg ctctgaaaac  60
gaaaaaaccg ccttgcaggg cggtttttcg aaggttctct gagctaccaa ctctttgaac  120
cgaggtaact ggcttggagg agcgcagtca ccaaaacttg tcctttcagt ttagccttaa  180
ccggcgcatg acttcaagac taactcctct aaatcaatta ccagtggctg ctgccagtgg  240
tgcttttgca tgtctttccg ggttggactc aagacgatag ttaccggata aggcgcagcg  300
gtcggactga acggggggtt cgtgcataca gtccagcttg gagcgaactg cctacccgga  360
actgagtgtc aggcgtggaa tgagacaaac gcggccataa cagcggaatg acaccggtaa  420
accgaaaggc aggaacagga gagcgcacga gggagccgcc agggggaaac gcctggtatc  480
tttatagtcc tgtcgggttt cgccaccact gatttgagcg tcagatttcg tgatgcttgt  540
caggggggcg gagcctatgg aaaaacggct ttgccgcggc cctctcactt ccctgttaag  600
tatcttcctg gcatcttcca ggaaatctcc gccccgttcg taagccattt ccgctcgccg  660
cagtcgaacg accgagcgta gcgagtcagt gagcgaggaa gcggaatata tcctgtatca  720
catattctgc tgacgcaccg gtgcagcctt ttttctcctg ccacatgaag cacttcactg  780
acaccctcat cagtgccaac atagtaagcc agtatacact ccgctagcgc tgatgtccgg  840
cggtgctttt gccgttacgc accaccccgt cagtagctga acaggaggga cagctgatag  900
```

-continued

```
aaacagaagc cactggagca cctcaaaaac accatcatac actaaatcag taagttggca  960
gcatcacccg acgcactttg cgccgaataa atacctgtga cggaagatca cttcgcagaa  1020
taaataaatc ctggtgtccc tgttgatacc gggaagcccc gggccaactt ttggcgaaaa  1080
tgagacgttg atcggcacgt aagaggttcc aactttcacc ataatgaaat aagatcacta  1140
ccgggcgtat tttttgagtt atcgagattt tcaggagcta aggaagctaa aatggagaaa  1200
aaaatcactg gatataccac cgttgatata tcccaatggc atcgtaaaga acattttgag  1260
gcatttcagt cagttgctca atgtacctat aaccagaccg ttcagctgga tattacggcc  1320
tttttaaaga ccgtaaagaa aaataagcac aagttttatc cggcctttat tcacattctt  1380
gcccgcctga tgaatgctca tccggaattc cgtatggcaa tgaaagacgg tgagctggtg  1440
atatgggata gtgttcaccc ttgttacacc gttttccatg agcaaactga aacgttttca  1500
tcgctctgga gtgaatacca cgacgatttc cggcagtttc tacacatata ttcgcaagat  1560
gtggcgtgtt acggtgaaaa cctggcctat ttccctaaag ggtttattga gaatatgttt  1620
ttcgtctcag ccaatccctg ggtgagtttc accagttttg atttaaacgt ggccaatatg  1680
gacaacttct tcgcccccgt tttcaccatg ggcaaatatt atacgcaagg cgacaaggtg  1740
ctgatgccgc tggcgattca ggttcatcat gccgtttgtg atggcttcca tgtcggcaga  1800
atgcttaatg aattacaaca gtactgcgat gagtggcagg gcggggcgta atttggtaca  1860
tctcaaataa aacgaaaggc tcagtcgaaa gactgggcct ttcgttttat ctgttgtttg  1920
tcggtgaacg ctctcgttaa ctagctatac tgatttcgtc agactcacag tcaaacatgc  1980
cggtcagttg gcctggtgat ggcgggatcg ttgtatattt cttgacacct tttcggcacc  2040
gccctaaaat tctgcgtcct cataatatat gaggcgattt attacgtgtt tacgaagcaa  2100
aagctaaaac caggagctat ttaatgccgg cagctaagaa aaagaaactg gatggcagcg  2160
tcgacatctt cgtggtgctg agcgtgaatc agttcagatg caaccccaac gccttcagac  2220
aagcctccat gaaaaccgac gacgagaaga aggacaccgc catcaagagc tacacaagct  2280
ggctgctgcc caacgacaga aaggagaagg acatggtgcg gagcttcctg gccctggacc  2340
aaggcagcag attctttttc gacctgatgc aagcctggta cggcggcctc acccccgaca  2400
tcatcaagag cgtgaccaag gagcgggacc tggtggacct gtggtgcgcc atctactggt  2460
tcagacccat gaagaaggag ctggcctccc accccatcga cagagtggac ctggccaaga  2520
cctttcagag atactacggc ggccccgcct ccgacgtggt gcaagagtac ctgagcgcct  2580
ccatcggcga ggactgctgc tggaacgact gcagacagaa gtaccaagag ttctgcaaga  2640
acctcggggt ggacttcacc cccgacctca agaccctggt gagagagaag ctgatcgccg  2700
tggccctgaa cgacggcagc caagccgcca tcagcaacct gttcggcaac ggcggcaagg  2760
aggacagaaa cgtgaaggtg aacatctgca agaagatcct gattgctctg gagaaggccg  2820
gcaaatccgt gaagtacgtg cgggacgtgc agagcatcat cctgaagtgc gccaacgcca  2880
aggacagaga ggacttcaac agaatctacg ccgacaagaa cggcagaccc ggcaccctgc  2940
tcctgctcct ggacagaaag ggcgagaaca cctacgacgc cgaggtgctg aagagatacc  3000
tgagaaagac catcaagagc aagaacgccc ccctggtgtg gaactacaat cagaagctgt  3060
tcgagtacat cgagagaggc atccggaatc tgctgagaag aaccatcaac tacgacgcct  3120
gggcctgggg cgagatgtgg agagtgggcc acaccccct gcagaccaag gccacaagaa  3180
actaccactt cgcccaagag cagctgaaga gacacagcga catcgccgcc gcttcccaaa  3240
gcagccacgc catcgccgtc gctctgaacg agttcttcga gagccccttc ttcgacggcg  3300
agaacccctt caccatctgc ccccaccacc tgggcaagaa cctggaaaag ctgttcaagg  3360
cctgggccga cgaaaaaaat cagaccgacg aggaggacgc cggcgaaacc gccatcaccg  3420
actactgcgc cgagttcaag gacggcttcg acagagagcc cattagaaac ctgctgagat  3480
acgtgtacgc ttccctgaga agcaagtaca gcgccaagga gctgatccaa gccgccaagt  3540
acaatcagca gttcgagaga tatcagagac agaaggccca ccccgtgacc cccgacaacc  3600
aaggctacac ctggcccgag gccgtgatca agcctagcaa ggccgagaga aagaacagag  3660
agaacagcct ggacacaaga atctgggtga gcgtgaagct gctgcaaaag gacggcacct  3720
gggagaagca ccacatcccc ttctacaacc tgagattctt cgaagaggtg tacgccgctg  3780
cctccatcgc cgaggacatg cctagcccca ccttcagaaa cagcagattc ggcttcaagc  3840
tgcccaagct gctgaacacc cacgccaaga tcaacaagaa aaagaaggac ggcaagaagg  3900
acaagaaggc cgtgaacgcc gccaagagag aggctagaat ctacctcgct gccaaggagg  3960
gcagactgcc cgccccctcc gtgcccctgg acaagctgag cgccgtgatc gctagagtga  4020
acggcaagtt ccaagtgacc gtgcccgtga agttcaaggt gaacaagcag cccaagtacc  4080
ccctgcctca gctggggcag atcatcctgg gctacgatca gaacctgacc gccaaccacg  4140
cctgggccct gttcgaggtg gtgaccgagg acacccccgg cgcccacttc tgcagaaatc  4200
agtacctgag agtgctcaag accggccaag tgagaagcat caccaagacc aaggacggcc  4260
aagagatcga tcagctgagc tacgacggcc tggagtacaa ggagtacggc gagtggagaa  4320
agcaagccaa gaagttcgcc tcccaatggt acatcaccac caaggtgaga aagggcaagg  4380
aaaccaccct gctgagccaa cccgccctgg agagattcga gagcatcgag aagtacaagc  4440
ccgccctgta cagattcaac aaggaatacg cccggctgct cctggccgtc atcagaagaa  4500
agaccctgaa cgagctggag gagatcagac ccgagatctt cagactggtg gagcaaggct  4560
tcggcatctg cagattcggc agcctgagcc tgagcagctt cgaggccatc agagccgcca  4620
aggccgtgat ctacggctac ttcagcaccg ccctgaagca cgaccacaac acccccatca  4680
cagatgacga gagacaagcc ttcgaccccg agctgttcgg cctgctgaac aagctggaaa  4740
ccctgagaca gaacaagggc gaggagaaga tcaacagagc cgctaacgcc ctgatcagaa  4800
tcgccctgga gaacaaggcc gacttcatca gaggcgaggg cgacctgccc accaccaaca  4860
agagcgtcaa gaaggggcag aacagcagaa gcatggactg gctggctaga ggcctgttca  4920
acaagatctg tcagctggcc gtgatgcaca acatcattcc caccgccgcc aacccccaca  4980
gcacaagcca ccaagacccc ttcgagcaca acaaggactt cgacgaccct cagcccgcca  5040
tgaagtgcag atacgctgag ttcaagatcg aggacatcgg cgacagcgtg ctggagagac  5100
tgggcacctc cctgagaaat gccaaggccg ggcagaccgg cgcctactat tacaagggcg  5160
cccaagactt cctggcccac tacggcctgc aagacatcga ggaagagctg aagaagtgca  5220
gaagaggcag aaaggccaac atgccctgct gggagctgca gaagagactg attcagaagc  5280
tgggcagcaa ggacgccgtg gtgtacatcc ccatgagagg cggccggatc tacctggcta  5340
cacacagcgt gaccaccggc gccaagccca tcatcttcaa cggcgaagag gtgtgggtga  5400
gcaacgccga cgagatcgcc gccgtgaaca tcggcctgac catcatcccc acaagcaaga  5460
aggacgagga gcaccccgac agagagaacg acgacaaggc catcagaaag agcgtcagac  5520
ggcctagaaa gagcggcgag agaagaagcg gcgacaagat gcccgccacc gctagaaaga  5580
ccacaggcgg cggccccggc ggcggcgccg ccgccggcag cggcagccct aagaaaaaac  5640
```

```
gaaaagttgg cagcggaagc aaaaggccgg cggccacgaa aaaggccggc caggcaaaaa  5700
agaaaaagct cgagtaccca tacgatgttc cagattacgc ttgagaattc ggtaccttga  5760
cagctagctc agtcctaggt ataatactag tgtaatgcgt ctcccattga cgccgcaatg  5820
atgatctccg agccgttcgg ccggcatggt cccagcctcc tcgctggcgc cggctgggca  5880
acatgcttcg gcatggcgaa tgggaccgta cgtcgacgct agcataaccc cttggggcct  5940
ctaaacgggt cttgaggggt tttttggat                                    5969

SEQ ID NO: 720         moltype = DNA  length = 28
FEATURE                Location/Qualifiers
source                 1..28
                       mol_type = other DNA
                       organism = synthetic construct
SEQUENCE: 720
cagcacaaaa ggaaactcac cctaactg                                     28

SEQ ID NO: 721         moltype = DNA  length = 20
FEATURE                Location/Qualifiers
source                 1..20
                       mol_type = other DNA
                       organism = synthetic construct
SEQUENCE: 721
tgtggcgcgt ggcggggtag                                              20

SEQ ID NO: 722         moltype = DNA  length = 23
FEATURE                Location/Qualifiers
source                 1..23
                       mol_type = other DNA
                       organism = synthetic construct
SEQUENCE: 722
catgagcatg cagaggtgag tat                                          23

SEQ ID NO: 723         moltype = DNA  length = 38
FEATURE                Location/Qualifiers
source                 1..38
                       mol_type = other DNA
                       organism = synthetic construct
SEQUENCE: 723
cattgacgcc atgagcatgc agaggtgagt attttttg                          38

SEQ ID NO: 724         moltype = DNA  length = 38
FEATURE                Location/Qualifiers
source                 1..38
                       mol_type = other DNA
                       organism = synthetic construct
SEQUENCE: 724
gtaccaaaaa atactcacct ctgcatgctc atggcgtc                          38

SEQ ID NO: 725         moltype = DNA  length = 8602
FEATURE                Location/Qualifiers
source                 1..8602
                       mol_type = other DNA
                       organism = synthetic construct
SEQUENCE: 725
tggcgaatgg gacgcgccct gtagcggcgc attaagcgcg gcgggtgtgg tggttacgcg  60
cagcgtgacc gctacacttg ccagcgccct agcgcccgct cctttcgctt tcttcccttc  120
ctttctcgcc acgttcgccg gctttccccg tcaagctcta aatcgggggc tccctttagg  180
gttccgattt agtgctttac ggcacctcga ccccaaaaaa cttgattagg gtgatggttc  240
acgtagtggg ccatcgccct gatagacggt ttttcgccct ttgacgttgg agtccacgtt  300
ctttaatagt ggactcttgt tccaaactgg aacaacactc aaccctatct cggtctattc  360
ttttgattta taagggattt tgccgatttc ggcctattgg ttaaaaaatg agctgattta  420
acaaaaattt aacgcgaatt ttaacaaaat attaacgttt acaatttcag gtggcacttt  480
tcggggaaat gtgcgcggaa cccctatttg tttatttttc taaatacatt caaatatgta  540
tccgctcatg aattaattct tagaaaaact catcgagcat caaatgaaac tgcaatttat  600
tcatatcagg attatcaata ccatattttt gaaaaagccg tttctgtaat gaaggagaaa  660
actcaccgag gcagttccat aggatggcaa gatcctggta tcggtctgcg attccgactc  720
gtccaacatc aatacaacct attaatttcc cctcgtcaaa aataaggtta tcaagtgaga  780
aatcaccatg agtgacgact gaatccggtg agaatggcaa aagtttatgc atttctttcc  840
agacttgttc aacaggccag ccattacgct cgtcatcaaa atcactcgca tcaaccaaac  900
cgttattcat tcgtgattgc gcctgagcga gacgaaatac gcgatcgctg ttaaaaggac  960
aattacaaac aggaatcgaa tgcaaccggc gcaggaacac tgccagcgca tcaacaatat  1020
tttcacctga atcaggatat tcttctaata cctggaatgc tgttttcccg gggatcgcag  1080
tggtgagtaa ccatgcatca tcaggagtac ggataaaatg cttgatggtc ggaagaggca  1140
taaattccgt cagccagttt agtctgacca tctcatctgt aacatcattg gcaacgctac  1200
ctttgccatg tttcagaaac aactctggcg catcgggctt cccatacaat cgatagattg  1260
tcgcacctga ttgcccgaca ttatcgcgag cccatttata cccatataaa tcagcatcca  1320
tgttggaatt taatcgcggc ctagagcaag acgtttcccg ttgaatatgg ctcataacac  1380
cccttgtatt actgtttatg taagcagaca gttttattgt tcatgaccaa aatcccttaa  1440
cgtgagtttt cgttccactg agcgtcagac cccgtagaaa agatcaaagg atcttcttga  1500
gatccttttt ttctgcgcgt aatctgctgc ttgcaaacaa aaaaaccacc gctaccagcg  1560
```

```
gtggtttgtt tgccggatca agagctacca actctttttc cgaaggtaac tggcttcagc  1620
agagcgcaga taccaaatac tgtccttcta gtgtagccgt agttaggcca ccacttcaag  1680
aactctgtag caccgcctac atacctcgct ctgctaatcc tgttaccagt ggctgctgcc  1740
agtggcgata agtcgtgtct taccgggttg gactcaagac gatagttacc ggataaggcg  1800
cagcggtcgg gctgaacggg gggttcgtgc acacagccca gcttggagcg aacgacctac  1860
accgaactga gatacctaca gcgtgagcta tgagaaagcg ccacgcttcc cgaagggaga  1920
aaggcggaca ggtatccggt aagcggcagg gtcggaacag gagagcgcac gagggagctt  1980
ccagggggaa acgcctggta tctttatagt cctgtcgggt ttcgccacct ctgacttgag  2040
cgtcgatttt tgtgatgctc gtcagggggg cggagcctat ggaaaaacgc cagcaacgcg  2100
gcctttttac ggttcctggc cttttgctgg ccttttgctc acatgttctt tcctgcgtta  2160
tcccctgatt ctgtggataa ccgtattacc gcctttgagt gagctgatac cgctcgccgc  2220
agccgaacga ccgagcgcag cgagtcagtg agcgaggaag cggaagagcg cctgatgcgg  2280
tattttctcc ttacgcatct gtgcggtatt tcacaccgca tatatggtgc actctcagta  2340
caatctgctc tgatgccgca tagttaagcc agtatacact ccgctatcgc tacgtgactg  2400
ggtcatggct gcgccccgac acccgccaac acccgctgac gcgccctgac gggcttgtct  2460
gctcccggca tccgcttaca gacaagctgt gaccgtctcc gggagctgca tgtgtcagag  2520
gttttcaccg tcatcaccga aacgcgcgag gcagctgcgg taaagctcat cagcgtggtc  2580
gtgaagcgat tcacagatgt ctgcctgttc atccgcgtcc agctcgttga gtttctccag  2640
aagcgttaat gtctggcttc tgataaagcg ggccatgtta agggcggttt tttcctgttt  2700
ggtcactgat gcctccgtgt aagggggatt tctgttcatg ggggtaatga taccgatgaa  2760
acgagagagg atgctcacga tacgggttac tgatgatgaa catgcccggt tactggaacg  2820
ttgtgagggt aaacaactgg cggtatggat gcggcgggac cagagaaaaa tcactcaggg  2880
tcaatgccag cgcttcgtta atacagatgt aggtgttcca cagggtagcc agcagcatcc  2940
tgcgatgcag atccggaaca taatggtgca gggcgctgac ttccgcgttt ccagacttta  3000
cgaaacacgg aaaccgaaga ccattcatgt tgttgctcag gtcgcagacg ttttgcagca  3060
gcagtcgctt cacgttcgct cgcgtatcgg tgattcattc tgctaaccag taaggcaacc  3120
ccgccagcct agccgggtcc tcaacgacag gagcacgatc atgcgcaccc gtggggccgc  3180
catgccggcg ataatggcct gcttctcgcc gaaacgtttg gtggcgggac cagtgacgaa  3240
ggcttgagcg agggcgtgca agattccgaa taccgcaagc gacaggccga tcatcgtcgc  3300
gctccagcga aagcggtcct cgccgaaaat gacccagagc gctgccggca cctgtcctac  3360
gagttgcatg ataaagaaga cagtcataag tgcggcgacg atagtcatgc cccgcgccca  3420
ccggaaggag ctgactgggt tgaaggctct caagggcatc ggtcgagatc ccggtgccta  3480
atgagtgagc taacttacat taattgcgtt gcgctcactg cccgctttcc agtcgggaaa  3540
cctgtcgtgc cagctgcatt aatgaatcgg ccaacgcgcg gggagaggcg gtttgcgtat  3600
tgggcgccag ggtggttttt cttttcacca gtgagacggg caacagctga ttgcccttca  3660
ccgcctggcc ctgagagagt tgcagcaagc ggtccacgct ggtttgcccc agcaggcgaa  3720
aatcctgttt gatggtggtt aacggcggga tataacatga gctgtcttcg gtatcgtcgt  3780
atcccactac cgagatatcc gcaccaacgc gcagcccgga ctcggtaatg gcgcgcattg  3840
cgcccagcgc catctgatcg ttggcaacca gcatcgcagt gggaacgatg ccctcattca  3900
gcatttgcat ggtttgttga aaaccggaca tggcactcca gtcgccttcc cgttccgcta  3960
tcggctgaat ttgattgcga gtgagatatt tatgccagcc agccagacgc agacgcgccg  4020
agacagaact taatgggccc gctaacagcg cgatttgctg gtgacccaat gcgaccagat  4080
gctccacgcc cagtcgcgta ccgtcttcat gggagaaaat aatactgttg atgggtgtct  4140
ggtcagagac atcaagaaat aacgccggaa cattagtgca ggcagcttcc acagcaatgg  4200
catcctggtc atccagcgga tagttaatga tcagcccact gacgcgttgc gcgagaagat  4260
tgtgcaccgc cgctttacag gcttcgacgc cgcttcgttc taccatcgac accaccacgc  4320
tggcacccag ttgatcggcg cgagatttaa tcgccgcgac aatttgcgac ggcgcgtgca  4380
gggccagact ggaggtggca acgccaatca gcaacgactg tttgcccgcc agttgttgtg  4440
ccacgcggtt gggaatgtaa ttcagctccg ccatcgccgc ttccactttt tcccgcgttt  4500
tcgcagaaac gtggctggcc tggttcacca cgcgggaaac ggtctgataa gagacaccgg  4560
catactctgc gacatcgtat aacgttactg gtttcacatt caccaccctg aattgactct  4620
cttccgggcg ctatcatgcc ataccgcgaa aggttttgcg ccattcgatg gtgtccggga  4680
tctcgacgct ctcccttatg cgactcctgc attaggaagc agcccagtag taggttgagg  4740
ccgttgagca ccgccgccgc aaggaatggt gcatgcaagg agatggcgcc caacagtccc  4800
ccggccacgg ggcctgccac catacccacg ccgaaacaag cgctcatgag cccgaagtgg  4860
cgagcccgat cttccccatc ggtgatgtcg gcgatatagg cgccagcaac cgcacctgtg  4920
gcgccggtga tgccggccac gatgcgtccg gcgtagagga tcgagatctc gatcccgcga  4980
aattaatacg actcactata ggggaattgt gagcggataa caattcccct ctagaaataa  5040
ttttgtttaa ctttaagaag gagatatacc atgggcagca gccatcatca tcatcatcac  5100
agcagcggcc tggtgccgcg cggcagccat atggctagca tgactggtgg acagcaaatg  5160
ggtcgcggat ccatgccggc agctaagaaa aagaaactgg atggcagcgt cgacatcttc  5220
cccacacaga gaagaaacac catgagcggc aacgtggtga gaagctacaa gagcgtgctc  5280
agacccaaca tcagaaagag agagctgctg gacgccacct tcaactggtt cgacagagcc  5340
tacaagaagt tcttcgacgt gttcgtgtgc ctgtacggcg gcgtggagca cgacaccgtg  5400
cacagcgccc tgctgaagga aaccaccgac cccgacctgg tgtgcgccac catgtggttc  5460
agagtggtgc ccaagagcag ctgcgacggc atcagcgccc aagagatgat cagaagattc  5520
ggcgtgtacg ccggccacga gcctagcgcc gtggccatga gctacctgac cggcaacttc  5580
gacgacaaga agaaccactg gatcgactgc agagagaagt tcgtggccct ggctagagac  5640
atggtggtga agcccgagag cctgagcatc gacatcaaga gcatgatcga gcacaagatc  5700
ctgcccatct gcagccaaga caactggcaa gcctggaacg ccatcagcca actgttcggc  5760
gagggcaaga aggagaacaa ggccgagaag gctcagatct tcgtggacgt ggtgagcatg  5820
ctgagcaaca acagcgtgca gacctgggag gactacaaag aggtgatcag caaggccacc  5880
ggctgcagaa ccgccggcga gatcaacagc aagttcggcg gcagacccgg catcctgagc  5940
gtggacttca gcaaggacga caccggcagc ctgcccaagg acttcatcga gagaagaatc  6000
aaggacctga gccaaaaggc caaggagaag agcgccgcct acgagctgcc caacagaatg  6060
agactgagag agctgatcgc tagcgtgatc ggccccctaca gactggaaac ctggagcagc  6120
gtggctcaga gagcctgcgg cgacatcaga agcaagaaca gcaacaacct gctgtacgct  6180
agcgagagat tcaacagaac caaggagatc gaggagatcc tgagcgccaa gggcgacgtg  6240
gctagagccc aaaacatcct agggcagttc agaagcggcg agttcaacga gttcgccgtg  6300
```

```
gagaagagac acctgggcaa cctggagagc ctgtacaaca tctggagcaa gagcgacatg  6360
gacaccggca tcgaggagta cagcagcatc cacaaggacg agtacgaccg ggaccccatc  6420
gtggacctgt acagacacat ctacccccac agagaggtga tcagcgccaa gaacttcatc  6480
gacgccgccg tgctgaacaa gctgctgaga ctgaacgcta gcagacacgt gcacccccacc 6540
gtgttcggca agaccgtgat cagcttcagc cccaagagca gcgcctacgg cagaatcacc  6600
ccccctagcg agatcgtgag aggcagaccc gccggcagcc acggcatgat ctggctgacc  6660
atggagctgt tcgacgacgg caagtggatc gagcaccacc tgcccttcca caacagcaga  6720
tactacgaag aggtgtactg ctaccaagag ggcctgcccg tgaaggacga gcctagaagc  6780
cccatgttcg gctacagagt gggcaacgcc atcgccgaca caagcaagat cgacaacaga  6840
cggagaaagg ctagcaagca gttcctgaga gctcagcaga acatcaccca caacgtgagc  6900
ttcgacgaga acaccgcctt cagcgtggtg agaaacggcg aggacttcag catcaccatc  6960
agcagcagaa tcaaggctag caatgctaag agcctgatga ccatcggcga cagaatcatg  7020
ggcatcgatc agaatcagac cgccgccaac acctacagca tctgggaggt ggtgggcgac  7080
ggcgacgccg gcagcattca gcacggcaac ctgagcctga agagaatcga ggacggccac  7140
atcacaagca tcatcagagg cagaggcggc aacttcgatc agctgaacta cggcggcctg  7200
agctacgcca agttcagcga gtggagaagc gctagactgg gcttcatcag cagcctgaac  7260
gccgagctgg ctagcaagat gaactgggac tggtgctgcc tgtacgagtg gaacgctaga  7320
tacgctagcg ccctgagaaa gatcatctac agccacaagg gcatcgacat cgagagagtg  7380
ttcagaagag agatcgagga cttcgtggag ggcgtgctga gaatcggcag cctgagcagc  7440
gacgccctgc agtgcctgac caacgccaag agcctgatca gcagctactt cttcctgaac  7500
ggcaagaagg agcccgagga gcagagaaag ttcgaccaag gcctgttcga cctgagcgcc  7560
aagattgaca agaagagagt gaacaagaga cagcaaaaga ccaagagaat catgagcagc  7620
atcatgcaga tcgctagaga cagaggcgtg agcttcatcg tggtggaggg caagctgagc  7680
accgccacca aggacaacaa gagcaaggcc aatcagaagg ccatcgactg gtgcgctaga  7740
gccgtggtgg agaacctgga gcacagctgc agcctggtgg gcatcaagct ggtggccatc  7800
gaccccatga acacaagcca cctggacccc ttcgtgtacg tgctcaagac aagcctgggc  7860
aaggaggcta gattcgctag cgtggtgccc gccaagatca acgctagaca catgaagaac  7920
ttcaagagct ggagcagcct gctggccggc aacggcaaga tcaaaaagac caccgacgcc  7980
atctacgtgg gcgccttcca agacttctgc agagagtacg gcttcgtggc cgaggacatc  8040
agcaagatga gccaaagcga gatccaagac aagctgagca gccatcagtt cgtgctggtg  8100
cctcagagag gcggcagagt gtacatgagc acccaccccg tgagcagcga ggccaagaag  8160
atcgtgtacg ccggcagaga gagatggtac aacaacgccg acgtggtggc cgccgtgaac  8220
atcaccctga gaggctgcga gagactgagc gctagcagaa agaccgctag cacaagaaca  8280
ggcggcggcc ccggcggcgg cgccgccgcc ggcagcggca gccctaagaa aaaacgaaaa  8340
gttggcagcg gaagcaaaag gccggcggcc acgaaaaagg ccggccaggc aaaaaagaaa  8400
aagctcgagt acccatacga tgttccagat tacgcttgac tcgagcacca ccaccaccac  8460
cactgagatc cggctgctaa caaagcccga aaggaagctg agttggctgc tgccaccgct  8520
gagcaataac tagcataacc ccttggggcc tctaaacggg tcttgagggg ttttttgctg  8580
aaaggaggaa ctatatccgg at                                           8602
```

```
SEQ ID NO: 726          moltype = RNA  length = 60
FEATURE                 Location/Qualifiers
source                  1..60
                        mol_type = other RNA
                        organism = synthetic construct
SEQUENCE: 726
atcgcaacat ctcagaaacc cgtcctaagt tgacgggtga gcaagggcga ggagctgttc  60
```

```
SEQ ID NO: 727          moltype = RNA  length = 62
FEATURE                 Location/Qualifiers
source                  1..62
                        mol_type = other RNA
                        organism = synthetic construct
SEQUENCE: 727
atcgcaacat ctcagaaacc cgtcctaagt tgacggcgca atgatgatct ccgagccgtt  60
cc                                                                62
```

```
SEQ ID NO: 728          moltype = AA  length = 1021
FEATURE                 Location/Qualifiers
source                  1..1021
                        mol_type = protein
                        organism = synthetic construct
SEQUENCE: 728
IFPTQRRNTM SGNVVRSYKS VLRPNIRKRE LLDATFNWFD RAYKKFFDVF VCLYGGVEHD  60
TVHSALLKET TDPDLVCATM WFRVVPKSSC DGISAQEMIR RFGVYAGHEP SAVAMSYLTG  120
NFDDKKNHWI DCREKFVALA RDMVVKPESL SIDIKSMIEH KILPICSQDN WQAWNAISQL  180
FGEGKKENKA EKAQIFVDVV SMLSNNSVQT WEDYKEVISK ATGCRTAGEI NSKFGGRPGI  240
LSVDFSKDDT GSLPKDFIER RIKDLSQKAK EKSAAYELPN RMRLRELIAS VIGPYRLETW  300
SSVAQRACGD IRSKNSNNLL YASERFNRTK EIEEILSAKG DVARAQSILG QFRSGEFNEF  360
AVEKRHLGNL ESLYNIWSKS DMDTGIEEYS SIHKDEYDRD PIVDLYRHIY PHREVISAKN  420
FIDAAVLNKL LRLNASRHVH PTVFGKTVIS FSPKSSAYGR ITPPSEIVRG RPAGSHGMIW  480
LTMELFDDGK WIEHHLPFHN SRYYEEVYCY QEGLPVKDEP RSPMFGYRVG NAIADTSKID  540
NRRRKASKQF LRAQQNITHN VSFDENTAFS VVRNGEDFSI TISSRIKASN AKSLMTIGDR  600
IMGIDQNQTA ANTYSIWEVV GDGDAGSIQH GNLSLKRIED GHITSIIRGR GGNFDQLNYG  660
GLSYAKFSEW RSARLGFISS LNAELASKMN WDWCCLYEWN ARYASALRKI IYSHKGIDIE  720
RVFRREIEDF VEGVLRIGSL SSDALQCLTN AKSLISSYFF LNGKKEPEEQ RKFDQGLFDL  780
SAKIDKKRVN KRQQKTKRIM SSIMQIARDR GVSFIVVEGK LSTATKDNKS KANQKAIDWC  840
ARAVVENLEH SCSLVGIKLV AIDPMNTSHL DPFVYVLKTS LGKEARFASV VPAKINARHM  900
KNFKSWSSLL AGNGKIKKTT DAIYVGAFQD FCREYGFVAE DISKMSQSEI QDKLSSHQFV  960
```

```
LVPQRGGRVY MSTHPVSSEA KKIVYAGRER WYNNADVVAA VNITLRGCER LSASRKTAST  1020
R                                                                 1021

SEQ ID NO: 729          moltype = DNA  length = 5629
FEATURE                 Location/Qualifiers
source                  1..5629
                        mol_type = other DNA
                        organism = synthetic construct
SEQUENCE: 729
atcataagat gatcttcttg agatcgtttt ggtctgcgcg taatctcttg ctctgaaaac  60
gaaaaaaccg ccttgcaggg cggtttttcg aaggttctct gagctaccaa ctctttgaac  120
cgaggtaact ggcttggagg agcgcagtca ccaaaacttg tcctttcagt ttagccttaa  180
ccggcgcatg acttcaagac taactcctct aaatcaatta ccagtggctg ctgccagtgg  240
tgcttttgca tgtctttccg ggttggactc aagacgatag ttaccggata aggcgcagcg  300
gtcggactga acggggggtt cgtgcataca gtccagcttg gagcgaactg cctacccgga  360
actgagtgtc aggcgtggaa tgagacaaac gcggccataa cagcggaatg acaccggtaa  420
accgaaaggc aggaacagga gagcgcacga gggagccgcc agggggaaac gcctggtatc  480
tttatagtcc tgtcgggttt cgccaccact gatttgagcg tcagatttcg tgatgcttgt  540
caggggggcg gagcctatgg aaaaacggct ttgccgcggc cctctcactt ccctgttaag  600
tatcttcctg gcatcttcca ggaaatctcc gccccgttcg taagccattt ccgctcgccg  660
cagtcgaacg accgagcgta gcgagtcagt gagcgaggaa gcggaatata tcctgtatca  720
catattctgc tgacgcaccg gtgcagcctt ttttctcctg ccacatgaag cacttcactg  780
acaccctcat cagtgccaac atagtaagcc agtatacact ccgctagcgc tgatgtccgg  840
cggtgctttt gccgttacgc accaccccgt cagtagctga acaggaggga cagctgatag  900
aaacagaagc cactggagca cctcaaaaac accatcatac actaaatcag taagttggca  960
gcatcacccg acgcactttg cgccgaataa atacctgtga cggaagatca cttcgcagaa  1020
taaataaatc ctggtgtccc tgttgatacc gggaagcccc gggccaactt ttggcgaaaa  1080
tgagacgttg atcggcacgt aagaggttcc aactttcacc ataatgaaat aagatcacta  1140
ccgggcgtat tttttgagtt atcgagattt tcaggagcta aggaagctaa aatggagaaa  1200
aaaatcactg gatataccac cgttgatata tcccaatggc atcgtaaaga acattttgag  1260
gcatttcagt cagttgctca atgtacctat aaccagaccg ttcagctgga tattacggcc  1320
tttttaaaga ccgtaaagaa aaataagcac aagttttatc cggcctttat tcacattctt  1380
gcccgcctga tgaatgctca tccggaattc cgtatggcaa tgaaagacgg tgagctggtg  1440
atatgggata gtgttcaccc ttgttacacc gttttccatg agcaaactga aacgttttca  1500
tcgctctgga gtgaatacca cgacgatttc cggcagtttc tacacatata ttcgcaagat  1560
gtggcgtgtt acggtgaaaa cctggcctat ttccctaaag ggtttattga gaatatgttt  1620
ttcgtctcag ccaatccctg ggtgagtttc accagttttg atttaaacgt ggccaatatg  1680
gacaacttct tcgcccccgt tttcaccatg ggcaaatatt atacgcaagg cgacaaggtg  1740
ctgatgccgc tggcgattca ggttcatcat gccgtttgtg atggcttcca tgtcggcaga  1800
atgcttaatg aattacaaca gtactgcgat gagtggcagg gcggggcgta atttggtaca  1860
tctcaaataa aacgaaaggc tcagtcgaaa gactgggcct ttcgttttat ctgttgtttg  1920
tcggtgaacg ctctcgttaa ctagctatac tgatttcgtc agactcacag tcaaacatgc  1980
cggtcagttg gcctggtgat ggcgggatcg ttgtatattt cttgacacct tttcggcacc  2040
gccctaaaat tctgcgtcct cataatatat gaggcgattt attacgtgtt tacgaagcaa  2100
aagctaaaac caggagctat ttaatgccgg cagctaagaa aaagaaactg gatggcagcg  2160
tcgacatctt ccccacacag agaagaaaca ccatgagcgg caacgtggtg agaagctaca  2220
agagcgtgct cagacccaac atcagaaaga gagagctgct ggacgccacc ttcaactggt  2280
tcgacagagc ctacaagaag ttcttcgacg tgttcgtgtg cctgtacggc ggcgtggagc  2340
acgacaccgt gcacagcgcc ctgctgaagg aaaccaccga ccccgacctg gtgtgcgcca  2400
ccatgtggtt cagagtggtg cccaagagca gctgcgacgg catcagcgcc caagagatga  2460
tcagaagatt cggcgtgtac gccggccacg agcctagcgc cgtggccatg agctacctga  2520
ccggcaactt cgacgacaag aagaaccact ggatcgactg cagagagaag ttcgtggccc  2580
tggctagaga catggtggtg aagcccgaga gcctgagcat cgacatcaag agcatgatcg  2640
agcacaagat cctgcccatc tgcagccaag acaactggca agcctggaac gccatcagcc  2700
aactgttcgg cgagggcaag aaggagaaca aggccgagaa ggctcagatc ttcgtggacg  2760
tggtgagcat gctgagcaac aacagcgtgc agacctggga ggactacaaa gaggtgatca  2820
gcaaggccac cggctgcaga accgccggcg agatcaacag caagttcggc ggcagacccg  2880
gcatcctgag cgtggacttc agcaaggacg acaccggcag cctgcccaag gacttcatcg  2940
agagaagaat caaggacctg agccaaaagg ccaaggagaa gagcgccgcc tacgagctgc  3000
ccaacagaat gagactgaga gagctgatcg ctagcgtgat cggcccctac agactggaaa  3060
cctggagcag cgtggctcag agagcctgcg gcgacatcag aagcaagaac agcaacaacc  3120
tgctgtacgc tagcgagaga ttcaacagaa ccaaggagat cgaggagatc ctgagcgcca  3180
agggcgacgt ggctagagcc caaagcatcc tagggcagtt cagaagcggc gagttcaacg  3240
agttcgccgt ggagaagaga cacctgggca acctggagag cctgtacaac atctggagca  3300
agagcgacat ggacaccggc atcgaggagt acagcagcat ccacaaggac gagtacgacc  3360
gggaccccat cgtggacctg tacagacaca tctaccccca cagagaggtg atcagcgcca  3420
agaacttcat cgacgccgcc gtgctgaaca agctgctgag actgaacgct agcagacacg  3480
tgcaccccac cgtgttcggc aagaccgtga tcagcttcag ccccaagagc agcgcctacg  3540
gcagaatcac ccccctagc gagatcgtga gaggcagacc cgccggcagc cacggcatga  3600
tctggctgac catggagctg ttcgacgacg gcaagtggat cgagcaccac ctgcccttcc  3660
acaacagcag atactacgaa gaggtgtact gctaccaaga gggcctgccc gtgaaggacg  3720
agcctagaag ccccatgttc ggctacagag tgggcaacgc catcgccgac acaagcaaga  3780
tcgacaacag acggagaaag gctagcaagc agttcctgag agctcagcag aacatcaccc  3840
acaacgtgag cttcgacgag aacaccgcct tcagcgtggt gagaaacggc gaggacttca  3900
gcatcaccat cagcagcaga atcaaggcta gcaatgctaa gagcctgatg accatcggcg  3960
acagaatcat gggcatcgat cagaatcaga ccgccgccaa cacctacagc atctgggagg  4020
tggtgggcga cggcgacgcc ggcagcattc agcacggcaa cctgagcctg aagagaatcg  4080
aggacggcca catcacaagc atcatcagag gcagaggcgg caacttcgat cagctgaact  4140
acggcggcct gagctacgcc aagttcagcg agtggagaag cgctagactg ggcttcatca  4200
```

```
gcagcctgaa cgccgagctg gctagcaaga tgaactggga ctggtgctgc ctgtacgagt  4260
ggaacgctag atacgctagc gccctgagaa agatcatcta cagccacaag ggcatcgaca  4320
tcgagagagt gttcagaaga gagatcgagg acttcgtgga gggcgtgctg agaatcggca  4380
gcctgagcag cgacgccctg cagtgcctga ccaacgccaa gagcctgatc agcagctact  4440
tcttcctgaa cggcaagaag gagcccgagg agcagagaaa gttcgaccaa ggcctgttcg  4500
acctgagcgc caagattgac aagaagagag tgaacaagag acagcaaaag accaagagaa  4560
tcatgagcag catcatgcag atcgctagag acagaggcgt gagcttcatc gtggtggagg  4620
gcaagctgag caccgccacc aaggacaaca agagcaaggc caatcagaag gccatcgact  4680
ggtgcgctag agccgtggtg gagaacctgg agcacagctg cagcctggtg ggcatcaagc  4740
tggtggccat cgaccccatg aacacaagcc acctggaccc cttcgtgtac gtgctcaaga  4800
caagcctggg caaggaggct agattcgcta gcgtggtgcc cgccaagatc aacgctagac  4860
acatgaagaa cttcaagagc tggagcagcc tgctggccgg caacggcaag atcaaaaaga  4920
ccaccgacgc catctacgtg ggcgccttcc aagacttctg cagagagtac ggcttcgtgg  4980
ccgaggacat cagcaagatg agccaaagcg agatccaaga caagctgagc agccatcagt  5040
tcgtgctggt gcctcagaga ggcggcagag tgtacatgag cacccacccc gtgagcagcg  5100
aggccaagaa gatcgtgtac gccggcagag agagatggta caacaacgcc gacgtggtgg  5160
ccgccgtgaa catcaccctg agaggctgcg agagactgag cgctagcaga aagaccgcta  5220
gcacaagaac aggcggcggc cccggcggcg gcgccgccgc cggcagcggc agccctaaga  5280
aaaaacgaaa agttggcagc ggaagcaaaa ggccggcggc cacgaaaaag gccggccagg  5340
caaaaaagaa aaagctcgag tacccatacg atgttccaga ttacgcttga gaattcggta  5400
ccttgacagc tagctcagtc ctaggtataa tactagtatc gcaacatctc agaaacccgt  5460
cctaagttga cggcgcaatg atgatctccg agccgttcgg ccggcatggt cccagcctcc  5520
tcgctggcgc cggctgggca acatgcttcg gcatggcgaa tgggaccgta cgtcgacgct  5580
agcataaccc cttggggcct ctaaacgggt cttgaggggt tttttggat             5629
```

```
SEQ ID NO: 730          moltype = DNA  length = 8134
FEATURE                 Location/Qualifiers
source                  1..8134
                        mol_type = other DNA
                        organism = synthetic construct
SEQUENCE: 730
acgcgtgtag tcttatgcaa tactcttgta gtcttgcaac atggtaacga tgagttagca  60
acatgcctta caaggagaga aaaagcaccg tgcatgccga ttggtggaag taaggtggta  120
cgatcgtgcc ttattaggaa ggcaacagac gggtctgaca tggattggac gaaccactga  180
attgccgcat tgcagagata ttgtatttaa gtgcctagct cgatacaata aacgggtctc  240
tctggttaga ccagatctga gcctgggagc tctctggcta actagggaac ccactgctta  300
agcctcaata aagcttgcct tgagtgcttc aagtagtgtg tgcccgtctg ttgtgtgact  360
ctggtaacta gagatccctc agaccctttt agtcagtgtg gaaaatctct agcagtggcg  420
cccgaacagg gacctgaaag cgaaagggaa accagagctc tctcgacgca ggactcggct  480
tgctgaagcg cgcacggcaa gaggcgaggg gcggcgactg gtgagtacgc caaaaatttt  540
gactagcgga ggctagaagg agagagatgg gtgcgagagc gtcagtatta agcgggggag  600
aattagatcg cgatgggaaa aaattcggtt aaggccaggg ggaaagaaaa aatataaatt  660
aaaacatata gtatgggcaa gcagggagct agaacgattc gcagttaatc ctggcctgtt  720
agaaacatca gaaggctgta gacaaatact gggacagcta caaccatccc ttcagacagg  780
atcagaagaa cttagatcat tatataatac agtagcaacc ctctattgtg tgcatcaaag  840
gatagagata aaagacacca aggaagcttt agacaagata gaggaagagc aaaacaaaag  900
taagaccacc gcacagcaag cggccactga tcttcagacc tggaggagga gatatgaggg  960
acaattggag aagtgaatta tataaatata aagtagtaaa aattgaacca ttaggagtag  1020
cacccaccaa ggcaaagaga agagtggtgc agagagaaaa aagagcagtg ggaataggag  1080
ctttgttcct tgggttcttg ggagcagcag gaagcactat gggcgcagcc tcaatgacgc  1140
tgacggtaca ggccagacaa ttattgtctg gtatagtgca gcagcagaac aatttgctga  1200
gggctattga ggcgcaacag catctgttgc aactcacagt ctggggcatc aagcagctcc  1260
aggcaagaat cctggctgtg gaaagatacc taaaggatca acagctcctg gggatttggg  1320
gttgctctgg aaaactcatt tgcaccactg ctgtgccttg gaatgctagt tggagtaata  1380
aatctctgga acagattgga atcacacgac ctggatggag tgggacagag aaattaacaa  1440
ttacacaagc ttaatacact ccttaattga agaatcgcaa aaccagcaag aaaagaatga  1500
acaagaatta ttggaattag ataaatgggc aagtttgtgg aattggttta acataacaaa  1560
ttggctgtgg tatataaaat tattcataat gatagtagga ggcttggtag gtttaagaat  1620
agtttttgct gtactttcta tagtgaatag agttaggcag ggatattcac cattatcgtt  1680
tcagacccac ctcccaaccc cgaggggacc cgacaggccc gaaggaatag aagaagaagg  1740
tggagagaga gacagagaca gatccattcg attagtgaac ggatctcgac ggtatcggtt  1800
aacttttaaa agaaaagggg ggattggggg gtacagtgca ggggaaagaa tagtagacat  1860
aatagcaaca gacatacaaa ctaaagaatt acaaaaacaa attacaaaat tcaaaatttt  1920
atcgatacta gtattatgcc cagtacatga ccttatggga ctttcctact tggcagtaca  1980
tctacgtatt agtcatcgct attaccatgg tgatgcggtt ttggcagtac atcaatgggc  2040
gtggatagcg gtttgactca cggggatttc caagtctcca ccccattgac gtcaatggga  2100
gtttgttttg gcaccaaaat caacgggact ttccaaaatg tcgtaacaac tccgccccat  2160
tgacgcaaat gggcggtagg cgtgtacggt gggaggttta tataagcaga gctcgtttag  2220
tgaaccgtca gatcgcctgg agacgccatc cacgctgttt tgacctccat agaagattct  2280
agagcgagaa aagccttgtt tgccaccatg gaacggctcg gagatcatca ttgcgnaang  2340
tgagcaaggg cgaggagctg ttcaccgggg tggtgcccat cctggtcgag ctggacggcg  2400
acgtaaacgg ccacaagttc agcgtgtccg gcgagggcga gggcgatgcc acctacggca  2460
agctgaccct gaagttcatc tgcaccaccg gcaagctgcc cgtgccctgg cccaccctcg  2520
tgaccaccct gacctacggc gtgcagtgct tcagccgcta ccccgaccac atgaagcagc  2580
acgacttctt caagtccgcc atgcccgaag gctacgtcca ggagcgcacc atcttcttca  2640
aggacgacgg caactacaag acccgcgccg aggtgaagtt cgagggcgac accctggtga  2700
accgcatcga gctgaagggc atcgacttca aggaggacgg caacatcctg gggcacaagc  2760
tggagtacaa ctacaacagc cacaacgtct atatcatggc cgacaagcag aagaacggca  2820
tcaaggtgaa cttcaagatc cgccacaaca tcgaggacgg cagcgtgcag ctcgccgacc  2880
```

```
actaccagca gaacaccccc atcggcgacg gccccgtgct gctgcccgac aaccactacc  2940
tgagcaccca gtccaagctg agcaaagacc ccaacgagaa gcgcgatcac atggtcctgc  3000
tggagttcgt gaccgccgcc gggatcactc tcggcatgga cgagctgtac aagtaactcg  3060
aggcggccgc gaaggatctg cgatcgctcc ggtgcccgtc agtgggcaga gcgcacatcg  3120
cccacagtcc ccgagaagtt ggggggaggg gtcggcaatt gaacgggtgc ctagagaagg  3180
tggcgcgggg taaactggga aagtgatgtc gtgtactggc tccgcctttt tcccgagggt  3240
gggggagaac cgtatataag tgcagtagtc gccgtgaacg ttctttttcg caacgggttt  3300
gccgccagaa cacagctgaa gcttcgaggg gctcgcatct ctccttcacg cgcccgccgc  3360
cctacctgag gccgccatcc acgccggttg agtcgcgttc tgccgcctcc cgcctgtggt  3420
gcctcctgaa ctgcgtccgc cgtctaggta agtttaaagc tcaggtcgag accgggcctt  3480
tgtccggcgc tcccttggag cctacctaga ctcagccggc tctccacgct ttgcctgacc  3540
ctgcttgctc aactctacgt ctttgtttcg ttttctgttc tgcgccgtta cagatccaag  3600
ctgtgaccgg cgcctacgct agatgaccga gtacaagccc acggtgcgcc tcgccacccg  3660
cgacgacgtc cccagggccg tacgcaccct cgccgccgcg ttcgccgact accccgccac  3720
gcgccacacc gtcgatccgg accgccacat cgagcgggtc accgagctgc aagaactctt  3780
cctcacgcgc gtcgggctcg acatcggcaa ggtgtgggtc gcggacgacg gcgccgcggt  3840
ggcggtctgg accacgccgg agagcgtcga agcgggggcg gtgttcgccg agatcggccc  3900
gcgcatggcc gagttgagcg gttcccggct ggccgcgcag caacagatgg aaggcctcct  3960
ggcgccgcac cggcccaagg agcccgcgtg gttcctggcc accgtcggcg tctcgcccga  4020
ccaccagggc aagggtctgg gcagcgccgt cgtgctcccc ggagtggagg cggccgagcg  4080
cgccggggtg cccgccttcc tggagacctc cgcgccccgc aacctcccct tctacgagcg  4140
gctcggcttc accgtcaccg ccgacgtcga ggtgcccgaa ggaccgcgca cctggtgcat  4200
gacccgcaag cccggtgcct gagtcgacaa tcaacctctg gattacaaaa tttgtgaaag  4260
attgactggt attcttaact atgttgctcc ttttacgcta tgtggatacg ctgctttaat  4320
gcctttgtat catgctattg cttcccgtat ggctttcatt ttctcctcct tgtataaatc  4380
ctggttgctg tctctttatg aggagttgtg gcccgttgtc aggcaacgtg gcgtggtgtg  4440
cactgtgttt gctgacgcaa cccccactgg ttggggcatt gccaccacct gtcagctcct  4500
ttccgggact ttcgctttcc ccctccctat tgccacggcg gaactcatcg ccgcctgcct  4560
tgcccgctgc tggacagggg ctcggctgtt gggcactgac aattccgtgg tgttgtcggg  4620
gaaatcatcg tcctttcctt ggctgctcgc ctgtgttgcc acctggattc tgcgcgggac  4680
gtccttctgc tacgtccctt cggccctcaa tccagcggac cttccttccc gcggcctgct  4740
gccggctctg cggcctcttc cgcgtcttcg ccttcgccct cagacgagtc ggatctccct  4800
ttgggccgcc tccccgcctg gtacctttaa gaccaatgac ttacaaggca gctgtagatc  4860
ttagccactt tttaaaagaa aaggggggac tggaagggct aattcactcc caacgaaaat  4920
aagatctgct ttttgcttgt actgggtctc tctggttaga ccagatctga gcctgggagc  4980
tctctggcta actagggaac ccactgctta agcctcaata aagcttgcct tgagtgcttc  5040
aagtagtgtg tgcccgtctg ttgtgtgact ctggtaacta gagatccctc agaccctttt  5100
agtcagtgtg gaaaatctct agcagtagta gttcatgtca tcttattatt cagtatttat  5160
aacttgcaaa gaaatgaata tcagagagtg agaggaactt gtttattgca gcttataatg  5220
gttacaaata aagcaatagc atcacaaatt tcacaaataa agcatttttt tcactgcatt  5280
ctagttgtgg tttgtccaaa ctcatcaatg tatcttatca tgtctggctc tagctatccc  5340
gcccctaact ccgcccagtt ccgcccattc tccgccccat ggctgactaa ttttttttat  5400
ttatgcagag gccgaggccg cctcggcctc tgagctattc cagaagtagt gaggaggctt  5460
ttttggaggc ctagactttt gcagagacgg cccaaattcg taatcatggt catagctgtt  5520
tcctgtgtga aattgttatc cgctcacaat tccacacaac atacgagccg gaagcataaa  5580
gtgtaaagcc tggggtgcct aatgagtgag ctaactcaca ttaattgcgt tgcgctcact  5640
gcccgctttc cagtcgggaa acctgtcgtg ccagctgcat taatgaatcg gccaacgcgc  5700
ggggagaggc ggtttgcgta ttgggcgctc ttccgcttcc tcgctcactg actcgctgcg  5760
ctcggtcgtt cggctgcggc gagcggtatc agctcactca aaggcggtaa tacggttatc  5820
cacagaatca ggggataacg caggaaagaa catgtgagca aaaggccagc aaaaggccag  5880
gaaccgtaaa aaggccgcgt tgctggcgtt tttccatagg ctccgccccc ctgacgagca  5940
tcacaaaaat cgacgctcaa gtcagaggtg gcgaaacccg acaggactat aaagatacca  6000
ggcgtttccc cctggaagct ccctcgtgcg ctctcctgtt ccgaccctgc cgcttaccgg  6060
atacctgtcc gcctttctcc cttcgggaag cgtggcgctt tctcatagct cacgctgtag  6120
gtatctcagt tcggtgtagg tcgttcgctc caagctgggc tgtgtgcacg aaccccccgt  6180
tcagcccgac cgctgcgcct tatccggtaa ctatcgtctt gagtccaacc cggtaagaca  6240
cgacttatcg ccactggcag cagccactgg taacaggatt agcagagcga ggtatgtagg  6300
cggtgctaca gagttcttga agtggtggcc taactacggc tacactagaa ggacagtatt  6360
tggtatctgc gctctgctga agccagttac cttcggaaaa agagttggta gctcttgatc  6420
cggcaaacaa accaccgctg gtagcggtgg tttttttgtt tgcaagcagc agattacgcg  6480
cagaaaaaaa ggatctcaag aagatccttt gatcttttct acggggtctg acgctcagtg  6540
gaacgaaaac tcacgttaag ggattttggt catgagatta tcaaaaagga tcttcaccta  6600
gatcctttta aattaaaaat gaagttttaa atcaatctaa agtatatatg agtaaacttg  6660
gtctgacagt taccaatgct taatcagtga ggcacctatc tcagcgatct gtctatttcg  6720
ttcatccata gttgcctgac tccccgtcgt gtagataact acgatacggg agggcttacc  6780
atctggcccc agtgctgcaa tgataccgcg agacccacgc tcaccggctc cagatttatc  6840
agcaataaac cagccagccg gaagggccga gcgcagaagt ggtcctgcaa ctttatccgc  6900
ctccatccag tctattaatt gttgccggga agctagagta agtagttcgc cagttaatag  6960
tttgcgcaac gttgttgcca ttgctacagg catcgtggtg tcacgctcgt cgtttggtat  7020
ggcttcattc agctccggtt cccaacgatc aaggcgagtt acatgatccc ccatgttgtg  7080
caaaaaagcg gttagctcct tcggtcctcc gatcgttgtc agaagtaagt tggccgcagt  7140
gttatcactc atggttatgg cagcactgca taattctctt actgtcatgc catccgtaag  7200
atgcttttct gtgactggtg agtactcaac caagtcattc tgagaatagt gtatgcggcg  7260
accgagttgc tcttgcccgg cgtcaatacg ggataatacc gcgccacata gcagaacttt  7320
aaaagtgctc atcattggaa aacgttcttc ggggcgaaaa ctctcaagga tcttaccgct  7380
gttgagatcc agttcgatgt aacccactcg tgcacccaac tgatcttcag catcttttac  7440
tttcaccagc gtttctgggt gagcaaaaac aggaaggcaa aatgccgcaa aaaagggaat  7500
aagggcgaca cggaaatgtt gaatactcat actcttcctt tttcaatatt attgaagcat  7560
ttatcagggt tattgtctca tgagcggata catatttgaa tgtatttaga aaaataaaca  7620
```

```
aatagggggtt ccgcgcacat ttccccgaaa agtgccacct gacgtctaag aaaccattat  7680
tatcatgaca ttaacctata aaaataggcg tatcacgagg ccctttcgtc tcgcgcgttt  7740
cggtgatgac ggtgaaaacc tctgacacat gcagctcccg gagacggtca cagcttgtct  7800
gtaagcggat gccgggagca gacaagcccg tcagggcgcg tcagcgggtg ttggcgggtg  7860
tcggggctgg cttaactatg cggcatcaga gcagattgta ctgagagtgc accatatgcg  7920
gtgtgaaata ccgcacagat gcgtaaggag aaaataccgc atcaggcgcc attcgccatt  7980
caggctgcgc aactgttggg aagggcgatc ggtgcgggcc tcttcgctat tacgccagct  8040
ggcgaaaggg ggatgtgctg caaggcgatt aagttgggta acgccagggt tttcccagtc  8100
acgacgttgt aaaacgacgg ccagtgccaa gctg                              8134

SEQ ID NO: 731         moltype = DNA  length = 27
FEATURE                Location/Qualifiers
source                 1..27
                       mol_type = other DNA
                       organism = synthetic construct
SEQUENCE: 731
ccaagctggc tagcgtttaa acttaag                                      27

SEQ ID NO: 732         moltype = DNA  length = 26
FEATURE                Location/Qualifiers
source                 1..26
                       mol_type = other DNA
                       organism = synthetic construct
SEQUENCE: 732
atgatctccg agccgttttt ggtacc                                       26

SEQ ID NO: 733         moltype = DNA  length = 31
FEATURE                Location/Qualifiers
source                 1..31
                       mol_type = other DNA
                       organism = synthetic construct
SEQUENCE: 733
gctgaagaga cacagcagaa tcgccgccgc t                                 31

SEQ ID NO: 734         moltype = DNA  length = 30
FEATURE                Location/Qualifiers
source                 1..30
                       mol_type = other DNA
                       organism = synthetic construct
SEQUENCE: 734
gggaagcggc ggcgattctg ctgtgtctct                                   30

SEQ ID NO: 735         moltype = DNA  length = 22
FEATURE                Location/Qualifiers
source                 1..22
                       mol_type = other DNA
                       organism = synthetic construct
SEQUENCE: 735
ctcacctcgc gacgcaatga tg                                           22

SEQ ID NO: 736         moltype = DNA  length = 26
FEATURE                Location/Qualifiers
source                 1..26
                       mol_type = other DNA
                       organism = synthetic construct
SEQUENCE: 736
gcgacgcaat gatgtttttc ggtacc                                       26

SEQ ID NO: 737         moltype = DNA  length = 9036
FEATURE                Location/Qualifiers
source                 1..9036
                       mol_type = other DNA
                       organism = synthetic construct
SEQUENCE: 737
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
```

-continued

```
gtttaaactt aagcttaccg gtgccaccat gccggcagct aagaaaaaga aactggatgg  960
cagcgtcgac atcttcccca cacagagaag aaacaccatg agcggcaacg tggtgagaag  1020
ctacaagagc gtgctcagac ccaacatcag aaagagagag ctgctggacg ccaccttcaa  1080
ctggttcgac agagcctaca agaagttctt cgacgtgttc gtgtgcctgt acggcggcgt  1140
ggagcacgac accgtgcaca gcgccctgct gaaggaaacc accgaccccg acctggtgtg  1200
cgccaccatg tggttcagag tggtgcccaa gagcagctgc gacggcatca gcgcccaaga  1260
gatgatcaga agattcggcg tgtacgccgg ccacgagcct agcgccgtgg ccatgagcta  1320
cctgaccggc aacttcgacg acaagaagaa ccactggatc gactgcagag agaagttcgt  1380
ggccctggct agagacatgg tggtgaagcc cgagagcctg agcatcgaca tcaagagcat  1440
gatcgagcac aagatcctgc ccatctgcag ccaagacaac tggcaagcct ggaacgccat  1500
cagccaactg ttcggcgagg gcaagaagga gaacaaggcc gagaaggctc agatcttcgt  1560
ggacgtggtg agcatgctga gcaacaacag cgtgcagacc tgggaggact acaaagaggt  1620
gatcagcaag gccaccggct gcagaaccgc cggcgagatc aacagcaagt tcggcggcag  1680
acccggcatc ctgagcgtgg acttcagcaa ggacgacacc ggcagcctgc ccaaggactt  1740
catcgagaga agaatcaagg acctgagcca aaaggccaag gagaagagcg ccgcctacga  1800
gctgcccaac agaatgagac tgagagagct gatcgctagc gtgatcggcc cctacagact  1860
ggaaacctgg agcagcgtgg ctcagagagc ctgcggcgac atcagaagca agaacagcaa  1920
caacctgctg tacgctagcg agagattcaa cagaaccaag gagatcgagg agatcctgag  1980
cgccaagggc gacgtggcta gagcccaaaa catcctaggg cagttcagaa gcggcgagtt  2040
caacgagttc gccgtggaga agagacacct gggcaacctg gagagcctgt acaacatctg  2100
gagcaagagc gacatggaca ccggcatcga ggagtacagc agcatccaca aggacgagta  2160
cgaccgggac cccatcgtgg acctgtacag acacatctac ccccacagag aggtgatcag  2220
cgccaagaac ttcatcgacg ccgccgtgct gaacaagctg ctgagactga acgctagcag  2280
acacgtgcac ccccaccgtgt tcggcaagac cgtgatcagc ttcagcccca agagcagcgc  2340
ctacggcaga atcacccccc ctagcgagat cgtgagaggc agacccgccg gcagccacgg  2400
catgatctgg ctgaccatgg agctgttcga cgacggcaag tggatcgagc accacctgcc  2460
cttccacaac agcagatact acgaagaggt gtactgctac caagagggcc tgcccgtgaa  2520
ggacgagcct agaagcccca tgttcggcta cagagtgggc aacgccatcg ccgacacaag  2580
caagatcgac aacagacgga gaaaggctag caagcagttc ctgagagctc agcagaacat  2640
cacccacaac gtgagcttcg acgagaacac cgccttcagc gtggtgagaa acggcgagga  2700
cttcagcatc accatcagca gcagaatcaa ggctagcaat gctaagagcc tgatgaccat  2760
cggcgacaga atcatgggca tcgatcagaa tcagaccgcc gccaacacct acagcatctg  2820
ggaggtggtg ggcgacggcg acgccggcag cattcagcac ggcaacctga gcctgaagag  2880
aatcgaggac ggccacatca caagcatcat cagaggcaga ggcggcaact tcgatcagct  2940
gaactacggc ggcctgagct acgccaagtt cagcgagtgg agaagcgcta gactgggctt  3000
catcagcagc ctgaacgccg agctggctag caagatgaac tgggactggt gctgcctgta  3060
cgagtggaac gctagatacg ctagcgccct gagaaagatc atctacagcc acaagggcat  3120
cgacatcgag agagtgttca gaagagagat cgaggacttc gtggagggcg tgctgagaat  3180
cggcagcctg agcagcgacg ccctgcagtg cctgaccaac gccaagagcc tgatcagcag  3240
ctacttcttc ctgaacggca agaaggagcc cgaggagcag agaaagttcg accaaggcct  3300
gttcgacctg agcgccaaga ttgacaagaa gagagtgaac aagagacagc aaaagaccaa  3360
gagaatcatg agcagcatca tgcagatcgc tagagacaga ggcgtgagct tcatcgtggt  3420
ggagggcaag ctgagcaccg ccaccaagga caacaagagc aaggccaatc agaaggccat  3480
cgactggtgc gctagagccg tggtggagaa cctggagcac agctgcagcc tggtgggcat  3540
caagctggtg gccatcgacc ccatgaacac aagccacctg gacccccttcg tgtacgtgct  3600
caagacaagc ctgggcaagg aggctagatt cgctagcgtg gtgcccgcca agatcaacgc  3660
tagacacatg aagaacttca agagctggag cagcctgctg gccggcaacg gcaagatcaa  3720
aaagaccacc gacgccatct acgtgggcgc cttccaagac ttctgcagag agtacggctt  3780
cgtggccgag gacatcagca agatgagcca aagcgagatc caagacaagc tgagcagcca  3840
tcagttcgtg ctggtgcctc agagaggcgg cagagtgtac atgagcaccc accccgtgag  3900
cagcgaggcc aagaagatcg tgtacgccgg cagagagaga tggtacaaca acgccgacgt  3960
ggtggccgcc gtgaacatca ccctgagagg ctgcgagaga ctgagcgcta gcagaaagac  4020
cgctagcaca agaacaggcg gcggccccgg cggcggcgcc gccgccggca gcggcagccc  4080
taagaaaaaa cgaaaagttg gcagcggaag caaaaggccg gcggccacga aaaaggccgg  4140
ccaggcaaaa aagaaaaagc tcgagtaccc atacgatgtt ccagattacg cttgagaatt  4200
ccccttgagc atctgacttc tggctaataa aggaaattta ttttcattgc aatagtgtgt  4260
tggaattttt tgtgtctctc aggtaccaaa aacggctcgg agatcatcat tgcgccgtca  4320
acttaggacg ggtttctgag atgttgcgat cggtgtttcg tcctttccac aagatatata  4380
aagccaagaa atcgaaatac tttcaagtta cggtaagcat atgatagtcc attttaaaac  4440
ataattttaa aactgcaaac tacccaagaa attattactt tctacgtcac gtattttgta  4500
ctaatatctt tgtgtttaca gtcaaattaa ttccaattat ctctctaaca gccttgtatc  4560
gtatatgcaa atatgaagga atcatgggaa ataggccctc tagagggccc gtttaaaccc  4620
gctgatcagc ctcgactgtg ccttctagtt gccagccatc tgttgtttgc ccctcccccg  4680
tgccttcctt gaccctggaa ggtgccactc ccactgtcct ttcctaataa aatgaggaaa  4740
ttgcatcgca ttgtctgagt aggtgtcatt ctattctggg gggtggggtg gggcaggaca  4800
gcaaggggga ggattgggaa gacaatagca ggcatgctgg ggatgcggtg ggctctatgg  4860
cttctgaggc ggaaagaacc agctggggct ctagggggta tccccacgcg ccctgtagcg  4920
gcgcattaag cgcggcgggt gtggtggtta cgcgcagcgt gaccgctaca cttgccagcg  4980
ccctagcgcc cgctcctttc gctttcttcc cttcctttct cgccacgttc gccggctttc  5040
cccgtcaagc tctaaatcgg gggctccctt tagggttccg atttagtgct ttacggcacc  5100
tcgaccccaa aaaacttgat tagggtgatg gttcacgtag tgggccatcg ccctgataga  5160
cggtttttcg ccctttgacg ttggagtcca cgttctttaa tagtggactc ttgttccaaa  5220
ctggaacaac actcaaccct atctcggtct attcttttga tttataaggg attttgccga  5280
tttcggccta ttggttaaaa aatgagctga tttaacaaaa atttaacgcg aattaattct  5340
gtggaatgtg tgtcagttag ggtgtggaaa gtccccaggc tccccagcag gcagaagtat  5400
gcaaagcatg catctcaatt agtcagcaac caggtgtgga aagtccccag gctccccagc  5460
aggcagaagt atgcaaagca tgcatctcaa ttagtcagca accatagtcc cgcccctaac  5520
tccgcccatc ccgcccctaa ctccgcccag ttccgcccat tctccgcccc atggctgact  5580
aattttttt atttatgcag aggccgaggc cgcctctgcc tctgagctat tccagaagta  5640
```

```
gtgaggaggc tttttggag gcctaggctt ttgcaaaaag ctcccgggag cttgtatatc  5700
cattttcgga tctgatcaag agacaggatg aggatcgttt cgcatgattg aacaagatgg  5760
attgcacgca ggttctccgg ccgcttgggt ggagaggcta ttcggctatg actgggcaca  5820
acagacaatc ggctgctctg atgccgccgt gttccggctg tcagcgcagg ggcgcccggt  5880
tctttttgtc aagaccgacc tgtccggtgc cctgaatgaa ctgcaggacg aggcagcgcg  5940
gctatcgtgg ctggccacga cgggcgttcc ttgcgcagct gtgctcgacg ttgtcactga  6000
agcgggaagg gactggctgc tattgggcga agtgccgggg caggatctcc tgtcatctca  6060
ccttgctcct gccgagaaag tatccatcat ggctgatgca atgcggcggc tgcatacgct  6120
tgatccggct acctgcccat tcgaccacca agcgaaacat cgcatcgagc gagcacgtac  6180
tcggatggaa gccggtcttg tcgatcagga tgatctggac gaagagcatc aggggctcgc  6240
gccagccgaa ctgttcgcca ggctcaaggc gcgcatgccc gacggcgagg atctcgtcgt  6300
gacccatggc gatgcctgct tgccgaatat catggtggaa aatggccgct tttctggatt  6360
catcgactgt ggccggctgg gtgtggcgga ccgctatcag gacatagcgt tggctacccg  6420
tgatattgct gaagagcttg gcggcgaatg ggctgaccgc ttcctcgtgc tttacggtat  6480
cgccgctccc gattcgcagc gcatcgcctt ctatcgcctt cttgacgagt tcttctgagc  6540
gggactctgg ggttcgaaat gaccgaccaa gcgacgccca acctgccatc acgagatttc  6600
gattccaccg ccgccttcta tgaaaggttg ggcttcggaa tcgttttccg ggacgccggc  6660
tggatgatcc tccagcgcgg ggatctcatg ctggagttct tcgcccaccc caacttgttt  6720
attgcagctt ataatggtta caaataaagc aatagcatca caaatttcac aaataaagca  6780
tttttttcac tgcattctag ttgtggtttg tccaaactca tcaatgtatc ttatcatgtc  6840
tgtataccgt cgacctctag ctagagcttg gcgtaatcat ggtcatagct gtttcctgtg  6900
tgaaattgtt atccgctcac aattccacac aacatacgag ccggaagcat aaagtgtaaa  6960
gcctggggtg cctaatgagt gagctaactc acattaattg cgttgcgctc actgcccgct  7020
ttccagtcgg gaaacctgtc gtgccagctg cattaatgaa tcggccaacg cgcggggaga  7080
ggcggtttgc gtattgggcg ctcttccgct tcctcgctca ctgactcgct gcgctcggtc  7140
gttcggctgc ggcgagcggt atcagctcac tcaaaggcgg taatacggtt atccacagaa  7200
tcaggggata acgcaggaaa gaacatgtga gcaaaaggcc agcaaaaggc caggaaccgt  7260
aaaaaggccg cgttgctggc gtttttccat aggctccgcc cccctgacga gcatcacaaa  7320
aatcgacgct caagtcagag gtggcgaaac ccgacaggac tataaagata ccaggcgttt  7380
ccccctggaa gctccctcgt gcgctctcct gttccgaccc tgccgcttac cggatacctg  7440
tccgcctttc tcccttcggg aagcgtggcg ctttctcata gctcacgctg taggtatctc  7500
agttcggtgt aggtcgttcg ctccaagctg ggctgtgtgc acgaaccccc cgttcagccc  7560
gaccgctgcg ccttatccgg taactatcgt cttgagtcca acccggtaag acacgactta  7620
tcgccactgg cagcagccac tggtaacagg attagcagag cgaggtatgt aggcggtgct  7680
acagagttct tgaagtggtg gcctaactac ggctacacta gaagaacagt atttggtatc  7740
tgcgctctgc tgaagccagt taccttcgga aaaagagttg gtagctcttg atccggcaaa  7800
caaaccaccg ctggtagcgg tttttttgtt tgcaagcagc agattacgcg cagaaaaaaa  7860
ggatctcaag aagatccttt gatcttttct acggggtctg acgctcagtg gaacgaaaac  7920
tcacgttaag ggattttggt catgagatta tcaaaaagga tcttcaccta gatcctttta  7980
aattaaaaat gaagttttaa atcaatctaa agtatatatg agtaaacttg gtctgacagt  8040
taccaatgct taatcagtga ggcacctatc tcagcgatct gtctatttcg ttcatccata  8100
gttgcctgac tccccgtcgt gtagataact acgatacggg agggcttacc atctggcccc  8160
agtgctgcaa tgataccgcg agacccacgc tcaccggctc cagatttatc agcaataaac  8220
cagccagccg gaagggccga gcgcagaagt ggtcctgcaa ctttatccgc ctccatccag  8280
tctattaatt gttgccggga agctagagta agtagttcgc cagttaatag tttgcgcaac  8340
gttgttgcca ttgctacagg catcgtggtg tcacgctcgt cgtttggtat ggcttcattc  8400
agctccggtt cccaacgatc aaggcgagtt acatgatccc ccatgttgtg caaaaaagcg  8460
gttagctcct tcggtcctcc gatcgttgtc agaagtaagt tggccgcagt gttatcactc  8520
atggttatgg cagcactgca taattctctt actgtcatgc catccgtaag atgcttttct  8580
gtgactggtg agtactcaac caagtcattc tgagaatagt gtatgcggcg accgagttgc  8640
tcttgcccgg cgtcaatacg ggataatacc gcgccacata gcagaacttt aaaagtgctc  8700
atcattggaa aacgttcttc ggggcgaaaa ctctcaagga tcttaccgct gttgagatcc  8760
agttcgatgt aacccactcg tgcacccaac tgatcttcag catcttttac tttcaccagc  8820
gtttctgggt gagcaaaaac aggaaggcaa aatgccgcaa aaaagggaat aagggcgaca  8880
cggaaatgtt gaatactcat actcttcctt tttcaatatt attgaagcat ttatcagggt  8940
tattgtctca tgagcggata catatttgaa tgtatttaga aaaataaaca aataggggtt  9000
ccgcgcacat ttccccgaaa agtgccacct gacgtc                           9036

SEQ ID NO: 738          moltype = AA  length = 7
FEATURE                 Location/Qualifiers
source                  1..7
                        mol_type = protein
                        organism = synthetic construct
SEQUENCE: 738
PKKKRKV                                                           7

SEQ ID NO: 739          moltype = AA  length = 16
FEATURE                 Location/Qualifiers
source                  1..16
                        mol_type = protein
                        organism = synthetic construct
SEQUENCE: 739
KRPAATKKAG QAKKKK                                                 16

SEQ ID NO: 740          moltype = AA  length = 9
FEATURE                 Location/Qualifiers
source                  1..9
                        mol_type = protein
                        organism = synthetic construct
```

```
SEQUENCE: 740
PAAKRVKLD                                                   9

SEQ ID NO: 741          moltype = AA  length = 11
FEATURE                 Location/Qualifiers
source                  1..11
                        mol_type = protein
                        organism = synthetic construct
SEQUENCE: 741
RQRRNELKRS P                                                11

SEQ ID NO: 742          moltype = AA  length = 38
FEATURE                 Location/Qualifiers
source                  1..38
                        mol_type = protein
                        organism = synthetic construct
SEQUENCE: 742
NQSSNFGPMK GGNFGGRSSG PYGGGGQYFA KPRNQGGY                   38

SEQ ID NO: 743          moltype = AA  length = 42
FEATURE                 Location/Qualifiers
source                  1..42
                        mol_type = protein
                        organism = synthetic construct
SEQUENCE: 743
RMRIZFKNKG KDTAELRRRR VEVSVELRKA KKDEQILKRR NV              42

SEQ ID NO: 744          moltype = AA  length = 8
FEATURE                 Location/Qualifiers
source                  1..8
                        mol_type = protein
                        organism = synthetic construct
SEQUENCE: 744
VSRKRPRP                                                    8

SEQ ID NO: 745          moltype = AA  length = 8
FEATURE                 Location/Qualifiers
source                  1..8
                        mol_type = protein
                        organism = synthetic construct
SEQUENCE: 745
PPKKARED                                                    8

SEQ ID NO: 746          moltype = AA  length = 8
FEATURE                 Location/Qualifiers
source                  1..8
                        mol_type = protein
                        organism = synthetic construct
SEQUENCE: 746
PQPKKKPL                                                    8

SEQ ID NO: 747          moltype = AA  length = 12
FEATURE                 Location/Qualifiers
source                  1..12
                        mol_type = protein
                        organism = synthetic construct
SEQUENCE: 747
SALIKKKKKM AP                                               12

SEQ ID NO: 748          moltype = AA  length = 5
FEATURE                 Location/Qualifiers
source                  1..5
                        mol_type = protein
                        organism = synthetic construct
SEQUENCE: 748
DRLRR                                                       5

SEQ ID NO: 749          moltype = AA  length = 7
FEATURE                 Location/Qualifiers
source                  1..7
                        mol_type = protein
                        organism = synthetic construct
SEQUENCE: 749
PKQKKRK                                                     7

SEQ ID NO: 750          moltype = AA  length = 10
FEATURE                 Location/Qualifiers
source                  1..10
                        mol_type = protein
```

```
                         organism = synthetic construct
SEQUENCE: 750
RKLKKKIKKL                                                    10

SEQ ID NO: 751           moltype = AA  length = 10
FEATURE                  Location/Qualifiers
source                   1..10
                         mol_type = protein
                         organism = synthetic construct
SEQUENCE: 751
REKKKFLKRR                                                    10

SEQ ID NO: 752           moltype = AA  length = 20
FEATURE                  Location/Qualifiers
source                   1..20
                         mol_type = protein
                         organism = synthetic construct
SEQUENCE: 752
KRKGDEVDGV DEVAKKKSKK                                         20

SEQ ID NO: 753           moltype = AA  length = 17
FEATURE                  Location/Qualifiers
source                   1..17
                         mol_type = protein
                         organism = synthetic construct
SEQUENCE: 753
RKCLQAGMNL EARKTKK                                            17

SEQ ID NO: 754           moltype = DNA  length = 38
FEATURE                  Location/Qualifiers
source                   1..38
                         mol_type = other DNA
                         organism = synthetic construct
SEQUENCE: 754
gtaccgaaaa acatcattgc gtcgcgaggt gaggcgtc                     38

SEQ ID NO: 755           moltype = DNA  length = 38
FEATURE                  Location/Qualifiers
source                   1..38
                         mol_type = other DNA
                         organism = synthetic construct
SEQUENCE: 755
cattgacgcc tcacctcgcg acgcaatgat gtttttcg                     38

SEQ ID NO: 756           moltype = DNA  length = 28
FEATURE                  Location/Qualifiers
source                   1..28
                         mol_type = other DNA
                         organism = synthetic construct
SEQUENCE: 756
gagttcaaga gaggcttcga cagagagc                                28

SEQ ID NO: 757           moltype = DNA  length = 30
FEATURE                  Location/Qualifiers
source                   1..30
                         mol_type = other DNA
                         organism = synthetic construct
SEQUENCE: 757
tcgaagcctc tcttgaactc ggcgcagtag                              30

SEQ ID NO: 758           moltype = DNA  length = 26
FEATURE                  Location/Qualifiers
source                   1..26
                         mol_type = other DNA
                         organism = synthetic construct
SEQUENCE: 758
aaccaggaga cagaacaagg gcgagg                                  26

SEQ ID NO: 759           moltype = DNA  length = 34
FEATURE                  Location/Qualifiers
source                   1..34
                         mol_type = other DNA
                         organism = synthetic construct
SEQUENCE: 759
ccttgttctg tctcctggtt tccagcttgt tcag                         34

SEQ ID NO: 760           moltype = AA  length = 1139
FEATURE                  Location/Qualifiers
source                   1..1139
```

```
                        mol_type = protein
                        organism = synthetic construct
SEQUENCE: 760
RFVVLSVNQF RCNPNAFRQA SMKTDDEKKD TAIKSYTSWL LPNDRKEKDM VRSFLALDQG  60
SRFFFDLMQA WYGGLTPDII KSVTKERDLV DLWCAIYWFR PMKKELASHP IDRVDLAKTF  120
QRYYGGPASD VVQEYLSASI GEDCCWNDCR QKYQEFCKNL GVDFTPDLKT LVREKLIAVA  180
LNDGSRAAIS NLFGNGGKED RNVKVNICKK ILIALEKAGK SVKYVRDVQS IILKCANAKD  240
REDFNRIYAD KNGRPGTLLL LLDRKGENTY DAEVLKRYLR KTIKSKNAPL VWNYNQKLFE  300
YIERGIRNLL RRTINYDAWA WGEMWRVGHT PLQTKATRNY HFAQEQLKRH SRIAAASQSS  360
HAIAVALNEF FESPPFFDGEN PFTICPHHLG KNLEKLFKAW ADEKNQTDEE DAGETAITDY  420
CAEFKRGFDR EPIRNLLRYV YASLRSKYSA KELIQAAKYN QQFERYQRQK AHPVTPDNQG  480
YTWPEAVIKP SKAERKNREN SLDTRIWVSV KLLQKDGTWE KHHIPFYNLR FFEEVYAAAS  540
IAEDMPSPTF RNSRFGFKLP KLLNTHAKIN KKKKDGKKDK KAVNAAKREA RIYLAAKEGR  600
LPAPSVPLDK LSAVIARVNG KFQVTVPVKF KVNKQPKYPL PQLGQIILGY DQNLTANHAW  660
ALFEVVTEDT PGAHFCRNQY LRVLKTGQVR SITKTKDGQE IDQLSYDGLE YKEYGEWRKQ  720
AKKFASQWYI TTKVRKGKET TLLSQPALER FESIEKYKPA LYRFNKEYAR LLLAVIRRKT  780
LNELEEIRPE IFRLVEQGFG ICRFGSLSLS SFEAIRAAKA VIYGYFSTAL KHDHNTPITD  840
DERQARDPEL FGLLNKLRTR RQNKGEEKIN RAANALIRIA LENKADFIRG EGDLPTTNKS  900
VKKGQNSRSM DWLARGLFNK ICQLAVMHNI IPTAANPHST SHQDPFEHNK DFDDPQPAMK  960
CRYAEFKIED IGDSVLERLG TSLRNAKAGQ TGAYYYKGAQ DFLAHYGLQD IEEELKKCRR  1020
GRKANMPCWE LQKRLIQKLG SKDAVVYIPM RGGRIYLATH SVTTGAKPII FNGEEVWVSN  1080
ADEIAAVNIG LTIIPTSKKD EEHPDRENDD KAIRKSVRRP RKSGERRSGD KMPATARKT   1139

SEQ ID NO: 761          moltype = DNA  length = 23
FEATURE                 Location/Qualifiers
source                  1..23
                        mol_type = other DNA
                        organism = synthetic construct
SEQUENCE: 761
tcctataagg tgtgaaagtc tgg                                          23

SEQ ID NO: 762          moltype = DNA  length = 20
FEATURE                 Location/Qualifiers
source                  1..20
                        mol_type = other DNA
                        organism = synthetic construct
SEQUENCE: 762
cagtaagatt tggtgtctat                                              20

SEQ ID NO: 763          moltype = DNA  length = 23
FEATURE                 Location/Qualifiers
source                  1..23
                        mol_type = other DNA
                        organism = synthetic construct
SEQUENCE: 763
tatatccctt ctacaaattc ctc                                          23

SEQ ID NO: 764          moltype = DNA  length = 24
FEATURE                 Location/Qualifiers
source                  1..24
                        mol_type = other DNA
                        organism = synthetic construct
SEQUENCE: 764
gtgtctgagg ctggccctac ggtg                                         24

SEQ ID NO: 765          moltype = DNA  length = 23
FEATURE                 Location/Qualifiers
source                  1..23
                        mol_type = other DNA
                        organism = synthetic construct
SEQUENCE: 765
agaaaggctg ctgatgacac ctg                                          23

SEQ ID NO: 766          moltype = DNA  length = 24
FEATURE                 Location/Qualifiers
source                  1..24
                        mol_type = other DNA
                        organism = synthetic construct
SEQUENCE: 766
gcatctcccc attccatgag catg                                         24

SEQ ID NO: 767          moltype = DNA  length = 22
FEATURE                 Location/Qualifiers
source                  1..22
                        mol_type = other DNA
                        organism = synthetic construct
SEQUENCE: 767
acagccaacg actccggccc cg                                           22
```

SEQ ID NO: 768 moltype = DNA length = 23
FEATURE Location/Qualifiers
source 1..23
mol_type = other DNA
organism = synthetic construct
SEQUENCE: 768
tagaagggat atacaaagtg gaa 23

SEQ ID NO: 769 moltype = DNA length = 24
FEATURE Location/Qualifiers
source 1..24
mol_type = other DNA
organism = synthetic construct
SEQUENCE: 769
tagatgctgt ccgaggcagt cctg 24

SEQ ID NO: 770 moltype = DNA length = 23
FEATURE Location/Qualifiers
source 1..23
mol_type = other DNA
organism = synthetic construct
SEQUENCE: 770
ggtgtctatt tccactttgt ata 23

SEQ ID NO: 771 moltype = DNA length = 24
FEATURE Location/Qualifiers
source 1..24
mol_type = other DNA
organism = synthetic construct
SEQUENCE: 771
ctgaacacat gcacggccac attg 24

SEQ ID NO: 772 moltype = DNA length = 23
FEATURE Location/Qualifiers
source 1..23
mol_type = other DNA
organism = synthetic construct
SEQUENCE: 772
cccagaggca aatggctccc agg 23

SEQ ID NO: 773 moltype = DNA length = 23
FEATURE Location/Qualifiers
source 1..23
mol_type = other DNA
organism = synthetic construct
SEQUENCE: 773
ctcctcagtt gtgagcccat gca 23

SEQ ID NO: 774 moltype = DNA length = 23
FEATURE Location/Qualifiers
source 1..23
mol_type = other DNA
organism = synthetic construct
SEQUENCE: 774
gccagccttg ccttgaccaa tag 23

SEQ ID NO: 775 moltype = DNA length = 23
FEATURE Location/Qualifiers
source 1..23
mol_type = other DNA
organism = synthetic construct
SEQUENCE: 775
accaatagtc ttagagtatc cag 23

SEQ ID NO: 776 moltype = DNA length = 23
FEATURE Location/Qualifiers
source 1..23
mol_type = other DNA
organism = synthetic construct
SEQUENCE: 776
ccttgtcaag gctattggtc aag 23

SEQ ID NO: 777 moltype = DNA length = 23
FEATURE Location/Qualifiers
source 1..23
mol_type = other DNA
organism = synthetic construct
SEQUENCE: 777
ccttgaccaa tagccttgac aag 23

```
SEQ ID NO: 778         moltype = DNA  length = 23
FEATURE                Location/Qualifiers
source                 1..23
                       mol_type = other DNA
                       organism = synthetic construct
SEQUENCE: 778
accaatagcc ttgacaaggc aaa                                          23

SEQ ID NO: 779         moltype = DNA  length = 23
FEATURE                Location/Qualifiers
source                 1..23
                       mol_type = other DNA
                       organism = synthetic construct
SEQUENCE: 779
gtcaaggcaa ggctggccaa ccc                                          23

SEQ ID NO: 780         moltype = DNA  length = 21
FEATURE                Location/Qualifiers
source                 1..21
                       mol_type = other DNA
                       organism = synthetic construct
SEQUENCE: 780
gtcaagtttg cctgtcaagg c                                            21

SEQ ID NO: 781         moltype = DNA  length = 23
FEATURE                Location/Qualifiers
source                 1..23
                       mol_type = other DNA
                       organism = synthetic construct
SEQUENCE: 781
tcaaggctat tggtcaaggc aag                                          23

SEQ ID NO: 782         moltype = DNA  length = 24
FEATURE                Location/Qualifiers
source                 1..24
                       mol_type = other DNA
                       organism = synthetic construct
SEQUENCE: 782
acaaggcaaa cttgaccaat agtc                                         24

SEQ ID NO: 783         moltype = RNA  length = 45
FEATURE                Location/Qualifiers
source                 1..45
                       mol_type = other RNA
                       organism = synthetic construct
SEQUENCE: 783
gtaatgcgtc tcccattgac gccatgagca tgcagaggtg agtat                  45

SEQ ID NO: 784         moltype = RNA  length = 45
FEATURE                Location/Qualifiers
source                 1..45
                       mol_type = other RNA
                       organism = synthetic construct
SEQUENCE: 784
gtaatgcgtc tcccattgac gctcctataa ggtgtgaaag tctgg                  45

SEQ ID NO: 785         moltype = RNA  length = 42
FEATURE                Location/Qualifiers
source                 1..42
                       mol_type = other RNA
                       organism = synthetic construct
SEQUENCE: 785
gtaatgcgtc tcccattgac gccagtaaga tttggtgtct at                     42

SEQ ID NO: 786         moltype = RNA  length = 45
FEATURE                Location/Qualifiers
source                 1..45
                       mol_type = other RNA
                       organism = synthetic construct
SEQUENCE: 786
gtaatgcgtc tcccattgac gctatatccc ttctacaaat tcctc                  45

SEQ ID NO: 787         moltype = RNA  length = 46
FEATURE                Location/Qualifiers
source                 1..46
                       mol_type = other RNA
                       organism = synthetic construct
SEQUENCE: 787
```

```
gtaatgcgtc tcccattgac gcgtgtctga ggctggccct acggtg                46

SEQ ID NO: 788          moltype = RNA  length = 45
FEATURE                 Location/Qualifiers
source                  1..45
                        mol_type = other RNA
                        organism = synthetic construct
SEQUENCE: 788
gtaatgcgtc tcccattgac gcagaaaggc tgctgatgac acctg                 45

SEQ ID NO: 789          moltype = RNA  length = 46
FEATURE                 Location/Qualifiers
source                  1..46
                        mol_type = other RNA
                        organism = synthetic construct
SEQUENCE: 789
gtaatgcgtc tcccattgac gcgcatctcc ccattccatg agcatg                46

SEQ ID NO: 790          moltype = RNA  length = 45
FEATURE                 Location/Qualifiers
source                  1..45
                        mol_type = other RNA
                        organism = synthetic construct
SEQUENCE: 790
gtaatgcgtc tcccattgac gcacagccaa cgactccggc ccccg                 45

SEQ ID NO: 791          moltype = RNA  length = 45
FEATURE                 Location/Qualifiers
source                  1..45
                        mol_type = other RNA
                        organism = synthetic construct
SEQUENCE: 791
gtaatgcgtc tcccattgac gctagaaggg atatacaaag tggaa                 45

SEQ ID NO: 792          moltype = RNA  length = 46
FEATURE                 Location/Qualifiers
source                  1..46
                        mol_type = other RNA
                        organism = synthetic construct
SEQUENCE: 792
gtaatgcgtc tcccattgac gctagatgct gtccgaggca gtcctg                46

SEQ ID NO: 793          moltype = RNA  length = 45
FEATURE                 Location/Qualifiers
source                  1..45
                        mol_type = other RNA
                        organism = synthetic construct
SEQUENCE: 793
gtaatgcgtc tcccattgac gcggtgtcta tttccacttt gtata                 45

SEQ ID NO: 794          moltype = RNA  length = 46
FEATURE                 Location/Qualifiers
source                  1..46
                        mol_type = other RNA
                        organism = synthetic construct
SEQUENCE: 794
gtaatgcgtc tcccattgac gcctgaacac atgcacggcc acattg                46

SEQ ID NO: 795          moltype = RNA  length = 45
FEATURE                 Location/Qualifiers
source                  1..45
                        mol_type = other RNA
                        organism = synthetic construct
SEQUENCE: 795
gtaatgcgtc tcccattgac gccccagagg caaatggctc ccagg                 45

SEQ ID NO: 796          moltype = RNA  length = 45
FEATURE                 Location/Qualifiers
source                  1..45
                        mol_type = other RNA
                        organism = synthetic construct
SEQUENCE: 796
gtaatgcgtc tcccattgac gcctcctcag ttgtgagccc atgca                 45

SEQ ID NO: 797          moltype = RNA  length = 45
FEATURE                 Location/Qualifiers
source                  1..45
                        mol_type = other RNA
                        organism = synthetic construct
```

```
SEQUENCE: 797
gtaatgcgtc tcccattgac gcgccagcct tgccttgacc aatag                45

SEQ ID NO: 798         moltype = RNA  length = 45
FEATURE                Location/Qualifiers
source                 1..45
                       mol_type = other RNA
                       organism = synthetic construct
SEQUENCE: 798
gtaatgcgtc tcccattgac gcaccaatag tcttagagta tccag                45

SEQ ID NO: 799         moltype = RNA  length = 45
FEATURE                Location/Qualifiers
source                 1..45
                       mol_type = other RNA
                       organism = synthetic construct
SEQUENCE: 799
gtaatgcgtc tcccattgac gcccttgtca aggctattgg tcaag                45

SEQ ID NO: 800         moltype = RNA  length = 45
FEATURE                Location/Qualifiers
source                 1..45
                       mol_type = other RNA
                       organism = synthetic construct
SEQUENCE: 800
gtaatgcgtc tcccattgac gcccttgacc aatagccttg acaag                45

SEQ ID NO: 801         moltype = RNA  length = 45
FEATURE                Location/Qualifiers
source                 1..45
                       mol_type = other RNA
                       organism = synthetic construct
SEQUENCE: 801
gtaatgcgtc tcccattgac gcaccaatag ccttgacaag gcaaa                45

SEQ ID NO: 802         moltype = RNA  length = 45
FEATURE                Location/Qualifiers
source                 1..45
                       mol_type = other RNA
                       organism = synthetic construct
SEQUENCE: 802
gtaatgcgtc tcccattgac gcgtcaaggc aaggctggcc aaccc                45

SEQ ID NO: 803         moltype = RNA  length = 44
FEATURE                Location/Qualifiers
source                 1..44
                       mol_type = other RNA
                       organism = synthetic construct
SEQUENCE: 803
gtaatgcgtc tcccattgac gcgtcaagtt tgccttgtca aggc                 44

SEQ ID NO: 804         moltype = RNA  length = 45
FEATURE                Location/Qualifiers
source                 1..45
                       mol_type = other RNA
                       organism = synthetic construct
SEQUENCE: 804
gtaatgcgtc tcccattgac gctcaaggct attggtcaag gcaag                45

SEQ ID NO: 805         moltype = RNA  length = 46
FEATURE                Location/Qualifiers
source                 1..46
                       mol_type = other RNA
                       organism = synthetic construct
SEQUENCE: 805
gtaatgcgtc tcccattgac gcacaaggca aacttgacca atagtc               46

SEQ ID NO: 806         moltype = DNA  length = 25
FEATURE                Location/Qualifiers
source                 1..25
                       mol_type = other DNA
                       organism = synthetic construct
SEQUENCE: 806
gaacgaatgt tccgatgctc taatc                                      25

SEQ ID NO: 807         moltype = DNA  length = 28
FEATURE                Location/Qualifiers
source                 1..28
                       mol_type = other DNA
```

```
                        organism = synthetic construct
SEQUENCE: 807
aatgaggtag aatgctcaga gttcaagt                                        28

SEQ ID NO: 808          moltype = DNA  length = 26
FEATURE                 Location/Qualifiers
source                  1..26
                        mol_type = other DNA
                        organism = synthetic construct
SEQUENCE: 808
caactgttct caggggacct attttc                                          26

SEQ ID NO: 809          moltype = DNA  length = 26
FEATURE                 Location/Qualifiers
source                  1..26
                        mol_type = other DNA
                        organism = synthetic construct
SEQUENCE: 809
ctctactgtc tgcccctaaa tgatgc                                          26

SEQ ID NO: 810          moltype = DNA  length = 28
FEATURE                 Location/Qualifiers
source                  1..28
                        mol_type = other DNA
                        organism = synthetic construct
SEQUENCE: 810
tgccatttaa tttcagttag gagttttc                                        28

SEQ ID NO: 811          moltype = DNA  length = 23
FEATURE                 Location/Qualifiers
source                  1..23
                        mol_type = other DNA
                        organism = synthetic construct
SEQUENCE: 811
cagacctccg agaagccaga tgt                                             23

SEQ ID NO: 812          moltype = DNA  length = 27
FEATURE                 Location/Qualifiers
source                  1..27
                        mol_type = other DNA
                        organism = synthetic construct
SEQUENCE: 812
caagacctga ctctgtactc ctgctct                                         27

SEQ ID NO: 813          moltype = DNA  length = 25
FEATURE                 Location/Qualifiers
source                  1..25
                        mol_type = other DNA
                        organism = synthetic construct
SEQUENCE: 813
atttggatct ctcctagcgt tctgc                                           25

SEQ ID NO: 814          moltype = DNA  length = 23
FEATURE                 Location/Qualifiers
source                  1..23
                        mol_type = other DNA
                        organism = synthetic construct
SEQUENCE: 814
acggctgaca aaagaagtcc tgg                                             23

SEQ ID NO: 815          moltype = DNA  length = 22
FEATURE                 Location/Qualifiers
source                  1..22
                        mol_type = other DNA
                        organism = synthetic construct
SEQUENCE: 815
catgggtaga caaccaggag cc                                              22

SEQ ID NO: 816          moltype = AA  length = 1139
FEATURE                 Location/Qualifiers
source                  1..1139
                        mol_type = protein
                        organism = synthetic construct
SEQUENCE: 816
RFVVLSVNQF RCNPNAFRQA SMKTDDEKKD TAIKSYTSWL LPNDRKEKDM VRSFLALDQG  60
SRFFFDLMQA WYGGLTPDII KSVTKERDLV DLWCAIYWFR PMKKELASHP IDRVDLAKTF  120
QRYYGGPASD VVQEYLSASI GEDCCWNDCR QKYQEFCKNL GVDFTPDLKT LVREKLIAVA  180
LNDGSRAAIS NLFGNGGKED RNVKVNICKK ILIALEKAGK SVKYVRDVQS IILKCANAKD  240
REDFNRIYAD KNGRPGTLLL LLDRKGENTY DAEVLKRYLR KTIKSKNAPL VWNYNQKLFE  300
```

-continued

```
YIERGIRNLL RRTINYDAWA WGEMWRVGHT PLQTKATRNY HFAQEQLKRH SRIAAASQSS  360
HAIAVALNEF FESPPFFDGEN PFTICPHHLG KNLEKLFKAW ADEKNQTDEE DAGETAITDY  420
CAEFKRGFDR EPIRNLLRYV YASLRSKYSA KELIQAAKYN QQFERYQRQK AHPVTPDNQG  480
YTWPEAVIKP SKAERKNREN SLDTRIWVSV KLLQKDGTWE KHHIPFYNLR FFEEVYAAAS  540
IAEDMPSPTF RNSRFGFKLP KLLNTHAKIN KKKKDGKKDK KAVNAAKREA RIYLAAKEGR  600
LPAPSVPLDK LSAVIARVNG KFQVTVPVKF KVNKQPKYPL PQLGQIILGY AQNLTANHAW  660
ALFEVVTEDT PGAHFCRNQY LRVLKTGQVR SITKTKDGQE IDQLSYDGLE YKEYGEWRKQ  720
AKKFASQWYI TTKVRKGKET TLLSQPALER FESIEKYKPA LYRFNKEYAR LLLAVIRRKT  780
LNELEEIRPE IFRLVEQGFG ICRFGSLSLS SFEAIRAAKA VIYGYFSTAL KHDHNTPITD  840
DERQARDPEL FGLLNKLRTR RQNKGEEKIN RAANALIRIA LENKADFIRG AGDLPTTNKS  900
VKKGQNSRSM DWLARGLFNK ICQLAVMHNI IPTAANPHST SHQDPFEHNK DFDDPQPAMK  960
CRYAEFKIED IGDSVLERLG TSLRNAKAGQ TGAYYYKGAQ DFLAHYGLQD IEEELKKCRR  1020
GRKANMPCWE LQKRLIQKLG SKDAVVYIPM RGGRIYLATH SVTTGAKPII FNGEEVWVSN  1080
AAEIAAVNIG LTIIPTSKKD EEHPDRENDD KAIRKSVRRP RKSGERRSGD KMPATARKT   1139

SEQ ID NO: 817          moltype = RNA  length = 70
FEATURE                 Location/Qualifiers
source                  1..70
                        mol_type = other RNA
                        organism = synthetic construct
SEQUENCE: 817
atgtgttttt gtcaaaagac cttttgtaat gcgtctccca ttgacgccat gagcatgcag  60
aggtgagtat                                                          70

SEQ ID NO: 818          moltype = RNA  length = 45
FEATURE                 Location/Qualifiers
source                  1..45
                        mol_type = other RNA
                        organism = synthetic construct
SEQUENCE: 818
gtaatgcgtc tcccattgac gccatgagca tgcagaggtg agtat                  45

SEQ ID NO: 819          moltype = RNA  length = 59
FEATURE                 Location/Qualifiers
source                  1..59
                        mol_type = other RNA
                        organism = synthetic construct
SEQUENCE: 819
gttgcaatcc caaggtaatg cgtctcccat tgacgccatg agcatgcaga ggtgagtat   59

SEQ ID NO: 820          moltype = RNA  length = 45
FEATURE                 Location/Qualifiers
source                  1..45
                        mol_type = other RNA
                        organism = synthetic construct
SEQUENCE: 820
gtaatgcgtc tcccattgac gccatgagca tgcagaggtg agtat                  45

SEQ ID NO: 821          moltype = RNA  length = 25
FEATURE                 Location/Qualifiers
source                  1..25
                        mol_type = other RNA
                        organism = synthetic construct
SEQUENCE: 821
atgtgttttt gtcaaaagac ctttt                                        25

SEQ ID NO: 822          moltype = RNA  length = 14
FEATURE                 Location/Qualifiers
source                  1..14
                        mol_type = other RNA
                        organism = synthetic construct
SEQUENCE: 822
gttgcaatcc caag                                                    14

SEQ ID NO: 823          moltype = DNA  length = 29
FEATURE                 Location/Qualifiers
source                  1..29
                        mol_type = other DNA
                        organism = synthetic construct
SEQUENCE: 823
gcgtaactta atccagactt tcacacctt                                    29

SEQ ID NO: 824          moltype = DNA  length = 26
FEATURE                 Location/Qualifiers
source                  1..26
                        mol_type = other DNA
                        organism = synthetic construct
SEQUENCE: 824
ggtcattcat caccttcctt aggaca                                       26
```

SEQ ID NO: 825 moltype = RNA length = 23
FEATURE Location/Qualifiers
source 1..23
mol_type = other RNA
organism = synthetic construct
SEQUENCE: 825
ctggagcctg tgataaaagc aac 23

SEQ ID NO: 826 moltype = RNA length = 23
FEATURE Location/Qualifiers
source 1..23
mol_type = other RNA
organism = synthetic construct
SEQUENCE: 826
aagctaacag ttgcttttat cac 23

SEQ ID NO: 827 moltype = RNA length = 23
FEATURE Location/Qualifiers
source 1..23
mol_type = other RNA
organism = synthetic construct
SEQUENCE: 827
cattgagata gtgtggggaa ggg 23

SEQ ID NO: 828 moltype = RNA length = 23
FEATURE Location/Qualifiers
source 1..23
mol_type = other RNA
organism = synthetic construct
SEQUENCE: 828
gcattgagat agtgtgggga agg 23

SEQ ID NO: 829 moltype = RNA length = 23
FEATURE Location/Qualifiers
source 1..23
mol_type = other RNA
organism = synthetic construct
SEQUENCE: 829
agatagtgtg gggaaggggc ccc 23

SEQ ID NO: 830 moltype = RNA length = 23
FEATURE Location/Qualifiers
source 1..23
mol_type = other RNA
organism = synthetic construct
SEQUENCE: 830
ggggcccctt ccccacacta tct 23

SEQ ID NO: 831 moltype = RNA length = 23
FEATURE Location/Qualifiers
source 1..23
mol_type = other RNA
organism = synthetic construct
SEQUENCE: 831
cctcttgggg gccccttccc cac 23

SEQ ID NO: 832 moltype = RNA length = 23
FEATURE Location/Qualifiers
source 1..23
mol_type = other RNA
organism = synthetic construct
SEQUENCE: 832
tcctcttggg ggccccttcc cca 23

SEQ ID NO: 833 moltype = RNA length = 23
FEATURE Location/Qualifiers
source 1..23
mol_type = other RNA
organism = synthetic construct
SEQUENCE: 833
gcagtatcct cttgggggcc cct 23

SEQ ID NO: 834 moltype = RNA length = 23
FEATURE Location/Qualifiers
source 1..23
mol_type = other RNA
organism = synthetic construct
SEQUENCE: 834

```
cccacactat ctcaatgcaa ata                                          23

SEQ ID NO: 835         moltype = RNA  length = 23
FEATURE                Location/Qualifiers
source                 1..23
                       mol_type = other RNA
                       organism = synthetic construct
SEQUENCE: 835
cagacagata tttgcattga gat                                          23

SEQ ID NO: 836         moltype = RNA  length = 23
FEATURE                Location/Qualifiers
source                 1..23
                       mol_type = other RNA
                       organism = synthetic construct
SEQUENCE: 836
agccagggac cgtttcagac aga                                          23

SEQ ID NO: 837         moltype = RNA  length = 23
FEATURE                Location/Qualifiers
source                 1..23
                       mol_type = other RNA
                       organism = synthetic construct
SEQUENCE: 837
acaaggcaaa cttgaccaat agt                                          23

SEQ ID NO: 838         moltype = RNA  length = 23
FEATURE                Location/Qualifiers
source                 1..23
                       mol_type = other RNA
                       organism = synthetic construct
SEQUENCE: 838
atccctagcc agccgccggc ccc                                          23

SEQ ID NO: 839         moltype = RNA  length = 23
FEATURE                Location/Qualifiers
source                 1..23
                       mol_type = other RNA
                       organism = synthetic construct
SEQUENCE: 839
tagggtaccc tcgtgcaccc ggg                                          23

SEQ ID NO: 840         moltype = RNA  length = 23
FEATURE                Location/Qualifiers
source                 1..23
                       mol_type = other RNA
                       organism = synthetic construct
SEQUENCE: 840
cgcggcagcc actcgctggt atc                                          23

SEQ ID NO: 841         moltype = RNA  length = 23
FEATURE                Location/Qualifiers
source                 1..23
                       mol_type = other RNA
                       organism = synthetic construct
SEQUENCE: 841
gtccttgagg acagacacca ctg                                          23

SEQ ID NO: 842         moltype = RNA  length = 23
FEATURE                Location/Qualifiers
source                 1..23
                       mol_type = other RNA
                       organism = synthetic construct
SEQUENCE: 842
atccttgttt tccagtggtg tct                                          23

SEQ ID NO: 843         moltype = RNA  length = 23
FEATURE                Location/Qualifiers
source                 1..23
                       mol_type = other RNA
                       organism = synthetic construct
SEQUENCE: 843
gaagagttga ccatcagtta tgg                                          23

SEQ ID NO: 844         moltype = RNA  length = 23
FEATURE                Location/Qualifiers
source                 1..23
                       mol_type = other RNA
                       organism = synthetic construct
```

```
SEQUENCE: 844
ctctactcct caagaaaaca cca                                         23

SEQ ID NO: 845         moltype = RNA  length = 23
FEATURE                Location/Qualifiers
source                 1..23
                       mol_type = other RNA
                       organism = synthetic construct
SEQUENCE: 845
acacagaacc ctgccattct aaa                                         23

SEQ ID NO: 846         moltype = RNA  length = 23
FEATURE                Location/Qualifiers
source                 1..23
                       mol_type = other RNA
                       organism = synthetic construct
SEQUENCE: 846
agtctgcaca acaaaaacaa gca                                         23

SEQ ID NO: 847         moltype = RNA  length = 23
FEATURE                Location/Qualifiers
source                 1..23
                       mol_type = other RNA
                       organism = synthetic construct
SEQUENCE: 847
gggtgatagg tgcagatggt ccg                                         23

SEQ ID NO: 848         moltype = RNA  length = 23
FEATURE                Location/Qualifiers
source                 1..23
                       mol_type = other RNA
                       organism = synthetic construct
SEQUENCE: 848
cccaacagtt ggtataaatt gtg                                         23

SEQ ID NO: 849         moltype = RNA  length = 23
FEATURE                Location/Qualifiers
source                 1..23
                       mol_type = other RNA
                       organism = synthetic construct
SEQUENCE: 849
cagtctgcac aacaaaaaca agc                                         23

SEQ ID NO: 850         moltype = RNA  length = 23
FEATURE                Location/Qualifiers
source                 1..23
                       mol_type = other RNA
                       organism = synthetic construct
SEQUENCE: 850
aggtggtccc ttagtttgca aac                                         23

SEQ ID NO: 851         moltype = RNA  length = 23
FEATURE                Location/Qualifiers
source                 1..23
                       mol_type = other RNA
                       organism = synthetic construct
SEQUENCE: 851
ggggtgtaca tggaagctac atc                                         23

SEQ ID NO: 852         moltype = RNA  length = 23
FEATURE                Location/Qualifiers
source                 1..23
                       mol_type = other RNA
                       organism = synthetic construct
SEQUENCE: 852
cctattaaag tacagtcccg gag                                         23

SEQ ID NO: 853         moltype = RNA  length = 23
FEATURE                Location/Qualifiers
source                 1..23
                       mol_type = other RNA
                       organism = synthetic construct
SEQUENCE: 853
tagcggtagg tgttcctccg gga                                         23

SEQ ID NO: 854         moltype = RNA  length = 23
FEATURE                Location/Qualifiers
source                 1..23
                       mol_type = other RNA
```

```
                       organism = synthetic construct
SEQUENCE: 854
cgtgctcggg tgcttcggcc agg                                          23

SEQ ID NO: 855         moltype = RNA  length = 23
FEATURE                Location/Qualifiers
source                 1..23
                       mol_type = other RNA
                       organism = synthetic construct
SEQUENCE: 855
cccctccacg gtaccgggcg gat                                          23

SEQ ID NO: 856         moltype = RNA  length = 23
FEATURE                Location/Qualifiers
source                 1..23
                       mol_type = other RNA
                       organism = synthetic construct
SEQUENCE: 856
atccgcccgg taccgtggag ggg                                          23

SEQ ID NO: 857         moltype = RNA  length = 23
FEATURE                Location/Qualifiers
source                 1..23
                       mol_type = other RNA
                       organism = synthetic construct
SEQUENCE: 857
gcagttgagc acgcgcaggc tgc                                          23

SEQ ID NO: 858         moltype = RNA  length = 23
FEATURE                Location/Qualifiers
source                 1..23
                       mol_type = other RNA
                       organism = synthetic construct
SEQUENCE: 858
gccacgccgg catcccggcc gct                                          23

SEQ ID NO: 859         moltype = RNA  length = 23
FEATURE                Location/Qualifiers
source                 1..23
                       mol_type = other RNA
                       organism = synthetic construct
SEQUENCE: 859
aggacgcggc tgtacccacc cgc                                          23

SEQ ID NO: 860         moltype = RNA  length = 23
FEATURE                Location/Qualifiers
source                 1..23
                       mol_type = other RNA
                       organism = synthetic construct
SEQUENCE: 860
ggccgctgtg tggacctctt tgc                                          23

SEQ ID NO: 861         moltype = RNA  length = 23
FEATURE                Location/Qualifiers
source                 1..23
                       mol_type = other RNA
                       organism = synthetic construct
SEQUENCE: 861
tctacggcgt aggcccccag gac                                          23

SEQ ID NO: 862         moltype = RNA  length = 23
FEATURE                Location/Qualifiers
source                 1..23
                       mol_type = other RNA
                       organism = synthetic construct
SEQUENCE: 862
cccaagtctc caacatgcct aat                                          23

SEQ ID NO: 863         moltype = RNA  length = 23
FEATURE                Location/Qualifiers
source                 1..23
                       mol_type = other RNA
                       organism = synthetic construct
SEQUENCE: 863
cccacacctt cactggtcca tta                                          23

SEQ ID NO: 864         moltype = RNA  length = 23
FEATURE                Location/Qualifiers
source                 1..23
```

```
                        mol_type = other RNA
                        organism = synthetic construct
SEQUENCE: 864
atgcttcccc acaccttcac tgg                                              23

SEQ ID NO: 865          moltype = RNA  length = 23
FEATURE                 Location/Qualifiers
source                  1..23
                        mol_type = other RNA
                        organism = synthetic construct
SEQUENCE: 865
agcatcttgt tacctctctt cat                                              23

SEQ ID NO: 866          moltype = RNA  length = 23
FEATURE                 Location/Qualifiers
source                  1..23
                        mol_type = other RNA
                        organism = synthetic construct
SEQUENCE: 866
ggcaatgtga ctgctgacaa aga                                              23

SEQ ID NO: 867          moltype = RNA  length = 23
FEATURE                 Location/Qualifiers
source                  1..23
                        mol_type = other RNA
                        organism = synthetic construct
SEQUENCE: 867
agcacgcaca cggccttcgt cgc                                              23

SEQ ID NO: 868          moltype = RNA  length = 23
FEATURE                 Location/Qualifiers
source                  1..23
                        mol_type = other RNA
                        organism = synthetic construct
SEQUENCE: 868
aaggactgac tgaaggcctg cat                                              23

SEQ ID NO: 869          moltype = RNA  length = 23
FEATURE                 Location/Qualifiers
source                  1..23
                        mol_type = other RNA
                        organism = synthetic construct
SEQUENCE: 869
agggggaagc cagcaccaca aag                                              23

SEQ ID NO: 870          moltype = RNA  length = 23
FEATURE                 Location/Qualifiers
source                  1..23
                        mol_type = other RNA
                        organism = synthetic construct
SEQUENCE: 870
cctcttagta caactatgac aag                                              23

SEQ ID NO: 871          moltype = RNA  length = 23
FEATURE                 Location/Qualifiers
source                  1..23
                        mol_type = other RNA
                        organism = synthetic construct
SEQUENCE: 871
ccagtcatct cactctacct aat                                              23

SEQ ID NO: 872          moltype = RNA  length = 23
FEATURE                 Location/Qualifiers
source                  1..23
                        mol_type = other RNA
                        organism = synthetic construct
SEQUENCE: 872
ccctctcccc agtgcacgat gag                                              23

SEQ ID NO: 873          moltype = RNA  length = 23
FEATURE                 Location/Qualifiers
source                  1..23
                        mol_type = other RNA
                        organism = synthetic construct
SEQUENCE: 873
agcagggaga tgtcatcagc aaa                                              23

SEQ ID NO: 874          moltype = RNA  length = 23
FEATURE                 Location/Qualifiers
```

```
source                  1..23
                        mol_type = other RNA
                        organism = synthetic construct
SEQUENCE: 874
ggtagagtga gatgactggg aaa                                          23

SEQ ID NO: 875          moltype = RNA  length = 23
FEATURE                 Location/Qualifiers
source                  1..23
                        mol_type = other RNA
                        organism = synthetic construct
SEQUENCE: 875
cccctcaacc agtctgaagt gct                                          23

SEQ ID NO: 876          moltype = RNA  length = 23
FEATURE                 Location/Qualifiers
source                  1..23
                        mol_type = other RNA
                        organism = synthetic construct
SEQUENCE: 876
agatcctgtc cattgatctc cac                                          23

SEQ ID NO: 877          moltype = RNA  length = 23
FEATURE                 Location/Qualifiers
source                  1..23
                        mol_type = other RNA
                        organism = synthetic construct
SEQUENCE: 877
gcacgcacag tgacgttggg gcc                                          23

SEQ ID NO: 878          moltype = DNA  length = 65
FEATURE                 Location/Qualifiers
source                  1..65
                        mol_type = other DNA
                        organism = synthetic construct
SEQUENCE: 878
ccatggaacg gctcggagat catcattgcg nnnnnnngtg agcaagggcg aggagctgtt  60
caccg                                                              65

SEQ ID NO: 879          moltype = DNA  length = 67
FEATURE                 Location/Qualifiers
source                  1..67
                        mol_type = other DNA
                        organism = synthetic construct
SEQUENCE: 879
ggtaccttgc cgagcctctc tagtagtaac gcnnnnnnnc actcgttccc gctcctcgac  60
aagtggc                                                            67

SEQ ID NO: 880          moltype = DNA  length = 24
FEATURE                 Location/Qualifiers
source                  1..24
                        mol_type = other DNA
                        organism = synthetic construct
SEQUENCE: 880
gtgagcaagg gcgaggagct gttc                                         24

SEQ ID NO: 881          moltype = DNA  length = 26
FEATURE                 Location/Qualifiers
source                  1..26
                        mol_type = other DNA
                        organism = synthetic construct
SEQUENCE: 881
ccttgccgag cctctagtag taacgc                                       26

SEQ ID NO: 882          moltype = DNA  length = 272
FEATURE                 Location/Qualifiers
source                  1..272
                        mol_type = other DNA
                        organism = synthetic construct
SEQUENCE: 882
ttattatttt aaaaaacagc acaaaaggaa actcacccta actgtaaagt aattgtgtgt  60
tttgagacta taaatatgca tgcgagaaaa gccttgtttg ccaccatgga acggctcgga  120
gatcatcatt gcgnnnnnnn accgagtaca agcccacggt gcgcctcgcc acccgcgcga  180
cgacgtcccc agggccgtac gcaccctcgc cgccgcgttc gccgactacc ccgccacgcg  240
ccacaccgtc gatccggacc gccacatcga gc                                272

SEQ ID NO: 883          moltype = DNA  length = 269
FEATURE                 Location/Qualifiers
source                  1..269
```

```
                         mol_type = other DNA
                         organism = synthetic construct
SEQUENCE: 883
aataataaaa tttttgtcg tgttttcctt tgagtgggat tgacatttca ttaacacaca  60
aaactctgat atttatacgt acgctctttt cggaacaaac ggtggtacct tgccgagcct  120
ctagtagtaa cgcnnnnnnt ggctcatgtt cgggtgccac gcggagcggt gggcgctgct  180
gcaggggtcc cggcatgcgt gggagcggcg gcgcaagcgg ctgatggggc ggtgcgcggt  240
gtggcagcta ggcctggcgg tgtagctcg                                   269

SEQ ID NO: 884           moltype = AA  length = 43
FEATURE                  Location/Qualifiers
source                   1..43
                         mol_type = protein
                         organism = synthetic construct
SEQUENCE: 884
TEYKPTVRLA TRDDVPRAVR TLAAAFADYP ATRHTVDPDR HIE                   43

SEQ ID NO: 885           moltype = AA  length = 55
FEATURE                  Location/Qualifiers
source                   1..55
                         mol_type = protein
                         organism = synthetic construct
SEQUENCE: 885
MERLGDHHCX XXPSTSPRCA SPPATTSPGP YAPSPPRSPT TPPRATPSIR TATSS       55

SEQ ID NO: 886           moltype = DNA  length = 20
FEATURE                  Location/Qualifiers
source                   1..20
                         mol_type = other DNA
                         organism = synthetic construct
SEQUENCE: 886
gatggggcgg tgcgcggtgt                                             20

SEQ ID NO: 887           moltype = DNA  length = 60
FEATURE                  Location/Qualifiers
source                   1..60
                         mol_type = other DNA
                         organism = synthetic construct
SEQUENCE: 887
ctccccattc catgagcatg cagaggtgag tatacagacc ttcgagggtt gttttggttt  60

SEQ ID NO: 888           moltype = DNA  length = 60
FEATURE                  Location/Qualifiers
source                   1..60
                         mol_type = other DNA
                         organism = synthetic construct
SEQUENCE: 888
ctccccagtc catgagcatg cagaggtgag tatacagacc ttcgagggtt gttttggttt  60

SEQ ID NO: 889           moltype = DNA  length = 46
FEATURE                  Location/Qualifiers
source                   1..46
                         mol_type = other DNA
                         organism = synthetic construct
SEQUENCE: 889
ctccccattc catgagcatg cagaccttcg agggttgttt tggttt                46

SEQ ID NO: 890           moltype = DNA  length = 55
FEATURE                  Location/Qualifiers
source                   1..55
                         mol_type = other DNA
                         organism = synthetic construct
SEQUENCE: 890
ctccccattc catgagcatg cagaggtgac agaccttcga gggttgtttt ggttt       55

SEQ ID NO: 891           moltype = DNA  length = 58
FEATURE                  Location/Qualifiers
source                   1..58
                         mol_type = other DNA
                         organism = synthetic construct
SEQUENCE: 891
ctccccattc catgagcatg cagaggtgag tacagacctt cgagggttgt tttggttt    58

SEQ ID NO: 892           moltype = DNA  length = 50
FEATURE                  Location/Qualifiers
source                   1..50
                         mol_type = other DNA
                         organism = synthetic construct
SEQUENCE: 892
```

```
ctccccattc catgagcatg cagacagacc ttcgagggtt gttttggttt            50

SEQ ID NO: 893         moltype = DNA  length = 51
FEATURE                Location/Qualifiers
source                 1..51
                       mol_type = other DNA
                       organism = synthetic construct
SEQUENCE: 893
ctccccattc catgagcatg cagaggtgac cttcgagggt tgttttggtt t           51

SEQ ID NO: 894         moltype = DNA  length = 54
FEATURE                Location/Qualifiers
source                 1..54
                       mol_type = other DNA
                       organism = synthetic construct
SEQUENCE: 894
ctccccattc catgagcatg cagaggtgca gaccttcgag ggttgttttg gttt        54

SEQ ID NO: 895         moltype = DNA  length = 58
FEATURE                Location/Qualifiers
source                 1..58
                       mol_type = other DNA
                       organism = synthetic construct
SEQUENCE: 895
ctccccattc catgagcatg cagaggtgag tatagacctt cgagggttgt tttggttt    58

SEQ ID NO: 896         moltype = DNA  length = 56
FEATURE                Location/Qualifiers
source                 1..56
                       mol_type = other DNA
                       organism = synthetic construct
SEQUENCE: 896
ctccccattc catgagcatg cagaggtgag tagaccttcg agggttgttt tggttt      56

SEQ ID NO: 897         moltype = DNA  length = 53
FEATURE                Location/Qualifiers
source                 1..53
                       mol_type = other DNA
                       organism = synthetic construct
SEQUENCE: 897
ctccccattc catgagcatg cagaggtcag accttcgagg gttgttttgg ttt         53

SEQ ID NO: 898         moltype = DNA  length = 52
FEATURE                Location/Qualifiers
source                 1..52
                       mol_type = other DNA
                       organism = synthetic construct
SEQUENCE: 898
ctccccattc catgagcatg cagaggcaga ccttcgaggg ttgttttggt tt          52

SEQ ID NO: 899         moltype = DNA  length = 57
FEATURE                Location/Qualifiers
source                 1..57
                       mol_type = other DNA
                       organism = synthetic construct
SEQUENCE: 899
ctccccattc catgagcatg cagaggtgag tcagaccttc gagggttgtt ttggttt     57

SEQ ID NO: 900         moltype = DNA  length = 49
FEATURE                Location/Qualifiers
source                 1..49
                       mol_type = other DNA
                       organism = synthetic construct
SEQUENCE: 900
ctccccattc catgagcatg cagaagacct tcgagggttg ttttggttt              49

SEQ ID NO: 901         moltype = DNA  length = 48
FEATURE                Location/Qualifiers
source                 1..48
                       mol_type = other DNA
                       organism = synthetic construct
SEQUENCE: 901
ctccccattc catgagcatg cagagacctt cgagggttgt tttggttt               48

SEQ ID NO: 902         moltype = DNA  length = 49
FEATURE                Location/Qualifiers
source                 1..49
                       mol_type = other DNA
                       organism = synthetic construct
```

```
SEQUENCE: 902
ctccccattc catgagcatg cagcagacct tcgagggttg ttttggttt             49

SEQ ID NO: 903          moltype = DNA  length = 51
FEATURE                Location/Qualifiers
source                 1..51
                       mol_type = other DNA
                       organism = synthetic construct
SEQUENCE: 903
ctccccattc catgagcatg cagagcagac cttcgagggt tgttttggtt t          51

SEQ ID NO: 904          moltype = DNA  length = 53
FEATURE                Location/Qualifiers
source                 1..53
                       mol_type = other DNA
                       organism = synthetic construct
SEQUENCE: 904
ctccccattc catgagcatg cagaggtgag accttcgagg gttgttttgg ttt        53

SEQ ID NO: 905          moltype = DNA  length = 59
FEATURE                Location/Qualifiers
source                 1..59
                       mol_type = other DNA
                       organism = synthetic construct
SEQUENCE: 905
ctccccattc catgagcatg cagaggtgag tatcagacct tcgagggttg ttttggttt  59

SEQ ID NO: 906          moltype = DNA  length = 54
FEATURE                Location/Qualifiers
source                 1..54
                       mol_type = other DNA
                       organism = synthetic construct
SEQUENCE: 906
ctccccattc catgagcatg cagaggtgaa gaccttcgag ggttgttttg gttt       54

SEQ ID NO: 907          moltype = DNA  length = 56
FEATURE                Location/Qualifiers
source                 1..56
                       mol_type = other DNA
                       organism = synthetic construct
SEQUENCE: 907
ctccccattc catgagcatg cagaggtgag cagaccttcg agggttgttt tggttt     56

SEQ ID NO: 908          moltype = DNA  length = 52
FEATURE                Location/Qualifiers
source                 1..52
                       mol_type = other DNA
                       organism = synthetic construct
SEQUENCE: 908
ctccccattc catgagcatg cagaggtaga ccttcgaggg ttgttttggt tt         52

SEQ ID NO: 909          moltype = DNA  length = 55
FEATURE                Location/Qualifiers
source                 1..55
                       mol_type = other DNA
                       organism = synthetic construct
SEQUENCE: 909
ctccccattc catgagcatg cagaggtatc agaccttcga gggttgtttt ggttt      55

SEQ ID NO: 910          moltype = DNA  length = 47
FEATURE                Location/Qualifiers
source                 1..47
                       mol_type = other DNA
                       organism = synthetic construct
SEQUENCE: 910
ctccccattc catgagcatg cagaaccttc gagggttgtt ttggttt               47

SEQ ID NO: 911          moltype = DNA  length = 54
FEATURE                Location/Qualifiers
source                 1..54
                       mol_type = other DNA
                       organism = synthetic construct
SEQUENCE: 911
ctccccattc catgagcatg cagaggtaca gaccttcgag ggttgttttg gttt       54

SEQ ID NO: 912          moltype = DNA  length = 55
FEATURE                Location/Qualifiers
source                 1..55
                       mol_type = other DNA
```

```
                         organism = synthetic construct
SEQUENCE: 912
ctccccattc catgagcatg cagaggtgag tgaccttcga gggttgtttt ggttt       55

SEQ ID NO: 913           moltype = DNA  length = 60
FEATURE                  Location/Qualifiers
source                   1..60
                         mol_type = other DNA
                         organism = synthetic construct
SEQUENCE: 913
ctccccattc catgagcatg cagatgtgag tatacagacc ttcgagggtt gttttggttt  60

SEQ ID NO: 914           moltype = DNA  length = 60
FEATURE                  Location/Qualifiers
source                   1..60
                         mol_type = other DNA
                         organism = synthetic construct
SEQUENCE: 914
ctccccattc catgatcatg cagaggtgag tatacagacc ttcgagggtt gttttggttt  60

SEQ ID NO: 915           moltype = DNA  length = 60
FEATURE                  Location/Qualifiers
source                   1..60
                         mol_type = other DNA
                         organism = synthetic construct
SEQUENCE: 915
ctccccattc catgagcatg cagaggtgag tatacagacc ttcgagtgtt gttttggttt  60

SEQ ID NO: 916           moltype = DNA  length = 52
FEATURE                  Location/Qualifiers
source                   1..52
                         mol_type = other DNA
                         organism = synthetic construct
SEQUENCE: 916
ctccccattc catgagcatg cagatacaga ccttcgaggg ttgttttggt tt          52

SEQ ID NO: 917           moltype = RNA  length = 23
FEATURE                  Location/Qualifiers
source                   1..23
                         mol_type = other RNA
                         organism = synthetic construct
SEQUENCE: 917
ccgcagttac cctctgcgta atg                                          23

SEQ ID NO: 918           moltype = RNA  length = 22
FEATURE                  Location/Qualifiers
source                   1..22
                         mol_type = other RNA
                         organism = synthetic construct
SEQUENCE: 918
cgcagttacc ctctgcgtaa tg                                           22

SEQ ID NO: 919           moltype = DNA  length = 300
FEATURE                  Location/Qualifiers
source                   1..300
                         mol_type = other DNA
                         organism = synthetic construct
SEQUENCE: 919
tataagcaga gctcgtttag tgaaccgtca gatcgcctgg agacgccatc cacgctgttt  60
tgacctccat agaagattct agagcgagaa aagccttgtt tgccaccatg gaacggctcg  120
gagatcatca ttgcgtcgcg aggtgagcaa gggcgaggag ctgttcaccg gggtggtgcc  180
catcctggtc gagctggacg gcgacgtaaa cggccacaag ttcagcgtgt ccggcgaggg  240
cgagggcgat gccacctacg gcaagctgac cctgaagttc atctgcacca ccggcaagct  300

SEQ ID NO: 920           moltype = DNA  length = 303
FEATURE                  Location/Qualifiers
source                   1..303
                         mol_type = other DNA
                         organism = synthetic construct
SEQUENCE: 920
atattcgtct cgagcaaatc acttggcagt ctagcggacc tctgcggtag gtgcgacaaa  60
actggaggta tcttctaaga tctcgctctt ttcggaacaa acggtggtac cttgccgagc  120
ctctagtagt aacgcagcgc tccactcgtt cccgctcctc gacaagtggc cccaccacca  180
cgggtaggac cagctcgacc tgccgctgca tttgccggtg ttcaagtcgc acaggccgct  240
cccgctcccg ctacggtgga tgccgttcga ctgggacttc aagtagacgt ggtggccgtt  300
cga                                                                303

SEQ ID NO: 921           moltype = AA  length = 53
FEATURE                  Location/Qualifiers
```

```
source                  1..53
                        mol_type = protein
                        organism = synthetic construct
SEQUENCE: 921
VSKGEELFTG VVPILVELDG DVNGHKFSVS GEGEGDATYG KLTLKFICTT GKL         53

SEQ ID NO: 922          moltype = DNA  length = 300
FEATURE                 Location/Qualifiers
source                  1..300
                        mol_type = other DNA
                        organism = synthetic construct
SEQUENCE: 922
tataagcaga gctcgtttag tgaaccgtca gatcgcctgg agacgccatc cacgctgttt  60
tgacctccat agaagattct agagcgagaa aagccttgtt tgccaccatg gaacggctcg  120
gagatcatca ttgcgnaang tgagcaaggg cgaggagctg ttcaccgggg tggtgcccat  180
cctggtcgag ctggacggcg acgtaaacgg ccacaagttc agcgtgtccg gcgagggcga  240
gggcgatgcc acctacggca agctgaccct gaagttcatc tgcaccaccg gcaagctgcc  300

SEQ ID NO: 923          moltype = DNA  length = 300
FEATURE                 Location/Qualifiers
source                  1..300
                        mol_type = other DNA
                        organism = synthetic construct
SEQUENCE: 923
atattcgtct cgagcaaatc acttggcagt ctagcggacc tctgcggtag gtgcgacaaa  60
actggaggta tcttctaaga tctcgctctt ttcggaacaa acggtggtac cttgccgagc  120
ctctagtagt aacgcnttnc actcgttccc gctcctcgac aagtggcccc accacgggta  180
ggaccagctc gacctgccgc tgcatttgcc ggtgttcaag tcgcacaggc cgctcccgct  240
cccgctacgg tggatgccgt tcgactggga cttcaagtag acgtggtggc cgttcgacgg  300

SEQ ID NO: 924          moltype = AA  length = 54
FEATURE                 Location/Qualifiers
source                  1..54
                        mol_type = protein
                        organism = synthetic construct
SEQUENCE: 924
VSKGEELFTG VVPILVELDG DVNGHKFSVS GEGEGDATYG KLTLKFICTT GKLP        54

SEQ ID NO: 925          moltype = DNA  length = 79
FEATURE                 Location/Qualifiers
source                  1..79
                        mol_type = other DNA
                        organism = synthetic construct
SEQUENCE: 925
atctccccat tccatgagca tgcagaggtg agtatacaga ccttcgaggg ttgttttggt  60
tttggttttt gcttttggc                                               79

SEQ ID NO: 926          moltype = DNA  length = 65
FEATURE                 Location/Qualifiers
source                  1..65
                        mol_type = other DNA
                        organism = synthetic construct
SEQUENCE: 926
atctccccat tccatgagca tgcagacctt cgagggttgt tttggttttg gtttttgctt  60
ttggc                                                              65

SEQ ID NO: 927          moltype = DNA  length = 58
FEATURE                 Location/Qualifiers
source                  1..58
                        mol_type = other DNA
                        organism = synthetic construct
SEQUENCE: 927
atctccccat tccatgagca tgcagagggt tgttttggtt ttggtttttg cttttggc    58

SEQ ID NO: 928          moltype = DNA  length = 69
FEATURE                 Location/Qualifiers
source                  1..69
                        mol_type = other DNA
                        organism = synthetic construct
SEQUENCE: 928
atctccccat tccatgagca tgcagacaga ccttcgaggg ttgttttggt tttggttttt  60
gcttttggc                                                          69

SEQ ID NO: 929          moltype = DNA  length = 70
FEATURE                 Location/Qualifiers
source                  1..70
                        mol_type = other DNA
                        organism = synthetic construct
SEQUENCE: 929
```

```
atctccccat tccatgagca tgcagaggtg accttcgagg gttgttttgg ttttggtttt  60
tgcttttggc                                                         70

SEQ ID NO: 930         moltype = DNA  length = 71
FEATURE                Location/Qualifiers
source                 1..71
                       mol_type = other DNA
                       organism = synthetic construct
SEQUENCE: 930
atctccccat tccatgagca tgcagataca gaccttcgag ggttgttttg gttttggttt  60
ttgcttttgg c                                                       71

SEQ ID NO: 931         moltype = DNA  length = 73
FEATURE                Location/Qualifiers
source                 1..73
                       mol_type = other DNA
                       organism = synthetic construct
SEQUENCE: 931
atctccccat tccatgagca tgcagaggta cagaccttcg agggttgttt tggttttggt  60
tttgcttttt ggc                                                     73

SEQ ID NO: 932         moltype = DNA  length = 77
FEATURE                Location/Qualifiers
source                 1..77
                       mol_type = other DNA
                       organism = synthetic construct
SEQUENCE: 932
atctccccat tccatgagca tgcagaggtg agtacagacc ttcgagggtt gttttggttt  60
tggtttttgc ttttggc                                                 77

SEQ ID NO: 933         moltype = DNA  length = 73
FEATURE                Location/Qualifiers
source                 1..73
                       mol_type = other DNA
                       organism = synthetic construct
SEQUENCE: 933
atctccccat tccatgagca tgcagaggtg cagaccttcg agggttgttt tggttttggt  60
tttgcttttt ggc                                                     73

SEQ ID NO: 934         moltype = DNA  length = 72
FEATURE                Location/Qualifiers
source                 1..72
                       mol_type = other DNA
                       organism = synthetic construct
SEQUENCE: 934
atctccccat tccatgagca tgcagaggtc agaccttcga gggttgtttt ggttttggtt  60
tttgcttttg gc                                                      72

SEQ ID NO: 935         moltype = DNA  length = 74
FEATURE                Location/Qualifiers
source                 1..74
                       mol_type = other DNA
                       organism = synthetic construct
SEQUENCE: 935
atctccccat tccatgagca tgcagaggtg acagaccttc gagggttgtt ttggttttgg  60
tttttgcttt tggc                                                    74

SEQ ID NO: 936         moltype = DNA  length = 67
FEATURE                Location/Qualifiers
source                 1..67
                       mol_type = other DNA
                       organism = synthetic construct
SEQUENCE: 936
atctccccat tccatgagca tgcagagacc ttcgagggtt gttttggttt tggtttttgc  60
ttttggc                                                            67

SEQ ID NO: 937         moltype = DNA  length = 74
FEATURE                Location/Qualifiers
source                 1..74
                       mol_type = other DNA
                       organism = synthetic construct
SEQUENCE: 937
atctccccat tccatgagca tgcagaggta tcagaccttc gagggttgtt ttggttttgg  60
tttttgcttt tggc                                                    74

SEQ ID NO: 938         moltype = DNA  length = 70
FEATURE                Location/Qualifiers
source                 1..70
                       mol_type = other DNA
```

```
                         organism = synthetic construct
SEQUENCE: 938
atctccccat tccatgagca tgcagagcag accttcgagg gttgttttgg ttttggtttt  60
tgcttttggc                                                         70

SEQ ID NO: 939           moltype = DNA  length = 68
FEATURE                  Location/Qualifiers
source                   1..68
                         mol_type = other DNA
                         organism = synthetic construct
SEQUENCE: 939
atctccccat tccatgagca tgcagcagac cttcgagggt tgttttggtt ttggtttttg  60
cttttggc                                                           68

SEQ ID NO: 940           moltype = DNA  length = 70
FEATURE                  Location/Qualifiers
source                   1..70
                         mol_type = other DNA
                         organism = synthetic construct
SEQUENCE: 940
atctccccat tccatgagca tgcagtacag accttcgagg gttgttttgg ttttggtttt  60
tgcttttggc                                                         70

SEQ ID NO: 941           moltype = DNA  length = 71
FEATURE                  Location/Qualifiers
source                   1..71
                         mol_type = other DNA
                         organism = synthetic construct
SEQUENCE: 941
atctccccat tccatgagca tgcagaggca gaccttcgag ggttgttttg gttttggttt  60
ttgcttttgg c                                                       71

SEQ ID NO: 942           moltype = DNA  length = 72
FEATURE                  Location/Qualifiers
source                   1..72
                         mol_type = other DNA
                         organism = synthetic construct
SEQUENCE: 942
atctccccat tccatgagca tgcagagtac agaccttcga gggttgtttt ggttttggtt  60
tttgcttttg gc                                                      72

SEQ ID NO: 943           moltype = DNA  length = 66
FEATURE                  Location/Qualifiers
source                   1..66
                         mol_type = other DNA
                         organism = synthetic construct
SEQUENCE: 943
atctccccat tccatgagca tgcagaacct tcgagggttg ttttggtttt ggtttttgct  60
tttggc                                                             66

SEQ ID NO: 944           moltype = DNA  length = 56
FEATURE                  Location/Qualifiers
source                   1..56
                         mol_type = other DNA
                         organism = synthetic construct
SEQUENCE: 944
atctccccat tccatgacct tcgagggttg ttttggtttt ggtttttgct tttggc      56

SEQ ID NO: 945           moltype = DNA  length = 56
FEATURE                  Location/Qualifiers
source                   1..56
                         mol_type = other DNA
                         organism = synthetic construct
SEQUENCE: 945
atctccccat tccatgagca tgcagggttg ttttggtttt ggtttttgct tttggc      56

SEQ ID NO: 946           moltype = DNA  length = 74
FEATURE                  Location/Qualifiers
source                   1..74
                         mol_type = other DNA
                         organism = synthetic construct
SEQUENCE: 946
atctccccat tccatgagca tgcagaggtt acagaccttc gagggttgtt ttggttttgg  60
tttttgcttt tggc                                                    74

SEQ ID NO: 947           moltype = DNA  length = 63
FEATURE                  Location/Qualifiers
source                   1..63
                         mol_type = other DNA
```

```
                        organism = synthetic construct
SEQUENCE: 947
atctccccat tccatgagca tgcagattcg agggttgttt tggttttggt ttttgctttt  60
ggc                                                                 63

SEQ ID NO: 948          moltype = DNA  length = 39
FEATURE                 Location/Qualifiers
source                  1..39
                        mol_type = other DNA
                        organism = synthetic construct
SEQUENCE: 948
ccttcgaggg ttgttttggt tttggttttt gcttttggc                          39

SEQ ID NO: 949          moltype = DNA  length = 70
FEATURE                 Location/Qualifiers
source                  1..70
                        mol_type = other DNA
                        organism = synthetic construct
SEQUENCE: 949
atctccccat tccatgagca tgcagaacag accttcgagg gttgttttgg ttttggtttt  60
tgcttttggc                                                          70

SEQ ID NO: 950          moltype = DNA  length = 38
FEATURE                 Location/Qualifiers
source                  1..38
                        mol_type = other DNA
                        organism = synthetic construct
SEQUENCE: 950
cttcgagggt tgttttggtt ttggttttttg cttttggc                          38

SEQ ID NO: 951          moltype = DNA  length = 57
FEATURE                 Location/Qualifiers
source                  1..57
                        mol_type = other DNA
                        organism = synthetic construct
SEQUENCE: 951
atctccccat tccatgagca tgcagaggtt gttttggttt tggtttttgc ttttggc      57

SEQ ID NO: 952          moltype = DNA  length = 64
FEATURE                 Location/Qualifiers
source                  1..64
                        mol_type = other DNA
                        organism = synthetic construct
SEQUENCE: 952
atctccccat tccatgagca tgcagacttc gagggttgtt ttggttttgg tttttgcttt  60
tggc                                                                64

SEQ ID NO: 953          moltype = DNA  length = 69
FEATURE                 Location/Qualifiers
source                  1..69
                        mol_type = other DNA
                        organism = synthetic construct
SEQUENCE: 953
atctccccat tccatgagca tgcagaggta ccttcgaggg ttgttttggt tttggttttt  60
gcttttggc                                                           69

SEQ ID NO: 954          moltype = DNA  length = 30
FEATURE                 Location/Qualifiers
source                  1..30
                        mol_type = other DNA
                        organism = synthetic construct
SEQUENCE: 954
gttgttttgg ttttggtttt tgcttttggc                                    30

SEQ ID NO: 955          moltype = DNA  length = 75
FEATURE                 Location/Qualifiers
source                  1..75
                        mol_type = other DNA
                        organism = synthetic construct
SEQUENCE: 955
atctccccat tccatgagca tgcagaggtg tacagacctt cgagggttgt tttggttttg  60
gtttttgctt ttggc                                                    75

SEQ ID NO: 956          moltype = DNA  length = 71
FEATURE                 Location/Qualifiers
source                  1..71
                        mol_type = other DNA
                        organism = synthetic construct
SEQUENCE: 956
```

```
atctccccat tccatgagca tgcagaggta gaccttcgag ggttgttttg gttttggttt  60
ttgcttttgg c                                                       71

SEQ ID NO: 957         moltype = DNA  length = 65
FEATURE                Location/Qualifiers
source                 1..65
                       mol_type = other DNA
                       organism = synthetic construct
SEQUENCE: 957
atctccccat tccatgagca tgcagaggtt cgagggttgt tttggttttg gtttttgctt  60
ttggc                                                              65

SEQ ID NO: 958         moltype = DNA  length = 60
FEATURE                Location/Qualifiers
source                 1..60
                       mol_type = other DNA
                       organism = synthetic construct
SEQUENCE: 958
atctccccat tccatgagca tgcttcgagg gttgttttgg ttttggtttt tgcttttggc  60

SEQ ID NO: 959         moltype = DNA  length = 49
FEATURE                Location/Qualifiers
source                 1..49
                       mol_type = other DNA
                       organism = synthetic construct
SEQUENCE: 959
atctccccat tccatgaggg ttgttttggt tttggttttt gcttttggc              49

SEQ ID NO: 960         moltype = DNA  length = 68
FEATURE                Location/Qualifiers
source                 1..68
                       mol_type = other DNA
                       organism = synthetic construct
SEQUENCE: 960
atctccccat tccatgagca tgcagaagac cttcgagggt tgttttggtt ttggtttttg  60
cttttggc                                                           68

SEQ ID NO: 961         moltype = DNA  length = 75
FEATURE                Location/Qualifiers
source                 1..75
                       mol_type = other DNA
                       organism = synthetic construct
SEQUENCE: 961
atctccccat tccatgagca tgcagaggta tacagacctt cgagggttgt tttggttttg  60
gtttttgctt ttggc                                                   75

SEQ ID NO: 962         moltype = DNA  length = 76
FEATURE                Location/Qualifiers
source                 1..76
                       mol_type = other DNA
                       organism = synthetic construct
SEQUENCE: 962
atctccccat tccatgagca tgcagaggtg atacagacct tcgagggttg ttttggtttt  60
ggtttttgct tttggc                                                  76

SEQ ID NO: 963         moltype = DNA  length = 68
FEATURE                Location/Qualifiers
source                 1..68
                       mol_type = other DNA
                       organism = synthetic construct
SEQUENCE: 963
atctccccat tccatgagca tgcagaggac cttcgagggt tgttttggtt ttggtttttg  60
cttttggc                                                           68

SEQ ID NO: 964         moltype = DNA  length = 78
FEATURE                Location/Qualifiers
source                 1..78
                       mol_type = other DNA
                       organism = synthetic construct
SEQUENCE: 964
atctccccat tccatgagca tgcagaggtg agtatcagac cttcgagggt tgttttggtt  60
ttggtttttg cttttggc                                                78

SEQ ID NO: 965         moltype = DNA  length = 24
FEATURE                Location/Qualifiers
source                 1..24
                       mol_type = other DNA
                       organism = synthetic construct
SEQUENCE: 965
```

```
atctccccat tccatgagca tgca                                        24

SEQ ID NO: 966         moltype = DNA  length = 69
FEATURE                Location/Qualifiers
source                 1..69
                       mol_type = other DNA
                       organism = synthetic construct
SEQUENCE: 966
atctccccat tccatgagca tgcagaggtg ccttcgaggg ttgttttggt tttggttttt  60
gcttttggc                                                         69

SEQ ID NO: 967         moltype = DNA  length = 77
FEATURE                Location/Qualifiers
source                 1..77
                       mol_type = other DNA
                       organism = synthetic construct
SEQUENCE: 967
atctccccat tccatgagca tgcagaggtg agtatagacc ttcgagggtt gttttggttt  60
tggtttttgc ttttggc                                                77

SEQ ID NO: 968         moltype = DNA  length = 68
FEATURE                Location/Qualifiers
source                 1..68
                       mol_type = other DNA
                       organism = synthetic construct
SEQUENCE: 968
atctccccat tccatgagca tgcagaggtc cttcgagggt tgttttggtt ttggtttttg  60
cttttggc                                                          68

SEQ ID NO: 969         moltype = DNA  length = 67
FEATURE                Location/Qualifiers
source                 1..67
                       mol_type = other DNA
                       organism = synthetic construct
SEQUENCE: 969
atctccccat tccatgagca tgcagaggtc ttcgagggtt gttttggttt tggtttttgc  60
ttttggc                                                           67

SEQ ID NO: 970         moltype = DNA  length = 67
FEATURE                Location/Qualifiers
source                 1..67
                       mol_type = other DNA
                       organism = synthetic construct
SEQUENCE: 970
atctccccat tccatgagca tgcacagacc ttcgagggtt gttttggttt tggtttttgc  60
ttttggc                                                           67

SEQ ID NO: 971         moltype = DNA  length = 62
FEATURE                Location/Qualifiers
source                 1..62
                       mol_type = other DNA
                       organism = synthetic construct
SEQUENCE: 971
atctccccat tccatgagca tgaccttcga gggttgtttt ggttttggtt tttgcttttg  60
gc                                                                62

SEQ ID NO: 972         moltype = DNA  length = 68
FEATURE                Location/Qualifiers
source                 1..68
                       mol_type = other DNA
                       organism = synthetic construct
SEQUENCE: 972
atctccccat tccatgagca tgcagaggta cttcgagggt tgttttggtt ttggtttttg  60
cttttggc                                                          68

SEQ ID NO: 973         moltype = DNA  length = 72
FEATURE                Location/Qualifiers
source                 1..72
                       mol_type = other DNA
                       organism = synthetic construct
SEQUENCE: 973
atctccccat tccatgagca tgcagaggac agaccttcga gggttgtttt ggttttggtt  60
tttgcttttg gc                                                     72

SEQ ID NO: 974         moltype = DNA  length = 61
FEATURE                Location/Qualifiers
source                 1..61
                       mol_type = other DNA
                       organism = synthetic construct
```

```
SEQUENCE: 974
atctccccat tccatgagca tgccttcgag ggttgttttg gttttggttt ttgcttttgg  60
c                                                                    61

SEQ ID NO: 975         moltype = AA  length = 1139
FEATURE                Location/Qualifiers
source                 1..1139
                       mol_type = protein
                       organism = synthetic construct
SEQUENCE: 975
RFRVLSVNQF RCNPNAFRQA SMKTDDEKKD TAIKSYTSWL LPNDRKEKDM VRSFLALDQG  60
SRFFFDLMQA WYGGLTPDII KSVTKERDLV DLWCAIYWFR PMKKELASHP IDRVDLAKTF  120
QRYYGGPASD VVQEYLSASI GEDCCWNDCR QKYQEFCKNL GVDFTPDLKT LVREKLIAVA  180
LNDGSRAAIS NLFGNGGKED RNVKVNICKK ILIALEKAGK SVKYVRDVQS IILKCANAKD  240
REDFNRIYAD KNGRPGTLLL LLDRKGENTY DAEVLKRYLR KTIKSKNAPL VWNYNQKLFE  300
YIERGIRNLL RRTINYDAWA WGEMWRVGHT PLQTKATRNY HFAQEQLKRH SRIAAASQSS  360
HAIAVALNEF FESPFFDGEN PFTICPHHLG KNLEKLFKAW ADEKNQTDEE DAGETAITDY  420
CAEFKRGFDR EPIRNLLRYV YASLRSKYSA KELIQAAKYN QQFERYQRQK AHPVTPDNQG  480
YTWPEAVIKP SKAERKNREN SLDTRIWVSV KLLQKDGTWE KHHIPFYNLR FFEEVYAAAS  540
IAEDMPSPTF RNSRFGFKLP KLLNTHAKIN KKKKDGKKDK KAVNAAKREA RIYLAAKEGR  600
LPAPSVPLDK LSAVIARVNG KFQVTVPVKF KVNKQPKYPL PQLGQIILGY AQNLTANHAW  660
ALFEVVTEDT PGAHFCRNQY LRVLKTGQVR SITKTKDGQE IDQLSYDGLE YKEYGEWRKQ  720
AKKFASQWYI TTKVRKGKET TLLSQPALER FESIEKYKPA LYRFNKEYAR LLLAVIRRKT  780
LNELEEIRPE IFRLVEQGFG ICRFGSLSLS SFEAIRAAKA VIYGYFSTAL KHDHNTPITD  840
DERQARDPEL FGLLNKLRTR RQNKGEEKIN RAANALIRIA LENKADFIRG AGDLPTTNKS  900
VKKGQNSRSM DWLARGLFNK ICQLAVMHNI IPTAANPHST SHQDPFEHNK DFDDPQPAMK  960
CRYAEFKIED IGDSVLERLG TSLRNAKAGQ TGAYYYKGAQ DFLAHYGLQD IEEELKKCRR  1020
GRKANMPCWE LQKRLIQKLG SKDAVVYIPM RGGRIYLATH SVTTGAKPII FNGEEVWVSN  1080
AAEIAAVNIG LTIIPTSKKD EEHPDRENDD KAIRKSVRRP RKSGERRSGD KMPATARKT   1139

SEQ ID NO: 976         moltype = DNA  length = 10255
FEATURE                Location/Qualifiers
source                 1..10255
                       mol_type = other DNA
                       organism = synthetic construct
SEQUENCE: 976
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
cgggccacca tgggaaaacg gacagccgac ggaagcgagt tcgagtcacc aaagaagaag  960
cggaaagtct ctgaagtcga gtttagccac gagtattgga tgaggcacgc actgaccctg  1020
gcaaagcgag catgggatga aagagaagtc cccgtgggcg ccgtgctggt gcacaacaat  1080
agagtgatcg gagagggatg gaacaggcca atcggccgcc acgaccctac cgcacacgca  1140
gagatcatgg cactgaggca gggaggcctg gtcatgcaga attaccgcct gatcgatgcc  1200
accctgtatg tgacactgga gccatgcgtg atgtgcgcag gagcaatgat ccacagcagg  1260
atcggaagag tggtgttcgg agcacgggac gccaagaccg gcgcagcagg ctccctgatg  1320
gatgtgctgc accaccccgg catgaaccac cgggtggaga tcacagaggg aatcctggca  1380
gacgagtgcg ccgccctgct gagcgatttc tttagaatgc ggagacagga gatcaaggcc  1440
cagaagaagg cacagagctc caccgactct ggaggatcta gcggaggatc ctctggaagc  1500
gagacaccag gcacaagcga gtccgccaca ccagagagct ccggcggctc ctccggagga  1560
tcctctgagg tggagttttc ccacgagtac tggatgagac atgccctgac cctggccaag  1620
agggcacggg atgagaggga ggtgcctgtg ggagccgtgc tggtgctgaa caatagagtg  1680
atcggcgagg gctggaacag agccatcggc ctgcacgacc caacagccca tgccgaaatt  1740
atggccctga gacagggcgg cctggtcatg cagaactaca gactgattga cgccaccctg  1800
tacgtgacat tcgagccttg cgtgatgtgc gccggcgcca tgatccactc taggatcggc  1860
cgcgtggtgt ttggcgtgag gaactcaaaa agaggcgccg caggctccct gatgaacgtg  1920
ctgaactacc ccggcatgaa tcaccgcgtc gaaattaccg agggaatcct ggcagatgaa  1980
tgtgccgccc tgctgtgcga tttctatcgg atgcctagac aggtgttcaa tgctcagaag  2040
aaggcccaga gctccatcaa ctctggagga tctagcggag gatcctctgg cagcgagaca  2100
ccaggaacaa gcgagtcagc aacaccagag agcagtggcg gcagcagcgg cggcagcccc  2160
aagaaaaaac gcaaggtggg aagcaggttc agggtgctga gcgtgaatca gttcagatgc  2220
aaccccaacg ccttcagaca agcctccatg aaaaccgacg acgagaagaa ggacaccgcc  2280
atcaagagct acacaagctg gctgctgccc aacgacagaa aggagaagga catggtgcgg  2340
agcttcctgg ccctggacca aggcagcaga ttctttttcg acctgatgca agcctggtac  2400
ggcggcctca cccccgacat catcaagagc gtgaccaagg agcgggacct ggtggacctg  2460
tggtgcgcca tctactggtt cagacccatg aagaaggagc tggcctccca ccccatcgac  2520
agagtggacc tggccaagac ctttcagaga tactacggcg gccccgcctc cgacgtggtg  2580
```

-continued

```
caagagtacc tgagcgcctc catcggcgag gactgctgct ggaacgactg cagacagaag  2640
taccaagagt tctgcaagaa cctcggggtg gacttcaccc ccgacctcaa gaccctggtg  2700
agagagaagc tgatcgccgt ggccctgaac gacggcagca gagccgccat cagcaacctg  2760
ttcggcaacg gcggcaagga ggacagaaac gtgaaggtga acatctgcaa gaagatcctg  2820
attgctctgg agaaggccgg caaatccgtg aagtacgtgc gggacgtgca gagcatcatc  2880
ctgaagtgcg ccaacgccaa ggacagagag gacttcaaca gaatctacgc cgacaagaac  2940
ggcagacccg gcaccctgct cctgctcctg gacagaaagg gcgagaacac ctacgacgcc  3000
gaggtgctga agagatacct gagaaagacc atcaagagca agaacgcccc cctggtgtgg  3060
aactacaatc agaagctgtt cgagtacatc gagagaggca tccggaatct gctgagaaga  3120
accatcaact acgacgcctg ggcctggggc gagatgtgga gagtgggcca caccccccctg  3180
cagaccaagg ccacaagaaa ctaccacttc gcccaagagc agctgaagag acacagcaga  3240
atcgccgccg cttcccaaag cagccacgcc atcgccgtcg ctctgaacga gttcttcgag  3300
agccccttct tcgacggcga gaacccccttc accatctgcc cccaccacct gggcaagaac  3360
ctggaaaagc tgttcaaggc ctgggccgac gaaaaaaatc agaccgacga ggaggacgcc  3420
ggcgaaaccg ccatcaccga ctactgcgcc gagttcaaga gaggcttcga cagagagccc  3480
attagaaacc tgctgagata cgtgtacgct tccctgagaa gcaagtacag cgccaaggag  3540
ctgatccaag ccgccaagta caatcagcag ttcgagagat atcagagaca gaaggcccac  3600
cccgtgaccc ccgacaacca aggctacacc tggcccgagg ccgtgatcaa gcctagcaag  3660
gccgagagaa agaacagaga gaacagcctg gacacaagaa tctgggtgag cgtgaagctg  3720
ctgcaaaagg acggcacctg ggagaagcac cacatcccct tctacaacct gagattcttc  3780
gaagaggtgt acgccgctgc ctccatcgcc gaggacatgc ctagccccac cttcagaaac  3840
agcagattcg gcttcaagct gcccaagctg ctgaacaccc acgccaagat caacaagaaa  3900
aagaaggacg gcaagaagga caagaaggcc gtgaacgccg ccaagagaga ggctagaatc  3960
tacctcgctg ccaaggaggg cagactgccc gccccctccg tgcccctgga caagctgagc  4020
gccgtgatcg ctagagtgaa cggcaagttc caagtgaccg tgcccgtgaa gttcaaggtg  4080
aacaagcagc ccaagtaccc cctgcctcag ctggggcaga tcatcctggg ctacgcccag  4140
aacctgaccg ccaaccacgc ctgggccctg ttcgaggtgg tgaccgagga cacccccggc  4200
gcccacttct gcagaaatca gtacctgaga gtgctcaaga ccggccaagt gagaagcatc  4260
accaagacca aggacggcca agagatcgat cagctgagct acgacggcct ggagtacaag  4320
gagtacggcg agtggagaaa gcaagccaag aagttcgcct cccaatggta catcaccacc  4380
aaggtgagaa agggcaagga aaccaccctg ctgagccaac ccgccctgga gagattcgag  4440
agcatcgaga agtacaagcc cgccctgtac agattcaaca aggaatacgc ccggctgctc  4500
ctggccgtca tcagaagaaa gaccctgaac gagctggagg agatcagacc cgagatcttc  4560
agactggtgg agcaaggctt cggcatctgc agattcggca gcctgagcct gagcagcttc  4620
gaggccatca gagccgccaa ggccgtgatc tacggctact tcagcaccgc cctgaagcac  4680
gaccacaaca cccccatcac agatgacgag agacaagcca gagaccccga gctgttcggc  4740
ctgctgaaca agctgagaac caggagacag aacaagggcg aggagaagat caacagagcc  4800
gctaacgccc tgatcagaat cgccctggag aacaaggccg acttcatcag aggcgccggc  4860
gacctgccca ccaccaacaa gagcgtcaag aaggggcaga acagcagaag catggactgg  4920
ctggctagag gcctgttcaa caagatctgt cagctggccg tgatgcacaa catcattccc  4980
accgccgcca acccccacag cacaagccac caagacccct tcgagcacaa caaggacttc  5040
gacgaccctc agcccgccat gaagtgcaga tacgctgagt tcaagatcga ggacatcggc  5100
gacagcgtgc tggagagact gggcacctcc ctgagaaatg ccaaggccgg gcagaccggc  5160
gcctactatt acaagggcgc ccaagacttc ctggcccact acggcctgca agacatcgag  5220
gaagagctga agaagtgcag aagaggcaga aaggccaaca tgccctgctg ggagctgcag  5280
aagagactga ttcagaagct gggcagcaag gacgccgtgg tgtacatccc catgagaggc  5340
ggccggatct acctggctac acacagcgtg accaccggcg ccaagcccat catcttcaac  5400
ggcgaagagg tgtgggtgag caacgccgcc gagatcgccg ccgtgaacat cggcctgacc  5460
atcatcccca caagcaagaa ggacgaggag caccccgaca gagagaacga cgacaaggcc  5520
atcagaaaga gcgtcagacg gcctagaaag agcggcgaga gaagaagcgg cgacaagatg  5580
cccgccaccg ctagaaagac cacaggcggc ggcccggcg gcggcgccgc cgccggcagc  5640
ggcagcccta agaaaaaacg aaaagttggc agcggaagca aaaggccggc ggccacgaaa  5700
aaggccggcc aggcaaaaaa gaaaaagctc gagcctgctg ccaaacgcgt taaactagac  5760
gactataagg accacgacgg agactacaag gatcatgata ttgattacaa agacgatgac  5820
gataagtgag tttaaacccg ctgatcagcc tcgactgtgc cttctagttg ccagccatct  5880
gttgtttgcc cctcccccgt gccttccttg accctggaag gtgccactcc cactgtcctt  5940
tcctaataaa atgaggaaat tgcatcgcat tgtctgagta ggtgtcattc tattctgggg  6000
ggtggggtgg ggcaggacag caagggggag gattgggaag acaatagcag gcatgctggg  6060
gatgcggtgg gctctatggc ttctgaggcg gaaagaacca gctggggctc taggggtat  6120
ccccacgcgc cctgtagcgg cgcattaagc gcggcgggtg tggtggttac gcgcagcgtg  6180
accgctacac ttgccagcgc cctagcgccc gctcctttcg ctttcttccc ttcctttctc  6240
gccacgttcg ccggctttcc ccgtcaagct ctaaatcggg ggctcccttt agggttccga  6300
tttagtgctt tacggcacct cgaccccaaa aaacttgatt agggtgatgg ttcacgtagt  6360
gggccatcgc cctgatagac ggtttttcgc cctttgacgt tggagtccac gttctttaat  6420
agtggactct tgttccaaac tggaacaaca ctcaacccta tctcggtcta ttcttttgat  6480
ttataaggga ttttgccgat ttcggcctat tggttaaaaa atgagctgat ttaacaaaaa  6540
tttaacgcga attaattctg tggaatgtgt gtcagttagg gtgtggaaag tccccaggct  6600
ccccagcagg cagaagtatg caaagcatgc atctcaatta gtcagcaacc aggtgtggaa  6660
agtccccagg ctccccagca ggcagaagta tgcaaagcat gcatctcaat tagtcagcaa  6720
ccatagtccc gcccctaact ccgcccatcc cgcccctaac tccgcccagt tccgcccatt  6780
ctccgcccca tggctgacta attttttta tttatgcaga ggccgaggcc gcctctgcct  6840
ctgagctatt ccagaagtag tgaggaggct tttttggagg cctaggcttt tgcaaaaagc  6900
tcccgggagc ttgtatatcc attttcggat ctgatcaaga gacaggatga ggatcgtttc  6960
gcatgattga acaagatgga ttgcacgcag gttctccggc cgcttgggtg gagaggctat  7020
tcggctatga ctgggcacaa cagacaatcg gctgctctga tgccgccgtg ttccggctgt  7080
cagcgcaggg gcgcccggtt ctttttgtca agaccgacct gtccggtgcc ctgaatgaac  7140
tgcaggacga ggcagcgcgg ctatcgtggc tggccacgac gggcgttcct tgcgcagctg  7200
tgctcgacgt tgtcactgaa gcgggaaggg actggctgct attgggcgaa gtgccggggc  7260
aggatctcct gtcatctcac cttgctcctg ccgagaaagt atccatcatg gctgatgcaa  7320
```

```
tgcggcggct gcatacgctt gatccggcta cctgcccatt cgaccaccaa gcgaaacatc  7380
gcatcgagcg agcacgtact cggatggaag ccggtcttgt cgatcaggat gatctggacg  7440
aagagcatca ggggctcgcg ccagccgaac tgttcgccag gctcaaggcg cgcatgcccg  7500
acggcgagga tctcgtcgtg acccatggcg atgcctgctt gccgaatatc atggtggaaa  7560
atggccgctt ttctggattc atcgactgtg gccggctggg tgtggcggac cgctatcagg  7620
acatagcgtt ggctacccgt gatattgctg aagagcttgg cggcgaatgg gctgaccgct  7680
tcctcgtgct ttacggtatc gccgctcccg attcgcagcg catcgccttc tatcgccttc  7740
ttgacgagtt cttctgagcg ggactctggg gttcgaaatg accgaccaag cgacgcccaa  7800
cctgccatca cgagatttcg attccaccgc cgccttctat gaaaggttgg gcttcggaat  7860
cgttttccgg gacgccggct ggatgatcct ccagcgcggg gatctcatgc tggagttctt  7920
cgcccacccc aacttgttta ttgcagctta taatggttac aaataaagca atagcatcac  7980
aaatttcaca aataaagcat ttttttcact gcattctagt tgtggtttgt ccaaactcat  8040
caatgtatct tatcatgtct gtataccgtc gacctctagc tagagcttgg cgtaatcatg  8100
gtcatagctg tttcctgtgt gaaattgtta tccgctcaca attccacaca acatacgagc  8160
cggaagcata aagtgtaaag cctggggtgc ctaatgagtg agctaactca cattaattgc  8220
gttgcgctca ctgcccgctt tccagtcggg aaacctgtcg tgccagctgc attaatgaat  8280
cggccaacgc gcggggagag gcggtttgcg tattgggcgc tcttccgctt cctcgctcac  8340
tgactcgctg cgctcggtcg ttcggctgcg gcgagcggta tcagctcact caaaggcggt  8400
aatacggtta tccacagaat caggggataa cgcaggaaag aacatgtgag caaaaggcca  8460
gcaaaaggcc aggaaccgta aaaaggccgc gttgctggcg tttttccata ggctccgccc  8520
ccctgacgag catcacaaaa atcgacgctc aagtcagagg tggcgaaacc cgacaggact  8580
ataaagatac caggcgtttc cccctggaag ctccctcgtg cgctctcctg ttccgaccct  8640
gccgcttacc ggatacctgt ccgcctttct cccttcggga agcgtggcgc tttctcatag  8700
ctcacgctgt aggtatctca gttcggtgta ggtcgttcgc tccaagctgg gctgtgtgca  8760
cgaacccccc gttcagcccg accgctgcgc cttatccggt aactatcgtc ttgagtccaa  8820
cccggtaaga cacgacttat cgccactggc agcagccact ggtaacagga ttagcagagc  8880
gaggtatgta ggcggtgcta cagagttctt gaagtggtgg cctaactacg gctacactag  8940
aagaacagta tttggtatct gcgctctgct gaagccagtt accttcggaa aaagagttgg  9000
tagctcttga tccggcaaac aaaccaccgc tggtagcggt ttttttgttt gcaagcagca  9060
gattacgcgc agaaaaaaag gatctcaaga agatcctttg atcttttcta cggggtctga  9120
cgctcagtgg aacgaaaact cacgttaagg gattttggtc atgagattat caaaaaggat  9180
cttcacctag atccttttaa attaaaaatg aagttttaaa tcaatctaaa gtatatatga  9240
gtaaacttgg tctgacagtt accaatgctt aatcagtgag gcacctatct cagcgatctg  9300
tctatttcgt tcatccatag ttgcctgact ccccgtcgtg tagataacta cgatacggga  9360
gggcttacca tctggcccca gtgctgcaat gataccgcga gacccacgct caccggctcc  9420
agatttatca gcaataaacc agccagccgg aagggccgag cgcagaagtg gtcctgcaac  9480
tttatccgcc tccatccagt ctattaattg ttgccgggaa gctagagtaa gtagttcgcc  9540
agttaatagt ttgcgcaacg ttgttgccat tgctacaggc atcgtggtgt cacgctcgtc  9600
gtttggtatg gcttcattca gctccggttc ccaacgatca aggcgagtta catgatcccc  9660
catgttgtgc aaaaaagcgg ttagctcctt cggtcctccg atcgttgtca gaagtaagtt  9720
ggccgcagtg ttatcactca tggttatggc agcactgcat aattctctta ctgtcatgcc  9780
atccgtaaga tgcttttctg tgactggtga gtactcaacc aagtcattct gagaatagtg  9840
tatgcggcga ccgagttgct cttgcccggc gtcaatacgg gataataccg cgccacatag  9900
cagaacttta aaagtgctca tcattggaaa acgttcttcg gggcgaaaac tctcaaggat  9960
cttaccgctg ttgagatcca gttcgatgta acccactcgt gcacccaact gatcttcagc  10020
atcttttact ttcaccagcg tttctgggtg agcaaaaaca ggaaggcaaa atgccgcaaa  10080
aaagggaata agggcgacac ggaaatgttg aatactcata ctcttccttt ttcaatatta  10140
ttgaagcatt tatcagggtt attgtctcat gagcggatac atatttgaat gtatttagaa  10200
aaataaacaa ataggggttc cgcgcacatt tccccgaaaa gtgccacctg acgtc       10255
```

```
SEQ ID NO: 977         moltype = RNA  length = 22
FEATURE                Location/Qualifiers
source                 1..22
                       mol_type = other RNA
                       organism = synthetic construct
SEQUENCE: 977
gtaatgcggc tcccattgcc gc                                           22

SEQ ID NO: 978         moltype = RNA  length = 22
FEATURE                Location/Qualifiers
source                 1..22
                       mol_type = other RNA
                       organism = synthetic construct
SEQUENCE: 978
gtaatgcgcc tcccattggc gc                                           22

SEQ ID NO: 979         moltype = RNA  length = 22
FEATURE                Location/Qualifiers
source                 1..22
                       mol_type = other RNA
                       organism = synthetic construct
SEQUENCE: 979
gtaatgcgtc tcccagtgac gc                                           22

SEQ ID NO: 980         moltype = RNA  length = 22
FEATURE                Location/Qualifiers
source                 1..22
                       mol_type = other RNA
                       organism = synthetic construct
```

```
SEQUENCE: 980
gtaatgcgtc tcccatggac gc                                          22

SEQ ID NO: 981          moltype = AA  length = 35
FEATURE                 Location/Qualifiers
source                  1..35
                        mol_type = protein
                        organism = synthetic construct
SEQUENCE: 981
GVEDDSRLLL GIYEHGYGNW ELIKTDPELK LTDKL                            35

SEQ ID NO: 982          moltype = AA  length = 225
FEATURE                 Location/Qualifiers
source                  1..225
                        mol_type = protein
                        organism = synthetic construct
SEQUENCE: 982
MSCESSMVLG YWDIRGLAHA IRLLLEFTDT SYEEKRYTCG EAPDYDRSQW LDVKFKLDLD  60
FPNLPYLLDG KNKITQSNAI LRYIARKHNM CGETEEEKIR VDIIENQVMD FRTQLIRLCY  120
SSDHEKLKPQ YLEELPGQLK QFSMFLGKFS WFAGEKLTFV DFLTYDILDQ NRIFDPKCLD  180
EFPNLKAFMC RFEALEKIAA YLQSDQFCKM PINNKMAQWG NKPVC                  225

SEQ ID NO: 983          moltype = AA  length = 272
FEATURE                 Location/Qualifiers
source                  1..272
                        mol_type = protein
                        organism = synthetic construct
SEQUENCE: 983
MAAEEPQQQK QEPLGSDSEG VNCLAYDEAI MAQQDRIQQE IAVQNPLVSE RLELSVLYKE  60
YAEDDNIYQQ KIKDLHKKYS YIRKTRPDGN CFYRAFGFSH LEALLDDSKE LQRFKAVSAK  120
SKEDLVSQGF TEFTIEDFHN TFMDLIEQVE KQTSVADLLA SFNDQSTSDY LVVYLRLLTS  180
GYLQRESKFF EHFIEGGRTV KEFCQQEVEP MCKESDHIHI IALAQALSVS IQVEYMDRGE  240
GGTTNPHIFP EGSEPKVYLL YRPGHYDILY KE                                272

SEQ ID NO: 984          moltype = AA  length = 291
FEATURE                 Location/Qualifiers
source                  1..291
                        mol_type = protein
                        organism = synthetic construct
SEQUENCE: 984
MACLSPSQLQ KFQQDGFLVL EGFLSAEECV AMQQRIGEIV AEMDVPLHCR TEFSTQEEEQ  60
LRAQGSTDYF LSSGDKIRFF FEKGVFDEKG NFLVPPEKSI NKIGHALHAH DPVFKSITHS  120
FKVQTLARSL GLQMPVVVQS MYIFKQPHFG GEVSPHQDAS FLYTEPLGRV LGVWIAVEDA  180
TLENGCLWFI PGSHTSGVSR RMVRAPVGSA PGTSFLGSEP ARDNSLFVPT PVQRGALVLI  240
HGEVVHKSKQ NLSDRSRQAY TFHLMEASGT TWSPENWLQP TAELPFPQLY T           291

SEQ ID NO: 985          moltype = AA  length = 276
FEATURE                 Location/Qualifiers
source                  1..276
                        mol_type = protein
                        organism = synthetic construct
SEQUENCE: 985
MDSSREPTLG RLDAAGFWQV WQRFDADEKG YIEEKELDAF FLHMLMKLGT DDTVMKANLH  60
KVKQQFMTTQ DASKDGRIRM KELAGMFLSE DENFLLLFRR ENPLDSSVEF MQIWRKYDAD  120
SSGFISAAEL RNFLRDLFLH HKKAISEAKL EEYTGTMMKI FDRNKDGRLD LNDLARILAL  180
QENFLLQFKM DACSTEERKR DFEKIFAYYD VSKTGALEGP EVDGFVKDMM ELVQPSISGV  240
DLDKFREILL RHCDVNKDGK IQKSELALCL GLKINP                            276

SEQ ID NO: 986          moltype = AA  length = 134
FEATURE                 Location/Qualifiers
source                  1..134
                        mol_type = protein
                        organism = synthetic construct
SEQUENCE: 986
MDVFMKGLSM AKEGVVAAAE KTKQGVTEAA EKTKEGVLYV GSKTREGVVQ GVASVAEKTK  60
EQASHLGGAV FSGAGNIAAA TGLVKREEFP TDLKPEEVAQ EAAEEPLIEP LMEPEGESYE  120
DPPQEEYQEY EPEA                                                    134

SEQ ID NO: 987          moltype = AA  length = 28
FEATURE                 Location/Qualifiers
source                  1..28
                        mol_type = protein
                        organism = synthetic construct
SEQUENCE: 987
MFRRPVLQVL RQFVRHESET TTSLVLER                                    28

SEQ ID NO: 988          moltype = AA  length = 63
FEATURE                 Location/Qualifiers
source                  1..63
```

```
                         mol_type = protein
                         organism = synthetic construct
SEQUENCE: 988
ATVKFKYKGE EKEVDISKIK KVWRVGKMIS FTYDEGGGKT GRGAVSEKDA PKELLQMLEK  60
QKK                                                               63

SEQ ID NO: 989           moltype = AA  length = 244
FEATURE                  Location/Qualifiers
source                   1..244
                         mol_type = protein
                         organism = synthetic construct
SEQUENCE: 989
MEVTGVSAPT VTVFISSSLN TFRSEKRYSR SLTIAEFKCK LELLVGSPAS CMELELYGVD  60
DKFYSKLDQE DALLGSYPVD DGCRIHVIDH SGARLGEYED VSRVEKYTIS QEAYDQRQDT  120
VRSFLKRSKL GRYNEEERAQ QEAEAAQRLA EEKAQASSIP VGSRCEVRAA GQSPRRGTVM  180
YVGLTDFKPG YWIGVRYDEP LGKNDGSVNG KRYFECQAKY GAFVKPAVVT VGDFPEEDYG  240
LDEI                                                              244

SEQ ID NO: 990           moltype = AA  length = 270
FEATURE                  Location/Qualifiers
source                   1..270
                         mol_type = protein
                         organism = synthetic construct
SEQUENCE: 990
MARFALTVVR HGETRFNKEK IIQGQGVDEP LSETGFKQAA AAGIFLNNVK FTHAFSSDLM  60
RTKQTMHGIL ERSKFCKDMT VKYDSRLRER KYGVVEGKAL SELRAMAKAA REECPVFTPP  120
GGETLDQVKM RGIDFFEFLC QLILKEADQK EQFSQGSPSN CLETSLAEIF PLGKNHSSKV  180
NSDSGIPGLA ASVLVVSHGA YMRSLFDYFL TDLKCSLPAT LSRSELMSVT PNTGMSLFII  240
NFEEGREVKP TVQCICMNLQ DHLNGLTETR                                  270

SEQ ID NO: 991           moltype = AA  length = 16
FEATURE                  Location/Qualifiers
source                   1..16
                         mol_type = protein
                         organism = synthetic construct
SEQUENCE: 991
ATGWSAFFID GKWTEA                                                 16

SEQ ID NO: 992           moltype = AA  length = 223
FEATURE                  Location/Qualifiers
source                   1..223
                         mol_type = protein
                         organism = synthetic construct
SEQUENCE: 992
MQLKPMEINP EMLNKVLSRL GVAGQWRFVD VLGLEEESLG SVPAPACALL LLFPLTAQHE  60
NFRKKQIEEL KGQEVSPKVY FMKQTIGNSC GTIGLIHAVA NNQDKLGFED GSVLKQFLSE  120
TEKMSPEDRA KCFEKNEAIQ AAHDAVAQEG QCRVDDKVNF HFILFNNVDG HLYELDGRMP  180
FPVNHGASSE DTLLKDAAKV CREFTEREQG EVRFSAVALC KAA                   223

SEQ ID NO: 993           moltype = AA  length = 245
FEATURE                  Location/Qualifiers
source                   1..245
                         mol_type = protein
                         organism = synthetic construct
SEQUENCE: 993
MEKTELIQKA KLAEQAERYD DMATCMKAVT EQGAELSNEE RNLLSVAYKN VVGGRRSAWR  60
VISSIEQKTD TSDKKLQLIK DYREKVESEL RSICTTVLEL LDKYLIANAT NPESKVFYLK  120
MKGDYFRYLA EVACGDDRKQ TIDNSQGAYQ EAFDISKKEM QPTHPIRLGL ALNFSVFYYE  180
ILNNPELACT LAKTAFDEAI AELDTLNEDS YKDSTLIMQL LRDNLTLWTS DSAGEECDAA  240
EGAEN                                                             245

SEQ ID NO: 994           moltype = AA  length = 119
FEATURE                  Location/Qualifiers
source                   1..119
                         mol_type = protein
                         organism = synthetic construct
SEQUENCE: 994
NTYSITLPWP PSNNRYYRHN RGRTHVSAEG QAYRDNVARI IKNAMLDIGL AMPVKIRIEC  60
HMPDRRRRNL DNLQKAAFDA LTKAGFWLDD AQVVDYRVVK MPVTKGGRLE LTITEMGNE   119

SEQ ID NO: 995           moltype = AA  length = 87
FEATURE                  Location/Qualifiers
source                   1..87
                         mol_type = protein
                         organism = synthetic construct
SEQUENCE: 995
MDNVVLIGKK PVMNYVVAVL TQLTSNDEVI IKARGKAINK AVDVAEMIRN RFIKDIKIKK  60
IEIGTDKVKN PDGREVNVST IEIVLAK                                     87
```

```
SEQ ID NO: 996          moltype = AA  length = 85
FEATURE                 Location/Qualifiers
source                  1..85
                        mol_type = protein
                        organism = synthetic construct
SEQUENCE: 996
MYIVVVYDVG VERVNKVKKF LRMHLNWVQN SVFEGEVTLA EFERIKEGLK KIIDENSDSV  60
IIYKLRSMPP RETLGIEKNP IEEII                                        85

SEQ ID NO: 997          moltype = AA  length = 25
FEATURE                 Location/Qualifiers
source                  1..25
                        mol_type = protein
                        organism = synthetic construct
SEQUENCE: 997
MKKSIRRSGG KSKGARLWYV GGTQY                                        25

SEQ ID NO: 998          moltype = AA  length = 78
FEATURE                 Location/Qualifiers
source                  1..78
                        mol_type = protein
                        organism = synthetic construct
SEQUENCE: 998
MSYNYVVTAQ KPTAVNGCVT GHFTSAEDLN LLIAKNTRLE IYVVTAEGLR PVKEVGMYGK  60
IAVMELFRPK GEKNLENE                                                78

SEQ ID NO: 999          moltype = AA  length = 96
FEATURE                 Location/Qualifiers
source                  1..96
                        mol_type = protein
                        organism = synthetic construct
SEQUENCE: 999
MSELGNLETT VTGKIKRFNN GGGYYYTTVV SPAADAYSFP PVIRIKSKKS LGRVGDEIAD  60
IHCRITGYER SFPYTDKQTG EQSRGFNVDM LLELLE                            96

SEQ ID NO: 1000         moltype = AA  length = 32
FEATURE                 Location/Qualifiers
source                  1..32
                        mol_type = protein
                        organism = synthetic construct
SEQUENCE: 1000
MNKGELVDAV MAKATVTKKQ ADAFILALDI VA                                32

SEQ ID NO: 1001         moltype = AA  length = 96
FEATURE                 Location/Qualifiers
source                  1..96
                        mol_type = protein
                        organism = synthetic construct
SEQUENCE: 1001
MNKKSKQQEK LYNFIIAKSF QQPVGSTFTY GELRKKYNVV CSTNDQREVG RRFAYWIKYT  60
PGLPFKIVGT KNGSLLYQKI GINPCNNSTP SKGGDC                            96

SEQ ID NO: 1002         moltype = AA  length = 275
FEATURE                 Location/Qualifiers
source                  1..275
                        mol_type = protein
                        organism = synthetic construct
SEQUENCE: 1002
ASRRNLMIVD GTNLGFRFKH NNSKKPFASS YVSTIQSLAK SYSARTTIVL GDKGKSVFRL  60
EHLPEYKGNR DEKYAQRTEE EKALDEQFFE YLKDAFELCK TTFPTFTIRG VEADDMAAYI  120
VKLIGHLYDH VWLISTDGDW DTLLTDKVSR FSFTTRREYH LRDMYEHHNV DDVEQFISLK  180
AIMGDLGDNI RGVEGIGAKR GYNIIREFGN VLDIIDQLPL PGKQKYIQNL NASEELLFRN  240
LILVDLPTYC VDAIAAVGQD VLDKFTKDIL EIAEQ                             275

SEQ ID NO: 1003         moltype = DNA  length = 123
FEATURE                 Location/Qualifiers
source                  1..123
                        mol_type = other DNA
                        organism = synthetic construct
SEQUENCE: 1003
ggtggaggag gtgggtctgg cgtggaggac gacagccgcc tgctgctggg catctacgag  60
cacggctacg gcaactggga gctgatcaag accgaccccg agctgaagct gaccgacaag  120
ctg                                                                123

SEQ ID NO: 1004         moltype = DNA  length = 39
FEATURE                 Location/Qualifiers
source                  1..39
                        mol_type = other DNA
                        organism = synthetic construct
```

```
SEQUENCE: 1004
gcaaaaaaga aaaagctcga gggtggagga ggtgggtct                       39

SEQ ID NO: 1005        moltype = DNA  length = 63
FEATURE                Location/Qualifiers
source                 1..63
                       mol_type = other DNA
                       organism = synthetic construct
SEQUENCE: 1005
atctggaaca tcgtatgggt actccagctt gtcggtcagc ttcagctcgg ggtcggtctt  60
gat                                                                63

SEQ ID NO: 1006        moltype = DNA  length = 9071
FEATURE                Location/Qualifiers
source                 1..9071
                       mol_type = other DNA
                       organism = synthetic construct
SEQUENCE: 1006
cggatcggga gatctcccga tcccctatgg tgcactctca gtacaatctg ctctgatgcc  60
gcatagttaa gccagtatct gctccctgct tgtgtgttgg aggtcgctga gtagtgcgcg  120
agcaaaattt aagctacaac aaggcaaggc ttgaccgaca attgcatgaa gaatctgctt  180
agggttaggc gttttgcgct gcttcgcgat gtacgggcca gatatacgcg ttgacattga  240
ttattgacta gttattaata gtaatcaatt acggggtcat tagttcatag cccatatatg  300
gagttccgcg ttacataact tacggtaaat ggcccgcctg gctgaccgcc caacgacccc  360
cgcccattga cgtcaataat gacgtatgtt cccatagtaa cgccaatagg gactttccat  420
tgacgtcaat gggtggagta tttacggtaa actgcccact tggcagtaca tcaagtgtat  480
catatgccaa gtacgccccc tattgacgtc aatgacggta aatggcccgc ctggcattat  540
gcccagtaca tgaccttatg ggactttcct acttggcagt acatctacgt attagtcatc  600
gctattacca tggtgatgcg gttttggcag tacatcaatg ggcgtggata gcggtttgac  660
tcacggggat ttccaagtct ccaccccatt gacgtcaatg ggagtttgtt ttggcaccaa  720
aatcaacggg actttccaaa atgtcgtaac aactccgccc cattgacgca aatgggcggt  780
aggcgtgtac ggtgggaggt ctatataagc agagctctct ggctaactag agaacccact  840
gcttactggc ttatcgaaat taatacgact cactataggg agacccaagc tggctagcgt  900
ttaaacttaa gcttaccggt gccaccatgc cggcagctaa gaaaaagaaa ctggatggca  960
gcgtcgacag attcgtggtg ctgagcgtga atcagttcag atgcaacccc aacgccttca  1020
gacaagcctc catgaaaacc gacgacgaga agaaggacac cgccatcaag agctacacaa  1080
gctggctgct gcccaacgac agaaaggaga aggacatggt gcggagcttc ctggccctgg  1140
accaaggcag cagattcttt ttcgacctga tgcaagcctg gtacggcggc ctcacccccg  1200
acatcatcaa gagcgtgacc aaggagcggg acctggtgga cctgtggtgc gccatctact  1260
ggttcagacc catgaagaag gagctggcct cccaccccat cgacagagtg gacctggcca  1320
agacctttca gagatactac ggcggccccg cctccgacgt ggtgcaagag tacctgagcg  1380
cctccatcgg cgaggactgc tgctggaacg actgcagaca gaagtaccaa gagttctgca  1440
agaacctcgg ggtggacttc acccccgacc tcaagaccct ggtgagagag aagctgatcg  1500
ccgtggccct gaacgacggc agcagagccg ccatcagcaa cctgttcggc aacggcggca  1560
aggaggacag aaacgtgaag gtgaacatct gcaagaagat cctgattgct ctggagaagg  1620
ccggcaaatc cgtgaagtac gtgcgggacg tgcagagcat catcctgaag tgcgccaacg  1680
ccaaggacag agaggacttc aacagaatct acgccgacaa gaacggcaga cccggcaccc  1740
tgctcctgct cctggacaga aagggcgaga acacctacga cgccgaggtg ctgaagagat  1800
acctgagaaa gaccatcaag agcaagaacg ccccccctggt gtggaactac aatcagaagc  1860
tgttcgagta catcgagaga ggcatccgga atctgctgag aagaaccatc aactacgacg  1920
cctgggcctg gggcgagatg tggagagtgg gccacacccc cctgcagacc aaggccacaa  1980
gaaactacca cttcgcccaa gagcagctga agagacacag cagaatcgcc gccgcttccc  2040
aaagcagcca cgccatcgcc gtcgctctga acgagttctt cgagagcccc ttcttcgacg  2100
gcgagaaccc cttcaccatc tgcccccacc acctgggcaa gaacctggaa aagctgttca  2160
aggcctgggc cgacgaaaaa aatcagaccg acgaggagga cgccggcgaa accgccatca  2220
ccgactactg cgccgagttc aagagaggct tcgacagaga gcccattaga aacctgctga  2280
gatacgtgta cgcttccctg agaagcaagt acagcgccaa ggagctgatc caagccgcca  2340
agtacaatca gcagttcgag agatatcaga gacagaaggc ccaccccgtg acccccgaca  2400
accaaggcta cacctggccc gaggccgtga tcaagcctag caaggccgag agaaagaaca  2460
gagagaacag cctggacaca agaatctggg tgagcgtgaa gctgctgcaa aaggacggca  2520
cctgggagaa gcaccacatc cccttctaca acctgagatt cttcgaagag gtgtacgccg  2580
ctgcctccat cgccgaggac atgcctagcc ccaccttcag aaacagcaga ttcggcttca  2640
agctgcccaa gctgctgaac acccacgcca agatcaacaa gaaaaagaag gacggcaaga  2700
aggacaagaa ggccgtgaac gccgccaaga gagaggctag aatctacctc gctgccaagg  2760
agggcagact gcccgccccc tccgtgcccc tggacaagct gagcgccgtg atcgctagag  2820
tgaacggcaa gttccaagtg accgtgcccg tgaagttcaa ggtgaacaag cagcccaagt  2880
acccccctgcc tcagctgggg cagatcatcc tgggctacga tcagaacctg accgccaacc  2940
acgcctgggc cctgttcgag gtggtgaccg aggacacccc cggcgcccac ttctgcagaa  3000
atcagtacct gagagtgctc aagaccggcc aagtgagaag catcaccaag accaaggacg  3060
gccaagagat cgatcagctg agctacgacg gcctggagta caaggagtac ggcgagtgga  3120
gaaagcaagc caagaagttc gcctcccaat ggtacatcac caccaaggtg agaaagggca  3180
aggaaaccac cctgctgagc caacccgccc tggagagatt cgagagcatc gagaagtaca  3240
agcccgccct gtacagattc aacaaggaat acgcccggct gctcctggcc gtcatcagaa  3300
gaaagaccct gaacgagctg gaggagatca gacccgagat cttcagactg gtggagcaag  3360
gcttcggcat ctgcagattc ggcagcctga gcctgagcag cttcgaggcc atcagagccg  3420
ccaaggccgt gatctacggc tacttcagca ccgccctgaa gcacgaccac aacaccccca  3480
tcacagatga cgagagacaa gccagagacc ccgagctgtt cggcctgctg aacaagctga  3540
gaaccaggag acagaacaag ggcgaggaga agatcaacag agccgctaac gccctgatca  3600
gaatcgccct ggagaacaag gccgacttca tcagaggcga gggcgacctg cccaccacca  3660
```

```
acaagagcgt caagaagggg cagaacagca gaagcatgga ctggctggct agaggcctgt  3720
tcaacaagat ctgtcagctg gccgtgatgc acaacatcat tcccaccgcc gccaaccccc  3780
acagcacaag ccaccaagac cccttcgagc acaacaagga cttcgacgac cctcagcccg  3840
ccatgaagtg cagatacgct gagttcaaga tcgaggacat cggcgacagc gtgctggaga  3900
gactgggcac ctccctgaga aatgccaagg ccgggcagac cggcgcctac tattacaagg  3960
gcgcccaaga cttcctggcc cactacggcc tgcaagacat cgaggaagag ctgaagaagt  4020
gcagaagagg cagaaaggcc aacatgccct gctgggagct gcagaagaga ctgattcaga  4080
agctgggcag caaggacgcc gtggtgtaca tccccatgag aggcggccgg atctacctgg  4140
ctacacacag cgtgaccacc ggcgccaagc ccatcatctt caacggcgaa gaggtgtggg  4200
tgagcaacgc cgacgagatc gccgccgtga acatcggcct gaccatcatc cccacaagca  4260
agaaggacga ggagcacccc gacagagaga acgacgacaa ggccatcaga aagagcgtca  4320
gacggcctag aaagagcggc gagagaagaa gcggcgacaa gatgcccgcc accgctagaa  4380
agaccacagg cggcggcccc ggcggcggcg ccgccgccgg cagcggcagc cctaagaaaa  4440
aacgaaaagt tggcagcgga agcaaaaggc cggcggccac gaaaaaggcc ggccaggcaa  4500
aaaagaaaaa gctcgagggt ggaggaggtg ggtctggcgt ggaggacgac agccgcctgc  4560
tgctgggcat ctacgagcac ggctacggca actgggagct gatcaagacc gaccccgagc  4620
tgaagctgac cgacaagctg gagtacccat acgatgttcc agattacgct tgagaattcc  4680
ccttgagcat ctgacttctg gctaataaag gaaatttatt ttcattgcaa tagtgtgttg  4740
gaattttttg tgtctctcag gtaccgaaaa acatcattgc gtcgcgaggt gaggcgtcaa  4800
tgggagacgc attacggtgt ttcgtccttt ccacaagata tataaagcca agaaatcgaa  4860
atactttcaa gttacggtaa gcatatgata gtccatttta aaacataatt ttaaaactgc  4920
aaactaccca agaaattatt actttctacg tcacgtattt tgtactaata tctttgtgtt  4980
tacagtcaaa ttaattccaa ttatctctct aacagccttg tatcgtatat gcaaatatga  5040
aggaatcatg ggaaataggc cctctagagg gcccgtttaa acccgctgat cagcctcgac  5100
tgtgccttct agttgccagc catctgttgt ttgcccctcc cccgtgcctt ccttgaccct  5160
ggaaggtgcc actcccactg tcctttccta ataaaatgag gaaattgcat cgcattgtct  5220
gagtaggtgt cattctattc tggggggtgg ggtggggcag gacagcaagg gggaggattg  5280
ggaagacaat agcaggcatg ctggggatgc ggtgggctct atggcttctg aggcggaaag  5340
aaccagctgg ggctctaggg ggtatcccca cgcgccctgt agcggcgcat taagcgcggc  5400
gggtgtggtg gttacgcgca gcgtgaccgc tacacttgcc agcgccctag cgcccgctcc  5460
tttcgctttc ttcccttcct ttctcgccac gttcgccggc tttccccgtc aagctctaaa  5520
tcgggggctc cctttagggt tccgatttag tgctttacgg cacctcgacc ccaaaaaact  5580
tgattagggt gatggttcac gtagtgggcc atcgccctga tagacggttt ttcgcccttt  5640
gacgttggag tccacgttct ttaatagtgg actcttgttc caaactggaa caacactcaa  5700
ccctatctcg gtctattctt ttgatttata agggattttg ccgatttcgg cctattggtt  5760
aaaaaatgag ctgatttaac aaaaatttaa cgcgaattaa ttctgtggaa tgtgtgtcag  5820
ttagggtgtg gaaagtcccc aggctcccca gcaggcagaa gtatgcaaag catgcatctc  5880
aattagtcag caaccaggtg tggaaagtcc ccaggctccc cagcaggcag aagtatgcaa  5940
agcatgcatc tcaattagtc agcaaccata gtcccgcccc taactccgcc catcccgccc  6000
ctaactccgc ccagttccgc ccattctccg ccccatggct gactaatttt ttttatttat  6060
gcagaggccg aggccgcctc tgcctctgag ctattccaga agtagtgagg aggctttttt  6120
ggaggcctag gcttttgcaa aaagctcccg ggagcttgta tatccatttt cggatctgat  6180
caagagacag gatgaggatc gtttcgcatg attgaacaag atggattgca cgcaggttct  6240
ccggccgctt gggtggagag gctattcggc tatgactggg cacaacagac aatcggctgc  6300
tctgatgccg ccgtgttccg gctgtcagcg caggggcgcc cggttctttt tgtcaagacc  6360
gacctgtccg gtgccctgaa tgaactgcag gacgaggcag cgcggctatc gtggctggcc  6420
acgacgggcg ttccttgcgc agctgtgctc gacgttgtca ctgaagcggg aagggactgg  6480
ctgctattgg gcgaagtgcc ggggcaggat ctcctgtcat ctcaccttgc tcctgccgag  6540
aaagtatcca tcatggctga tgcaatgcgg cggctgcata cgcttgatcc ggctacctgc  6600
ccattcgacc accaagcgaa acatcgcatc gagcgagcac gtactcggat ggaagccggt  6660
cttgtcgatc aggatgatct ggacgaagag catcaggggc tcgcgccagc cgaactgttc  6720
gccaggctca aggcgcgcat gcccgacggc gaggatctcg tcgtgaccca tggcgatgcc  6780
tgcttgccga atatcatggt ggaaaatggc cgcttttctg gattcatcga ctgtggccgg  6840
ctgggtgtgg cggaccgcta tcaggacata gcgttggcta cccgtgatat tgctgaagag  6900
cttggcggcg aatgggctga ccgcttcctc gtgctttacg gtatcgccgc tcccgattcg  6960
cagcgcatcg ccttctatcg ccttcttgac gagttcttct gagcgggact ctggggttcg  7020
aaatgaccga ccaagcgacg cccaacctgc catcacgaga tttcgattcc accgccgcct  7080
tctatgaaag gttgggcttc ggaatcgttt tccgggacgc cggctggatg atcctccagc  7140
gcggggatct catgctggag ttcttcgccc accccaactt gtttattgca gcttataatg  7200
gttacaaata aagcaatagc atcacaaatt tcacaaataa agcatttttt tcactgcatt  7260
ctagttgtgg tttgtccaaa ctcatcaatg tatcttatca tgtctgtata ccgtcgagtt  7320
aacggaaccg taaaaaggcc gcgttgctgg cgtttttcca taggctccgc ccccctgacg  7380
agcatcacaa aaatcgacgc tcaagtcaga ggtggcgaaa cccgacagga ctataaagat  7440
accaggcgtt tccccctgga agctccctcg tgcgctctcc tgttccgacc ctgccgctta  7500
ccggatacct gtccgccttt ctcccttcgg gaagcgtggc gctttctcat agctcacgct  7560
gtaggtatct cagttcggtg taggtcgttc gctccaagct gggctgtgtg cacgaacccc  7620
ccgttcagcc cgaccgctgc gccttatccg gtaactatcg tcttgagtcc aacccggtaa  7680
gacacgactt atcgccactg gcagcagcca ctggtaacag gattagcaga gcgaggtatg  7740
taggcggtgc tacagagttc ttgaagtggt ggcctaacta cggctacact agaagaacag  7800
tatttggtat ctgcgctctg ctgaagccag ttaccttcgg aaaaagagtt ggtagctctt  7860
gatccggcaa acaaaccacc gctggtagcg gtggtttttt tgtttgcaag cagcagatta  7920
cgcgcagaaa aaaaggatct caagaagatc ctttgatctt ttctacgggg tctgacgctc  7980
agtggaacga aaactcacgt taagggattt tggtcatgag attatcaaaa aggatcttca  8040
cctagatcct tttaaattaa aaatgaagtt ttaaatcaat ctaaagtata tatgagtaaa  8100
cttggtctga cagttagaaa aactcatcga gcatcaaatg aaactgcaat ttattcatat  8160
caggattatc aataccatat ttttgaaaaa gccgtttctg taatgaagga gaaaactcac  8220
cgaggcagtt ccataggatg gcaagatcct ggtatcggtc tgcgattccg actcgtccaa  8280
catcaataca acctattaat ttcccctcgt caaaaataag gttatcaagt gagaaatcac  8340
catgagtgac gactgaatcc ggtgagaatg gcaaaagttt atgcatttct ttccagactt  8400
```

-continued

```
gttcaacagg ccagccatta cgctcgtcat caaaatcact cgcatcaacc aaaccgttat 8460
tcattcgtga ttgcgcctga gcgaaacgaa atacgcgatc gctgttaaaa ggacaattac 8520
aaacaggaat cgaatgcaac cggcgcagga acactgccag cgcatcaaca atattttcac 8580
ctgaatcagg atattcttct aatacctgga atgctgtttt cccagggatc gcagtggtga 8640
gtaaccatgc atcatcagga gtacggataa aatgcttgat ggtcggaaga ggcataaatt 8700
ccgtcagcca gtttagtctg accatctcat ctgtaacatc attggcaacg ctacctttgc 8760
catgtttcag aaacaactct ggcgcatcgg gcttcccata caatcgatag attgtcgcac 8820
ctgattgccc gacattatcg cgagcccatt tatacccata taaatcagca tccatgttgg 8880
aatttaatcg cggcctagag caagacgttt cccgttgaat atggctcata ctcttccttt 8940
ttcaatatta ttgaagcatt tatcagggtt attgtctcat gagcggatac atatttgaat 9000
gtatttagaa aaataaacaa ataggggttc cgcgcacatt tccccgaaaa gtgccacctg 9060
acgtccgtcg a                                                      9071
```

CAS12 PROTEINS AND USES THEREOF

CROSS REFERENCE TO RELATED APPLICATIONS

This application is a continuation-in-part application of International Application No. PCT/CN2024/119862, filed on Sep. 19, 2024, which claims priority to Chinese Patent Application No. 202311214330.6, filed on Sep. 19, 2023, and Chinese Patent Application No. 202410388592.2, filed on Apr. 1, 2024, the entire contents of each of which are incorporated herein by reference.

SEQUENCE LISTING

The instant application contains a Sequence Listing which has been submitted electronically in XML format and is hereby incorporated by reference in its entirety. The XML copy, created on Sep. 28, 2025, is named "2025 Sep. 28-Sequence Listing-20954-0003US00", and is 1,060,505 bytes in size.

TECHNICAL FIELD

The present disclosure relates to the field of CRISPR gene editing, and, more particularly, to Cas12 proteins and uses thereof.

BACKGROUND

A CRISPR-Cas system is an adaptive immune defense developed by bacteria and archaea over a long period of time, which is used to fight against invading viruses and exogenous DNA. The clustered regularly interspaced short palindromic repeat (CRISPR) and the CRISPR-associated protein system (CRISPR-Cas system) can be used to make changes to gene sequences directly in cells, which is a fast and effective manner.

Many researchers in this field are working on finding new Cas12 proteins and CRISPR-Cas12 gene editing systems.

SUMMARY

The present disclosure provides Cas12 proteins and uses thereof.

Embodiments of the present disclosure provide a Cas12 protein. In some embodiments, the Cas12 protein is selected from the group consisting of a CLUSTER1 protein, a CLUSTER2 protein, a CLUSTER3 protein, a CLUSTER4 protein, a CLUSTER5 protein, a CLUSTER6 protein, a CLUSTER7 protein, a CLUSTER8 protein, a CLUSTER9 protein, a CLUSTER10 protein, a CLUSTER11 protein, a CLUSTER12 protein, and a CLUSTER13 protein. As used herein, a CLUSTER refers to a Cas12 protein family classified according to a phylogenetic analysis as shown in FIG. 1A.

In some embodiments, the Cas12 protein comprises an amino acid sequence having at least 50% sequence identity to any one of the amino acid sequences shown in SEQ ID NO: 1-53, SEQ ID NO: 696, or SEQ ID NO: 728.

In some embodiments, the Cas12 protein comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity to any one of the amino acid sequences shown in SEQ ID NO: 1-53, SEQ ID NO: 696, or SEQ ID NO: 728.

In some embodiments, the Cas12 protein comprises an amino acid sequence having at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to any one of the amino acid sequences shown in SEQ ID NO: 1-53, SEQ ID NO: 696, or SEQ ID NO: 728.

In some embodiments, the Cas12 protein comprises an amino acid sequence having at least 80% sequence identity to any one of the amino acid sequences shown in SEQ ID NO: 1-53, SEQ ID NO: 696, or SEQ ID NO: 728. In some embodiments, the Cas12 protein comprises an amino acid sequence having at least 85% sequence identity to any one of the amino acid sequences shown in SEQ ID NO: 1-53, SEQ ID NO: 696, or SEQ ID NO: 728. In some embodiments, the Cas12 protein comprises an amino acid sequence having at least 90% sequence identity to any one of the amino acid sequences shown in SEQ ID NO: 1-53, SEQ ID NO: 696, or SEQ ID NO: 728. In some embodiments, the Cas12 protein comprises an amino acid sequence having at least 95% sequence identity to any one of the amino acid sequences shown in SEQ ID NO: 1-53, SEQ ID NO: 696, or SEQ ID NO: 728. In some embodiments, the Cas12 protein comprises an amino acid sequence having at least 97% sequence identity to any one of the amino acid sequences shown in SEQ ID NO: 1-53, SEQ ID NO: 696, or SEQ ID NO: 728. In some embodiments, the Cas12 protein comprises an amino acid sequence having at least 98% sequence identity to any one of the amino acid sequences shown in SEQ ID NO: 1-53, SEQ ID NO: 696, or SEQ ID NO: 728. In some embodiments, the Cas12 protein comprises an amino acid sequence having at least 99% sequence identity to any one of the amino acid sequences shown in SEQ ID NO: 1-53, SEQ ID NO: 696, or SEQ ID NO: 728. In some embodiments, the Cas12 protein comprises an amino acid sequence having at least 99.5% sequence identity to any one of SEQ ID NO: 1-53, SEQ ID NO: 696, or SEQ ID NO: 728. In some embodiments, the Cas12 protein comprises an amino acid sequence having at least 99.7% sequence identity to any one of the amino acid sequences shown in SEQ ID NO: 1-53, SEQ ID NO: 696, or SEQ ID NO: 728. In some embodiments, the Cas12 protein comprises an amino acid sequence having at least 99.8% sequence identity to any one of the amino acid sequences shown in SEQ ID NO: 1-53, SEQ ID NO: 696, or SEQ ID NO: 728. In some embodiments, the Cas12 protein comprises an amino acid sequence having at least 100% sequence identity to any one of the amino acid sequences shown in SEQ ID NO: 1-53, SEQ ID NO: 696, or SEQ ID NO: 728.

In some embodiments, the Cas12 protein retains a function of a protein having an amino acid sequence as shown in any one of SEQ ID NO: 1-53, SEQ ID NO: 696, or SEQ ID NO: 728.

In some embodiments, the Cas12 protein forms a complex with a guide polynucleotide. In some embodiments, the Cas12 protein and the guide polynucleotide specifically bind to a target nucleic acid.

In some embodiments, the Cas12 protein forms a complex with a guide polynucleotide, and the complex specifically binds to a target nucleic acid. In some embodiments, the Cas12 protein forms a complex with a guide polynucleotide, and the complex specifically binds to a target DNA.

In some embodiments, the Cas 12 protein and a guide polynucleotide specifically binds to and cleaves a target nucleic acid. In some embodiments, the Cas12 protein and a guide polynucleotide specifically binds to and cleaves a target DNA. In some embodiments, the Cas12 protein forms a complex with a guide polynucleotide, and the complex specifically binds and cleaves a target nucleic acid. In some embodiments, the Cas12 protein forms a complex with the guide polynucleotide, and the complex specifically binds and cleaves the target DNA.

As used herein, the phrase "retaining a function of a protein having an amino acid sequence as shown in any one of SEQ ID NO: 1-53, SEQ ID NO: 696, or SEQ ID NO: 728" refers to retaining the ability to form a complex with a guide polynucleotide, retaining the ability to bind a target nucleic acid complementary to the guide sequence, retaining the ability to specifically cleave the target nucleic acid with the guide polynucleotide, and/or retaining the ability to process an RNA transcript containing the guide sequence into guide polynucleotide molecules.

In some embodiments, the retaining a function of a protein having an amino acid sequence as shown in any one of SEQ ID NO: 1-53, SEQ ID NO: 696, or SEQ ID NO: 728 refers to retaining the ability to form a complex with a guide polynucleotide.

In some embodiments, the retaining a function of a protein having an amino acid sequence as shown in any one of SEQ ID NO: 1-53, SEQ ID NO: 696, or SEQ ID NO: 728 refers to retaining the ability to bind a target nucleic acid complementary to the guide sequence of the guide polynucleotide.

In some embodiments, the retaining a function of a protein having an amino acid sequence as shown in any one of SEQ ID NO: 1-53, SEQ ID NO: 696, or SEQ ID NO: 728 refers to retaining the ability to specifically cleave a target nucleic acid with a guide polynucleotide.

In some embodiments, the retaining a function of a protein having an amino acid sequence as shown in any one of SEQ ID NO: 1-53, SEQ ID NO: 696, or SEQ ID NO: 728 refers to retaining the ability to process the RNA transcript containing the guide sequence into guide polynucleotide molecules.

In some embodiments, the Cas12 protein comprises an amino acid sequence as shown in any one of SEQ ID NO: 1-53, SEQ ID NO: 696, or SEQ ID NO: 728.

In some embodiments, a protospacer adjacent motif (PAM) sequence (5→3') recognized by the Cas12 protein is selected from any one or more of the following:

A, C, T, G,

TA, TC, GN, AA, AG, TG, AN, GG, CG, TN, NT, NG, GT, NA, CC, AC, GC, AT, CT, GA, TT,
CN, NC, CA,

NTN, ANN, TTN, ATC, NAC, AGA, TGC, TCT, NGN, CGC, NTC, GCA, TCG, TTT, CCG,
GGG, NAG, ACA, CGG, CNG, ACN, GTG, CNT, TTG, TCN, GGT, TNC, CCN, CGT, TGG,
CGA, NGG, TCC, AGT, NCA, CAN, TCA, NNG, TAC, CCT, NTG, CGN, TGN, CAT, NGC,
GNG, GNC, NNA, GAA, TTC, CTT, ATA, TAT, GCT, NCC, TTA, AGN, GNN, CAA, CAC,
AGG, NTT, ANG, GNA, GTT, NGA, TAA, GTA, GGN, GNT, NCG, ATT, CCA, CNN, AAA,
AAC, ATN, GAG, CTG, ACG, NAA, TAN, NAT, CNA, GCN, GTC, NCN, CTN, CNC, ANT,
NNC, CAG, NAN, ATG, NCT, CCC, AAN, TGT, TNA, ACC, GAT, ACT, AAT, GGA, GAN,
ANC, GAC, NNT, CTA, TNN, GCG, GTN, TNT, AAG, TAG, NGT, NTA, ANA, CTC, GCC,
TGA, GGC, AGC, TNG,

NGAA, GANC, GCNC, NTNT, TGGG, AAGG, AAGN, NTNN, TCGT, CNTG, NTGG, CCGN,
ATAT, TGCA, NGGT, TGNT, NNTG, NCCG, ACAT, GNTG, CGCG, GACN, NTCG, TCNG,
CTGC, TNNC, GGTN, CGNN, TCCA, AGCN, TNAG, GGAC, GATC, AANA, NATG, CCAG,
NAAT, TCNT, CACT, CGGC, CGAN, CNCA, ATNT, NNNG, NGCT, CTGG, GGAN, NTNC,
ATTC, AATG, CNTC, TGGN, NATC, GTCG, ACNC, GCNN, GACT, CTNT, NCTT, NAGG,
NANC, CTTA, GTCT, ANAG, NGCN, CNNA, TCAG, ACAC, NCGG, TNNT, CAAG, ACCT,
CCCA, GTNC, ANTC, GACC, AACG, TTAA, TCCG, CGCC, NCCN, TTNA, NCNT, NGCA,
AGNN, AATC, GGGA, GNAN, NAGA, CGNA, GTAT, GTNA, ATNC, ACNA, GGAA,
NTCC, GGCG, AATN, CNNT, AGGC, GCGN, GTGC, TTGA, AAGC, GAAG, ATNG, TGCT,
TACT, CTAN, GGCT, GNGC, GTCN, CGAA, CNAC, GCCT, TAGG, ANGC, TNAA, GANT,
NCNA, NCCT, AGAN, GTAA, TTTN, ATGA, TGNA, CANC, ACGA, CCAC, CCGG, CTNG,
CNGN, GGTA, NGNC, GTTT, CTAA, TNCT, CTGN, NGAC, TGTA, TANN, GCNT, GCTC,
CNCG, AAAN, CCNT, GANA, CACA, CTNA, ANTN, TTNT, CCTG, TNTT, CANA, NTAN,

-continued

CACG, GGAT, TTTC, GNCG, TACA, GTAC, GAGC, ACNN, ATGG, AANT, ATCC, ACCG, AGNC, TGTT, NCAT, ATTA, GNTT, GAGN, TNAC, GCCG, NTNG, GTGG, GNGN, ACCA, NTAA, ACTN, NCTG, NCTA, TTTT, GCNG, NTAG, CAAA, GGNA, CNTN, TTAG, TCTG, NCTN, TATG, GCGT, TANT, GGGT, NACN, ACTG, CCNG, GNNT, CCAT, GNTA, NANT, TACN, TGTN, ATCT, NCAN, TNGG, CNNN, AAGT, ATTN, GGNN, CAGC, CGTN, GCCC, GCTT, CNAT, NANA, CCNN, GNGA, TNGN, GCAG, CGNG, CCTT, NGAG, NCNG,

AANG, GGTC, ACTC, TGAA, NAGN, NNCA, ACGG, TGAC, TCCN, ANNN, TCGN, TAAN, CAGG, TTAN, NGAN, NTGC, CCNC, TNTN, ATGN, GTGN, GCAT, NNGN, NNCC, CCNA, CNAG, GNAC, CGNT, TTCN, TAGN, ANCT, NATN, GTGA, TNGT, CTAT, CCCG, TNCA, NGTA, NNGA, CGTG, TAAT, CGCA, NNCG, NGTC, NAGT, GNAT, TNTC, NCGC, NGGN, CATN, GTTN, AGTA, GNNG, TTNN, TGNC, NAAA, TNCC, CACC, CTCT, TTGN, GCTA, NTTT, TGAN, TNAN, NGAT, CCTN, GAAT, GTCA, NTCN, GCCA, ANTG, TGGC, CAAC, TTTA, TGTC, CGGA, NCGN, AGNT, NCGA, ANCG, ACAA, TAGT, CGAG, NCAA, AATA, AGGG, GNGT, CAGA, AGGT, GGGG, ANAC, TGGT, GTGT, GNCA, GTTA, NGTT, TNNG, NCAG, CACN, GCAN, GAAC, NCCA, TTCC, NCNN, GNNN, ANGT, NTNA, CCCT, GNAA, TTNG, GTNN, GGNG, TCTA, NCAC, GANG, TTCG, CCTC, CNGG, ANNA, TCAN, ATCG, NTGA, CGTA, TTAC, GCTN, GCTG, NGTG, TCCC, CANN, NNNA, TAGA, ACGT, AGAT, GATG, GCCN, TGNG, GCGC, CCGA, GNCN, NTTG, NNAT, TNCG, NANG, GGTG, NCCC, GNCC, CAAT, CGCN, CNGA, NTTC, TTCT, NGGA, AGTC, CNNC, NACG, AGTN, NANN, ACAG, GNCT, TACC, CNTA, TGTG, CATC, GACA, TCTT, NTCT, CTGA, AGGA, GATA, TNAT, CCTA, GGAG, ANCC, AANC, GTAN, GCNA, TGNN, TANC, GNTN, AGCG, CTAG, NNAA, AGTT, CTAC, TACG, TTNC, TNTA, ANTT, ATAC, TCCT, TCAC, NGGC, NTTN, NNTC, CANT, ATAA, TGCC, CTCC, TNNA, GING, ACGN, GGCA, AAAG, TTGT, NGNA, NAAN, TATN, CGGG, CATA, ATGC, ACGC, ACCN, ATTT, TCNA, TNGC, NACA, NACC, CTCN, GGCC, TANG, AGAA, TNGA, TAGC, CAGN, GGCN, ANNT, NNNC, TCAT, CATT, TAAA, ATGT, TGAG, CGCT, TCGG, GCAC, GTAG, NTCA, NATT, ANTA, CCCN, ACTA, AAAA, GAAN, TATT, NNAC, TGAT, GGGN, CCAA, GNGG, CCAN, GTCC, NNCT, AGNG, CNTT, CNCT, GANN, GGTT, AGCT, CATG, NTAC, TNCN, NNTN, TGGA, GATT, AGCA, TAAG, GCGA, ACTT, ANGN, NTGN, AACN, AACT, TCAA, NTAT, TCGA, NCTC, NNGG, ANGG, NNTT, GTNT, CTNN, CGGN, TAAC, GGNC, GAAA, ACNG, GNAG, TTGG, CTTC, CNGT, TNNN, TNTG, GTTG, TCNN, CGGT, GAGA, CNNG, NCNC, GAGG, AGCC, ATNN, NNNT, AGAC, AACC, ANNC, ANNG, ACAN, GTTC, TATA, GNTC, NCGT, NGNT, CGTC, CCGC, CGAC, GACG, ATTG, GNNC, CNAA, TATC, AGNA, CTNC, TTCA, ANCA, ACCC, AGTG, CCGT, ANAT, CTGT, GGGC, NTTA, NAAG, AANN, CNAN, NNCN, ANAA,

ANAN, CTTG, NGNN, AGAG, TANA, TCNC, GCAA, NGNG, NAGC, NATA, ATCN, CGTT, CNGC, GATN, NNTA, AAGA, CTTT, AAAC, AGGN, ACNT, NTGT, CTTN, ATCA, NACT, NNAG, NGTN, NAAC, TGCG, GGNT, ATAN, TTGC, ANCN, CCCC, ANGA, NGCG, TCTC, CTCG, ATNA, AATT, NNAN, NNGT, TCGC, ATAG, CAAN, AACA, TTAT, CAGT, GNNA, TGCN, GCGG, NGGG, CANG, TTTG, GAGT, AAAT, CTCA, CNCN, CNCC, TCTN, CGNC, NGCC, CGAT, NNGC.

N is A, T, C, or G.

In some embodiments, a PAM sequence recognized by the Cas 12 protein is 5'-T-3'.

In some embodiments, a PAM sequence recognized by the Cas12 protein is 5'-G-3'.

In some embodiments, a PAM sequence recognized by the Cas 12 protein is 5'-A-3'.

In some embodiments, a PAM sequence recognized by the Cas 12 protein is 5'-C-3'.

In some embodiments, a PAM sequence recognized by the Cas12 protein is 5'-TA-3'.

In some embodiments, a PAM sequence recognized by the Cas12 protein is 5'-TC-3'.

In some embodiments, a PAM sequence recognized by the Cas 12 protein is 5'-TG-3'.

In some embodiments, a PAM sequence recognized by the Cas 12 protein is S'-TT-3'.

In some embodiments, a PAM sequence recognized by the Cas 12 protein is 5'-TN-3'.

In some embodiments, a PAM sequence recognized by the Cas12 protein is 5'-TTN-3'.

In some embodiments, a PAM sequence recognized by the Cas 12 protein is 5'-TTT-3'.

In some embodiments, a PAM sequence recognized by the Cas 12 protein is 5'-TTG-3', In some embodiments, a PAM sequence recognized by the Cas 12 protein is 5'-TTC-3'.

In some embodiments, a PAM sequence recognized by the Cas12 protein is 5'-TTA-3'.

In some embodiments, a PAM sequence recognized by the Cas12 protein is 5'-WTN-3'.

In some embodiments, a PAM sequence recognized by the Cas12 protein is 5'-ATN-3'.

N is A, T, C, or G, and W is A or T.

In some embodiments of the present disclosure, the Cas12 protein is an inactivated Cas12 mutant. In some embodiments of the present disclosure, the Cas12 protein is a nuclease-inactivated mutant. In some embodiments of the present disclosure, the Cas12 protein is a dead Cas12 mutant or a nickase Cas12 mutant. In some embodiments, the Cas12 protein has an inactivated Ruvc domain.

In some embodiments of the present disclosure, the Cas12 protein is selected from an active fragment constituting the Cas12 protein described in the present disclosure.

In some embodiments of the present disclosure, the Cas12 protein comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity to any one of the amino acid sequences shown in SEQ ID NO: 46, SEQ ID NO: 696, SEQ ID NO: 52, or SEQ ID NO: 728.

In some embodiments, the Cas12 protein forms a complex with a guide polynucleotide. Further, the complex specifically binds to a target nucleic acid. Further, the complex cleaves the target nucleic acid, modifies the target nucleic acid, and/or modulates the expression of the target nucleic acid.

In some embodiments, the Cas12 protein forms a complex with a guide polynucleotide, and the guide polynucleotide comprises a guide sequence that is reverse complementary to a target nucleic acid. Further, the guide polynucleotide comprises a scaffold sequence that interacts with the Cas 12 protein. Further, the scaffold sequence comprises a direct repeat (DR) sequence. Further, the DR sequence comprises a nucleotide sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to any one of the sequences shown in SEQ ID NO: 704, SEQ ID NO: 529, or SEQ ID NO: 534.

In some embodiments, the scaffold sequence does not comprise a tracrRNA sequence.

In some embodiments, a PAM sequence recognized by the Cas12 protein is 5-TTN-3' and/or 5'-TTNC-3'. N may be A, T, C, or G.

Some embodiments of the present disclosure provide a Cas12 protein. The Cas12 protein comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity to the amino acid sequence shown in SEQ ID NO: 46.

In some embodiments, the Cas12 protein forms a complex with a guide polynucleotide. Further, the complex specifically binds to a target nucleic acid. Further, the complex cleaves the target nucleic acid, modifies the target nucleic acid, and/or modulates an expression of the target nucleic acid.

In some embodiments, the Cas12 protein forms a complex with a guide polynucleotide, and the guide polynucleotide comprises a guide sequence that is reverse complementary to the target nucleic acid. Further, the guide polynucleotide comprises a scaffold sequence that interacts with the Cas12 protein. Further, the scaffold sequence comprises a DR sequence. Further, the scaffold sequence comprises a sequence having at least 80%, at least 85%, at least 90%, at least 95%, at least 96%, or at least 97% sequence identity to the sequence shown in SEQ ID NO: 704.

Some embodiments of the present disclosure provide a Cas12 protein. In some embodiments, the Cas12 protein comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity to the amino acid sequence shown in SEQ ID NO: 696

In some embodiments, the Cas12 protein forms a complex with a guide polynucleotide. Further, the complex specifically binds to a target nucleic acid. Further, the complex cleaves the target nucleic acid, modifies the target nucleic acid, and/or modulates the expression of the target nucleic acid.

In some embodiments, the Cas12 protein forms a complex with a guide polynucleotide, and the guide polynucleotide comprises a guide sequence that is reverse complementary to a target nucleic acid. Further, the guide polynucleotide comprises a scaffold sequence that interacts with the Cas12 protein. Further, the scaffold sequence comprises a DR sequence. Further, the scaffold sequence comprises a sequence having at least 80%, at least 85%, at least 90%, at least 95%, at least 96%, or at least 97% sequence identity to the sequence shown in SEQ ID NO: 704.

Some embodiments of the present disclosure provide a Cas12 protein. The Cas12 protein comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity to the amino acid sequence shown in SEQ ID NO: 52.

In some embodiments, the Cas12 protein forms a complex with a guide polynucleotide. Further, the complex specifically binds to a target nucleic acid. Further, the complex cleaves the target nucleic acid, modifies the target nucleic acid, and/or modulates the expression of the target nucleic acid.

In some embodiments, the Cas12 protein forms a complex with a guide polynucleotide, and the guide polynucleotide comprises a guide sequence that is reverse complementary to a target nucleic acid. Further, the guide polynucleotide comprises a scaffold sequence that interacts with the Cas12 protein. Further, the scaffold sequence comprises a DR sequence. Further, the scaffold sequence comprises a sequence having at least 80%, at least 85%, at least 90%, at least 95%, at least 96%, or at least 97% sequence identity to the sequence shown in SEQ ID NO: 534.

Some embodiments of the present disclosure provide a Cas12 protein. The Cas12 protein comprises an amino acid sequence having at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity to the amino acid sequence shown in SEQ ID NO: 728.

In some embodiments, the Cas12 protein forms a complex with a guide polynucleotide. Further, the complex specifically binds to a target nucleic acid. Further, the complex cleaves the target nucleic acid, modifies the target nucleic acid, and/or modulates the expression of the target nucleic acid.

In some embodiments, the Cas12 protein forms a complex with a guide polynucleotide, and the guide polynucleotide comprises a guide sequence that is reverse complementary to a target nucleic acid. Further, the guide polynucleotide comprises a scaffold sequence that interacts with the Cas12 protein. Further, the scaffold sequence comprises a DR sequence. Further, the scaffold sequence comprises a sequence having at least 80%, at least 85%, at least 90%, at least 95%, at least 96%, or at least 97% sequence identity to the sequence shown in SEQ ID NO: 534.

In some embodiments of the present disclosure, the Cas12 protein comprises an amino acid sequence having at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity to the amino acid sequence shown in SEQ ID NO: 46.

The Cas12 protein forms a complex with a guide polynucleotide; and the guide polynucleotide comprises a guide sequence that is reverse complementary to a target nucleic acid and a DR sequence.

In some embodiments, the DR sequence comprises a nucleotide sequence having at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the sequence shown in SEQ ID NO: 704

In some embodiments, the complex binds to the target nucleic acid under the guidance of the guide sequence.

In some embodiments, a PAM sequence recognized by the Cas 12 protein is 5'-TTN-3'.

N may be A, T, C or G.

In some embodiments of the present disclosure, the Cas12 protein comprises an amino acid sequence having at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity to the amino acid sequence shown in SEQ ID NO: 696.

The Cas12 protein may form a complex with a guide polynucleotide; and the guide polynucleotide comprises a guide sequence that is reverse complementary to a target nucleic acid and a DR sequence.

In some embodiments, the DR sequence comprises a nucleotide sequence having at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the sequence shown in the SEQ ID NO: 704.

In some embodiments, the complex binds to the target nucleic acid under the guidance of the guide sequence.

In some embodiments, a PAM sequence recognized by the Cas12 protein is 5'-TTN-3' In some embodiments, a PAM sequence recognized by the Cas12 protein is 5'-ATN-3'. In some embodiments, a PAM sequence recognized by the Cas 12 protein is 5'-WTN-3'.

In some embodiments of the present disclosure, the Cas12 protein comprises an amino acid sequence having at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity to the amino acid sequence shown in SEQ ID NO: 52

The Cas12 protein may form a complex with a guide polynucleotide; and the guide polynucleotide comprises a guide sequence that is reverse complementary to a target nucleic acid and a DR sequence.

In some embodiments, the DR sequence comprises a nucleotide sequence having at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the sequence shown in SEQ ID NO: 534.

In some embodiments, the complex binds to the target nucleic acid under the guidance of the guide sequence.

In some embodiments, a PAM sequence recognized by the Cas 12 protein is 5'-TTN-3'.

In some embodiments of the present disclosure, the Cas12 protein comprises an amino acid sequence having at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity to the amino acid sequence shown in SEQ ID NO: 728.

The Cas12 protein may form a complex with a guide polynucleotide; and the guide polynucleotide comprises a guide sequence that is reverse complementary to a target nucleic acid and a DR sequence.

In some embodiments, the DR sequence comprises a nucleotide sequence having at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the sequence shown in SEQ ID NO: 534.

In some embodiments, the complex binds to the target nucleic acid under the guidance of the guide sequence.

In some embodiments, a PAM sequence recognized by the Cas 12 protein is 5'-TTN-3', N may be A, T, C, or G.

In some embodiments, the reverse complementation is partially complementary or fully complementary. In some embodiments, the guide sequence hybridizes to the target nucleic acid.

In some embodiments, the Cas12 protein is a mutant of a Cas protein having an amino acid sequence shown in any one of SEQ ID NO: 1-53, 696, or 728.

In some embodiments, the Cas12 protein is an inactivated mutant of a Cas protein having an amino acid sequence shown in any one of SEQ ID NO: 1-53, 696, or 728.

In some embodiments, the Cas12 protein provided herein comprises one, two, or more mutations as compared to the Cas protein with the sequence shown in any one of SEQ ID NO: 1-53, SEQ ID NO: 696, and SEQ ID NO: 728, such as a single amino acid insertion, a single amino acid deletion, a single amino acid substitution, or combinations thereof. In some examples, compared to the Cas protein with the sequence shown in any one of SEQ ID NO: 1-53, SEQ ID NO: 696, and SEQ ID NO: 728, the Cas12 protein comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, or 130 amino acid changes (e.g., insertions, deletions, or substitutions) while retaining the ability to bind the target nucleic acid molecule complementary to the guide sequence of the guide polynucleotide, and/or retaining the ability to process an RNA transcript containing the guide sequence into the guide polynucleotide molecules. In some embodiments, compared to the Cas protein with the sequence shown in any one of SEQ ID NO: 1-53, SEQ ID NO: 696, and SEQ ID NO: 728, the Cas12 protein comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, or 130 amino acid changes (e.g., insertions, deletions, or substitutions) while retaining the ability to bind the target nucleic acid molecule complementary to the guide sequence of the guide polynucleotide.

In some embodiments of the present disclosure, the Cas12 protein comprises a mutation at any amino acid residue corresponding to the sequence shown in SEQ ID NO: 696. In some embodiments, the mutation is a mutation to any other natural amino acid residue. In some embodiments, the mutation is a mutation to residue R, H, K, or A. In some embodiments, the mutation is a mutation to residue R. In some embodiments, the mutation is a mutation to residue A. In some embodiments, the mutation is mutated to residue H. In some embodiments, the mutation is a mutation to residue K.

In some embodiments of the present disclosure, the Cas12 protein has mutations at the amino acid residues corresponding to positions 1-41, 42-195, 196-290, 291-358, 359-479, 480-636, 637-689, 690-846, 847-884, 885-959, 960-1080 or 1081-1139 of the sequence shown in SEQ ID NO: 696.

In some embodiments of the present disclosure, the Cas12 protein has the mutation in the RuvC domain corresponding to the sequence shown in SEQ ID NO: 696. In some embodiments of the present disclosure, the Cas 12 protein has mutations at the amino acid residues corresponding to positions 637-689, 885-959, or 1081-1139 of the sequence shown in SEQ ID NO: 696.

In some embodiments of the present disclosure, the Cas12 protein has the mutation in a helical domain corresponding to the sequence shown in SEQ ID NO: 696. In some embodiments of the present disclosure, the Cas12 protein has the mutations at the amino acid residues corresponding to positions 42-195, 291-479, or 690-846 of the sequence as shown in SEQ ID NO: 696.

In some embodiments of the present disclosure, the Cas12 protein has the mutation at the amino acid residue corresponding to positions 1-41 of the sequence as shown in SEQ ID NO: 696. In some embodiments of the present disclosure, the Cas12 protein has the mutation at the amino acid residue corresponding to positions 42-195 of the sequence as shown in SEQ ID NO: 696. In some embodiments of the present disclosure, the Cas12 protein has the mutation at the amino acid residue corresponding to positions 196-290 of the sequence as shown in SEQ ID NO: 696. In some embodiments of the present disclosure, the Cas12 protein has the mutation at the amino acid residue corresponding to positions 291-358 of the sequence as shown in SEQ ID NO: 696. In some embodiments of the present disclosure, the Cas12 protein has the mutation at the amino acid residue corresponding to positions 359-479 of the sequence as shown in SEQ ID NO: 696. In some embodiments of the present disclosure, the Cas12 protein has the mutation at the amino acid residue corresponding to positions 480-636 of the sequence as shown in SEQ ID NO: 696. In some embodiments of the present disclosure, the Cas12 protein has the mutation at the amino acid residue corresponding to positions 637-689 of the sequence as shown in SEQ ID NO: 696. In some embodiments of the present disclosure, the Cas12 protein has the mutation at the amino acid residue corresponding to positions 690-846 of the sequence as shown in SEQ ID NO: 696. In some embodiments of the present disclosure, the Cas12 protein has the mutation at the amino acid residue corresponding to positions 847-884 of the sequence as shown in SEQ ID NO: 696. In some embodiments of the present disclosure, the Cas12 protein has the mutation at the amino acid residue corresponding to positions 885-959 of the sequence as shown in SEQ ID NO: 696. In some embodiments of the present disclosure, the Cas12 protein has the mutation at the amino acid residue corresponding to positions 960-1080 of the sequence as shown in SEQ ID NO: 696. In some embodiments of the present disclosure, the Cas12 protein has the mutation at the amino acid residue corresponding to positions 1081-1139 of the sequence as shown in SEQ ID NO: 696.

In some embodiments of the present disclosure, at the amino acid residues corresponding to positions 1-41 of the sequence as shown in SEQ ID NO: 696, the Cas12 protein has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity to the sequence shown in SEQ ID NO: 696. In some embodiments of the present disclosure, at the amino acid residues corresponding to positions 42-195 of the sequence as shown in SEQ ID NO: 696, the Cas12 protein has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity to the sequence shown in SEQ ID NO: 696. In some embodiments of the present disclosure, at the amino acid residues corresponding to positions 196-290 of the sequence as shown in SEQ ID NO: 696, the Cas12 protein has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity to the sequence shown in SEQ ID NO: 696. In some embodiments of the present disclosure, at the amino acid residues corresponding to positions 291-358 of the sequence as shown in SEQ ID NO: 696, the Cas 12 protein has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity to the sequence shown in SEQ ID NO: 696. In some embodiments of the present disclosure, at the amino acid residues corresponding to positions 359-479 of the sequence as shown in SEQ ID NO: 696, the Cas12 protein has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity to the sequence shown in SEQ ID NO: 696. In some embodiments of the present disclosure, at the amino acid residues corresponding to positions 480-636 of the sequence as shown in SEQ ID NO: 696, the Cas 12 protein has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity to the sequence shown in SEQ ID NO: 696. In some embodiments of the present disclosure, at the amino acid residues corresponding to positions 637-689 of the sequence as shown in SEQ ID NO: 696, the Cas12 protein has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity to the sequence shown in SEQ ID NO: 696. In some embodiments of the present disclosure, at the amino acid residues corresponding to positions 690-846 of the sequence as shown in SEQ ID NO: 696, the Cas12 protein has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity to the sequence shown in SEQ ID NO: 696. In some embodiments of the present disclosure, at the amino acid residues corresponding to positions 847-884 of the sequence as shown in SEQ ID NO: 696, the Cas12 protein has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity to the sequence shown in SEQ ID NO: 696. In some embodiments of the present disclosure, at the amino acid residues corresponding to positions 885-959 of the sequence as shown in SEQ ID NO: 696, the Cas12 protein has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity to the sequence shown in SEQ ID NO: 696. In some embodiments of the present disclosure, at the amino acid residues corresponding to positions 960-1080 of the sequence as shown in SEQ ID NO: 696, the Cas12 protein has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity to the sequence shown in SEQ ID NO: 696. In some embodiments of the present disclosure, at the amino acid residues corresponding to positions 1081-1139 of the sequence as shown in SEQ ID NO: 696, the Cas 12 protein has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity to the sequence shown in SEQ ID NO: 696.

In some embodiments of the present disclosure, the Cas12 protein has at least one mutation in at least 1, at least 2, at least 3, at least 4, at least 5, at least 6, at least 7, at least 8, at least 9, at least 10, at least 11, or at least 12 of the amino acid residues corresponding to positions 1, 2, 3, 4, 5, 6, 7, 8, 9, 10, 12, 13, 14, 15, 16, 19, 21, 22, 23, 24, 25, 26, 27, 28, 29, 30, 32, 33, 34, 35, 36, 37, 38, 39, 40, 41, 42, 43, 44, 46, 47, 48, 49, 50, 51, 53, 54, 55, 56, 57, 58, 59, 60, 61, 62, 64, 65, 66, 67, 68, 69, 70, 71, 72, 73, 74, 75, 76, 77, 78, 79, 80, 81, 82, 83, 84, 85, 86, 88, 89, 90, 91, 92, 93, 94, 95, 96, 97, 98, 99, 101, 102, 103, 104, 105, 106, 108, 109, 110, 111, 112, 114, 115, 116, 117, 118, 119, 120, 121, 123, 124, 125, 126, 127, 128, 129, 130, 131, 132, 133, 134, 135, 136, 137, 138, 139, 140, 141, 142, 143, 144, 145, 146, 147, 148, 149, 151, 152, 153, 154, 155, 156, 157, 158, 159, 160, 161, 162, 163, 164, 165, 166, 167, 169, 170, 171, 172, 174, 175, 176, 177, 178, 179, 180, 182, 183, 184, 185, 186, 187, 188, 189, 190, 191, 192, 194, 195, 196, 197, 198, 199, 200, 202, 203, 204, 205, 206, 207, 208, 209, 210, 211, 212, 213, 214, 215, 216, 217, 218, 219, 220, 221, 222, 223, 224, 225, 227, 228, 229, 230, 231, 232, 233, 234, 235, 236, 237, 238, 239, 240, 242, 243, 244, 245, 247, 248, 249, 250, 251, 252, 253, 255, 256, 257, 258, 259, 260, 261, 262, 263, 265, 266, 267, 268, 269, 270, 271, 272, 273, 274, 275, 276, 278, 279, 281, 282, 283, 284, 285, 286, 287, 288, 289, 290, 291, 292, 293, 294, 295, 296, 297, 298, 299, 300, 301, 302, 303, 305, 306, 308, 309, 310, 313, 315, 316, 317, 318, 319, 320, 321, 322, 323, 324, 325, 327, 328, 329, 330, 331, 332, 333, 334, 335, 336, 337, 339, 340, 341, 342, 343, 344, 345, 346, 347, 348, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 431, 432, 433, 435, 436, 437, 439, 440, 441, 442, 443, 444, 446, 447, 448, 449, 450, 451, 452, 453, 454, 455, 456, 457, 458, 459, 460, 461, 462, 463, 464, 467, 469, 470, 471, 472, 473, 474, 475, 476, 477, 478, 479, 480, 481, 482, 483, 484, 485, 486, 487, 488, 489, 490, 491, 492, 493, 494, 496, 497, 499, 500, 501, 502, 503, 504, 506, 507, 508, 509, 510, 511, 512, 513, 514, 515, 516, 517, 518, 519, 520, 521, 522, 523, 524, 525, 526, 527, 528, 529, 531, 532, 533, 534, 535, 536, 537, 538, 539, 540, 541, 542, 543, 544, 545, 546, 547, 548, 549, 550, 552, 553, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 589, 590, 592, 593, 594, 595, 596, 597, 598, 599, 601, 602, 603, 604, 605, 606, 607, 608, 609, 610, 611, 612, 613, 614, 615, 616, 618, 619, 620, 621, 622, 623, 624, 625, 626, 627, 628, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 678, 679, 680, 681, 683, 684, 685, 686, 688, 689, 691, 692, 693, 694, 695, 696, 697, 698, 699, 700, 701, 702, 703, 704, 705, 706, 707, 708, 709, 710, 711, 712, 713, 715, 716, 717, 719, 720, 721, 722, 723, 724, 725, 727, 728, 729, 730, 731, 732, 733, 734, 736, 737, 738, 739, 740, 741, 742, 743, 744, 745, 746, 747, 748, 749, 751, 752, 753, 754, 755, 756, 758, 759, 760, 761, 762, 764, 765, 766, 767, 768, 769, 771, 772, 773, 774, 775, 776, 779, 780, 781, 782, 783, 784, 785, 786, 787, 789, 790, 791, 792, 794, 795, 797, 798, 800, 801, 802, 804, 805, 806, 807, 808, 809, 810, 811, 812, 813, 814, 815, 817, 818, 819, 821, 822, 823, 824, 825, 826, 827, 828, 829, 830, 831, 832, 833, 834, 835, 836, 837, 838, 839, 840, 841, 842, 844, 845, 846, 847, 848, 849, 850, 851, 852, 853, 854, 855, 856, 857, 858, 859, 860, 862, 863, 864, 865, 866, 867, 868, 870, 872, 873, 874, 875, 876, 877, 879, 880, 881, 882, 883, 884, 885, 886, 887, 888, 890, 891, 892, 893, 894, 895, 896, 897, 898, 899, 900, 901, 902, 903, 904, 905, 906, 909, 910, 911, 912, 913, 914, 916, 917, 918, 919, 920, 921, 922, 923, 924, 925, 926, 927, 928, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 963, 964, 965, 966, 967, 968, 969, 970, 971, 972, 973, 974, 975, 976, 977, 979, 980, 981, 982, 983, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1021, 1023, 1024, 1025, 1026, 1027, 1028, 1029, 1030, 1031, 1032, 1033, 1035, 1036, 1037, 1038, 1039, 1040, 1041, 1042, 1043, 1044, 1045, 1046, 1047, 1048, 1049, 1050, 1052, 1053, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1100, 1101, 1102, 1103, 1104, 1105, 1107, 1108, 1109, 1110, 1111, 1112, 1113, 1115, 1116, 1117, 1120, 1122, 1123, 1124, 1125, 1128, 1129, 1130, 1131, 1132, 1133, 1134, and 1135 of the amino acid sequence shown in SEQ ID NO: 696. In some embodiments, the mutation is a mutation to any other natural amino acid residue. In some embodiments, the mutation is a mutation to residue R, H, K, or A. In some embodiments, the mutation is a mutation to residue R. In some embodiments, the mutation is a mutation to residue A. In some embodiments, the mutation is a mutation to residue H. In some embodiments, the mutation is a mutation to residue K.

In some embodiments of the present disclosure, the Cas12 protein has at least one mutation in at least 1, at least 2, at least 3, at least 4, at least 5, at least 6, at least 7, at least 8, at least 9, at least 10, at least 11, or at least 12 of the amino acid residues corresponding to positions 1, 2, 3, 4, 5, 7, 10, 24, 30, 48, 51, 55, 58, 59, 66, 108, 118, 138, 141, 175, 178, 185, 186, 257, 333, 352, 356, 375, 376, 378, 379, 383, 397, 400, 416, 426, 443, 449, 456, 459, 462, 469, 484, 485, 509, 561, 597 607, 609, 623, 638, 639, 640, 697, 722, 731, 733, 755, 758, 771, 773, 779, 781, 784, 785, 786, 789, 792, 794, 798, 822, 823, 825, 826, 829, 830, 833, 834, 836, 842, 845, 846, 847, 850, 851, 853, 855, 856, 858, 859, 860, 866, 884, 892, 893, 900, 904, 926, 956, 985, 988, 989, 992, 993, 996, 1016, 1033, 1045, 1050, 1073, 1074, 1095, 1100, 1124, 1129, and 1132 of the amino acid sequence shown in SEQ ID NO: 696. In some embodiments, the mutation is a mutation to residue R, H, or K. In some embodiments, the mutation is a mutation to residue R.

In some embodiments of the present disclosure, the Cas12 protein has at least one mutation in at least 1, at least 2, at least 3, at least 4, at least 5, at least 6, at least 7, at least 8, at least 9, at least 10, at least 11, or at least 12 of the amino acid residues corresponding to positions 12, 29, 35, 36, 40, 53, 57, 60, 64, 71, 72, 73, 75, 94, 95, 96, 97, 99, 137, 148, 149, 153, 164, 167, 171, 172, 174, 177, 190, 192, 194, 199, 204, 207, 208, 211, 215, 228, 232, 236, 238, 244, 248, 253, 256, 258, 261, 262, 275, 282, 286, 292, 298, 300, 302, 320, 324, 328, 332, 336, 339, 366, 373, 374, 384, 389, 393, 395, 415, 432, 436, 440, 453, 458, 460, 471, 472, 474, 506, 508, 510, 519, 523, 526, 528, 531, 534, 544, 550, 570, 571, 573, 592, 594, 596, 613, 615, 616, 619, 622, 624, 626, 648, 650, 651, 652, 658, 661, 663, 684, 686, 689, 693, 704, 744, 783, 787, 800, 849, 854, 876, 888, 890, 891, 894, 912, 940, 941, 942, 945, 946, 948, 961, 971, 979, 987, 998, 1000, 1002, 1006, 1013, 1015, 1035, 1042, 1048, 1049, 1052, 1053, 1057, 1058, 1063, 1079, 1081, 1082, 1083, 1084, 1085, 1086, 1087, 1088, 1089, 1090, and 1091 of the amino acid sequence shown in SEQ ID NO: 696. In some embodiments, the mutation is a mutation to residue A.

In some embodiments of the present disclosure, the Cas12 protein has the mutations at the amino acid residues corresponding to any 1, any 2, any 3, any 4, any 5, any 6, any 7, any 8, any 9, any 10, any 11, any 12, any 13, any 14, any 15, any 16, or more positions in the amino acid sequence shown in SEQ ID NO: 696, and the positions are selected from I33, G184, S185, Q186, G194, N195, G196, G197, N245, G256, L260, Y278, S285, Y316, H350, D352, A355, A356, C385, P386, H387, G390, K391, N392, D429, Q461, Q462, Q469, E485, S491, K521, P525, L611, K629, K631, N633, D841, N898, K987, A988, G989, Q990, T991, D1010, E1013, A1136, K1138, and T1139.

In some embodiments of the present disclosure, the Cas 12 protein has any 1, any 2, any 3, any 4, any 5, any 6, any 7, any 8, any 9, any 10, any 11, any 12, any 13, any 14, any 15, any 16, or more amino acid mutations of the amino acid sequence shown in SEQ ID NO: 696 at positions corresponding to the amino acid sequence shown in SEQ ID NO: 696, and the amino acid mutations are selected from I33R, G184R, S185R, Q186R, G194R, N195R, G196R, G197R, N245R, G256R, L260R, Y278R, S285R, Y316R, H350R, D352R, A355R, A356R, C385R, P386R, H387R, G390R, K391R, N392R, D429R, Q461R, Q462R, Q469R, E485R, S491R, K521R, P525R, L611R, K629R, K631R, N633R, D841R, N898R, K987R, A988R, G989R, Q990R, T991R, D1010R, E1013R, A1136R, K1138R, and T1139R.

In some embodiments of the present disclosure, the Cas 12 protein has any 1, any 2, any 3, any 4, any 5, or more amino acid mutation combinations of the amino acid sequence shown in SEQ ID NO: 696 at the position corresponding to the amino acid sequence shown in SEQ ID NO: 696, and the amino acid mutation combinations are selected from 186+352+1+426+846+858+860, 186+352+1+426+846+860, 186+352+1+5+426+858+860, 186+352+1+3+426+858+860, 186+352+3+426+860, 186+352+1+333+426+858+860, 186+352+1+426+485+858+860, 186+352+1+5+426+860, 186+352+3+426+858+860, 186+352+5+426+858+860, 186+352+333+426+858+860, 186+352+333+426+860, 186+352+426+846+860, 186+352+5+426+860, 186+352+1+3+426+860, 5+426+860, 186+352+426+846+85+860, 186+352+1+426+485+860, 426+858+860, 7+426+858, 186+352+426+860, 186+352+426+485+858+860, 186+352+426+485+860, 426+846+858+860, 7+426+846, 186+352+860, 184+186+352+376+1132, 5+333+426, 5+426+858, 186+352+1+333+426+860, 184+186+352+3+107+426, 186+352+5+426, 333+376+426, 186+352+5, 2+5+846+858, 186+352+3+426, 5+846+858, 186+352+426+846, 186+352+7, 186+352+3+376+426, 186+352+376+426+860+865, 186+352+376+426, 3+846+860, 846+858+988, 3+426+858, 3+846+858+860, 3+858+860, 186+352+858, 184+186+352+860, 333+426, 184+186+352+3+376, 3+426+860, 846+860+988, 3+860, 184+186+352+3+639, 186+352+333+426, 846+585+860, 186+352+426, 333+426+846, 333+426+485, 5+846+860, 3+846+988, 184+186+352+376, 3+333+426, 186+352+426+485, 333+426+858, 333+426+1132, 428+485, 186+352+333+352+376+426, 858+860, 186+352+376+426+485+860, 184+186+352+426, 186+352+639, 5+858+988, 3+858+988, 5+858, 3+858, 184+186+352+846, 184+186+352+639, 858+988, 184+186+352+426+1132, 186+352+1132, 184+186+352+5, 184+186+352+858, 858+860+1132, 3+5, 426+649, 186+352+426+485+860, 186+352+333, 184+186+352, 186+376, 846+860, 858+988+1132, 846+858, 333+376, 376+426, 184+186+352+3, 3+846+1132, 5+846+1132, 186+352+426+1132, 376+426+485+660, 426, 5+846, 846+860+1132, 333+376+485, 184+186+352+639+1132, 352+426, 333+485, 184+186+352+333, 846+858+1132, 333+426+860, 186+352+988, 5+860, 846+988, 186+352, 3+846, 846+1132, 184+186+352+1132, 186+485, 988+1132, 184+186+352+485, 376+485, 5+1132, 3+7, 186+352+485, 184+186+352+7, 184+186+352+333+336, 3+1132, 426+858+988, 186+352+376, 186+352+3, and 186+352+333+336+352+376+426 (mutation combinations are separated by commas). In some embodiments, the mutation is a mutation to residue R or A.

In some embodiments of the present disclosure, the Cas12 protein has any one amino acid mutation combination of the amino acid sequence shown in SEQ ID NO: 696 at a position corresponding to the amino acid sequence shown in SEQ ID NO: 696, and the amino acid mutation combination is selected from 186+352+1+426+846+858+860, 186+352+1+426+846+860, 186+352+1+5+426+858+860, 186+352+1+3+426+858+860, 186+352+3+426+860, 186+352+1+333+426+858+860, 186+352+1+426+485+858+860, 186+352+1+5+426+860, 186+352+3+426+858+860, 186+352+5+426+858+860, 186+352+333+426+858+860, 186+352+333+426+860, 186+352+426+846+860, 186+352+5+426+860, 186+352+1+3+426+860, 5+426+860, 186+352+426+846+858+860, 186+352+1+426+485+860, 426+858+860, 7+426+858, 186+352+426+860, 186+352+426+485+858+860, 186+352+426+485+860, 426+846+858+860, 7+426+846, and 186+352+860 (mutation combinations are separated by commas). In some embodiments, the mutation is a mutation to residue R or A.

In some embodiments of the present disclosure, the Cas12 protein has any 1, any 2, any 3, any 4, any 5, or more amino acid mutations of the amino acid sequence shown in SEQ ID NO: 696 at the position corresponding to the amino acid sequence shown in SEQ ID NO: 696, and the amino acid mutations are selected from D352R+Q186R, D352R+L260R, D352R+A355R, A355R+L260R, P386R+C385R, E485R+Q462R, D352R+Q186R, A355R+L260R, G184R+R186Q, D352R+Q186R+I33R, D352R+Q186R+G184R, D352R+Q186R+S185R, D352R+Q186R+G256R, D352R+Q186R+Y278R, D352R+Q186R+S285R, D352R+Q186R+Y316R, D352R+Q186R+H350R, D352R+Q186R+A356R, D352R+Q186R+Q469R, D352R+Q186R+S491R, D352R+Q186R+K521R, D352R+Q186R+P525R, D352R+Q186R+K629R, D352R+Q186R+N633R, D352R+Q186R+D841R, D352R+Q186R+N898R, D352R+Q186R+K987R, D352R+Q186R+T991R, D352R+Q186R+D1010R, and D352R+Q186R+E1013R.

In some embodiments of the present disclosure, the Cas12 protein comprises a mutation at an amino acid residue corresponding to position 1 of the sequence as shown in SEQ ID NO: 696. In some embodiments of the present disclosure, the Cas12 protein comprises a mutation at an amino acid residue corresponding to position 2 of the sequence as shown in SEQ ID NO: 696. In some embodiments of the present disclosure, the Cas12 protein comprises a mutation at an amino acid residue corresponding to position 3 of the sequence as shown in SEQ ID NO: 696. In some embodiments of the present disclosure, the Cas12 protein comprises a mutation at an amino acid residue corresponding to position 4 of the sequence as shown in SEQ ID NO: 696. In some embodiments of the present disclosure, the Cas12 protein comprises a mutation at an amino acid residue corresponding to position 5 of the sequence as shown in SEQ ID NO: 696. In some embodiments of the present disclosure, the Cas12 protein comprises a mutation at an amino acid residue corresponding to position 7 of the sequence as shown in SEQ ID NO: 696. In some embodiments of the present disclosure, the Cas12 protein comprises a mutation at an amino acid residue corresponding to position 10 of the sequence as shown in SEQ ID NO: 696. In some embodiments of the present disclosure, the Cas12 protein comprises a mutation at an amino acid residue corresponding to position 24 of the sequence as shown in SEQ ID NO: 696. In some embodiments of the present disclosure, the Cas12 protein comprises a mutation at amino acid residue corresponding to position 30 of the as shown in SEQ ID NO: 696. In some embodiments of the present disclosure, the Cas12 protein comprises a mutation at an amino acid residue corresponding to position 48 of the sequence as shown in SEQ ID NO: 696. In some embodiments of the present disclosure, the Cas12 protein comprises a mutation at an amino acid residue corresponding to position 51 of the sequence as shown in SEQ ID NO: 696. In some embodiments of the present disclosure, the Cas12 protein comprises a mutation at an amino acid residue corresponding to position 55 of the sequence as shown in SEQ ID NO: 696. In some embodiments of the present disclosure, the Cas12 protein comprises a mutation at an amino acid residue corresponding to position 58 of the sequence as shown in SEQ ID NO: 696. In some embodiments of the present disclosure, the Cas12 protein comprises a mutation at an amino acid residue corresponding to position 59 of the sequence as shown in SEQ ID NO: 696. In some embodiments of the present disclosure, the Cas12 protein comprises a mutation at an amino acid residue corresponding to position 66 of the sequence as shown in SEQ ID NO: 696. In some embodiments of the present disclosure, the Cas12 protein comprises a mutation at amino acid residue corresponding to position 108 of the sequence as shown in SEQ ID NO: 696. In some embodiments of the present disclosure, the Cas12 protein comprises a mutation at an amino acid residue corresponding to position 118 of the sequence as shown in SEQ ID NO: 696. In some embodiments of the present disclosure, the Cas12 protein comprises a mutation at an amino acid residue corresponding to position 138 of the sequence as shown in SEQ ID NO: 696. In some embodiments of the present disclosure, the Cas12 protein comprises a mutation at an amino acid residue corresponding to position 141 of the sequence as shown in SEQ ID NO: 696. In some embodiments of the present disclosure, the Cas12 protein comprises a mutation at an amino acid residue corresponding to position 175 of the sequence as shown in SEQ ID NO: 696. In some embodiments of the present disclosure, the Cas12 protein comprises a mutation at an amino acid residue corresponding to position 178 of the sequence as shown in SEQ ID NO: 696. In some embodiments of the present disclosure, the Cas12 protein comprises a mutation at an amino acid residue corresponding to position 185 of the sequence as shown in SEQ ID NO: 696. In some embodiments of the present disclosure, the Cas12 protein comprises a mutation at an amino acid residue corresponding to position 186 of the sequence as shown in SEQ ID NO: 696. In some embodiments of the present disclosure, the Cas12 protein comprises a mutation at an amino acid residue corresponding to position 257 of the sequence as shown in SEQ ID NO: 696. In some embodiments of the present disclosure, the Cas12 protein comprises a mutation at an amino acid residue corresponding to position 333 of the sequence as shown in SEQ ID NO: 696. In some embodiments of the present disclosure, the Cas12 protein comprises a mutation at an amino acid residue corresponding to position 352 of the sequence as shown in SEQ ID NO: 696. In some embodiments of the present disclosure, the Cas12 protein comprises a mutation at an amino acid residue corresponding to position 356 of the sequence as shown in SEQ ID NO: 696. In some embodiments of the present disclosure, the Cas12 protein comprises a mutation at an amino acid residue corresponding to position 375 of the sequence as shown in SEQ ID NO: 696. In some embodiments of the present disclosure, the Cas12 protein comprises a mutation at an amino acid residue corresponding to position 376 of the sequence as shown in SEQ ID NO: 696. In some embodiments of the present disclosure, the Cas12 protein comprises a mutation at an amino acid residue corresponding to position 378 of the sequence as shown in SEQ ID NO: 696. In some embodiments of the present disclosure, the Cas12 protein comprises a mutation at an amino acid residue corresponding to position 379 of the sequence as shown in SEQ ID NO: 696. In some embodiments of the present disclosure, the Cas12 protein comprises a mutation at an amino acid residue corresponding to position 383 of the sequence as shown in SEQ ID NO: 696. In some embodiments of the present disclosure, the Cas12 protein comprises a mutation at an amino acid residue corresponding to position 397 of the sequence as shown in SEQ ID NO: 696. In some embodiments of the present disclosure, the Cas12 protein comprises a mutation at an amino acid residue corresponding to position 400 of the sequence as shown in SEQ ID NO: 696. In some embodiments of the present disclosure, the Cas12 protein comprises a mutation at an amino acid residue corresponding to position 416 of the sequence as shown in SEQ ID NO: 696. In some embodiments of the present disclosure, the Cas12 protein comprises a mutation at an amino acid residue corresponding to position 426 of the sequence as shown in SEQ ID NO: 696. In some embodiments of the present disclosure, the Cas12 protein comprises a mutation at an amino acid residue corresponding to position 443 of the sequence as shown in SEQ ID NO: 696. In some embodiments of the present disclosure, the Cas12 protein comprises a mutation at an amino acid residue corresponding to position 449 of the sequence as shown in SEQ ID NO: 696. In some embodiments of the present disclosure, the Cas12 protein comprises a mutation at an amino acid residue corresponding to position 456 of the sequence as shown in SEQ ID NO: 696. In some embodiments of the present disclosure, the Cas12 protein comprises a mutation at an amino acid residue corresponding to position 459 of the sequence as shown in SEQ ID NO: 696. In some embodiments of the present disclosure, the Cas12 protein comprises a mutation at an amino acid residue corresponding to position 462 of the sequence as shown in SEQ ID NO: 696. In some embodiments of the present disclosure, the Cas12 protein comprises a mutation at an amino acid residue corresponding to position 469 of the sequence as shown in SEQ ID NO: 696. In some embodiments of the present disclosure, the Cas12 protein comprises a mutation at an amino acid residue corresponding to position 484 of the sequence as shown in SEQ ID NO: 696. In some embodiments of the present disclosure, the Cas12 protein comprises a mutation at an amino acid residue corresponding to position 485 of the sequence as shown in SEQ ID NO: 696. In some embodiments of the present disclosure, the Cas12 protein comprises a mutation at an acid residue corresponding to position 509 of the sequence as shown in SEQ ID NO: 696. In some embodiments of the present disclosure, the Cas12 protein comprises a mutation at an amino acid residue corresponding to position 561 of the sequence as shown in SEQ ID NO: 696. In some embodiments of the present disclosure, the Cas12 protein comprises a mutation at an amino acid residue corresponding to position 597 of the sequence as shown in SEQ ID NO: 696. In some embodiments of the present disclosure, the Cas12 protein comprises a mutation at an amino acid residue corresponding to position 607 of the sequence as shown in SEQ ID NO: 696. In some embodiments of the present disclosure, the Cas12 protein comprises a mutation at an amino acid residue corresponding to position 609 of the sequence as shown in SEQ ID NO: 696. In some embodiments of the present disclosure, the Cas12 protein comprises a mutation at an amino acid residue corresponding to position 623 of the sequence as shown in SEQ ID NO: 696. In some embodiments of the present disclosure, the Cas12 protein comprises a mutation at an amino acid residue corresponding to position 638 of the sequence as shown in SEQ ID NO: 696. In some embodiments of the present disclosure, the Cas12 protein comprises a mutation at an amino acid residue corresponding to position 639 of the sequence as shown in SEQ ID NO: 696. In some embodiments of the present disclosure, the Cas12 protein comprises a mutation at an amino acid residue corresponding to position 640 of the sequence as shown in SEQ ID NO: 696. In some embodiments of the present disclosure, the Cas12 protein comprises a mutation at an amino acid residue corresponding to position 697 of the sequence as shown in SEQ ID NO: 696. In some embodiments of the present disclosure, the Cas12 protein comprises a mutation at an amino acid residue corresponding to position 722 of the sequence as shown in SEQ ID NO: 696. In some embodiments of the present disclosure, the Cas12 protein comprises a mutation at an amino acid residue corresponding to position 731 of the sequence as shown in SEQ ID NO: 696. In some embodiments of the present disclosure, the Cas12 protein comprises a mutation at an amino acid residue corresponding to position 733 of the sequence as shown in SEQ ID NO: 696. In some embodiments of the present disclosure, the Cas12 protein comprises a mutation at an amino acid residue corresponding to position 755 of the sequence as shown in SEQ ID NO: 696. In some embodiments of the present disclosure, the Cas12 protein comprises a mutation at an amino acid residue corresponding to position 758 of the sequence as shown in SEQ ID NO: 696. In some embodiments of the present disclosure, the Cas12 protein comprises a mutation at an amino acid residue corresponding to position 771 of the sequence as shown in SEQ ID NO: 696. In some embodiments of the present disclosure, the Cas12 protein comprises a mutation at an amino acid residue corresponding to position 773 of the sequence as shown in SEQ ID NO: 696. In some embodiments of the present disclosure, the Cas12 protein comprises a mutation at an amino acid residue corresponding to position 779 of the sequence as shown in SEQ ID NO: 696. In some embodiments of the present disclosure, the Cas12 protein comprises a mutation at an amino acid residue corresponding to position 781 of the sequence as shown in SEQ ID NO: 696. In some embodiments of the present disclosure, the Cas12 protein comprises a mutation at an amino acid residue corresponding to position 784 of the sequence as shown in SEQ ID NO: 696. In some embodiments of the present disclosure, the Cas12 protein comprises a mutation at an amino acid residue corresponding to position 785 of the sequence as shown in SEQ ID NO: 696. In some embodiments of the present disclosure, the Cas12 protein comprises a mutation at an amino acid residue corresponding to position 786 of the sequence as shown in SEQ ID NO: 696. In some embodiments of the present disclosure, the Cas12 protein comprises a mutation at an amino acid residue corresponding to position 789 of the sequence as shown in SEQ ID NO: 696. In some embodiments of the present disclosure, the Cas12 protein comprises a mutation at an amino acid residue corresponding to position 792 of the sequence as shown in SEQ ID NO: 696. In some embodiments of the present disclosure, the Cas12 protein comprises a mutation at an amino acid residue corresponding to position 794 of the sequence as shown in SEQ ID NO: 696. In some embodiments of the present disclosure, the Cas12 protein comprises a mutation at an amino acid residue corresponding to position 798 of the sequence as shown in SEQ ID NO: 696. In some embodiments of the present disclosure, the Cas12 protein comprises a mutation at an amino acid residue corresponding to position 822 of the sequence as shown in SEQ ID NO: 696. In some embodiments of the present disclosure, the Cas12 protein comprises a mutation at an amino acid residue corresponding to position 823 of the sequence as shown in SEQ ID NO: 696. In some embodiments of the present disclosure, the Cas12 protein comprises a mutation at an amino acid residue corresponding to position 825 of the sequence as shown in SEQ ID NO: 696. In some embodiments of the present disclosure, the Cas12 protein comprises a mutation at an amino acid residue corresponding to position 826 of the sequence as shown in SEQ ID NO: 696. In some embodiments of the present disclosure, the Cas12 protein comprises a mutation at an amino acid residue corresponding to position 829 of the sequence as shown in SEQ ID NO: 696. In some embodiments of the present disclosure, the Cas12 protein comprises a mutation at an amino acid residue corresponding to position 830 of the sequence as shown in SEQ ID NO: 696. In some embodiments of the present disclosure, the Cas12 protein comprises a mutation at an amino acid residue corresponding to position 833 of the sequence as shown in SEQ ID NO: 696. In some embodiments of the present disclosure, the Cas12 protein comprises a mutation at an amino acid residue corresponding to position 834 of the sequence as shown in SEQ ID NO: 696. In some embodiments of the present disclosure, the Cas12 protein comprises a mutation at an amino acid residue corresponding to position 836 of the sequence as shown in SEQ ID NO: 696. In some embodiments of the present disclosure, the Cas12 protein comprises a mutation at an amino acid residue corresponding to position 842 of the sequence as shown in SEQ ID NO: 696. In some embodiments of the present disclosure, the Cas12 protein comprises a mutation at an amino acid residue corresponding to position 845 of the sequence as shown in SEQ ID NO: 696. In some embodiments of the present disclosure, the Cas12 protein comprises a mutation at an amino acid residue corresponding to position 846 of the sequence as shown in SEQ ID NO: 696. In some embodiments of the present disclosure, the Cas12 protein comprises a mutation at an amino acid residue corresponding to position 847 of the sequence as shown in SEQ ID NO: 696. In some embodiments of the present disclosure, the Cas12 protein comprises a mutation at an amino acid residue corresponding to position 850 of the sequence as shown in SEQ ID NO: 696. In some embodiments of the present disclosure, the Cas12 protein comprises a mutation at an amino acid residue corresponding to position 851 of the sequence as shown in SEQ ID NO: 696. In some embodiments of the present disclosure, the Cas12 protein comprises a mutation at an amino acid residue corresponding to position 853 of the sequence as shown in SEQ ID NO: 696. In some embodiments of the present disclosure, the Cas12 protein comprises a mutation at an amino acid residue corresponding to position 855 of the sequence as shown in SEQ ID NO: 696. In some embodiments of the present disclosure, the Cas12 protein comprises a mutation at an amino acid residue corresponding to position 856 of the sequence as shown in SEQ ID NO: 696. In some embodiments of the present disclosure, the Cas12 protein comprises a mutation at an amino acid residue corresponding to position 858 of the sequence as shown in SEQ ID NO: 696. In some embodiments of the present disclosure, the Cas12 protein comprises a mutation at an amino acid residue corresponding to position 859 of the sequence as shown in SEQ ID NO: 696. In some embodiments of the present disclosure, the Cas12 protein comprises a mutation at an amino acid residue corresponding to position 860 of the sequence as shown in SEQ ID NO: 696. In some embodiments of the present disclosure, the Cas12 protein comprises a mutation at an amino acid residue corresponding to position 866 of the sequence as shown in SEQ ID NO: 696. In some embodiments of the present disclosure, the Cas12 protein comprises a mutation at an amino acid residue corresponding to position 884 of the sequence as shown in SEQ ID NO: 696. In some embodiments of the present disclosure, the Cas12 protein comprises a mutation at an amino acid residue corresponding to position 892 of the sequence as shown in SEQ ID NO: 696. In some embodiments of the present disclosure, the Cas12 protein comprises a mutation at an amino acid residue corresponding to position 893 of the sequence as shown in SEQ ID NO: 696. In some embodiments of the present disclosure, the Cas12 protein comprises a mutation at an amino acid residue corresponding to position 900 of the sequence as shown in SEQ ID NO: 696. In some embodiments of the present disclosure, the Cas12 protein comprises a mutation at an amino acid residue corresponding to position 904 of the sequence as shown in SEQ ID NO: 696. In some embodiments of the present disclosure, the Cas12 protein comprises a mutation at an amino acid residue corresponding to position 926 of the sequence as shown in SEQ ID NO: 696. In some embodiments of the present disclosure, the Cas12 protein comprises a mutation at an amino acid residue corresponding to position 956 of the sequence as shown in SEQ ID NO: 696. In some embodiments of the present disclosure, the Cas12 protein comprises a mutation at an amino acid residue corresponding to position 985 of the sequence as shown in SEQ ID NO: 696. In some embodiments of the present disclosure, the Cas12 protein comprises a mutation at an amino acid residue corresponding to position 988 of the sequence as shown in SEQ ID NO: 696. In some embodiments of the present disclosure, the Cas12 protein comprises a mutation at an amino acid residue corresponding to position 989 of the sequence as shown in SEQ ID NO: 696. In some embodiments of the present disclosure, the Cas12 protein comprises a mutation at an amino acid residue corresponding to position 992 of the sequence as shown in SEQ ID NO: 696. In some embodiments of the present disclosure, the Cas12 protein comprises a mutation at an amino acid residue corresponding to position 993 of the sequence as shown in SEQ ID NO: 696. In some embodiments of the present disclosure, the Cas12 protein comprises a mutation at an amino acid residue corresponding to position 996 of the sequence as shown in SEQ ID NO: 696. In some embodiments of the present disclosure, the Cas12 protein comprises a mutation at an amino acid residue corresponding to position 1016 of the sequence as shown in SEQ ID NO: 696. In some embodiments of the present disclosure, the Cas12 protein comprises a mutation at an amino acid residue corresponding to position 1033 of the sequence as shown in SEQ ID NO: 696. In some embodiments of the present disclosure, the Cas12 protein comprises a mutation at an amino acid residue corresponding to position 1045 of the sequence as shown in SEQ ID NO: 696. In some embodiments of the present disclosure, the Cas12 protein comprises a mutation at an amino acid residue corresponding to position 1050 of the sequence as shown in SEQ ID NO: 696. In some embodiments of the present disclosure, the Cas12 protein comprises a mutation at an amino acid residue corresponding to position 1073 of the sequence as shown in SEQ ID NO: 696. In some embodiments of the present disclosure, the Cas12 protein comprises a mutation at an amino acid residue corresponding to position 1074 of the sequence as shown in SEQ ID NO: 696. In some embodiments of the present disclosure, the Cas12 protein comprises a mutation at an amino acid residue corresponding to position 1095 of the sequence as shown in SEQ ID NO: 696. In some embodiments of the present disclosure, the Cas12 protein comprises a mutation at an amino acid residue corresponding to position 1100 of the sequence as shown in SEQ ID NO: 696. In some embodiments of the present disclosure, the Cas12 protein comprises a mutation at an amino acid residue corresponding to position 1124 of the sequence as shown in SEQ ID NO: 696. In some embodiments of the present disclosure, the Cas12 protein comprises a mutation at an amino acid residue corresponding to position 1129 of the sequence as shown in SEQ ID NO: 696. In some embodiments of the present disclosure, the Cas12 protein comprises a mutation at an amino acid residue corresponding to position 1132 of the sequence as shown in SEQ ID NO: 696. In some embodiments, the mutation is a mutation to residue R.

In some embodiments of the present disclosure, the Cas12 protein comprises a mutation at an amino acid residue corresponding to position 651 of the sequence as shown in SEQ ID NO: 696. In some embodiments, the mutation is a mutation to residue A.

In some embodiments of the present disclosure, the Cas12 protein comprises a mutation at an amino acid residue corresponding to position 891 of the sequence as shown in SEQ ID NO: 696. In some embodiments, the mutation is a mutation to residue A.

In some embodiments of the present disclosure, the Cas12 protein comprises a mutation at an amino acid residue corresponding to position 1082 of the sequence as shown in SEQ ID NO: 696. In some embodiments, the mutation is a mutation to residue A.

In some embodiments of the present disclosure, the Cas12 protein has mutations at amino acid residues corresponding to any 1, any 2, any 3, any 4, any 5, any 6, any 7, any 8, any 9, any 10, any 11, any 12, any 13, any 14, any 15, any 16, or more positions of the amino acid sequence shown in SEQ ID NO: 52, and the positions are selected from V15, Q172, A173, G182, E183, G184, K185, K186, G239, V243, D264, E271, Y295, L297, N317, T329, E331, I335, K339, N347, E363, H366, V426, K429, S430, L433, S452, S455, S465, E493, P497, K587, E768, T825, A911, G914, K915, 1916, K918, T919, T920, A922, and E940.

In some embodiments of the present disclosure, the Cas12 protein has any 1, any 2, any 3, any 4, any 5, any 6, any 7, any 8, any 9, any 10, any 11, any 12, any 13, any 14, any 15, any 16, or more amino acid mutations of the amino acid sequence shown in SEQ ID NO: 52 at positions corresponding to the amino acid sequence shown in SEQ ID NO: 52, and the amino acid mutations are selected from V15R, Q172R, A173W, G182R, E183R, G184R, K185R, K186R, G239R, V243R, D264R, E271R, Y295R, L297R, N317R, T329R, E331R, 1335R, K339R, N347E, E363R, H366R, V426R, K429R, S430R, L433R, S452R, S455R, S465R, E493R, P497R, K587R, E768R, T825R, A911R, G914R, K915R, 1916R, K918R, T919R, T920R, A922R, and E940R.

In some embodiments of the present disclosure, the Cas12 protein has any 1, any 2, any 3, any 4, any 5, or more amino acid mutations of the amino acid sequence shown in SEQ ID NO: 52 at positions corresponding to the amino acid sequence shown in SEQ ID NO: 52, and the amino acid mutations are selected from N347E+K339R, Q172R+S452R, Q172R+T920R, Q172R+V426R, S452R+T920R, V426R+S452R, V426R+T920R.

In some embodiments of the present disclosure, the Cas12 protein comprises a mutation at an amino acid residue corresponding to position 15 of the sequence as shown in SEQ ID NO: 52. In some embodiments of the present disclosure, the Cas12 protein comprises a mutation at an amino acid residue corresponding to position 172 of the sequence as shown in SEQ ID NO: 52. In some embodiments of the present disclosure, the Cas12 protein comprises a mutation at an amino acid residue corresponding to position 173 of the sequence as shown in SEQ ID NO: 52. In some embodiments of the present disclosure, the Cas12 protein comprises a mutation at an amino acid residue corresponding to position 182 of the sequence as shown in SEQ ID NO: 52. In some embodiments of the present disclosure, the Cas12 protein comprises a mutation at an amino acid residue corresponding to position 183 of the sequence as shown in SEQ ID NO: 52. In some embodiments of the present disclosure, the Cas12 protein comprises a mutation at an amino acid residue corresponding to position 184 of the sequence as shown in SEQ ID NO: 52. In some embodiments of the present disclosure, the Cas12 protein comprises a mutation at an amino acid residue corresponding to position 185 of the sequence as shown in SEQ ID NO: 52. In some embodiments of the present disclosure, the Cas12 protein comprises a mutation at an amino acid residue corresponding to position 186 of the sequence as shown in SEQ ID NO: 52. In some embodiments of the present disclosure, the Cas12 protein comprises a mutation at an amino acid residue corresponding to position 239 of the sequence as shown in SEQ ID NO: 52. In some embodiments of the present disclosure, the Cas12 protein comprises a mutation at an amino acid residue corresponding to position 243 of the sequence as shown in SEQ ID NO: 52. In some embodiments of the present disclosure, the Cas12 protein comprises a mutation at an amino acid residue corresponding to position 264 of the sequence as shown in SEQ ID NO: 52. In some embodiments of the present disclosure, the Cas12 protein comprises a mutation at an amino acid residue corresponding to position 271 of the sequence as shown in SEQ ID NO: 52. In some embodiments of the present disclosure, the Cas12 protein comprises a mutation at an amino acid residue corresponding to position 295 of the sequence as shown in SEQ ID NO: 52. In some embodiments of the present disclosure, the Cas12 protein comprises a mutation at an amino acid residue corresponding to position 297 of the sequence as shown in SEQ ID NO: 52. In some embodiments of the present disclosure, the Cas12 protein comprises a mutation at an amino acid residue corresponding to position 317 of the sequence as shown in SEQ ID NO: 52. In some embodiments of the present disclosure, the Cas12 protein comprises a mutation at an amino acid residue corresponding to position 329 of the sequence as shown in SEQ ID NO: 52. In some embodiments of the present disclosure, the Cas12 protein comprises a mutation at an amino acid residue corresponding to position 331 of the sequence as shown in SEQ ID NO: 52. In some embodiments of the present disclosure, the Cas 12 protein comprises a mutation at an amino acid residue corresponding to position 335 of the sequence as shown in SEQ ID NO: 52. In some embodiments of the present disclosure, the Cas12 protein comprises a mutation at an amino acid residue corresponding to position 339 of the sequence as shown in SEQ ID NO: 52. In some embodiments of the present disclosure, the Cas12 protein comprises a mutation at an amino acid residue corresponding to position 347 of the sequence as shown in SEQ ID NO: 52. In some embodiments of the present disclosure, the Cas12 protein comprises a mutation at an amino acid residue corresponding to position 363 of the sequence as shown in SEQ ID NO: 52. In some embodiments of the present disclosure, the Cas12 protein comprises a mutation at an amino acid residue corresponding to position 366 of the sequence as shown in SEQ ID NO: 52. In some embodiments of the present disclosure, the Cas12 protein comprises a mutation at an amino acid residue corresponding to position 426 of the sequence as shown in SEQ ID NO: 52. In some embodiments of the present disclosure, the Cas12 protein comprises a mutation at an amino acid residue corresponding to position 429 of the sequence as shown in SEQ ID NO: 52. In some embodiments of the present disclosure, the Cas12 protein comprises a mutation at an amino acid residue corresponding to position 430 of the sequence as shown in SEQ ID NO: 52. In some embodiments of the present disclosure, the Cas12 protein comprises a mutation at an amino acid residue corresponding to position 433 of the sequence as shown in SEQ ID NO: 52. In some embodiments of the present disclosure, the Cas12 protein comprises a mutation at an amino acid residue corresponding to position 452 of the sequence as shown in SEQ ID NO: 52. In some embodiments of the present disclosure, the Cas12 protein comprises a mutation at an amino acid residue corresponding to position 455 of the sequence as shown in SEQ ID NO: 52. In some embodiments of the present disclosure, the Cas12 protein comprises a mutation at an amino acid residue corresponding to position 465 of the sequence as shown in SEQ ID NO: 52. In some embodiments of the present disclosure, the Cas12 protein comprises a mutation at an amino acid residue corresponding to position 493 of the sequence as shown in SEQ ID NO: 52. In some embodiments of the present disclosure, the Cas12 protein comprises a mutation at an amino acid residue corresponding to position 497 of the sequence as shown in SEQ ID NO: 52. In some embodiments of the present disclosure, the Cas12 protein comprises a mutation at an amino acid residue corresponding to position 587 of the sequence as shown in SEQ ID NO: 52. In some embodiments of the present disclosure, the Cas12 protein comprises a mutation at an amino acid residue corresponding to position 768 of the sequence as shown in SEQ ID NO: 52. In some embodiments of the present disclosure, the Cas12 protein comprises a mutation at an amino acid residue corresponding to position 825 of the sequence as shown in SEQ ID NO: 52. In some embodiments of the present disclosure, the Cas12 protein comprises a mutation at an amino acid residue corresponding to position 911 of the sequence as shown in SEQ ID NO: 52. In some embodiments of the present disclosure, the Cas12 protein comprises a mutation at an amino acid residue corresponding to position 914 of the sequence as shown in SEQ ID NO: 52.

In some embodiments of the present disclosure, the Cas12 protein comprises a mutation at an amino acid residue corresponding to position 915 of the sequence as shown in SEQ ID NO: 52. In some embodiments of the present disclosure, the Cas12 protein comprises a mutation at an amino acid residue corresponding to position 916 of the sequence as shown in SEQ ID NO: 52. In some embodiments of the present disclosure, the Cas12 protein comprises a mutation at an amino acid residue corresponding to position 918 of the sequence as shown in SEQ ID NO: 52. In some embodiments of the present disclosure, the Cas12 protein comprises a mutation at an amino acid residue corresponding to position 919 of the sequence as shown in SEQ ID NO: 52. In some embodiments of the present disclosure, the Cas12 protein comprises a mutation at an amino acid residue corresponding to position 920 of the sequence as shown in SEQ ID NO: 52. In some embodiments of the present disclosure, the Cas12 protein comprises a mutation at an amino acid residue corresponding to position 922 of the sequence as shown in SEQ ID NO: 52. In some embodiments of the present disclosure, the Cas12 protein comprises a mutation at an amino acid residue corresponding to position 940 of the sequence as shown in SEQ ID NO: 52. In some embodiments, the mutation is a mutation to residue R.

Embodiments of the present disclosure provides a guide polynucleotide, wherein the guide polynucleotide comprises (i) a scaffold sequence, and (ii) a guide sequence. The guide sequence has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to a sequence shown in any one of SEQ ID NO: 722, SEQ ID NO: 761-782, and SEQ ID NO: 825-877. The guide polynucleotide is able to form a complex with a nucleic acid-binding polypeptide and guide a sequence-specific binding of the complex to a target nucleic acid.

In some embodiments, the guide sequence may be obtained by adding and/or deleting 1, 2, 3, 4, 5, 6, or 7 nucleotides to/from the sequence shown in any one of SEQ ID NO: 722, SEQ ID NO: 761-782, and SEQ ID NO: 825-877. In some embodiments, the guide sequence is as shown in any one of SEQ ID NO: 722, SEQ ID NO: 761-782, and SEQ ID NO: 825-877.

In some embodiments, the guide sequence hybridizes to the target nucleic acid. In some embodiments, the target nucleic acid is randomly selected from TTR, HBG, BCL11A, BACH2, KLKB1, PCSK9, SOD1, and BACE1 genes.

In some embodiments, the guide sequence is located at the 5' end or 3' end of the scaffold sequence.

In some embodiments, the nucleic acid-binding polypeptide and the guide polynucleotide form a complex. Further, the complex specifically binds to a target nucleic acid. Further, the complex cleaves the target nucleic acid, modifies the target nucleic acid, and/or modulates an expression of the target nucleic acid.

In some embodiments, the nucleic acid-binding polypeptide comprises a DNA-binding polypeptide. In some embodiments, the nucleic acid-binding polypeptide comprises an RNA-binding polypeptide. In some embodiments, the nucleic acid-binding polypeptide comprises a TALEN nuclease, a zinc finger nuclease, a CRISPR-Cas nuclease, or a meganuclease. In some embodiments, the nucleic acid-binding polypeptide is an RNA-guided nuclease. In some embodiments, the DNA-binding polypeptide is a CRISPR-associated nuclease, i.e., a Cas enzyme (also known as a Cas protein, a CRISPR-Cas nuclease). In some embodiments, the nucleic acid-binding polypeptide is selected from Cas1, Cas1B, Cas2, Cas3, Cas4, Cas5, Cas5d, Cas5t, Cas5h, Cas5a, Cas6, Cas7, Cas8, Cas8a, Cas8b, Cas8c, Cas9, Cas10, Cas10d, Cas12a/Cpf1, Cas12b/C2c1, Cas12c/C2c3, Cas12d/CasY, Cas12e/CasX, Cas12f/CasZ, Cas12g, Cas12h, Cas12i, Csy1, Csy2, Csy3, Csy4, Cse1, Cse2, Cse3, Cse4, Cse5e, Csc1, Csc2, Csa5, Csn1, Csn2, Csm1, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csx11, Csf1, Csf2, CsO, Csf4, Csd1, Csd2, Cst1, Cst2, Csh1, Csh2, Csa1, Csa2, Csa3, Csa4, Csa5, Cas13a, Cas13b, Cas13c, Cas13d, Cas13c, Cas13f, TnpB, IscB, IsrB, and Fancor, or fragments thereof. Non-limiting examples of the fragments include nucleic acid-binding domain fragments. In some embodiments, the nucleic acid-binding polypeptide is selected from Cas9, Cas12, Cas13, TnpB, IscB, IsrB, Fancor nuclease, or fragments thereof, including but not limited to the nucleic acid-binding domain fragments. In some embodiments, the Cas9 is selected from SpCas9, SaCas9, Nme2Cas9, Nme3Cas9, CjCas9, NmCas9, FnCas9, PpnCas9, FrCas9, SauCas9, SauriCas9, ScaCas9, StlCas9, BlatCas9, CdiCas9, GeoCas9, fragments thereof, and mutations thereof or fragments of the mutations. In some embodiments, the nucleic acid-binding polypeptide is selected from AsCpf1, enAsCas12a (addgene plasmid #196724), dFnCas12a (addgene plasmid #136379), ErCas12a, LbCas12a D832A, LbCas12a H759A, LbCas12a E795L, FnCas12a3, FnCas12a D917A, AsCas12a R1226A, AsCas12a D908A, AsCas12a E174R/S542R, AsCas12a (S542R/K548V/N552R), PrCas12a, PxCas12a, PcCas12a, PdCas12a, Mb2Cas12a, Mb3Cas12a, MICas12a, CMaCas12a, CMtCas12a, HkCas12a, Lb5Cas12a, ErCas12a, TsCas12a, FnCpf1, LbCas12a, dLbCpf1, ttHsCas12a, AaCas12b, AaCas12b D570A, AaCas12b Q119F/E475R/E758R, BhCas12b, BvCas12b, BrCas12b, AkCas12b, AmCas12b, BsCas12b, OspCas12c, Cas12c2 (addgene plasmid #183072), Cas12c_4 (addgene plasmid #183071), Cas12c1 (addgene plasmid #120872), CasY.1 (from Katanobacteria), CasY.2 (from Vogelbacteria), CasY.3 (from Vogelbacteria), CasY.4 (fromParcubacteria), CasY.5 (from Komcilibacteria), CasY.6 (from Kerfeldbacteria), PlmCasX, DpbCasX, Un1Cas12f, CnCas12f1, enRhCas12f1, AsCas12f1, SpaCas12f1, Cas12g1 (addgene plasmid #120879), Cas12 h from the international application WO2021113522A1 (SEQ ID NO: 1 from the application), Cas12i1 (addgene plasmid #171670), Cas1212 (addgene plasmid #188275), Cas12i1 (addgene plasmid #120882), Cas1212 (addgene plasmid #120883), Cas12i protein named as Cas12f.4/Cas12f.5/Cas12f.6 in CN111757889B, dSiCas12i (D1049A), SiCas12i, Si2Cas12i, WiCas12i, Wi2Cas12i, Wi3Cas12i, SaCas12i, Sa2Cas12i, Sa3Cas12i, WaCas12i, Wa2Cas12i, xCas12i, hfCas12Max, Cas12i-Max (addgene plasmid #188276), Cas12i1 D647A (addgene plasmid #171671), Cas12i-HiFi (addgene plasmid #188269), Cas12i1 D647A, Cas12j3 (addgene plasmid #188497), Cas12j2 (addgene plasmid #188498), AsCas12j-2 (addgene plasmid #191655), Cas12j-8 (addgene plasmid #194966), ShCas12k, N7Cas12k, AcCas12k, Cas12k-TniQ (addgene plasmid #181787), Cas12k-TnsC (addgene plasmid #181789), Cas121, MmCas12m, MmCas12m ΔZF (H549A, C552A), dCas12m-ΔZF (D485A, H549A, C552A), AcCas12n, dAcCas12n (D240), TnpB Actinomadura_cellulosilytica_strain_DSM_45823, TnpB TnpB Actinomadura_namibiensis_strain_DSM_44197, Actinomadura_umbrina_strain- _DSM_43927_$, TnpB *Actinoplanes_lobatus*_strain_DSM_43150 (TnpB-1 and TnpB-2), TnpB Alicyclobacillus_macrosporagiidus_strain-_DSM_17980, TnpB Haloactinospora_alba_Strain-_DSM_45015, TnpB Lipingzhangella_halophila_strain-_DSM_102030, TnpB Meiothermus_Silvanus_DSM_9946, TnpB QNFX01000004, ISDra2 TnpB (PDB: 8H1J), KralscB-1, AwaIscB, OgeuIscB, GtFz1 (from Guillardia theta), SpuFz1 (fromSpizellomyces punctatus), NlovFz2 (from Percolozoa *Naegleria* lovaniensis), and MmeFz2 (from Mercenaria mercenaria), fragments thereof, and mutations thereof or fragments of the mutationss. In some embodiments, the DNA-binding polypeptide is able to cleave one strand of a double-stranded nucleic acid molecule (e.g., a double-stranded DNA molecule). Alternatively, the DNA-binding polypeptide is an RNA-guided nuclease with nickase activity. In some embodiments, the Cas enzyme cleaves a target strand of a double-stranded nucleic acid molecule, which means that the Cas enzyme cleaves the strand that is base-paired (complementary) with gRNA (e.g., sgRNA) bound to the Cas enzyme. In some embodiments, the nucleic acid-binding polypeptide is an RNA-guided nuclease with inactivated nuclease activity. In some embodiments, the nucleic acid-binding polypeptide is a completely inactivated mutant relative to nuclease activity of the wild-type RNA-guided nuclease, such as a dCas enzyme, which comprises but is not limited to Cas9, Cas12, Cas13, TnpB, IscB, IsrB, and Fancor with completely inactivated nuclease activity (which are referred to as dead Cas9, dead Cas12, dead Cas13, dead TnpB, dead IscB, dead IsrB, and dead Fancor); or fragments or mutations thereof, such as a SpRYs Cas9 mutant. In some embodiments of the present disclosure, the nucleic acid-binding polypeptide is a partially inactivated mutant relative to nuclease activity of a wild-type RNA-guided nuclease, such as an nCas enzyme, e.g., a polypeptide fragment that retains the nuclease activity for cleavage of a single strand of double-stranded DNA, which comprises but is not limited to nickase Cas9 and nickase Cas12.

Some embodiments of the present disclosure provide a guide polynucleotide comprising (i) a DR sequence having at least 50% sequence identity to the sequence shown in any one of SEQ ID NO: 54-583 or 704, and (ii) a guide sequence engineered to hybridize to a target nucleic acid. The DR sequence is linked to the guide sequence, and the guide polynucleotide forms a complex with a Cas12 protein, and guide sequence-specific binding of the complex to the target nucleic acid.

In some embodiments of the present disclosure, the DR sequence has at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to the sequence shown in any one of SEQ ID NO: 54-583 or 704.

In some embodiments of the present disclosure, the DR sequence has at least 60% sequence identity to the sequence shown in any one of SEQ ID NO: 54-583 or 704.

In some embodiments of the present disclosure, the DR sequence has at least 65% sequence identity to the sequence shown in any one of SEQ ID NO: 54-583 or 704.

In some embodiments of the present disclosure, the DR sequence has at least 70% sequence identity to the sequence shown in any one of SEQ ID NO: 54-583 or 704.

In some embodiments of the present disclosure, the DR sequence has at least 75% sequence identity to the sequence shown in any one of SEQ ID NO: 54-583 or 704.

In some embodiments of the present disclosure, the DR sequence has at least 80% sequence identity to the sequence shown in any one of SEQ ID NO: 54-583 or 704.

In some embodiments of the present disclosure, the DR sequence has at least 85% sequence identity to the sequence shown in any one of SEQ ID NO: 54-583 or 704.

In some embodiments of the present disclosure, the DR sequence has at least 90% sequence identity to the sequence shown in any one of SEQ ID NO: 54-583 or 704.

In some embodiments of the present disclosure, the DR sequence has at least 95% sequence identity to the sequence shown in any one of SEQ ID NO: 54-583 or 704.

In some embodiments of the present disclosure, the DR sequence has at least 96% sequence identity to the sequence shown in any one of SEQ ID NO: 54-583 or 704.

In some embodiments of the present disclosure, the DR sequence has at least 97% sequence identity to the sequence shown in any one of SEQ ID NO: 54-583 or 704.

In some embodiments of the present disclosure, the DR sequence has at least 98% sequence identity to the sequence shown in any one of SEQ ID NO: 54-583 or 704.

In some embodiments of the present disclosure, the DR sequence has at least 100% sequence identity to the sequence shown in any one of SEQ ID NO: 54-583 or 704.

In some embodiments, the Cas12 protein is a Cas12 protein as described herein.

In some embodiments, the guide sequence comprises 15-60 nucleotides. In some embodiments, the guide sequence comprises 15-50 nucleotides. In some embodiments, the guide sequence comprises 15-40 nucleotides. In some embodiments, the guide sequence comprises 15-35 nucleotides. In some embodiments, the guide sequence comprises 15-30 nucleotides. In some embodiments, the guide sequence comprises 15-25 nucleotides. In some embodiments, the guide sequence comprises 18-25 nucleotides. In some embodiments, the guide sequence comprises 20-25 nucleotides. In some embodiments, the guide sequence comprises 18-22 nucleotides. In some embodiments, the guide sequence comprises 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides.

In some embodiments, the guide sequence hybridizes to the target nucleic acid, and the guide sequence is 90%-100% complementary to the target nucleic acid.

In some embodiments, the guide sequence hybridizes to the target nucleic acid.

In some embodiments, the guide sequence hybridizes to the target nucleic acid, and the guide sequence is mismatched to the target nucleic acid by no more than one nucleotide.

In some embodiments, the DR sequence comprises 15-100 nucleotides. In some embodiments, the DR sequence comprises 15-90 nucleotides. In some embodiments, the DR sequence comprises 15-80 nucleotides. In some embodiments, the DR sequence comprises 15-70 nucleotides. In some embodiments, the DR sequence comprises 15-60 nucleotides. In some embodiments, the guide sequence comprises 15-50 nucleotides. In some embodiments, the guide sequence comprises 15-40 nucleotides. In some embodiments, the guide sequence comprises 20-40 nucleotides. In some embodiments, the guide sequence comprises 20-30 nucleotides. In some embodiments, the guide sequence comprises 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides.

In some embodiments, the guide sequence is located at the 3' end of the DR sequence.

In some embodiments, the guide sequence is located at the 5' end of the DR sequence. In some embodiments, the guide polynucleotide further comprises tracrRNA.

In some embodiments of the present disclosure, the tracrRNA sequence has at least 50% sequence identity to any one of the sequences shown in SEQ ID NO: 584-695. In some embodiments of the present disclosure, the tracrRNA sequence has at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% sequence identity to any one of the sequences shown in SEQ ID NO: 584-695.

In some embodiments of the present disclosure, the tracrRNA sequence is selected from the sequences shown in SEQ ID NO: 584-695.

In some embodiments, the tracrRNA is complementarily paired with the DR sequence. In general, the complementary pairing is a complementary pairing for partial bases. In some embodiments, the tracrRNA interacts with the DR sequence.

In some embodiments, the tracrRNA sequence is linked to the DR sequence. In some embodiments, the tracrRNA sequence is linked to the DR sequence by a nucleotide sequence. In some embodiments, the tracrRNA sequence is linked to the DR sequence by a nucleotide sequence including 1-10 nucleotides. In some embodiments, the tracrRNA sequence is linked to the DR sequence by a nucleotide sequence including 1, 2, 3, 4, 5, 6, 7, 8, 9, or 10 nucleotides. In some embodiments, the tracrRNA sequence is linked to the DR sequence by a nucleotide sequence including 4 nucleotides. In some embodiments, the tracrRNA sequence is linked to the DR sequence by a 5'-GAAA-3' linker.

In some embodiments, the tracrRNA sequence is located at the 3' end of the DR sequence.

In some embodiments, the tracrRNA sequence is located at the 5' end of the DR sequence.

In some embodiments, the tracrRNA comprises 10-200 nucleotides. In some embodiments, the tracrRNA comprises 10-190, 10-180, 10-170, 10-160, 10-150, 10-140, 10-130, 10-120, 10-110, 10-100, 10-90, 10-80, 10-70, 10-60, 10-50, 10-40, 10-30, 10-20, 20-100, 30-100, 40-100, 20-90, 20-80, 20-70, 20-60, 20-50, or 30-50 nucleotides. In some embodiments, the tracrRNA comprises 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

SEQ ID NO: 1-53 shows the amino acid sequence of the Cas protein.

SEQ ID NO: 54-583 shows the DR sequence corresponding to the Cas protein. When more than one DR sequences corresponding to a particular Cas protein are listed, any one DR sequence may be used.

SEQ ID NO: 584-695 shows the tracrRNA sequence corresponding to the Cas protein. When SEQ ID NO: 584-695 does not list the tracrRNA sequence corresponding to a specific Cas protein, then gRNA may comprise only the guide sequence and the DR sequence, and do not comprise the tracrRNA sequence. When SEQ ID NO: 584-695 lists the tracrRNA sequence corresponding to the particular Cas protein, then the gRNA may comprise the guide sequence and the DR sequence and optionally comprise the tracrRNA sequence. When more than one tracrRNA sequences corresponding to the particular Cas protein are listed, any one of the tracrRNA sequences may be selected for use.

Some embodiments of the present disclosure provide an inactivated Cas12 mutant. The inactivated Cas 12 mutant is a nuclease-inactivated mutant of the Cas12 protein as described in the present disclosure.

In the present disclosure, depending on the context, a reference scope of the Cas 12 protein may encompass the inactivated Cas12 mutant. However, given the importance of the inactivated Cas12 mutant (non-limiting examples including that the inactivated Cas12 mutant is fused with a deaminase for single-base editing, fused with a transcriptional activation domain or a transcriptional repression domain for transcription regulation, etc.), the inactivated Cas12 mutant may be described separately and in detail herein; which does not imply that the reference scope of the Cas12 protein necessarily excludes the inactivated Cas12 mutant.

In some embodiments, the inactivated Cas12 mutant is a mutant in which the nuclease activity is completely inactivated, i.e., a dead Cas12 mutant (dCas12). The dCas12 only binds the target nucleic acid under the mediation of the guide polynucleotide and has no or negligible cleavage activity against the target nucleic acid. For example, a target nucleic acid cleavage efficiency of the dCas12 is no more than 20%, 15%, 10%, 5%, 4%, 3%, 2%, or 1% of the target nucleic acid cleavage efficiency of the Cas12 protein before inactivating mutation.

In some embodiments, the inactivated Cas12 mutant is a mutant in which the nuclease activity is partially inactivated. Further, the mutant with partially inactivated nuclease activity is a nickase Cas12 (nCas12), which binds the target nucleic acid under mediation of the guide polynucleotide, and then cleaves one single strand of the double-stranded target nucleic acid without cleaving the other single strand.

In some embodiments, the inactivated Cas12 mutant is a Cas12 protein with an inactivated Ruvc domain.

In some embodiments, the inactivated Cas 12 mutant is a Cas 12 protein with an inactivated Ruvc-I, Ruvc-II, or Ruvc-III domain.

In some embodiments, the inactivated Cas12 mutant is obtained by introducing the inactivating mutation into the Ruvc-I, Ruvc-II, or Ruvc-III domain of the Cas12 protein.

In some embodiments, the inactivating mutation is selected from one or more of D651A, E891A, and D1082A corresponding to the amino acid sequence as shown in SEQ ID NO: 696.

In some embodiments, the inactivating mutation is D651A, E891A, and D1082A corresponding to the amino acid sequence shown in SEQ ID NO: 696.

In some embodiments, a PAM sequence recognized by the inactivated Cas12 mutant is the same as the PAM sequence recognized by the Cas12 protein.

In some embodiments, the PAM sequence (5'→3') recognized by the inactivated Cas12 mutant is selected from any one or more of the following: A, C, T, G, TA, TC, GN, AA, AG, TG, AN, GG, CG, TN, NT, NG, GT, NA, CC, AC, GC, AT, CT, GA, TT, CN, NC, CA, NTN, ANN, TTN, ATC, NAC, AGA, TGC, TCT, NGN, CGC, NTC, GCA, TCG, TTT, CCG, GGG, NAG, ACA, CGG, CNG, ACN, GTG, CNT, TTG, TCN, GGT, TNC, CCN, CGT, TGG, CGA, NGG, TCC, AGT, NCA, CAN, TCA, NNG, TAC, CCT, NTG, CGN, TGN, CAT, NGC, GNG, GNC, NNA, GAA, TTC, CTT, ATA, TAT, GCT, NCC, TTA, AGN, GNN, CAA, CAC, AGG, NTT, ANG, GNA, GTT, NGA, TAA, GTA, GGN, GNT, NCG, ATT, CCA, CNN, AAA, AAC, ATN, GAG, CTG, ACG, NAA, TAN, NAT, CNA, GCN, GTC, NCN, CTN, CNC, ANT, NNC, CAG, NAN, ATG, NCT, CCC, AAN, TGT, TNA, ACC, GAT, ACT, AAT, GGA, GAN, ANC, GAC, NNT, CTA, TNN, GCG, GTN, TNT, AAG, TAG, NGT, NTA, ANA, CTC, GCC, TGA, GGC, AGC, TNG, NGAA, GANC, GCNC, NINT, TGGG, AAGG, AAGN, NTNN, TCGT, CNTG, NTGG, CCGN, ATAT, TGCA, NGGT, TGNT, NNTG, NCCG, ACAT, GNTG, CGCG, GACN, NTCG, TCNG, CTGC, TNNC, GGTN, CGNN, TCCA, AGCN, TNAG, GGAC, GATC, AANA, NATG, CCAG, NAAT, TCNT, CACT, CGGC, CGAN, CNCA, ATNT, NNNG, NGCT, CTGG, GGAN, NINC, ATTC, AATG, CNTC, TGGN, NATC, GTCG, ACNC, GCNN, GACT, CTNT, NCTT, NAGG, NANC, CTTA, GTCT, ANAG, NGCN, CNNA, TCAG, ACAC, NCGG, TNNT, CAAG, ACCT, CCCA, GTNC, ANTC, GACC, AACG, TTAA, TCCG, CGCC, NCCN, TTNA, NCNT, NGCA, AGNN, AATC, GGGA, GNAN, NAGA, CGNA, GTAT, GTNA, ATNC, ACNA, GGAA, NTCC, GGCG, AATN, CNNT, AGGC, GCGN, GTGC, TTGA, AAGC, GAAG, ATNG, TGCT, TACT, CTAN, GGCT, GNGC, GTCN, CGAA, CNAC, GCCT, TAGG, ANGC, TNAA, GANT, NCNA, NCCT, AGAN, GTAA, TTTN, ATGA, TGNA, CANC, ACGA, CCAC, CCGG, CTNG, CNGN, GGTA, NGNC, GTTT, CTAA, TNCT, CTGN, NGAC, TGTA, TANN, GCNT, GCTC, CNCG, AAAN, CCNT, GANA, CACA, CTNA, ANTN, TTNT, CCTG, TNTT, CANA, NTAN, CACG, GGAT, TTTC, GNCG, TACA, GTAC, GAGC, ACNN, ATGG, AANT, ATCC, ACCG, AGNC, TGTT, NCAT, ATTA, GNTT, GAGN, TNAC, GCCG, NING, GTGG, GNGN, ACCA, NTAA, ACTN, NCTG, NCTA, TTTT, GONG, NTAG, CAAA, GGNA, CNTN, TTAG, TCTG, NCTN, TATG, GCGT, TANT, GGGT, NACN, ACTG, CCNG, GNNT, CCAT, GNTA, NANT, TACN, TGTN, ATCT, NCAN, TNGG, CNNN, AAGT, ATTN, GGNN, CAGC, CGTN, GCCC, GCTT, CNAT, NANA, CCNN, GNGA, TNGN, GCAG, CGNG, CCTT, NGAG, NCNG, AANG, GGTC, ACTC, TGAA, NAGN, NNCA, ACGG, TGAC, TCCN, ANNN, TCGN, TAAN, CAGG, TTAN, NGAN, NTGC, CCNC, TNTN, ATGN, GTGN, GCAT, NNGN, NNCC, CCNA, CNAG, GNAC, CGNT, TTCN, TAGN, ANCT, NATN, GTGA, TNGT, CTAT, CCCG, TNCA, NGTA, NNGA, CGTG, TAAT, CGCA, NNCG, NGTC, NAGT, GNAT, TNTC, NCGC, NGGN, CATN, GTTN, AGTA, GNNG, TTNN, TGNC, NAAA, TNCC, CACC, CTCT, TTGN, GCTA, NTTT, TGAN, TNAN, NGAT, CCTN, GAAT, GTCA, NTCN, GCCA, ANTG, TGGC, CAAC, TTTA, TGTC, CGGA, NCGN, AGNT, NCGA, ANCG, ACAA, TAGT, CGAG, NCAA, AATA, AGGG, GNGT, CAGA, AGGT, GGGG, ANAC, TGGT, GTGT, GNCA, GTTA, NGTT, TNNG, NCAG, CACN, GCAN, GAAC, NCCA, TTCC, NCNN, GNNN, ANGT, NTNA, CCCT, GNAA, TTNG, GTNN, GGNG, TCTA, NCAC, GANG, TTCG, CCTC, CNGG, ANNA, TCAN, ATCG, NTGA, CGTA, TTAC, GCTN, GCTG, NGTG, TCCC, CANN, NNNA, TAGA, ACGT, AGAT, GATG, GCCN, TGNG, GCGC, CCGA, GNCN, NTTG, NNAT, TNCG, NANG, GGTG, NCCC, GNCC, CAAT, CGCN, CNGA, NTTC, TTCT, NGGA, AGTC, CNNC, NACG, AGTN, NANN, ACAG, GNCT, TACC, CNTA, TGTG, CATC, GACA, TCTT, NTCT, CTGA, AGGA, GATA, TNAT, CCTA, GGAG, ANCC, AANC, GTAN, GCNA, TGNN, TANC, GNTN, AGCG, CTAG, NNAA, AGTT, CTAC, TACG, TINC, TNTA, ANTT, ATAC, TCCT, TCAC, NGGC, NTTN, NNTC, CANT, ATAA, TGCC, CTCC, TNNA, GING, ACGN, GGCA, AAAG, TTGT, NGNA, NAAN, TATN, CGGG, CATA, ATGC, ACGC, ACCN, ATTT, TCNA, TNGC, NACA, NACC, CTCN, GGCC, TANG, AGAA, INGA, TAGC, CAGN, GGCN, ANNT, NNNC, TCAT, CATT, TAAA, ATGT, TGAG, CGCT, TCGG, GCAC, GTAG, NTCA, NATT, ANTA, CCCN, ACTA, AAAA, GAAN, TATT, NNAC, TGAT, GGGN, CCAA, GNGG, CCAN, GTCC, NNCT, AGNG, CNTT, CNCT, GANN, GGTT, AGCT, CATG, NTAC, TNCN, NNTN, TGGA, GATT, AGCA, TAAG, GCGA, ACTT, ANGN, NTGN, AACN, AACT, TCAA, NTAT, TCGA, NCTC, NNGG, ANGG, NNTT, GTNT, CTNN, CGGN, TAAC, GGNC, GAAA, ACNG, GNAG, TTGG, CTTC, CNGT, TNNN, TNTG, GTTG, TCNN, CGGT, GAGA, CNNG, NCNC, GAGG, AGCC, ATNN, NNNT, AGAC, AACC, ANNC, ANNG, ACAN, GTTC, TATA, GNTC, NCGT, NGNT, CGTC, CCGC, CGAC, GACG, ATTG, GNNC, CNAA, TATC, AGNA, CTNC, TTCA, ANCA, ACCC, AGTG, CCGT, ANAT, CTGT, GGGC, NTTA, NAAG, AANN, CNAN, NNCN, ANAA, ANAN, CTTG, NGNN, AGAG, TANA, TCNC, GCAA, NGNG, NAGC, NATA, ATCN, CGTT, CNGC, GATN, NNTA, AAGA, CTTT, AAAC, AGGN, ACNT, NTGT, CTTN, ATCA, NACT, NNAG, NGTN, NAAC, TGCG, GGNT, ATAN, TTGC, ANCN, CCCC, ANGA, NGCG, TCTC, CTCG, ATNA, AATT, NNAN, NNGT, TCGC, ATAG, CAAN, AACA, TTAT, CAGT, GNNA, TGCN, GCGG, NGGG, CANG, TTTG, GAGT, AAAT, CTCA, CNCN, CNCC, TCTN, CGNC, NGCC, CGAT, and NNGC.

N is A, T, C, or G.

Some embodiments of the present disclosure provide a fusion protein or conjugate. The fusion protein or conjugate comprises: (1) the Cas12 protein as described herein, or the inactivated Cas12 mutant as described herein; and (2) a homologous or heterologous functional domain.

In the present disclosure, depending on the context, the reference scope of the Cas12 protein may encompass the inactivated Cas12 mutant. However, given the importance of the inactivated Cas12 mutant (non-limiting examples including the fusion of the inactivated Cas12 mutant with the deaminase for single base editing, fusion with a transcriptional activation domain or a transcriptional repression domain for transcriptional regulation, etc.), the inactivated Cas12 mutant is described separately and in detail herein, which does not imply that the reference scope of the Cas12 protein necessarily excludes the inactivated Cas12 mutant.

In some embodiments of the present disclosure, a fusion protein is provided. The fusion protein comprises (1) the Cas12 protein as described herein, or the inactivated Cas12 mutant as described herein; and (2) the homologous or heterologous functional domain.

In some embodiments of the present disclosure, a fusion protein is provided. The fusion protein comprises (1) the Cas12 protein as described herein; and (2) the homologous or heterologous functional domain.

In some embodiments, a conjugate is provided. The conjugate comprises (1) the Cas12 protein as described herein, or the inactivated Cas12 mutant as described herein; and (2) the homologous or heterologous functional domain.

In some embodiments, a conjugate is provided. The conjugate comprises (1) the Cas12 protein as described herein; and (2) the homologous or heterologous functional domain.

In some embodiments, the functional domain has an enzyme activity for modifying the target nucleic acid sequence; the enzyme activity comprising a nuclease activity, a methyltransferase activity, a demethylase activity, a DNA repair activity, a DNA damage activity, a deamination activity, a dismutase activity, an alkylation activity, a depurination activity, an oxidation activity, a pyrimidine dimer formation activity, an integrase activity, a transposase activity, a recombinase activity, a polymerase activity, a ligase activity, a helicase activity, a photolyase activity, a glycosylase activity, a deglycosylation activity, an acetyltransferase activity, a deacetylase activity, a kinase activity, a phosphatase activity, a ubiquitin ligase activity, a deubiquitination activity, an adenylylation activity, a deadenylation activity, a SUMOylating activity, a deSUMOylating activity, a myristoylation activity, and/or a demyristoylation activity.

In some embodiments, the inactivating mutation is selected from one or more of D651A, E891A, and D1082A corresponding to the amino acid sequence shown in SEQ ID NO: 696.

In some embodiments, the inactivating mutation is D651A, E891A, and D1082A corresponding to the amino acid sequence as shown in SEQ ID NO: 696.

In some embodiments, the functional domain is selected from one or more of the following: a nuclease (e.g., FokI), a DNA methyltransferase, a DNA demethylase, a histone methyltransferase, a histone demethylase, a histone acetylase domain, a histone deacetylase domain, a DNA repair enzyme, a DNA damage enzyme, a deaminase, a dismutase, an alkylase, a depurinase, an oxidase, a pyrimidine dimer-forming enzyme, an integrase, a transposase, a recombinase, a polymerase, a ligase, a helicase, a photolyase, a glycosylase, a deglycosylase, an acetyltransferase, a deacetylase, a kinase, a phosphatase, a ubiquitin ligase, a deubiquitinating enzyme, an adenylylase, a deadenylase, a SUMOylating enzyme, a deSUMOylating enzyme, a myristoylase, and/or a demyristoylase.

In some embodiments, the homologous or heterologous functional domain is selected from any one, two, three, four, or more of the following: a subcellular positioning signal, a DNA binding domain, a protease domain, a transcriptional activation domain, a transcriptional repression domain, a nuclease domain, a deaminase domain, a uracil DNA glycosylase domain (UDG), a uracil DNA glycosylase inhibitory domain (UGI), a DNA methyltransferase, a DNA demethylase, a histone methyltransferase, a histone demethylase, a transcription release factor, a histone acetylase domain, a histone deacetylase domain, a DNA ligase, an affinity tag, a reporter tag, an affinity domain, and a reporter domain.

In some embodiments, the homologous or heterologous functional domain comprises a transcriptional repressor. In some embodiments, the homologous or heterologous functional domain comprises a DNA methyltransferase. In some embodiments, the homologous or heterologous functional domain comprises a histone methyltransferase. In some embodiments, the homologous or heterologous functional domain comprises a histone domain. In some embodiments, the homologous or heterologous functional domain is selected from one, two, three, or more of the following: a transcriptional repressor, a DNA methyltransferase, a histone methyltransferase, and a histone domain.

In some embodiments, the transcriptional repressor is randomly selected from: Kruppel-associated Box (KRAB), Enhancer of Zeste Homolog 2 (EZH2), Zinc Finger Protein 57 (ZFP57), Zinc Finger Protein 445 (ZNF445), Tripartite Motif Containing 28 (TRIM28, also known as KAP1), Methyl-CpG Binding Protein (MeCP, such as MeCP2), Sin3 Interaction Domain (SID), Tandem Repeat of Sin3 Interaction Domain (SID4X), Methyl-CpG Binding Domain Protein 2 (MBD2), Methyl-CpG Binding Domain Protein 3 (MBD3), DNA Methyltransferase 1 (DNMT1), DNA Methyltransferase 3 Alpha (DNMT3A), DNA Methyltransferase 3 Beta (DNMT3B), RE1-Silencing Transcription Factor (REST), Neuron-Restrictive Silencer Factor (NRSF, alias for REST), TGF-β-Inducible Early Gene (TIEG, also known as KLF10), Corepressor of REST (CoREST), G9a (Euchromatic Histone-Lysine N-Methyltransferase 2, also known as EHMT2), Suppressor of Variegation 3-9 Homolog 1 (SUV39H1), SET Domain, Bifurcated 1 (SETDB1), Histone Deacetylase 1 (HDAC1), Histone Deacetylase 2 (HDAC2), Histone Deacetylase 3 (HDAC3), Silencing Mediator for Retinoid and Thyroid Hormone Receptors (SMRT), Nuclear Receptor Corepressor (NCoR), ERG-Associated Protein with SET Domain (ESET, also referred to as SETDB1), Zinc Finger and BTB Domain Containing 33 (ZBTB33, also known as KAISO), Viral Oncogene Homolog of Thyroid Hormone Receptor (v-ERB-A), Transducin Beta-Like 1 (TBL1), Transducin Beta-Like Related 1 (TBLR1), Lysine-Specific Histone Demethylase 1A (LSD1, also known as KDMIA), C-terminal Binding Protein 1 (CtBP1), C-terminal Binding Protein 2 (CtBP2), *Arabidopsis* Histone Deacetylase 2A (AtHD2A), BCL6 Corepressor (BCOR), Mesoderm Induction Early Response 1 (MIER1), Zinc Finger Protein 10 (ZNF10), Zinc Finger Protein 91 (ZNF91), Zinc Finger Protein 809 (ZFP809), Bromo Adjacent Homology Domain Containing 1 (BAHD1), Retinoblastoma Binding Protein 4 (RBBP4), Retinoblastoma Binding Protein 7 (RBBP7), Heterochromatin Protein 1 Alpha (HP1α, also known as CBX5), Heterochromatin Protein 1 Beta (HP1β, also known as CBX1), Chromobox Protein Homolog 3 (CBX3), Chromobox Protein Homolog 7 (CBX7), PR Domain Zinc Finger Protein 1 (PRDMI, also known as BLIMP-1), PR Domain Zinc Finger Protein 14 (PRDM14), Nuclear Receptor Corepressor 2 (NCOR2, also known as SMRT), Metastasis Associated 1 (MTA1), Metastasis Associated 2 (MTA2), Metastasis Associated 3 (MTA3), Chromodomain Helicase DNA Binding Protein 4 (CHD4), and Lysine Demethylase 5B, also known as JARID1B (KDM5B).

In some embodiments, the DNA methyltransferase is selected from DNMT3A, DNMT3B, DNMT3L, DRM, UHRF1, DNMT1, dim-2, M.Sssl, M.Pvull (N4C), DMS3, and T4Dam (N6C).

In some embodiments, the DNA methyltransferase is selected from DNA (Cytosine-5)-Methyltransferase 1 (DNMT1), DNA (Cytosine-5)-Methyltransferase 3 Alpha (DNMT3A), DNA (Cytosine-5)-Methyltransferase 3 Beta (DNMT3B), DNA (Cytosine-5)-Methyltransferase 3-Like (DNMT3L), tRNA Aspartic Acid Methyltransferase 1 (DNMT2), Ubiquitin-like with PHD and RING Finger Domains 1 (UHRF1), Ubiquitin-like with PHD and RING Finger Domains 2 (UHRF2), Helicase, Lymphoid Specific (HELLS, also known as LSH), Cell Division Cycle Associated 7 (CDCA7), Nuclear Protein 95 (NP95, the obsolete name of UHRF1), tRNA aspartic acid methyltransferase 1 (TRDMT1, alias for DNMT2), DNA (Cytosine-5)-Methyltransferase 3C (DNMT3C, a new type of DNA methyltransferase unique to mice, used for transposon silencing in male germ cells), and KIAA1429 (also known as VIRMA, which regulates m6A but may be related to methylation regulation). In some embodiments, the DNA methyltransferase is selected from Methyltransferase 1 (METI, functionally analogous to mammalian DNMT1), Chromomethylase 3 (CMT3, mediating CHG site methylation), Chromomethylase 2 (CMT2, mediating CHH methylation), Domains Rearranged Methyltransferase 1 (DRM1), and Domains Rearranged Methyltransferase 2 (DRM2, functionally analogous to mammalian DNMT3, mediating de novo methylation). In some embodiments, the DNA methyltransferase is selected from Repeat-Induced Point mutation defective protein (RID, involved in RIP mutation and DNA methylation) and Methyltransferase associated with sexual cycle 1 (Masc1). In some embodiments, the DNA methyltransferase is selected from CpG-specific DNA methyltransferase from Spiroplasma species (M.SssI, intended to be used as a model enzyme for specifically methylation of CpG sites), DNA adenine methyltransferase (Dam, an adenine methyltransferase for methylation of GATC sites, commonly used in prokaryotic regulation research), and DNA cytosine methyltransferase (Dcm, a cytosine methyltransferase for specifically methylation of the CCWGG sequence).

In some embodiments, the histone domain is selected from a histone H3 domain, a histone H2 domain, and a histone H4 domain. In some embodiments, the histone domain is selected from a histone H3 tail domain, a histone H2 tail domain, and a histone H4 tail domain.

In some embodiments of the present disclosure, the subcellular positioning signal is selected from a nuclear localization signal, a nuclear export signal, a mitochondrial localization signal, and a chloroplast localization signal.

In some embodiments, the fusion protein or conjugate comprises 1, 2, 3, 4, 5, 6, 7, 8, 9, or more homologous or heterologous functional domains, and the functional domains are identical or different.

In some embodiments, the fusion protein or conjugate connects 0, 1, 2, 3, 4, 5, 6, 7, 8, or more functional domains at the N-terminal and/or C-terminal of the Cas12 protein.

In some embodiments, the fusion protein comprises 1, 2, 3, 4, or more nuclear positioning signals.

In some embodiments, the fusion protein is used to achieve base editing, such as in conjunction with the guide polynucleotide to achieve the base editing. In some embodiments, the fusion protein comprises the nuclear positioning signal and the deaminase domain.

In some embodiments, the fusion protein comprises the nuclear positioning signal, a cytidine deaminase domain, and optionally 1 or 2 UGI domains. The fusion protein is used to achieve C→T base editing of the target nucleic acid.

In some embodiments, the fusion protein comprises the nuclear positioning signal and the adenosine deaminase domain. The fusion protein is used to achieve A→G base editing of the target nucleic acid.

In some embodiments, the fusion protein comprises the nuclear positioning signal, the cytidine deaminase domain, and the adenosine deaminase domain. In some embodiments, the fusion protein comprises 1, 2, or 3 nuclear positioning signals, and the deaminase domain. In some embodiments, the fusion protein comprises the UGI domain. In some embodiments, the fusion protein comprises 1, 2, or 3 nuclear positioning signals, the deaminase domain, and 1 or 2 UGI domains.

In some embodiments, the fusion protein is used to achieve the transcriptional activation of a specific target gene, such as in conjunction with the guide polynucleotide for achieving the transcriptional activation of the specific target gene. In some embodiments, the fusion protein comprises the nuclear positioning signal and the transcriptional activation domain.

In some embodiments, the fusion protein is used to achieve the transcriptional repression of a specific target gene, such as in conjunction with the guide polynucleotide for achieving the transcriptional repression of the specific target gene. In some embodiments, the fusion protein comprises the nuclear positioning signal and the transcriptional repression domain.

In some embodiments, the fusion protein is used to achieve methylation of a specific target sequence, such as in conjunction with the guide polynucleotide for achieving methylation of the specific target sequence. In some embodiments, the fusion protein comprises the nuclear positioning signal and the DNA methylation domain.

In some embodiments, the fusion protein is used to achieve demethylation of a specific target sequence, such as in conjunction with the guide polynucleotide for achieving demethylation of the specific target sequence. In some embodiments, the fusion protein comprises the nuclear positioning signal and the DNA demethylation domain.

In some embodiments, the nuclease domain comprises a polypeptide with an ssDNA cleavage activity and/or a polypeptide with a dsDNA cleavage activity.

In some embodiments, the nuclease domain comprises a polypeptide with an ssDNA cleavage activity.

In some embodiments, the nuclease domain comprises a polypeptide with a dsDNA cleavage activity.

In some embodiments, the Cas12 protein or inactivated Cas12 mutant is directly or indirectly linked to the homologous or heterologous functional domain.

In some embodiments, the direct linkage is a covalent linkage, and the indirect linkage is a linkage through an amino acid linker or a non-amino acid linker.

In some embodiments, the homologous or heterologous functional domain is fused or conjugated at the N-terminal, C-terminal, or internally with respect to the Cas12 protein or inactivated Cas12 mutant.

In the present disclosure, the fusion protein is obtained by connecting (1) to (2) through a peptide linker or directly connecting (1) to (2); and the conjugate is obtained by connecting (1) to (2) through a non-peptide chemical bond.

In some embodiments, the PAM sequence recognized by the fusion protein or the conjugate is the same as the PAM sequence recognized by the Cas12 protein.

In some embodiments, the PAM sequence (5'→3') recognized by the fusion protein or conjugate is selected from any one or more of the following: A, C, T, G, TA, TC, GN, AA, AG, TG, AN, GG, CG, TN, NT, NG, GT, NA, CC, AC, GC, AT, CT, GA, TT, CN, NC, CA, NTN, ANN, TTN, ATC, NAC, AGA, TGC, TCT, NGN, CGC, NTC, GCA, TCG, TTT, CCG, GGG, NAG, ACA, CGG, CNG, ACN, GTG, CNT, TTG, TCN, GGT, TNC, CCN, CGT, TGG, CGA, NGG, TCC, AGT, NCA, CAN, TCA, NNG, TAC, CCT, NTG, CGN, TGN, CAT, NGC, GNG, GNC, NNA, GAA, TTC, CTT, ATA, TAT, GCT, NCC, TTA, AGN, GNN, CAA, CAC, AGG, NTT, ANG, GNA, GTT, NGA, TAA, GTA, GGN, GNT, NCG, ATT, CCA, CNN, AAA, AAC, ATN, GAG, CTG, ACG, NAA, TAN, NAT, CNA, GCN, GTC, NCN, CTN, CNC, ANT, NNC, CAG, NAN, ATG, NCT, CCC, AAN, TGT, TNA, ACC, GAT, ACT, AAT, GGA, GAN, ANC, GAC, NNT, CTA, TNN, GCG, GTN, TNT, AAG, TAG, NGT, NTA, ANA, CTC, GCC, TGA, GGC, AGC, TNG, NGAA, GANC, GCNC, NTNT, TGGG, AAGG, AAGN, NTNN, TCGT, CNTG, NTGG, CCGN, ATAT, TGCA, NGGT, TGNT, NNTG, NCCG, ACAT, GNTG, CGCG, GACN, NTCG, TCNG, CTGC, TNNC, GGTN, CGNN, TCCA, AGCN, TNAG, GGAC, GATC, AANA, NATG, CCAG, NAAT, TCNT, CACT, CGGC, CGAN, CNCA, ATNT, NNNG, NGCT, CTGG, GGAN, NTNC, ATTC, AATG, CNTC, TGGN, NATC, GTCG, ACNC, GCNN, GACT, CTNT, NCTT, NAGG, NANC, CTTA, GTCT, ANAG, NGCN, CNNA, TCAG, ACAC, NCGG, TNNT, CAAG, ACCT, CCCA, GTNC, ANTC, GACC, AACG, TTAA, TCCG, CGCC, NCCN, TTNA, NCNT, NGCA, AGNN, AATC, GGGA, GNAN, NAGA, CGNA, GTAT, GTNA, ATNC, ACNA, GGAA, NTCC, GGCG, AATN, CNNT, AGGC, GCGN, GTGC, TTGA, AAGC, GAAG, ATNG, TGCT, TACT, CTAN, GGCT, GNGC, GTCN, CGAA, CNAC, GCCT, TAGG, ANGC, TNAA, GANT, NCNA, NCCT, AGAN, GTAA, TTTN, ATGA, TGNA, CANC, ACGA, CCAC, CCGG, CTNG, CNGN, GGTA, NGNC, GTTT, CTAA, TNCT, CTGN, NGAC, TGTA, TANN, GCNT, GCTC, CNCG, AAAN, CCNT, GANA, CACA, CTNA, ANTN, TTNT, CCTG, TNTT, CANA, NTAN, CACG, GGAT, TTTC, GNCG, TACA, GTAC, GAGC, ACNN, ATGG, AANT, ATCC, ACCG, AGNC, TGTT, NCAT, ATTA, GNTT, GAGN, TNAC, GCCG, NING, GTGG, GNGN, ACCA, NTAA, ACTN, NCTG, NCTA, TTTT, GONG, NTAG, CAAA, GGNA, CNTN, TTAG, TCTG, NCTN, TATG, GCGT, TANT, GGGT, NACN, ACTG, CCNG, GNNT, CCAT, GNTA, NANT, TACN, TGTN, ATCT, NCAN, TNGG, CNNN, AAGT, ATTN, GGNN, CAGC, CGTN, GCCC, GCTT, CNAT, NANA, CONN, GNGA, TNGN, GCAG, CGNG, CCTT, NGAG, NCNG, AANG, GGTC, ACTC, TGAA, NAGN, NNCA, ACGG, TGAC, TCCN, ANNN, TCGN, TAAN, CAGG, TTAN, NGAN, NTGC, CCNC, TNTN, ATGN, GTGN, GCAT, NNGN, NNCC, CCNA, CNAG, GNAC, CGNT, TTCN, TAGN, ANCT, NATN, GTGA, TNGT, CTAT, CCCG, TNCA, NGTA, NNGA, CGTG, TAAT, CGCA, NNCG, NGTC, NAGT, GNAT, TNTC, NCGC, NGGN, CATN, GTTN, AGTA, GNNG, TTNN, TGNC, NAAA, TNCC, CACC, CTCT, TTGN, GCTA, NTTT, TGAN, TNAN, NGAT, CCTN, GAAT, GTCA, NTCN, GCCA, ANTG, TGGC, CAAC, TTTA, TGTC, CGGA, NCGN, AGNT, NCGA, ANCG, ACAA, TAGT, CGAG, NCAA, AATA, AGGG, GNGT, CAGA, AGGT, GGGG, ANAC, TGGT, GTGT, GNCA, GTTA, NGTT, TNNG, NCAG, CACN, GCAN, GAAC, NCCA, TTCC, NCNN, GNNN, ANGT, NTNA, CCCT, GNAA, TTNG, GTNN, GGNG, TCTA, NCAC, GANG, TTCG, CCTC, CNGG, ANNA, TCAN, ATCG, NTGA, CGTA, TTAC, GCTN, GCTG, NGTG, TCCC, CANN, NNNA, TAGA, ACGT, AGAT, GATG, GCCN, TGNG, GCGC, CCGA, GNCN, NTTG, NNAT, TNCG, NANG, GGTG, NCCC, GNCC, CAAT, CGCN, CNGA, NTTC, TTCT, NGGA, AGTC, CNNC, NACG, AGTN, NANN, ACAG, GNCT, TACC, CNTA, TGTG, CATC, GACA, TCTT, NTCT, CTGA, AGGA, GATA, TNAT, CCTA, GGAG, ANCC, AANC, GTAN, GCNA, TGNN, TANC, GNTN, AGCG, CTAG, NNAA, AGTT, CTAC, TACG, TINC, TNTA, ANTT, ATAC, TCCT, TCAC, NGGC, NTTN, NNTC, CANT, ATAA, TGCC, CTCC, TNNA, GTNG, ACGN, GGCA, AAAG, TTGT, NGNA, NAAN, TATN, CGGG, CATA, ATGC, ACGC, ACCN, ATTT, TCNA, TNGC, NACA, NACC, CTCN, GGCC, TANG, AGAA, INGA, TAGC, CAGN, GGCN, ANNT, NNNC, TCAT, CATT, TAAA, ATGT, TGAG, CGCT, TCGG, GCAC, GTAG, NTCA, NATT, ANTA, CCCN, ACTA, AAAA, GAAN, TATT, NNAC, TGAT, GGGN, CCAA, GNGG, CCAN, GTCC, NNCT, AGNG, CNTT, CNCT, GANN, GGTT, AGCT, CATG, NTAC, TNCN, NNTN, TGGA, GATT, AGCA, TAAG, GCGA, ACTT, ANGN, NTGN, AACN, AACT, TCAA, NTAT, TCGA, NCTC, NNGG, ANGG, NNTT, GTNT, CTNN, CGGN, TAAC, GGNC, GAAA, ACNG, GNAG, TTGG, CTTC, CNGT, TNNN, TNTG, GTTG, TCNN, CGGT, GAGA, CNNG, NCNC, GAGG, AGCC, ATNN, NNNT, AGAC, AACC, ANNC, ANNG, ACAN, GTTC, TATA, GNTC, NCGT, NGNT, CGTC, CCGC, CGAC, GACG, ATTG, GNNC, CNAA, TATC, AGNA, CTNC, TTCA, ANCA, ACCC, AGTG, CCGT, ANAT, CTGT, GGGC, NTTA, NAAG, AANN, CNAN, NNCN, ANAA, ANAN, CTTG, NGNN, AGAG, TANA, TCNC, GCAA, NGNG, NAGC, NATA, ATCN, CGTT, CNGC, GATN, NNTA, AAGA, CTTT, AAAC, AGGN, ACNT, NTGT, CTTN, ATCA, NACT, NNAG, NGTN, NAAC, TGCG, GGNT, ATAN, TTGC, ANCN, CCCC, ANGA, NGCG, TCTC, CTCG, ATNA, AATT, NNAN, NNGT, TCGC, ATAG, CAAN, AACA, TTAT, CAGT, GNNA, TGCN, GCGG, NGGG, CANG, TTTG, GAGT, AAAT, CTCA, CNCN, CNCC, TCTN, CGNC, NGCC, CGAT, and NNGC.

N is A, T, C, or G.

In some embodiments, a PAM sequence recognized by the fusion protein is 5'-TTN-3'.

In some embodiments, a PAM sequence recognized by the fusion protein is 5'-TTNC-3'.

In some embodiments, a PAM sequence recognized by the fusion protein is 5'-WTN-3'.

In some embodiments, a PAM sequence recognized by the fusion protein is 5'-ATN-3'.

In some embodiments, a PAM sequence recognized by the fusion protein is 5'-TTN-3'.

In some embodiments, a PAM sequence recognized by the fusion protein is 5'-TTNC-3'.

In some embodiments, a PAM sequence recognized by the fusion protein is 5'-WTN-3'.

In some embodiments, a PAM sequence recognized by the fusion protein is 5'-ATN-3'.

Some embodiments of the present disclosure provide an isolated nucleic acid. The nucleic acid encodes the Cas12 protein, the inactivated Cas12 mutant, or the fusion protein or conjugate as described herein.

In some embodiments of the present disclosure, the nucleic acid encodes the Cas12 protein or the fusion protein as described herein.

In some embodiments, the nucleic acid is codon optimized for expression in cells.

In some embodiments, the nucleic acid is codon optimized for expression in a eukaryote, a mammal such as a human or non-human mammal, a plant, an insect, a bird, a reptile, a rodent (e.g., a mouse, a rat), a fish, a worm/nematode, or a yeast.

Some embodiments of the present disclosure provide a CRISPR-Cas12 system. In some embodiments, the CRISPR-Cas12 system comprises:

a. the Cas12 protein, the inactivated Cas12 mutant, the fusion protein or conjugate, or the isolated nucleic acid as described herein; and
b. a guide polynucleotide, or a polynucleotide sequence encoding the guide polynucleotide.

The Cas12 protein, the inactivated Cas12 mutant, or the fusion protein or conjugate forms a complex with the guide polynucleotide; and the guide polynucleotide comprises a guide sequence engineered to guide a sequence-specific binding of the complex to the target nucleic acid.

The isolated nucleic acid encodes the Cas12 protein, the inactivated Cas12 mutant, or the fusion protein or conjugate as described herein.

In some embodiments, the guide polynucleotide comprises a DR sequence linked to a guide sequence.

In some embodiments, the DR sequence has at least 50% sequence identity to the sequence shown in any one of SEQ ID NO: 54-583 or 704.

In some embodiments, the guide polynucleotide comprises a DR sequence linked to a guide sequence. Further, in some embodiments, the DR sequence has at least 50% sequence identity to the sequence shown in any one of SEQ ID NO: 54-583 or 704. In some embodiments, the DR sequence has at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity to the sequence shown in any one of SEQ ID NO: 54-583 or 704. Further, in some embodiments, the DR sequence comprises or is the sequence shown in any one of SEQ ID NO: 54-583 or 704.

In some embodiments, the guide sequence comprises 15-60 nucleotides. In some embodiments, the guide sequence comprises 15-50 nucleotides. In some embodiments, the guide sequence comprises 15-40 nucleotides. In some embodiments, the guide sequence comprises 15-35 nucleotides. In some embodiments, the guide sequence comprises 15-30 nucleotides. In some embodiments, the guide sequence comprises 15-25 nucleotides. In some embodiments, the guide sequence comprises 18-25 nucleotides. In some embodiments, the guide sequence comprises 20-25 nucleotides. In some embodiments, the guide sequence comprises 18-22 nucleotides. In some embodiments, the guide sequence comprises 20-22 nucleotides. In some embodiments, the guide sequence comprises 15, 16, 17, 18, 19, 20, 21, 22, 23, 24, 25, 26, 27, 28, 29, 30, 31, 32, 33, 34, 35, 36, 37, 38, 39, or 40 nucleotides.

In some embodiments, the guide sequence hybridizes to the target nucleic acid, and the guide sequence is 90%-100% complementary to the target nucleic acid.

In some embodiments, the guide sequence hybridizes to the target nucleic acid.

In some embodiments, the guide sequence hybridizes to the target nucleic acid, and the guide sequence is mismatched to the target nucleic acid by no more than one nucleotide.

In some embodiments, the DR sequence comprises 15-100 nucleotides. In some embodiments, the DR sequence comprises 15-90 nucleotides. In some embodiments, the DR sequence comprises 15-80 nucleotides. In some embodiments, the DR sequence comprises 15-70 nucleotides. In some embodiments, the DR sequence comprises 15-60 nucleotides. In some embodiments, the guide sequence comprises 15-50 nucleotides. In some embodiments, the guide sequence comprises 15-40 nucleotides. In some embodiments, the guide sequence comprises 20-40 nucleotides. In some embodiments, the guide sequence comprises 20-30 nucleotides. In some embodiments, the guide sequence comprises 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides.

In some embodiments, the guide sequence is located at the 3' end of the DR sequence.

In some embodiments, the guide sequence is located at the 5' end of the DR sequence.

In some embodiments, the guide polynucleotide further comprises the tracrRNA.

In some embodiments of the present disclosure, the tracrRNA sequence has at least 50% sequence identity to the sequence shown in any one of SEQ ID NO: 584-695. In some embodiments of the present disclosure, the tracrRNA sequence has at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity to the sequence shown in any one of SEQ ID NO: 584-695.

In some embodiments, the tracrRNA is complementarily paired with the DR sequence. In general, the complementary pairing is complementary pairing for partial bases. In some embodiments, the tracrRNA interacts with the DR sequence.

In some embodiments, the tracrRNA sequence is linked to the DR sequence. In some embodiments, the tracrRNA sequence is linked to the DR sequence by a nucleotide sequence. In some embodiments, the tracrRNA sequence is linked to the DR sequence by the nucleotide sequence including 1-10 nucleotides. In some embodiments, the tracrRNA sequence is linked to the DR sequence by the nucleotide sequence including 1, 2, 3, 4, 5, 6, 7, 8, 9, or 10 nucleotides. In some embodiments, the tracrRNA sequence is linked to the DR sequence by the nucleotide sequence including 4 nucleotides. In some embodiments, the tracrRNA sequence is linked to the DR sequence by a 5'-GAAA-3' sequence.

In some embodiments, the tracrRNA sequence is located at the 3' end of the DR sequence.

In some embodiments, the tracrRNA sequence is located at the 5' end of the DR sequence.

In some embodiments, the tracrRNA comprises 10-200 nucleotides. In some embodiments, the tracrRNA comprises 10-190, 10-180, 10-170, 10-160, 10-150, 10-140, 10-130, 10-120, 10-110, 10-100, 10-90, 10-80, 10-70, 10-60, 10-50, 10-40, 10-30, 10-20, 20-100, 30-100, 40-100, 20-90, 20-80, 20-70, 20-60, 20-50, or 30-50 nucleotides. In some embodiments, the tracrRNA comprises 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides.

In some embodiments, the guide polynucleotide is the guide polynucleotide as described herein.

In some embodiments, the target nucleic acid is DNA or RNA. In some embodiments, dsDNA or ssDNA.

In some embodiments, the DNA is the eukaryotic DNA. In some embodiments, the eukaryotic DNA is non-human mammalian DNA, non-human primate DNA, human DNA, plant DNA, insect DNA, bird DNA, reptile DNA, rodent DNA, fish DNA, worm/nematode DNA, or yeast DNA.

In some embodiments, the target nucleic acid is a disease or a condition-related gene or a signaling biochemical pathway-related gene, or the target nucleic acid is a reporter gene. For example, the disease or disorder is a hematologic disease or disorder, an ophthalmic disease or disorder, a neurological disease or disorder, a respiratory disease or disorder, a hepatic disease or disorder, a metabolic disease or disorder, a cancer, or an infectious disease.

In some embodiments, the target nucleic acid is a gene as listed in Table 27.

In some embodiments, the target nucleic acid is a disease or disorder related gene, the disease or disorder being selected from: hemophilia A, Best yolk-like macular dystrophy, B-cell acute lymphoblastic leukemia, hemophilia B, CDKL5 deficiency, CLN2 disease, Niemann-Pick disease type C, Dravet syndrome, FOXG1 syndrome, GM1ganglioside storage disease, GM2 ganglioside deposition disease, HIV infection, HSV infection, Usher syndrome type IB, Usher syndrome type IIA, Mucopolysaccharidosis type IIIA, Mucopolysaccharidosis type IIIB, Gaucher disease type III, Mucopolysaccharidosis type II, type II diabetes, Mucopolysaccharidosis type IV, Gaucher disease type I, Mucopolysaccharidosis type I, type I diabetes, Usher syndrome type I, KCNQ2 epileptic encephalopathy, Leber hereditary optic neuropathy, Leigh syndrome, Prader-Willi syndrome, SLC13A5 deficiency, X-linked myotubular myopathy, X-linked retinoschisis, X-linked retinitis pigmentosa, α1-antitrypsin deficiency, α-mannoside storage disease, α-thalassemia, β-thalassemia, Alzheimer's disease, Bardet-Biedl syndrome, white dot retinal degeneration, leukocyte adhesion deficiency type I, galactosemia, bladder cancer, overactive bladder, phenylketonuria, nasopharyngeal carcinoma, Bietti's crystalline dystrophy, pyruvate kinase deficiency, erectile dysfunction, autosomal recessive congenital ichthyosis, adult glucan body disease, traumatic arthritis, homozygous familial hypercholesterolemia, Fragile X syndrome, thalassemia, hypophosphatasia, epilepsy, multiple myeloma, multiple system atrophy, frontotemporal dementia, catecholamine-sensitive polymorphic ventricular tachycardia, Fabry's disease, Fanconi's anemia, aromatic L-amino acid decarboxylase deficiency, radiation-induced xerostomia, non-Hodgkin's lymphoma, non-muscle invasive bladder carcinoma, non-alcoholic fatty liver disease, non-small cell lung cancer, hypertrophic cardiomyopathy, hypertrophic scar, obesity, peroneal muscular dystrophy type 1A, peroneal muscular dystrophy type 2A, pulmonary hypertension, Friedrich's ataxia, peritoneal carcinoma, liver cancer, hepatocellular carcinoma, dry age-related macular degeneration, sicca syndrome, hyperuricemia, hyperlipidemia, Gaucher disease, autism spectrum disorders, osteoarthritis, bone marrow failure syndromes, citrullinemia type I, coronary heart disease, cystinosis, melanoma, Huntington's disease, amyotrophic lateral sclerosis, urge incontinence, acute intermittent porphyria, acute lymphoblastic leukemia, spinal cerebellar ataxia, spinal muscular atrophy with respiratory distress type 1, spinal muscular atrophy, Tay-Sachs disease, methylmalonic acidemia, thyroid carcinoma, pseudohypertrophic muscular dystrophy, anaplastic astrocytoma, intermittent claudication, junctional epidermolysis bullosa, glioma, glioblastoma, corneal graft rejection, colorectal cancer, progressive multifocal leukoencephalopathy, progressive familial intrahepatic cholestasis, giant-axonal neuropathy, Canavan's disease, cocaine addiction, Klaber's disease, Kriegler-Najjar syndrome, oral cancer, Angelman syndrome, diffuse intrinsic pontine glioma, Lafora's disease, rheumatoid arthritis, sickle cell disease, lymphedema, ovarian cancer, chronic lymphocytic leukemia, chronic granulomatous disease, chronic nephrogenic anemia, chronic pain, chronic hepatitis B, Menkes' disease, cystic fibrosis, Netherseton's syndrome, ornithine transcarbamylase deficiency, Parkinson's disease, Pompe's disease, uveitis, prostate cancer, vestibular schwannoma, ankylosing muscular dystrophy, ankylosing spondylitis, castration-resistant prostate cancer, glaucoma, achromatopsia, ischemic heart failure, lysosomal storage disease, sarcoma, breast cancer, Rett's syndrome, triple-negative breast cancer, Sandhoff's disease, color blindness, heart failure with reduced ejection fraction, neuronal ceroid lipofuscinosis, adrenoleukodystrophy, renal cell carcinoma, wet age-related macular degeneration, eczema, thrombocytopenia with immunodeficiency syndrome, esophageal cancer, optic neuropathy, optic nerve atrophy, retinal vein occlusion, retinitis pigmentosa, rhodopsin-mediated autosomal dominant retinitis pigmentosa, ependymoma, fallopian tube carcinoma, bilateral vestibulopathies, Stargardt's disease, diabetic macular edema, diabetic neuropathy, diabetic retinopathy, diabetic peripheral neuralgia, diabetic foot, glycogenosis, glycogenosis type Ia, glycogenosis type IIb, atopic dermatitis, hearing loss, hearing impairment, head and neck cancer, squamous cell carcinoma of the head and neck, Wilson's disease, stable angina pectoris, Usher's syndrome, choroideremia, Leber's congenital amaurosis, congenital adrenal hyperplasia, cardiomyopathy, angina pectoris, heart failure, COVID-19 infection, pleural mesothelioma, acne vulgaris, severe combined immunodeficiency diseases, severe limb ischemia, oculopharyngeal muscular dystrophy, pancreatic cancer, graft-versus-host disease, hereditary retinal dystrophy, hereditary angioedema, hepatitis B, heterotrophic cerebral leukoencephalic dystrophy, psoriatic arthritis, recessive genetic dystrophic epidermolysis bullosa, infantile malignant osteosclerosis, dystrophic epidermolysis bullosa, morphea, primary immune deficiency, heterozygous familial hypercholesterolemia, limb-girdle muscular dystrophy type 2B, limb-girdle muscular dystrophy type 2C, limb-girdle muscular dystrophy type 2D, limb-girdle muscular dystrophy type 2E, limb-girdle muscular dystrophy type 2I, limb-girdle muscular dystrophy type 2L, limb ischemic disease, lipoprotein lipase deficiency, severe congenital neutrophilic dysphoria, wrinkles, stroke, sciatica, schizophrenia, depression, drug addiction, autism, idiopathic pulmonary fibrosis, hyperlipidemia, transthyretin (ATTR) amyloidosis, alpha-1-antitrypsin deficiency (AATD) liver disease, and AATD lung disease.

In some embodiments, genes associated with ATTR amyloidosis comprise, but are not limited to, ATTR.

Genes associated with Leber hereditary optic neuropathy comprise, but are not limited to, MT-ND4.

Genes associated with the AATD liver disease comprise, but are not limited to, AATD.

Genes associated with the AATD lung disease comprise, but are not limited to, AATD.

Genes associated with the graft-versus-host disease comprise, but are not limited to, thymidine kinase genes.

Genes associated with hereditary retinal dystrophy comprise, but are not limited to, RPE65.

Genes associated with spinal muscular atrophy comprise, but are not limited to, SMN1.

Genes associated with osteoarthritis comprise, but are not limited to, TGF-β1.

Genes associated with hemophilia A comprise, but are not limited to, factor VIII.

Genes associated with hemophilia B comprise, but are not limited to, factor IX.

Genes associated with cystic fibrosis comprise, but are not limited to, CFTR.

Genes associated with Parkinson's disease comprise, but are not limited to, Gad1, Gad2, PTBP1, KEAP1, RE1, Amigo1, Gprc5c, Let-7a, Pnky, LRRK2, SNCA, GBA, miR-92b, miR-9, miR-124, miR-181, HMGB1, TRIM72, GPNMB, and REST.

Genes associated with Usher syndrome comprise, but are not limited to, USH2A.

Genes associated with α-thalassemia, β-thalassemia, and sickle cell disease comprise, but are not limited to, BCL11A, HBG, HBA, and HBB.

Genes associated with pulmonary hypertension comprise, but are not limited to, eNOS.

Genes associated with Stargardt's disease comprise, but are not limited to, ABCA4.

Genes associated with age-related macular degeneration comprise, but are not limited to, VEGFA, VEGFR, IL17, Kir7.1, LCN-2, IRAK-M, CD59, LTA4H, GPX4, GLS1, PAPP-A, cGAS, STING, mTOR, GCN2, Nrf2, Ang 2, CTGF, complement C3, complement C5, CHFR4b, DOCK6, CTSS, ELN, and FGF2.

Genes associated with glaucoma comprise, but are not limited to, AQP1, ADRB2, NMNTA2, NRP1, Hrh1, Anxa2, OPA1, Cx43, ANGPTL7, MYOC, ROCK, ROCK2, TIMP1, TIMP2, TIMP3, TIMP4, carbonic anhydrase CA2, carbonic anhydrase CA4, and carbonic anhydrase CA12.

Genes associated with idiopathic pulmonary fibrosis comprise, but are not limited to, CTGF.

Genes associated with hyperlipidemia comprise, but are not limited to, PCSK9.

Genes associated with Alzheimer's disease comprise, but are not limited to, NGF.

Genes associated with coronary heart disease comprise, but are not limited to, VEGFA and bFGF Genes associated with chronic nephrogenic anemia comprise, but are not limited to, EPO.

Genes associated with congenital amaurosis comprise, but are not limited to, RPE65.

Genes associated with retinitis pigmentosa comprise, but are not limited to, PDE6B.

Genes associated with phenylketonuria comprise, but are not limited to, PAH.

Genes associated with epilepsy comprise, but are not limited to, GAT1.

Some embodiments of the present disclosure provide a vector system. The vector system comprises one or more recombinant vectors. The recombinant vectors comprise the isolated nucleic acid or the CRISPR-Cas12 system as described herein.

In some embodiments, the recombinant vector further comprises a regulatory sequence.

In some embodiments, the vector system comprises one or more recombinant vectors comprising a polynucleotide sequence encoding the Cas12 protein, the inactivated Cas12 mutant, or the fusion proteins or conjugate as described herein and a polynucleotide sequence encoding the guide polynucleotide.

In some embodiments, the polynucleotide sequence encoding the Cas12 protein, the inactivated Cas12 mutant, or the fusion protein or conjugate is operably linked to the regulatory sequence 1.

In some embodiments, the polynucleotide sequence encoding the guide polynucleotide is operably linked to the regulatory sequence 2.

Further, in some embodiments, the regulatory sequence 1 is the same as or different from the regulatory sequence 2.

In some embodiments, the regulatory sequence is optionally selected from one or more of: a promoter, an enhancer, an internal ribosome entry site, and a transcription termination signal. The promoter comprises a constitutive promoter, an inducible promoter, a broad-spectrum promoter, or a tissue-specific promoter, and/or the transcriptional termination signal comprises a polyadenylation signal or a poly-U sequence.

In some embodiments, a scaffold of the one or more recombinant vectors is an adeno-associated virus vector, a lentiviral vector, or a virus-like particle.

In some embodiment of the present disclosure, when the scaffold is the adeno-associated virus vector, the adeno-associated virus vector is a recombinant adeno-associated virus vector of serotype AAV1, AAV2, AAV4, AAV5, AAV6, AAV7, AAVrh74, AAV8, AAV9, AAV10, AAV11, AAV12, or AAV13; when the scaffold is the lentiviral vector, the lentiviral vector is pseudotyped with an envelope protein; in some embodiments, the isolated nucleic acid is linked to an aptamer sequence; and when the scaffold is the virus-like particle, the isolated nucleic acid is linked to a gene encoding a gag protein.

Some embodiments of the present disclosure provide a delivery system. The delivery system comprises (1) a delivery tool, and (2) the Cas12 protein, the guide polynucleotide, the inactivated Cas12 mutant, the fusion protein or conjugate, the isolated nucleic acid, the CRISPR-Cas12 system, or the vector system as described herein.

In some embodiments, the delivery tool is a virus, a lipid nanoparticle, a nanoparticle, a liposome, an exosome, a microbubble, or a gene gun.

In some embodiments, the delivery tool is the lipid nanoparticle comprising the guide polynucleotide and mRNA encoding the Cas 12 protein, the inactivated Cas 12 mutant, or the fusion protein or conjugate.

Some embodiments of the present disclosure provide a cell comprising the Cas 12 protein, the guide polynucleotide, the inactivated Cas12 mutant, the fusion protein or conjugate, the isolated nucleic acid, the CRISPR-Cas12 system, or the vector system as described herein.

In some embodiments of the present disclosure, the cell is a prokaryotic cell.

In some embodiments of the present disclosure, the cell is a eukaryotic cell.

In some embodiments of the present disclosure, the eukaryotic cell is a mammalian cell.

Some embodiments of the present disclosure provide a pharmaceutical composition, wherein the pharmaceutical composition comprises the Cas12 protein, the guide polynucleotide, the inactivated Cas 12 mutant, the fusion protein or conjugate, the nucleic acid, the CRISPR-Cas12 system, the vector system, the delivery system, or the cell as described herein.

In some embodiments, the pharmaceutical composition further comprises pharmaceutically acceptable excipients.

Some embodiments of the present disclosure provide a kit, wherein the kit comprises the Cas12 protein, the guide polynucleotide, the inactivated Cas12 mutant, the fusion protein or conjugate, the isolated nucleic acid, the CRISPR-Cas12 system, the vector system, the delivery system, or the cell as described herein.

In some embodiments, the kit further comprises a cut buffer. The cut buffer is any buffer known in the art suitable for cleaving the target nucleic acid by the Cas12 protein.

Some embodiments of the present disclosure provide a use of the Cas12 protein, the guide polynucleotide, the inactivated Cas12 mutant, the fusion protein or conjugate, the nucleic acid, the CRISPR-Cas12 system, the vector system, the delivery system, the cell, the pharmaceutical composition, or the kit as described herein in preparing a reagent or medicament for diagnosing, treating, or preventing a disease or disorder associated with a target nucleic acid, In some embodiments, the disease or disorder is a hematologic disease or disorder, an ophthalmic disease or disorder, a neurological disease or disorder, a respiratory disease or disorder, a hepatic disease or disorder, a metabolic disease or disorder, a cancer, or an infectious disease. In some embodiments, the reagent or medicament is used to: cleave one or more target nucleic acid molecules or introduce nicks into the one or more target nucleic acid molecules, activate or upregulate an expression of the one or more target nucleic acid molecules, activate or inhibit transcription of the one or more target nucleic acid molecules, inactivate the one or more target nucleic acid molecules, visualize, label, or detect the one or more target nucleic acid molecules, bind the one or more target nucleic acid molecules, transport the one or more target nucleic acid molecules, and mask the one or more target nucleic acid molecules.

In some embodiments, the target nucleic acid is optionally selected from the genes as listed in Table 27, and the disease or disorder is the disease or disorder as listed in Table 27.

In some embodiments, the disease or disorder is selected from: hemophilia A, Best yolk-like macular dystrophy, B-cell acute lymphoblastic leukemia, hemophilia B, CDKL5deficiency, CLN2 disease, Niemann-Pick disease type C, Dravet syndrome, FOXG1syndrome, GM1 ganglioside storage disease, GM2 ganglioside deposition disease, HIV infection, HSV infection, Usher syndrome type IB, Usher syndrome type IIA, Mucopolysaccharidosis type IIIA, Mucopolysaccharidosis type IIIB, Gaucher disease type III, Mucopolysaccharidosis type II, type II diabetes, Mucopolysaccharidosis type IV, Gaucher disease type I, Mucopolysaccharidosis type I, type I diabetes, Usher syndrome type I, KCNQ2 epileptic encephalopathy, Leber hereditary optic neuropathy, Leigh syndrome, Prader-Willi syndrome, SLC13A5deficiency, X-linked myotubular myopathy, X-linked retinoschisis, X-linked retinitis pigmentosa, α1-antitrypsin deficiency, α-mannoside storage disease, α-thalassemia, β-thalassemia, Alzheimer's disease, Bardet-Biedl syndrome, white dot retinal degeneration, leukocyte adhesion deficiency type I, galactosemia, bladder cancer, overactive bladder, phenylketonuria, nasopharyngeal carcinoma, Bietti's crystalline dystrophy, pyruvate kinase deficiency, erectile dysfunction, autosomal recessive congenital ichthyosis, adult glucan body disease, traumatic arthritis, homozygous familial hypercholesterolemia, Fragile X syndrome, thalassemia, hypophosphatasia, epilepsy, multiple myeloma, multiple system atrophy, frontotemporal dementia, catecholamine-sensitive polymorphic ventricular tachycardia, Fabry's disease, Fanconi's anemia, aromatic L-amino acid decarboxylase deficiency, radiation-induced xerostomia, non-Hodgkin's lymphoma, non-muscle invasive bladder carcinoma, non-alcoholic fatty liver disease, non-small cell lung cancer, hypertrophic cardiomyopathy, hypertrophic scar, obesity, peroneal muscular dystrophy type 1A, peroneal muscular dystrophy type 2A, pulmonary hypertension, Friedrich's ataxia, peritoneal carcinoma, liver cancer, hepatocellular carcinoma, dry age-related macular degeneration, sicca syndrome, hyperuricemia, hyperlipidemia, Gaucher disease, autism spectrum disorders, osteoarthritis, bone marrow failure syndromes, citrullinemia type I, coronary heart disease, cystinosis, melanoma, Huntington's disease, amyotrophic lateral sclerosis, urge incontinence, acute intermittent porphyria, acute lymphoblastic leukemia, spinal cerebellar ataxia, spinal muscular atrophy with respiratory distress type 1,spinal muscular atrophy, Tay-Sachs disease, methylmalonic acidemia, thyroid carcinoma, pseudohypertrophic muscular dystrophy, anaplastic astrocytoma, intermittent claudication, junctional epidermolysis bullosa, glioma, glioblastoma, corneal graft rejection, colorectal cancer, progressive multifocal leukoencephalopathy, progressive familial intrahepatic cholestasis, giant-axonal neuropathy, Canavan's disease, cocaine addiction, Klaber's disease, Kriegler-Najjar syndrome, oral cancer, Angelman syndrome, diffuse intrinsic pontine glioma, Lafora's disease, rheumatoid arthritis, sickle cell disease, lymphedema, ovarian cancer, chronic lymphocytic leukemia, chronic granulomatous disease, chronic nephrogenic anemia, chronic pain, chronic hepatitis B, Menkes' disease, cystic fibrosis, Netherseton's syndrome, ornithine transcarbamylase deficiency, Parkinson's disease, Pompe's disease, uveitis, prostate cancer, vestibular schwannoma, ankylosing muscular dystrophy, ankylosing spondylitis, castration-resistant prostate cancer, glaucoma, achromatopsia, ischemic heart failure, lysosomal storage disease, sarcoma, breast cancer, Rett's syndrome, triple-negative breast cancer, Sandhoff's disease, color blindness, heart failure with reduced ejection fraction, neuronal ceroid lipofuscinosis, adrenoleukodystrophy, renal cell carcinoma, wet age-related macular degeneration, eczema, thrombocytopenia with immunodeficiency syndrome, esophageal cancer, optic neuropathy, optic nerve atrophy, retinal vein occlusion, retinitis pigmentosa, rhodopsin-mediated autosomal dominant retinitis pigmentosa, ependymoma, fallopian tube carcinoma, bilateral vestibulopathies, Stargardt's disease, diabetic macular edema, diabetic neuropathy, diabetic retinopathy, diabetic peripheral neuralgia, diabetic foot, glycogenosis, glycogenosis type Ia, glycogenosis type IIb, atopic dermatitis, hearing loss, hearing impairment, head and neck cancer, squamous cell carcinoma of the head and neck, Wilson's disease, stable angina pectoris, Usher's syndrome, choroideremia, Leber's congenital amaurosis, congenital adrenal hyperplasia, cardiomyopathy, angina pectoris, heart failure, COVID-19 infection, pleural mesothelioma, acne vulgaris, severe combined immunodeficiency diseases, severe limb ischemia, oculopharyngeal muscular dystrophy, pancreatic cancer, graft-versus-host disease, hereditary retinal dystrophy, hereditary angioedema, hepatitis B, heterotrophic cerebral leukoencephalic dystrophy, psoriatic arthritis, recessive genetic dystrophic epidermolysis bullosa, infantile malignant osteosclerosis, dystrophic epidermolysis bullosa, morphea, primary immune deficiency, heterozygous familial hypercholesterolemia, limb-girdle muscular dystrophy type 2B, limb-girdle muscular dystrophy type 2C, limb-girdle muscular dystrophy type 2D, limb-girdle muscular dystrophy type 2E, limb-girdle muscular dystrophy type 2I, limb-girdle muscular dystrophy type 2L, limb ischemic disease, lipoprotein lipase deficiency, severe congenital neutrophilic dysphoria, wrinkles, stroke, sciatica, schizophrenia, depression, drug addiction, autism, idiopathic pulmonary fibrosis, hyperlipidemia, transthyretin (ATTR) amyloidosis, alpha-1-antitrypsin deficiency (AATD) liver disease, and AATD lung disease.

In some embodiments, genes associated with the ATTR amyloidosis comprise, but is not limited to, ATTR.

Genes associated with the Leber hereditary optic neuropathy comprise, but are not limited to, MT-ND4.

Genes associated with the AATD liver disease comprise, but are not limited to, AATD.

the genes associated with the AATD lung disease comprise, but are not limited to, AATD.

Genes associated with the graft-versus-host disease comprise, but are not limited to, thymidine kinase genes.

Genes associated with the hereditary retinal dystrophy comprise, but are not limited to, RPE65.

Genes associated with the spinal muscular atrophy comprise, but are not limited to, SMN1.

Genes associated with the osteoarthritis comprise, but are not limited to, TGF-β1.

Genes associated with the hemophilia A comprise, but are not limited to, factor VIII.

Genes associated with the hemophilia B comprise, but are not limited to, factor IX.

Genes associated with the cystic fibrosis comprise, but are not limited to, CFTR.

Genes associated with the Parkinson's disease comprise, but are not limited to, Gad1, Gad2, PTBP1, KEAP1, RE1, Amigo1, Gprc5c, Let-7a, Pnky, LRRK2, SNCA, GBA gene, miR-92b, miR-9, miR-124, miR-181, HMGB1, TRIM72, GPNMB, and REST.

Genes associated with Usher syndrome comprise, but are not limited to, USH2A.

Genes associated with α-thalassemia, β-thalassemia, and sickle cell disease comprise, but are not limited to, BCL11A, HBG, HBA, and HBB.

Genes associated with the pulmonary hypertension comprise, but are not limited to, eNOS. Genes associated with the Stargardt's disease comprise, but are not limited to, ABCA4.

Genes associated with the age-related macular degeneration comprise, but are not limited to, VEGFA, VEGFR, IL17, Kir7.1, LCN-2, IRAK-M, CD59, LTA4H, GPX4, GLS1, PAPP-A, cGAS, STING, mTOR, GCN2, Nrf2, Ang 2, CTGF, complement C3, complement C5, CHFR4b, DOCK6, CTSS, ELN, and FGF2.

Genes associated with the glaucoma comprise, but are not limited to, AQP1, ADRB2, NMNTA2, NRP1, Hrh1, Anxa2, OPA1, Cx43, ANGPTL7, MYOC, ROCK1, ROCK2, TIMP1, TIMP2, TIMP3, TIMP4, carbonic anhydrase CA2, carbonic anhydrase CA4, and carbonic anhydrase CA12.

Genes associated with the idiopathic pulmonary fibrosis comprise, but are not limited to, CTGF.

Genes associated with cardiovascular diseases such as hyperlipidemia comprise, but are not limited to, PCSK9 (Proprotein Convertase Subtilisin/Kexin Type 9), ANGPTL3 (Angiopoietin Like 3), LPA (Lipoprotein (a)), APOC3 (Apolipoprotein C3), and APOB (Apolipoprotein B). Genes associated with hypertension comprise, but are not limited to, AGT (Angiotensinogen). Genes associated with ATTR comprise, but are not limited to, TTR (Transthyretin). Genes associated with obesity comprise, but are not limited to, INHBE (Inhibin Subunit Beta E).

Genes associated with the Alzheimer's disease comprise, but are not limited to, NGF.

Genes associated with the coronary heart disease comprise, but are not limited to, VEGFA and bFGF.

Genes associated with the chronic nephrogenic anemia comprise, but are not limited to, EPO.

Genes associated with the congenital amaurosis comprise, but are not limited to, RPE65.

Genes associated with the retinitis pigmentosa comprise, but are not limited to, PDE6B.

Genes associated with the phenylketonuria comprise, but are not limited to, PAH.

Genes associated with the epilepsy comprise, but are not limited to, GAT1.

Some embodiments of the present disclosure provide a method for detecting, binding, or cleaving a target nucleic acid, comprising: using the Cas12 protein, the guide polynucleotide, the inactivated Cas12 mutant, the fusion protein or conjugate, the nucleic acid, the CRISPR-Cas12 system, the vector system, the delivery system, the cell, the pharmaceutical composition, or the kit as described herein to contact the target nucleic acid.

In some embodiments, the method is for non-diagnostic and/or non-therapeutic purposes; and/or the fusion protein or conjugate comprises a detectable marker, such as a marker detectable by fluorescence, DNA blotting, or FISH.

In some embodiments, when the method is for cleaving the target nucleic acid, the method further comprises performing a cleavage reaction using a cut buffer. The cut buffer may be any buffer known in the art suitable for cleaving the target nucleic acid by the Cas12 protein.

Some embodiments of the present disclosure provide is a method for altering a cell state, comprising using the Cas12 protein, the guide polynucleotide, the inactivated Cas12 mutant, the fusion protein or conjugate, the isolated nucleic acid, the CRISPR-Cas12 system, the vector system, the delivery system, the cell, the pharmaceutical composition, or the kit as described herein to contact the cell to alter a cell state.

In some embodiments of the present disclosure, the method results in one or more of: an increase or decrease in an expression of a specific gene, an induction of cellular senescence in vitro or in vivo, an induction of cellular cycle arrest in vitro or in vivo, a cellular growth promotion and/or a cellular growth inhibition in vitro or in vivo, an induction of anergy in vitro or in vivo, an induction of apoptosis in vitro or in vivo, and an induction of necrosis in vitro or in vivo.

In some embodiments, the method is for non-diagnostic and/or non-therapeutic purposes.

Some embodiments of the present disclosure provide a method for diagnosing, treating, or preventing a disease or disorder associated with a target nucleic acid, comprising applying the Cas12 protein, the guide polynucleotide, the inactivated Cas12 mutant, the fusion protein or conjugate, the isolated nucleic acid, the CRISPR-Cas12 system, the vector system, the delivery system, the cell, the pharmaceutical composition, or the kit as described herein to a sample from a subject in need or the subject in need.

In some embodiments, the target nucleic acid is optionally selected from genes as listed in Table 27, and the disease or disorder is the disease or disorder as listed in Table 27.

In some embodiments, the disease or disorder is a hematologic disease or disorder, an ophthalmic disease or disorder, a neurological disease or disorder, a respiratory disease or disorder, a hepatic disease or disorder, a metabolic disease or disorder, a cancer, or an infectious disease.

Some embodiments of the present disclosure provide a use of the Cas12 protein, the guide polynucleotide, the inactivated Cas12 mutant, the fusion proteins or conjugate, the isolated nucleic acid, the CRISPR-Cas12 system, the vector system, the delivery system, the cell, the pharmaceutical composition, or the kit as described herein in diagnosing, treating, or preventing a disease or disorder associated with the target nucleic acid.

In some embodiments, the target nucleic acid is optionally selected from genes as listed in Table 27, and the disease or disorder is the disease or disorder as listed in Table 27.

In some embodiments, the disease or disorder is a hematologic disease or disorder, an ophthalmic disease or disorder, a neurological disease or disorder, a respiratory disease or disorder, a hepatic disease or disorder, a metabolic disease or disorder, a cancer, or an infectious disease.

On the basis of conforming to the common knowledge in the field, the above preferred conditions may be arbitrarily combined, thereby obtaining the preferred embodiments of the present disclosure.

BRIEF DESCRIPTION OF THE DRAWINGS

FIG. 1B shows the proteins according to some embodiments of the present disclosure;

Figure 2:
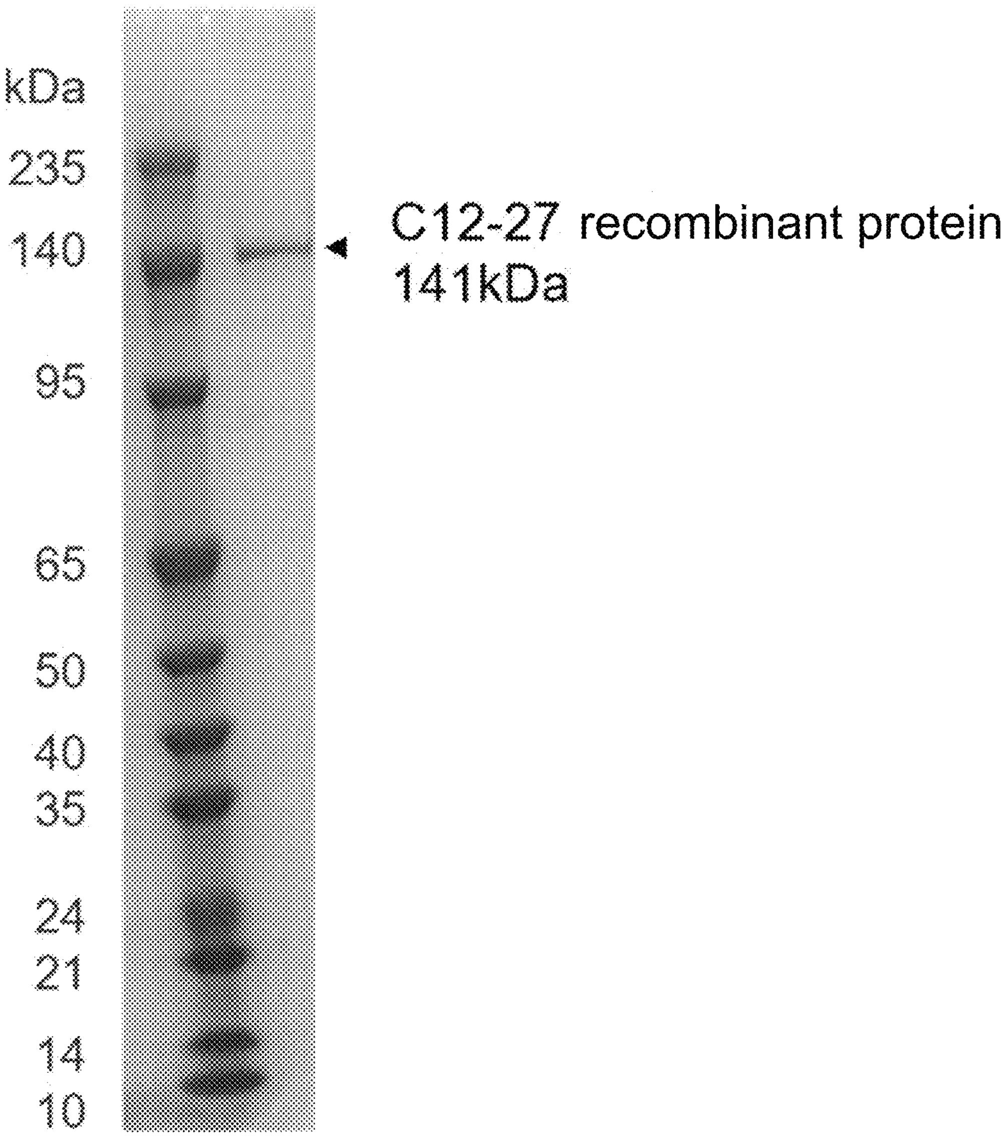
Figure 3:
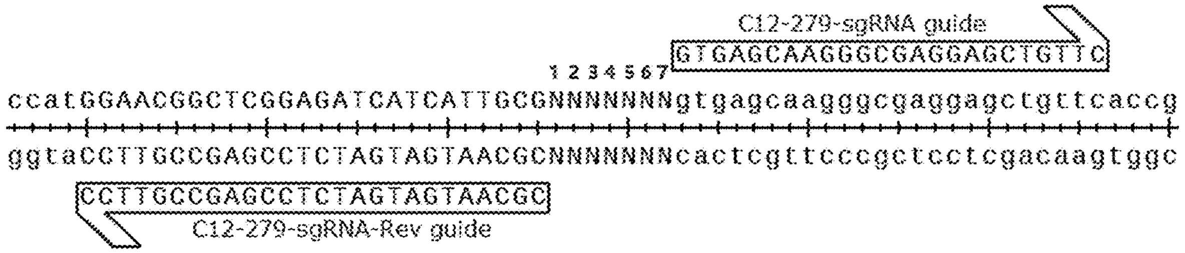
Figure 4:
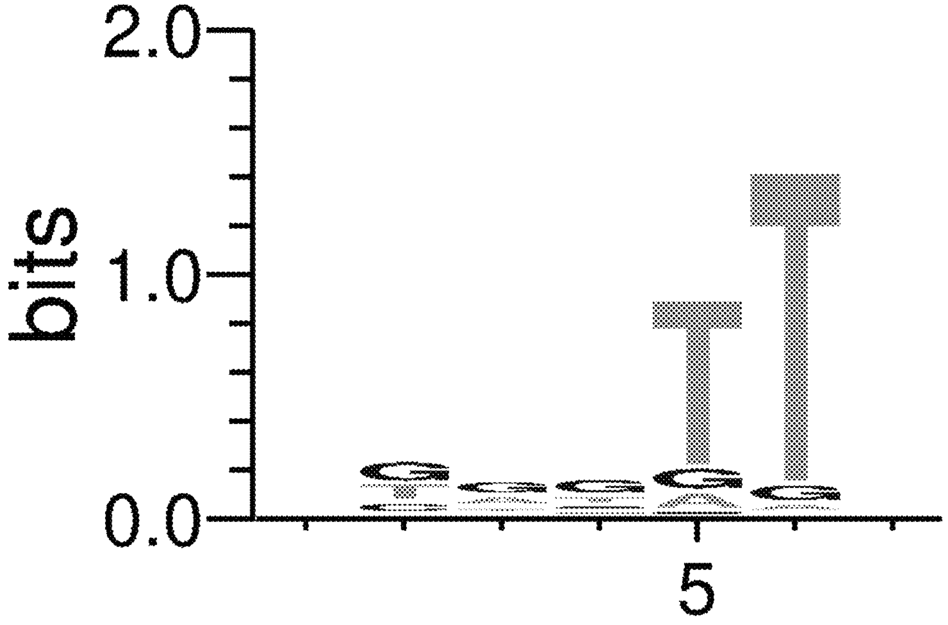
Figure 5:
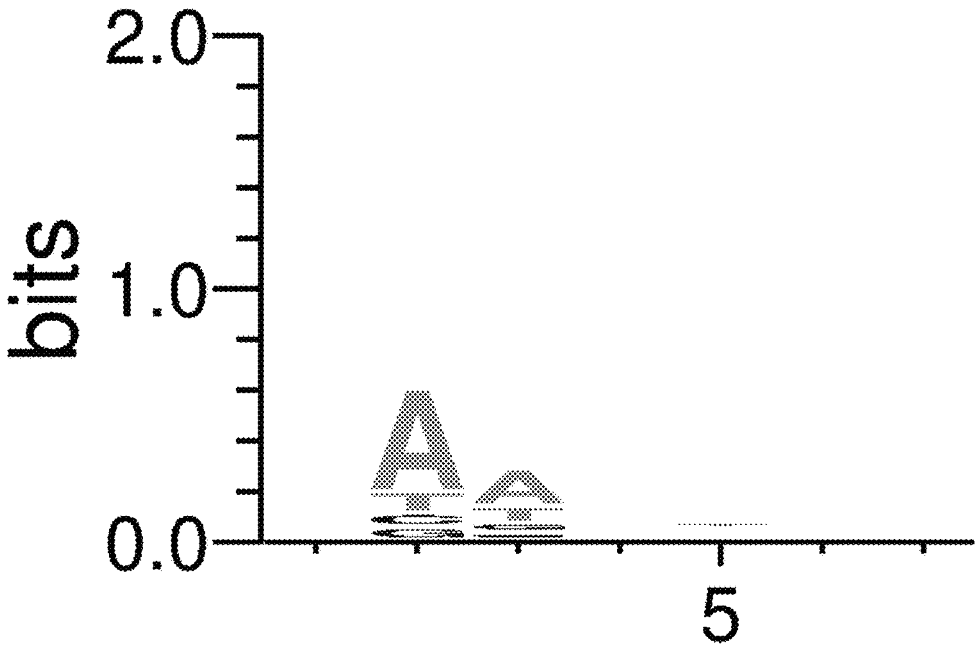
Figure 6:
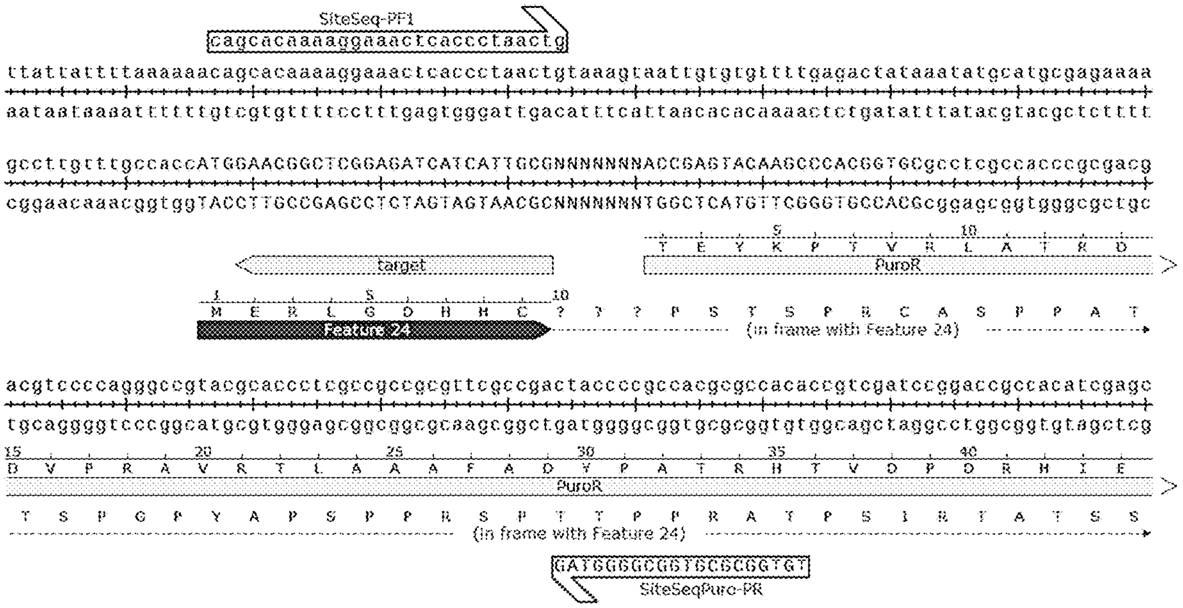
Figure 7:
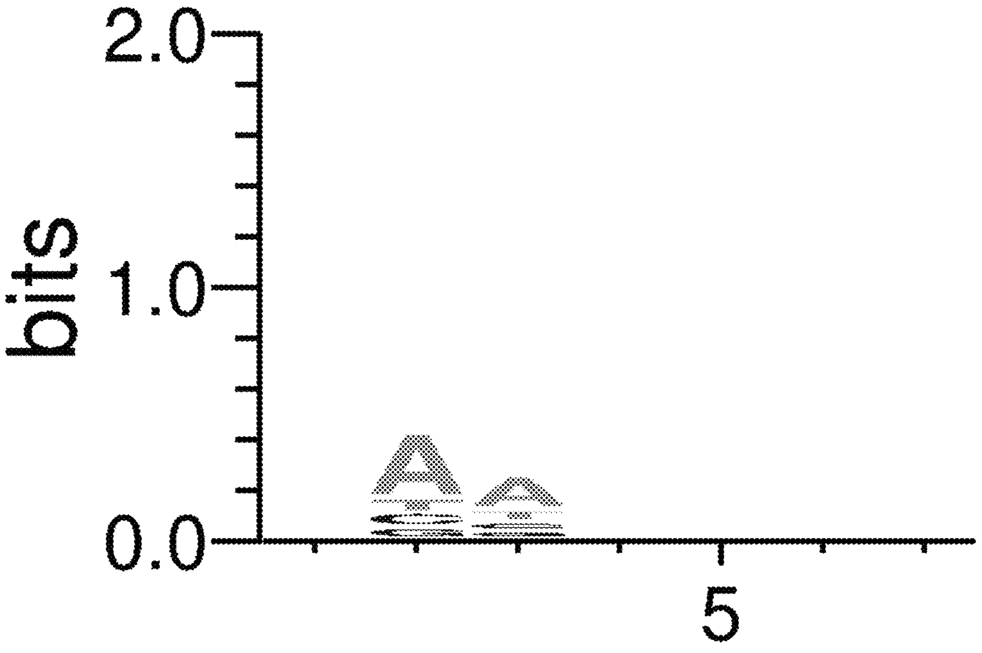
Figure 8:
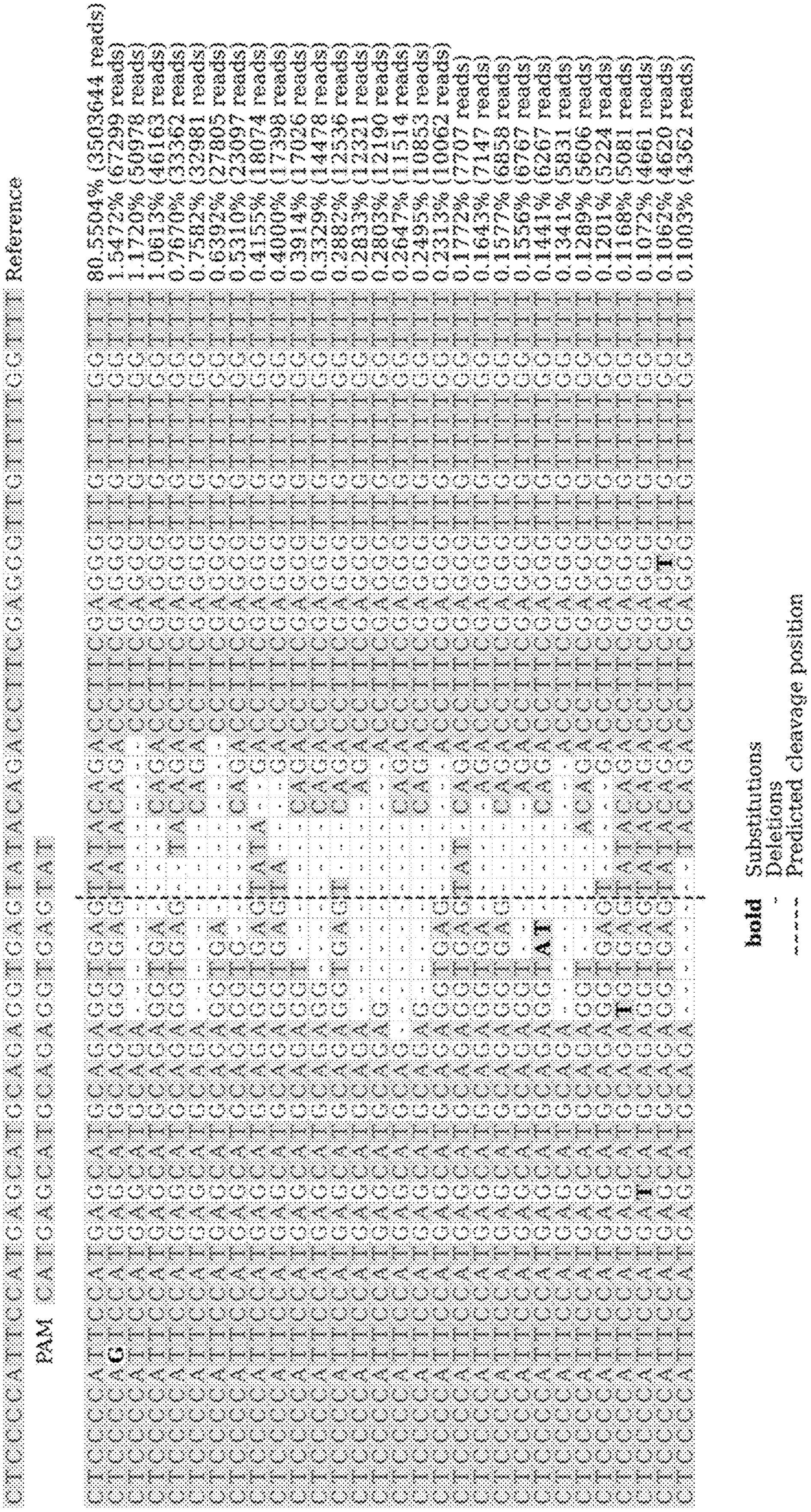

In the evolutionary tree, some proteins of the present disclosure form a separate and distinctly separated branch (a different cluster [CLUSTER]) compared to the known Cas12 isoform proteins, i.e., the proteins of the present disclosure are not mixed with the known Cas12 isoform proteins; and evalue of the alignment between these proteins in the present disclosure (FIG. 1B) and the existing Cas12 HMM Profile model is greater than 1e-5. These proteins of the present disclosure comprise CLUSTER1-CLUSTER13 proteins shown in FIG. 1B. Overall, this suggests that these Cas proteins may be novel subgroups, e.g., new Cas12 isoform proteins;

FIG. 2 is an SDS-PAGE electrophoresis pattern of a C12-279 recombinant protein according to some embodiment of the present disclosure;

FIG. 3 shows a PAM library for in vitro cleavage by Cas12 protein according to some embodiments of the present disclosure, and sequences in FIG. 3 are shown in SEQ ID NO: 878-881;

FIG. 4 shows a motif identified after C12-279-sgRNA targeting a 7nt random sequence according to some embodiments of the present disclosure;

FIG. 5 shows a motif identified after C12-279-sgRNA-Rev targeting a 7nt random sequence according to some embodiments of the present disclosure;

FIG. 6 shows fragments of plasmids containing 7nt random sequences in a plasmid elimination assay according to some embodiments of the present disclosure, and the sequences in FIG. 6 are shown in SEQ ID NO: 720 and SEQ ID NO: 882-886;

FIG. 7 shows a motif identified in the plasmid elimination assay for C12-279 according to some embodiments of the present disclosure;

FIG. 8 shows a partial indel result generated after C12-279 editing TTR genes according to some embodiments of the present disclosure, and the sequences in the FIG. 8 are shown in SEQ ID NO: 722 and SEQ ID NO: 887-916;

FIG. 9 shows that a CI1062732 protein (SEQ ID NO: 46) with dozens of amino acid residues deletion at an N-terminal of the C12-279 protein (SEQ ID NO: 696), in combination with a gRNA containing the DR sequence (GTAATGCGTCTCCCATTGACGCC) (SEQ ID NO: 529), targets a 7nt random sequence plasmid library in bacteria, grabbing a "false" PAM motif of 5'-TTNC-3.

Figure 10:
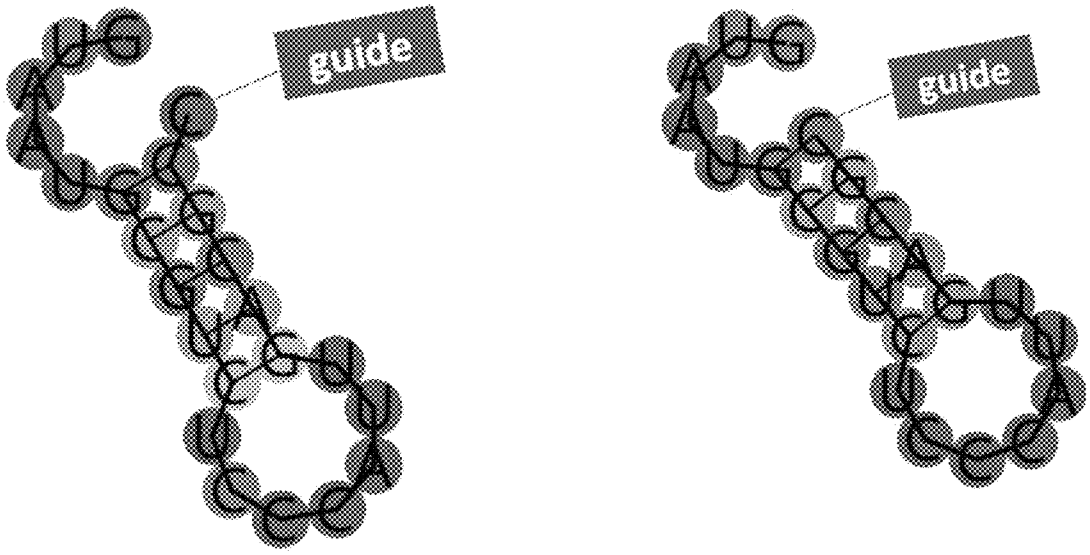

FIG. 10 is a diagram of a secondary structure of a "false" DR sequence according to some embodiments of the present disclosure, hypothesizing that the 3'-end base C of the identified "false" PAM motif TTNC is caused by an extra C at the 3' end of the DR, and the sequences in FIG. 10 are shown in SEQ ID NO: 917 and SEQ ID NO: 918.

Figure 11:
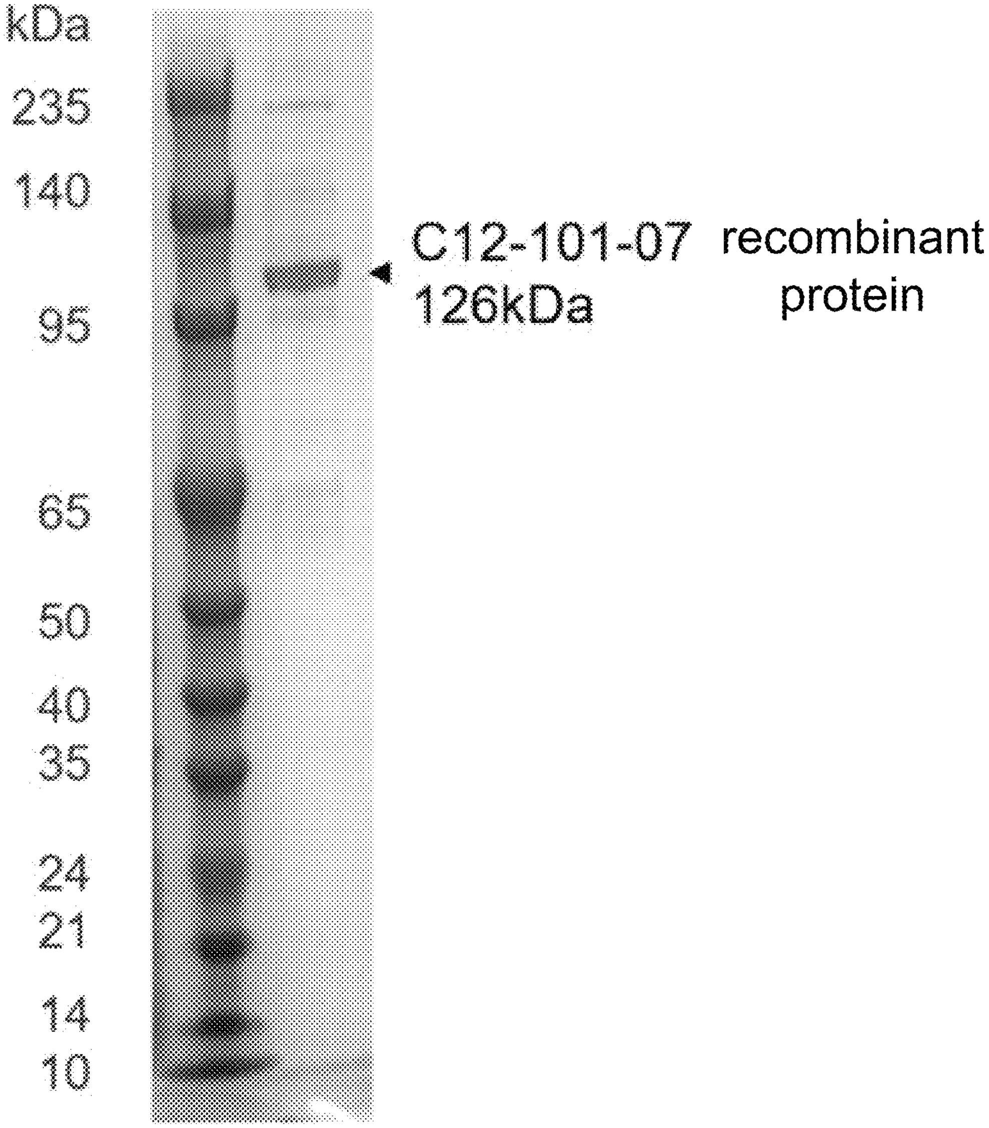
Figure 12:
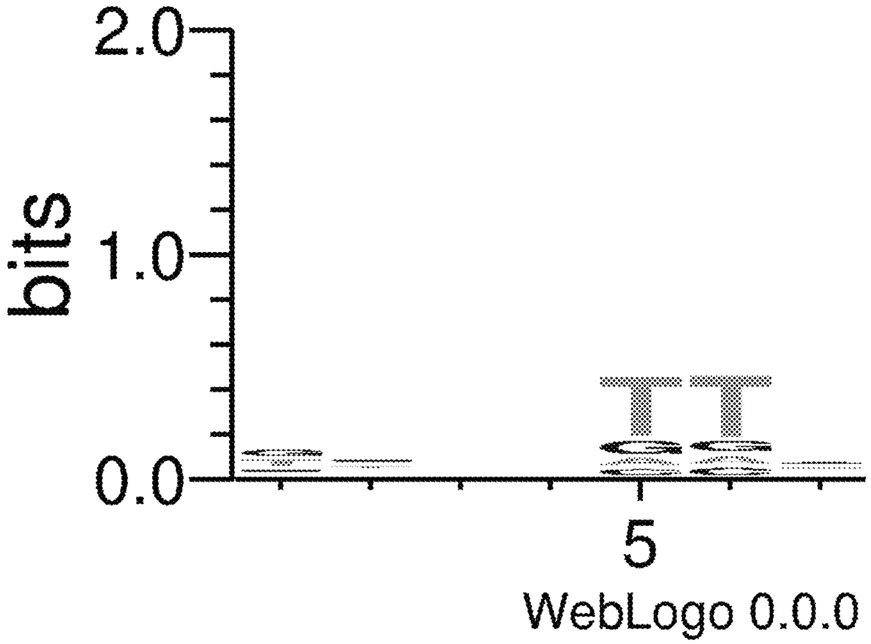
Figure 13:
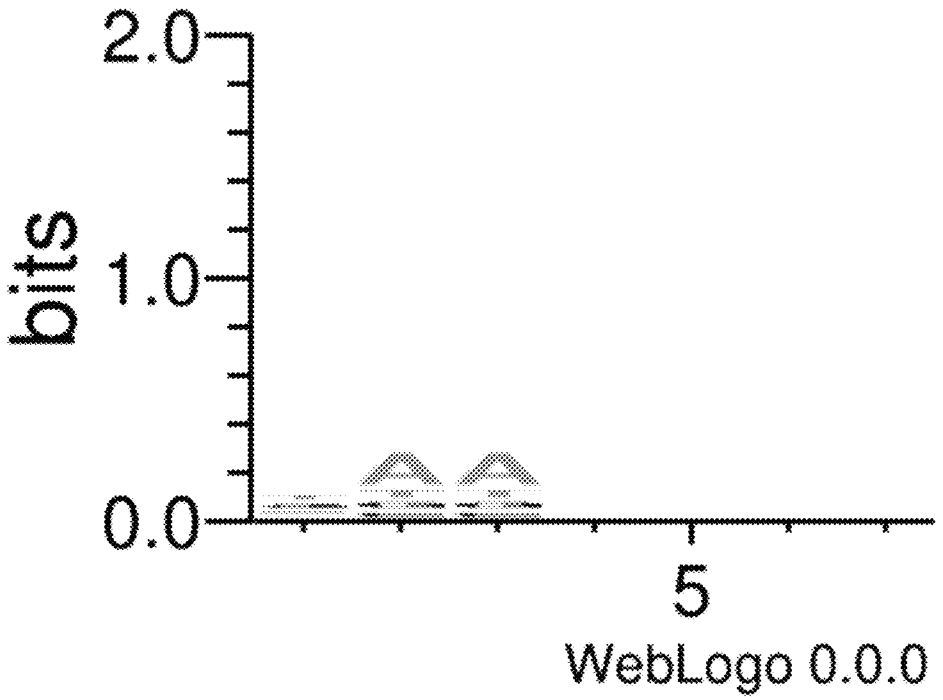
Figure 14:
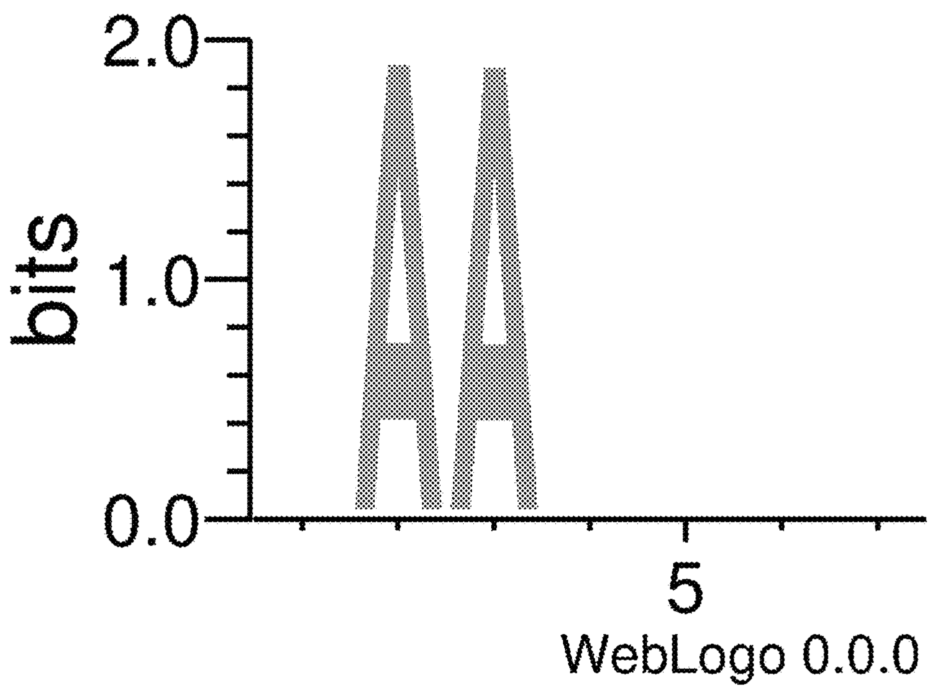
Figure 15A:
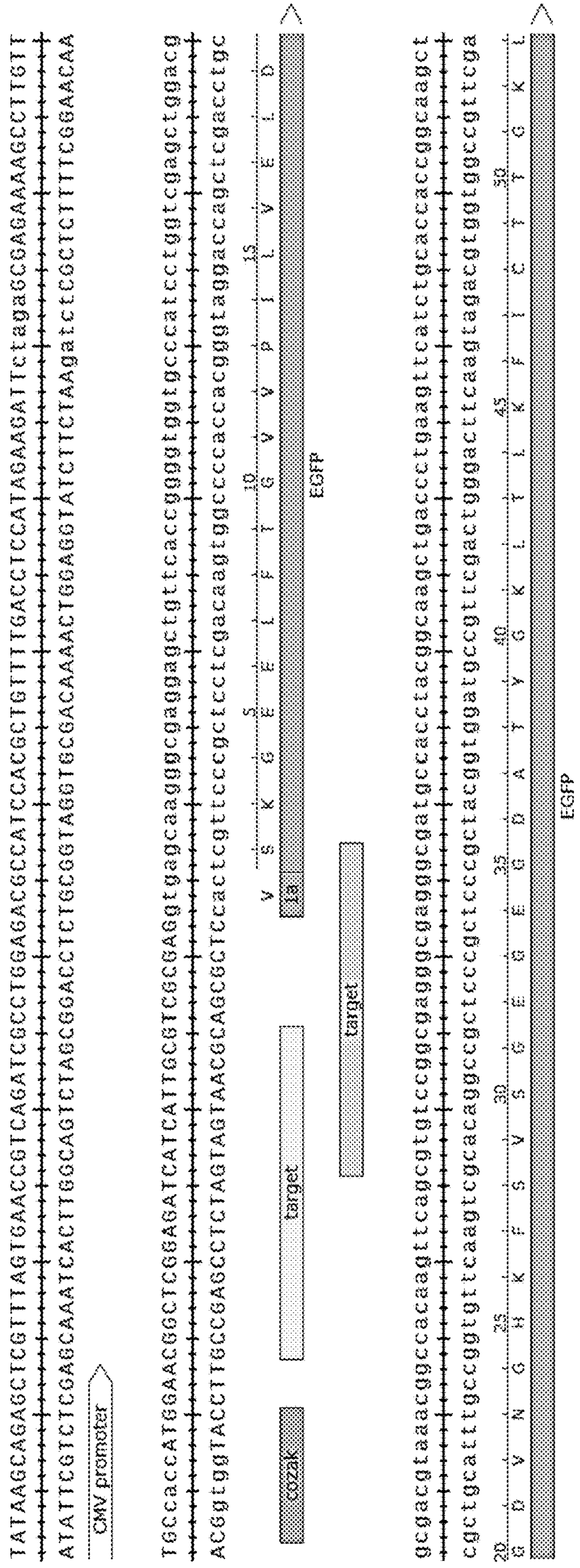
Figure 15B:
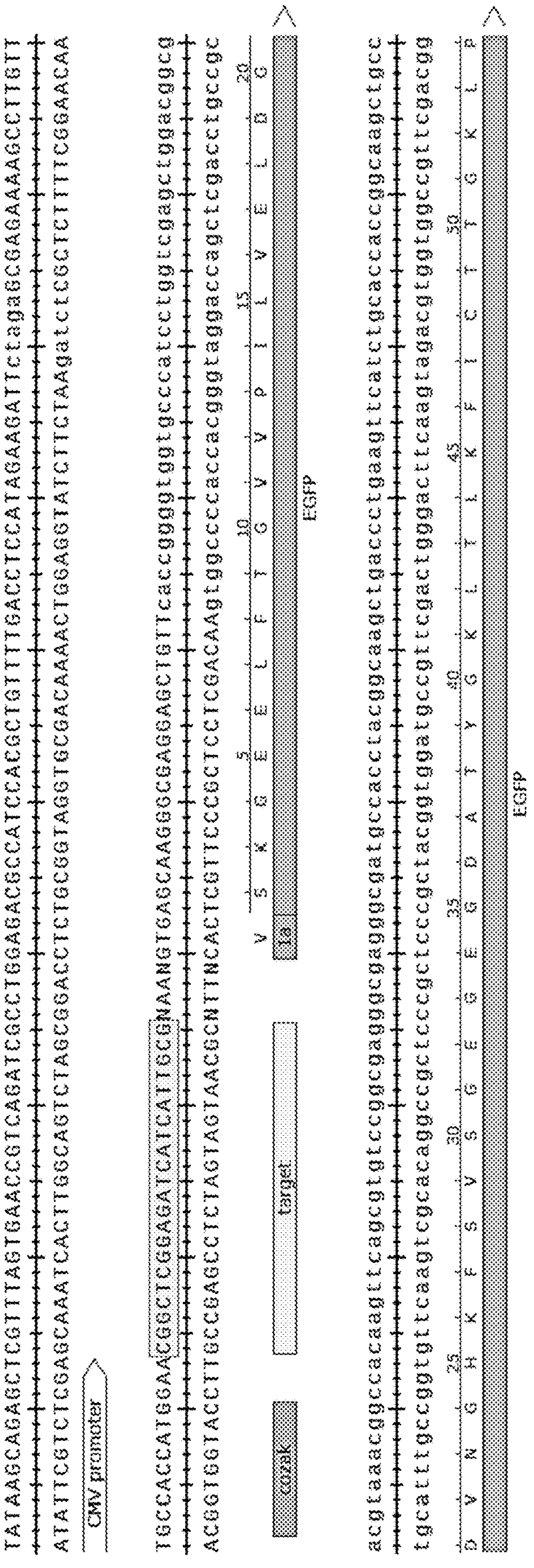
Figure 16:
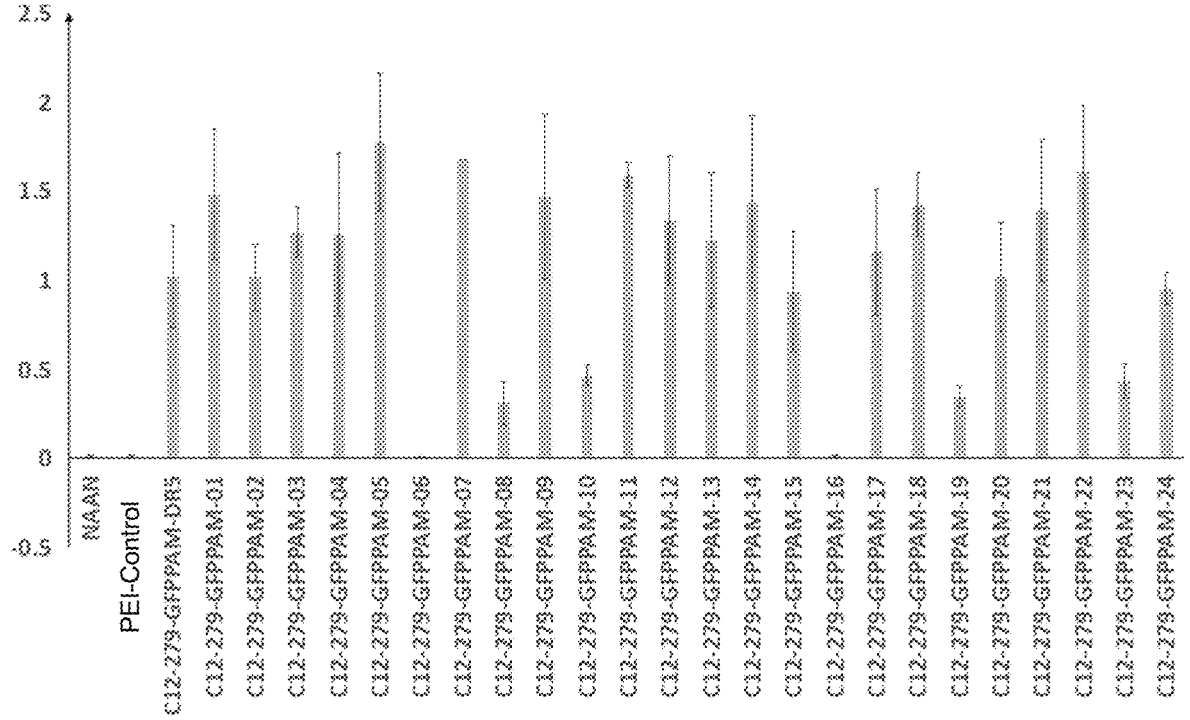
Figure 17:
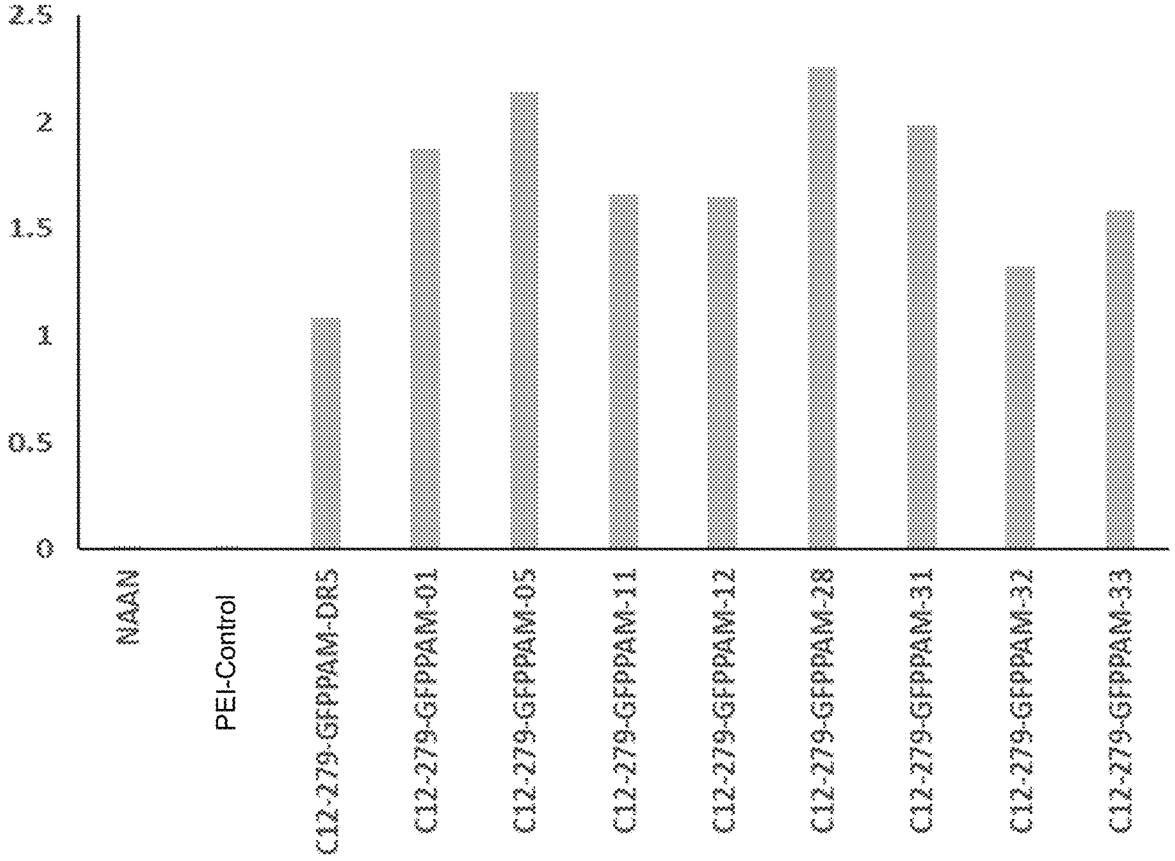
Figure 18:
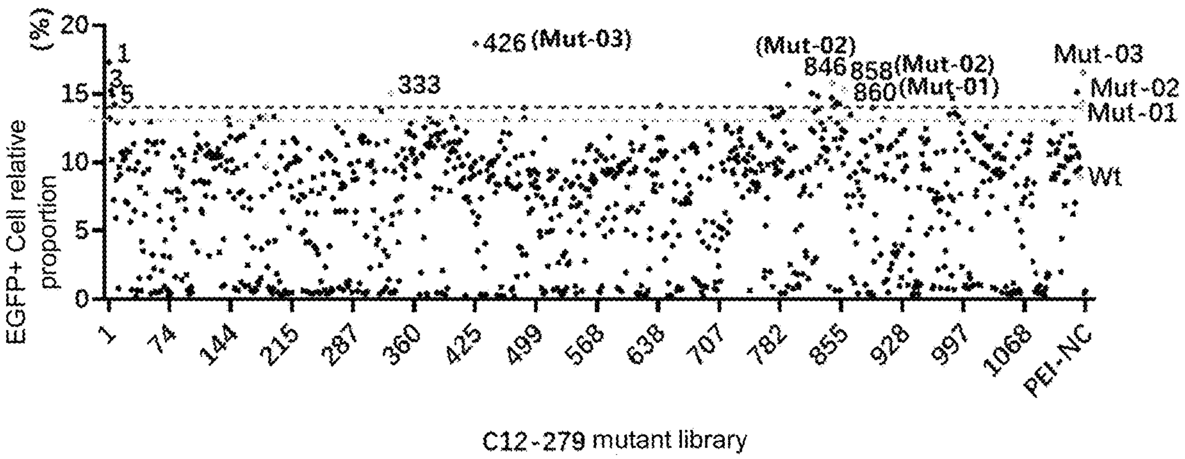
Figure 19:
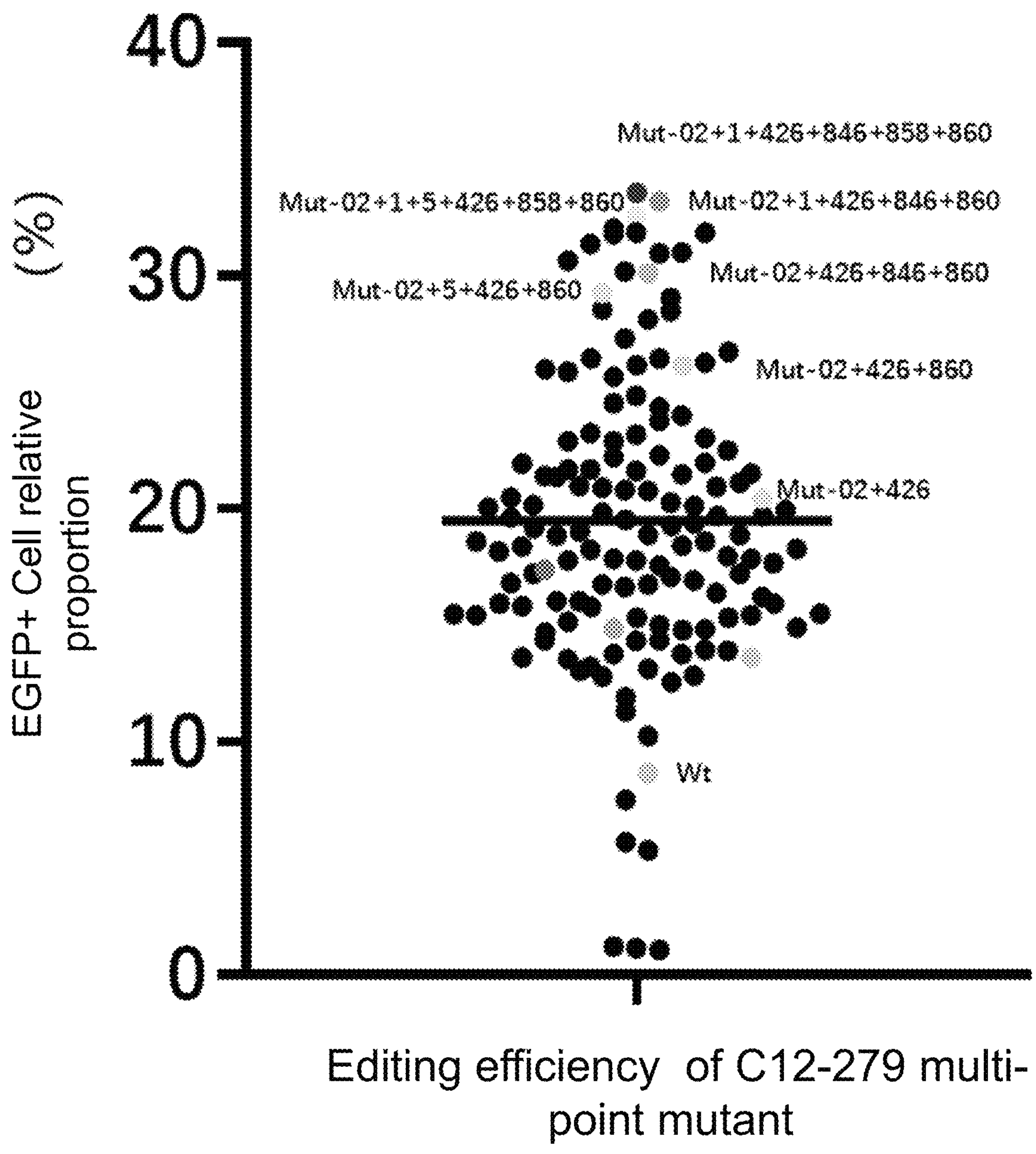
Figure 20A:
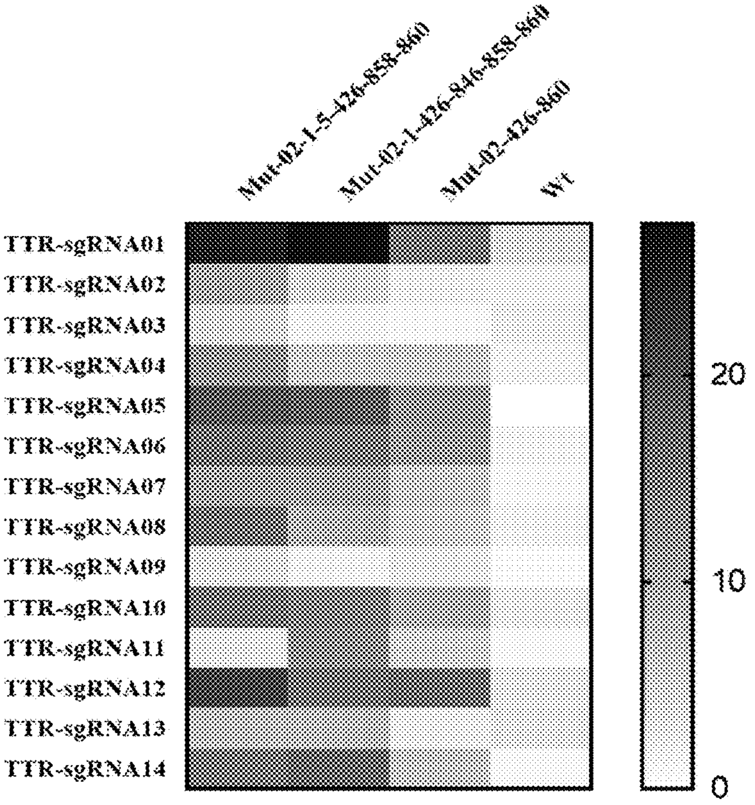
Figure 20B:
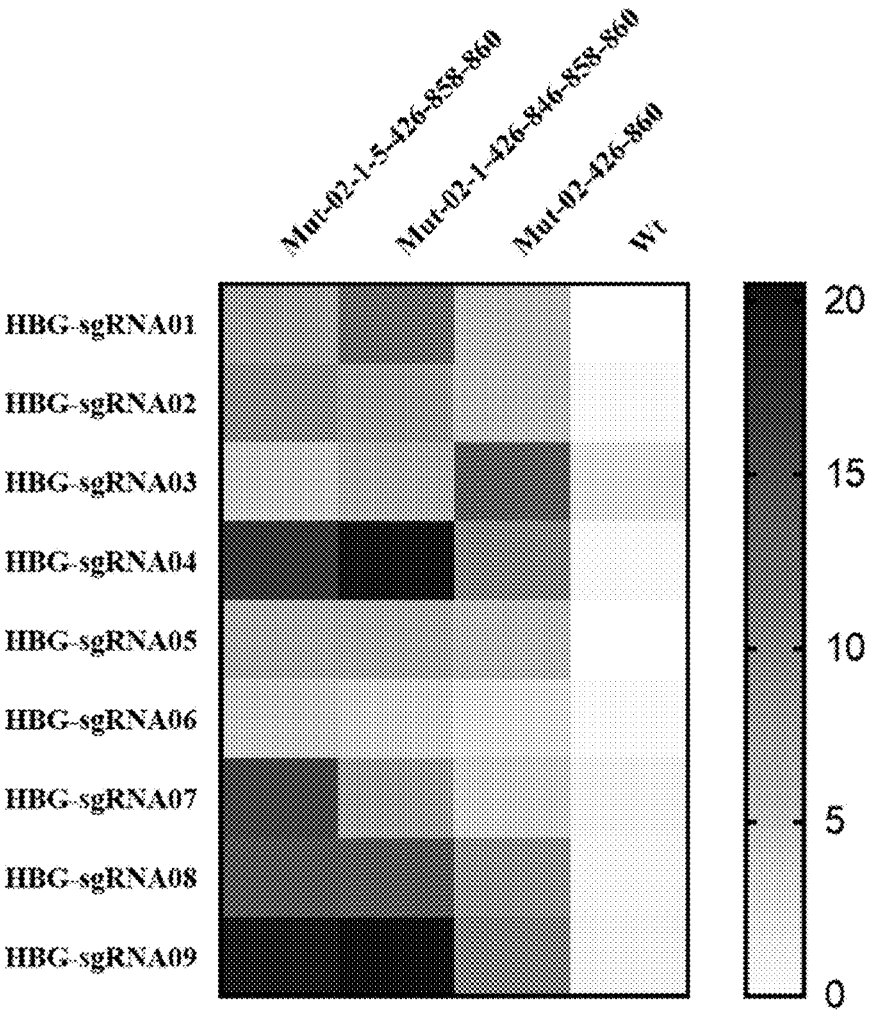
Figure 21:
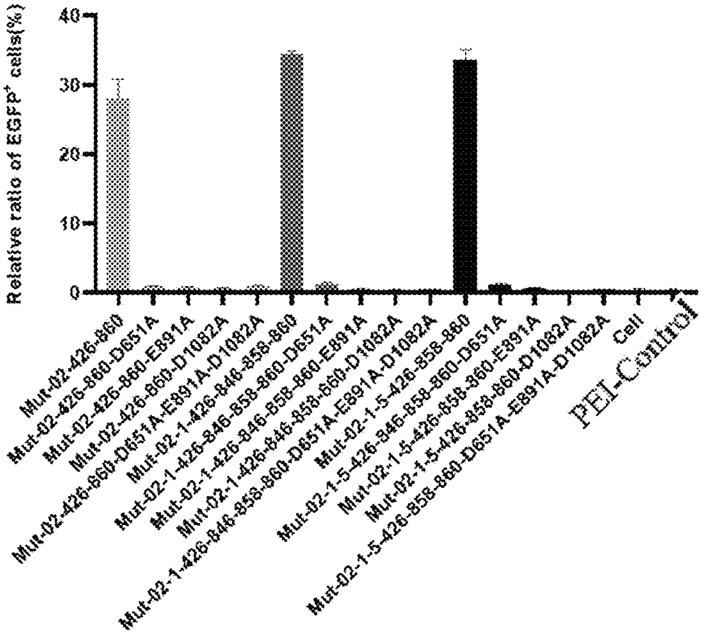
Figure 22:
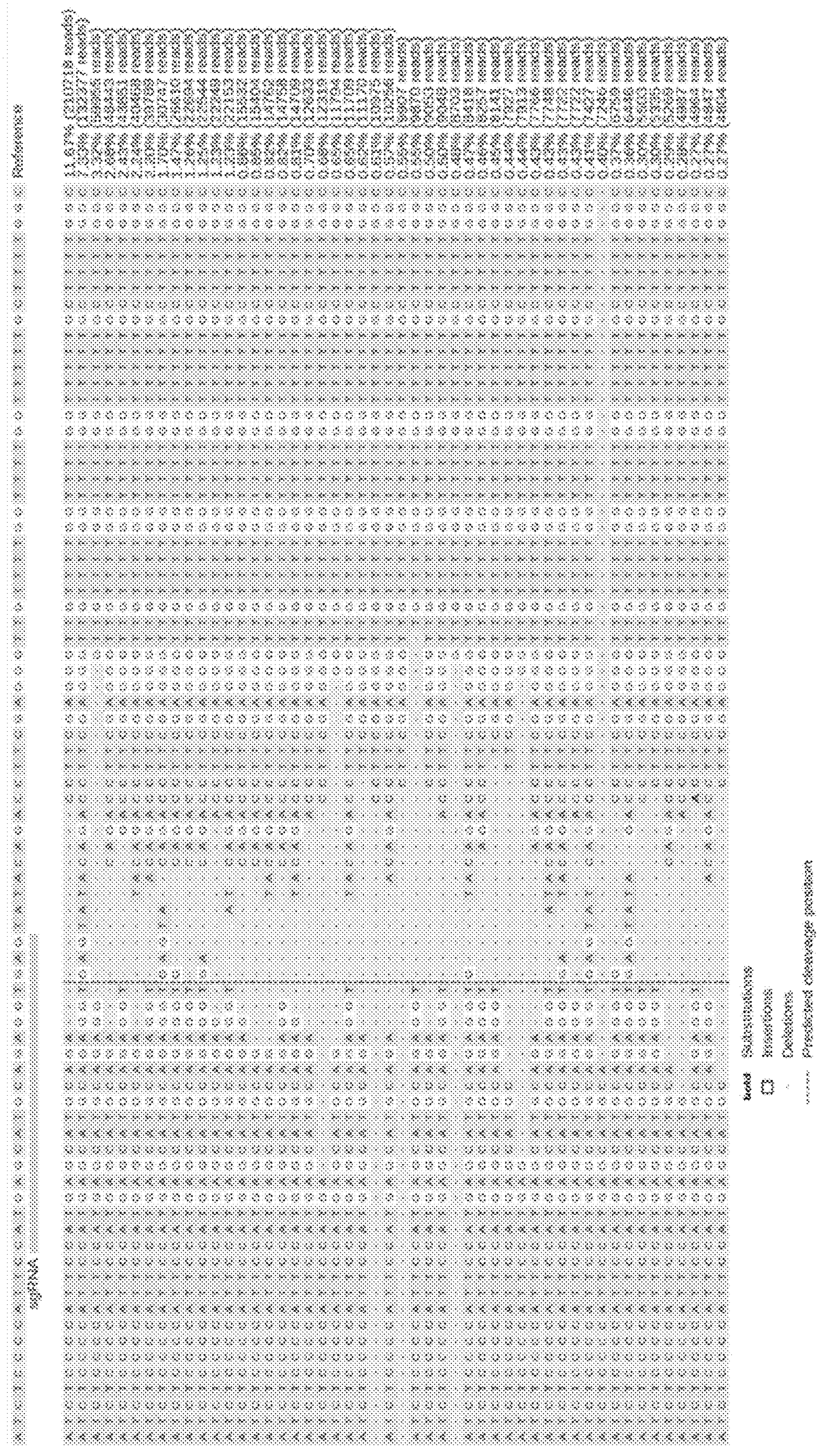
Figure 23:
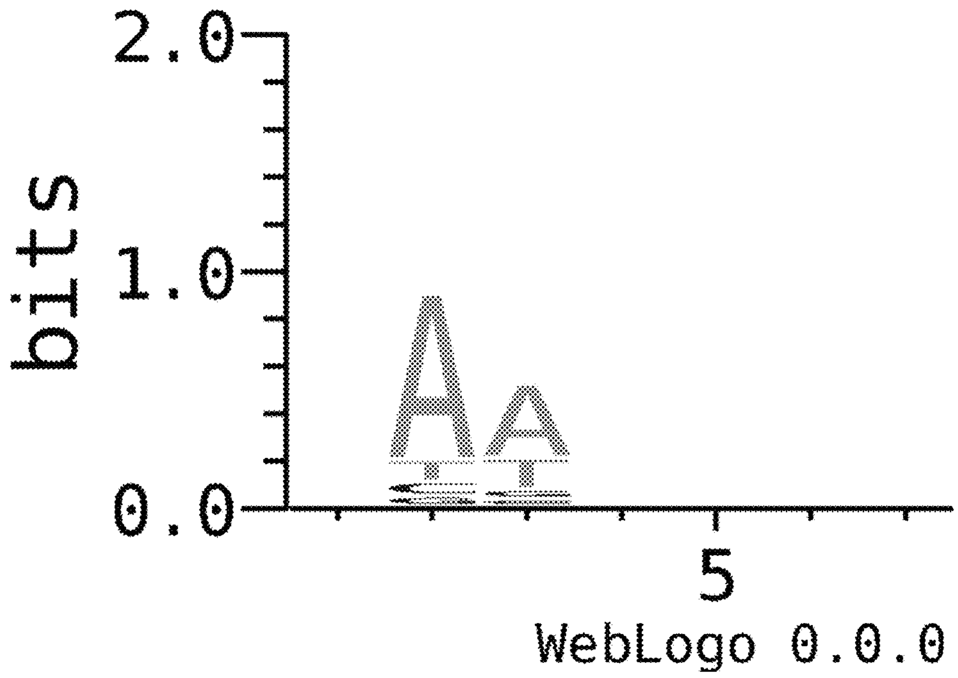
Figure 24:
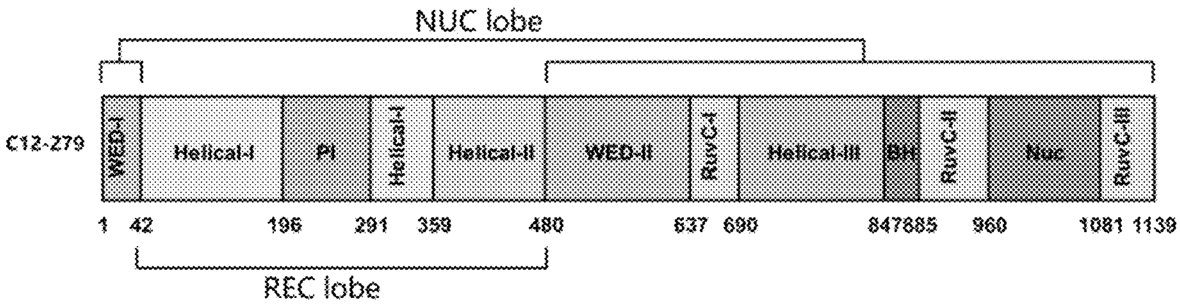

FIG. 11 is an SDS-PAGE electrophoresis pattern of a C12-101-07 recombinant protein (126 KDa) according to some embodiments of the present disclosure;

FIG. 12 shows a motif identified after C12-101-07-sgRNA targeting a 7nt random sequence according to some embodiments of the present disclosure;

FIG. 13 shows a motif identified after C12-101-07-sgRNA-Rev targeting a 7nt random sequence according to some embodiments of the present disclosure;

FIG. 14 shows a motif identified in a plasmid elimination assay for C12-101-09 according to some embodiments of the present disclosure;

FIG. 15A shows fragments of pCDH-CMV-EGFP-reporter3-EF1-Puro plasmid according to some embodiments of the present disclosure; the sequences in FIG. 15A are shown in SEQ ID NO: 919-921; FIG. 15B shows fragments of a plasmid library with a PAM sequence of NAAN according to some embodiments of the present disclosure; and the sequences in FIG. 15B are shown in SEQ ID NO: 922-924;

FIG. 16 shows the editing efficiency of different C12-279 mutants in NAAN cells, expressed as multiples of the editing efficiency of C12-279, according to some embodiments of the present disclosure;

FIG. 17 shows the editing efficiency of different C12-279 mutants in NAAN cells, expressed as multiples of the editing efficiency of C12-279, according to some embodiments of the present disclosure;

FIG. 18 shows editing efficiency test results of different mutants targeting a reporter system according to some embodiments of the present disclosure, where Wt denotes a wild type C12-279; the marked number n indicates that the amino acid residue at position n is mutated to arginine R; Mut-01 is a mutant C12-279-pCDH-05 (Q186R mutant), Mut-02 is a mutant C12-279-pCDH-28 (double point mutation of Q186R and D352R), and Mut-03 is a mutant C12-279-pCDH-35 (triple point mutation of G184R, Q186R, and D352R); a lower dashed line indicates a 50% increase in editing efficiency compared to the wild type C12-279; an upper dashed line indicates an editing efficiency equal to the editing efficiency of Mut-02;

FIG. 19 shows editing efficiency test results of different multipoint mutants in the reporter system according to some embodiments of the present disclosure; where Mut-02-1-5-426-858-860 denotes a multipoint mutant obtained by additionally introducing mutations at positions 1, 5, 426, 858, and 860 (all mutate to arginine R) based on the Mut-02 mutant, i.e., the multipoint mutant contains the following mutations: amino acid residues at positions 1, 5, 186, 352, 426, 858, and 860 are all mutated to R; and other mutants are similar;

FIG. 20A shows an efficiency of multipoint mutants combined with different gRNAs in editing TTR gene according to some embodiments of the present disclosure; FIG. 20B shows an efficiency of multipoint mutants combined with different gRNAs in editing HBG gene according to some embodiments of the present disclosure; where Mut-02-1-5-426-858-860 denotes a multipoint mutant obtained by additionally introducing mutations at positions 1, 5, 426, 858, and 860 (all mutated to arginine R) based on the Mut-02 mutant, i.e., the multipoint mutant contains the following mutations: all amino acid residues at positions 1, 5, 186, 352, 426, 858, and 860 are mutated to R; and other mutants are similar;

FIG. 21 shows editing activity test results of dCas12-279 according to some embodiments of the present disclosure; where Mut-02-426-860 denotes a multipoint mutant obtained by additionally introducing 426R and 860R mutations based on the Mut-02 mutant; Mut-02-426-860-D651A denotes a multipoint mutant obtained by additionally introducing 426R, 860R, and 651A mutations based on the Mut-02 mutant; and other mutants are similar;

FIG. 22 shows NGS sequencing results after the coding mRNA of the mutant Mut-02-1-5-426-858-860 is combined with the modified gRNA (C279-dmTTR01-02) for electroporation of HEK293 cells and editing of TTR gene, with an editing efficiency up to 92.18%, according to some embodiments of the present disclosure; and the sequences in FIG. 22 are shown as SEQ ID NO: 925-974;

FIG. 23 shows a PAM recognized by C12-279 mutant Mut-02-1-426-846-858-860 according to some embodiments of the present disclosure; and FIG. 24 is a schematic diagram illustrating a structure of C12-279 according to some embodiments of the present disclosure.

DETAILED DESCRIPTION

In the present disclosure, scientific and technical terms used herein have the meanings commonly understood by those of skill in the art unless otherwise indicated. Additionally, the procedures involving molecular genetics, nucleic acid chemistry, chemistry, molecular biology, biochemistry, cell culture, microbiology, cell biology, genomics, and recombinant DNA, as used herein, are all standard techniques widely employed in their respective fields. At the same time, for better understanding of the present disclosure, definitions and explanations of relevant terms are provided below.

In the present disclosure, the term "several" refers to a quantity greater than or equal to 2. In the present disclosure, the term "multiple" refers to a quantity greater than or equal to 2.

In the present disclosure, depending on the context, the term "cleavage" refers to cutting of a main chain of a polynucleotide chain; and non-limiting examples include complete cleavage of a single-stranded DNA, cleavage of one strand of a double-stranded DNA, or cleavage of both strands of a double-stranded DNA.

In the present disclosure, depending on the context, the term "modification" refers to other forms of chemical reactions of nucleic acid strands other than "cleavage". It includes, but is not limited to, base substitution, addition, and/or deletion, as well as methylation and demethylation of nucleic acid strands. Non-limiting examples include base substitution on a target nucleic acid strand through single-base editing (e.g., the Cas12 of the present disclosure is fused with a deaminase domain and combined with gRNA), such as A→G, C→T, T→C, or G→A nucleotide mutations, as well as other types of nucleotide mutations (e.g., A→T, C→G, T→A, G→C, etc.). Other examples include base substitution, addition, or deletion through Prime editing technology (e.g., the Cas12 of the present disclosure is fused with a reverse transcriptase and combined with pegRNA), or base substitution, addition, or deletion through homology-directed repair (HDR) (e.g., the Cas12 of the present disclosure is combined with gRNA and a donor template). In addition, the Cas12 of the present disclosure is also fused with a DNA methyltransferase or a DNA demethylase and combined with gRNA for targeted modification.

In the present disclosure, depending on the context, the term "modulating an expression of a target nucleic acid" refers to modulation of the transcription of the target nucleic acid. Non-limiting examples include enhancing or suppressing the transcription of the target nucleic acid using CRISPRa or CRISPRi technologies, by means of a transcriptional activation or repression domain fused to Cas12.

In the present disclosure, letters in amino acid sequences denote single-letter abbreviations for amino acids well known in the art, as described in *J. Biol. Chem,* 243, p3558 (1968), Alanine: Ala-A, Arginine: Arg-R, Aspartic acid: Asp-D, Cysteine: Cys-C, Glutamine: Gln-Q, Glutamic acid: Glu-E, Histidine: His-H, Glycine: Gly-G, Asparagine: Asn-N, Tyrosine: Tyr-Y, Proline: Pro-P, Serine: Ser-S, Methionine: Met-M, Lysine: Lys-K, Valine: Val-V, Isoleucine: Ile-I, Phenylalanine: Phe-F, Leucine: Leu-L, Tryptophan: Trp-W, and Threonine: Thr-T.

In the present disclosure, the term "amino acid difference" refers to the difference of amino acid residues at specific positions in the protein's amino acid sequence, including substitution, addition, or deletion.

In the present disclosure, a mutation of an amino acid residue at a specific position refers to the substitution, addition, or deletion of the amino acid residue at that position.

It is well known to those skilled in the art that in proteins or peptides, two adjacent amino acids each lose an OH or H through dehydration condensation to form a peptide bond, and each amino acid exists in the form of an amino acid residue. Thus, in the present disclosure, the terms "amino acid" and "amino acid residue" refer to the same meaning. Further, in the present disclosure, to simplify the expression, the amino acid residue before the substitution is retained before the position of the amino acid residue; the letter before the position indicates the original amino acid residue, and the letter after the position indicates the substituted amino acid residue. For example, "S211" represents that the original amino acid residue at position 211 is S, and when it is substituted with R, it may be expressed as "S211R".

In the present disclosure, the symbol "+" is sometimes used to connect one amino acid mutation on each side, indicating that both point mutations are present simultaneously in a single mutant; if two or more point mutations are connected by two or more "+", it represents that these point mutations are present simultaneously.

In the present disclosure, if an amino acid is substituted, it refers to that it is substituted with another amino acid residue different from the original amino acid residue. If the original amino acid is a positively charged amino acid and is substituted with a positively charged amino acid, it refers to that it is substituted with another positively charged amino acid residue different from the original one. For example, if an original amino acid residue is R and is substituted with a positively charged amino acid, it refers to that it is substituted with H or K.

In the present disclosure, when referring to an "RNA sequence", "T" in the sequence is used interchangeably with "U". When referring to a "guide sequence", "T" in the sequence is used interchangeably with "U". When referring to a "direct repeat (DR) sequence", "T" in the sequence is used interchangeably with "U".

In the present disclosure, when referring to the numbering of a Cas protein, C12-n and Cas12-n refer to the same protein. For example, Cas12-279 and C12-279 are used interchangeably.

Sequence Identity

As used herein, the term "identity" refers to a sequence matching degree between two polypeptides or between two nucleic acids. The terms "identity", "percent identity", and "sequence identity" are used interchangeably. When a given position in two compared sequences are occupied by the same base or amino acid monomeric subunit (for example, if the same position in each of two DNA molecules is occupied by adenine, or the same position in each of two polypeptides is occupied by lysine), the molecules are considered to be identical at that position. The percent identity between two sequences is calculated by a function: the number of matching positions shared by the two sequences/the total number of compared positions×100%. For example, if there are 6 matching positions in 10 positions of two sequences, then the two sequences have 60% sequence identity. Typically, the alignment is performed by aligning the two sequences to generate the maximum sequence identity. Such alignment may be performed by using published and commercially available alignment algorithms and programs, including but not limited to CLUSTER Q, MAFFT, Probcons, T-Coffee, Probalign, and BLAST, which may be reasonably selected and used by one of ordinary skill in the art. Those skilled in the art can determine appropriate parameters for sequence alignment, including any algorithm required to achieve an optimal or best alignment for the full length of the compared sequences, as well as any algorithm required to achieve an optimal or best alignment for the local region of the compared sequences.

CRISPR-Cas12 System

As used herein, the terms "clustered regularly interspaced short palindromic repeats (CRISPR)—CRISPR-Cas system" or "CRISPR system" are used interchangeably and have the meanings commonly understood by those of skill in the art, which generally comprise transcription products or other elements associated with the expression of a CRISPR-associated (Cas) gene or transcription products or other elements capable of guiding the activity of the Cas gene. Such transcription products or other elements may comprise sequences encoding Cas effector proteins and guide polynucleotides.

Zhang Feng et al. discovered Cas12a in 2015, categorized as type V in the Class II CRISPR-Cas system. After detailed studies of subtype V-A (Cas12a), Zhang Feng et al. reported Cas12b (C2C1) in 2015. In 2017, Burstein et al. reported the Cas12e (CasX) nuclease. In 2019, Winston X. Yan et al. reported the newly discovered type V Cas effector proteins Cas12c, Cas12h, Cas12i, and Cas12g in detail by bioinformatics analysis.

In some embodiments, a Cas12 protein as described herein refers to a protein having an amino acid sequence, the amino acid sequence having at least 50%, 55%, 60%, 65%, 70%, 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% sequence identity to any one of sequences shown in SEQ ID NO: 1-53, SEQ ID NO: 696, or SEQ ID NO: 728. When the CRISPR-Cas12 system comprises a fusion protein or a conjugate comprising the Cas12 protein and a functional domain, a percent sequence identity between the Cas 12 portion of the fusion protein or the conjugate and a reference sequence is calculated.

In the present disclosure, the CRISPR-Cas12 system comprises the Cas12 protein with the amino acid sequence having at least 50% sequence identity to any one of sequences shown in SEQ ID NO: 1-53, SEQ ID NO: 696, and SEQ ID NO: 728, or a nucleic acid encoding the Cas12 protein; and a guide polynucleotide or a nucleic acid encoding the guide polynucleotide; the guide polynucleotide comprises a DR sequence linked to a guide sequence, the guide sequence is engineered to hybridize with a target nucleic acid, and the guide polynucleotide is capable of forming a complex with the Cas12 protein and guiding the sequence-specific binding of the complex to the target nucleic acid.

Guide Polynucleotide

As used herein, the term "guide polynucleotide" refers to a molecule in a CRISPR-Cas system that forms a complex with the Cas protein and guides the complex to a target sequence. Typically, the guide polynucleotide comprises a scaffold sequence that is linked to a guide sequence, and the guide sequence may hybridize to the target sequence. Typically, the scaffold sequence comprises a DR sequence, and sometimes, the scaffold sequence comprises a tracrRNA sequence. In some embodiments, the guide polynucleotide does not comprise a tracrRNA sequence. In some embodiments, the guide polynucleotide comprises a tracrRNA sequence.

In some embodiments, the guide polynucleotide of the CRISPR-Cas12 system is a guide RNA. In some embodiments, the guide polynucleotide is a chemically modified guide polynucleotide. In some embodiments, the guide polynucleotide comprises at least one chemically modified nucleotide.

In some embodiments, the chemically modified nucleotide comprises a base-modified nucleotide, a phosphate-modified nucleotide, and a ribose-modified nucleotide.

In some embodiments, the base-modified nucleotide is selected from nucleotides containing non-natural bases.

In some embodiments, the phosphate-modified nucleotide is selected from an aminophosphate nucleotide, a phosphorothioate nucleotide, a dithiophosphate nucleotide, a methylphosphonate nucleotide, a 5'-phosphate nucleotide, an alkyl phosphate nucleotide, and a borane phosphate nucleotide.

In some embodiments, the ribose-modified nucleotide is selected from a deoxynucleotide, a 3'-terminal deoxythymidine (dT) nucleotide, a 2'-O-methyl-modified nucleotide, a 2'-fluoro-modified nucleotide, a 2'-deoxy-modified nucleotide, a 2'-amino-modified nucleotide, a 2'-O-allyl-modified nucleotide, a 2'-C-alkyl-modified nucleotide, a 2'-hydroxy-modified nucleotide, a 2'-methoxyethyl-modified nucleotide, a 2'-O-alkyl-modified nucleotide, and a morpholino nucleotide.

In some embodiments, the base-modified nucleotide is selected from nucleotides containing non-natural bases, for example, 5-methylcytosine, 5-hydroxymethylcytosine, pseudouridine, 2,6-diaminopurine, 2-thiopurine, 7-methylguanosine, 8-bromoguanosine, 5-iodouracil, 5-bromouracil, 5-propargyluracil, 5-methyluracil, 1-methylpseudouridine, N6-methyladenosine, N6-methylthioadenosine, 2-aminopurine, isocytosine, isoguanine, and isoguanine. In some embodiments, the phosphate-modified nucleotide is selected from an aminophosphate nucleotide, a phosphorothioate nucleotide, a phosphorodithioate nucleotide, a methylphosphonate nucleotide, a 5'-phosphorylated nucleotide, an alkylphosphate nucleotide, a boranephosphonate nucleotide, a phosphoroselenoate nucleotide, a fluorophosphonate nucleotide, an allylphosphate nucleotide, a benzylphosphate nucleotide, a cyanophosphonate nucleotide, and a sulfonate-modified nucleotide. In some embodiments, the ribose-modified nucleotide is selected from deoxynucleotide, 3'-deoxythymidine nucleotide, 2'-O-methyl nucleotide, 2'-fluoro nucleotide, 2'-deoxy nucleotide, 2'-amino nucleotide, 2'-O-allyl nucleotide, 2'-C-alkyl nucleotide, 2'-hydroxy nucleotide, 2'-O-methoxyethyl (MOE) nucleotide, 2'-O-alkyl nucleotide, morpholino nucleotide (PMO), locked nucleic acid (LNA), thio-sugar nucleotide, 2'-O-methoxy nucleotide, 4'-methyl nucleotide, 3'-O-alkyl nucleotide, 3'-amino nucleotide, 4'-thionucleotide, cyclo-nucleotide, peptide nucleic acid (PNA), β-deoxyinosine nucleotide, 2'-fluoro-deoxynucleotide, 2'-protected nucleotide (for stabilizing CRISPR RNP), methylated ribose-modified nucleotide, and hydrophobic-tailed nucleotide (for cell membrane penetration).

In some embodiments, the guide polynucleotide comprises a chemically modified nucleotide at a 5' end and/or a 3' end.

In some embodiments, the guide polynucleotide comprises a deoxynucleotide at the 5' end; and the deoxynucleotide has a length in a range of 10 to 25 nt, e.g., 14 nt or 25 nt.

In some embodiments, the guide polynucleotide comprises a nucleotide with phosphorothioate group and 2'-O-methyl modifications at the 5' end or the 3' end.

In some embodiments, the guide polynucleotide comprises at least one guide sequence (or referred to as a spacer sequence) linked to at least one DR sequence. In some embodiments, the guide sequence is located at the 3' end of the DR sequence. In some embodiments, the guide sequence is located at the 5' end of the DR sequence.

In some embodiments, the tracrRNA sequence is linked to the DR sequence.

In some embodiments, the tracrRNA sequence is located at the 5' end or 3' end of the DR sequence. In some embodiments, the tracrRNA sequence is located at the 5' end of the DR sequence. In some embodiments, the tracrRNA sequence is located at the 3' end of the DR sequence.

In some embodiments, a nucleotide sequence of the guide polynucleotide comprises the tracrRNA, the DR sequence, and the guide sequence in order from the 5' end to the 3' end.

In some embodiments, the nucleotide sequence of the guide polynucleotide comprises the tracrRNA, a linker sequence, the DR sequence, and the guide sequence in order from the 5' end to the 3' end.

In some embodiments, the nucleotide sequence of the guide polynucleotide comprises the tracrRNA, a loop sequence, the DR sequence, and the guide sequence in order from the 5' end to the 3' end.

In some embodiments, a structure of the guide polynucleotide is as follows: 5'-tracrRNA-loop sequence-DR sequence-guide sequence-3'.

In some embodiments, the tracrRNA and the DR sequence of the guide polynucleotide are linked by a nucleotide sequence.

In some embodiments, the tracrRNA sequence is linked to the DR sequence by a nucleotide sequence including 1, 2, 3, 4, 5, 6, 7, 8, 9, or 10 nucleotides. In some embodiments, the tracrRNA sequence is linked to the DR sequence by a nucleotide sequence including 4 nucleotides. In some embodiments, the tracrRNA sequence is linked to the DR sequence by a 5'-GAAA-3' sequence.

In some embodiments, the guide sequence is sufficiently complementary to a target nucleic acid to hybridize with the target nucleic acid and to guide sequence-specific binding of a CRISPR-Cas12 complex to the target nucleic acid. In some embodiments, the guide sequence has 100% complementarity with the target nucleic acid, but the guide sequence may also have less than 100% complementarity with the target nucleic acid, for example, at least 80%, at least 85%, at least 90%, at least 95%, at least 98%, or at least 99% complementarity.

In some embodiments, the guide sequence is engineered to hybridize to the target nucleic acid and is mismatched to the target nucleic acid by no more than two nucleotides. In some embodiments, the guide sequence is engineered to hybridize to the target nucleic acid and is mismatched to the target nucleic acid by no more than one nucleotide. In some embodiments, the guide sequence is engineered to hybridize to the target nucleic acid and is not mismatched or is mismatched to the target nucleic acid.

In some embodiments of the present disclosure, the guide sequence has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, or 100% sequence identity to any one of sequences shown in SEQ ID NO: 722, SEQ ID NO: 761-782, and SEQ ID NO: 825-877. In some embodiments of the present disclosure, the guide sequence is shown in any one of SEQ ID NO: 722, SEQ ID NO: 761-782, and SEQ ID NO: 825-877.

In some embodiments, the CRISPR-Cas12 system comprises at least 2, at least 3, at least 4, at least 5, at least 10, or at least 20 different guide polynucleotides. In some embodiments, the guide polynucleotide targets at least 2, at least 3, at least 4, at least 5, at least 10, or at least 20 different target nucleic acid molecules, or targets at least 2, at least 3, at least 4, at least 5, at least 10, or at least 20 different regions of one or more target nucleic acid molecules.

In some embodiments, the guide polynucleotide comprises a constant DR sequence located upstream of a variable guide sequence. In some embodiments, a plurality of guide polynucleotides is a portion of an array, which may be a portion of a vector, such as a viral vector or plasmid. For example, a guide array that comprises a sequence: DR sequence-spacer-DR sequence-spacer-DR sequence-spacer- . . . -DR sequence-spacer may comprise a plurality of unique unprocessed guide polynucleotides (one for each DR sequence-spacer or space-DR sequence). Once introduced into a cell or cell-free system, the array is processed by the Cas12 protein into several individual mature guide polynucleotides. This allows for multiplexing, such as delivering a plurality of guide polynucleotides into the cell or system to target a plurality of target nucleic acids or a plurality of regions within a single target nucleic acid.

The ability of the guide polynucleotide to guide the sequence-specific binding of the complex (a CRISPR complex) to the target nucleic acid may be assessed by any suitable assay. For example, components of the CRISPR system sufficient to form the complex (the CRISPR complex), including a guide polynucleotide to be tested, may be delivered to a host cell containing the corresponding target nucleic acid molecules, such as by transfection with a vector encoding the components of the CRISPR complex, followed by assessment of preferential cleavage within a target sequence. Similarly, cleavage of the target nucleic acid sequence may be assessed in vitro by providing the target nucleic acid and the components of the CRISPR complex including the guide polynucleotide to be tested and a control guide polynucleotide different from the guide polynucleotide to be tested, and then comparing the ability of the guide polynucleotide to be tested and the control guide polynucleotide to bind the target nucleic acid or the rate of the guide polynucleotide to be tested and the control guide polynucleotide to cleave the target nucleic acid. The ability of the CRISPR complex to cleave or bind the target nucleic acid may also be assessed by the manner described above.

Cas12 Mutant

As described herein, when referring to "a position corresponding to a sequence shown in SEQ ID NO: XX" or a similar textual description, the position may be determined by amino acid sequence alignment. Typically, the alignment is made when two sequences are aligned to produce a maximum sequence identity. Such an alignment may be performed by using published and commercially available alignment algorithms and programs such as, but not limited to, Clustal Ω, MAFFT, Probcons, T-Coffee, Probalign, and BLAST, which may be reasonably selected by one of ordinary skill in the art. One skilled in the art can determine appropriate parameters for sequence alignment, including any algorithm needed to achieve an optimal or best alignment for the full length of the compared sequences, as well as any algorithm required to achieve an optimal or best local alignment for the local region of the compared sequences.

In some embodiments, the corresponding position is determined by performing an online sequence alignment of an amino acid sequence of the Cas12 protein with any one of sequences shown in SEQ ID NO: 1-53, SEQ ID NO: 696, and SEQ ID NO: 728 using the MAFFT version 7 tool (mafft.cbrc.jp), with the following parameters: G-INS-i (Very slow; recommended for <200 sequences with global homology; 2 iterative cycles only), Try to align gappy regions anyway, Scoring matrix for amino acid sequences-BLOSUM62, Gap opening penalty 1.53, Offset value 0.0, and Mafft-homologs-Use UniRef50 (more comprehensive and requires longer search time).

In some embodiments, the corresponding position is determined by performing an online sequence alignment of the amino acid sequence of the Cas12 protein with the sequence shown in SEQ ID NO: 696 using the MAFFT version 7 tool (mafft.cbrc.jp), with the following parameters: G-INS-i (very slow; recommended for <200 sequences with global homology; 2 iterative cycles only), Try to align gappy regions anyway, Scoring matrix for amino acid sequences-BLOSUM62, Gap opening penalty 1.53, Offset value 0.0, Mafft-homologs-Use UniRef50 (more comprehensive and requires longer search time).

In some embodiments, the Cas12 protein herein comprises one or more mutations, e.g., a single amino acid insertion, a single amino acid deletion, a single amino acid substitution, or any combination thereof compared to the Cas12 protein with a sequence shown in any one of SEQ ID NO: 1-53, SEQ ID NO: 696, and SEQ ID NO: 728. In some embodiments, compared to the Cas 12 protein with the sequence shown in any one of SEQ ID NO: 1-53, SEQ ID NO: 696, and SEQ ID NO: 728, the Cas12 protein comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, or 130 amino acid changes (e.g., insertions, deletions, or substitutions), but retains the ability to bind to a target nucleic acid molecule that is complementary to a guide sequence of a guide polynucleotide, and/or the ability to process an RNA transcript containing a guide sequence into a guide polynucleotide molecule. In some embodiments, compared to the Cas 12 protein with the sequence shown in any one of SEQ ID NO: 1-53, SEQ ID NO: 696, and SEQ ID NO: 728, the Cas12 protein comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, or 130 amino acid changes (e.g., insertions, deletions, or substitutions), but retains the ability to bind a target nucleic acid molecule that is complementary to the guide sequence of the guide polynucleotide.

One type of modification or mutation comprises replacing an amino acid residue with an amino acid having similar biochemical properties, i.e., a conservative substitution. Usually, the conservative substitution has little or no effect on the activity of the resulting protein or peptide. For example, the conservation substitution refers to a substitution of an amino acid residue in the Cas12 protein that does not substantially affect the binding between the Cas12 protein and a target nucleic acid molecule that is complementary to a guide sequence of a gRNA molecule, and/or the process of processing a guide array RNA transcript into gRNA molecules.

More substantial changes may be introduced by using fewer conservative substitutions, e.g., by selecting residues that differ more significantly in maintaining the following effects: (a) the polypeptide backbone structure in the region where the substitution occurs, such as a helical or folded conformation; (b) the charge or hydrophobicity of the region interacted with the target site; or (c) the bulk of the amino acid side chain. The substitutions that are generally expected to produce the greatest changes in peptide function are (a): a substitution between hydrophilic residues (e.g., serine or threonine) and hydrophobic residues (e.g., leucine, isoleucine, phenylalanine, valine, or alanine); (b) a substitution between cysteine or proline and any other residue; (c) a substitution between residues with a positively charged side chain (e.g., lysine, arginine, or histidine) and residues with a negatively charged residue (e.g., glutamic acid or aspartic acid); or (d) a substitution between a residue having a bulky side chain (e.g., phenylalanine) and a residue not having a side chain (e.g., glycine).

Cas12 Active Fragment

In the present disclosure, the Cas12 protein may comprise only a WED-I domain, a Helical-I1 domain, a PI domain, a Helical-I2 domain, a Helical-II domain, a WED-II domain, a Ruvc-I domain, a Helical-III domain, a BH domain, a Ruvc-II domain, a Nuc domain, and/or a Ruvc-III domain.

The Cas12 protein described herein, in addition to including the domains described above, may also comprise domains of the Cas12 proteins in the prior art, which together form a complete structure of the Cas12 protein to fulfill the function of the Cas12 protein described in the present disclosure. The function comprises, but is not limited to, retaining the ability of the Cas12 protein to form a complex with a gRNA, retaining the ability of the Cas12 protein to form a complex with a gRNA and target a target nucleic acid, retaining the ability of the complex formed by the Cas12 protein with the gRNA to target and modulate the expression of the target nucleic acid, retaining the ability of the complex formed by the Cas12 protein with the gRNA to target and cleave a single strand or double strands of a target nucleic acid, retaining the ability of the Cas12 protein to bind a target nucleic acid molecule that is complementary to a guide sequence of a guide polynucleotide, and/or retaining the ability to process RNA transcripts containing the guide sequence into guide polynucleotide molecules.

For example, in some embodiments, the Cas12 active fragment comprises only the PAM-interacting (PI) domain of C12-279 or a homologous sequence thereof. Such active fragment is capable of recognizing a PAM sequence on the target nucleic acid. Furthermore, the active fragment may be used to replace a PI domain in another Cas12 protein (e.g., a Cas12i protein, which is known in the literature to typically recognize a TTN PAM), such that the newly formed chimeric protein can recognize a WTN or ATN PAM.

In some other embodiments, the Cas12 active fragment comprises only the REC lobe of C12-279 or a homologous sequence thereof. Such active fragment may retain the ability to bind a guide polynucleotide and/or a target nucleic acid.

In some other embodiments, the Cas12 active fragment comprises only the RuvC nuclease domain(s) of C12-279 or homologous sequences thereof. Such a fragment may retain the ability to cleave a target nucleic acid when provided in combination with a guide polynucleotide. For example, the RuvC domain may be fused to heterologous DNA-binding domains, or other CRISPR effector proteins to generate engineered nucleases with altered specificity or activity.

Inactivated Cas12 Mutant

By inactivating the RuvC domain of Cas12 through introducing point mutations, the Cas12 protein loses its endonuclease activity, resulting in a dCas12 that can only bind to a target gene under the mediation of the guide polynucleotide but does not possess the function of cleaving DNA.

Point mutations may also be introduced to partially inactivate the RuvC domain of Cas12, resulting in a nickase Cas12 (nCas12), which can bind to a target gene and cleave only one strand of the double-stranded nucleic acid under the mediation of the guide polynucleotide, while leaving the other strand intact.

Accordingly, the dCas12 or the nCas12 may be fused or conjugated with other domains (including, but not limited to, deaminase domains, transcriptional activation domains, transcriptional repression domains, methylation domains, demethylation domains, histone acetylation domains, and histone deacetylation domains), and guided to a target sequence of a target nucleic acid by the guide polynucleotide, to exert corresponding functions through the other domains. For example, the conversion of cytosine (C) to thymine (T) in the target nucleic acid is achieved by deamination of the cytosine base; the conversion of adenine (A) to guanine (G) is achieved by deamination of the adenine base; the transcriptional repression of the target nucleic acid is achieved using the transcriptional repression domain KRAB; and the transcriptional activation is promoted using the transcriptional activation domain VP64.

Functional Domain

In some embodiments, the Cas12 protein or the inactivated Cas12 mutant is covalently linked or fused to a homologous or heterologous functional domain.

In some embodiments, the functional domain has an enzyme activity that modifies a target nucleic acid sequence; the enzyme activity comprising a nuclease activity, a methyltransferase activity, a demethylase activity, a DNA repair activity, a DNA damage activity, a deamination activity, a dismutase activity, an alkylation activity, a depurination activity, an oxidation activity, a pyrimidine dimer formation activity, an integrase activity, a transposase activity, a recombinase activity, a polymerase activity, a ligase activity, a helicase activity, a photolyase activity, a glycosylase activity, a deglycosylation activity, an acetyltransferase activity, a deacetylase activity, a kinase activity, a phosphatase activity, a ubiquitin ligase activity, a deubiquitination activity, an adenylylation activity, a deadenylation activity, a SUMOylating activity, a deSUMOylating activity, a myristoylation activity, and/or a demyristoylation activity.

In some embodiments, the functional domain is selected from one or more of the following: a nuclease (e.g., FokI), a methyltransferase, a demethylase, a DNA repair enzyme, a DNA damage enzyme, a deaminase, a dismutase, an alkylase, a depurinase, an oxidase, a pyrimidine dimer-forming enzyme, an integrase, a transposase, a recombinase, a polymerase, a ligase, a helicase, a photolyase, a glycosylase, a deglycosylase, an acetyltransferase, a deacetylase, a kinase, a phosphatase, a ubiquitin ligase, a deubiquitinating enzyme, an adenylylase, a deadenylase, a SUMOylating enzyme, a deSUMOylating enzyme, a myristoylase, and/or a demyristoylase.

In some embodiments, the functional domain is selected from one, two, three, four, or more of the following: a subcellular positioning signal, a DNA binding domain, a protease domain, a transcriptional activation domain, a transcriptional repression domain, a nuclease domain, a deaminase domain, a uracil DNA glycosylase domain (UDG), a uracil DNA glycosylase inhibitory domain (UGI), a methylase, a demethylase, a transcription release factor, a histone acetylase domain, a histone deacetylase domain, a DNA ligase, an affinity tag, a reporter tag, an affinity domain, and a reporter domain.

In some embodiments of the present disclosure, the deaminase domain is selected from the following: APOBEC1, APOBEC3A, APOBEC3B, APOBEC3C, APOBEC3D, APOBEC3F, an activation-induced cytidine deaminase (AID), cytidine deaminase (CDA) from lamprey, and engineered mutants of adenosine deaminase (TadA) that act on DNA.

In some embodiments, the transcriptional activation domain is selected from the following: P65, VPR, VP16, VP64, VTR1, VTR2, VTR3, p65, MyoD1, HSF1, RTA, SET7/9, and a histone acetyltransferase. In some embodiments, the transcriptional activation domain is selected from the following: the sequence ETFSDLWKL from p53 TAD1, the sequence DDIEQWFTE from p53 TAD2, the sequence SDIMDFVLK from MLL, the sequence DLLDFSMMF from E2A, the sequence ETLDFSLVT from Rtg3, the sequence RKILNDLSS from CREB, the sequence EAILAELKK from CREBaB6, the sequence DDVVQYLNS from Gli3, the sequence DDVYNYLFD from Gal4, the sequence DLFDYDFLV from Oaf1, the sequence DFFDYDLLF from Pip2, the sequence EDLYSILWS from Pdr1, and the sequence TDLYHTLWN from Pdr3.

In some embodiments, the transcriptional repression domain is selected from: KRAB domain of KOX1, KRAB domain of KAP-1, MAD, FKHR, EGR-1, ERD, SID, a tandem repeat of SID (e.g., SID4X), KRAB domain of TIEG, v-ERB-A, MBD2, MBD3, TRa, a histone methyltransferase, a histone deacetylase (HDAC), a nuclear hormone receptor (e.g., an estrogen receptor or a thyroid hormone receptor), members of the DNMT family (e.g., DNMT1, DNMT3A, DNMT3B), the KRAB domain of MeCP2, ROM2, and AtHD2A.

In some embodiments, the transcriptional repression domain is a KRAB domain. In some embodiments, the transcriptional repression domain is a KRAB domain from a KOX1 protein.

In some embodiments, the nuclease domain is selected from the following: FokI, a polypeptide with single-stranded DNA (ssDNA) cleavage activity, or a polypeptide with double-stranded DNA (dsDNA) cleavage activity.

In some embodiments, the methylase domain is selected from a DNA methylase, including, but not limited to, DNMT1, DNMT3a, and DNMT3b.

In some embodiments, the demethylase is selected from TET1CD, TET1, ROS1, DME, DML2, and DML3.

Methylation and demethylation are recognized in the field as important modes of epigenetic gene modulation.

In some embodiments, the homologous or heterologous functional domain refers to a sequence tag useful for the solubility, purification, or detection of the fusion protein or conjugate. Suitable protein tag sequences are provided in the present disclosure, which include, but are not limited to, a biotin carboxylase carrier protein (BCCP) tag, a myc tag, a calmodulin tag, a FLAG tag, a hemagglutinin (HA) tag, a polyhistidine tag (also known as His tag), a maltose-binding protein (MBP) tag, a nus tag, and a glutathione-S-transferase (GST) tag, a green fluorescent protein (GFP) tag, a thioredoxin tag, a S-tag, a Softag (e.g., Softag 1, Softag 3), a strep-tag, a biotin ligase tag, a FLASH tag, a V5 tag, and a SBP tag. Additional suitable sequences are apparent to those of ordinary skill in the art.

In some embodiments of the present disclosure, a single-base editor is constructed by fusing a Mut-02-1-426-846-858-860-D651A-E891A-D1082A mutant with a deaminase domain and a nuclear localization signal (NLS). In some embodiments of the present disclosure, a single-base editor is constructed by fusing a Mut-02-1-426-846-858-860-D651A-E891A-D1082A mutant with an APOBEC3A domain and an SV40 NLS.

In some embodiments of the present disclosure, a transcriptional repression epigenetic editor is constructed by fusing a Mut-02-1-426-846-858-860-D651A-E891A-D1082A mutant with a KRAB domain and an SV40 NLS. In some embodiments of the present disclosure, a transcriptional activation epigenetic editor is constructed by fusing a Mut-02-1-426-846-858-860-D651A-E891A-D1082A mutant with a VP64 domain and an SV40 NLS.

Subcellular Localization Signal

In some embodiments, the Cas12 protein is fused to at least one type of homologous or heterologous subcellular localization signal. In some embodiments, the Cas12 protein is fused to at least one homologous or heterologous subcellular localization signal. Exemplarily, the subcellular localization signal comprises an organelle localization signal, such as a nuclear localization signal (NLS), a nuclear export signal (NES), or a mitochondrial localization signal.

Non-limiting examples of NLS include NLS sequences derived from: an NLS of SV40 large T antigen having the amino acid sequence PKKKKRKV (SEQ ID NO: 738); an NLS of a nucleoplasmic protein (e.g., a sequence KRPAATKKKAGQAKKKKK, SEQ ID NO: 739); an NLS of c-myc having the amino acid sequence PAAKRVKLD (SEQ ID NO: 740) or the amino acid sequence RQRRNELKRSP (SEQ ID NO: 741); an NLS of hRNPA1 M9 having the amino acid sequence NQSSNFGPMKGGGNFGGRSSGPYGGGGGQYFAKPRNQGGY (SEQ ID NO: 742); a sequence RMRIZFKNKGKDTAELRRRRVEVSVELRKKAKKDEQILKRRNV (SEQ ID NO: 743) derived from an IBB domain; a sequence VSRKRPRP (SEQ ID NO: 744) and a sequence PPKKARED (SEQ ID NO: 745) of the rhabdomyosarcoma T-protein; a sequence PQPKKKPL of human p53 (SEQ ID NO: 746); a sequence SALIKKKKKKMAP (SEQ ID NO: 747) of mouse c-ablIV; a sequence DRLRR (SEQ ID NO: 748) and a sequence PKQKKRK (SEQ ID NO: 749) of influenza virus NS1; and a sequence RKLKKKKKKL (SEQ ID NO: 750) of hepatitis virus delta antigen; a sequence REKKKKFLKRR (SEQ ID NO: 751) of mouse Mx1 protein; a sequence KRKGDEVDGVDEVAKKKSKK (SEQ ID NO: 752) of human poly(ADP-ribose) polymerase; and a sequence RKCLQAGMNLEARKTKKK (SEQ ID NO: 753) of steroid hormone receptor. In some embodiments, the nuclear localization sequence has sufficient strength to drive the accumulation of the fusion protein or conjugate described herein within the nucleus of a eukaryotic cell to a detectable level. In summary, the strength of the nuclear localization activity may be derived from a count of the NLS, one or more specific used NLSs, or any combination of these factors. The accumulation within the nucleus may be detected using any suitable technique. For example, a detectable marker may be fused to the Cas protein to allow visualization of its intracellular location, such as in combination with detection methods of nuclear location (e.g., nucleus-specific dyes such as DAPI)). As another example, the cell nucleus may be isolated from the cell, and its contents are subsequently analyzed using any appropriate method for detecting protein, including but not limited to immunohistochemistry, western blotting, or enzymatic activity assays. As another example, the accumulation within the nucleus may also be indirectly determined, for example, by assessing the effect of the formation of a nucleic acid-targeting complex (e.g., measuring DNA or RNA cleavage or mutation at a target sequence, or measuring changes in gene expression activity resulting from the formation of a DNA-targeting complex or a RNA-targeting complex and/or the activity of a DNA-targeting Cas protein or a RNA-targeting Cas protein), compared with a control group that is not exposed to a nucleic acid-targeting Cas protein or complex, or exposed to a nucleic acid-targeting Cas protein lacking one or more NLSs.

Vector System

Some embodiments of the present disclosure relate to a vector system comprising the CRISPR-Cas12 system described herein. The vector system comprises one or more recombinant vectors, and the recombinant vector comprises a polynucleotide sequence encoding the Cas12 protein and a polynucleotide sequence encoding the guide polynucleotide.

In some embodiments, the vector system comprises at least one plasmid or viral recombinant vector (e.g., retrovirus, lentivirus, adenovirus, adeno-associated virus, or herpes simplex virus). In some embodiments, the polynucleotide sequence encoding the Cas12 protein and the polynucleotide sequence encoding the guide polynucleotide are located at the same recombinant vector. In some embodiments, the polynucleotide sequence encoding the Cas12 protein and the polynucleotide sequence encoding the guide polynucleotide are located at a plurality of recombinant vectors.

In some embodiments, the polynucleotide sequence encoding the Cas12 protein and/or the polynucleotide sequence encoding the guide polynucleotide is operably linked to a regulatory sequence (also known as a regulatory element). The regulatory element comprises a promoter, an enhancer, an internal ribosome entry site (IRES), and other expression control elements (e.g., a transcriptional termination signal such as a polyadenylation signal and a poly-U sequence). The regulatory element comprises an element that enables constitutive expression of the nucleotide sequence in many types of host cell types, as well as an element that restrict expression to specific host cells (e.g., a tissue-specific regulatory sequence). A tissue-specific promoter can be directly expressed primarily in the desired tissue of interest, e.g., muscle, neurons, bone, skin, blood, specific organs (e.g., liver, pancreas), or specific cell types (e.g., lymphocytes). The regulatory element may also guide expression in a time-dependent manner, e.g., in a cell-cycle-dependent or developmental-stage-dependent manner, which may or may not also be tissue-type specific or cell-type specific. In some embodiments, the regulatory element is enhancer elements, such as a WPRE, a CMV enhancer, an R-U5 segment in the LTR of HTLV-1, an SV40 enhancer, or an intronic sequence between exons 2 and 3 of the rabbit β-globin.

In some embodiments, the recombinant vector comprises a polymerase III (pol III) promoter (e.g., a U6 promoter and an H1 promoter), a polymerase II (pol II) promoter (e.g., the retroviral Rous sarcoma virus (RSV) long terminal repeat (LTR) promoter (optionally with an RSV enhancer), a cytomegalovirus (CMV) promoter (optionally with a CMV enhancer), an SV40 promoter, a dihydrofolate reductase promoter, a β-actin promoter, a phosphoglycerol kinase (PGK) promoter, or an EF1α promoter), or both a pol III promoter and a pol II promoter.

In some embodiments, the promoter is a constitutive promoter, which is continuously active and not modulated by external signals or molecules. Suitable constitutive promoters include, but are not limited to, CMV, RSV, SV40, EF1α, CAG, and β-actin promoters. In some embodiments, the promoter is an inducible promoter modulated by an external signal or molecule (e.g., a transcription factor).

In some embodiments, the promoter is a tissue-specific promoter, which may be used to drive tissue-specific expression of the Cas12 protein. Suitable muscle-specific promoters include, but are not limited to, CK8, MHCK7, a myoglobin (Mb) promoter, a desmin promoter, a muscle creatine kinase (MCK) promoter and mutants thereof, and an SPc5-12 synthesis promoter. Suitable immune cell-specific promoters include, but are not limited to, a B29 promoter (B cells), a CD14 promoter (monocytes), a CD43 promoter (leukocytes and platelets), a CD68 (macrophages) promoter, and an SV40/CD43 promoter (leukocytes and platelets). Suitable blood cell-specific promoters include, but are not limited to, a CD43 promoter (leukocytes and platelets), a CD45 promoter (hematopoietic cells), INF-β (hematopoietic cells), a WASP promoter (hematopoietic cells), an SV40/CD43 promoter (leukocytes and platelets), and an SV40/CD45 promoter (hematopoietic cells). Suitable pancreas-specific promoters include, but are not limited to, an elastase-1 promoter. Suitable endothelial cell-specific promoters include, but are not limited to, a Fit-1 promoter and an ICAM-2 promoter. Suitable neuronal tissue/cell-specific promoters include, but are not limited to, a GFAP promoter (astrocytes), an SYN1 promoter (neurons), and NSE/RU5' (mature neurons). Suitable kidney-specific promoters include, but are not limited to, a NphsI promoter (podocytes). Suitable bone-specific promoters include, but are not limited to, an OG-2 promoter (osteoblasts, dentinogenic cells). Suitable lung-specific promoters include, but are not limited to, an SP-B promoter (lung). Suitable liver-specific promoters include, but are not limited to, an SV40/Alb promoter. Suitable heart-specific promoters include, but are not limited to, α-MHC. In some embodiments, the tissue-specific promoter is selected from liver-specific promoters such as an albumin (ALB) promoter, an alpha-fetoprotein (AFP) promoter, a transthyretin (TTR) promoter, a hepatocyte nuclear factor 4 alpha (HNF4α) promoter, an apolipoprotein B (APOB) promoter, a carbamoyl-phosphate synthase 1 (CPS1) promoter, and a coagulation factor VII promoter (F7 promoter); a hematopoietic stem/progenitor cell (HSC)-specific promoter such as a cluster of differentiation 34 (CD34) promoter, a stem cell leukemia (SCL) promoter, a KIT proto-oncogene (c-Kit) promoter, a GATA binding protein 2 (GATA2) promoter, a LIM domain only 2 (LM02) promoter, and a runt-related transcription factor 1 (RUNX1) promoter; a nerve-specific promoter such as a synapsin I promoter, a neuron-specific enolase (NES) promoter, a tyrosine hydroxylase (TH) promoter, a glial fibrillary acidic protein (GFAP) promoter, and a myelin basic protein (MBP) promoter; muscle-specific promoters such as a muscle creatine kinase (MCK) promoter, a desmin promoter, an alpha-myosin heavy chain (α-MHC) promoter, and a myogenin promoter; immune/hematopoietic lineage-specific promoters such as a cluster of differentiation 19 (CD19) promoter, a cluster of differentiation 3 epsilon (CD3ε) promoter, a CD8 promoter, a Integrin alpha M (CD11b) promoter, an interleukin-2 (IL-2) promoter, and a lymphocyte-specific protein tyrosine kinase (Lck) promoter; lung-specific promoters such as a surfactant protein C (SP-C) promoter, a clara cell 10-kDa protein (CC10) promoter, and a forkhead box protein J1 (FOXJ1) promoter; heart-specific promoters such as an alpha-myosin heavy chain (α-MHC) promoter, a cardiac troponin T (cTnT) promoter, a myosin light chain 2 ventricular (MLC-2v) promoter; and kidney-specific promoters such as a nephrin (NPHS1) promoter and an aquaporin 2 (AQP2) promoter.

In some embodiments, the tissue-specific promoter is selected from pancreatic/islet β-cell-specific promoters such as an insulin (INS) promoter, a pancreatic and duodenal homeobox 1 (PDX1) promoter, and a glucose transporter type 2 (GLUT2) promoter; and an intestinal-specific promoter such as a villin promoter, a mucin-2 (MUC2) promoter, and a fatty acid binding protein 2 (FABP2) promoter.

Adeno-Associated Virus (AAV) Vector

Some embodiments of the present disclosure relate to an AAV vector comprising the CRISPR-Cas12 system, and the AAV vector comprises DNA encoding the Cas12 protein and the guide polynucleotide.

Delivery of the CRISPR-Cas system via the AAV vector was described in Maeder et al., *Nature Medicine* 25:229-233 (2019). It clinically demonstrated the safety and efficacy of subretinal delivery of AAV. Localized delivery via subretinal injection, the natural tropism of AAV5 for photoreceptor cells, and the use of the photoreceptor-specific GRKI promoter were all employed to restrict expression of the CRISPR/Cas system to the therapeutic target tissue and cell types. The entire contents of this reference are incorporated herein by reference. In some embodiments, the AAV vector comprises a ssDNA genome that comprises coding sequences for the Cas 12 protein and a guide polynucleotide flanked by inverted terminal repeats (ITRs).

In some embodiments, the CRISPR-Cas12 system is packaged into the AAV vector, such as AAV1, AAV2, AAV3, AAV4, AAV5, AAV6, AAV7, AAV8, AAV9, or AAVrh74. In some embodiments, the CRISPR-Cas12 system described herein is packaged into the AAV vector including an engineered capsid with tissue tropism, such as an engineered muscle-tropic capsid. Taboada et al., *Cell* 184:4919-4938 (2021) described the engineering of tissue-tropic AAV capsids through directed evolution and identifying a class of capsids containing an RGD motif, and systemic injection of MyoAAV enables efficient transduction of muscle tissue in non-human primates. The entire contents of this reference are incorporated herein by reference.

Lipid Nanoparticle

Some embodiments of the present disclosure relate to a lipid nanoparticle (LNP) comprising the CRISPR-Cas12 system, and the LNP comprises the guide polynucleotide and mRNA encoding the Cas12 protein as described herein.

The LNP delivery of the CRISPR-Cas system was described in Gillmore et al., *N. Engl. J. Med.* 385:493-502 (2021). The LNP is composed of four lipids, including a proprietary ionizable lipid LP000001, DSPC, cholesterol, and DMG-PEG2k. An LNP suspension is formulated in an aqueous buffer including Tris, NaCl, and sucrose at pH of 7.4. The entire contents of this reference are incorporated herein by reference. In some embodiments, in addition to RNA payload (Cas12 mRNA and a guide polynucleotide), the LNP further comprises four components: a cationic or ionizable lipid, cholesterol, a helper lipid, and a PEG-lipid. In some embodiments, the cationic or ionizable lipid comprises cKK-E12, C12-200, ALC-0315, DLin-MC3-DMA, DLin-KC2-DMA, FTT5, Moderna SM-102, and Intellia LP01. In some embodiments, the PEG-lipid comprises PEG-2000-C-DMG, PEG-2000-DMG, or ALC-0159. In some embodiments, the helper lipid comprises DSPC. The components of LNP were described in Panuska et al., *Nature Reviews Genetics* 23:265-280 (2022). FDA-approved LNP comprises mutants of four basic components: a cationic or ionizable lipid, cholesterol, a helper lipid, and polyethylene glycol (PEG) lipid. The entire contents of this reference are incorporated herein by reference.

Lentiviral Vector

Some embodiments of the present disclosure relate to a lentiviral vector comprising the CRISPR-Cas12 system described herein, and the lentiviral vector comprises the guide polynucleotide and mRNA encoding the Cas12 protein described herein. In some embodiments, the lentiviral vector is pseudotyped with homologous or heterologous envelope proteins such as VSV-G. In some embodiments, the mRNA encoding the Cas12 protein is linked to an aptamer sequence.

Ribonucleoprotein (RNP) Complex

Some embodiments of the present disclosure relate to a RNP complex comprising the CRISPR-Cas12 system, and the RNP complex is formed by the guide polynucleotide and the Cas12 protein described herein. In some embodiments, the RNP complex may be delivered into eukaryotic cells, mammalian cells, or human cells via microinjection or electroporation. In certain embodiments, the RNP complex may be packaged into virus-like particles and delivered in vivo to mammalian or human subjects.

Virus-Like Particle (VLP)

Some embodiments of the present disclosure relate to a VLP comprising the CRISPR-Cas12 system, and the VLP comprises the guide polynucleotide and the Cas12 protein described herein, or the RNP complex formed by the guide polynucleotide and the Cas12 protein.

The development and application of DNA-free virus-like particles (eVLPs) for efficient packaging and delivery of base editors or Cas9 ribonucleoproteins was described in Banskota et al., *Cell* 185 (2): 250-265 (2022). Mangeot et al., *Nature Communications* 10 (1): 1-15 (2019) revealed engineered murine leukemia virus-like particles (Nanoblades) loaded with Cas9-sgRNA ribonucleoproteins to induce efficient genome editing in cell lines and primary cells (including human induced pluripotent stem cells, human hematopoietic stem cells, and mouse bone marrow cells). Campbell et al., *Molecular Therapy* 27:151-163 (2019) revealed specialized extracellular vesicles called “gesicles” to efficiently yet transiently deliver Cas9 ribonucleoproteins targeting the HIV long terminal repeat (LTR) sequence. Gesicles are produced by expressing vesicular stomatitis virus glycoprotein and packaging proteins (as their cargo), thus eliminating the need for transgenic delivery and enabling more precise control over Cas9 expression. Mangeot et al., *Molecular Therapy* 19 (9): 1656-1666 (2011) revealed that overexpression of the vesicular stomatitis virus glycoprotein (VSV-G) in human cells induces the release of fusogenic vesicles (named gesicles). Biochemical and functional studies showed that glial cells incorporate proteins from producer cells and can deliver them to recipient cells. This protein transduction method enables the direct transfer of cytoplasmic, nuclear, or surface proteins in target cells. These references all describe engineered VLPs, the entire contents of each of which are incorporated herein by reference.

In some embodiments, the engineered VLP is pseudotyped with homologous or heterologous envelope proteins such as VSV-G. In some embodiments, the Cas12 protein is fused to a gag protein (e.g., MLV gag) via a cleavable linker, and cleavage of the linker in the target cell exposes a nuclear localization signal (NLS) located between the linker and the Cas12 protein. In some embodiments, the fusion protein or conjugate comprises (e.g., from the 5' end to the 3' end) the gag protein (e.g., MLV gag), one or more nuclear export signals (NES), a cleavable linker, one or more NLS, and Cas12, as described in Banskota et al., *Cell* 185 (2): 250 265 (2022).

In some embodiments, the Cas12 protein is fused to a first dimerization domain that is capable of dimerizing or heterodimerizing with a second dimerization domain fused to a membrane protein, and the presence of a ligand promotes such dimerization and facilitates the enrichment of the Cas12 protein or the fusion protein or conjugate thereof into the VLP, as described in Campbell et al., *Molecular Therapy* 27:151-163 (2019).

Cell

Some embodiments of the present disclosure relate to a cell comprising the CRISPR-Cas12 system described herein. The cell (e.g., used to generate a cell-free system) may be prokaryotic or eukaryotic. For example, the cell comprises, but is not limited to, bacteria, archaea, plant, fungi, yeast, insect, and mammalian cell, such as *Lactobacillus, Lactococcus, Bacillus* (e.g., *B. subtilis*), *Escherichia* (e.g., *Escherichia coli*), *Clostridium, Saccharomyces* or *Pichia* (e.g., *Saccharomyces cerevisiae* or *Pichia pastoris*), *Kluyveromyces lactis, Salmonella typhimurium, Drosophila cells, Caenorhabditis elegans* cell, *Xenopus laevis* cell, SF9 cells, C129 cells, HEK293 cells, *Neurospora*, and immortalized mammalian cell line (e.g., HeLa, bone marrow cell line, and lymphoid cell line).

In some embodiments, the cell is a prokaryotic cell, such as a bacterial cell (e.g., *Escherichia coli*). In some embodiments, the cell is a eukaryotic cell, such as a mammalian or human cell. In some embodiments, the cell is a primary eukaryotic cell, a stem cell, a tumor/cancer cell, a circulating tumor cell (CTC), a blood cell (e.g., T cell, B cell, NK cell, regulatory T cell (Treg), etc.), a hematopoietic stem cell, a specialized immune cell (e.g., tumor-infiltrating lymphocyte or tumor-suppressive lymphocyte), or a stromal cell in the tumor microenvironment (e.g., cancer-associated fibroblast). In some embodiments, the cell is a brain or neuronal cell of the central or peripheral nervous system (e.g., neuron, astrocyte, microglial cell, retinal ganglion cell, rod or cone cell).

Target Nucleic Acid or Target DNA

In some embodiments, the target nucleic acid is a target DNA.

The CRISPR-Cas12 system described herein may be used to target one or more target nucleic acid molecules, such as target nucleic acid molecules present in biological samples or environmental samples (e.g., soil, air, or water samples).

In some embodiments of the present disclosure, the target nucleic acid is a gene associated with a disease or disorder. In some embodiments, the target nucleic acid is a disease-associated gene. In some embodiments, the disease-associated gene is a pathogenic gene that directly causes the disease. In some embodiments, the disease-associated gene is an aberrant gene that directly causes the disease or a gene exhibiting abnormal expression. For example, the gene undergoes deleterious mutations, leading to occurrence of disease. As another example, the gene may be overexpressed or underexpressed, resulting in occurrence of disease. In some embodiments, overexpression of the gene leads to disease. In some embodiments, underexpression of the gene leads to disease. In some embodiments, the overexpression of the gene is associated with the occurrence of disease. In some embodiments, the underexpression of the gene is associated with the occurrence of disease.

In some embodiments of the present disclosure, the disease or disorder is a hematologic disease or disorder, an ophthalmic disease or disorder, a neurological disease or disorder, a respiratory disease or disorder, a hepatic disease or disorder, a metabolic disease or disorder, a cancer, or an infectious disease.

In some embodiments of the present disclosure, the target nucleic acid is selected from any one of the genes listed in Table 27, and the disease or disorder is listed in Table 27. Table 27 shows target nucleic acids and a disease or disorder corresponding to each target nucleic acid.

In some embodiments of the present disclosure, the disease or disorder is selected from: hemophilia A, Best yolk-like macular dystrophy, B-cell acute lymphoblastic leukemia, hemophilia B, CDKL5 deficiency, CLN2 disease, Niemann-Pick disease type C, Dravet syndrome, FOXG1 syndrome, GM1 ganglioside storage disease, GM2 ganglioside deposition disease, HIV infection, HSV infection, Usher syndrome type IB, Usher syndrome type IIA, Mucopolysaccharidosis type IIIA, Mucopolysaccharidosis type IIIB, Gaucher disease type III, Mucopolysaccharidosis type II, type II diabetes, Mucopolysaccharidosis type IV, Gaucher disease type I, Mucopolysaccharidosis type I, type I diabetes, Usher syndrome type I, KCNQ2 epileptic encephalopathy, Leber hereditary optic neuropathy, Leigh syndrome, Prader-Willi syndrome, SLC13A5 deficiency, X-linked myotubular myopathy, X-linked retinoschisis, X-linked retinitis pigmentosa, al-antitrypsin deficiency, α-mannoside storage disease, α-thalassemia, β-thalassemia, Alzheimer's disease, Bardet-Biedl syndrome, white dot retinal degeneration, leukocyte adhesion deficiency type I, galactosemia, bladder cancer, overactive bladder, phenylketonuria, nasopharyngeal carcinoma, Bietti's crystalline dystrophy, pyruvate kinase deficiency, erectile dysfunction, autosomal recessive congenital ichthyosis, adult glucan body disease, traumatic arthritis, homozygous familial hypercholesterolemia, Fragile X syndrome, thalassemia, hypophosphatasia, epilepsy, multiple myeloma, multiple system atrophy, frontotemporal dementia, catecholamine-sensitive polymorphic ventricular tachycardia, Fabry's disease, Fanconi's anemia, aromatic L-amino acid decarboxylase deficiency, radiation-induced xerostomia, non-Hodgkin's lymphoma, non-muscle invasive bladder carcinoma, non-alcoholic fatty liver disease, non-small cell lung cancer, hypertrophic cardiomyopathy, hypertrophic scar, obesity, peroneal muscular dystrophy type 1A, peroneal muscular dystrophy type 2A, pulmonary hypertension, Friedrich's ataxia, peritoneal carcinoma, liver cancer, hepatocellular carcinoma, dry age-related macular degeneration, sicca syndrome, hyperuricemia, hyperlipidemia, Gaucher disease, autism spectrum disorders, osteoarthritis, bone marrow failure syndromes, citrullinemia type I, coronary heart disease, cystinosis, melanoma, Huntington's disease, amyotrophic lateral sclerosis, urge incontinence, acute intermittent porphyria, acute lymphoblastic leukemia, spinal cerebellar ataxia, spinal muscular atrophy with respiratory distress type 1, spinal muscular atrophy, Tay-Sachs diesease, methylmalonic acidemia, thyroid carcinoma, pseudohypertrophic muscular dystrophy, anaplastic astrocytoma, intermittent claudication, junctional epidermolysis bullosa, glioma, glioblastoma, corneal graft rejection, colorectal cancer, progressive multifocal leukoencephalopathy, progressive familial intrahepatic cholestasis, giant-axonal neuropathy, Canavan's disease, cocaine addiction, Klaber's disease, Kriegler-Najjar syndrome, oral cancer, Angelman syndrome, diffuse intrinsic pontine glioma, Lafora's disease, rheumatoid arthritis, sickle cell disease, lymphedema, ovarian cancer, chronic lymphocytic leukemia, chronic granulomatous disease, chronic nephrogenic anemia, chronic pain, chronic hepatitis B, Menkes' disease, cystic fibrosis, Netherseton's syndrome, ornithine transcarbamylase deficiency, Parkinson's disease, Pompe's disease, uveitis, prostate cancer, vestibular schwannoma, ankylosing muscular dystrophy, ankylosing spondylitis, castration-resistant prostate cancer, glaucoma, achromatopsia, ischemic heart failure, lysosomal storage disease, sarcoma, breast cancer, Rett's syndrome, triple-negative breast cancer, Sandhoff's disease, color blindness, heart failure with reduced ejection fraction, neuronal ceroid lipofuscinosis, adrenoleukodystrophy, renal cell carcinoma, wet age-related macular degeneration, eczema, thrombocytopenia with immunodeficiency syndrome, esophageal cancer, optic neuropathy, optic nerve atrophy, retinal vein occlusion, retinitis pigmentosa, rhodopsin-mediated autosomal dominant retinitis pigmentosa, ependymoma, fallopian tube carcinoma, bilateral vestibulopathies, Stargardt's disease, diabetic macular edema, diabetic neuropathy, diabetic retinopathy, diabetic peripheral neuralgia, diabetic foot, glycogenosis, glycogenosis type Ia, glycogenosis type IIb, atopic dermatitis, hearing loss, hearing impairment, head and neck cancer, squamous cell carcinoma of the head and neck, Wilson's disease, stable angina pectoris, Usher's syndrome, choroideremia, Leber's congenital amaurosis, congenital adrenal hyperplasia, cardiomyopathy, angina pectoris, heart failure, COVID-19 infection, pleural mesothelioma, acne vulgaris, severe combined immunodeficiency diseases, severe limb ischemia, oculopharyngeal muscular dystrophy, pancreatic cancer, graft-versus-host disease, hereditary retinal dystrophy, hereditary angioedema, hepatitis B, heterotrophic cerebral leukoencephalic dystrophy, psoriatic arthritis, recessive genetic dystrophic epidermolysis bullosa, infantile malignant osteosclerosis, dystrophic epidermolysis bullosa, morphea, primary immune deficiency, heterozygous familial hypercholesterolemia, limb-girdle muscular dystrophy type 2B, limb-girdle muscular dystrophy type 2C, limb-girdle muscular dystrophy type 2D, limb-girdle muscular dystrophy type 2E, limb-girdle muscular dystrophy type 2I, limb-girdle muscular dystrophy type 2L, limb ischemic disease, lipoprotein lipase deficiency, severe congenital neutrophilic dysphoria, wrinkles, stroke, sciatica, schizophrenia, depression, drug addiction, autism, idiopathic pulmonary fibrosis, hyperlipidemia, transthyretin (ATTR) amyloidosis, alpha-1-antitrypsin deficiency (AATD) liver disease, and AATD lung disease.

Genes associated with ATTR amyloidosis comprise, but are not limited to, ATTR.

Genes associated with Leber hereditary optic neuropathy comprise, but are not limited to, MT-ND4.

Genes associated with AATD liver disease comprise, but are not limited to, AATD.

Genes associated with AATD lung disease comprise, but are not limited to, AATD.

Genes associated with the graft-versus-host disease comprise, but are not limited to, thymidine kinase genes.

Genes associated with hereditary retinal dystrophy comprise, but are not limited to, RPE65.

Genes associated with spinal muscular atrophy comprise, but are not limited to, SMN1.

Genes associated with osteoarthritis comprise, but are not limited to, TGF-β1.

Genes associated with hemophilia A comprise, but are not limited to, factor VIII.

Genes associated with hemophilia B comprise, but are not limited to, factor IX.

Genes associated with cystic fibrosis comprise, but are not limited to, CFTR.

Genes associated with Parkinson's disease comprise, but are not limited to, Gad1, Gad2, PTBP1, KEAP1, RE1, Amigo1, Gprc5c, Let-7a, Pnky, LRRK2, SNCA, GBA, miR-92b, miR-9, miR-124, miR-181, HMGB1, TRIM72, GPNMB, and REST.

Genes associated with Usher syndrome comprise, but are not limited to, USH2A.

Genes associated with α-thalassemia, β-thalassemia, and the sickle cell disease comprise, but are not limited to, BCL11A, HBG, HBA, and HBB.

Genes associated with pulmonary hypertension comprise, but are not limited to, eNOS.

Genes associated with Stargardt's disease comprise, but are not limited to, ABCA4.

Genes associated with age-related macular degeneration comprise, but are not limited to, VEGFA, VEGFR, IL17, Kir7.1, LCN-2, IRAK-M, CD59, LTA4H, GPX4, GLS1, PAPP-A, cGAS, STING, mTOR, GCN2, Nrf2, Ang 2, CTGF, Complement C3, Complement C5, CHFR4b, DOCK6, CTSS, ELN, and FGF2.

Genes associated with glaucoma comprise, but are not limited to, AQP1, ADRB2, NMNTA2, NRP1, Hrh1, Anxa2, OPA1, Cx43, ANGPTL7, MYOC, ROCK1, ROCK2, TIMP1, TIMP2, TIMP3, TIMP4, carbonic anhydrase CA2, carbonic anhydrase CA4, and carbonic anhydrase CA12.

Genes associated with idiopathic pulmonary fibrosis comprise, but are not limited to, CTGF.

Genes associated with hyperlipidemia comprise, but are not limited to, PCSK9.

Genes associated with Alzheimer's disease comprise, but are not limited to, NGF.

Genes associated with coronary heart disease comprise, but are not limited to, VEGFA and bFGF.

Genes associated with chronic nephrogenic anemia related comprise, but are not limited to, EPO.

Genes associated with Leber's congenital amaurosis comprise, but are not limited to, RPE65.

Genes associated with retinitis pigmentosa comprise, but are not limited to, PDE6B.

Genes associated with phenylketonuria comprise, but are not limited to, PAH.

Genes associated with epilepsy comprise, but are not limited to, GAT1.

In some embodiments of the present disclosure, a sequence of the target nucleic acid is as shown in any one of sequences shown in SEQ ID NO: 761-782.

Non-limiting examples of the target nucleic acid also include target nucleic acids disclosed in U.S. Provisional Patent Application No. 61/736,527, filed on Dec. 12, 2012, U.S. Provisional Patent Application No. 61/748,427, filed on Jan. 2, 2013, and International Application No. PCT/US2013/074667, filed on Dec. 12, 2013, the entire contents of each of which are incorporated herein by reference.

In some embodiments, the target nucleic acid is a reporter gene. Examples of the reporter gene include, but are not limited to, glutathione-S-transferase (GST), horseradish peroxidase (HRP), chloramphenicol acetyltransferase (CAT), β-galactosidase, β-glucuronidase, luciferase, green fluorescent protein (GFP), HcRed, DsRed, cyan fluorescent protein (CFP), yellow fluorescent protein (YFP), and autofluorescent protein including blue fluorescent protein (BFP)

Use for Treatment or Prevention of Disease

Some embodiments of the present disclosure relate to a pharmaceutical composition comprising the Cas12 protein, the guide polynucleotide, the inactivated Cas12 mutant, the fusion protein or conjugate, the isolated nucleic acid, the CRISPR-Cas12 system, the vector system, the delivery system, or the cell, which are all described in the present disclosure. For example, the pharmaceutical composition may comprise an AAV vector encoding the Cas12 protein or the inactivated Cas12 mutant and the guide polynucleotide. For example, the pharmaceutical composition may comprise a lipid nanoparticle comprising the guide polynucleotide and mRNA encoding the Cas12 protein. For example, the pharmaceutical compositions may comprise a lentiviral vector comprising the guide polynucleotide and the mRNA encoding the Cas12 protein. For example, the pharmaceutical composition may comprise a virus-like particle comprising the guide polynucleotide and the Cas12 protein, or a ribonucleoprotein complex formed by the guide polynucleotide and the Cas12 protein.

Some embodiments of the present disclosure relate to use of the Cas12 protein, the guide polynucleotide, the inactivated Cas12 mutant, the fusion protein or conjugate, the isolated nucleic acid, the CRISPR-Cas12 system, the vector system, the delivery system, the cell, the pharmaceutical composition, or the kit described herein in cleaving or editing a target nucleic acid in a mammalian cell.

Some embodiments of the present disclosure relate to use of the Cas12 protein, the guide polynucleotide, the inactivated Cas12 mutant, the fusion protein or conjugate, the isolated nucleic acid, the CRISPR-Cas 12 system, the vector system, the delivery system, the cell, the pharmaceutical composition, or the kit described herein in any of the following: cleaving one or more target nucleic acid molecules or introducing nicks into the one or more target nucleic acid molecules, activating or upmodulating an expression of the one or more target nucleic acid molecules, activating or inhibiting transcription of the one or more target nucleic acid molecules, inactivating the one or more target nucleic acid molecules, visualizing, labeling, or detecting the one or more target nucleic acid molecules, binding the one or more target nucleic acid molecules, transporting the one or more target nucleic acid molecules, and masking the one or more target nucleic acid molecules.

Some embodiments of the present disclosure relate to use of the Cas12 protein, the guide polynucleotide, the inactivated Cas12 mutant, the fusion protein or conjugate, the isolated nucleic acid, the CRISPR-Cas12 system, the vector system, the delivery system, the cell, the pharmaceutical composition, or the kit described herein in modifying one or more target nucleic acid molecules, and the modifying one or more target nucleic acid molecules comprises one or more of: nucleic acid base substitution, nucleic acid base deletion, nucleic acid base insertion, breakage of a target nucleic acid, nucleic acid methylation, and nucleic acid demethylation.

Some embodiments of the present disclosure relate to use of the Cas12 protein, the guide polynucleotide, the inactivated Cas12 mutant, the fusion protein or conjugate, the isolated nucleic acid, the CRISPR-Cas12 system, the vector system, the delivery system, the cell, the pharmaceutical composition, or the kit described herein in diagnosing, treating, or preventing a disease or disorder associated with the target nucleic acid.

Some embodiments of the present disclosure relate to use of the Cas12 protein, the guide polynucleotide, the inactivated Cas12 mutant, the fusion protein or conjugate, the isolated nucleic acid, the CRISPR-Cas12 system, the vector system, the delivery system, the cell, the pharmaceutical composition, or the kit described herein in preparing a medicament for diagnosing, treating, or preventing a disease or disorder associated with the target nucleic acid.

In some embodiments of the present disclosure, the target nucleic acid is optionally selected from genes as listed in Table 27, and the disease or disorder is as listed in Table 27.

Table 27 shows target nucleic acids and a disease or disorder corresponding to each target nucleic acid.

In some embodiments of the present disclosure, specific genes, such as those listed in Table 27, are subjected to targeted cleavage by the CRISPR-Cas12 system, thereby preventing, diagnosing, or treating the corresponding disease or disorder in Table 27. After targeted cleavage, indels are introduced through cellular repair, resulting in the knockout of the target gene, thereby suppressing its function.

In some embodiments of the present disclosure, specific genes, such as those listed in Table 27, are subjected to targeted modification by the CRISPR-Cas12 system, thereby preventing, diagnosing, or treating the corresponding disease or disorder in Table 27.

In some embodiments of the present disclosure, an expression of specific genes, such as those listed in Table 27, is subjected to targeted modulation by the CRISPR-Cas12 system, thereby preventing, diagnosing, or treating the corresponding disease or disorder in Table 27.

In some embodiments, the pharmaceutical composition is delivered in vivo to a human subject. The pharmaceutical composition may be delivered by any effective route. Exemplary routes of administration include, but are not limited to, intravenous infusion, intravenous injection, intraperitoneal injection, intramuscular injection, intratumoral injection, subcutaneous injection, intradermal injection, intraventricular injection, intravascular injection, intracerebellar injection, intraocular injection, subretinal injection, intravitreal injection, intracameral injection, intratympanic injection, intranasal injection, and inhalation.

Diagnostic Application

Some embodiments of the present disclosure relate to an in vitro composition, comprising the CRISPR-Cas12 system described herein and a marked detector DNA that does not hybridize with the guide polynucleotide described herein.

Some embodiments of the present disclosure relate to the use of the CRISPR-Cas12 system in detecting a target nucleic acid in a nucleic acid sample suspected of containing a target nucleic acid.

Some embodiments of the present disclosure relate to the use of the CRISPR-Cas12 system in detecting a target nucleic acid in a nucleic acid sample containing the target nucleic acid.

In some embodiments, the detected target nucleic acid is a target RNA.

In some embodiments, the detected target nucleic acid is a target DNA. In some embodiments, a method for detecting the target DNA comprises fusing a Cas12 protein to a fluorescent protein or other detectable marker and a guide sequence of a guide polynucleotide being specific to the target DNA. The binding of Cas12 to the target DNA may be visualized by microscopy or other imaging manners.

In some embodiments, a method for detecting a target nucleic acid in a cell-free system results in the generation of a detectable marker or enzymatic activity. For example, by using the Cas12 protein, the guide polynucleotide comprising the guide sequence specific to the target DNA, and the detectable marker, the target nucleic acid may be recognized by Cas12. Binding of Cas12 to the target nucleic acid triggers its DNase activity, which results in cleavage of the target nucleic acid and the detectable marker.

In some embodiments, the detectable marker is DNA linked to a fluorescent probe and a quencher. The complete detectable DNA ligates to the fluorescent probe and quencher, suppressing fluorescence. After the detectable DNA is cleaved by Cas12, the fluorescent probe is released from the quencher and exhibits fluorescent activity. This method may be used to determine whether the target DNA is present in lysed cell samples, lysed tissue samples, blood samples, saliva samples, environmental samples (e.g., water, soil, or air samples), or other lysed cell or cell-free samples. This method may also be used to detect pathogens such as viruses or bacteria, or to diagnose disease states such as cancer.

In some embodiments, the detection of the target nucleic acid is conducive to diagnosing a disease and/or pathological condition, or the presence of viral or bacterial infection.

Table 27 Target nucleic acid/target gene and corresponding disease or disorder (when there are two or more target sites in a specific cell, it means that two or more target genes are targeted simultaneously, the targeting including targeted knockout, single-base editing, homologous recombination, targeted enhancement of transcription, and targeted inhibition of transcription)

| Target site (gene) | Disease name |
|---|---|
| 17β-HSD13 | Non-alcoholic steatohepatitis (NASH) |
| 17β-HSD13 | Metabolic dysfunction-associated fatty liver disease (MAFLD) |
| 17β-HSD5, PSMA | Castration-resistant prostate cancer |
| 23S rRNA | Klebsiella pneumoniae infection |
| 4-1BB, BCMA | Refractory plasma cell myeloma |
| 4-1BB, BCMA | Relapsed Multiple myeloma |
| 4-1BB, BCMA | Multiple myeloma |
| 4-1BB, CD19 | Myasthenia gravis |
| 4-1BB, CD19 | Small lymphocytic lymphoma |
| 4-1BB, CD19 | Systemic sclerosis |
| 4-1BB, CD19 | Systemic lupus erythematosus |
| 4-1BB, CD19 | Idiopathic inflammatory myopathy |
| 4-1BB, CD19 | Dermatomyositis |
| HLA | Head and neck tumor |
| HLA | Hemophagocytic lymphohistiocytosis |
| HLA | Breast cancer |
| HLA | Prostate cancer |
| HLA | Diffuse large B-cell lymphoma |
| HLA | Ovarian cancer |
| HLA | Colorectal cancer |
| HLA | Refractory plasma cell myeloma |
| HLA | Acquired immunodeficiency syndrome (AIDS) |
| HLA | Melanoma |
| HLA | Relapsed Multiple myeloma |
| HLA | Lung cancer |
| HLA | Bladder cancer |
| 4-1BB, CD19 | Chronic lymphocytic leukemia |
| 4-1BB, CD19 | Lymphocytic leukemia |
| 4-1BB, CD19 | Lupus nephritis |
| 4-1BB, CD19 | Non-Hodgkin lymphoma |
| 4-1BB, CD19, CD3ζ, EGFR | Chronic lymphocytic leukemia (CLL) |
| 4-1BB, CD19, CD3ζ, EGFR | Acute lymphoblastic leukemia (ALL) |
| 4-1BB, CD19, CD3ζ, EGFR | Non-Hodgkin lymphoma |
| 4-1BB, CD40 | Biliary tract tumor |
| 4-1BB, CD40L, CTLA4 | Metastatic hepatocellular carcinoma |
| 4-1BB, CD40L, CTLA4 | Microsatellite-stable colorectal cancer (MSS CRC) |
| 4-1BB, CD40L, CTLA4 | Advanced malignant solid tumor |
| 4-1BB, CD40L, CTLA4 | Solid tumor |
| 4-1BB, CD40L, | Locally advanced head and neck squamous cell |

| Target site (gene) | Disease name |
|---|---|
| CTLA4 4-1BB, | carcinoma (HNSCC) Locally advanced |
| CD40L, CTLA4 | hepatocellular carcinoma (HCC) |
| HLA | Epstein-Barr virus infection |
| HLA class II antigen, MAGEA3 | Tumor |
| HLA class II antigen, TERT | Solid tumor |
| HLA class I antigen | Myxoid liposarcoma |
| HLA class I antigen | Synovial sarcoma |
| HLA class I antigen | Non-small cell lung cancer (NSCLC) |
| HLA class I antigen, HLA class II antigen | Type 1 diabetes |
| HLA class I antigen, KKLC1 | Solid tumor |
| HLA, MAGEA3 | Malignant epithelial tumor |
| HLA, NY-ESO-1, transforming growth factor β (TGFβ) receptor | Tumor |
| HLA, TGFBR2 | Tumor |
| HLA-A2 | Renal transplant rejection |
| HLA-A2 | Liver transplant rejection |
| HLA-A2 | Liver failure |
| 4-1BB, CD40L, CTLA4 | Recurrent head and neck squamous cell carcinoma (Recurrent HNSCC) |
| 4-1BB, EBV protein | Nasopharyngeal carcinoma (NPC) |
| 4-1BB, EBV protein | Niemann-Pick disease type C |
| 4-1BB, HPV E7, IL2RA | Advanced cancer |
| 4-1BB, HPV E7, IL2RA | Head and neck tumor |
| 4-1BB, HPV E7, IL2RA | Human papillomavirus type 16 positive (HPV-16 positive) |
| 4-1BB, HPV E7, IL2RA | Cervical cancer |
| 4-1BB, HPV E7, IL2RA | Anal tumor |
| 4-1BB, HPV E7, IL2RA | HPV16 infection |
| 4-1BB, IL-12R | Advanced malignant solid tumor |
| 4-1BB, IL-12R | Head and neck squamous cell carcinoma (HNSCC) |
| 4-1BB, IL-12R | Triple-negative breast cancer (TNBC) |
| 4-1BB, IL-12R | Cutaneous melanoma |
| 4-1BB, IL-12R | Urothelial carcinoma |
| 4-1BB, IL-12R | Melanoma |
| 4-1BB, IL-12R | Non-small cell lung cancer (NSCLC) |
| 4-1BB, IL-12R | Bladder urothelial carcinoma |
| 4-1BBL, CD19, PSCA | Tumor |
| 4-1BBL, IL15R | Solid tumor |
| 5T4 | Solid tumor |
| 5T4 | Locally advanced malignant solid tumor |
| 5T4 | Acute myeloid leukemia (AML) |
| HLA-A2, NY-ESO-1 | Triple-negative breast cancer (TNBC) |
| HLA-A2, NY-ESO-1 | Sarcoma |
| HLA-G | Metastatic clear cell renal cell carcinoma |
| HLA-G | Hematologic malignancy |
| HLA-G | Solid tumor |

| Target site (gene) | Disease name |
|---|---|
| HLA-G | Renal cell carcinoma |
| HLA-G | Ovarian cancer |
| HLA-G | Locally advanced clear cell renal cell carcinoma |
| HLA-G | Acute myeloid leukemia (AML) |
| HMGB1 | Fibrosis |
| HMGB1 | Pain |
| HMGB1 | Sepsis |
| HMGB1 | Pulmonary fibrosis |
| HP-NAP | Breast cancer |
| HPV E6 | Cervical cancer |
| HPV E6, HPV E7 | HPV16-positive solid tumor |
| HPV E7 | Cervical dysplasia |
| HPV E7 | Tumor metastasis |
| HPV E7 | Vaginal adenocarcinoma |
| HPV E7 | Novel coronavirus infection |
| HPV E7 | Vulvar tumor |
| HPV E7 | Vulvar intraepithelial neoplasia (VIN) |
| 5T4 | Unresectable malignant solid tumor |
| A1AT | Liver fibrosis |
| A1AT | Liver disease |
| A1AT | Scar |
| A1AT | Alpha-1 antitrypsin deficiency |
| A1R | Asthma |
| ABCA4 | Mucopolysaccharidosis type I (MPS I) |
| ABCA4 | Cystic fibrosis |
| ABCA4 | Huntington's disease |
| ABCA4 | Alzheimer's disease |
| ABCA4 | Stargardt disease type 4 |
| ABCA4 | Friedreich's ataxia |
| ABCD1 | Adrenoleukodystrophy (ALD) |
| ABCD1 | Hypertriglyceridemia |
| AC | Heart failure |
| ACE2 | Primary sclerosing cholangitis |
| ACE2 | Coronavirus infection |
| AChE | Myasthenia gravis |
| AChE | Inflammatory bowel disease |
| AChE | Amyotrophic lateral sclerosis |
| ACTG2 | Megacystis-microcolon-intestinal hypoperistalsis syndrome (MMIHS) |
| ACVR2B | Cachexia |
| ADA | Severe combined immunodeficiency |
| ADA | Adenosine deaminase deficiency |
| ADAM8 | Tumor |
| ADAMTS5 | Osteoarthritis |
| ADAMTS5, TNF | Rheumatoid arthritis |
| ADAMTS5, | Osteoarthritis |
| HPV E7 | Head and neck tumor |
| HPV E7 | Papillomavirus infection |
| HPV E7 | HPV-associated vulvar squamous cell carcinoma |
| HPV E7 | HPV-associated penile squamous cell carcinoma |
| HPV E7 | HPV-associated cervical cancer |
| HPV E7 | Squamous cell tumor |
| HPV E7 | Squamous intraepithelial lesion (SIL) |
| HPV E7 | Oropharyngeal tumor |
| HPV E7 | Glioblastoma |
| HPV E7 | Spinal cord injury |
| HPV E7 | Macular degeneration |
| HPV E7 | Laryngeal tumor |
| HPV E7 | Cervical intraepithelial neoplasia (CIN) |
| HPV E7 | Cervical cancer |
| HPV E7 | Polyomavirus infection |
| HPV E7 | HPV-associated squamous cell carcinoma |
| HPV E7 | HPV16-positive solid tumor |
| HS | Mucopolysaccharidosis type III (MPS III) |

-continued

| Target site (gene) | Disease name |
|---|---|
| Hsp27 | Pancreatic cancer |
| Hsp27 | Prostate cancer |
| Hsp27 | Non-small cell lung cancer (NSCLC) |
| Hsp27 | Bladder cancer |
| Hsp47 | Fibrosis |
| Hsp47 | Systemic sclerosis |
| Hsp47 | Idiopathic pulmonary fibrosis |
| HSP70 heat-shock proteins | Non-small cell lung cancer (NSCLC) |
| HSPA1A, p53 | Tumor |
| HSPA9 | Ovarian cancer |
| ADAR | Novel coronavirus infection |
| ADAR | Decompensated liver cirrhosis |
| ADAR | Immunoglobulin A nephropathy |
| ADARB1 | Amyotrophic lateral sclerosis |
| ADP | Tumor |
| ADP, thymidine kinase | Pancreatic cancer |
| aFGF | Peripheral arterial occlusive disease |
| aFGF | Eczema |
| aFGF | Chronic limb-threatening ischemia |
| aFGF | Intermittent claudication |
| aFGF | Arterial occlusive disease |
| AFP | Liver cancer |
| AGER | Inflammation |
| AGER | Asthma |
| AGL | Glycogen storage disease type III (GSD III) |
| AGRE2, CLL-1 | Relapsed acute myeloid leukemia |
| AGT | Preeclampsia |
| AGT | Heart failure with reduced ejection fraction |
| AGT | Chronic heart failure |
| AGT | Hypertension |
| HSPGs, MMPs, TGF-β1 | Tumor |
| HSPGs, MMPs, TGF-β1 | Trauma and injury |
| HTATIP2 | Complement disorder |
| HTT | Hodgkin lymphoma |
| HTT | Huntington's disease |
| Hyaluronic acid | Metastatic pancreatic adenocarcinoma |
| Hyaluronic acid | Secondary malignant neoplasm of pancreas |
| Hyaluronic acid | Retinoblastoma |
| Hyaluronic acid | Brain cancer |
| Hyaluronic acid | Melanoma |
| Hypoxia-inducible factor 1 | Myocardial ischemia |
| Hypoxia-inducible factor 1 | Peripheral vascular disease |
| Hypoxia-inducible factor 1 | Peripheral arterial disease |
| Hypoxia-inducible factor 1 | Intermittent claudication |
| Hypoxia-inducible factor 1 | Atherosclerosis |
| ICAM-1 | Inflammatory bowel disease |
| ICAM-1 | Inflammation |

-continued

| Target site (gene) | Disease name |
|---|---|
| ICAM-1 | Ulcerative colitis |
| ICAM-1 | Anaplastic thyroid carcinoma |
| ICAM-1 carcinoma | Poorly differentiated thyroid |
| AGT | Alzheimer's disease |
| AGT, ANGPTL3 | Cardiovascular disease |
| AGT, APOC3 | Hypertension |
| AGT, APOC3 | Hypertriglyceridemia |
| AIPL1 | Cone dystrophy |
| AIPL1 | Retinitis pigmentosa |
| AIPL1 | Leber congenital amaurosis |
| Akt, PTEN | Tumor |
| Akt-1 | Metastatic renal cell carcinoma |
| Akt-1 | Secondary malignant neoplasm of pancreas |
| Akt-1 | Pancreatic cancer |
| Akt-1 | Advanced renal cell carcinoma |
| Akt-1 | Advanced hepatocellular carcinoma |
| Akt-1 | Advanced malignant solid tumor |
| Akt-1 | Renal cell carcinoma |
| ALAS1 | Acute hepatic porphyria |
| ALAS1 | Hepatic porphyria |
| ALDH2 | Esophageal cancer |
| ALDH2 | Alcohol use disorder |
| ALDH2 | Glioblastoma |
| ALDH2 | Glioma |
| ALDH2 | Osteoporosis |
| ALK5 | Ocular disease |
| ALPP | Endometrial cancer |
| ALPP | Ovarian cancer |
| ALPPL2 | Solid tumor |
| AMHR2 | Tumor |
| AML1-ETO fusion protein | Acute myeloid leukemia |
| Ang2 | Retinal disorder |
| Ang2 | Prostate cancer |
| Ang2 | Sepsis |
| Ang2 | Acute lung injury |
| Ang2 | Acute lung injury |
| ICAM-1 | Recurrent thyroid cancer |
| ICAM-1 | Non-small cell lung cancer |
| ICE1, caspase | Neurofibroma |
| ID1 | Tumor |
| IDS | Mucopolysaccharidosis type II |
| IDUA | Mucopolysaccharidosis type I |
| IFN α | Head and neck tumor |
| IFN α | Melanoma |
| IFNAR | Pleural effusion |
| IFNAR | Rheumatoid arthritis |
| IFNAR | Colorectal cancer |
| IFNAR | Glioblastoma |
| IFNAR | Non-muscle-invasive bladder tumor |
| IFNAR | Malignant pleural mesothelioma |
| IFNAR | Pleomorphic glioblastoma |
| IFNAR | Hepatitis C |
| IFNAR | Bladder cancer |
| IFNAR | Bladder cancer |
| IFNGR | Tumor |
| IFNGR | Heart failure |
| IFNGR | Perioperative ischemia |
| IFNGR | Peripheral vascular disease |
| IFNGR | Neurodegenerative disease |
| IFNGR | Cutaneous T-cell lymphoma |
| IFNGR | Candidemia |
| IFNGR | Brain injury |
| IFNGR | Basal cell nevus syndrome |
| IFNGR | Melanoma |
| IFNGR | Lung disease |
| IFNGR | Type 1 diabetes |

-continued

| Target site (gene) | Disease name |
|---|---|
| IFNα2 | Melanoma |
| IFNβ | Endometrial cancer |
| IFNβ | Glioma |
| Ang2, VEGF | Wet age-related macular degeneration |
| Angiostatin | Corneal transplant rejection |
| ANGPTL3 | Primary hypercholesterolemia |
| ANGPTL3 | Hypertriglyceridemia |
| ANGPTL3 | Homozygous familial hypercholesterolemia |
| ANGPTL3 | Type II hyperlipoproteinemia |
| ANO5 | Limb-girdle muscular dystrophy |
| AP4M1 | Autosomal recessive spastic paraplegia type 50 |
| APN | B-cell lymphoma |
| APN, DPP-4 | Organ transplant rejection |
| APOA1 | Hypercholesterolemia |
| APOB | Heterozygous familial hypercholesterolemia |
| APOB | Neonatal disease |
| APOB | Congenital malformation |
| APOB | Coronary artery disease |
| APOB | Coronary heart disease |
| APOB | High and low density lipoprotein cholesterolemia |
| APOB | Hypercholesterolemia |
| APOB | Homozygous familial hypercholesterolemia |
| APOB | Type II hyperlipoproteinemia |
| APOB | Type IIa hyperlipoproteinemia |
| APOC3 | Combined lipase deficiencies |
| APOC3 | Dyslipidemia |
| APOC3 | Hemophilia B |
| APOC3 | Familial chylomicronemia syndrome |
| APOC3 | Hyperlipidemia |
| APOC3 | Hypertriglyceridemia |
| APOC3 | Non-alcoholic steatohepatitis |
| APOC3 | Atherosclerosis |
| IFNβ | Acute myeloid leukemia |
| IFNβ | Multiple sclerosis |
| IFNβ | Multiple myeloma |
| IFNβ | T-cell lymphoma |
| IFNβ, NIS | Neuroendocrine carcinoma |
| IFNβ, NIS | Refractory malignant solid tumor |
| IFNβ, NIS | Colorectal cancer |
| IFNβ, NIS | Acute myeloid leukemia |
| IFNβ, NIS | Liver cancer |
| IFNβ, NIS | Malignant solid tumor |
| IFNβ, NIS | Multiple myeloma |
| IFNβ, NIS | T-cell lymphoma |
| IFNβ, TLR9 | Inflammation |
| IFNγ | Castration-resistant prostate cancer |
| IFNγ, TERT | Tumor |
| IgE | Immune system disease |
| IgE | Hypersensitivity |
| IgE receptors | Asthma |
| IGF-1 | Tumor |
| IGF-1 | Alzheimer's disease |
| IGF-1 | Type 1 diabete |
| IGF-1R | Psoriasis |
| IGF-1R | Fibrosis |
| IGF-1R | Head and neck tumor |
| IGF-1R | Glaucoma |
| IGF-1R | Prostate cancer |

-continued

| Target site (gene) | Disease name |
|---|---|
| IGF-1R | Ovarian cancer |
| IGF-1R | Glioblastoma |
| IGF-1R | Amyotrophic lateral sclerosis |
| APOC3 | Type I hyperlipoproteinemia |
| APOC3, PCSK9 | Dyslipidemia |
| APOC3, PCSK9 | Metabolic disease |
| APOC3, TMPRSS6 | Hemochromatosis |
| APOC3, TMPRSS6 | Hypertriglyceridemia |
| ApoE2 | Alzheimer's disease |
| APP | Down syndrome |
| APP | Cerebral amyloid angiopathy |
| APP | Alzheimer's disease |
| APRIL | Refractory plasma cell myeloma |
| APRIL | Relapsed Multiple myeloma |
| AQP1 | Parotid gland disease |
| AQP1 | Xerostomia |
| AR | Androgenic alopecia |
| AR | Castration-resistant prostate cancer |
| AR | Prostate cancer |
| AR | Prostate cancer |
| AR | Bone cancer |
| AR, mTOR | Benign prostatic hyperplasia |
| AR, mTOR | Prostate cancer |
| AR, PRLR, aromatase | Tumor |
| ARHGAP45 | Primary myelofibrosis |
| ARHGAP45 | Hematologic malignancy |
| ARHGAP45 | Solid tumor |
| ARHGAP45 | Chronic myeloid leukemia |
| ARHGAP45 | Lymphoma |
| ARHGAP45 | Acute myeloid leukemia |
| ARHGAP45 | Acute lymphoblastic leukemia |
| ARHGAP45 | Myelodysplastic syndrome |
| ARHGAP45 | Myelofibrosis |
| ARHGAP45 | Multiple myeloma |
| ASA | Metachromatic leukoencephalopathy |
| ASC2 | Inflammation |
| IGF-1R | Graves' ophthalmopathy |
| IGF-1R | Hepatocellular carcinoma |
| IGF-1R | Laron syndrome |
| IGFBP2, IGFBP5 | Breast cancer |
| IGHMBP2 | Charcot-Marie-Tooth disease type 2S |
| IKKγ, NF-κB | Tumor |
| IL-10R | Autoimmune hepatitis |
| IL-10R | Inflammation |
| IL-10R | Solid tumor |
| IL-10R | Amyotrophic lateral sclerosis |
| IL-10R | Musculoskeletal pain |
| IL-10R | Arthralgia |
| IL-10R | Multiple sclerosis |
| IL-10R | Back pain |
| IL-12 | Metastatic melanoma |
| IL-12 | Tumor |
| IL-12 | Pancreatic cancer |
| IL-12 | Adverse drug reaction |
| IL-12 | Novel coronavirus infection |
| IL-12 | Head and neck tumor |
| IL-12 | Head and neck tumor |
| IL-12 | Triple-negative breast cancer |
| IL-12 | Breast cancer |
| IL-12 | Prostate cancer |
| IL-12 | Skin tumor |
| IL-12 | Cutaneous T-cell lymphoma |
| IL-12 | Diffuse intrinsic pontine glioma |
| IL-12 | Merkel cell carcinoma |
| IL-12 | Ovarian cancer |

-continued

| Target site (gene) | Disease name |
|---|---|
| IL-12 | Squamous cell carcinoma |
| IL-12 | Locally advanced melanoma |
| IL-12 | Glioblastoma |
| IL-12 | Acute myeloid leukemia |
| ASGR1, L-lactate dehydrogenase | End-stage renal disease |
| ASGR1, L-lactate dehydrogenase | Primary hyperoxaluria type 2 |
| ASGR1, L-lactate dehydrogenase | Primary hyperoxaluria type 1 |
| ASGR1, L-lactate dehydrogenase | Primary hyperoxaluria |
| ASN | Metastatic pancreatic ductal adenocarcinoma |
| ASN | Advanced pancreatic ductal adenocarcinoma |
| ASS | Citrullinemia |
| ASXL1, RUNX1, p53 | Acute myeloid leukemia |
| AT III | Hemophilia B |
| AT III | Hemophilia A |
| AT III | Venous thromboembolism |
| AT III | Atherosclerosis |
| AT III | Hemorrhage |
| ATM | Ataxia-telangiectasia |
| ATOH1 | Hearing loss |
| ATP7A | Menkes syndrome |
| ATP7B | Wilson's disease |
| ATXN1 | Spinocerebellar ataxia |
| ATXN2 | Amyotrophic lateral sclerosis |
| ATXN3 | Machado-Joseph disease |
| ATXN7 | Ataxia |
| Autotaxin | Idiopathic pulmonary fibrosis |
| IL-12 | Melanoma |
| IL-12 | Lung cancer |
| IL-12 | HPV-associated cancer |
| IL-12, IL-15 | Advanced malignant solid tumor |
| IL-12, IL-15, PDL1 | Solid tumor |
| IL-12, IL-2 | Melanoma |
| IL-12, MUC16 | Ovarian cancer |
| IL-12, PD-1 | Glioblastoma |
| IL-12, PD-1 | Glioma |
| IL-12, PD-1 | Recurrent glioblastoma |
| IL-12, PD-1 | Glioblastoma multiforme |
| IL-12, thymidine kinase | Astrocytoma |
| IL-12, thymidine kinase | Recurrent prostate cancer |
| IL-12R | Metastatic breast cancer |
| IL-12R | Metastatic colorectal cancer |
| IL-12R | Primary peritoneal carcinoma |
| IL-12R | Pediatric cerebellar astrocytoma |
| IL-12R | Advanced malignant solid tumor |
| IL-12R | Head and neck tumor |
| IL-12R | Fallopian tube cancer |
| IL-12R | Gliosarcoma |
| IL-12R | Mucolipidosis type II |
| AXL | Sarcoma |
| AXL | Ovarian cancer |
| AXL | Osteosarcoma |
| B2M, HLA-B | Head and neck tumor |
| B2M, HLA-B | Renal tumor |
| B2M, HLA-B | Breast cancer |
| B2M, HLA-B | Lymphoma |
| B2M, HLA-B | Colorectal cancer |
| B2M, HLA-B | Melanoma |
| B4GALT1 | Cardiovascular disease |
| B7-H4 | Solid tumor |
| BAFF | Autoimmune disease |
| BAFF | Systemic lupus erythematosus |
| BAFF | Refractory non-Hodgkin lymphoma |

-continued

| Target site (gene) | Disease name |
|---|---|
| BAFF | Refractory plasma cell myeloma |
| BAFF | Sjögren's syndrome |
| BAFF | Relapsed non-Hodgkin lymphoma |
| BAFF | Relapsed Multiple myeloma |
| BAFF | B-cell lymphoma |
| BAFF | B-cell malignancy |
| BAFF, CD19 | Autoimmune disease |
| BAFF-R | Refractory transformed chronic lymphocytic leukemia |
| BAFF-R | Refractory small lymphocytic lymphoma |
| BAFF-R | Refractory mantle cell lymphoma |
| BAFF-R | Refractory diffuse large B-cell lymphoma |
| BAFF-R | Refractory chronic lymphocytic leukemia |
| IL-12R | Diffuse intrinsic pontine glioma |
| IL-12R | Ovarian epithelial carcinoma |
| IL-12R | Ovarian cancer |
| IL-12R | Locally advanced breast cancer |
| IL-12R | Colorectal cancer with liver metastasis |
| IL-12R | Colorectal cancer |
| IL-12R | Glioblastoma |
| IL-12R | Glioma |
| IL-12R | Melanoma |
| IL-12R | Secondary malignant neoplasm of peritoneum |
| IL-12R | Peritoneal cancer |
| IL-12R | Recurrent breast cancer |
| IL-12R | Recurrent glioblastoma |
| IL-12R | Recurrent malignant glioma |
| IL-12R | Glioblastoma multiforme |
| IL-12R | Metabolic bone disease |
| IL-12R | Unresectable melanoma |
| IL-12R | WHO grade III mixed glioma |
| IL-12R, decorin | Gastrointestinal tumor |
| IL-12R, decorin | Myeloproliferative disorder |
| IL-12R, decorin | Multiple myeloma |
| IL-12R, IL15R | Solid tumor |
| IL-12R, IL15R | Renal cell carcinoma |
| IL-12R, IL15R | Breast cancer |
| IL-12R, IL15R | Ovarian cancer |
| IL-12R, IL-15Rα | Hematologic malignancy |
| BAFF-R | Refractory follicular lymphoma |
| BAFF-R | Diffuse large B-cell lymphoma |
| BAFF-R | Relapsed transformed chronic lymphocytic leukemia |
| BAFF-R | Relapsed mantle cell lymphoma |
| BAFF-R | Relapsed chronic lymphocytic leukemia |
| BAFF-R | Relapsed follicular lymphoma |
| BAFF-R | Relapsed marginal zone lymphoma |
| BAFF-R | Refractory marginal zone lymphoma |
| BAFF-R | B-cell malignancy |
| BAG3 | Dilated cardiomyopathy |
| BCL11A | Sickle cell disease |
| BCL11A | β-thalassemia |
| BCL11A, Hemoglobins | Sickle cell disease |
| BCL11A, β-globin | Transfusion-dependent β-thalassemia |
| BCL11A, β-globin | Sickle cell disease |
| BCL11A, β-globin | β-thalassemia |
| Bcl-2 | Metastatic renal cell carcinoma |
| IL-12R, IL-15Rα | Solid tumor |
| IL-12R, IL-15Rα, PDL1 | Metastatic gastric adenocarcinoma |
| IL-12R, IL-15Rα, PDL1 | Metastatic gastroesophageal adenocarcinoma |

-continued

| Target site (gene) | Disease name |
|---|---|
| IL-12R, IL-15Rα, PDL1 | Metastatic gastroesophageal junction adenocarcinoma |
| IL-12R, IL-15Rα, PDL1 | Advanced pancreatic adenocarcinoma |
| IL-12R, IL-15Rα, PDL1 | Advanced hepatocellular carcinoma |
| IL-12R, IL-15Rα, PDL1 | Advanced malignant solid tumor |
| IL-12R, IL-15Rα, PDL1 | Osteosarcoma |
| IL-12R, IL-15Rα, PDL1 | Hepatocellular carcinoma |
| IL-12R, IL-15Rα, PDL1 | Intrahepatic cholangiocarcinoma |
| IL-12R, IL-15Rα, PDL1 | Liver cancer |
| IL-12R, IL-15Rα, PDL1 | Cholangiocarcinoma |
| IL-12R, IL-7Rα | Metastatic solid tumor |
| IL-12R, IL-7Rα | Advanced cancer |
| IL-12R, NY-ESO-1 | Tumor |
| IL-12R, PD-1 | Endometrial cancer |
| IL-12R, PD-1 | Metastatic colorectal cancer |
| Bcl-2 | Metastatic breast cancer |
| Bcl-2 | Intraocular lymphoma |
| Bcl-2 | Recurrent small cell lung cancer |
| Bcl-2 | Small lymphocytic lymphoma |
| Bcl-2 | Small intestine cancer |
| Bcl-2 | Gastrointestinal stromal tumor |
| Bcl-2 | Advanced malignant solid tumor |
| Bcl-2 | Peripheral T-cell lymphoma |
| Bcl-2 | Mantle cell lymphoma |
| Bcl-2 | Breast cancer |
| Bcl-2 | Prostate cancer |
| Bcl-2 | Cutaneous T-cell lymphoma |
| Bcl-2 | Refractory acute myeloid leukemia |
| Bcl-2 | Refractory non-Hodgkin lymphoma |
| Bcl-2 | Male breast tumor |
| Bcl-2 | Immunoblastic large cell lymphoma |
| Bcl-2 | Diffuse large B-cell lymphoma |
| Bcl-2 | Merkel cell carcinoma |
| Bcl-2 | Chronic lymphocytic leukemia |
| Bcl-2 | Follicular lymphoma |
| Bcl-2 | Lymphocytic leukemia |
| Bcl-2 | Lymphoblastic lymphoma |
| Bcl-2 | Reye's syndrome |
| Bcl-2 | Macroglobulinemia |
| IL-12R, PD-1 | Advanced malignant solid tumor |
| IL-12R, PD-1 | Head and neck squamous cell carcinoma |
| IL-12R, PD-1 | Esophageal cancer |
| IL-12R, PD-1 | Breast cancer |
| IL-12R, PD-1 | Sarcoma |
| IL-12R, PD-1 | Skin tumor |
| IL-12R, PD-1 | Ovarian cancer |
| IL-12R, PD-1 | Lymphoma |
| IL-12R, PD-1 | Colorectal cancer with liver metastasis |
| IL-12R, PD-1 | Colorectal cancer |
| IL-12R, PD-1 | Melanoma |
| IL-12R, PD-1 | Liver cancer |
| IL-12R, PD-1 | Non-small cell lung cancer |
| IL-12R, PD-1 | Malignant pleural mesothelioma |
| IL-12R, PD-1 | Bladder cancer |
| IL-12R, RIG-I | Non-muscle-invasive bladder tumor |

-continued

| Target site (gene) | Disease name |
|---|---|
| IL-12R, STEAP1 | Prostate cancer |
| IL-13R, IL-4Rα | Asthma |
| IL-13R, IL-4Rα | Allergic asthma |
| IL-13R, IL-4Rα | Rhinitis |
| IL-13Rα2 | Brain metastases |
| IL-13Rα2 | Glioblastoma |
| IL-13Rα2 | Glioma |
| IL-13Rα2 | Melanoma |
| Bcl-2 | Locally advanced breast cancer |
| Bcl-2 | Glioblastoma |
| Bcl-2 | Plasmacytoma |
| Bcl-2 | Acute myeloid leukemia |
| Bcl-2 | Acute lymphoblastic leukemia |
| Bcl-2 | Hodgkin lymphoma |
| Bcl-2 | Refractory Waldenstrom's macroglobulinemia |
| Bcl-2 | Melanoma |
| Bcl-2 | Extensive-stage small cell lung cancer |
| Bcl-2 | Testicular disorders |
| Bcl-2 | Liver cancer |
| Bcl-2 | Recurrent mantle cell lymphoma |
| Bcl-2 | Recurrent diffuse large B-cell lymphoma |
| Bcl-2 | Recurrent acute myeloid leukemia |
| Bcl-2 | Recurrent Hodgkin lymphoma |
| Bcl-2 | Recurrent non-Hodgkin lymphoma |
| Bcl-2 | Recurrent adult grade III lymphogranuloma |
| Bcl-2 | Relapsed marginal zone lymphoma |
| Bcl-2 | Relapsed B-cell lymphoma |
| Bcl-2 | Recurrent Grade 3a Follicular Lymphoma |
| Bcl-2 | Lung cancer |
| Bcl-2 | Non-small cell lung cancer |
| Bcl-2 | Non-Hodgkin lymphoma |
| Bcl-2 | Multiple myeloma |
| Bcl-2 | Adult T-cell leukemia/lymphoma |
| IL-13Rα2 | High-grade astrocytoma |
| IL-13Rα2 | Recurrent glioblastoma |
| IL-13Rα2 | Recurrent malignant glioma |
| IL-13Rα2 | Pleomorphic glioblastoma |
| IL-15 | Metastatic melanoma |
| IL-15 | Metastatic non-small cell lung cancer |
| IL-15 | Tumor |
| IL-15 | Gastric cancer |
| IL-15 | Solid tumor |
| IL-15 | Lymphoma |
| IL-15 | Colorectal cancer |
| IL-15 | Secondary malignant lung tumor |
| IL-15 | Melanoma |
| IL-15 | Non-small cell lung cancer |
| IL-15, IL-2 | Tumor |
| IL-15, PDL1 | Non-small cell lung cancer |
| IL-15, PSCA | Pancreatic acinar cell carcinoma |
| IL-15, PSCA | Gastric cancer |
| IL-15, PSCA | Prostate cancer |
| IL-15, PSCA | Bladder cancer |
| IL15R, MUC16 | Fallopian tube cancer |
| IL15R, MUC16 | Refractory ovarian cancer |
| IL15R, MUC16 | Ovarian cancer |
| IL15R, MUC16 | Peritoneal cancer |
| IL15R, | Recurrent primary |

-continued

| Target site (gene) | Disease name |
|---|---|
| MUC16 | peritoneal cancer |
| Bcl-2 | Burkitt lymphoma |
| Bcl-2 | Marginal zone B-cell lymphoma |
| Bcl-2 | Triple-Negative Breast Cancer |
| Bcl-2 | Type 1 diabetes |
| Bcl-2, c-Myc | Ovarian cancer |
| Bcl-2, c-Myc | Lung cancer |
| Bcl-xl | Tumor |
| Bcl-xl | Colorectal cancer |
| Bcl-xl, Mcl-1 | Head and neck tumor |
| Bcl-xl, Mcl-1 | Bladder cancer |
| BCMA | Autoimmune disease |
| BCMA | Myasthenia gravis |
| BCMA | End-stage renal disease |
| BCMA | Smoldering Multiple myeloma |
| BCMA | Systemic lupus erythematosus |
| BCMA | Peripheral T-cell lymphoma |
| BCMA | Aquaporin 4 antibody-positive neuromyelitis optica spectrum disorder |
| BCMA | Neuromyelitis optica |
| BCMA | Precursor T-cell acute lymphoblastic leukemia/lymphoma |
| BCMA | Immunoblastic lymphadenopathy |
| BCMA | Chronic inflammatory demyelinating polyneuropathy |
| BCMA | Extranodal NK-T cell lymphoma |
| BCMA | Refractory Multiple myeloma |
| IL15R, MUC16 | Recurrent ovarian cancer |
| IL15R, MUC16 | Recurrent platinum-resistant primary peritoneal cancer |
| IL15R, MUC16 | Platinum-resistant fallopian tube cancer |
| IL15R, MUC16 | Platinum-resistant ovarian cancer |
| IL15R, PD-1 | Lung cancer |
| IL15R, PD-1 | Non-small cell lung cancer |
| IL-15Rα, NKG2D | Metastatic colorectal cancer |
| IL-15Rα, NKG2D | Osteosarcoma |
| IL-15Rα, NKG2D | Hepatocellular carcinoma |
| IL-15Rα, NKG2D | Intrahepatic cholangiocarcinoma |
| IL-17RA | Psoriasis |
| IL-17RA | Congenital ichthyosis erythroderma |
| IL-17RA | Hair loss |
| IL-18 | Hematologic malignancy |
| IL-18 | Solid tumor |
| IL-18 | Renal cell carcinoma |
| IL-18 | Neuralgia |
| IL-1R, MMPs | Liver cirrhosis |
| IL1R1 | Gout |
| IL1R1 | Arthritis |
| IL-1RA | Knee arthritis |
| IL-1RA, PRG4 | Osteoarthritis |
| IL-1α | Osteoarthritis |
| BCMA | Plasma cell leukemia |
| BCMA | Anaplastic large cell lymphoma |
| BCMA | Necrotizing myopathy |
| BCMA | Multiple myeloma |
| BCMA | Enteropathy-associated T-cell lymphoma |
| BCMA | CD7-positive hematological malignancy |
| BCMA, CD138, CD19, CD38 | Multiple myeloma |
| BCMA, CD16a, IL-15Rα | Refractory Multiple myeloma |

-continued

| Target site (gene) | Disease name |
|---|---|
| BCMA, CD16a, IL-15Rα | Relapsed Multiple myeloma |
| BCMA, CD16a, NKp46 | Immunoglobulin light chain amyloidosis |
| BCMA, CD16a, NKp46 | Refractory Multiple myeloma |
| BCMA, CD16a, NKp46 | Myelodysplastic syndrome |
| BCMA, CD16a, NKp46 | Relapsed Multiple myeloma |
| BCMA, CD19 | Autoimmune hemolytic anemia |
| BCMA, CD19 | Vasculitis |
| BCMA, CD19 | Systemic lupus erythematosus |
| BCMA, CD19 | Precursor B-cell lymphoblastic leukemia/lymphoma |
| BCMA, CD19 | Precursor/B-cell lymphoblastic leukemia lymphoma |
| BCMA, CD19 | Sjögren's syndrome |
| IL-2 | Primary peritoneal adenocarcinoma |
| IL-2 | Primary peritoneal cancer |
| IL-2 | Adenocarcinoma |
| IL-2 | Head and neck tumor |
| IL-2 | Fallopian tube cancer |
| IL-2 | Renal cell carcinoma |
| IL-2 | Neuroblastoma |
| IL-2 | Breast cancer |
| IL-2 | Prostate cancer |
| IL-2 | Skin tumor |
| IL-2 | Ovarian adenocarcinoma |
| IL-2 | Ovarian serous adenocarcinoma |
| IL-2 | Colon cancer |
| IL-2 | Serous cystadenocarcinoma |
| IL-2 | Mesothelioma |
| IL-2 | Melanoma |
| IL-2 | Melanoma |
| IL-2 | Hepatocellular carcinoma |
| IL-2 | Lung cancer |
| BCMA, CD19 | Non-Hodgkin lymphoma |
| BCMA, CD19 | Multiple myeloma |
| BCMA, CD19 | Multiple myeloma |
| BCMA, CD19 | Amyloidosis |
| BCMA, CD19 | Relapsed T-cell acute lymphoblastic leukemia |
| BCMA, CD19 | POEMS syndrome |
| BCMA, CD19 | Crouzon syndrome with acanthosis nigricans |
| BCMA, CD19 | B-cell lymphoma |
| BCMA, CD19, HER2, Trop-2 | Tumor |
| BCMA, CD20 | Autoimmune disease |
| BCMA, CD3 | Tumor |
| BCMA, CD38 | Tumor |
| BCMA, CD4 | Tumor |
| BCMA, CD5 | Tumor |
| BCMA, CD7 | Multiple myeloma |
| BCMA, CD70 | Renal cell carcinoma |
| BCMA, CD70 | Refractory plasma cell myeloma |
| BCMA, CD70 | Multiple myeloma |
| BCMA, CD8 | Tumor |
| BCMA, GPRC5D | Multiple myeloma |
| BCMA, GPRC5D, NKG2D | Myeloid leukemia |
| BCMA, HPK1 | Myeloproliferative disorder |
| BCMA, SLAMF7 | Multiple myeloma |
| IL-2, TNF | Renal cell carcinoma |
| IL-2, TNF | Colon cancer |
| IL-2, TNF | Melanoma |
| IL-2, TNF-α | Metastatic melanoma |
| IL-2, TNF-α | Head and neck squamous cell carcinoma |
| IL-2, TNF-α | Solid tumor |
| IL-2, TNF-α | Ovarian cancer |

-continued

| Target site (gene) | Disease name |
|---|---|
| IL-2, TNF-α | Melanoma |
| IL-2, TNF-α | Non-small cell lung cancer |
| IL-21 | Pancreatic cancer |
| IL-21 | Pulmonary arterial hypertension |
| IL-21R | Poxvirus infection |
| IL-23 | Tumor |
| IL-24 | Pancreatic cancer |
| IL-24 | Head and neck tumor |
| IL-24 | Breast cancer |
| IL-24 | Melanoma |
| IL-24 | Hepatocellular carcinoma |
| IL-24 | Lung cancer |
| IL-24, THBS1 | Leukemia |
| IL-24, TRAIL | Hepatocellular carcinoma |
| IL-27 | Tumor |
| IL-2R | Metastatic melanoma |
| BCMA, TACI | Refractory plasma cell myeloma |
| BCMA, TACI | Relapsed Multiple myeloma |
| BCMA, TGF-β | Refractory B-cell acute lymphoblastic leukemia |
| BCMA, TGF-β | Multiple myeloma |
| BCMA, TGF-β | Relapsed T-cell acute lymphoblastic leukemia |
| BCMA, VISTA | Multiple myeloma |
| BDNF | Glaucoma |
| BDNF | Alzheimer's disease |
| beclin-1 | Multiple myeloma |
| BEST1 | Vitelliform macular dystrophy |
| BET, RPE65 | Biallelic RPE65 Mutation-associated Retinal Degeneration |
| bFGF | Perioperative ischemia |
| bFGF | Achondroplasia |
| BMP4 | Glioblastoma |
| BMP6 | Sjögren's syndrome |
| BMPR2, VEGF | Fracture |
| BRAF | Tumor |
| BRCA1 | Ovarian cancer |
| BRD4 | Solid tumor |
| BSG | Liver cancer |
| BSG | Recurrent glioblastoma |
| BSG | Recurrent malignant glioma |
| BSG, IL-24 | Hepatocellular carcinoma |
| BTK | Bruton's agammaglobulinemia |
| BTN3A1 | Acute myeloid leukemia |
| BTN3A1 | Myelodysplastic syndrome |
| BTN3A1 | Multiple myeloma |
| IL-2R | Gastrointestinal tumor |
| IL-2R | Renal tumor |
| IL-2R | Renal tumor |
| IL-2R | Renal cell carcinoma |
| IL-2R | Prostate cancer |
| IL-2R | Mesothelioma |
| IL-2R | Melanoma |
| IL-2R | Recurrent prostate cancer |
| IL-2R | Lung cancer |
| IL-2R, LMP2 | Cancer |
| IL2RA | Tumor |
| IL2RA | Hematologic malignancy |
| IL-2Rγ | Immunodeficiency syndrome |
| IL-2Rγ | X-linked severe combined immunodeficiency |
| IL-3 | CD123-positive acute myeloid leukemia |
| IL-33R | Asthma |
| IL-4Rα | Asthma |
| IL-6R | Inflammation |
| IL-6R | Arthritis |
| IL-6RA | Rheumatoid arthritis |
| IL-7 | Tumor |
| IL-7 | Melanoma |
| IL-7Rα | Head and neck tumor |

-continued

| Target site (gene) | Disease name |
|---|---|
| IL-7Rα | Cervical cancer |
| IL-8 | Pathological neovascularization |
| influenza virus M1 | Influenza virus infection |
| influenza virus M1 | Influenza A virus infection |
| C1-INH | Hereditary angioedema |
| C1-INH | Liver disease |
| C3 | Paroxysmal nocturnal hemoglobinuria |
| C3 | Neurodegenerative disease |
| C3 | Immune system disease |
| C3 | Immunoglobulin A nephropathy |
| C3 | Liver disease |
| C3 | Complement dysregulation |
| C3 | C3 glomerulopathy |
| C3, C5 | Geographic atrophy |
| C5 | Myasthenia gravis |
| C5 | Paroxysmal nocturnal hemoglobinuria |
| C5 | Stargardt disease |
| C5 | Age-related macular degeneration |
| C5 | Immune system disease |
| C5 | Immunoglobulin A nephropathy |
| C5 | Macular degeneration |
| C5 | Geographic atrophy |
| C5, C5AR1 | Sepsis |
| C5, CFB | Genetic disorder |
| C5a | Community-acquired pneumonia |
| C5a | Lung cancer |
| C9orf72 | Pick's disease dementia |
| C9orf72 | Amyotrophic lateral sclerosis |
| C9orf72 | Frontotemporal dementia |
| CA4 | Ocular hypertension |
| CA8 | Knee arthritis |
| CA8 | Erythromelalgia |
| CADM1 | Hepatocellular carcinoma |
| CADM1 | Non-small cell lung cancer |
| CAG repeat expansion | Machado-Joseph disease |
| CAG repeat expansion | Spinocerebellar ataxia |
| ING4 | Relapsed acute myeloid leukemia |
| INHBE | Abdominal obesity |
| INSR | Diabetic macular edema |
| INSR | Diabetes |
| INSR | Wet age-related macular degeneration |
| INSR | Ischemic central retinal vein occlusion |
| INSR | Choroidal neovascularization |
| INSR | Corneal transplant rejection |
| INSR | Macular degeneration |
| INSR | Bladder cancer |
| INSR | Type 1 diabetes |
| Insulin | Type 1 diabetes |
| Integrin | Tumor |
| Integrin | Prostate adenocarcinoma |
| Integrin | Localized prostate cancer |
| Ion channels | Idiopathic pulmonary fibrosis |
| Ion channels | Trigeminal neuralgia |
| Ion channels | Partial seizures |
| IRAK1 | Hepatocellular carcinoma |
| IRAK1 | Trauma and injury |
| IRF4 | Refractory plasmacytoma |
| IRF4 | Recurrent multiple myeloma |
| IRF5 | Rheumatoid arthritis |
| ISG15 | Hepatitis C |
| ITGB7 | Multiple myeloma |
| JAK1 | Autoimmune disease |
| JAK1 | Inflammation |
| KHK | Obesity |

| Target site (gene) | Disease name |
|---|---|
| KHK | Type 2 diabetes |
| Kir7.1 | Leber congenital amaurosis |
| KKLC1 | Pancreatic acinar cell carcinoma |
| KKLC1 | Gastric cancer |
| CAG repeat expansion | Hodgkin lymphoma |
| CAG repeat expansion | Huntington's disease |
| CAIX | Advanced renal cell carcinoma |
| CAIX | Solid tumor |
| CAIX, PDL1 | Tumor |
| CAIX, PSMA | Renal cell carcinoma |
| CAIX, PSMA | Renal clear cell carcinoma |
| CaN | Liver transplant rejection |
| CAPN2 | Amyotrophic lateral sclerosis |
| CAPN3 | Limb-girdle muscular dystrophy |
| CAPN3 | Limb-girdle muscular dystrophy type 2A |
| Caspase 2 | Optic nerve injury |
| Caspase 2 | Ischemic optic neuropathy |
| Caspase 2 | Glaucoma |
| Caspase 2 | Angle-closure glaucoma |
| CASQ2 | Ventricular tachycardia |
| CAV1 | Amyotrophic lateral sclerosis |
| Caveolin | Wet age-related macular degeneration |
| Cbl-b | Endometrial cancer |
| Cbl-b | Pancreatic cancer |
| Cbl-b | Advanced cancer |
| Cbl-b | Renal cell carcinoma |
| Cbl-b | Glioblastoma multiforme |
| Cbl-b | Cervical cancer |
| Cbl-b | Recurrent melanoma |
| Cbl-b | Platinum-resistant ovarian cancer |
| KKLC1 | Breast cancer |
| KKLC1 | Cervical cancer |
| KKLC1 | Liver cancer |
| KKLC1 | Lung cancer |
| KKLC1 | Non-small cell lung cancer |
| KLB | Alzheimer's disease |
| KLK2 | Metastatic castration-resistant prostate cancer |
| KLK3 | Prostate cancer |
| KLK5 | Netherton syndrome |
| KLKB1 | Hereditary angioedema |
| KMA | Multiple myeloma |
| KRAS | Tumor |
| KRAS | Pancreatic cancer |
| KRAS | Immune system disease |
| KRAS | Colorectal cancer |
| KRAS | Muscle disorders |
| KRAS | Lung cancer |
| KRAS | Non-small cell lung cancer |
| KRAS | KRAS-mutant tumor |
| KRAS G12A | Lung cancer |
| KRAS G12C | Tumor |
| KRAS G12C | Lung cancer |
| KRAS G12C | Non-small cell lung cancer |
| KRAS G12C, KRAS G12D | Pancreatic ductal adenocarcinoma |
| KRAS G12C, KRAS G12D | Colorectal cancer |
| KRAS G12C, KRAS G12D, KRAS G12V | Tumor |
| Cbl-b | Stage IIB melanoma |
| cccDNA | Hepatitis B |
| CCL19, | Diffuse large B-cell |

| Target site (gene) | Disease name |
|---|---|
| CD19, IL-7Rα | lymphoma |
| CCL19, IL-7, MAGEA4 | Solid tumor |
| CCL2 | Diabetic nephropathy |
| CCL21 | Lung cancer |
| CCL4, CTLA4, Flt3L, IL-12, PD-1 | Advanced malignant solid tumor |
| CCL4, CTLA4, Flt3L, IL-12, PD-1 | Head and neck squamous cell carcinoma |
| CCL4, CTLA4, Flt3L, IL-12, PD-1 | Triple-negative breast cancer |
| CCL4, CTLA4, Flt3L, IL-12, PD-1 | Colorectal cancer |
| KRAS G12C, KRAS G12D, KRAS G12V | Pancreatic cancer |
| KRAS G12C, KRAS G12D, KRAS G12V | Colon cancer |
| KRAS G12C, KRAS G12D, KRAS G12V | Lung cancer |
| KRAS G12C, KRAS G12D, PI3Kα, p53 R175H | Tumor |
| KRAS G12D | Endometrial cancer |
| KRAS G12D | Metastatic pancreatic ductal adenocarcinoma |
| KRAS G12D | Rectal cancer |
| KRAS G12D | Pancreatic acinar cell carcinoma |
| KRAS G12D | Pancreatic ductal adenocarcinoma |
| KRAS G12D | Pancreatic cancer |
| CCL4, CTLA4, Flt3L, IL-12, PD-1 | Melanoma |
| CCL4, CTLA4, Flt3L, IL-12, PD-1 | Liver metastasis |
| CCL4, CTLA4, Flt3L, IL-12, PD-1 | Liver cancer |
| CCL4, CXCL10, IL-12 | Tumor |
| CCL5 | Hepatocellular carcinoma |
| CCL5, CD19, IL-12, PD-1, Trop-2 | Solid tumor |
| CCNB1, WT1 | Breast cancer |
| CCND1, ITGB7, MAdCAM-1, α4β7 | Inflammatory bowel disease |
| CCND1, Raf kinase | Tumor |
| CCR1, EGFR | Glioblastoma |
| CCR2, IL-2, leptin | Solid tumor |
| CCR3, IL-3R, IL-3Rβ | Asthma |
| CCR3, IL-3R, IL-3Rβ | Allergic asthma |
| CCR5 | Breast cancer |
| CCR5 | Lymphoma |
| CCR5 | HIV infection |
| CCR5, CD4 | HIV infection |

-continued

| Target site (gene) | Disease name |
|---|---|
| KRAS G12D | Gastric cancer |
| KRAS G12D | Solid tumor |
| KRAS G12D | Locally advanced pancreatic adenocarcinoma |
| KRAS G12D | Colorectal cancer |
| KRAS G12D | Colon cancer |
| KRAS G12D | Lung cancer |
| KRAS G12D | Non-small cell lung cancer |
| KRAS G12D, KRAS G12V | Solid tumor |
| KRAS G12V | Metastatic pancreatic adenocarcinoma |
| KRAS G12V | Metastatic non-small cell lung cancer |
| KRAS G12V | Tumor |
| KRAS G12V | Pancreatic ductal adenocarcinoma |
| KRAS G12V | Pancreatic cancer |
| KRAS G12V | Solid tumor |
| KRAS G12V | Colorectal cancer |
| KRAS G12V | Lung cancer |
| KRAS G12V | Non-small cell lung cancer |
| CCR5, TRIM5 | Pancytopenia |
| CCR5, TRIM5 | X-linked severe combined immunodeficiency |
| CD103, CD39, CD8 | Tumor |
| CD123 | Acute myeloid leukemia |
| CD123 | Acute lymphoblastic leukemia |
| CD123 | Myelodysplastic syndrome |
| CD123 | Blastic plasmacytoid dendritic cell neoplasm |
| CD123, CD33 | Tumor |
| CD123, CD33, CD38, CD56, CLL-1, MUC1 | Tumor |
| CD123, CD33, CLL-1 | Tumor |
| CD123, TIM3 | Acute myeloid leukemia |
| CD133 | Retinal disease |
| CD133 | Glioblastoma |
| CD133, EGFR | Glioblastoma |
| CD138 | Tumor |
| CD138, NY-ESO-1, SLAMF7, WT1 | Multiple myeloma |
| CD16a | Pancreatic cancer |
| CD16a | Novel Coronavirus Infection |
| CD16a | Advanced solid malignant tumor |
| CD16a | Fallopian tube cancer |
| CD16a | Breast cancer |
| KRAS G12V | Colonic adenocarcinoma |
| KRAS G12V | Intestinal tumor |
| KRAS G13D | Pancreatic cancer |
| KRAS, c-Myc | Lung cancer |
| KRT6A | Congenital pachyonychia |
| Ku70/80, MRN, PARP1 | Metastatic solid tumor |
| Ku70/80, MRN, PARP1 | Breast cancer |
| Ku70/80, MRN, PARP1 | Prostate cancer |
| Ku70/80, MRN, PARP1 | Recurrent ovarian cancer |
| Kv7.2 | epilepsy |
| L1CAM | Neuroendocrine prostate cancer |
| L1CAM | Neuroblastoma |
| L1CAM | leukemia |
| L1CAM | CD22-positive acute lymphoblastic leukemia |
| LICAM | CD19 expressing malignancy |
| LAG3 | Tumor |
| LAGE-1a, NY-ESO-1 | Solid tumor |
| LAMA1 | Muscular dystrophy |
| LAMP-1, TERT | Acute myeloid leukemia |

-continued

| Target site (gene) | Disease name |
|---|---|
| LAMP-2 | Glycogen storage disease type IIb |
| LAMP-2 | Diverticular disease |
| CD16a | Hypoxia |
| CD16a | Ovarian epithelial carcinoma |
| CD16a | Colorectal cancer |
| CD16a | Acute myeloid leukemia |
| CD16a | Liver cancer |
| CD16a | Peritoneal cancer |
| CD16a | Lung cancer |
| CD16a | Glioblastoma multiforme |
| CD16a | B-cell lymphoma |
| CD16a, CD19, IL-15Rα | Mantle cell lymphoma |
| CD16a, CD19, IL-15Rα | Diffuse large B-cell lymphoma |
| CD16a, CD19, IL-15Rα | Chronic lymphocytic leukemia |
| CD16a, CD19, IL-15Rα | Follicular lymphoma |
| CD16a, CD19, IL-15Rα | Indolent non-Hodgkin lymphoma |
| CD16a, CD19, IL-15Rα | Marginal zone B-cell lymphoma |
| CD16a, CD19, IL-15Rα | B-cell lymphoma |
| CD16a, CD276, IL-7 | Solid tumor |
| CD16a, HER2 | HER2-positive breast cancer |
| CD16a, IL-15 | Advanced solid tumor |
| CD16a, IL-15 | Refractory plasma cell myeloma |
| CD16a, IL-15 | Acute myeloid leukemia |
| CD16a, IL-15 | Relapsed Multiple myeloma |
| CD16a, IL-15 | Multiple myeloma |
| LAMP-2 | Huntington's disease |
| LCA5 | Retinal degeneration |
| LCA5 | Leber congenital amaurosis type 5 |
| LCN2 | Pancreatic cancer |
| LDLR | Hypercholesterolemia |
| LECT2 | Amyloidosis |
| LEKTI | Netherton syndrome |
| lepB | Pseudomonas aeruginosa infection |
| Lewis-Y antigen | Advanced cancer |
| Lewis-Y antigen | Acute myeloid leukemia |
| LGR5 | Metastatic colorectal cancer |
| LGR5 | Hematologic malignancy |
| LGR5 | Ovarian cancer |
| LGR5 | Colorectal cancer |
| L-HBsAg | Hepatitis B |
| L-HBsAg | Fibrosis |
| L-HBsAg | Chronic hepatitis B |
| L-HBsAg | Chronic hepatitis D |
| LIGHT | Glioblastoma |
| LILRB4 | Refractory acute myeloid leukemia |
| LILRB4 | Chronic myelomonocytic leukemia |
| LILRB4 | Acute myeloid leukemia |
| LILRB4 | Acute myelomonocytic leukemia |
| CD16a, IL-15, MICA, MICB | Pancreatic cancer |
| CD16a, IL-15, MICA, MICB | Gastroesophageal junction cancer |
| CD16a, IL-15, MICA, MICB | Advanced solid tumor |
| CD16a, IL-15, MICA, MICB | Head and neck tumor |
| CD16a, IL-15, MICA, MICB | Breast cancer |
| CD16a, IL-15, MICA, MICB | Ovarian cancer |
| CD16a, IL-15, MICA, MICB | Colorectal cancer |
| CD16a, IL-15, MICA, MICB | Non-small cell lung cancer |
| CD18 | Leukocyte Adhesion Deficiency Type 1 |
| CD19 | Autoimmune disease |
| CD19 | Myasthenia gravis |

-continued

| Target site (gene) | Disease name |
|---|---|
| CD19 | End-stage renal disease |
| CD19 | Primary progressive multiple sclerosis |
| CD19 | Graft-versus-host disease |
| CD19 | Pancreatic cancer |
| CD19 | Inflammation |
| CD19 | Small lymphocytic lymphoma |
| CD19 | Microscopic polyangiitis |
| CD19 | Systemic scleroderma |
| CD19 | Systemic lupus erythematosus |
| LILRB4 | Acute monocytic leukemia |
| LILRB4 | Relapsed acute myeloid leukemia |
| LILRB4 | Multiple myeloma |
| LIN28B | Pancreatic cancer |
| LIPG | Coronary heart disease |
| lipoprotein(a) | Aortic stenosis |
| lipoprotein(a) | Cardiovascular disease |
| lipoprotein(a) | Neurodegenerative disease |
| lipoprotein(a) | Hyperlipoproteinemia |
| lipoprotein(a) | Liver disease |
| lipoprotein(a) | Atherosclerosis |
| lipoprotein(a) | Hypobetalipoproteinemia |
| LIV-1 | Breast cancer |
| LMNA | Premature aging |
| LMNA | Myocardial disease |
| LMNA | Dilated cardiomyopathy |
| LMP1 | Hematologic malignancy |
| LMP1 | Nasopharyngeal carcinoma |
| LMP1, LMP2 | Leiomyosarcoma |
| LMP1, LMP2 | Hodgkin lymphoma |
| CD19 | Gastric cancer |
| CD19 | Idiopathic inflammatory myopathy |
| CD19 | Mantle cell lymphoma |
| CD19 | Granulomatosis with polyangiitis |
| CD19 | Precursor B-cell acute lymphoblastic leukemia |
| CD19 | Precursor B-cell lymphoblastic leukemia lymphoma |
| CD19 | Dermatomyositis |
| CD19 | Refractory acute leukemia |
| CD19 | Refractory non-Hodgkin lymphoma |
| CD19 | Refractory B-cell lymphoma |
| CD19 | Refractory B-type acute lymphoblastic leukemia |
| CD19 | Diffuse scleroderma |
| CD19 | Hairy cell leukemia |
| CD19 | Chronic lymphocytic leukemia |
| CD19 | Chronic myeloid leukemia |
| CD19 | Lymphomatoid granulomatosis |
| CD19 | Lymphoma |
| CD19 | Lupus nephritis |
| CD19 | Antineutrophil cytoplasmic antibody-associated vasculitis |
| CD19 | Secondary progressive multiple sclerosis |
| CD19 | Acute lymphoblastic leukemia |
| CD19 | Macular degeneration |
| CD19 | Philadelphia chromosome-negative acute lymphoblastic leukemia |
| LMP1, LMP2 | Non-Hodgkin lymphoma |
| LMP1, LMP2 | Nasopharyngeal carcinoma |
| LMP1, MAVS | Vaccination |
| LMP1, MAVS | HIV infection |
| LMP2 | Head and neck tumor metastasis |
| LMP2 | Recurrent nasopharyngeal carcinoma |
| LPL | Type V hyperlipoproteinemia |
| LPL | Hyperlipoproteinemia type I |
| LptD | Pseudomonas aeruginosa infection |
| LpxC | Pseudomonas aeruginosa infection |
| LRRC15 | Tumor |
| LRRK2 | Parkinson's disease |
| L-sel | Inflammation |

-continued

| Target site (gene) | Disease name |
|---|---|
| LXR | Nonalcoholic steatohepatitis |
| LXR | Type II hyperlipoproteinemia |
| LY86 | Duchenne muscular dystrophy |
| LZTS1, LZTS2 | Tumor |
| MAFA, PDX1 | Type 1 diabetes |
| MAGEA1 | Tumor |
| MAGEA1 | Head and neck tumor |
| MAGEA1 | Solid tumor |
| MAGEA1 | Triple-negative breast cancer |
| MAGEA1 | Urothelial carcinoma |
| CD19 | Non-Hodgkin lymphoma |
| CD19 | Fanconi anemia |
| CD19 | Multiple sclerosis |
| CD19 | Residual tumor |
| CD19 | AIDS-related lymphoma |
| CD19 | CD19-positive B-cell acute lymphoblastic leukemia |
| CD19 | CD19-positive B-cell acute lymphoblastic leukemia |
| CD19 | B-cell lymphoma |
| CD19 | Type 2 diabetes |
| CD19, CD20 | Purpura hepatitis |
| CD19, CD20 | Precursor B-cell acute lymphoblastic leukemia |
| CD19, CD20 | Chronic lymphocytic leukemia |
| CD19, CD20 | Philadelphia chromosome-negative acute lymphoblastic leukemia |
| CD19, CD20, CD22 | Refractory non-Hodgkin lymphoma |
| CD19, CD20, CD22 | Refractory indolent non-Hodgkin lymphoma |
| CD19, CD20, CD22 | Chronic lymphocytic leukemia |
| CD19, CD20, CD22 | Acute lymphoblastic leukemia |
| CD19, CD20, CD22 | Relapsed transformed chronic lymphocytic leukemia |
| CD19, CD20, CD22 | Relapsed chronic lymphocytic leukemia |
| CD19, CD20, CD22 | Relapsed acute lymphoblastic leukemia |
| CD19, CD20, CD22 | Relapsed non-Hodgkin lymphoma |
| CD19, CD20, CD22 | Relapsed indolent non-Hodgkin lymphoma |
| CD19, CD20, CD22 | Relapsed B-type acute lymphoblastic leukemia |
| CD19, CD20, CD22 | B-cell lymphoma |
| CD19, CD22 | Autoimmune disease |
| CD19, CD22 | Purpura hepatitis |
| CD19, CD22 | Hematologic malignancy |
| MAGEA1 | Ovarian cancer |
| MAGEA1 | Melanoma |
| MAGEA1 | Melanoma |
| MAGEA1 | Cervical cancer |
| MAGEA1 | Hepatocellular carcinoma |
| MAGEA1 | Liver cancer |
| MAGEA1 | Non-small cell lung cancer |
| MAGEA1 | HPV-related cancers |
| MAGEA1, PRAME | Solid tumor |
| MAGEA10 | Head and neck tumor |
| MAGEA10 | Urothelial carcinoma |
| MAGEA10 | Melanoma |
| MAGEA10 | Non-small cell lung cancer |
| MAGEA10 | Malignant epithelial tumor |
| MAGEA12, MAGEA3 | Metastatic melanoma |
| MAGEA12, MAGEA3 | Tumor metastasis |
| MAGEA12, MAGEA3 | Kidney tumor |
| MAGEA3 | Kidney tumor |
| MAGEA3 | Breast cancer |
| MAGEA3 | Melanoma |

-continued

| Target site (gene) | Disease name |
|---|---|
| MAGEA3 | Cervical cancer |
| MAGEA3 | Lung cancer |
| MAGEA3, MAGEA6 | Tumor |
| MAGEA3, MAGEA6 | Solid tumor |
| MAGEA4 | Endometrial cancer |
| MAGEA4 | Liposarcoma |
| MAGEA4 | Myxoid liposarcoma |
| CD19, CD22 | Blood disorder |
| CD19, CD22 | Precursor B-cell acute lymphoblastic leukemia |
| CD19, CD22 | Precursor B-cell lymphoblastic leukemia lymphoma |
| CD19, CD22 | Refractory B-type acute lymphoblastic leukemia |
| CD19, CD22 | Relapsed B-type acute lymphoblastic leukemia |
| CD19, CD22 | Philadelphia chromosome-negative acute lymphoblastic leukemia |
| CD19, CD22 | Philadelphia chromosome-positive acute lymphoblastic leukemia |
| CD19, CD22 | Non-Hodgkin lymphoma |
| CD19, CD22 | Residual tumor |
| CD19, CD22 | Ph-like acute lymphoblastic leukemia |
| CD19, CD22 | CD22-positive B-cell precursor acute lymphoblastic leukemia |
| CD19, CD22 | CD22-positive acute lymphoblastic leukemia |
| CD19, CD22 | CD22-positive B-cell acute lymphoblastic leukemia |
| CD19, CD22 | CD19-positive B-cell precursor acute lymphoblastic leukemia |
| CD19, CD22 | CD19-positive B-cell acute lymphoblastic leukemia |
| CD19, CD22 | B-cell lymphoma |
| CD19, CD22, CD8 | Chronic lymphocytic leukemia |
| CD19, CD22, CD8 | Acute lymphoblastic leukemia |
| CD19, CD22, CD8 | Non-Hodgkin lymphoma |
| CD19, CD276 | Ewing sarcoma |
| MAGEA4 | Gastroesophageal junction malignant tumor |
| MAGEA4 | Gastric cancer |
| MAGEA4 | Gastric cancer |
| MAGEA4 | Esophageal cancer |
| MAGEA4 | Solid tumor |
| MAGEA4 | Solid tumor |
| MAGEA4 | Neurofibrosarcoma |
| MAGEA4 | Neuroblastoma |
| MAGEA4 | sarcoma |
| MAGEA4 | Urothelial carcinoma |
| MAGEA4 | Ovarian cancer |
| MAGEA4 | Ovarian cancer |
| MAGEA4 | Synovial sarcoma |
| MAGEA4 | Melanoma |
| MAGEA4 | Osteosarcoma |
| MAGEA4 | Recurrent solid tumor |
| MAGEA4 | Non-small cell lung cancer |
| MAGEA4 | Bladder cancer |
| MAGEA4, MAGEA8 | Solid tumor |
| MAGEA4, NY-ESO-1, PRAME, SSX2, survivin | Hematologic malignancy |
| CD19, CD276 | Clear cell sarcoma |
| CD19, CD276 | Retinoblastoma |
| CD19, CD276 | Wilms tumor |
| CD19, CD276 | Neurofibrosarcoma |
| CD19, CD276 | Neuroblastoma |
| CD19, CD276 | sarcoma |
| CD19, CD276 | Synovial sarcoma |
| CD19, CD276 | Rhabdoid tumor |
| MAGEA4, NY-ESO-1, PRAME, SSX2, survivin | Acute myeloid leukemia |
| MAGEA4, NY-ESO-1, PRAME, SSX2, survivin | Hodgkin lymphoma |
| MAGEA4, NY-ESO-1, PRAME, SSX2, survivin | Non-Hodgkin lymphoma |
| MAGEA4, NY-ESO-1, PRAME, SSX2, WT1, survivin | Pancreatic cancer |
| MAGEA4, NY-ESO-1, PRAME, SSX2, WT1, survivin | Refractory lymphoma |
| MAGEA4, NY-ESO-1, PRAME, SSX2, WT1, survivin | Refractory non-Hodgkin lymphoma |
| MAGEA4, NY-ESO-1, PRAME, SSX2, WT1, survivin | Hodgkin lymphoma |
| MAGEA4, NY-ESO-1, PRAME, SSX2, WT1, survivin | Relapsed lymphoma |
| CD19, CD276 | Rhabdomyosarcoma |
| CD19, CD276 | Melanoma |
| CD19, CD276 | Hepatoblastoma |
| CD19, CD276 | Recurrent solid tumor |
| CD19, CD276 | Malignant epithelial tumor |
| CD19, CD276 | Desmoplastic small round cell tumor |
| CD19, CD3 | Severe combined immunodeficiency |
| CD19, CD3 | Common variable immunodeficiency |
| CD19, CD3 | Refractory B-cell lymphoma |
| CD19, CD3 | Immunodeficiency syndrome |
| CD19, CD3 | Mendelian susceptibility to mycobacterial disease |
| CD19, CD3 | Chronic granulomatous disease |
| CD19, CD3 | Lymphoma |
| CD19, CD3 | Relapsed B-cell lymphoma |
| CD19, CD3 | Wiskott-Aldrich syndrome |
| CD19, CD3 | Job syndrome |
| CD19, CD3 | B-cell lymphoma |
| CD19, CD4 | Chronic lymphocytic leukemia |
| CD19, CD4 | Non-Hodgkin lymphoma |
| MAGEA4, NY-ESO-1, PRAME, SSX2, WT1, survivin | Relapsed non-Hodgkin lymphoma |
| MAGEC2 | Head and neck tumor |
| MAGEC2 | Solid tumor |
| MAGEC2 | Ovarian cancer |
| MAGEC2 | Melanoma |
| MAGEC2 | Hepatocellular carcinoma |
| MAGEC2 | Non-small cell lung cancer |
| MALAT1 | Tumor |
| MALAT1 | Breast cancer |
| MAX, c-Myc | Tumor |
| MBP | Multiple sclerosis |
| MCM7 | Tumor |

-continued

| Target site (gene) | Disease name |
|---|---|
| M-CSF | Tumor |
| MDA5, RIG-I, TLR3 | Myxoid MFH |
| MDA5, RIG-I, TLR3 | Head and Neck Squamous Cell Carcinoma |
| MDA5, RIG-I, TLR3 | Neurofibrosarcoma |
| MDA5, RIG-I, TLR3 | Breast cancer |
| MDA5, RIG-I, TLR3 | Sarcoma |
| MDA5, RIG-I, TLR3 | Dedifferentiated liposarcoma |
| CD19, CD7 | Precursor B-cell acute lymphoblastic leukemia |
| CD19, CD7 | Acute lymphoblastic leukemia |
| CD19, CD7 | B-cell leukemia |
| CD19, CD70 | Refractory B-cell lymphoma |
| CD19, CD70 | Lymphoma |
| CD19, CD70 | Acute myeloid leukemia |
| CD19, CD70 | Relapsed B-cell lymphoma |
| CD19, CD70 | Non-Hodgkin lymphoma |
| CD19, CD70 | B-cell lymphoma |
| CD19, CD79B | Non-Hodgkin lymphoma |
| CD19, CD8 | Precursor B-cell lymphoblastic leukemia lymphoma |
| CD19, CD8 | Chronic lymphocytic leukemia |
| CD19, CD8 | Non-Hodgkin lymphoma |
| CD19, CLDN18.2 | Gastric cancer |
| CD19, DR5 | B-cell lymphoma |
| CD19, EBV protein | Acute lymphoblastic leukemia |
| CD19, EBV protein | B-cell lymphoma |
| CD19, EGFR | Tumor |
| CD19, HPK1 | Acute lymphoblastic leukemia |
| CD19, HPK1 | B-cell lymphoma |
| MDA5, RIG-I, TLR3 | Leiomyosarcoma |
| MDA5, RIG-I, TLR3 | Synovial sarcoma |
| MDA5, RIG-I, TLR3 | Rhabdomyosarcoma |
| MDA5, RIG-I, TLR3 | Hepatoembryosarcoma |
| MDA5, RIG-I, TLR3 | Retroperitoneal sarcoma |
| MDA5, RIG-I, TLR3 | Non-small cell lung cancer |
| MDA5, RIG-I, TLR3 | Malignant fibrous histiocytoma |
| MDH1, MDH2 | Non-small cell lung cancer |
| MECOM | Ovarian cancer |
| MECOM | Lung cancer |
| MECP2 | Lubbs sex-linked mental retardation syndrome |
| MECP2 | Spinal muscular atrophy with respiratory distress type 1 |
| MECP2 | Charcot-Marie-Tooth Disease Type 2S |
| MECP2 | Rett syndrome |
| melan-A | Metastatic melanoma |
| melan-A | Melanoma |
| melan-A | Melanoma |
| MerTK | Retinitis pigmentosa |
| MEX3B | Severe asthma |
| MFN2 | Charcot-Marie-Tooth Disease |
| CD19, IL15R | Small lymphocytic lymphoma |
| CD19, IL15R | Mantle cell lymphoma |
| CD19, IL15R | Precursor B-cell acute lymphoblastic leukemia |
| CD19, IL15R | Chronic lymphocytic leukemia |
| CD19, IL15R | Lupus nephritis |
| CD19, IL15R | Macroglobulinemia |

-continued

| Target site (gene) | Disease name |
|---|---|
| CD19, IL15R | Large B-cell lymphoma |
| CD19, IL15R | B-cell malignancy |
| CD19, IL-18 | Acute lymphoblastic leukemia |
| CD19, IL-18 | B-cell lymphoma |
| CD19, IL18R1 | Refractory B-type acute lymphoblastic leukemia |
| CD19, IL18R1 | Chronic lymphocytic leukemia |
| CD19, IL18R1 | Acute lymphoblastic leukemia |
| CD19, IL18R1 | Relapsed acute lymphoblastic leukemia |
| CD19, IL18R1 | Relapsed and refractory acute lymphoblastic leukemia |
| CD19, IL18R1 | Non-Hodgkin lymphoma |
| CD19, IL18R1 | CD19 expressing malignancy |
| CD19, IL-2Rβ | Tumor |
| CD19, IL-2Rβ | Small lymphocytic lymphoma |
| CD19, IL-2Rβ | Mantle cell lymphoma |
| CD19, IL-2Rβ | Diffuse large B-cell lymphoma |
| MFSD8 | Neuronal ceroid lipofuscinosis |
| MFSD8 | Lysosomal storage disease |
| MGMT | Glioblastoma |
| MICA | Hepatocellular carcinoma |
| MICA, MICB | Tumor |
| MICA, MICB, ULBP1 | Solid tumor |
| micro-dystrophin | Duchenne muscular dystrophy |
| microRNA let-7i-5p | Hepatocellular carcinoma |
| MicroRNAs | Alzheimer's disease |
| Microtubule-associated proteins | Myocardial infarction |
| Microtubule-associated proteins | Nerve damage |
| Microtubule-associated proteins | burn |
| miHAs | Hematopoietic stem cell transplantation |
| miHAs | Hematologic malignancy |
| miHAs | Hematologic malignancy |
| miHAs | Acute myeloid leukemia |
| miHAs | Acute lymphoblastic leukemia |
| miHAs | Myelodysplastic syndrome |
| miHAs | leukemia |
| mini-dystrophin | Duchenne muscular dystrophy |
| MIR 103A1, miR-107 | Nonalcoholic steatohepatitis |
| CD19, IL-2Rβ | Chronic lymphocytic leukemia |
| CD19, IL-2Rβ | Follicular lymphoma |
| CD19, IL-2Rβ | Indolent B-cell non-Hodgkin lymphoma |
| CD19, IL-2Rβ | Large B-cell lymphoma |
| CD19, IL-2Rβ | CD19 expressing malignancy |
| CD19, MUC1 | Tumor |
| CD19, PD-1 | Solid tumor |
| CD19, PD-1 | Refractory cancer |
| CD19, PD-1 | Refractory B-cell lymphoma |
| CD19, PD-1 | Relapsed non-Hodgkin lymphoma |
| CD19, PD-1 | Non-Hodgkin lymphoma |
| CD19, PD-1 | Mesothelin-positive tumor |
| CD19, PD-1 | CD19 expressing malignancy |
| CD19, PD-1 | Carney complex |
| CD19, PD-1 | B-cell lymphoma |
| CD19, PD-1, TIGIT | Mediastinal large B-cell lymphoma |
| CD19, PD-1, TIGIT | Follicular lymphoma |

-continued

| Target site (gene) | Disease name |
|---|---|
| CD19, PD-1, TIGIT | High-grade B-cell lymphoma |
| CD19, PD-1, TIGIT | Large B-cell lymphoma |
| CD19, STING | Solid tumor |
| CD19, TGF-β2 | Non-Hodgkin lymphoma |
| CD19, TGF-β2 | CD19-positive diffuse large B-cell lymphoma |
| CD19, TGF-β2 | CD19-positive B-cell acute lymphoblastic leukemia |
| CD1A | Precursor T-lymphocytic leukemia lymphoma |
| CD1A | Precursor T-lymphocytic leukemia lymphoma |
| miR-10b | Pancreatic cancer |
| miR-10b | Small cell lung cancer |
| miR-10b | Advanced solid tumor |
| miR-10b | Breast cancer |
| miR-10b | Ovarian cancer |
| miR-10b | Colon cancer |
| miR-10b | Glioblastoma |
| miR-10b | Osteosarcoma |
| miR-10b, miR-21 | Glioblastoma |
| miR-122 | Hepatitis C |
| miR-126 | Chronic myeloid leukemia |
| miR-126 | Acute myeloid leukemia in adults |
| miR-132 | Heart failure |
| miR-132 | Cardiac hypertrophy |
| miR-132 | Heart failure with preserved ejection fraction |
| miR-132 | Dilated cardiomyopathy |
| miR-132 | Acute myocardial infarction |
| MIR135A1 | Depression |
| miR-143 | Colorectal cancer |
| miR-145 | Pulmonary hypertension |
| miR-150 | Rectal cancer |
| miR-150 | Colorectal cancer |
| miR-155 | Wet macular degeneration |
| miR-155 | Cutaneous T-cell lymphoma |
| miR-17 | Autosomal dominant polycystic kidney disease |
| CD1A | Lymphoma |
| CD1A | T-cell acute lymphoblastic leukemia/lymphoma |
| CD2 | Sezary syndrome |
| CD20 | Mediastinal large B-cell lymphoma |
| CD20 | Autoimmune disease |
| CD20 | Metastatic melanoma |
| CD20 | Hematologic malignancy |
| CD20 | Small lymphocytic lymphoma |
| CD20 | Skin melanoma |
| CD20 | Refractory mantle cell lymphoma |
| CD20 | Refractory B-cell lymphoma |
| CD20 | Chronic lymphocytic leukemia |
| CD20 | Follicular lymphoma |
| CD20 | Waldenstrom's macroglobulinemia is refractory |
| CD20 | Melanoma |
| CD20 | Relapsed mantle cell lymphoma |
| CD20 | Relapsed chronic lymphocytic leukemia |
| CD20 | Recurrent macroglobulinemia |
| CD20 | Relapsed B-cell lymphoma |
| CD20 | Marginal zone B-cell lymphoma |
| CD20 | CD20-positive B-cell lymphoma |
| CD20, CD22 | Precursor B-cell lymphoblastic leukemia lymphoma |
| CD20, CD22 | Refractory B-cell lymphoma |
| CD20, CD22 | Non-Hodgkin lymphoma |
| CD20, CD22, CD38 | Breast cancer |
| CD20, CD23, TLR9 | Hematologic malignancy |

-continued

| Target site (gene) | Disease name |
|---|---|
| MIR181A2 | Chondrosarcoma |
| miR-193a-3p | Advanced solid tumor |
| miR-193a-3p | Melanoma |
| miR-193a-3p | Liver cancer |
| miR-195 | Liver cancer |
| miR-195 | Bile duct tumor |
| miR-21 | Post-COVID-19 Syndrome |
| miR-21 | Nephritis |
| miR-21 | Triple-negative breast cancer |
| miR-21 | Lung cancer |
| miR-21 | Non-small cell lung cancer |
| miR-21 | Bladder cancer |
| miR-21, miR-34a | Triple-negative breast cancer |
| miR-22 | Fatty liver |
| miR-22 | Optic nerve disease |
| miR-22 | Obesity |
| miR-22 | Nonalcoholic steatohepatitis |
| miR-22 | Metabolic disease |
| miR-22 | Metabolic fatty liver disease |
| miR-22 | Type 2 diabetes |
| miR-23b | Osteoarthritis |
| miR-29 | Fibrosis |
| miR-29 | Idiopathic pulmonary fibrosis |
| miR-328 | Shortsighted |
| miR-33a | Idiopathic pulmonary fibrosis |
| miR-34a | Small cell carcinoma |
| CD20, CD79A | Non-Hodgkin lymphoma |
| CD200R | Immune system disorder |
| CD22 | Autoimmune disease |
| CD22 | Hairy cell leukemia |
| CD22 | Acute lymphoblastic leukemia |
| CD22 | Non-Hodgkin lymphoma |
| CD22 | B-cell leukemia |
| CD22, CD37 | Hematologic malignancy |
| CD22, PDL1 | sarcoma |
| CD22, PDL1 | Cervical cancer |
| CD22, PDL1 | Non-small cell lung cancer |
| CD24 | Tumor |
| CD276 | Diffuse midline glioma with K27M point mutation in histone H3 |
| CD276 | Pancreatic ductal adenocarcinoma |
| CD276 | Pancreatic cancer |
| CD276 | Medulloblastoma |
| CD276 | Ependymoma |
| CD276 | Neuroblastoma |
| CD276 | Brain malignant glioma |
| CD276 | Refractory acute myeloid leukemia |
| CD276 | Diffuse intrinsic pontine glioma |
| CD276 | Ovarian epithelial carcinoma |
| CD276 | Colorectal cancer |
| CD276 | Colorectal cancer |
| CD276 | Glioblastoma |
| CD276 | Glioma |
| CD276 | Acute myeloid leukemia |
| CD276 | Melanoma |
| CD276 | Liver cancer |
| CD276 | Recurrent platinum-resistant ovarian cancer |
| miR-34a | Renal cell carcinoma |
| miR-34a | Lymphoma |
| miR-34a | Melanoma |
| miR-34a | Liver cancer |
| miR-34a | Non-small cell lung cancer |
| miR-34a | Multiple myeloma |
| MIR 449A | Breathing disorders |
| MIR92A1 | Heart failure |
| miR-96 | Diabetic nephropathy |
| MIRN122 microRNA | Parkinson's disease |
| MIRN122 microRNA | Amyotrophic lateral sclerosis |
| MIRN122 microRNA | Cholestasis |

-continued

| Target site (gene) | Disease name |
|---|---|
| MIRN122 microRNA | Hepatitis C |
| MIRN122 microRNA | Alzheimer's disease |
| Mitochondrial proteins | sarcoma |
| Mitochondrial proteins | Skin tumor |
| Mitochondrial proteins | Basal cell carcinoma |
| Mitochondrial proteins | Melanoma |
| MKI67 | Bladder cancer |
| MLC | White matter disease |
| MMP1 | Tumor |
| MMP1 | Systemic scleroderma |
| MMP1 | Skin laxity |
| MMP1 | Facial wrinkle |
| MMP1 | aging |
| MMP1 | Trauma and Injury |
| MMP2 | Prostate cancer |
| MMP2 | Colorectal cancer |
| MMP2 | Glioblastoma |
| MMP2 | Melanoma |
| CD276 | Lung cancer |
| CD276 | Atypical teratoma |
| CD276 | Recurrent ovarian tumor of low malignant potential |
| CD276 | CD276-positive solid tumor |
| CD276, FGFR4 | Rhabdomyosarcoma |
| CD276, HER2 | Tumor |
| CD276, IL-13Rα2 | Solid tumor |
| CD28, CD80, p53 | Tumor |
| CD28, CSF-2R, CTLA4 | Tumor |
| CD29, EGFR, LAMA4 | Metastatic non-small cell lung cancer |
| CD29, EGFR, LAMA4 | Breast cancer |
| CD29, EGFR, LAMA4 | Glioma |
| CD3 | Tumor |
| CD3, CD7 | Acute lymphoblastic leukemia |
| CD3, CD80 | Tumor |
| CD3, CD86, PD-1 | Endometrial cancer |
| MMP2 | MMP2-positive glioblastoma |
| MMP-7 | Idiopathic pulmonary fibrosis |
| MNK1 | Non-small cell lung cancer |
| MnSOD | Colorectal cancer |
| MnSOD, TRAIL | Non-small cell lung cancer |
| MnSOD, transcription factors, and related regulatory factors | Motor neurone disease |
| MnSOD, transcription factors, and related regulatory factors | Traumatic brain injury |
| MnSOD, transcription factors, and related regulatory factors | Alzheimer's disease |
| MSH3 | Spinocerebellar ataxia |
| MSH3 | Myotonic dystrophy |

-continued

| Target site (gene) | Disease name |
|---|---|
| MSH3 | Huntington's disease |
| MSLN | Mediastinal large B-cell lymphoma |
| MSLN | Metastatic non-small cell lung cancer |
| MSLN | Tumor |
| MSLN | Primary peritoneal cancer |
| MSLN | Pancreatic acinar cell carcinoma |
| CD3, CD86, PD-1 | Bronchogenic carcinoma |
| CD3, CD86, PD-1 | Pancreatic cancer |
| CD3, CD86, PD-1 | Pharyngeal tumor |
| CD3, CD86, PD-1 | Small cell lung cancer |
| CD3, CD86, PD-1 | Gastrointestinal tumor |
| CD3, CD86, PD-1 | Gastric cancer |
| CD3, CD86, PD-1 | Advanced malignant solid tumor |
| CD3, CD86, PD-1 | Advanced cancer |
| CD3, CD86, PD-1 | Head and neck tumor |
| CD3, CD86, PD-1 | Fallopian tube cancer |
| CD3, CD86, PD-1 | Esophageal cancer |
| CD3, CD86, PD-1 | Kidney tumor |
| CD3, CD86, PD-1 | Soft tissue sarcoma |
| CD3, CD86, PD-1 | Breast cancer |
| CD3, CD86, PD-1 | Sarcoma |
| CD3, CD86, PD-1 | Female genitor tumor |
| CD3, CD86, PD-1 | Brain cancer |
| CD3, CD86, PD-1 | Ovarian cancer |
| CD3, CD86, PD-1 | Colorectal cancer |
| CD3, CD86, PD-1 | Laryngeal tumor |
| CD3, CD86, PD-1 | Melanoma |
| CD3, CD86, PD-1 | Osteosarcoma |
| MSLN | Pancreatic adenocarcinoma |
| MSLN | Pancreatic cancer |
| MSLN | Adenocarcinoma |
| MSLN | Gastric cancer |
| MSLN | Advanced cancer |
| MSLN | Fallopian tube cancer |
| MSLN | Solid tumor |
| MSLN | Triple-negative breast cancer |
| MSLN | Breast cancer |
| MSLN | Refractory B-cell lymphoma |
| MSLN | Follicular lymphoma |
| MSLN | Ovarian adenocarcinoma |
| MSLN | Ovarian epithelial cancer |
| MSLN | Ovarian epithelial cancer |
| MSLN | Ovarian serous adenocarcinoma |
| MSLN | High-grade serous ovarian adenocarcinoma |
| MSLN | Ovarian cancer |
| MSLN | Ovarian cancer |
| MSLN | Colorectal cancer |
| MSLN | Mesothelioma |

| Target site (gene) | Disease name |
|---|---|
| MSLN | Mesothelioma |
| MSLN | Malignant peritoneal mesothelioma |
| CD3, CD86, PD-1 | Bone cancer |
| CD3, CD86, PD-1 | Cervical cancer |
| CD3, CD86, PD-1 | Liver cancer |
| CD3, CD86, PD-1 | Peritoneal cancer |
| CD3, CD86, PD-1 | Recurrent Head and neck tumor |
| CD3, CD86, PD-1 | Recurrent ovarian cancer |
| CD3, CD86, PD-1 | Lung cancer |
| CD3, CD86, PD-1 | Non-small cell lung cancer |
| CD3, CD86, PD-1 | Ear tumor |
| CD3, CD86, PD-1 | Malignant epithelial tumor |
| CD3, CD86, PD-1 | Nasal tumor |
| CD3, EGFR | Pancreatic adenocarcinoma |
| CD3, EGFR | Pancreatic cancer |
| CD3, EGFR | Glioblastoma |
| CD3, EGFRvIII, IL-13Rα2 | Glioblastoma |
| CD3, EpCAM | Tumor |
| CD3, EphA2 | Tumor |
| CD3, FAP | Tumor metastasis |
| CD3, FAP | Adenoepithelial tumor |
| CD3, FAP | Malignant epithelial tumor |
| CD3, gp100 | Uveal melanoma |
| CD3, gp100 | Cutaneous melanoma |
| CD3, gp100 | Residual tumor |
| CD3, GPC3 | Solid tumor |
| CD3, GPRC5D | Tumor |
| MSLN | Lung cancer |
| MSLN | Non-small cell lung cancer |
| MSLN | Malignant pleural mesothelioma |
| MSLN | Cholangiocarcinoma |
| MSLN | Cholangiocarcinoma |
| MSLN | Diffuse large B-cell lymphoma |
| MSLN | Mesothelin-expressing tumor |
| MSLN | Mesothelin-expressing solid tumor |
| MSLN, MUC16 | Pancreatic acinar cell carcinoma |
| MSLN, MUC16 | Ovarian epithelial cancer |
| MSLN, PD-1 | Advanced malignant solid tumor |
| MSLN, PD-1 | Breast cancer |
| MSLN, PD-1 | Mesothelioma |
| MSLN, PD-1 | Mesothelioma |
| MSLN, PD-1 | Mesothelin-expressing solid tumor |
| MSLN, PDL1 | Ovarian cancer |
| MSP-1 | Malaria |
| MSTN | Muscle atrophy |
| MSTN | Duchenne muscular dystrophy |
| MSTN | Inclusion body myositis |
| MTM1 | Congenital myopathy |
| MTM1 | Rheumatoid arthritis |
| MTM1 | Muscle disorders |
| MT-ND1 | Leber Hereditary Optic Neuropathy, ND1 mutation |
| MT-ND4 | Leber Hereditary Optic Neuropathy, ND4 mutation |
| CD3, HER2 | Breast cancer |
| CD3, IL-13Rα2, PDL1 | Glioblastoma |
| CD3, IL-13Rα2, PDL1 | Glioma |
| CD3, MUC1 | Advanced pancreatic adenocarcinoma |
| CD3, MUC1 | Advanced gastric cancer |
| CD3, MUC1 | Advanced breast cancer |
| CD3, MUC1 | Kidney tumor |
| CD3, MUC1 | Colorectal cancer |

| Target site (gene) | Disease name |
|---|---|
| CD3, MUC1 | Liver cancer |
| CD3, MUC1 | Lung cancer |
| CD3, PDL1 | Solid tumor |
| CD3, PDL1 | Recurrent cervical cancer |
| CD3, PRAME | Advanced malignant solid tumor |
| CD3, PRAME | Cutaneous melanoma |
| CD3, PRAME | Melanoma |
| CD3, SLAMF7 | Refractory plasma cell myeloma |
| CD3, SLAMF7 | Relapsed Multiple myeloma |
| CD30 | Peripheral T-cell lymphoma |
| CD30 | Diffuse large B-cell lymphoma |
| CD30 | Anaplastic large cell lymphoma |
| CD30 | Anaplastic large cell lymphoma |
| CD30 | Hodgkin lymphoma |
| CD30 | T-cell lymphoma |
| CD30 | CD30-positive lymphoma |
| CD30 | CD30-positive Hodgkin lymphoma |
| CD30 | CD30-positive diffuse large B-cell lymphoma |
| CD30 | CD19-positive lymphoma |
| CD30 | CD19 expressing malignancy |
| CD30 | B-cell lymphoma |
| CD30 | B-cell leukemia |
| CD33 | Graft-versus-host disease |
| mTOR | Tumor |
| mTOR | Hemophilia A |
| mTOR | Diabetic retinopathy |
| mTOR | Retinal disease |
| mTOR | Methylmalonic acidemia |
| MUC1 | Metastatic solid tumor |
| MUC1 | Metastatic breast cancer |
| MUC1 | Pancreatic acinar cell carcinoma |
| MUC1 | Pancreatic ductal carcinoma |
| MUC1 | Pancreatic cancer |
| MUC1 | Gastric cancer |
| MUC1 | Advanced gastric cancer |
| MUC1 | Advanced malignant solid tumor |
| MUC1 | Head and neck squamous cell carcinoma |
| MUC1 | Fallopian tube cancer |
| MUC1 | Esophageal cancer |
| MUC1 | Renal cell carcinoma |
| MUC1 | Breast cancer |
| MUC1 | Prostate cancer |
| MUC1 | Brain malignant glioma |
| MUC1 | Ovarian epithelial carcinoma |
| MUC1 | Ovarian cancer |
| MUC1 | Colorectal cancer |
| MUC1 | Glioma |
| MUC1 | Hepatocellular carcinoma |
| MUC1 | Intrahepatic cholangiocarcinoma |
| MUC1 | Lung cancer |
| MUC1 | Non-small cell lung cancer |
| MUC1 | Non-small cell lung cancer |
| MUC1 | Multiple myeloma |
| MUC1 | Nasopharyngeal tumor |
| CD33 | Acute myeloid leukemia |
| CD33 | Alzheimer's disease |
| CD33, CLL-1 | Hematologic malignancy |
| CD33, CLL-1 | Chronic myeloid leukemia |
| CD33, CLL-1 | Chronic myelomonocytic leukemia |
| CD33, CLL-1 | Acute myeloid leukemia |
| CD33, CLL-1 | Acute myeloid leukemia |
| CD33, CLL-1 | Myelodysplastic syndrome |
| CD33, FLT3 | Hematologic malignancy |
| CD33, FLT3 | Refractory acute myeloblastic leukemia |
| CD33, FLT3 | Myelodysplastic syndrome |
| CD33, FLT3 | Relapsed acute myeloblastic leukemia |
| CD33, IL-15Rα, NKG2C | Acute myeloid leukemia |

-continued

| Target site (gene) | Disease name |
|---|---|
| CD33, NKG2A | Acute myeloid leukemia in adults |
| CD34 | Severe combined immunodeficiency |
| CD34 | Tumor |
| CD34 | Hematologic malignancy |
| CD34 | Adenosine deaminase deficiency |
| CD34 | Myeloid tumor |
| CD34 | Acute leukemia |
| CD34 | Myelodysplastic syndrome |
| CD34 | Multiple myeloma |
| CD34 | Wiskott-Aldrich syndrome |
| CD37 | Chronic lymphocytic leukemia |
| CD37 | T-cell lymphoma |
| CD37 | B-cell lymphoma |
| CD38 | Refractory acute myeloid leukemia |
| MUC1 | MUC1-expressing solid tumor |
| MUC16 | Breast cancer |
| MUC16 | Ovarian epithelial carcinoma |
| Mucin | Tumor |
| Mucin | Asthma |
| Mucin | Chronic obstructive pulmonary disease |
| MUSK | Myasthenia gravis |
| MUT | Methylmalonic acidemia |
| MUT, mTOR | Mesothelioma |
| MYB | Hematologic malignancy |
| MYB | Chronic myeloid leukemia |
| MYB | Leukemia |
| MYBPC3 | Hypertrophic cardiomyopathy |
| MYO6 | Hearing impairment |
| MYO7A | Usher syndrome |
| MYO7A | Usher syndrome type 1B |
| NaCT | Epilepsy |
| NAGA | Fabry disease |
| NAGLU | Lower urinary tract symptom |
| NAGLU | Mucopolysaccharidosis type III |
| Nav1.1 | Mucopolysaccharidosis type I |
| Nav1.1 | Rett syndrome |
| Nav1.1 | Dravet syndrome |
| Nav1.1 | CDKL5 Deficiency |
| Nav1.2 | Genetic disease |
| Nav1.2 | Precocious puberty |
| Nav1.2 | Epileptic encephalopathy |
| CD38 | Hepatocellular carcinoma |
| CD38 | Relapsed acute myeloid leukemia |
| CD38 | Multiple myeloma |
| CD38, CLL-1 | Cancer |
| CD38, DR5 | Multiple myeloma |
| CD38, GPRC5D | Tumor |
| CD39, CD73 | Rheumatoid arthritis |
| CD4 | Hematopoietic stem cell transplantation |
| CD4 | Graft-versus-host disease |
| CD4 | Precursor T-cell lymphocytic leukemia/lymphoma |
| CD4 | Chronic myelomonocytic leukemia |
| CD4 | T-cell lymphoma |
| CD4 | T-cell leukemia |
| CD4 | HIV infection |
| CD4, CD8 | Colorectal cancer |
| CD4, CD8 | HIV infection |
| CD40 | Autoimmune disease |
| CD40 | Tumor metastasis |
| CD40 | Adenoepithelial tumor |
| CD40 | Autoimmune neurological disorder |

-continued

| Target site (gene) | Disease name |
|---|---|
| CD40 | Organ transplant rejection |
| CD40 | Hypersensitivity reactions |
| CD40L | Metastatic renal cell carcinoma |
| CD40L | Tumor |
| CD40L | Chronic lymphocytic leukemia |
| CD40L | Vaccination |
| CD40L | Glioma |
| CD40L | Melanoma |
| Nav1.2 | SCN2A-related encephalopathy |
| Nav1.6 | Developmental and epileptic encephalopathy |
| Nav1.6 | CDKL5 deficiency |
| Nav1.7 | Small fiber neuropathy |
| Nav1.7 | Pain |
| Nav1.7 | Neuralgia |
| Nav1.7 | Erythromelalgia |
| Nav1.7, Nav1.8 | Pain |
| Nav1.7, Voltage-gated sodium channels | Neuralgia |
| Nav1.8 | Pain |
| Nav1.8, TRKA | Neurological disorders |
| NCALD | Spinal muscular atrophy |
| NCF1 | Chronic granulomatous disease |
| NCL | Tumor |
| NCL | Tumor |
| NCL | Triple-negative breast cancer |
| NCL | Myelodysplastic syndrome |
| NCOR2 | Tumor |
| NCR2, NKG2D | Advanced solid tumor |
| NCR3LG1 | Tumor |
| NCR3LG1 | Solid tumor |
| NECTIN2 | Tumor |
| Nectin-4 | Tumor |
| NEGF2 | Tumor |
| NEK2 | Pancreatic cancer |
| NEK2 | Cholangiocarcinoma |
| NF-κB | Atopic dermatitis |
| NF-κB | Sepsis |
| CD40L | Recurrent non-small cell lung cancer |
| CD40L | Non-muscle invasive bladder tumor |
| CD40L | Bladder urothelial bladder |
| CD40L | Bladder cancer |
| CD40L | Stage IV malignant non-small cell lung tumor |
| CD40L, CD70, TLR4 | Tumor |
| CD40L, CD70, TLR4 | Melanoma |
| CD40L, CD70, TLR4 | Stage IV malignant melanoma |
| CD40L, CD70, TLR4 | Unresectable melanoma |
| CD40L, IFNβ | Tumor |
| CD40L, OX40L | Tumor |
| CD40L, OX40L | Triple-negative breast cancer |
| CD40L, OX40L | Sarcoma |
| CD40L, OX40L | Melanoma |
| CD40L, OX40L | Non-small cell lung cancer |
| CD43 | T-cell lymphoma |
| CD43 | T-cell leukemia |

-continued

| Target site (gene) | Disease name |
|---|---|
| CD44 | Hematologic malignancy |
| CD44v6 | Solid tumor |
| CD44v6 | Acute myeloid leukemia |
| CD44v6 | Multiple myeloma |
| CD45 | Hematologic malignancy |
| CD45 | Bone marrow tumor |
| CD46 | Rectal cancer |
| CD46 | Head and neck tumor |
| CD46 | Renal cell carcinoma |
| CD46 | Ovarian cancer |
| CD46 | Colorectal cancer |
| CD46 | Non-small cell lung cancer |
| CD46 | Bladder cancer |
| CD46, PEDF | Geographic atrophy |
| NF-κB | Acute kidney injury |
| NF-κB | Obstetric delivery (premature birth) |
| NGF | Hearing loss |
| NGF | Retinitis pigmentosa |
| NGF | Retinal disease |
| NGF | Neuralgia |
| NGF | Glaucoma |
| NGF | Parkinson's disease |
| NGF | Stroke |
| NGF | Keratitis |
| NGF | Spinal cord injury |
| NGF | Macular degeneration |
| NGF | Huntington's disease |
| NGF | Osteoporosis |
| NGF | Osteoarthritis |
| NGF | Alzheimer's disease |
| NGLY1 | Genetic disease |
| NGLY1 | NGLY1 deficiency |
| Nicotine | Tobacco dependence |
| NIS | Pancreatic ductal adenocarcinoma |
| NIS | Fallopian tube cancer |
| NIS | Breast cancer |
| NIS | Prostate cancer |
| NIS | Ovarian cancer |
| NIS | Squamous cell carcinoma |
| NIS | Mesothelioma |
| NIS | Rhabdomyosarcoma |
| NIS | Peritoneal cancer |
| NIS | Multiple myeloma |
| NIS | Bladder cancer |
| NK1 | Hypertonia |
| CD47 | Hematologic malignancy |
| CD47 | Solid tumor |
| CD47 | Sickle cell disease |
| CD47 | Thalassemia |
| CD47, PHD2 | Tumor |
| CD47, PHD2 | Hematologic malignancy |
| CD47, PHD2 | Solid tumor |
| CD47, SIRPα | Tumor |
| CD47, SIRPα | Advanced malignant solid tumor |
| CD47, SIRPα | Solid tumor |
| CD47, SIRPα | Refractory non-Hodgkin lymphoma |
| CD47, SIRPα | Relapsed non-Hodgkin lymphoma |
| CD47, SIRPα | Atherosclerosis |
| CD49d | Multiple sclerosis |
| CD49d | Duchenne muscular dystrophy |
| CD5 | Mycosis fungoides |
| CD5 | Hematologic malignancy |
| CD5 | Peripheral T-cell lymphoma |
| CD5 | Precursor T-cell lymphocytic leukemia/lymphoma |
| CD5 | Precursor B-cell lymphoblastic leukemia/lymphoma |
| CD5 | Refractory T-cell acute lymphoblastic leukemia |
| CD5 | Refractory B-type acute lymphoblastic leukemia |
| CD5 | Lymphoma |
| CD5 | Acute lymphoblastic leukemia |

-continued

| Target site (gene) | Disease name |
|---|---|
| CD5 | Relapsed acute lymphoblastic leukemia |
| CD5 | Relapsed T-cell lymphoma |
| CD5 | Non-Hodgkin lymphoma |
| CD5 | T-cell lymphoma |
| CD5 | T-cell acute lymphoblastic leukemia/lymphoma |
| NK2R, mGluRs | Major depressive disorder |
| NKG2D | Metastatic solid tumor |
| NKG2D | Rectal cancer |
| NKG2D | Hematologic malignancy |
| NKG2D | Novel Coronavirus Infection |
| NKG2D | Medulloblastoma |
| NKG2D | Medulloblastoma |
| NKG2D | Refractory acute myeloid leukemia |
| NKG2D | Colorectal cancer |
| NKG2D | Colon cancer liver metastasis |
| NKG2D | Colon cancer |
| NKG2D | Glioblastoma |
| NKG2D | Glioblastoma |
| NKG2D | Acute myeloid leukemia |
| NKG2D | Acute myeloid leukemia |
| NKG2D | Myelodysplastic syndrome |
| NKG2D | Hepatocellular carcinoma |
| NKG2D | Relapsed acute myeloid leukemia |
| NKG2D | Unresectable colorectal cancer |
| NKG2D | NKG2DL-positive solid tumor |
| NLGase | Gaucher disease |
| NLRP1, NLRP3 | Neurodegenerative disease |
| NLRP3 | Inflammatory bowel disease |
| NLRP3 | Inflammation |
| NMNAT1 | Leber congenital amaurosis |
| N-Myc | Small cell lung cancer |
| N-Myc | Neuroblastoma |
| N-Myc | Soft tissue sarcoma |
| NOD2 | Crohn's disease |
| CD5, IL15R | Hematologic malignancy |
| CD56 | Extranodal NK-T-cell lymphoma |
| CD56 | Recurrent nasopharyngeal carcinoma |
| CD59 | Age-related macular degeneration |
| CD59 | Geographic atrophy |
| CD7 | Juvenile idiopathic arthritis |
| CD7 | Mycosis fungoides |
| CD7 | Peripheral T-cell lymphoma |
| CD7 | Sezary syndrome |
| CD7 | Precursor T-cell lymphocytic leukemia/lymphoma |
| CD7 | Dermatomyositis |
| CD7 | Refractory T-cell lymphocytic/lymphoma |
| CD7 | Refractory T-cell acute lymphoblastic leukemia |
| CD7 | Immunoblastic lymphadenopathy |
| CD7 | Lymphoblastic lymphoma |
| CD7 | Ulcerative colitis |
| CD7 | Crohn's disease |
| CD7 | Extranodal NK-T-cell lymphoma |
| CD7 | Anaplastic large cell lymphoma |
| CD7 | Acute myeloid leukemia |
| CD7 | Acute lymphoblastic leukemia |
| CD7 | Hepatosplenic T-cell lymphoma |
| CD7 | Relapsed T-cell lymphoma |
| CD7 | Non-Hodgkin lymphoma |
| CD7 | Large granular lymphocytic leukemia |
| CD7 | Adult T-cell lymphoma/leukemia |
| NOS | Head and neck tumor |
| NOS | Prostate cancer |
| NOS | Liver cancer |

-continued

| Target site (gene) | Disease name |
|---|---|
| NOS | Pulmonary hypertension due to lung disease |
| NOS | Pulmonary arterial hypertension |
| NOS2 | Vascular restenosis |
| NOS2 | Pulmonary arterial hypertension |
| NOX | Chronic granulomatous disease |
| NOX1 | Chronic granulomatous disease |
| NPC1 | Niemann-Pick disease type C |
| NPRA | Tumor |
| NPRA | Immune system disorder |
| NPY receptor | Epilepsy |
| NR2E3 | Retinitis pigmentosa |
| NR2E3 | Leber congenital amaurosis |
| NR2F6 | Tumor |
| NR2F6 | Solid tumor |
| NR2F6 | Myelodysplastic syndrome |
| NR2F6 | Leukemia |
| NRARP | Wet age-related macular degeneration |
| NRARP | Wet macular degeneration |
| NRARP | Choroidal neovascularization |
| NRARP | Macular degeneration |
| NRAS | Tumor |
| NRAS | Hematologic malignancy |
| NRAS | Solid tumor |
| CD7 | Adult T-cell leukemia/lymphoma |
| CD7 | Enteropathy-associated T-cell lymphoma |
| CD7 | Enteropathy-associated T-cell lymphoma |
| CD7 | T-cell lymphocytic leukemia |
| CD7 | T-cell lymphoma |
| CD7 | T-cell lymphoma |
| CD7 | Recurrent T-cell acute lymphoblastic leukemia |
| CD7 | T-cell acute lymphoblastic leukemia/lymphoma |
| CD7 | T-cell acute lymphoblastic leukemia/lymphoma |
| CD7 | NK-cell lymphoma |
| CD7 | CD7-positive tumor |
| CD7 | CD7-positive acute myeloid leukemia |
| CD70 | Metastatic clear cell renal cell carcinoma |
| CD70 | Tumor metastasis |
| CD70 | Pancreatic adenocarcinoma |
| CD70 | Hematologic malignancy |
| CD70 | Advanced renal cell carcinoma |
| CD70 | Advanced solid malignant tumor |
| CD70 | Advanced cancer |
| CD70 | Esophageal cancer |
| CD70 | Solid tumor |
| CD70 | Solid tumor |
| CD70 | Renal cell carcinoma |
| CD70 | Urologic tumor |
| CD70 | Ovarian cancer |
| CD70 | Lymphoma |
| CD70 | Acute myeloid leukemia |
| CD70 | Acute myeloid leukemia |
| CD70 | Cervical cancer |
| CD70 | Non-Hodgkin lymphoma |
| CD70 | Non-Hodgkin lymphoma |
| Nrf2 | Nonalcoholic steatohepatitis |
| Nrf2 | Arteriosclerosis |
| NRP-1 | Tumor |
| NRP-2 | Metastatic melanoma |
| NRP-2 | Tumor metastasis |
| NRP-2 | Tumor |
| NRP-2 | Kidney tumor |
| NRTN | Ocular disease |
| NRTN | Parkinson's disease |
| NRTN | Huntington's disease |
| NT-4 | Motor neurone disease |
| NT-4 | Hearing impairment |

-continued

| Target site (gene) | Disease name |
|---|---|
| NT-4 | Diabetic retinopathy |
| NT-4 | Glaucoma |
| NT-4 | Uveitis |
| NT-4 | Parkinson's disease |
| NT-4 | Huntington's disease |
| NTCP | Liver disease |
| NTCP | Cholestasis |
| NTF3 | Charcot-Marie-Tooth Disease |
| Nucleic acids | Duchenne muscular dystrophy |
| NXNL1 | Cone-rod dystrophy |
| NXNL1 | Retinitis pigmentosa |
| NY-ESO-1 | Metastatic solid tumor |
| NY-ESO-1 | Tumor |
| NY-ESO-1 | Myxoid liposarcoma |
| NY-ESO-1 | Advanced solid malignant tumor |
| NY-ESO-1 | Esophageal squamous cell carcinoma |
| NY-ESO-1 | Esophageal cancer |
| NY-ESO-1 | Esophageal cancer |
| NY-ESO-1 | Solid tumor |
| CD70 | Malignant pleural mesothelioma |
| CD70 | Multiple myeloma |
| CD70 | T-cell lymphoma |
| CD70 | CD70-positive tumor |
| CD70 | CD70-positive female genitor tumor |
| CD70, IL-15, TGF-β | Renal cell carcinoma |
| CD70, IL15R | Advanced renal cell carcinoma |
| CD70, IL15R | Mesothelioma |
| CD70, IL15R | Osteosarcoma |
| CD72 | Acute lymphoblastic leukemia |
| CD74 | Alzheimer's disease |
| CD79B | Refractory B-cell acute lymphoblastic leukemia |
| CD79B | Acute lymphoblastic leukemia |
| CD79B | B-cell lymphoma |
| CD79B | B-cell lymphoma |
| CD8 | Advanced Head and neck tumor |
| CD8 | Head and neck tumor |
| CD80, CD86, PDL1 | Non-small cell lung cancer |
| CD80, GM-CSF | Tumor |
| CD80, IFNα, MIP-1α | Solid tumor |
| CD83 | Tumor |
| CD84 | Adult acute myeloid leukemia |
| CD86 | Glioma |
| CD86 | Melanoma |
| CD86, HPV E6, HPV E7, IL-12, IL-2 | Solid tumor |
| NY-ESO-1 | Solid tumor |
| NY-ESO-1 | Neuroblastoma |
| NY-ESO-1 | Triple-negative breast cancer |
| NY-ESO-1 | Soft tissue sarcoma |
| NY-ESO-1 | Breast cancer |
| NY-ESO-1 | Breast cancer |
| NY-ESO-1 | Sarcoma |
| NY-ESO-1 | Meningioma |
| NY-ESO-1 | Refractory ovarian cancer |
| NY-ESO-1 | Epithelial ovarian carcinoma |
| NY-ESO-1 | Ovarian cancer |
| NY-ESO-1 | Synovial sarcoma |
| NY-ESO-1 | Synovial sarcoma |
| NY-ESO-1 | Melanoma |
| NY-ESO-1 | Hepatocellular carcinoma |
| NY-ESO-1 | Liver cancer |
| NY-ESO-1 | Recurrent primary peritoneal cancer |
| NY-ESO-1 | Lung cancer |
| NY-ESO-1 | Non-small cell lung cancer |
| NY-ESO-1 | Multiple myeloma |
| NY-ESO-1 | Platinum-resistant fallopian tube cancer |

-continued

| Target site (gene) | Disease name |
|---|---|
| NY-ESO-1 | Platinum-resistant ovarian cancer |
| NY-ESO-1 | Platinum-sensitive primary peritoneal carcinoma |
| NY-ESO-1 | Platinum-sensitive fallopian tube cancer |
| NY-ESO-1 | Platinum-resistant primary peritoneal cancer |
| CD86, HPV E6, HPV E7, IL-12, IL-2 | HPV16-positive solid tumor |
| CD8A, NY-ESO-1 | Solid tumor |
| CD94 | Plasmacytic leukemia |
| CD99 | Hematologic malignancy |
| CD99 | Myeloid leukemia |
| CD99 | Sarcoma |
| CDA | Gastrointestinal tumor |
| CDA | Glioblastoma |
| CDA | High-grade glioma |
| CDA | Recurrent glioblastoma |
| CDCP1 | Pancreatic ductal adenocarcinoma |
| CDH17 | Metastatic colorectal cancer |
| CDH17 | Pancreatic cancer |
| CDH17 | Neuroendocrine tumor |
| CDH17 | Colorectal cancer |
| CDH5 | Diabetic retinopathy |
| CDKL5 | Neurological disorder |
| CDKL5 | X-linked genetic disease |
| CDKL5 | CDKL5 Deficiency |
| CDKN1A | Non-muscle invasive bladder tumor |
| CDKs | Tumor |
| CDKs | Sensorineural hearing loss |
| CEA | Tumor metastasis |
| CEA | Rectal cancer |
| CEA | Pancreatic acinar carcinoma |
| CEA | Pancreatic cancer |
| NY-ESO-1 | Urothelial bladder cancer |
| NY-ESO-1 | Bladder cancer |
| NY-ESO-1 | FGF19-positive solid tumor |
| NY-ESO-1, PD-1 | Myxoid liposarcoma |
| NY-ESO-1, PD-1 | Synovial sarcoma |
| NY-ESO-1, PD-1 | Melanoma |
| NY-ESO-1, PD-1 | Multiple myeloma |
| NY-ESO-1, PRAME, WT1 | Acute myeloid leukemia |
| NY-ESO-1, PRAME, WT1 | Acute lymphoblastic leukemia |
| NY-ESO-1, TCR | Solid tumor |
| NY-ESO-1, TGF-β | Myxoid liposarcoma |
| NY-ESO-1, TGF-β | Synovial sarcoma |
| OPA1 | Optic atrophy |
| OPA1 | Autosomal dominant optic atrophy |
| OPCML | Ovarian cancer |
| OTCase | Urea cycle disorder |
| OTCase | Ornithine transcarbamylase deficiency |
| OTOF | Hearing loss |
| OTOF | Deafness |
| OX40 | Metastatic colorectal cancer |
| OX40 | Gastrointestinal stromal tumor |
| OX40 | Gastric cancer |
| OX40 | Kidney tumor |
| OX40 | Breast cancer |
| OX40 | Sarcoma |
| OX40 | Squamous cell carcinoma |
| CEA | Gastric cancer |
| CEA | Advanced solid malignant tumor |
| CEA | Esophageal cancer |
| CEA | Oligodendroglioma |
| CEA | Breast cancer |
| CEA | Ovarian cancer |
| CEA | Colorectal cancer |
| CEA | Colorectal cancer |
| CEA | Colon cancer |
| CEA | Colon cancer |
| CEA | Liver metastasis |
| CEA | Liver cancer |
| CEA | Peritoneal cancer |
| CEA | Recurrent cancer |
| CEA | Lung cancer |
| CEA | Cholangiocarcinoma |
| CEA | Biliary tract tumor |
| CEA, IL-15Rα, IL-21R | Colorectal cancer |
| CEACAM5 | Pancreatic acinar carcinoma |
| CEACAM5 | Pancreatic adenocarcinoma |
| CEACAM5 | Pancreatic cancer |
| CEACAM5 | Adenocarcinoma |
| CEACAM5 | Gastric cancer |
| CEACAM5 | Gastric cancer |
| CEACAM5 | Breast cancer |
| CEACAM5 | Breast cancer |
| CEACAM5 | Ovarian cancer |
| CEACAM5 | Squamous non-small cell lung cancer |
| CEACAM5 | Colorectal cancer |
| CEACAM5 | Colorectal cancer |
| CEACAM5 | Liver metastasis |
| CEACAM5 | Liver cancer |
| CEACAM5 | Lung cancer |
| CEACAM5 | Malignant ascites |
| CEACAM5, CEACAM6 | Tumor |
| OX40 | Colorectal cancer liver metastasis |
| OX40 | Melanoma |
| OX40 | Liver metastasis |
| OX40 | Abdominal tumor |
| OX40L | Lymphoma |
| p24 antigen | HIV infection |
| p53 | Delayed recovery of graft function |
| p53 | Transplant complication |
| p53 | Pancreatic cancer |
| p53 | Small lymphocytic lymphoma |
| p53 | Advanced solid malignant tumor |
| p53 | Advanced bile duct cancer |
| p53 | Head and neck tumor |
| p53 | Fallopian tube cancer |
| p53 | Leukoplakia |
| p53 | Chronic lymphocytic leukemia |
| p53 | Ovarian cancer |
| p53 | Glioblastoma |
| p53 | Acute myeloid leukemia |
| p53 | Acute kidney injury |
| p53 | Myelodysplastic syndrome |
| p53 | Liver cancer |
| p53 | Peritoneal cancer |
| p53 | Non-small cell lung cancer |
| p53 | Malignant ascites |
| p53 | Nasopharyngeal carcinoma |
| p53 | Bladder cancer |
| p53 | Vitiligo |
| p53 R175H | Metastatic solid tumor |
| p53 R175H | Pancreatic adenocarcinoma |
| p53 R175H | Head and Neck Squamous Cell Carcinoma |
| p53 R175H | Breast cancer |
| p53 R175H | Colorectal cancer |
| p53 R175H | Non-small cell lung cancer |
| p75NTR | Alzheimer's disease |
| CEACAM7 | Pancreatic cancer |
| CEBPA | Hepatitis B |
| CEBPA | Hepatocellular carcinoma |
| CEBPA | Liver cancer |
| CEBPA | Hepatitis C |
| CEBPB | Breast cancer |
| CEBPB | Melanoma |
| CEBPB | Hepatocellular carcinoma |

-continued

| Target site (gene) | Disease name |
|---|---|
| CEBPB | Bladder cancer |
| Cell adhesion molecules, NF-κB, eIF5A | Mantle cell lymphoma |
| Cell adhesion molecules, NF-κB, eIF5A | Diffuse large B-cell lymphoma |
| Cell adhesion molecules, NF-κB, eIF5A | Plasma cell leukemia |
| Cell adhesion molecules, NF-κB, eIF5A | Relapsed mantle cell lymphoma |
| Cell adhesion molecules, NF-κB, eIF5A | Relapsed diffuse large B-cell lymphoma |
| Cell adhesion molecules, NF-κB, eIF5A | Relapsed Multiple myeloma |
| Cell adhesion molecules, NF-κB, eIF5A | Relapsed B-cell lymphoma |
| PA protein, influenza virus M1 | Influenza virus infection |
| PABPN1 | Oculopharyngeal muscular dystrophy |
| PABPN1 | Swallowing disorders |
| PAH | Phenylketonuria |
| PAI-1, tPA, vWF | Thrombotic microangiopathy |
| PAI-1, tPA, vWF | Novel Coronavirus Infection |
| PAI-1, tPA, vWF | Veno-occlusive disease |
| PAI-1, tPA, vWF | High-risk neuroblastoma |
| PAI-1, tPA, vWF | Hepatic veno-occlusive disease |
| PAK4 | Non-muscle invasive bladder tumor |
| PAK4 | Bladder cancer |
| PARP | Tumor |
| PARP | Solid tumor |
| PARP1 | Tumor |
| PAX4 | Type 1 diabetes |
| PBGD | Acute intermittent porphyria |
| Cell adhesion molecules, NF-κB, eIF5A | Multiple myeloma |
| Cep290 | Retinal Degenerative Disease |
| Cep290 | Leber congenital amaurosis type 10 |
| Cep290, nuclease Cas9 | Hereditary retinal dystrophy |
| Cep290, nuclease Cas9 | Eye deformities |
| Cep290, nuclease Cas9 | Retinal degeneration |
| Cep290, nuclease Cas9 | Visual impairment |
| CFB | Age-related macular degeneration |
| CFB | Immune system disorders |
| CFB | Immunoglobulin A nephropathy |
| CFB | Geographic atrophy |
| CFH | Macular degeneration |
| CFI | Sagging skin |
| CFI | Age-related macular degeneration |
| CFI | Macular degeneration |
| CFI | Dry age-related macular degeneration |
| CFI | Geographic atrophy |
| CFI | Glycogen storage disease type II |
| CFLAR | Tumor |

-continued

| Target site (gene) | Disease name |
|---|---|
| CFTR | Retinal disease |
| CFTR | Cystic fibrosis |
| cGMP-PDE | Retinitis pigmentosa |
| PCSK9 | Lipid metabolism disorder |
| PCSK9 | Heterozygous familial hypercholesterolemia |
| PCSK9 | Primary hypercholesterolemia |
| PCSK9 | Hereditary Leiomyomatosis and Renal Cell Carcinoma |
| PCSK9 | Peripheral arterial disease |
| PCSK9 | Stroke |
| PCSK9 | Familial combined hyperlipidemia |
| PCSK9 | Coronary artery disease |
| PCSK9 | Hyperlipidemia |
| PCSK9 | hypertension |
| PCSK9 | Hypercholesterolemia |
| PCSK9 | Liver disease |
| PCSK9 | Atherosclerosis |
| PCSK9 | Homozygous familial hypercholesterolemia |
| PCSK9 | Type IIa hyperlipoproteinemia |
| PD-1 | Metastatic melanoma |
| PD-1 | Metastatic non-small cell lung cancer |
| PD-1 | Advanced non-small cell lung cancer |
| PD-1 | Advanced solid malignant tumor |
| PD-1 | Esophageal cancer |
| PD-1 | Triple-negative breast cancer |
| PD-1 | Skin tumor |
| Chk1 | Brain metastases |
| Chk1 | Glioblastoma |
| chloride channel | Cystic fibrosis |
| CHOP | Diabetic nephropathy |
| CHST15 | Ulcerative colitis |
| CHST15 | Crohn's disease |
| chymase | Heart failure |
| CIDEB | Nonalcoholic steatohepatitis |
| CISH | Gastrointestinal tumor |
| CISH, IL-15 | Hematologic malignancy |
| CISH, IL-15 | Solid tumor |
| CISH, TGFBR2 | Solid tumor |
| c-Jun | Basal cell carcinoma |
| c-Jun | Melanoma |
| c-Kit | Myocardial ischemia |
| c-Kit | Systemic mastocytosis |
| c-Kit | allergy |
| CLCN7 | Autosomal dominant osteopetrosis type II |
| CLDN18.2 | Autoimmune disease |
| CLDN18.2 | Pancreatic cancer |
| CLDN18.2 | Gastric adenocarcinoma |
| CLDN18.2 | Gastroesophageal junction adenocarcinoma |
| CLDN18.2 | Gastrointestinal tumor |
| CLDN18.2 | Gastric cancer |
| CLDN18.2 | Advanced solid malignant tumor |
| CLDN18.2 | Solid tumor |
| CLDN18.2 | Ovarian epithelial carcinoma |
| CLDN18.2 | Ovarian cancer |
| CLDN18.2 | Advanced gastric adenocarcinoma |
| CLDN18.2 | CLDN18.2-positive pancreatic cancer |
| PD-1 | Squamous cell carcinoma of the skin |
| PD-1 | Skin melanoma |
| PD-1 | Brain metastases |
| PD-1 | Refractory cancer |
| PD-1 | Urinary system tumor |
| PD-1 | Merkel cell carcinoma |
| PD-1 | Ovarian cancer |
| PD-1 | Colorectal cancer |

-continued

| Target site (gene) | Disease name |
|---|---|
| PD-1 | Glioma |
| PD-1 | Mesothelioma |
| PD-1 | Melanoma |
| PD-1 | Hepatocellular carcinoma |
| PD-1 | Non-small cell lung cancer stage III |
| PD-1 | Non-small cell lung cancer |
| PD-1 | Glioblastoma multiforme |
| PD-1 | Unresectable melanoma |
| PD-1 | Mesothelin-positive tumor |
| PD-1 | Mesothelin-positive solid tumor |
| PD-1 | IV Malignant Non-Small Cell Lung Tumor |
| PD-1 | Stage III colon cancer |
| PD-1 | Stage IIA non-small cell lung cancer |
| PD-1 | Carney complex |
| PD-1, PSCA, PSMA | Prostate cancer |
| PDCD5 | Leukemia |
| PDE4B, PDE4D, PDE7A | Chronic obstructive pulmonary disease |
| PDGFB | diabetic foot |
| PDGFB, VEGFR | Macular degeneration |
| PDGFR | Tumor |
| PDGFR | Ocular disease |
| PDGFR | Fibrosis |
| CLDN18.2 | CLDN18.2-positive gastroesophageal junction adenocarcinoma |
| CLDN18.2 | CLDN18.2-positive gastrointestinal tumor |
| CLDN18.2, CXCR4 | Pancreatic ductal adenocarcinoma |
| CLDN18.2, GluN2B, NAMPT, NKG2D, NMDA receptor | Pancreatic cancer |
| CLDN18.2, GluN2B, NAMPT, NKG2D, NMDA receptor | Gastric cancer |
| CLDN18.2, GluN2B, NAMPT, NKG2D, NMDA receptor | NKG2DL-positive solid tumor |
| CLDN18.2, GluN2B, NAMPT, NKG2D, NMDA receptor | CLDN18.2-positive solid tumor |
| CLDN18.2, IL-15 | Pancreatic cancer |
| CLDN18.2, IL-15 | Melanoma |
| CLDN18.2, PD-1 | Gastric cancer |
| CLDN18.2, PDL1 | CLDN18.2-positive solid tumor |
| CLDN6 | Solid tumor |
| CLDN6 | Ovarian cancer |
| CLDN6 | Testicular tumor |
| CLEC4K | Langerhans cell histiocytosis |
| CLL-1 | Chronic lymphocytic leukemia |
| CLL-1 | Acute myeloid leukemia |
| PDGFR | Hippel-Lindau syndrome |

-continued

| Target site (gene) | Disease name |
|---|---|
| PDGFR | Retinoblastoma |
| PDGFR | Wet age-related macular degeneration |
| PDGFR | Wet macular degeneration |
| PDGFR | Macular degeneration |
| PDGFR, VEGFR1 | Wet age-related macular Degeneration |
| PDGFRα | Glioma |
| PDGFRβ | Cirrhosis |
| PDHK1 | Allergic conjunctivitis |
| PDL1 | Autoimmune hepatitis |
| PDL1 | Metastatic head and neck squamous cell carcinoma |
| PDL1 | Tumor metastasis |
| PDL1 | Tumor |
| PDL1 | Hepatitis B |
| PDL1 | Graft-versus-host disease |
| PDL1 | Pancreatic ductal adenocarcinoma |
| PDL1 | Pancreatic cancer |
| CLL-1 | Relapsed acute myeloid leukemia |
| CLN3 | Neuronal ceroid lipofuscinosis |
| CLN5 | Neuronal ceroid lipofuscinosis 5 |
| CLN6 | Neuronal ceroid lipofuscinosis |
| CLN8 | Neuronal ceroid lipofuscinosis |
| CLRN1 | Usher syndrome |
| CLU | Metastatic castration-resistant prostate cancer |
| CLU | Metastatic non-small cell lung cancer |
| CLU | Pain |
| CLU | Castration-resistant prostate cancer |
| CLU | Non-small cell lung cancer |
| c-Met | Foot ulcer |
| c-Met | Perioperative ischemia |
| c-Met | Solid tumor |
| c-Met | Ulcer |
| c-Met | Cirrhosis |
| c-Met | Atherosclerosis obliterans |
| c-Met | Hyperlipoproteinemia type I |
| CMV IE2 | Cytomegalovirus retinitis |
| CMV IE2 | Cytomegalovirus infection |
| CMV IE2 | HIV infection |
| CMV pp65, LAMP-1 | Glioblastoma |
| CMV protein | Adenoviridae Infections |
| CMV protein | Organ transplant rejection |
| CMV protein | Cytomegalovirus infection |
| PDL1 | Gastric cancer |
| PDL1 | Triple-negative breast cancer |
| PDL1 | Ovarian epithelial carcinoma |
| PDL1 | Locally advanced malignant solid tumor |
| PDL1 | Glioblastoma |
| PDL1 | Hodgkin lymphoma |
| PDL1 | Melanoma |
| PDL1 | Peritoneal cancer |
| PDL1 | Recurrent squamous cell carcinoma of the head and neck |
| PDL1, TLR9 | Tumor |
| PDL1, VEGFR1 | Tumor |
| PDL1, VEGFR1 | Malignant ascites |
| PECAM1 | Solid tumor |
| PECAM1 | Lung damage |
| PEDF | Retinitis pigmentosa |

-continued

| Target site (gene) | Disease name |
|---|---|
| PfCSP | Plasmodium falciparum |
| PGF, VEGF-A, VEGF-B, VEGF-C | Diabetic macular edema |
| PGF, VEGF-A, VEGF-B, VEGF-C | Wet age-related macular degeneration |
| P-gp | Breast cancer |
| P-gp | Non-Hodgkin lymphoma |
| P-gp | Bladder cancer |
| PGRN | Frontotemporal dementia |
| PhD2 | Anemia |
| PhD2 | Acute kidney injury |
| Phospho-transferases | Restenosis |
| CMV protein | Polyomavirus infection |
| CMV protein | Epstein-Barr virus infection |
| CMV protein, EBV protein | Infect |
| c-Myc | Reperfusion injury |
| c-Myc | Primitive neuroectodermal tumor |
| c-Myc | Islet cell adenoma |
| c-Myc | Solid tumor |
| c-Myc | Lymphoma |
| c-Myc | Colorectal cancer |
| c-Myc | Huntington's disease |
| c-Myc | Coronary artery restenosis |
| c-Myc | Hepatocellular carcinoma |
| c-Myc | Non-small cell lung cancer |
| c-Myc | Non-Hodgkin lymphoma |
| c-Myc | Multiple myeloma |
| c-Myc | C-Myc positive solid tumor |
| CNGA3 | Color vision impairment |
| CNGA3 | Achromatopsia type 1 |
| CNGB1 | Retinitis pigmentosa |
| CNGB3 | Color vision impairment |
| CNGB3 | Color vision impairment |
| CNGB3 | Achromatopsia type 1 |
| CNTF | Retinitis pigmentosa |
| CNTFR | Autism Spectrum Disorders |
| CNTFR | Autism |
| CNTFR | Peripheral nerve damage |
| CNTFR | Retinitis pigmentosa |
| CNTFR | Retinal telangiectasia |
| Phospho-transferases, p38α | Tumor |
| Phospho-transferases, p38α | Restenosis |
| PI3K family, mTORC1, mTORC2 | Solid tumor |
| PI3Kα | Tumor |
| PI3Kα H1047R | Tumor |
| PI3Kα H1047R | Advanced breast cancer |
| PI3Kα H1047R | Advanced solid malignant tumor |
| PI3Kα H1047R | Advanced cancer |
| PI3Kα H1047R | Breast cancer |
| PIGF, VEGF-A, VEGF-B | Wet macular degeneration |
| PIKFYVE | Amyotrophic lateral sclerosis |
| PIKFYVE | Frontotemporal dementia |
| PIWIL1 | Pancreatic cancer |
| PIWIL1 | Gastrointestinal tumor |
| PIWIL1 | Colorectal cancer |
| PKA | Tumor |
| PKA | Solid tumor |
| PKA | Breast cancer |
| PKA | Ovarian cancer |
| PKA | Colon cancer |
| PKA | Lung cancer |
| PKCα | Lung cancer |
| PKCα | Non-small cell lung cancer |
| PKLR | Erythrocyte pyruvate kinase deficiency |

-continued

| Target site (gene) | Disease name |
|---|---|
| PKN3 | Pancreatic cancer |
| PKN3 | Advanced solid malignant tumor |
| PKN3 | Head and neck tumor |
| PLA2 | Tumor |
| CNTFR | Optic nerve disease |
| CNTFR | Color vision impairment |
| CNTFR | Glaucoma |
| CNTFR | Parkinson's disease |
| CNTFR | Acute lung injury |
| CNTFR | Amyotrophic lateral sclerosis |
| CNTFR | Huntington's disease |
| CNTFR | Multiple sclerosis |
| CNTFR | Geographic atrophy |
| CNTFR | Usher syndrome |
| Coagulation factor | Coagulation disorder |
| COL1A1 | Skin aging |
| COL3A1 | Ehlers-Danlos syndrome |
| COL3A1, elastin | Skin disorders |
| COL5A1 | Ehlers-Danlos syndrome |
| COL6A3 | Solid tumor |
| COL7A1 | Dystrophic epidermolysis bullosa |
| COL7A1 | Graft-versus-host disease |
| COL7A1 | Burn |
| COL7A1 exon 80 | Epidermolysis bullosa |
| Collagen | Dystrophic epidermolysis bullosa |
| Collagen | Penile edema |
| Collagen | Lower limb ulcers |
| Collagen | Knee Injury |
| Collagen | Tennis elbow |
| Collagen | Cartilage disease |
| Collagen | Tendon injuries |
| Collagen | Tendinopathy |
| Collagen | Osteoarthritis |
| Collagen | Epidermolysis bullosa |
| COP1 | Hepatocellular carcinoma |
| PLA2G6 | Neuroaxonal dystrophy |
| PLA2R | Membranous Glomerulonephritis |
| plakophilin-2 | Arrhythmic right ventricular dysplasia |
| plakophilin-2 | Myocardial disease |
| PLK1 | Advanced hepatocellular carcinoma |
| PLK1 | Advanced solid malignant tumor |
| PLK1 | Adrenal cortical carcinoma |
| PLK1 | Neuroendocrine tumor |
| PLK1 | Lymphoma |
| PLK1 | Hepatocellular carcinoma |
| PLK4 | Solid tumor |
| PLK4 | Breast cancer |
| PLP1 | Pelizaeus-Merzbacher disease |
| PMP22 | Charcot-Marie-Tooth Disease Type Ia |
| PMVK | Pancreatic cancer |
| PMVK | Non-small cell lung cancer |
| PNP | Pharyngeal tumor |
| PNP | Advanced Head and neck tumor |
| PNP | Head and neck tumor |
| PNP | Prostate cancer |
| PNP | Squamous cell carcinoma |
| PNPLA3 | Fatty liver |
| PNPLA3 | Cardiovascular disease |
| PNPLA3 | Fibrosis |
| PNPLA3 | hepatitis |
| PNPLA3 | Nonalcoholic steatohepatitis |
| PNPLA3 | Metabolic disease |
| PNPLA3 | Metabolic fatty liver disease |
| POSTN | Diabetic retinopathy |
| Potassium channel | Urge incontinence |
| Potassium channel | Overactive bladder |
| COPS5, WEE1 | Hepatitis B |

-continued

| Target site (gene) | Disease name |
|---|---|
| COX-2 | Prostate cancer |
| COX-2 | Basal cell carcinoma |
| COX-2, PGE2 | Colon cancer |
| COX-2, PGE2 | Liver cancer |
| COX-2, TGF-β1 | Carcinoma in situ |
| COX-2, TGF-β1 | Primary sclerosing cholangitis |
| COX-2, TGF-β1 | Solid tumor |
| COX-2, TGF-β1 | Breast cancer |
| COX-2, TGF-β1 | Prostate cancer |
| COX-2, TGF-β1 | Hypertrophic scars of the skin |
| COX-2, TGF-β1 | Squamous cell carcinoma of the skin |
| COX-2, TGF-β1 | Local obesity |
| COX-2, TGF-β1 | Basal cell carcinoma |
| COX-2, TGF-β1 | Liver metastasis |
| COX-2, TGF-β1 | Cirrhosis |
| COX-2, TGF-β1 | Hepatocellular carcinoma |
| COX-2, TGF-β1 | Obesity |
| COX-2, TGF-β1 | Cholangiocarcinoma |
| COX-2, TGF-β1 | Keloid |
| CRAF | Tumor |
| CRAF | Pancreatic cancer |
| CRAF | Small cell lung cancer |
| PPAR | Acne vulgaris |
| PPT1 | Neuronal ceroid lipofuscinosis |
| PR1 | Acute myeloid leukemia in adults |
| PRAME | Endometrial cancer |
| PRAME | Tumor |
| PRAME | Head and neck tumor |
| PRAME | Solid tumor |
| PRAME | Uveal melanoma |
| PRAME | Skin melanoma |
| PRAME | Ovarian cancer |
| PRAME | Acute myeloid leukemia |
| PRAME | Synovial sarcoma |
| PRAME | Melanoma |
| PRAME | Myelodysplastic syndrome |
| PRAME | Myelodysplastic syndrome |
| PRAME | Non-small cell lung cancer |
| PRAME, WT1 | Prostate cancer |
| PRAME, WT1, cyclin A1 | Acute myeloid leukemia |
| PRAME, WT1, cyclin A1 | Myelodysplastic syndrome |
| PRDM2 | Prostate cancer |
| PRDM2 | Liver cancer |
| PRDM2 | Non-small cell lung cancer |
| PRG4 | Osteoarthritis |
| CRAF | Diabetic macular edema |
| CRAF | Solid tumor |
| CRAF | Renal cell carcinoma |
| CRAF | Breast cancer |
| CRAF | Prostate cancer |
| CRAF | Ovarian cancer |
| CRAF | Colorectal cancer |
| CRAF | Macular degeneration |
| CRAF | Non-small cell lung cancer |
| CRP | Inflammation |
| CRP | Atrial fibrillation |
| CRP | Kidney disease |
| CRP | Rheumatoid arthritis |
| CRP | Crohn's disease |
| CRX | Cone-rod dystrophy |
| CRX | Retinitis pigmentosa |
| CRX | Retinal disease |
| CRX | Leber congenital amaurosis |
| CSF-2R | Metastatic solid tumor |
| CSF-2R | Metastatic breast cancer |
| CSF-2R | Metastatic biliary tract cancer |
| CSF-2R | Tumor |
| CSF-2R | Central nervous system tumor |
| CSF-2R | Mucinous adenocarcinoma |
| CSF-2R | Ewing sarcoma |
| CSF-2R | Signet ring cell carcinoma |
| CSF-2R | Secondary malignant tumor of the pancreas |
| CSF-2R | Mycosis fungoides |

-continued

| Target site (gene) | Disease name |
|---|---|
| CSF-2R | Eccrine sweat gland pore carcinoma |
| CSF-2R | Gastric cancer |
| CSF-2R | Microcystic adnexal carcinoma |
| CSF-2R | Advanced colorectal adenocarcinoma |
| PRNP | Prion disease |
| Protein kinases | Tumor |
| PRPF31 | Retinal degenerative disease associated with biallelic RPE65 mutations |
| PRPF31 | Retinitis pigmentosa type 11 |
| PSCA | Esophageal adenocarcinoma |
| PSCA | Bladder cancer |
| P-sel | Sickle cell disease |
| PSMA | Autoimmune disease |
| PSMA | Metastatic castration-resistant prostate cancer |
| PSMA | Tumor |
| PSMA | Mucoepidermoid carcinoma |
| PSMA | Adenoid cystic carcinoma |
| PSMA | Acinar cell carcinoma |
| PSMA | Salivary gland cancer |
| PSMA | Salivary gland tumor |
| PSMA | Renal cell carcinoma |
| PSMA | Breast cancer |
| PSMA | Castration-resistant prostate cancer |
| PSMA | Castration-resistant prostate cancer |
| PSMA | Prostate cancer |
| PSMA | Prostate cancer |
| PSMA | Colorectal cancer |
| PSMA | Non-small cell lung cancer |
| PSMA | Multiple myeloma |
| PSMA | Ductal carcinoma |
| PSMA | PSMA-positive tumor |
| PSMA, TCRDV2 | Metastatic castration-resistant prostate cancer |
| PSMA, TGF-β | Castration-resistant prostate cancer |
| PSMA, TGF-β | Prostate cancer |
| PSMA, Trop-2 | Prostate cancer |
| PTEN | Severe Acute Respiratory Syndrome |
| PTEN | Spinal cord injury |
| CSF-2R | Vulvar squamous cell carcinoma |
| CSF-2R | Head and neck tumor |
| CSF-2R | Retinoblastoma |
| CSF-2R | Esophageal cancer |
| CSF-2R | Solid tumor |
| CSF-2R | Wilms tumor |
| CSF-2R | Neuroblastoma |
| CSF-2R | Sezary syndrome |
| CSF-2R | Extramammary Paget's disease |
| CSF-2R | Ductal carcinoma |
| CSF-2R | Papillary adenocarcinoma |
| CSF-2R | Prostate cancer |
| CSF-2R | Sebaceous adenoma |
| CSF-2R | Skin tumor |
| CSF-2R | Squamous cell carcinoma of the skin |
| CSF-2R | Skin melanoma |
| CSF-2R | Skin adnexal cancer |
| CSF-2R | Brain malignant glioma |
| CSF-2R | Refractory lymphoma |
| CSF-2R | Refractory anaplastic large cell lymphoma |
| CSF-2R | Refractory T-cell lymphoma |
| CSF-2R | Merkel cell carcinoma |
| CSF-2R | Helical adenocarcinoma |
| CSF-2R | Lymphoma |
| CSF-2R | Locally advanced soft tissue |

-continued

| Target site (gene) | Disease name |
|---|---|
| | sarcoma |
| CSF-2R | Locally advanced bladder cancer |
| CSF-2R | Invasive breast cancer |
| CSF-2R | Colorectal cancer liver metastasis |
| CSF-2R | Colorectal cancer |
| CSF-2R | Keratoacanthoma |
| CSF-2R | Glioblastoma |
| CSF-2R | Mesothelioma |
| CSF-2R | Basal cell carcinoma |
| PTEN | Acute spinal cord injury |
| PTH | Postmenopausal osteoporosis |
| PTK7 | Colorectal cancer |
| PTP1B | obesity |
| PTP1B | Type 2 diabetes |
| PYK2 | Ovarian cancer |
| PYK2 | Colorectal cancer |
| PYK2 | Thyroid cancer |
| Raf kinase | Head and neck tumor |
| Raf kinase | Breast cancer |
| RAG-1 | Glioblastoma |
| RANGRF | Brugada syndrome |
| Ras | Tumor |
| Ras | Tumor |
| Ras | Pancreatic acinar carcinoma |
| Ras | Secondary malignant tumor of the pancreas |
| Ras | Advanced colorectal adenocarcinoma |
| Ras | Solid tumor |
| Ras | Breast cancer |
| Ras | Locally advanced pancreatic adenocarcinoma |
| Ras | Colorectal cancer |
| Ras | Recurrent colorectal cancer |
| Ras | Non-small cell lung cancer |
| RB1 | Pancreatic cancer |
| RB1 | Head and neck tumor |
| RB1 | Mesothelioma |
| RB1 | Lung cancer |
| RDH12 | Leber congenital amaurosis |
| RdRp | Novel Coronavirus Infection |
| Redd1 | Diabetic macular edema |
| Redd1 | Macular degeneration |
| regnase-1 | Fibrosis |
| regnase-1 | Adult respiratory distress syndrome |
| CSF-2R | Basal squamous cell carcinoma |
| CSF-2R | Muscle-Invasive Bladder Cancer |
| CSF-2R | Rhabdomyosarcoma |
| CSF-2R | Melanoma |
| CSF-2R | Sweat gland tumor |
| CSF-2R | Hepatocellular carcinoma |
| CSF-2R | Liver cancer |
| CSF-2R | Recurrent breast cancer |
| CSF-2R | Relapsed T-cell lymphoma |
| CSF-2R | Recurrent HER2-negative breast cancer |
| CSF-2R | Relapsed peripheral T-cell lymphoma |
| CSF-2R | Non-muscle invasive bladder tumor |
| CSF-2R | Malignant cylindrical tumor |
| CSF-2R | Malignant solid tumor |
| CSF-2R | Ductal carcinoma |
| CSF-2R | Unresectable melanoma |
| CSF-2R | Bladder metastases |
| CSF-2R | Bladder cancer |
| CSF-2R | NK cell lymphoma |
| CSF-2R, CTLA4 | Tumor |
| CSF-2R, CTLA4, GALV-GP | Microsatellite stable colorectal cancer |
| R-CSF-2R, CTLA4, GALV-GP | Solid tumor |
| R-CSF-2R, | Solid tumor |

-continued

| Target site (gene) | Disease name |
|---|---|
| GALV-GP | |
| R-CSF-2R, GALV-GP | Triple-negative breast cancer |
| R-CSF-2R, GALV-GP | Squamous cell carcinoma of the skin |
| R-CSF-2R, GALV-GP R- | Skin melanoma |
| RELA | Rheumatoid arthritis |
| RELA | Osteoarthritis |
| renin receptor | Diabetic retinopathy |
| renin receptor | Uveitis |
| renin receptor | Macular degeneration |
| REP1 | Choroideremia |
| REP1 | Retinal dysplasia |
| REP1 | X-linked retinitis pigmentosa |
| REV | HIV infection |
| RHO | Retinitis pigmentosa type 4 |
| RHO | Retinitis pigmentosa |
| RHO | Color vision impairment |
| RHO | Macular degeneration |
| RHO | Geographic atrophy |
| RHOK | Retinal disease |
| RIG-I | Tumor |
| RIG-I | Melanoma |
| RIG-I | Coronavirus infection |
| RIG-I, TLR3 | Viral infection |
| RLBP1 | Retinitis pigmentosa |
| RNAP | Hepatitis B |
| RNA binding proteins | Metastatic breast cancer |
| RNR | Metastatic solid tumor |
| RNR | Tumor |
| RNR | Rectal cancer |
| RNR | Primitive neuroectodermal tumor |
| CSF-2R, GALV-GP | Melanoma |
| R-CSF-2R, GALV-GP | Non-small cell lung cancer |
| R-CSF-2R, GALV-GP | MSI-H cancer |
| R-CSF-2R, PDL1 | Solid tumor |
| CSF-3R | Neutropenia |
| CSF-3R | Cytokine Release Syndrome |
| CSF-3R | Knee arthritis |
| CSF-3R | Advanced solid malignant tumor |
| CSF-3R | Community-acquired pneumonia |
| CSF-3R | Sepsis |
| CSF-3R | Urinary tract infection |
| CSF-3R | Mesothelioma |
| CSF-3R | Acute cholecystitis |
| CSF-3R | Abdominal infection |
| CSF-3R | Secondary malignant tumor of peritoneum |
| CSF-3R | Peritoneal cancer |
| CSF-3R | cholangitis |
| CTCFL | Breast cancer |
| CTGF | Head and neck tumor |
| CTGF | Idiopathic pulmonary fibrosis |
| CTGF | Hypertrophic scars of the skin |
| CTGF | Ovarian cancer |
| CTGF | Melanoma |
| CTGF | Cirrhosis |
| CTGF | Trauma and Injury |
| CTGF | Scar |
| CTGF, NF-κB | Duchenne muscular dystrophy |
| RNR | Solid tumor |
| RNR | Kidney tumor |
| RNR | Renal cell carcinoma |
| RNR | Breast cancer |
| RNR | Prostate cancer |
| RNR | Prostate cancer |
| RNR | Refractory undifferentiated acute leukemia |
| RNR | Supratentorial tumor |

-continued

| Target site (gene) | Disease name |
|---|---|
| RNR | Chronic myeloid leukemia |
| RNR | Lymphoma |
| RNR | Locally advanced non-small cell lung cancer |
| RNR | Colorectal cancer |
| RNR | Glioblastoma |
| RNR | Secondary myelodysplastic syndrome |
| RNR | Chronic myeloid leukemia in acute transformation |
| RNR | Acute promyelocytic leukemia |
| RNR | Acute leukemia |
| RNR | Myelodysplastic syndrome |
| RNR | Recurrent prostate cancer |
| RNR | Recurrent colon cancer |
| RNR | Relapsed acute myeloid leukemia |
| RNR | Recurrent non-small cell lung cancer |
| RNR | Relapsed adult acute lymphoblastic leukemia |
| RNR | Non-small cell lung cancer stage IIIB |
| RNR | Non-small cell lung cancer stage IIIA |
| RNR | Non-small cell lung cancer |
| RNR | Acute myeloid leukemia in adults |
| CTLA4 | Tumor |
| CTLA4 | Sjögren's syndrome |
| CTLA4, FLT3, IL-12R | Solid tumor |
| CTLA4, IL-12 | Metastatic non-small cell lung cancer |
| CTLA4, MSLN, PD-1 | Solid tumor |
| CTLA4, PD-1 | Advanced solid malignant tumor |
| CTLA4, PD-1 | Colon cancer |
| CTLA4, STAT3 | Tumor |
| CTNNB1 | Tumor |
| CTNNB1 | Type 2 diabetes |
| CTNS | Cystinosis |
| CXCR2, GPC3 | Liver cancer |
| CXCR3, IL-12, TGF-β | Tumor |
| CXCR4 | Primary myelofibrosis |
| CXCR4 | Heart failure |
| CXCR4 | Perioperative ischemia |
| CXCR4 | Peripheral arterial disease |
| CXCR4 | Surgical wound |
| CXCR4 | Myelofibrosis |
| CXCR5, EGFR | Non-small cell lung cancer |
| CYB5R3 | Tumor |
| CYBB | Chronic granulomatous disease |
| Cyclin G1 | Pancreatic cancer |
| Cyclin G1 | Solid tumor |
| Cyclin G1 | Breast cancer |
| Cyclin G1 | Sarcoma |
| Cyclin G1 | Colorectal cancer |
| RNR | Adult acute lymphoblastic leukemia |
| RNR | Bladder cancer |
| RNR | Acute myeloid leukemia with 11q23 abnormalities |
| RNR | IV malignant non-small cell lung tumor |
| ROBO1 | Tumor |
| ROBO1 | Pancreatic cancer |
| ROBO1 | Solid tumor |
| ROCK | Tumor |
| ROCK | Retinitis pigmentosa |
| ROCK | Corneal edema |
| ROCK | Corneal endotheliitis |
| ROCK | Bullous keratopathy |
| ROCK | Fuchs endothelial dystrophy |
| ROR1 | Metastatic non-small cell lung |

-continued

| Target site (gene) | Disease name |
|---|---|
| | cancer |
| ROR1 | Hematologic malignancy |
| ROR1 | Advanced breast cancer |
| ROR1 | Mantle cell lymphoma |
| ROR1 | Solid tumor |
| ROR1 | Triple-negative breast cancer |
| ROR1 | Breast cancer |
| ROR1 | Breast cancer |
| ROR1 | Refractory malignant solid tumor |
| ROR1 | Diffuse large B-cell lymphoma |
| ROR1 | Chronic lymphocytic leukemia |
| ROR1 | Ovarian cancer |
| ROR1 | Acute lymphoblastic leukemia |
| ROR1 | Recurrent breast cancer |
| Cyclin G1 | Osteosarcoma |
| CYP21A2 | Congenital adrenal hyperplasia |
| CYP27A1 | Cerebrotendinous xanthomatosis |
| CYP3A4 | Tumor |
| CYP4V2 | Retinal degeneration |
| CYP4V2 | Bietti crystal dystrophy |
| CYPs | Pancreatic cancer |
| CYPs | Colorectal cancer |
| Cytokines | Sarcoma |
| Cytokines | Melanoma |
| Cytokines | Malignant solid tumor |
| C-type lectin domain protein | Testicular tumor |
| DAF | Macular degeneration |
| DAF, ICAM-1 | Solid tumor |
| DAF, ICAM-1 | Non-small cell lung cancer |
| DAG1 | Muscular dystrophy |
| DAG1 | Duchenne muscular dystrophy |
| DAT | Parkinson's disease |
| DDC | Parkinson's disease |
| DDC | Aromatic amino acid decarboxylase deficiency |
| DGAT2 | Nonalcoholic steatohepatitis |
| DGAT2 | Type 2 diabetes |
| DGKK | Fragile X syndrome |
| DKK3 | Mesothelioma |
| DKK3 | Malignant pleural mesothelioma |
| DLL3 | Recurrence of small cell lung cancer |
| DLL3 | Small cell lung cancer |
| DLL3 | Large cell neuroendocrine carcinoma |
| DMD exon 055 | Muscular dystrophy |
| ROR1 | Recurrent non-small cell lung cancer |
| ROR1 | Non-Hodgkin lymphoma |
| ROR1 | Leukemia |
| ROR1 | B-cell malignancy |
| ROR2 | Pancreatic cancer |
| ROR2 | Gastric cancer |
| ROR2 | Kidney tumor |
| ROR2 | Renal cell carcinoma |
| ROR2 | Sarcoma |
| ROR2 | Recurrent solid tumor |
| ROR2 | Bladder cancer |
| RORG | Immune system disorders |
| RORα | Stargardt disease |
| RORα | Retinitis pigmentosa type 19 |
| RORα | Dry age-related macular degeneration |
| RORα | Geographic atrophy |
| RORα | Cone-rod dystrophy type 3 |
| RPE65 | Leber congenital amaurosis |
| RPE65 | Leber's hereditary optic atrophy |
| RPGR | Choroideremia |
| RPGR | Retinoschisis |
| RPGR | X-linked retinitis pigmentosa |
| RPN2 | Breast cancer |
| RRM2 | Tumor |
| RRM2 | Solid tumor |
| RT | Lymphoma |
| RT | HIV infection |

-continued

| Target site (gene) | Disease name |
|---|---|
| RTK | Ovarian cancer |
| RUNX3 | Tumor |
| DMD exon 44 | Muscular dystrophy |
| DMD exon 44 | Duchenne muscular dystrophy |
| DMD exon 45 | Duchenne muscular dystrophy |
| DMD exon 45, DMD exon 44 | Duchenne muscular dystrophy |
| DMD exon 50 | Duchenne muscular dystrophy |
| DMD exon 51 | Duchenne muscular dystrophy |
| DMD exon 52 | Muscular dystrophy |
| DMD exon 52 | Duchenne muscular dystrophy |
| DMD exon 53 | Duchenne muscular dystrophy |
| DMD exon 53 | Duchenne muscular dystrophy |
| DMD exon 55 | Duchenne muscular dystrophy |
| Dm-dNK | Breast cancer |
| Dm-dNK | Colorectal cancer |
| DMPK | Myotonic dystrophy |
| DNA | Pancreatic cancer |
| DNA polymerase, RT | Cytomegalovirus infection |
| DNA polymerase, RT | Herpes simplex |
| DNA polymerase, RT | Epstein-Barr virus infection |
| RYR2 | Catecholaminergic polymorphic ventricular tachycardia |
| SANS | Usher syndrome |
| SARM1 | Peripheral nervous system disease |
| SARS-CoV-2 3CLpro | Novel Coronavirus Infection |
| SARS-CoV-2 N protein, SARS-CoV-2 ORF1Ab | Novel Coronavirus Infection |
| SARS-CoV-2 S protein | Novel Coronavirus Infection |
| SARS-CoV-2 S protein | Coronavirus infection |
| SATB1 | Prostate cancer |
| SCAP | Dyslipidemia |
| SCAP | Metabolic fatty liver disease |
| SDF-1 | Hematopoietic stem cell transplantation |
| SDF-1 | Pancreatic cancer |
| SDF-1 | Heart damage |
| SDF-1 | Diabetic retinopathy |
| SDF-1 | Chronic lymphocytic leukemia |
| SDF-1 | Colorectal cancer |
| SDF-1 | Relapsed chronic lymphocytic leukemia |
| SDF-1 | Multiple myeloma |
| DNA polymerase, RT | HIV infection |
| DNA polymerase, thymidine kinase | Tumor |
| DNA-directed DNA polymerase | Autoimmune disease |
| DNA-directed DNA polymerase | Tumor |
| DNA-directed DNA polymerase | Inflammation |
| DNA-directed DNA polymerase | Influenza A virus infection |
| DNA-directed DNA polymerase | Dystonia |
| DNAJC15 | Acute kidney injury |
| DNAJC15 | Polycystic kidney disease |
| DNase I | Pancreatic acinar carcinoma |
| DNase I | Colorectal cancer |
| DNA repair proteins | Advanced cancer |
| DNA repair proteins | Melanoma |
| DNA-directed RNA polymerase | Bacterial infection |
| DNM2 | Muscle atrophy |
| DNMT1 | Head and neck tumor |
| DNMT1 | Kidney tumor |
| DNMT1 | Renal cell carcinoma |
| DNMT1 | Acute myeloid leukemia |
| DNMT1 | Myelodysplastic syndrome |
| DOK7 | Motor neurone disease |
| Selectins | Inflammation |
| Selectins | Colon cancer |
| Selectins | Melanoma |
| SEMA4A | Multiple myeloma |
| SERCA2 | Heart failure |
| SERCA2 | Diastolic heart failure |
| SERCA2 | Heart failure with preserved ejection fraction |
| SERCA2 | Ischemic cardiomyopathy |
| SERCA2 | Urinary incontinence |
| SERCA2 | Dilated cardiomyopathy |
| SERCA2 | Pulmonary hypertension |
| SERCA2 | Nonischemic cardiomyopathy |
| SERCA2 | Duchenne muscular dystrophy |
| SERCA2 | DMD-related dilated cardiomyopathy |
| SGCA | Limb-girdle muscular dystrophy |
| SGCA | Sarcoglycanosis |
| SGCB | Limb-girdle muscular dystrophy |
| SGCB | 2e type of muscular dystrophy |
| SGCG | Limb-girdle muscular dystrophy R5 |
| SGCG | Limb-girdle muscular dystrophy type 2C |
| SGLT2 | Type 2 diabetes |
| DOK7 | Congenital myasthenic syndrome |
| DR4, TRAIL | Kidney tumor |
| DR5 | Liver cancer |
| DRDs | Parkinson's disease |
| DSG1, DSG3 | Pemphigus |
| DSG3 | Pemphigus |
| DSG3 | Familial pemphigus vulgaris |
| DUSP1 | Heart failure |
| DUSP1 | Arrhythmias |
| DUSP1 | Heart failure NYHA class III |
| DUSP1 | Myocardial ischemia |
| DUSP1 | Diastolic heart failure |
| DUSP1 | Systolic heart failure |
| DUSP1 | Complication |
| DUX4 | Facioscapulohumeral muscular dystrophy |
| DUX4 | Facioscapulohumeral muscular dystrophy type 1a |
| DWORF | Heart failure with reduced ejection fraction |
| DWORF | Dilated cardiomyopathy |
| DYSF | Limb-girdle muscular dystrophy |
| DYSF | Miyoshi myopathy |
| DYSF | Myofibrillar myopathy |
| DYSF | Dysferlin myopathy |
| DYSF | Limb-Girdle Muscular Dystrophy Type 2B |
| Dystrophin | Angelman syndrome |
| Dystrophin | Muscular dystrophy |
| Dystrophin | Duchenne muscular dystrophy |
| E2F1 | End-stage renal disease |
| E2F1 | Hyperplasia |
| SGSH | Mucopolysaccharidosis type III |
| SGSH, SUMF1 | Mucopolysaccharidosis type III |
| SHANK3 | Autism Spectrum Disorders |
| SHANK3 | Phelan-McDermid syndrome |
| SIRPα | Tumor |

-continued

| Target site (gene) | Disease name |
|---|---|
| SIRT6 | Nonalcoholic steatohepatitis |
| SLAMF7 | Hematologic malignancy |
| SLAMF7 | Multiple myeloma |
| SLC6A8 | Duchenne muscular dystrophy |
| SMAC | Pancreatic cancer |
| SMAC, TRAIL | Hepatocellular carcinoma |
| SMAD2, TGFBR2, VEGF-A | Choroidal neovascularization |
| SMAD4 | Colorectal cancer |
| SMAD7 | Crohn's disease |
| SMAD7 | Cachexia |
| SMAD7 | Duchenne muscular dystrophy |
| SMAD7 | Inclusion body myositis |
| SMN1 | Spinal muscular atrophy |
| SMN1 | Muscular dystrophy |
| SMN1 | Spinal muscular atrophy type I |
| SMN2 | Infantile-onset spinocerebellar ataxia |
| SMN2 | Spinal muscular atrophy |
| SMN2 exon 7 | Spinal muscular atrophy |
| SMPD1 | Niemann-Pick disease |
| SNAP25 | Primary axillary hyperhidrosis |
| SOCS1 | Advanced solid malignant tumor |
| SOCS1 | Head and neck tumor |
| SOCS1 | Head and Neck Squamous Cell Carcinoma |
| E2F1 | Vascular graft obstruction |
| E2F1 | Perioperative ischemia |
| E2F1 | Peripheral vascular disease |
| E2F1 | Coronary artery restenosis |
| E2F1 | Coronary heart disease |
| E2F1 | Arterial occlusive disease |
| E6 | Penile tumor |
| E6 | Vaginal tumor |
| E6 | Vulvar tumor |
| E6 | Papillomavirus infection |
| E6 | Squamous intraepithelial lesion |
| E6 | Oropharyngeal tumor |
| E6 | Cervical cancer |
| E6 | Cervical cancer |
| E6 | Anal tumor |
| E6 | Polyomavirus infection |
| E6 | HPV16 infection |
| E6, HPV E7 | Head and neck tumor |
| E6, HPV E7 | Cervical cancer |
| E6, PD-1 | Metastatic cervical cancer |
| E6, PD-1 | Cervical cancer |
| EBNA1, LMP1, BARF1 proteins | Hodgkin lymphoma |
| EBNA1, LMP1, BARF1 proteins | Non-Hodgkin lymphoma |
| EBV proteins | Hematopoietic stem cell transplantation |
| EBV proteins | Transplant complications |
| EBV proteins | Hematologic malignancy |
| EBV proteins | Gastric cancer |
| EBV proteins | Leiomyosarcoma |
| EBV proteins | Nasopharyngeal carcinoma |
| SOCS1 | Melanoma |
| SOCS1 | Lung cancer |
| SOCS1 | Non-small cell lung cancer |
| SOCS3 | Hepatocellular carcinoma |
| SOD1 | Motor neurone disease |
| SOD1 | Motor neurone disease |
| SOD1 | Amyotrophic lateral sclerosis |
| SOD1 | Amyotrophic lateral sclerosis type 1 |
| SOS1 | Lung cancer |
| SOST | Tumor |
| SOST | Triple-negative breast cancer |
| SOST | Familial hypophosphatemic rickets |
| SOST | Osteoporosis |
| SOST | Osteogenesis imperfecta |
| SOST | Type 2 diabetes |
| SPAG9 | Prostate cancer |

-continued

| Target site (gene) | Disease name |
|---|---|
| SPAT | Primary hyperoxaluria |
| SPHK1 | Hepatocellular carcinoma |
| SPSB1 | Non-small cell lung cancer |
| SRY | Parkinson's disease |
| SSTR, thymidine kinase | Ovarian cancer |
| SSTR, thymidine kinase | Recurrent ovarian cancer |
| SSTR2 | Melanoma |
| ST13 | Colorectal cancer |
| ST13, TRAIL | Pancreatic ductal carcinoma |
| STAT1 | Asthma |
| STAT3 | Metastatic head and neck squamous cell carcinoma |
| STAT3 | Hereditary nonpolyposis colorectal cancer type 1 |
| STAT3 | Pancreatic acinar carcinoma |
| EBV proteins | Epstein-Barr virus-positive lymphoma |
| EBV proteins | Epstein-Barr virus-associated lymphoproliferative disease |
| EBV proteins | Epstein-Barr virus-associated nasopharyngeal carcinoma |
| EBV proteins | Ebola virus disease |
| EBV proteins | EBV-related post-transplant lymphoproliferative disorder |
| EGF | HER2-positive breast cancer |
| EGFR | Metastatic head and neck squamous cell carcinoma |
| EGFR | Ewing sarcoma |
| EGFR | Advanced solid malignant tumor |
| EGFR | Clear cell sarcoma |
| EGFR | Head and neck tumor |
| EGFR | Retinoblastoma |
| EGFR | Solid tumor |
| EGFR | Wilms tumor |
| EGFR | Neurofibrosarcoma |
| EGFR | Neuroblastoma |
| EGFR | Triple-negative breast cancer |
| EGFR | Squamous cell carcinoma |
| EGFR | Glioblastoma |
| EGFR | Synovial sarcoma |
| EGFR | Rhabdoid tumor |
| EGFR | Rhabdomyosarcoma |
| EGFR | Hepatocellular carcinoma |
| EGFR | Hepatoblastoma |
| EGFR | Recurrent solid tumor |
| EGFR | Non-small cell lung cancer |
| EGFR | Malignant epithelial tumor |
| EGFR | Desmoplastic small round cell tumor |
| EGFR | Trauma and Injury |
| STAT3 | Advanced colorectal adenocarcinoma |
| STAT3 | Advanced non-small cell lung cancer |
| STAT3 | Advanced solid malignant tumor |
| STAT3 | Head and neck tumor |
| STAT3 | Kidney tumor |
| STAT3 | Adrenoleukodystrophy |
| STAT3 | Breast cancer |
| STAT3 | Prostate cancer metastasis |
| STAT3 | Refractory colorectal cancer |
| STAT3 | Refractory lung cancer |
| STAT3 | Ovarian cysts |
| STAT3 | Glioma |
| STAT3 | Acute myeloid leukemia |
| STAT3 | Myelodysplastic syndrome |
| STAT3 | Hepatocellular carcinoma |
| STAT3 | Recurrent squamous cell carcinoma of the head and neck |
| STAT3 | Non-small cell lung cancer |
| STAT3 | Bladder cancer |
| STAT3 | MSI-H Colorectal Cancer |
| STAT3, mTOR | Pancreatic cancer |

-continued

| Target site (gene) | Disease name |
|---|---|
| STAT3, mTOR | Bladder cancer |
| STAT3, TLR9 | Tumor |
| STAT3, TLR9 | Acute myeloid leukemia |
| STAT3, TLR9 | B-cell lymphoma |
| STAT5 transcription factor | Breast cancer |
| STAT6 | Pancreatic acinar carcinoma |
| STAT6 | Gastric cancer |
| STAT6 | Advanced hepatocellular carcinoma |
| STAT6 | Breast cancer |
| EGFR | HER2-positive breast cancer |
| EGFR | EGFR mutant solid tumor |
| EGFR | EGFR mutant solid tumor |
| EGFR, c-Met | Nonalcoholic steatohepatitis |
| EGFR, EGFRvIII | Glioblastoma |
| EGFR, EGFRVIII, HER2, IL-13Rα2 | Recurrent glioblastoma |
| EGFR, IL-12 | Colorectal cancer |
| EGFR, IL-13Rα2 | Glioblastoma |
| EGFR, IL-13Rα2 | Recurrent glioblastoma |
| EGFR, IL-13Rα2 | EGFR-mutated glioblastoma |
| EGFR, IL-21R | Leukemia |
| EGFR, SSTR | Pancreatic cancer |
| EGFR, SSTR | Head and Neck Squamous Cell Carcinoma |
| EGFR, SSTR | Breast cancer |
| EGFR, SSTR | Colorectal cancer |
| EGFR, SSTR | Melanoma |
| EGFR, SSTR | Liver cancer |
| EGFR, TCRDV2 | Pancreatic ductal adenocarcinoma |
| EGFR, TCRDV2 | Head and Neck Squamous Cell Carcinoma |
| EGFR, TCRDV2 | Solid tumor |
| EGFR, TCRDV2 | Colorectal cancer |
| EGFR, TCRDV2 | Non-small cell lung cancer |
| EGFR, TGF-β | Tumor |
| EGFRvIII | Meningeal tumor |
| EGFRvIII | Glioblastoma |
| EGFRvIII | Liver cancer |
| STAT6 | Uveal melanoma |
| STAT6 | Ovarian epithelial carcinoma |
| STAT6 | Colorectal cancer |
| STAT6 | Glioma |
| STAT6 | Thyroid cancer |
| STAT6 | Liver metastasis |
| STAT6 | Liver cancer |
| STAT6 | Lung cancer |
| STEAP1 | Metastatic castration-resistant prostate cancer |
| STEAP1 | Prostate cancer metastasis |
| STEAP2, TGFBR2 | Prostate cancer metastasis |
| STEAP2, TGFBR2 | Prostate cancer |
| STING | Liver cancer |
| STMN1 | Solid tumor |
| STMN2 | Amyotrophic lateral sclerosis |
| STMN2 | Frontotemporal dementia |
| STRC | Hearing impairment |
| STRIP1 | Solid tumor |
| STRIP1 | Glioma |
| STXBP1 | STXBP1-related epileptic encephalopathy |
| SULF2, TGF-β1 | Pancreatic acinar carcinoma |
| SULF2, TGF-β1 | Liver cancer |
| SULF2, TGF-β1 | Lung cancer |
| SUMO1 | Heart failure |
| SURF1 | Leigh disease |
| Survivin | Metastatic non-small cell lung cancer |
| EGFRvIII | Lung cancer |

-continued

| Target site (gene) | Disease name |
|---|---|
| EGFRvIII | Glioblastoma multiforme |
| EGFRvIII, EphA2, HER2, IL-13Rα2 | Glioblastoma |
| EGR1 | Tumor |
| EGR1 | Postoperative pain |
| EHMT2 | Prader-Willi syndrome |
| EIF2AK4 | Tumor |
| EIF2AK4 | Immune system disorders |
| EIF4E | Tumor |
| EIF4E | Advanced cancer |
| EIF4E | Castration-resistant prostate cancer |
| EIF4E | Prostate cancer |
| EIF4E | Non-small cell lung cancer |
| ELA2 | Tumor |
| ELA2 | Duchenne muscular dystrophy |
| elastin | Skin disorders |
| ELAVL1 | Pancreatic cancer |
| ELAVL1 | Ovarian cancer |
| ELF3 | Tuberculosis |
| ELOVL2 | Dry age-related macular degeneration |
| ELP1, splicing factor | Familial dysautonomia |
| EMR1 | Leukemia |
| ENaC | Cystic fibrosis |
| enkephalinase | B-cell leukemia |
| eNOS | Myocardial infarction |
| eNOS | Peripheral vascular disease |
| eNOS | Pulmonary hypertension |
| env | Chronic hepatitis B |
| Survivin | Tumor |
| Survivin | Advanced hepatocellular carcinoma |
| Survivin | Solid tumor |
| Survivin | Castration-resistant prostate cancer |
| Survivin | Precursor T-lymphocytic leukemia lymphoma |
| Survivin | Prostate cancer |
| Survivin | Lymphoma |
| Survivin | Locally advanced non-small cell lung cancer |
| Survivin | Glioblastoma |
| Survivin | Acute myeloid leukemia |
| Survivin | Acute lymphoblastic leukemia |
| Survivin | Hepatocellular carcinoma |
| Survivin | Relapsed adult acute lymphoblastic leukemia |
| Survivin | Non-small cell lung cancer |
| SYF2 | Amyotrophic lateral sclerosis |
| SYF2 | Frontotemporal dementia |
| Syk | Inflammation |
| Syk | Asthma |
| SYT11 | Gastric cancer |
| SYT11 | Colorectal cancer |
| SYT11 | Lung cancer |
| TAG-72 | Ovarian cancer |
| TAG-72 | Platinum-resistant Ovarian epithelial carcinoma |
| TAG-72 | T-cell lymphoma |
| TAU | Mild cognitive impairment |
| TAU | Pick's disease dementia |
| TAU | Progressive supranuclear palsy |
| TAU | Dementia due to Alzheimer's disease |
| EpCAM | Digestive system tumor |
| EpCAM | Gastric cancer |
| EpCAM | Advanced Gastric Cancer |
| EpCAM | Solid tumor |
| EpCAM | Liver cancer |
| EphA2 | Pancreatic cancer |
| EphA2 | Solid tumor |

-continued

| Target site (gene) | Disease name |
|---|---|
| EphA2 | Ovarian cancer |
| EphA2 | Lymphoma |
| EphA2 | Locally advanced malignant solid tumor |
| EphA2 | Glioblastoma |
| EphA2 | Glioma |
| EphA2 | Lung cancer |
| EphA2, IL-13Rα2 | EGFR-mutated glioblastoma |
| EphA3 | Solid tumor |
| EPO receptor | End-stage renal disease |
| EPO receptor | Renal anemia |
| EPO receptor | Neurodegenerative disease |
| EPO receptor | Glaucoma |
| EPO receptor | Anemia |
| EPO receptor | Parkinson's disease |
| ERVE-1 | Kidney tumor |
| ERα | Tumor |
| E-sel | Thrombotic occlusive vasculitis |
| E-sel | Vascular disease |
| E-sel | Peripheral arterial disease |
| EWS-FLI1 | Ewing sarcoma |
| EZH2 | Solid tumor |
| F10 | Hemophilia A |
| F10, F8 | Hemophilia A |
| F11 | End-stage renal disease |
| F11 | Thromboembolism |
| F11 | Cardiovascular disease |
| TAU | Alzheimer's disease |
| TAU, α-synuclein | Neurodegenerative disease |
| TBX21 | Psoriasis |
| TBX21 | Chronic obstructive pulmonary disease |
| TBXA2R | Tumor |
| TBXA2R | Cardiovascular disease |
| TCF7L2 | Tumor |
| TCR | B-cell lymphoma |
| TCR, VCAM1 | Neuroblastoma |
| TDP43 | Amyotrophic lateral sclerosis |
| TDP43 | Frontotemporal dementia |
| TECPR2 | Spastic paraplegia |
| Telomerase | Gastroesophageal junction adenocarcinoma |
| Telomerase | Gastric cancer |
| Telomerase | Perioperative ischemia |
| Telomerase | Esophageal cancer |
| Telomerase | Glioblastoma |
| Telomerase | Melanoma |
| Telomerase | Liver cancer |
| Telomerase | Non-small cell lung cancer |
| TERC | Neutropenia |
| TERC | Juvenile myelomonocytic leukemia |
| TERC | Transfusion-dependent anemia |
| TERC | Acute myeloid leukemia |
| TERC | Myelodysplastic syndrome |
| TERC | Myelofibrosis |
| TERT | Advanced non-small cell lung cancer |
| TERT | Head and neck tumor |
| TERT | Glioblastoma |
| TERT | Melanoma |
| TERT | Hepatocellular carcinoma |
| TERT | Non-small cell lung cancer |
| TERT, c-Myc | Tumor |
| F11 | Myocardial infarction |
| F11 | Upper extremity deep vein thrombosis |
| F11 | Coagulation disorders |
| F11 | Stroke |
| F11 | Venous thrombosis |
| F11 | Arterial thrombosis |
| F11R | Androgenic Alopecia |
| F12 | Thromboembolism |
| F12 | Cardiovascular disease |
| F12 | Metabolic disease |
| F8 | Hemophilia A |

-continued

| Target site (gene) | Disease name |
|---|---|
| F8 | Antineutrophil cytoplasmic antibody-associated vasculitis |
| F8 | X-linked genetic disease |
| F8, factor IX | Hemophilia B |
| F8, factor IX | Hemophilia A |
| factor IX | Hemophilia B |
| factor IX | Venous thrombosis |
| factor IX | Acute Coronary Syndrome |
| factor IX | Acute Coronary Syndrome |
| factor IX | Coronary heart disease |
| factor IX | Nonalcoholic steatohepatitis |
| Factor VII | Thrombosis |
| Factor VII | Factor VII deficiency |
| FANCA | Tyrosinemia |
| FANCA | Fanconi anemia |
| FANCC | Fanconi anemia |
| FAP | Tumor |
| FAP, PDL1 | Solid tumor |
| FasL | Sarcoma |
| FasL | Lymphoma |
| FasL | Malignant epithelial tumor |
| FASN, MSLN | Fallopian tube cancer |
| TERT, αvβ3, αvβ5 | Tumor |
| TERT, αvβ5 | Tumor |
| TFDP3 | Tumor |
| TFPI | Hemophilia B |
| TFPI | Hemophilia A |
| TFPI | hemophilia |
| TfR1 | Neuromuscular disorders |
| TfR1 | Duchenne muscular dystrophy |
| TG | Brain metastases |
| TGFBI | Hereditary corneal dystrophy |
| TGFBR2 | Tumor |
| TGFBR2 | Pulmonary fibrosis |
| TGF-β | Heart failure |
| TGF-β | Gastric cancer |
| TGF-β | Solid tumor |
| TGF-β | Chondrosarcoma |
| TGF-β | Relapsed plasma cell myeloma |
| TGF-β | Multiple myeloma |
| TGF-β | Infectious mononucleosis |
| TGF-β | Nasopharyngeal carcinoma |
| TGF-β | Niemann-Pick disease type C |
| TGF-β1 | Novel Coronavirus Infection |
| TGF-β1 | Idiopathic pulmonary fibrosis |
| TGF-β1 | Corneal disease |
| TGF-β1 | Basal cell carcinoma |
| TGF-β1 | Osteoarthritis |
| TGF-β1 | Liver cancer |
| TGF-β1, VEGFR2 | Tumor |
| TGF-β1, α-Klotho | Joint disease |
| TGF-β2 | Metastatic solid tumor |
| TGF-β2 | Metastatic non-small cell lung cancer |
| TGF-β2 | Tumor |
| FASN, MSLN | Ovarian cancer |
| FASN, MSLN | Peritoneal cancer |
| FasR | Hepatitis |
| FasR | Liver failure |
| FasR, TNFR1 | Metastatic colorectal cancer |
| FasR, TNFR1 | Colorectal cancer liver metastasis |
| FasR, TNFR1 | Recurrent platinum-resistant ovarian cancer |
| FasR, TNFR1 | Glioblastoma multiforme |
| FGF19 | Nonalcoholic steatohepatitis |
| FGF21 | Heart failure |
| FGF21 | Myocardial disease |
| FGF21 | Familial partial lipid dystrophy |
| FGF21 | obesity |
| FGF21 | Metabolic fatty liver disease |
| FGF21, FGF21R | Nonalcoholic steatohepatitis |
| FGF21, TGF-β1 | Heart disease |
| FGF21, TGF-β1 | Senescence |
| FGF21, TGF-β1 | Kidney disease |

-continued

| Target site (gene) | Disease name |
|---|---|
| FGF21, TGF-β1 | Metabolic disease |
| FGF4 | Stable angina |
| FGF4 | Refractory angina |
| FGF4 | Coronary heart disease |
| FGFR3 | Chondrodysplasia |
| FGFR4 | Rhabdomyosarcoma |
| FGFR4 | Hepatocellular carcinoma |
| FGFR4 | Obesity |
| FGFRs | Hair loss |
| TGF-β2 | Bronchogenic carcinoma |
| TGF-β2 | Pancreatic cancer |
| TGF-β2 | Advanced non-small cell lung cancer |
| TGF-β2 | Diabetic macular edema |
| TGF-β2 | Solid tumor |
| TGF-β2 | Wet macular degeneration |
| TGF-β2 | Renal cell carcinoma |
| TGF-β2 | Diffuse midline glioma |
| TGF-β2 | Diffuse intrinsic pontine glioma |
| TGF-β2 | Glioblastoma |
| TGF-β2 | Glioma |
| TGF-β2 | Melanoma |
| TGF-β2 | Non-small cell lung cancer |
| TGF-β2 | Malignant pleural mesothelioma |
| TGM1 | Autosomal recessive ichthyosis |
| TGM2 | Tumor |
| TGM2 | Immune system disorders |
| THBS1 | Pancreatic cancer |
| THBS1 | Lung cancer |
| THPO | Thrombocytopenia |
| thrombin | Thrombosis |
| thrombin | heart disease |
| Thymidine kinase | Tumor |
| Thymidine kinase | Graft-versus-host disease |
| Thymidine kinase | Pancreatic adenocarcinoma |
| Thymidine kinase | Hematologic malignancy |
| Thymidine kinase | Gastric cancer |
| FGFRs | Multiple sclerosis |
| FGL1 | Tumor |
| FKRP | Limb-girdle muscular dystrophy |
| FKRP | Miyoshi myopathy |
| FLAP | Allergic conjunctivitis |
| FLT3 | Refractory acute myeloid leukemia |
| FLT3 | Acute myeloid leukemia |
| FLT3 | Relapsed acute myeloid leukemia |
| FLT3 | Leukemia |
| FLT3 | FLT3-positive acute myeloid leukemia |
| FMRP | Fragile X syndrome |
| FOLR1 | Mucinous cystadenocarcinoma |
| FOLR1 | Primary peritoneal serous adenocarcinoma |
| FOLR1 | Undifferentiated ovarian cancer |
| FOLR1 | Advanced solid tumor |
| FOLR1 | Fallopian tube clear cell adenocarcinoma |
| FOLR1 | Fallopian tube cancer |
| FOLR1 | Renal cell carcinoma |
| FOLR1 | Urothelial carcinoma |
| FOLR1 | Urothelial carcinoma |
| FOLR1 | Myxoma |
| FOLR1 | Ovarian endometrioid carcinoma |
| FOLR1 | Ovarian epithelial carcinoma |
| FOLR1 | Ovarian epithelial carcinoma |
| Thymidine kinase | Fallopian tube cancer |
| Thymidine kinase | Ovarian cancer |
| Thymidine kinase | Localized prostate cancer |
| Thymidine kinase | Colorectal cancer |
| Thymidine kinase | Glioma |
| Thymidine kinase | Melanoma |
| Thymidine kinase | Liver cancer |
| Thymidine kinase | Platinum-sensitive primary peritoneal carcinoma |

-continued

| Target site (gene) | Disease name |
|---|---|
| Thymidine kinase | Leukemia |
| Tie-2 | Diabetic retinopathy |
| TIGIT | Tumor |
| TLR | Hepatocellular carcinoma |
| TLR2 | Parkinson's disease |
| TLR3 | Breast cancer |
| TLR3 | Immune system disorders |
| TLR3 | Ovarian cancer |
| TLR4 | Stroke |
| TLR4 | Lymphatic malformations |
| TLR4 | Infect |
| TLR4 | Non-muscle invasive bladder tumor |
| TLR7 | Idiopathic pulmonary fibrosis |
| TLR7 | Non-small cell lung cancer |
| TLR7, TLR8 | Tumor |
| TLR7, TLR8 | Infect |
| FOLR1 | Ovarian mixed epithelial carcinoma |
| FOLR1 | Ovarian cancer |
| FOLR1 | Serous cystadenocarcinoma |
| FOLR1 | Osteosarcoma |
| FOLR1 | Peritoneal cancer |
| FOLR1 | Peritoneal cancer |
| FOLR1 | Recurrent primary peritoneal cancer |
| FOLR1 | Recurrent ovarian cancer |
| FOLR1 | Non-small cell lung cancer |
| FOXG1 | Neurological disorders |
| FOXO1 | Solid tumor |
| FSHR | Ovarian cancer |
| FtsZ | Acinetobacter baumannii infection |
| FUS | Amyotrophic lateral sclerosis |
| FUS | Amyotrophic lateral sclerosis |
| FXN | Friedreich's ataxia |
| G6PC1 | Glycogen storage disease |
| G6PC1 | Glycogen storage disease type I |
| GABA receptor | Temporal lobe epilepsy |
| TLR7, TLR8, TLR9 | psoriasis |
| TLR7, TLR8, TLR9 | Dermatomyositis |
| TLR7, TLR8, TLR9 | Refractory diffuse large B-cell lymphoma |
| TLR7, TLR8, TLR9 | Diffuse large B-cell lymphoma |
| TLR7, TLR8, TLR9 | Macroglobulinemia |
| TLR7, TLR8, TLR9 | Muscular dystrophy |
| TLR7, TLR8, TLR9 | Waldenstrom's macroglobulinemia is refractory |
| TLR7, TLR8, TLR9 | Relapsed diffuse large B-cell lymphoma |
| TLR7, TLR8, TLR9 | Plaque psoriasis |
| TLR7, TLR9 | Tumor |
| TLR7, TLR9 | Inflammatory bowel disease |
| TLR7, TLR9 | Systemic lupus erythematosus |
| TLR7, TLR9 | Rheumatoid arthritis |
| TLR7, TLR9 | Hyperlipidemia |
| TLR7, TLR9 | Multiple sclerosis |
| TLR7, TLR9 | Plaque psoriasis |
| TLR9 | Autoimmune hepatitis |
| TLR9 | Metastatic head and neck squamous cell carcinoma |
| TLR9 | Metastatic breast cancer |
| GABA receptor | Drug-resistant epilepsy |
| GABA receptor | epilepsy |
| GAD | Parkinson's disease |
| GAD2, GDNF, IL-10 | Sciatica |
| GAD2, GDNF, IL-10 | Lumbar radiculopathy |
| GAD2, GDNF, IL-10 | Neuralgia |
| GAG | Mucopolysaccharidosis type II |

| Target site (gene) | Disease name |
|---|---|
| GAG | HIV infection |
| GALC | Globoid cell leukodystrophy |
| galectin-3 | Osteosarcoma |
| GALGT2 | Duchenne muscular dystrophy |
| GALT | Galactosemia |
| GATA3 | asthma |
| GATA3 | Chronic obstructive pulmonary disease |
| GATA3 | Ulcerative colitis |
| GBA | Parkinson's disease |
| GBA | Gaucher disease |
| GBA | Fabry disease |
| GBA | Gaucher disease type II |
| GBA, Phospho-transferases | Gaucher disease |
| GC-C | Pancreatic cancer |
| GC-C | Colorectal cancer |
| GCDH | Glutaric acidemia |
| GCGR | Type 2 diabetes |
| GCGR | Type 2 diabetes |
| GD2 | Phyllodes |
| GD2 | Small cell lung cancer |
| TLR9 | Metastatic melanoma |
| TLR9 | Metastatic non-small cell lung cancer |
| TLR9 | Myasthenia gravis |
| TLR9 | Primary malignant liver tumor |
| TLR9 | Psoriasis |
| TLR9 | Pancreatic ductal adenocarcinoma |
| TLR9 | Pancreatic cancer |
| TLR9 | Mycosis fungoides |
| TLR9 | asthma |
| TLR9 | Small lymphocytic lymphoma |
| TLR9 | Advanced pancreatic ductal adenocarcinoma |
| TLR9 | Advanced non-small cell lung cancer |
| TLR9 | Advanced non-small cell lung cancer |
| TLR9 | Head and neck tumor |
| TLR9 | Head and Neck Squamous Cell Carcinoma |
| TLR9 | Eosinophilic asthma |
| TLR9 | Renal cell carcinoma |
| TLR9 | Ductal carcinoma |
| TLR9 | Breast cancer |
| TLR9 | Uveal melanoma |
| TLR9 | Skin melanoma |
| TLR9 | Cutaneous T-cell lymphoma |
| TLR9 | Refractory non-Hodgkin lymphoma |
| TLR9 | Refractory malignant solid tumor |
| TLR9 | Diffuse large B-cell lymphoma |
| TLR9 | Merkel cell carcinoma |
| TLR9 | Chronic obstructive pulmonary disease |
| GD2 | Ependymoma |
| GD2 | Neuroblastoma |
| GD2 | sarcoma |
| GD2 | Uveal melanoma |
| GD2 | Brain cancer |
| GD2 | Refractory neuroblastoma |
| GD2 | Diffuse intrinsic pontine glioma |
| GD2 | Glioma |
| GD2 | Rhabdomyosarcoma |
| GD2 | Melanoma |
| GD2 | Osteosarcoma |
| GD2 | High-grade glioma |
| GD2 | Recurrent Ewing sarcoma |
| GD2 | Recurrent neuroblastoma |
| GD2 | Recurrent osteosarcoma |
| GD2 | Glioblastoma multiforme |
| GD2 | Gaucher disease type II |
| GD2, IL15R | Small cell lung cancer |
| GD2, IL15R | Non-small cell lung cancer |

| Target site (gene) | Disease name |
|---|---|
| GDNF | Parkinson's disease |
| GDNF | Amyotrophic lateral sclerosis |
| GFAP | Alexander disease |
| GFRA4 | Medullary thyroid cancer |
| GHR | Acromegaly |
| GHR | Acromegaly |
| GHRH | Anemia |
| GHRH | Cachexia |
| GITRL | Glioma |
| GJA1 | Arrhythmias |
| GJA1 | Myocardial disease |
| GJA1 | diabetic foot |
| TLR9 | Chronic lymphocytic leukemia |
| TLR9 | Chronic Hepatitis C Genotype 1 |
| TLR9 | Follicular lymphoma |
| TLR9 | Influenza virus infection |
| TLR9 | Squamous cell carcinoma |
| TLR9 | Ulcerative colitis |
| TLR9 | Macroglobulinemia |
| TLR9 | Locally advanced pancreatic adenocarcinoma |
| TLR9 | Locally advanced breast cancer |
| TLR9 | Colorectal cancer liver metastasis |
| TLR9 | Colorectal cancer |
| TLR9 | Conjunctival tumor |
| TLR9 | Hepatocellular carcinoma |
| TLR9 | Intrahepatic bile duct carcinoma |
| TLR9 | Relapsed mantle cell lymphoma |
| TLR9 | Relapsed marginal zone lymphoma |
| TLR9 | Relapsed grade 3a follicular lymphoma |
| TLR9 | Non-small cell lung cancer |
| TLR9 | Nonalcoholic steatohepatitis |
| TLR9 | Indolent B-cell non-Hodgkin lymphoma |
| TLR9 | Multiple sclerosis |
| TLR9 | Hepatitis C |
| TLR9 | T-cell lymphoma |
| TLR9 | EGFR-positive non-small cell lung cancer |
| TLR9 | CD20-positive non-Hodgkin lymphoma |
| TM4SF1 | Digestive system tumor |
| TMC1 | Hearing loss |
| TMPRSS6 | Polycythemia vera |
| TMPRSS6 | High-risk myelodysplastic syndrome |
| TMPRSS6 | Thalassemia |
| TNF | psoriasis |
| GJA1 | Corneal damage |
| GJB2 | Hearing loss |
| GLA | Fabry disease |
| GLA | Glycogen storage disease type II |
| GLA | Chagas cardiomyopathy |
| GlcCer | Neurodegenerative disease |
| GlcCer | Gaucher disease |
| GlcCer | Gaucher disease type I |
| GLI2 | Tumor |
| GLI2 | Prostate cancer |
| GLIPR1 | Prostate cancer |
| Globo H | Gastric cancer |
| GLP-1R | Weight loss |
| GLP-1R | Obesity |
| GLP-1R | Type 2 diabetes |
| glucokinase | Type 2 diabetes |
| Glucokinase, insulin | Diabetes |
| GluK2, Kainic acid receptor | Temporal lobe epilepsy |
| GluK2, Kainic acid receptor | Epilepsy |
| Glycogen | Glycogen storage disease type II |
| GM2 (ganglioside M2) | Solid tumor |

-continued

| Target site (gene) | Disease name |
|---|---|
| GM-CSF | Bladder cancer |
| GM-CSF, decorin | Colorectal cancer |
| GM-CSF, IFNα2, IL-12, IL-15 | Advanced solid tumor |
| GM-CSF, IFNα2, IL-12, IL-15 | Solid tumor |
| GM-CSF, IFNα2, IL-12, IL-15 | Melanoma |
| GM-CSF, RYBP | Tumor |
| TNF | Renal cell carcinoma |
| TNF | Prostate cancer |
| TNF | Brain cancer |
| TNF | Huntington's disease |
| TNF | Melanoma |
| TNF | Alzheimer's disease |
| TNF-α | Tumor |
| TNF-α | Rectal cancer |
| TNF-α | Psoriasis |
| TNF-α | Pancreatic cancer |
| TNF-α | Inflammation |
| TNF-α | Periodontal disease |
| TNF-α | Retinitis pigmentosa |
| TNF-α | Esophageal cancer |
| TNF-α | Sarcoma |
| TNF-α | Prostate cancer |
| TNF-α | Rheumatoid arthritis |
| TNF-α | Crohn's disease |
| TNF-α | Locally advanced prostate cancer |
| TNF-α | Colorectal cancer |
| TNF-α | Melanoma |
| TNF-α | Melanoma |
| TNF-α | Osteosarcoma |
| TNSALP | Hypoalkaline phosphatase |
| TOP1 | Tumor |
| TP63 | Colorectal cancer |
| TPP1 | Neuronal ceroid lipofuscinosis |
| GNE | Distal myopathy |
| GNE | Hereditary inclusion body myopathy |
| GOPC | Tumor |
| GOX | Primary hyperoxaluria type 1 |
| GOX | Primary hyperoxaluria |
| GOX | Kidney Stone Disease |
| gp100 | Melanoma |
| GPC1 | Pancreatic cancer |
| GPC2 | Small cell lung cancer |
| GPC2 | Neuroblastoma |
| GPC2 | Refractory neuroblastoma |
| GPC2 | High-risk neuroblastoma |
| GPC2 | Recurrent neuroblastoma |
| GPC2 | Bladder cancer |
| GPC3 | Ovarian cancer |
| GPC3 | Squamous cell lung cancer |
| GPC3 | Hepatocellular carcinoma |
| GPC3 | Lung cancer |
| GPC3 | Cholangiocarcinoma |
| GPC3, IL-15 | Solid tumor |
| GPC3, IL-15 | Hepatocellular carcinoma |
| GPC3, IL15R | Liver cancer |
| GPC3, IL-2Rβ | Solid tumor |
| GPC3, NKp46 | Hepatocellular carcinoma |
| GPCR | Retinitis pigmentosa |
| GPCR, β-adrenoceptors | Novel Coronavirus Infection |
| GPCR, β-adrenoceptors | Heart failure |
| GPCR, β-adrenoceptors | Chronic fatigue syndrome |
| GPCR, β-adrenoceptors | Dilated cardiomyopathy |
| TPP1 | Neuronal ceroid lipofuscinosis 2 |
| TRAIL | Metastatic non-squamous non-small cell lung cancer |
| TRAIL | Pancreatic cancer |
| TRAIL | Hepatocellular carcinoma |
| TRAIL | Lung adenocarcinoma |

-continued

| Target site (gene) | Disease name |
|---|---|
| TRBC1 | Immunoblastic lymphadenopathy |
| TRBC1 | Relapsed T-cell lymphoma |
| TRBC1 | TRBC1-positive T-cell lymphoma |
| TRBC2 | Peripheral T-cell lymphoma |
| TRKA | pain |
| Trop-2 | Breast cancer |
| Trop-2 | Colon cancer |
| Trop-2 | Lung cancer |
| Trop-2 | Malignant epithelial tumor |
| TRPV1 | Eye pain |
| TRPV1 | Dry eye syndrome |
| TRPV1 | Complex Regional Pain Syndrome |
| Trypsin | Cystic fibrosis |
| Trypsin | Chronic obstructive pulmonary disease |
| Trypsin | Respiratory syncytial virus infection |
| Trypsin | Emphysema |
| Trypsin | Alpha-1 antitrypsin deficiency |
| TSHR | Thyroid cancer |
| TSLPR | B-cell leukemia |
| TTK | Corneal disease |
| TTR | Transthyretin Amyloidosis |
| TTR | Transthyretin cardiac amyloidosis |
| TTR | Transthyretin-associated familial amyloid polyneuropathy |
| TTR | Hematopoietic stem cell transplantation |
| GPRC5D | Refractory plasma cell myeloma |
| GPRC5D | Plasma cell leukemia |
| GPRC5D | Plasma cell leukemia |
| GPRC5D | Relapsed Multiple myeloma |
| GPRC5D | Multiple myeloma |
| GPVI | Vascular disease |
| GR | Cushing syndrome |
| GR | Metabolic disease |
| GR | Type 2 diabetes |
| GRB2 | Endometrial cancer |
| GRB2 | Fallopian tube cancer |
| GRB2 | Ovarian epithelial carcinoma |
| GRB2 | Peritoneal cancer |
| GRB2 | Recurrent solid tumor |
| GSTP1 | Pancreatic cancer |
| GSTP1 | Colorectal cancer |
| GSTP1 | Non-small cell lung cancer |
| GSTP1 | KRAS-mutated non-small cell lung cancer |
| GTPCH1 | Immune system disorders |
| GUCY2D | Leber congenital amaurosis type 1 |
| GUCY2D | Leber congenital amaurosis |
| GYS1 | Glycogen storage disease type III |
| GYS1 | Lafora disease |
| GYS1 | Glycogen storage disease type II |
| GYS1 | Glycogen storage disease type II |
| H1 receptor, Opioid receptors | Upper respiratory tract allergies |
| H1 receptor, Opioid receptors | Common cold |
| H1 receptor, Opioid receptors | Cough |
| HAAH | Hematologic ma5lignancy |
| TTR | Stargardt disease |
| TTR | Senile cardiac amyloidosis |
| TTR | Transthyretin amyloid cardiomyopathy |
| TTR | Familial amyloid neuropathy |
| TTR | Polyneuropathy |
| TTR | Amyloidosis |
| TUBB4A | Type 6 myelin-reduced leukodystrophy |
| TUSC2 | Breast cancer |
| TUSC2 | Lung cancer |
| TUSC2 | Non-small cell lung cancer |
| TYK2 | Autoimmune disease |
| TYK2 | Novel Coronavirus Infection |
| TYMP | Mitochondrial encephalomyopathy |

-continued

| Target site (gene) | Disease name |
|---|---|
| TYMS | Pancreatic cancer |
| TYMS | Gastric cancer |
| TYMS | Prostate cancer |
| TYMS | Ovarian cancer |
| TYMS | Glioblastoma |
| TYMS | Bone cancer |
| TYR | Hyperpigmentation |
| TYR | Melanoma |
| UBE3A | Angelman syndrome |
| UCN2 | Heart failure |
| UCN2 | Abdominal obesity andmetabolic syndrome |
| UCN2 | Obesity |
| UCN2 | Nonalcoholic steatohepatitis |
| UCN2 | Type 2 diabetes |
| UGT1A1 | Nonalcoholic steatohepatitis |
| UGT1A1 | Crigler-Najjar syndrome |
| HAAH | Solid tumor |
| HAAH | Glioblastoma |
| harmonin | Usher syndrome |
| HBA1 | Beta thalassemia |
| HBG1 | Sickle cell disease |
| HBG1 | Beta thalassemia |
| HBG1, HBG2 | Sickle cell disease |
| HBG1, HBG2 | Beta thalassemia |
| HBG2 | Sickle cell disease |
| HBG2 | Beta thalassemia |
| HBsAg | Hepatitis B virus-related hepatocellular carcinoma |
| HBsAg | Hepatitis B |
| HBsAg | diabetic foot |
| HBsAg | Hepatocellular carcinoma |
| HBsAg | Hepatitis D |
| HBV pol | Hepatitis B |
| HBV RNA | Hepatitis B |
| HBV-X | Hepatitis B |
| HBV-X | Chronic hepatitis B |
| HBV-X | Hepatitis D |
| HBX | Hepatitis B |
| HCCS1 | Hepatocellular carcinoma |
| HDAC6 | Tumor |
| HDGFL3 | Tumor |
| hemagglutinin | Niemann-Pick disease type C2 |
| Hemoglobin HbA | Alpha thalassemia |
| Hemoglobins | Transfusion-dependent beta-thalassemia |
| Hemoglobins | Sickle cell disease |
| Hemoglobins | Thalassemia |
| Hemoglobins, KLKB1, TTR | Sickle cell disease |
| Hemoglobins, KLKB1, TTR | Beta thalassemia |
| ULBP1 | Hematologic malignancy |
| ULBP1 | Advanced solid tumor |
| ULBP1 | Advanced cancer |
| ULBP1 | Refractory cancer |
| UNC13A | Amyotrophic lateral sclerosis |
| UNC13A | Frontotemporal dementia |
| UPF1 | Amyotrophic lateral sclerosis |
| USH2A | Usher syndrome |
| UTRN | Duchenne muscular dystrophy |
| VAMP1 + VAMP2 | Nasopharyngeal tumor |
| VCAM1 | Inflammatory bowel disease |
| VDR | Multiple sclerosis |
| VEGF | Diabetic retinopathy |
| VEGF | Wet age-related macular degeneration |
| VEGF | Macular degeneration |
| VEGF-A | Myocardial ischemia |
| VEGF-A | Peripheral arterial disease |
| VEGF-A | Diabetic macular edema |
| VEGF-A | Retinal vein occlusion |
| VEGF-A | Wet age-related macular degeneration |
| VEGF-A | Breast cancer |

-continued

| Target site (gene) | Disease name |
|---|---|
| VEGF-A | Colorectal cancer |
| VEGF-A | Macular degeneration |
| VEGF-A | Liver cancer |
| VEGF-A | Malignant ascites |
| VEGF-A, VEGFR | Angina |
| VEGF-A, VEGFR | Ischemia |
| VEGF-A, VEGFR | Coronary heart disease |
| VEGF-C | Lymphedema |
| VEGF-D | Peripheral vascular disease |
| VEGFR | Tumor |
| Hepc | Tumor |
| Hepc | End-stage renal disease |
| Hepc | Inflammation |
| Hepc | Anemia |
| Hepc | endotoxemia |
| Hepc | Chronic |
| Hepc | Anemia with chronic kidney disease |
| Hepc, IL-10, TGF-β | Kidney disease |
| HER2 | Endometrial cancer |
| HER2 | Endometrial cancer |
| HER2 | Tumor metastasis |
| HER2 | Tumor |
| HER2 | Tumor |
| HER2 | Pancreatic cancer |
| HER2 | Inflammatory breast tumor |
| HER2 | Small cell lung cancer |
| HER2 | Gastroesophageal junction cancer |
| HER2 | Gastric cancer |
| HER2 | Head and neck tumor |
| HER2 | Breast cancer |
| HER2 | Prostate cancer |
| HER2 | Urothelial carcinoma |
| HER2 | Brain metastases |
| HER2 | Ovarian epithelial carcinoma |
| HER2 | Ovarian cancer |
| HER2 | Squamous cell carcinoma |
| HER2 | Colorectal cancer |
| HER2 | Glioma |
| HER2 | Mesothelioma |
| VEGFR | Head and Neck Squamous Cell Carcinoma |
| VEGFR | Retinal disease |
| VEGFR | Macular degeneration |
| VEGFR | Nasopharyngeal carcinoma |
| VEGFR1 | Preeclampsia |
| VEGFR1 | Age-related macular degeneration |
| VEGFR1 | Choroidal neovascularization |
| VEGFR1 | Macular degeneration |
| VEGFR1, VEGFR2, VEGFR3 | Mesothelioma |
| VEGFR2 | Tumor |
| VEGFR2 | Wet age-related macular degeneration |
| VEGFR2 | Hepatocellular carcinoma |
| Viral proteins | Hepatitis B |
| Viral proteins | Chronic hepatitis B |
| Viral proteins | Marburg virus disease |
| VP24 | Marburg virus disease |
| VP24, Viral RNA | Ebola virus disease |
| VP35, Viral RNA | Ebola virus disease |
| VSTM1 | Tumor |
| vWF | Hemophilia A |
| vWF | Thrombotic thrombocytopenia purpura |
| vWF | Thrombotic microangiopathy |
| vWF | Thrombosis |
| vWF | Hemolytic uremic syndrome |
| vWF | Intracranial embolism |
| vWF | Carotid artery stenosis |
| vWF | Acute ischemic stroke |

-continued

| Target site (gene) | Disease name |
|---|---|
| vWF | Acquired thrombotic thrombocytopenia purpura |
| vWF | Coronary artery thrombosis |
| HER2 | Chemotherapy-induced nausea and vomiting |
| HER2 | Osteosarcoma |
| HER2 | Cervical cancer |
| HER2 | Hepatocellular carcinoma |
| HER2 | Lung cancer |
| HER2 | Obesity |
| HER2 | Non-small cell lung cancer |
| HER2 | Ductal carcinoma |
| HER2 | Bile duct tumor |
| HER2 | Bladder cancer |
| HER2 | HER2-positive gastric cancer |
| HER2 | HER2-positive breast cancer |
| HER2 | Type 2 diabetes |
| HER2, HER3 | Triple-negative breast cancer |
| HER2, HER3 | Meningeal tumor |
| HER2, HER3 | HER2-positive breast cancer |
| HER2, HER3 | HER2-negative breast cancer |
| HER2, IL-13Rα2 | Ovarian cancer |
| HER2, IL15R | Gastric cancer |
| HER2, IL15R | Breast cancer |
| HER2, NKG2D | Solid tumor |
| HER2, PD-1 | Solid tumor |
| HER3 | Tumor |
| HER3 | Breast cancer |
| HER3 | Colon cancer |
| HER3 | Lung cancer |
| hERG | Atrial fibrillation |
| HEXA, HEXB | Tay-Sachs disease |
| HEXA, HEXB | Sandhoff disease |
| HEXA, HEXB | GM2 gangliosidosis |
| HGF | Autoimmune disease |
| HGF | Tumor |
| HGF | Myocardial ischemia |
| HGF | Lower limb ischemia |
| vWF | Von Willebrand disease |
| vWF | Von Willebrand disease type 2 |
| WASP | Angina |
| WASP | Wiskott-Aldrich syndrome |
| WT1 | Acute myeloid leukemia |
| WT1 | Myelodysplastic syndrome |
| WT1 | Multiple myeloma |
| XIAP | Pancreatic cancer |
| XIAP | Breast cancer |
| XIAP | Chronic lymphocytic leukemia |
| XIAP | Acute myeloid leukemia |
| XIAP | Acute myelomonocytic leukemia |
| XIAP | Hepatocellular carcinoma |
| XIAP | Non-small cell lung cancer |
| XIAP | Malignant epithelial tumor |
| XIAP | Multiple sclerosis |
| XIAP | B-cell lymphoma |
| XKR8 | Pancreatic cancer |
| XKR8 | Colon cancer |
| XLRS1 | Retinoschisis |
| XO | Gout |
| YAP1 | Advanced solid tumor |
| ZSCAN4 | Dyskeratosis congenita |
| ZSCAN4 | Pancytopenia |
| ZSCAN4 | Bone marrow failure disease |
| α-glucosidase | Glycogen storage disease type II |
| α-Klotho | Amyotrophic lateral sclerosis |
| α-synuclein | Parkinson's disease |
| α-synuclein | Parkinson's disease |
| α-synuclein | Multiple System Atrophy |
| αvβ3 | Breast cancer |
| αvβ3 | Melanoma |
| αvβ6 | Tumor |
| αvβ6 | Pancreatic cancer |
| HGF | Peripheral arterial disease |
| HGF | Diabetic peripheral neuropathy |
| HGF | Diabetic vascular disease |

-continued

| Target site (gene) | Disease name |
|---|---|
| HGF | Diabetic neuropathy |
| HGF | Diabetic nephropathy |
| HGF | Breast cancer |
| HGF | Ischemia |
| HGF | Chronic limb-threatening ischemia |
| HGF | Ulcer |
| HGF | Amyotrophic lateral sclerosis |
| HGF | Coronary heart disease |
| HGF | Type 1 diabetes |
| HIF-1α | Peripheral arterial disease |
| HIF-1α | Lymphoma |
| HIF-1α | Hepatocellular carcinoma |
| HIF-1α | Liver cancer |
| HIF-1α | Liver cancer |
| HIF-1α | Malignant epithelial tumor |
| αvβ6 | Amyotrophic lateral sclerosis |
| β2-adrenergic receptor | Glaucoma |
| β2-adrenergic receptor | Ocular hypertension |
| β-galactosidase | Gangliosidosis |
| β-galactosidase | GM1 gangliosidosis |
| β-globin | Sickle cell anemia |
| β-globin | Beta thalassemia |
| Amiloride-sensitive sodium channel | Cystic fibrosis |
| Amiloride-sensitive sodium channel | Chronic bronchitis |
| Intercellular adhesion molecule | Inflammation |
| Viral RNA | Pseudohyperkalemia Cardiff type |
| Viral RNA | Hepatitis C |
| Viral Protein | Merkel cell carcinoma |
| Viral Protein | Resectable Merkel cell carcinoma |
| Collagen I | Achilles tendinitis |
| Immunoglobulin light chain kappa | Lymphoma |
| Immunoglobulin light chain kappa | Multiple myeloma |
| Immunoglobulin light chain kappa | leukemia |
| HIF-1α, transcription factors, and related regulatory factors | Tumor |
| HIF-2α | Renal cell carcinoma |
| HIF-2α | Neuroblastoma |
| Histone H3 | Diffuse midline glioma, H3 K27M-mutant |
| HIV envelope protein gp120 | AIDS |
| HIV gag | AIDS |
| HIV gag | HIV infection |
| HIV-1 integrase | AIDS |
| HIV-1 integrase | HIV infection |
| HIV-1 pol | Opportunistic infections |
| HIV-1 pol | AIDS |
| HIV-1 pol | Hepatitis C |
| HIV-1 tat | HIV infection |
| HIV RNase H | HIV infection |
| HJV, Hepc | anemia |
| Endotoxin A | Prostate cancer |
| Coagulation Factor VIII | Hemophilia A |
| Human endogenous retroviral elements | Solid tumor |

-continued

| Target site (gene) | Disease name |
|---|---|
| Growth factor receptors | Neurodegenerative disease |
| Cell adhesion molecules | Inflammation |
| Cell adhesion molecules | Septic shock |
| SARS-CoV-2 Antigen | Novel Coronavirus Infection |
| Folate receptor | Tumor |
| Apolipoprotein | Alzheimer's disease |
| Tumor antigen MG7 | Liver cancer |
| Transforming growth factor β receptor | Tumor |
| Transcription factors and related regulatory factors | Larsen syndrome |
| Transcription factors and related regulatory factors | Fuchs endothelial corneal dystrophy type 3 |
| Transcription factors and related regulatory factors, c-Jun | Tumor |

EXAMPLES

The present disclosure is further described below by way of examples, but the present disclosure is not limited to the scope of the examples. The experimental methods without specific conditions in the following examples are performed according to conventional manners and conditions, or according to product specifications.

Example 1. Screening C12-279 Protein

Figure 1A:
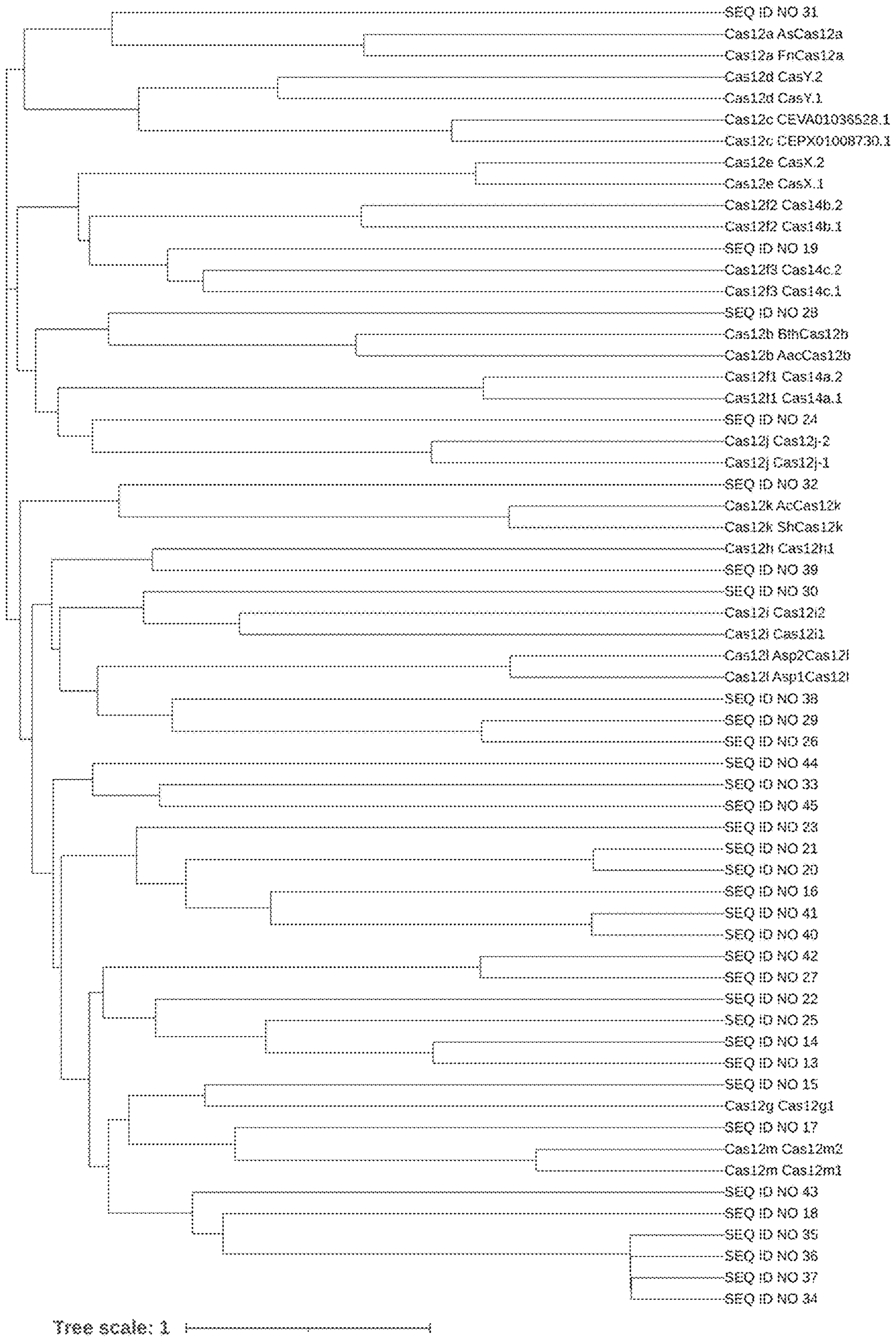
FIG. 1A is a diagram illustrating an evolutionary relationship of Cas proteins and known Cas12 isoform proteins (performing sequence alignment using MAFFT, then constructing an evolutionary tree using FastTree) according to embodiments of the present disclosure.

As shown in FIGS. 1A and 1B, the Cas12i protein C12-279 was finally obtained through screening, analysis, and designing using a complex bioinformatics manner.

An amino acid sequence of the C12-279 protein (SEQ ID NO: 696) is:

```
                                                    (SEQ ID NO: 696)
IFVVLSVNQFRCNPNAFRQASMKTDDEKKDTAIKSYTSWLLPNDRKEKDMVRSFLALD

QGSRFFFDLMQAWYGGLTPDIIKSVTKERDLVDLWCAIYWFRPMKKELASHPIDRVDLA

KTFQRYYGGPASDVVQEYLSASIGEDCCWNDCRQKYQEFCKNLGVDFTPDLKTLVREK

LIAVALNDGSQAAISNLFGNGGKEDRNVKVNICKKILIALEKAGKSVKYVRDVQSIILKC

ANAKDREDFNRIYADKNGRPGTLLLLLDRKGENTYDAEVLKRYLRKTIKSKNAPLVWN

YNQKLFEYIERGIRNLLRRTINYDAWAWGEMWRVGHTPLQTKATRNYHFAQEQLKRHS

DIAAASQSSHAIAVALNEFFESPFFDGENPFTICPHHLGKNLEKLFKAWADEKNQTDEED

AGETAITDYCAEFKDGFDREPIRNLLRYVYASLRSKYSAKELIQAAKYNQQFERYQRQK

AHPVTPDNQGYTWPEAVIKPSKAERKNRENSLDTRIWVSVKLLQKDGTWEKHHIPFYN

LRFFEEVYAAASIAEDMPSPTFRNSRFGFKLPKLLNTHAKINKKKKDGKKDKKAVNAAK

REARIYLAAKEGRLPAPSVPLDKLSAVIARVNGKFQVTVPVKFKVNKQPKYPLPQLGQII

LGYDQNLTANHAWALFEVVTEDTPGAHFCRNQYLRVLKTGQVRSITKTKDGQEIDQLSY

DGLEYKEYGEWRKQAKKFASQWYITTKVRKGKETTLLSQPALERFESIEKYKPALYRFN

KEYARLLLAVIRRKTLNELEEIRPEIFRLVEQGFGICRFGSLSLSSFEAIRAAKAVIYGYFST

ALKHDHNTPITDDERQAFDPELFGLLNKLETLRQNKGEEKINRAANALIRIALENKADFI

RGEGDLPTTNKSVKKGQNSRSMDWLARGLFNKICQLAVMHNIIPTAANPHSTSHQDPFE

HNKDFDDPQPAMKCRYAEFKIEDIGDSVLERLGTSLRNAKAGQTGAYYYKGAQDFLAH

YGLQDIEEELKKCRRGRKANMPCWELQKRLIQKLGSKDAVVYIPMRGGRIYLATHSVTT

GAKPIIFNGEEVWVSNADEIAAVNIGLTIIPTSKKDEEHPDRENDDKAIRKSVRRPRKSGE

RRSGDKMPATARKT.
```

A predicted structure of the C12-279 protein is shown in FIG. 24.

Example 2. Preparation and Purification of C12-279 Protein

1. Vector Construction

A pET28a vector plasmid was double digested with BamHI and XhoI, and a linearized vector was recovered by agarose gel electrophoresis. Using the prepared pXC12-279-GFPPAM-DR5 plasmid (SEQ ID NO: 697) as a template, DNA fragments containing coding sequences of the C12-279 protein was obtained by PCR amplification with primers ChkCas-pET28-PF1 (SEQ ID NO: 699) and ChkCas-pET28-PRI (SEQ ID NO: 700). The DNA fragments were inserted into a cloning region of the pET28a vector by homologous recombination (New England Biolabs (NEB™), Gibson Assembly® Master Mix) to construct a recombinant vector C12-279-pET28a-01 (SEQ ID NO: 698). A reaction solution was transformed into Stb13 competent cells, coated on an LB plate containing kanamycin sulfate, and cultured at 37° C. overnight, and clones were picked for sequencing and identification.

Positive clones with a correct sequence were selected and cultured overnight. Plasmids were extracted and transformed into an expression strain Rosetta (DE3), and then coated on the LB plate containing kanamycin sulfate and cultured at 37° C. overnight.

2. Protein Expression

A single clone was selected and inoculated into 5 mL of LB culture medium containing kanamycin sulfate and cultured at 37° C. overnight.

The selected single clone was reinoculated into 500 mL of LB culture medium containing kanamycin sulfate at a ratio of 1:100, cultured at 220 rpm and 37° C. until OD reached 0.6, added with IPTG to a final concentration of 0.2 mM, and induced at 16° C. for 24 h.

After rinsing with 15 mL PBS, the bacteria were collected by centrifugation, added with a lysis buffer for sonication disruption, a supernatant containing the recombinant protein was obtained by centrifuging at 10,000 g for 30 min, and the supernatant was filtered through a 0.45 μm filter membrane before being applied to column purification.

3. Protein Purification

The expressed recombinant protein has 1240 amino acids (aa) and a structure of His tag-NLS-C12-279-SV40 NLS-nucleoplasmin NLS. Using 6×His tag at an N-terminal as purification tags, the C12-279 recombinant protein was obtained by Immobilized Metal Ion Affinity Chromatography (IMAC) (Ni Sepharose™ 6 Fast Flow affinity chromatography media (Cytiva™)) and heparin affinity chromatography (POROS™ Heparin 50 μm chromatographic column, Thermo Scientific™). The purified recombinant protein was detected by SDS-PAGE electrophoresis, and results are shown in FIG. 2.

Example 3. In Vitro Cleavage of PAM Library and Grabbing of PAM by C12-279 Protein In this example, sgRNA containing a specific guide sequence and the C12-279 recombinant protein prepared and purified as described in Example 2 were mixed to cleave an in vitro cleavage substrate (containing a spacer sequence and a 7nt random sequence) (as shown in FIG. 3). After incubation at 37° C., purification and library construction were performed, followed by NGS sequencing to determine the PAM sequence of C12-279. Specific operations were as follows.

In Vitro Cleavage Substrate

The designed in vitro cleavage substrate sequence is as follows:

```
                                                                   (SEQ ID NO: 701)
ggagttcagacgtgtgctcttccgatctcagcacaaaggaaactcaccctaactgtaaagtaattgtgtgttttga

gactataaatatgcatgcgagaaaagccttgtttgccaccatGGAACGGCTCGGAGATCATCATTGCGNNNNNNNgt

gagcaagggcgaggagctgttcaccggggtggtgcccatcctggtcgagctggacggcgacgtaaacggccacaagt

tcagcgtgtccggcagatcggaagagcacacgtctgaactcc.
```

In the sequence, N represents any one of A, T, C, and G.

A double-stranded DNA containing the above sequence was prepared by PCR amplification and used as the in vitro cleavage substrate.

The cleavage substrate was sent to a sequencing company for PCR-free library construction and NGS sequencing. A complexity and abundance analysis on the PAM library composed of the 7nt random sequence were analyzed. The result is as follows.

Compositions of the four bases A, T, G, and C are basically the same. At the same time, the PAM library composed of the 7nt random sequence contains $4^7=16384$ different combinations, all of which (100%) are detected. The complexity and abundance of the PAM library are qualified.

B. Preparation of sgRNA

The sgRNA (C12-279-sgRNA) containing a specific guide sequence was synthesized by in vitro transcription at 37° C. in a system containing T7 RNA transcriptase, four ribonucleotide triphosphates, and a DNA template with a T7 promoter. A transcription product was precipitated and purified with LiCl. The sgRNA sequence is as follows:

```
>C12-279-sgRNA
                                          (SEQ ID NO: 702)
5'-gtaatgcgtctcccattgacgcGTGAGCAAGGGCGAGGAGCTGTT
C-3'.

>C12-279-sgRNA-Rev
                                          (SEQ ID NO: 703)
5'-gtaatgcgtctcccattgacgcCGCAATGATGATCTCCGAGCCGT
TCC-3'.

The sgRNA scaffold sequence (DR sequence) is:
                                          (SEQ ID NO: 704)
5'-gtaatgcgtctcccattgacgc-3'.
```

The uppercase bases are the guide sequence of the sgRNA.

C. NGS Library Construction and PAM Analysis

1) PAM Library Cleavage and T4 DNA Polymerase Treatment

Reaction systems containing the C12-279 protein, two different sgRNAs, the in vitro cleavage substrate, and a buffer were prepared (as shown in Table 1) and reacted at 37° C. for 3 h and at 75° C. for 15 min).

TABLE 1

| Reaction system for in vitro cleavage reaction | |
|---|---|
| Components | Addition amount (μL) |
| 10× Cut Buffer (500 mM Tris-HCl PH 8.0, 2M NaCl, 100 mM $MgCl_2$, 10 mM DTT) | 5 |
| Cleavage substrate (59.5 ng/μL) | 36.5 |
| C12-279- sgRNA or C12-279-sgRNA-Rev | 2.8 μg |
| C12-279 protein (10 mg/mL) | 0.5 |

2) T4 DNA Polymerase Treatment for Blunting Cleavage Product

The T4 DNA Polymerase (Thermo Scientific™) was added to the cleavage product. The specific reaction system was shown in Table 2. After addition, the reaction was performed at 37° C. for 20 min and at 85° C. for 10 min.

TABLE 2

| Reaction system for blunting the C12-279 cleavage product | |
|---|---|
| Component | Addition amount (μL) |
| C12-279 cleavage product | 50 |
| 5× T4 DNA Polymerase Buffer | 13 |
| T4 DNA Polymerase | 1 |
| dNTP(10 mM) | 0.65 |
| $ddH_2O$ | 0.35 |

3) 3' End A-Tailing and Addition of Biotin-Labeled Adapter a. 78 μL SPRISelect™ Beads (Beckman COULTER™) were added to the T4 DNA Polymerase reaction product and mixed well, the mixture was placed at room temperature for 5 min, the product was moved to a magnetic rack for adsorption for 5 min, the supernatant was transferred to a new 1.5 mL tube, 39 μL SPRISelect™ Beads (Beckman COULTER™) was added and mixed well, and placed at room temperature for 5 min. The product was moved to the magnetic rack for adsorption for 5 min. A supernatant was discarded, then the product was washed twice with 85% ethanol, placed at room temperature for 10 min for air drying, and added with 50 μL $ddH_2O$ for elution.

b. Using the SynplSeq DNA Library Prep Kit for Illumina® library prep kit, 3' A-tailing was performed on the product in step a according to the system in Table 3 at 37° C. for 10 min, 65° C. for 20 min, and 4° C. for later use.

TABLE 3

| 3' A-tailing of C12-279 cleavage product | |
|---|---|
| Component | Addition amount (μL) |
| Cleavage products of C12-279 with different sgRNA | 49 |
| Enhancer | 1.5 |
| End Prep Mix | 6 |
| End Prep Buffer 1 | 3 |
| $ddH_2O$ | 0.5 |
| Total | 60 |

c. Adapter 1 (obtained by annealing an upstream primer: 5'Biosg/gttgacatgctggattgagacttctacactctttccctacgacg ctcttccgatc*t (SEQ ID NO: 705) and a downstream primer: gatcggaagagcgtcgtgtagggaaaga gtgtaggaagtctcaatccagcatgtcaac (SEQ ID NO: 706)) was added according to the system in Table 4 and reacted at 20° C. for 30 min and at 16° C. overnight. The reaction product was purified using SPRISelect™ Beads, Biosg is a biotin modification, and "*" represents thiolation.

TABLE 4

| Reaction system added with Adapter 1 | |
|---|---|
| Component | Addition amount (μL) |
| Reaction product in step b | 60 |
| Adapter 1 | 2 |
| DNA Ligase | 1.2 |
| 3x Ligation Buffer 1 | 33 |
| $ddH_2O$ | 3.8 |
| Total | 100 |

d. The reaction product was purified using streptavidin-labeled magnetic beads Dynabeads® M-280 Streptavidin (Invitrogen™ Thermo Fisher Scientific)

e. Recover PCR

The primers in Table 5 were designed, and the Recover PCR reaction was performed using Q5® Hot Start High-Fidelty 2× Master Mix (NEB™) according to the system in Table 6 and the reaction program in Table 7.

TABLE 5

| Recover PCR primers | |
|---|---|
| Primer ID | sequence |
| Recovery PCR Forward | ggagttcagacgtgtgctc (SEQ ID NO: 707) |
| Recovery PCR Reverse | gttgacatgctggattgagacttc (SEQ ID NO: 708) |

TABLE 6

| Recover PCR reaction system | |
|---|---|
| Component | Addition amount (μL) |
| Streptavidin-labeled magnetic beads purification product | 22.5 |
| Recovery PCR Forward (10 uM) | 2.5 |
| Recovery PCR Reverse (10 uM) | 2.5 |
| Q5 ® Hot-Start 2x Master Mix | 22.5 |
| $ddH_2O$ | Up to 50 |

TABLE 7

| Recover PCR reaction program | | |
|---|---|---|
| Reaction temperature | Duration | Number of cycles |
| 98 °C | 2 min | 1 |
| 98 °C | 10 sec | 12 |
| 61 °C | 30 sec | |
| 72 °C | 2 min | |
| 72 °C | 2 min | 1 |
| 4 °C | ∞ | |

f. The Recover PCR product was moved to the magnetic rack and adsorbed for 5 min, the supernatant was moved to a new 1.5 mL centrifuge tube, 3 μL of the Recovery PCR product was taken, and 148.5 μL $ddH_2O$ was added to dilute.

g. Index PCR

The primers in Table 8 were selected, and the Index PCR was performed according to the system in Table 9 and the reaction program in Table 10.

TABLE 8

| Index PCR primers | |
|---|---|
| Primer | Sequence |
| IF501 | aatgatacggcgaccaccgagatctacactatagcctacactctttccctacacgacg (SEQ ID NO: 709) |
| IR701 | caagcagaagacggcatacgagatcgagtaatgtgactggagttcagacgtgtgctc (SEQ ID NO: 710) |

TABLE 9

| Index PCR reaction system | |
|---|---|
| Component | Addition amount (μL) |
| Recovery PCR dilution product | 12 |
| IF501(10 uM) | 4 |
| IR701(10 uM) | 4 |
| Q5 ® Hot-Start 2x Master Mix | 20 |
| Total | 40 |

TABLE 10

| Index PCR reaction program | | |
|---|---|---|
| Reaction temperature | Duration | Count of cycles |
| 98 °C | 2 min | 1 |
| 98 °C | 10 s | 12 |
| 60 °C | 30 s | |
| 72 °C | 2 min | |

TABLE 10-continued

| Index PCR reaction program | | |
|---|---|---|
| Reaction temperature | Duration | Count of cycles |
| 72 °C | 2 min | 1 |
| 4 °C | ∞ | |

h. 0.7×SPRISelect™ Beads were added to the Index PCR product for product purification, 38 μL $ddH_2O$ was added for elution, the concentration was measured using a Qubit® fluorometer (Thermo Fisher Scientific), and then sent for NGS sequencing.

i. Analysis of NGS results: through the NGS sequencing and analysis with WebLogo software by referring to the document (*A compact Cas9 ortholog from Staphylococcus Auricularis (SauriCas9) expands the DNA targeting scope. PLOS biology,* 2020, 18 (3), e3000686), the identified motifs were obtained as shown in FIGS. 4 and 5. Both FIGS. 4 and 5 demonstrate that the PAM recognized by the C12-279 is 5'-TTN-3'.

Example 4. Verification of PAM Based on In Vivo Editing Activity of C12-279 Protein in Bacteria In this example, a plasmid library containing a 7nt random sequence was first constructed, and then a bacterial expression plasmid containing the C12-279 protein coding sequence was constructed. After the expression plasmid was transformed into bacteria to prepare a competent cell, the 7nt random sequence plasmid library was electroporated. If the plasmid in the 7nt random sequence library could be recognized and targeted by C12-279, the plasmid may be removed from the library and the corresponding bacteria could not grow, as shown in FIG. 6.

The specific operations were as follows.

1. Construction of 7nt Random Sequence Plasmid Library pLVX-EFla-BSD vector plasmid (SEQ ID NO: 711) was double-digested by EcoRV and XhoI, and a linearized vector was recovered by agarose gel electrophoresis. Using the prepared pCDH-CMV-EGFP-reporter3-EF1-Puro plasmid (SEQ ID NO: 712) as a template, were used to the DNA fragment containing the coding sequence of the Puro resistance gene was obtained by PCR amplification with primers Puro-PF1 (SEQ ID NO: 714) and Puro-PRI (SEQ ID NO: 715). The DNA fragment was inserted into the pLVX-EF1a-BSD vector digested with enzymes by homologous recombination (NEB™, Gibson Assembly® Master Mix) to construct a recombinant vector pL VX-7NN-Puro library plasmid containing the 7NN random sequence (SEQ ID NO: 713). The reaction solution was transformed into Stb13 competent cells, coated on an LB plate containing ampicillin, and cultured overnight at 37° C. All colonies were scraped for extracting plasmids.

2. Construction of Bacterial Expression Plasmid P15A-C12-279 of C12-279 Protein and Preparation of Competent Cells Containing the Plasmid a. Construction of Bacterial Expression Plasmid of C12-279 Protein A P15A-Cas-NC03 vector plasmid (SEQ ID NO: 716) was digested with SalI, and the linearized vector was recovered by agarose gel electrophoresis. Using the prepared pXC12-279-GFPPAM-DR5 plasmid (SEQ ID NO: 697) was used as a template, the DNA fragment encoding the C12-279 protein and the fusion fragment expressing the sgRNA were obtained by PCR with the primers ChkNLS-PF1 (SEQ ID NO: 718) and the synthesized C12-279-sgRNA fragment (SEQ ID NO: 717). The fragments were inserted into the P15A-Cas-NC03 vector digested with enzymes by homologous recombination (NEB™, Gibson Assembly® Master Mix) to construct the recombinant vector P15A-C12-279 (SEQ ID NO: 719). The reaction solution was transformed into Stb13 competent cells, coated on the LB plate containing chloramphenicol, and cultured overnight at 37° C., and a single clone was picked for sequencing verification.

b. Preparation of Competent Cells Containing Bacterial Expression Plasmid P15A-C12-279

The P15A-C12-279 plasmid verified to be correct by sequencing was transformed into DH5a competent cells (Vidyabiotech™ CAT #: DL1001), and the single clone was picked and inoculated into LB medium containing chloramphenicol and cultured at 37° C. overnight.

Electrocompetent cells were prepared as follows.

The culture bacterial solution was inoculated into 100 mL of fresh LB medium containing chloramphenicol at a ratio of 1:100 for amplification culture at 37° C. and 220 rpm.

Then the culture bacterial solution was cultured until OD600 reached 0.5, the bacterial solution was transferred to a 50 mL centrifuge tube and pre-cooled on ice for 30 min.

Then the culture bacterial solution was centrifuged at 4000 rpm and 4° C. for 10 min, the cells were collected and resuspend in an equal volume of pre-cooled sterile water.

The above operations were repeated.

The cells were resuspended in 1/10 volume of pre-cooled sterile water containing 10% glycerol, divided into 50 μL/tube, and stored at −80° C. to obtain the P15A-C12-279 competent cells.

c. Performing Plasmid Elimination to Identify the PAM Sequence of the C12-279 Protein 100 ng of pLVX-7NN-Puro library plasmid was electroporated into the prepared P15A-C12-279 competent cells and DH5a electroporated cells, respectively, and marked as Lib1 (electroporated P15A-C12-279 competent cells) and Lib2 (electroporated DH5a competent cells), respectively.

After electroporation, 10 mL of LB medium was added, and the cells were revived and cultured at 37° C. and 220 rpm for 2 h.

The revived bacterial solution was centrifuged at 4000 rpm for 2 min to collect the bacteria, and then resuspended in 400 μL LB and coated on the LB plate. The electroporated DH5a bacterial solution was coated on the LB plate containing ampicillin, and the electroporated P15A-C12-279 competent cells were coated on the LB plate containing chloramphenicol and ampicillin and cultured at 37° C. overnight.

The bacterial cells were scraped from the culture plate and the plasmid DNA was extracted by alkaline lysis manner.

100 ng of each of the two extracted plasmid DNA samples was used as the PCR template, and a PCR amplification was performed using primers SiteSeq-PF1 (SEQ ID NO: 720) and SiteSeqPuro-PR (SEQ ID NO: 721). The obtained fragments were subjected to amplicon library construction using an NGS library construction kit (Xunshi Biotechnology, SynplSeq DNA Library Prep Kit for Illumina®), followed by NGS sequencing.

The NGS sequencing data from Lib1 and Lib2 cells is compared and analyzed, as shown in FIG. 7. It is proved that the PAM sequence recognized by the C12-279 is 5'-TTN-3'.

Example 5. Cleavage Activity of C12-279 Protein on Target Nucleic Acid in 293T Cells In this example, sgRNA targeting TTR genes in HEK293T cells was first designed and constructed into a pXC12-279-GFPPAM-DR5 plasmid (SEQ ID NO: 697) to obtain a plasmid pXC12-279-TTR01 targeting the TTR genes. After transfecting the HEK293T cells, an indel ratio was verified by NGS to verify the cleavage activity of the C12-279 protein in 293T cells. The specific operations were as follows.

1. Construction of sgRNA Plasmid

An sgRNA target site catgagcatgcagaggtgagtat (SEQ ID NO: 722) was designed based on TTR gene sequence information in a HEK293T cell line.

TABLE 11

| Plasmid name | Primer name | sgRNA annealing primer<br>Primer sequence |
|---|---|---|
| pXC12-279-TTR01 | TTR01-PF1 | cattgacgccatgagcatgcagaggtgagtatTTTTTG<br>(SEQ ID NO: 723) |
| | TTR01-PR1 | gtaccAAAAAatactcacctctgcatgctcatggcgtc<br>(SEQ ID NO: 724) |

The annealing primers were designed according to the sgRNA target site information, and the plasmid pXC12-279-GFPPAM-DR5 (SEQ ID NO: 697) was digested with BsmBI (Thermo Scientific™, ER0451) and Acc65I (Thermo Scientific™, ER0901). The primers (Table 11) were annealed and then connected with the vector to obtain a pXC12-279-TTR01 expression clone.

2. Detection of TTR Gene Editing Efficiency

Plating: 293T cell lines were plated when a confluency reached 70-80%, and a count of cells seeded in a 24-well plate was 5*10^5 cells/well.

Transfection: Transfection was performed 12-14 h after plating. 100 μLOpti-MEM™ reduced serum medium (Gibco, Thermo Fisher Scientific), 1.5 μL PEI (Yeasen Biotechnology™. Polyethylenimine Linear (PEI) MW25000), and 500 ng pXC12-279-TTR01 plasmid were added to each well of a 24-well plate, mixed, and added to 293T cells for cell transfection after placing at room temperature for 20 min. After overnight transfection, a fresh culture medium was replaced, and culture was continued.

DNA extraction, PCR amplification, and NGS library construction: After 72 h of culture, the cells were washed with PBS, and then 100 μL of cell lysis solution (Viagen™, DirectPCR® Lysis Reagent (Cell)) was added for lysis to obtain lysate containing genomic DNA. The region near the target sequence was amplified for the genomic DNA. The PCR product was subjected to the NGS library construction and sequencing, and the sequencing result was analyzed. The indel rate is higher than 14%, as shown in FIG. 8.

Example 6. PAM Recognition of CI1062732

Compared with the C12-279 protein (SEQ ID NO: 696), the protein CI1062732 (SEQ ID NO: 46) lacks dozens of amino acid residues at the N-terminal.

A PAM sequence recognized by CI1062732 was identified using a manner substantially the same as that in Example 4. A gRNA containing a "false" DR sequence (SEQ ID NO: 529)
GTAATGCGTCTCCCATTGACGCC was combined with CI1062732 to target a 7nt random sequence plasmid library in bacteria. The sequencing analysis (as shown in FIG. 9) indicates that a "false" PAM motif identified by CI1062732 is 5'-TTNC-3'.

Subsequently, by analyzing a secondary structure of the "false" DR sequence, it is hypothesized that the 3'-end C base of the identified "false" PAM motif TTNC might be caused by an extra C at the 3' end of DR (FIG. 10). Therefore, in subsequent CI1062732 test and C12-279 test, the DR sequence is (SEQ ID NO: 704)
GTAATGCGTCTCCCATTGACGC.

Example 7. Screening, Design, Preparation, and Testing of C12-101-07 Protein (1) The C12-101-07 protein was ultimately obtained through screening and design using complex bioinformatics manners.

An amino acid sequence of the C12-101-07 protein is:

(SEQ ID NO: 52)
IFPTQRRNTMSGNVVRSYKSVLRPNIRKRELLDATFNWFDRAYKKFFDVF
VCLYGGVEHDTVHSALLKETTDPDLVCATMWFRVVPKSSCDGISAQEMIR
RFGVYAGHEPSAVAMSYLTGNFDDKKNHWIDCREKFVALARDMVVKPESL
SIDIKSMIEHKILPICSQDNWQAWNAISQLFGEGKKENKAEKAQIFVDVV
SMLSNNSVQTWEDYKEVISKATGCRTAGEINSKFGGRPGILSVDFSKDDT
GSLPKDFIERRIKDLSQKAKEKSAAYELPNRMRLRELIASVIGPYRLETW
SSVAQRACGDIRSKNSNNLLYASERFNRTKEIEEILSAKGDVARAQNILG
QFRSGEFNEFAVEKRHLGNLESLYNIWSKSDMDTGIEEYSSIHKDEYDRD
PIVDLYRHIYPHREVISAKNFIDAAVLNKLLRLNASRHVHPTVFGKTVIS
FSPKSSAYGRITPPSEIVRGRPAGSHGMIWLTMELFDDGKWIEHHLPFHN
SRYYEEVYCYQEGLPVKDEPRSPMFGYRVGNAIADTSKIDNRRRKASKQF
LRAQQNITHNVSFDENTAFSVVRNGEDFSITISSRIKASNAKSLMTIGDR
IMGIDQNQTAANTYSIWEVVGDGDAGSIQHGNLSLKRIEDGHITSIIRGR

-continued
GGNFDQLNYGGLSYAKFSEWRSARLGFISSLNAELASKMNWDWCCLYEWN
ARYASALRKIIYSHKGIDIERVFRREIEDFVEGVLRIGSLSSDALQCLTN
AKSLISSYFFLNGKKEPEEQRKFDQGLFDLSAKIDKKRVNKRQQKTKRIM
SSIMQIARDRGVSFIVVEGKLSTATKDNKSKANQKAIDWCARAVVENLEH
SCSLVGIKLVAIDPMNTSHLDPFVYVLKTSLGKEARFASVVPAKINARHM
KNFKSWSSLLAGNGKIKKTTDAIYVGAFQDFCREYGFVAEDISKMSQSEI
QDKLSSHQFVLVPQRGGRVYMSTHPVSSEAKKIVYAGRERWYNNADVVAA
VNITLRGCERLSASRKTASTR.

The recombinant vector C12-101-07-pET28a-01 (SEQ ID NO: 725) was constructed by a manner substantially the same as that in Example 2, which was expressed and purified to obtain the C12-101-07 recombinant protein, with an amino acid count of 1122 aa and a structure of His tag-NLS-C12-101-07-SV40 NLS-nucleoplasmin NLS. The purified recombinant protein was detected by SDS-PAGE electrophoresis, and the result is shown in FIG. 11.

(2) The in vitro cleavage of PAM library by the C12-101-07 protein was prepared using a manner substantially the same as that in Example 3 to grab the PAM.

In vitro transcription was used to synthesize sgRNA containing a specific guide sequence, the sequence of which is as follows:

>C12-101-07-sgRNA
(SEQ ID NO: 726)
5'-atcgcaacatctcagaaacccgtcctaagttgacggGTGAGCAAGGG
CGAGGAGCTGTTC-3'.

>C12-101-07-sgRNA-Rev
(SEQ ID NO: 727)
5'-atcgcaacatctcagaaacccgtcctaagttgacggCGCAATGATGA
TCTCCGAGCCGTTCC-3'.

The sgRNA scaffold sequence is:
(SEQ ID NO: 534)
5'-atcgcaacatctcagaaacccgtcctaagttgacgg-3'.

The C12-101-07 protein was combined with forward and reverse gRNAs respectively for editing.

The PAM motifs shown in FIGS. 12 and 13 were identified during the experiment.

It is demonstrated that the PAM sequence recognized by C12-101-07 is 5'-TTN-3'.

Example 8. In Vivo Editing Activity of C12-101-09 Protein in Bacteria and Verification of PAM A similar protein C12-101-09 was designed based on C12-101-07, with the sequence as follows:

>C12-101-09
(SEQ ID NO: 728)
IFPTQRRNTMSGNVVRSYKSVLRPNIRKRELLDATFNWFDRAYKKFFDVF
VCLYGGVEHDTVHSALLKETTDPDLVCATMWFRVVPKSSCDGISAQEMIR
RFGVYAGHEPSAVAMSYLTGNFDDKKNHWIDCREKFVALARDMVVKPESL
SIDIKSMIEHKILPICSQDNWQAWNAISQLFGEGKKENKAEKAQIFVDVV
SMLSNNSVQTWEDYKEVISKATGCRTAGEINSKFGGRPGILSVDFSKDDT

-continued

GSLPKDFIERRIKDLSQKAKEKSAAYELPNRMRLRELIASVIGPYRLETW

SSVAQRACGDIRSKNSNNLLYASERFNRTKEIEEILSAKGDVARAQSILG

QFRSGEFNEFAVEKRHLGNLESLYNIWSKSDMDTGIEEYSSIHKDEYDRD

PIVDLYRHIYPHREVISAKNFIDAAVLNKLLRLNASRHVHPTVFGKTVIS

FSPKSSAYGRITPPSEIVRGRPAGSHGMIWLTMELFDDGKWIEHHLPFHN

SRYYEEVYCYQEGLPVKDEPRSPMFGYRVGNAIADTSKIDNRRRKASKQF

LRAQQNITHNVSFDENTAFSVVRNGEDFSITISSRIKASNAKSLMTIGDR

IMGIDQNQTAANTYSIWEVVGDGDAGSIQHGNLSLKRIEDGHITSIIRGR

GGNFDQLNYGGLSYAKFSEWRSARLGFISSLNAELASKMNWDWCCLYEWN

ARYASALRKIIYSHKGIDIERVFRREIEDFVEGVLRIGSLSSDALQCLTN

AKSLISSYFFLNGKKEPEEQRKFDQGLFDLSAKIDKKRVNKRQQKTKRIM

SSIMQIARDRGVSFIVVEGKLSTATKDNKSKANQKAIDWCARAVVENLEH

SCSLVGIKLVAIDPMNTSHLDPFVYVLKTSLGKEARFASVVPAKINARHM

KNFKSWSSLLAGNGKIKKTTDAIYVGAFQDFCREYGFVAEDISKMSQSEI

QDKLSSHQFVLVPQRGGRVYMSTHPVSSEAKKIVYAGRERWYNNADVVAA

VNITLRGCERLSASRKTASTR.

The recombinant vector plasmid P15A-C12-101-09 (SEQ ID NO: 729) was constructed by conventional manners, and then tests were performed using manners substantially the same as those in Example 4.

The motif recognized by C12-101-09 was identified, as shown in FIG. 14.

It is demonstrated that the PAM sequence recognized by C12-101-09 is 5'-TTN-3'.

Example 9. Construction of Cell Lines Containing Different PAM Reporter Systems Stable cell lines were prepared by lentiviral infection. By constructing lentiviral expression plasmids containing different PAM sequences, 293T cells were infected after virus packaging to construct cell lines containing GFP reporter systems with different PAM sequences for subsequent mutation screening.

(1) Construction of Lentiviral Expression Plasmids for GFP Reporter Systems with Different PAM Sequences In addition to the prepared plasmid pCDH-CMV-EGFP-reporter3-EF1-Puro (SEQ ID NO: 712), a plasmid library with a PAM composition of NAAN was simultaneously constructed. A specific construction scheme was as follows.

A mixed library of EGFP fragments containing a detection system was synthesized by gene synthesis, and digested with XbaI+NotI, then the digested fragments were ligated to the XbaI+NotI digested vector of the plasmid pCDH-CMV-EGFP-reporter3-EF1-Puro using T4 DNA ligase. The ligation products were transformed into Stb13 cells, and cultured on ampicillin-containing plates at 37° C. overnight.

For the mixed fragment library, multiple clones were picked for sequencing and identification to obtain 16 plasmids with different sequence compositions (i.e., PAM sequences being AAAA, AAAT, AAAG, AAAC, TAAA, TAAT, TAAG, TAAC, GAAA, GAAT, GAAG, GAAC, CAAA, CAAT, CAAG, CAAC), and then the plasmids were mixed at equal mass to obtain a Plasmid Lib (Puro-NAAN-eGFP-Lib, SEQ ID NO: 730) with a PAM sequence composition of NAAN for subsequent lentiviral packaging and construction of stable cell line.

In the unedited reporter system, there is a base insertion that is not a multiple of 3 from a start codon to a normal GFP reading frame (pCDH-CMV-EGFP-reporter3-EF1-Puro has a 32 bp base insertion, and the Plasmid Lib has a 29 bp base insertion, as shown in FIG. 15), which causes the GFP normal reading frame to be interrupted, and GFP is not expressed. Then an sgRNA target site was set inside a GFP expression frame, and indel was generated by the editing of Cas12, having a probability to restore the normal GFP reading frame, so that GFP was expressed normally, and the higher an editing efficiency, the higher the probability of the generated indel to restore the normal GFP reading frame. The editing efficiency of the Cas12 protein was characterized by counting GFP-expressing cells using flow cytometry.

(2) Lentiviral Packaging of GFP Reporter System Plasmids with Different PAM Sequences The constructed pCDH-CMV-EGFP-reporter3-EF1-Puro plasmid and Plasmid Lib were mixed with virus packaging auxiliary plasmids pMD2.G (Miaoling Biosciences) and psPAX2 (Miaoling Biosciences) at a molar ratio of 1:1:1, respectively, and then transfected into 293T cells using PEI. After 48 h of transfection, a culture supernatant was taken and filtered with 0.45 μm of a filter film to obtain two crude viruses, namely pCDH-CMV-EGFP-reporter3-EF1-Puro and Plasmid Lib.

(3) Construction of the Detection Cell Line by Infecting 293T Cells Using the Crude Viruses pCDH-CMV-EGFP-Reporter3-EF1-Puro and Plasmid Lib 293T cells were infected with ¼ volume of crude viruses pCDH-CMV-EGFP-reporter3-EF1-Puro and Plasmid Lib in culture medium. After 48 h of infection, the medium was changed and 2 μg/mL of Puromycin was added for screening.

For the 293T cells infected with pCDH-CMV-EGFP-reporter3-EF1-Puro, the screened cells were subjected to monoclonal screening by limited dilution, and the screened monoclonal cell lines were the cell line used for detection (namely, Reporter3 cell line).

For the 293T cells infected with Plasmid Lib, the cell pool obtained after drug screening was the cell line used for detection (namely, NAAN cell line).

Example 10. Design of C12-279 Protein Mutation and Detection of Editing Efficiency a. Determination of Mutation Position A 3D structure of C12-279 protein was predicted and simulated through bioinformatics analysis and AI manners. Possible binding, recognition and cleavage sites of DNA of C12-279 were identified in combination with the 3D structure. The molecular cloning point mutation manner was used to construct mutation clones for these sites.

First, the mutations shown in Table 12 were designed.

TABLE 12

Editing efficiency of different mutation positions of C12-279 in NAAN cell line

| Mutation position | Mutant vector | Editing efficiency in NAAN cell line, expressed as a multiple of the editing efficiency of C12-279 |
|---|---|---|
| D352R | C12-279-GFPPAM-01 | 1.45 ± 0.36 |
| K631R | C12-279-GFPPAM-02 | 0.99 ± 0.18 |

TABLE 12-continued

| Editing efficiency of different mutation positions of C12-279 in NAAN cell line | | |
|---|---|---|
| Mutation position | Mutant vector | Editing efficiency in NAAN cell line, expressed as a multiple of the editing efficiency of C12-279 |
| A988R | C12-279-GFPPAM-03 | 1.24 ± 0.14 |
| G989R | C12-279-GFPPAM-04 | 1.23 ± 0.44 |
| Q186R | C12-279-GFPPAM-05 | 1.74 ± 0.38 |
| G194R | C12-279-GFPPAM-06 | 0.01 |
| N195R | C12-279-GFPPAM-07 | 1.64 |
| G196R | C12-279-GFPPAM-08 | 0.31 ± 0.12 |
| G197R | C12-279-GFPPAM-09 | 1.44 ± 0.45 |
| N245R | C12-279-GFPPAM-10 | 0.46 ± 0.06 |
| L260R | C12-279-GFPPAM-11 | 1.56 ± 0.07 |
| A355R | C12-279-GFPPAM-12 | 1.31 ± 0.36 |
| C385R | C12-279-GFPPAM-13 | 1.20 ± 0.37 |
| P386R | C12-279-GFPPAM-14 | 1.40 ± 0.48 |
| H387R | C12-279-GFPPAM-15 | 0.92 ± 0.33 |
| G390R | C12-279-GFPPAM-16 | 0.00 |
| K391R | C12-279-GFPPAM-17 | 1.14 ± 0.34 |
| N392R | C12-279-GFPPAM-18 | 1.39 ± 0.18 |
| D429R | C12-279-GFPPAM-19 | 0.34 ± 0.06 |
| Q461R | C12-279-GFPPAM-20 | 0.99 ± 0.3 |
| Q462R | C12-280-GFPPAM-21 | 1.36 ± 0.39 |
| E485R | C12-280-GFPPAM-22 | 1.57 ± 0.37 |
| L611R | C12-280-GFPPAM-23 | 0.43 ± 0.09 |
| Q990R | C12-280-GFPPAM-24 | 0.94 ± 0.09 |
| A1136R | C12-280-GFPPAM-25 | Not detected |
| K1138R | C12-280-GFPPAM-26 | Not detected |
| T1139R | C12-280-GFPPAM-27 | Not detected |
| N/A | NAAN cell line | 0.00 |
| N/A | PEI-control | 0.00 |
| N/A | C12-279-GFPPAM-DR5 | 1.00 ± 0.28 |

b. Construction of Mutation Clones

After a specific mutation position was determined, the mutation base was introduced through primers to construct expression clones containing different mutation positions. The following was an example of the construction of a D352R mutation clone.

TABLE 13

| Primer sequences for the construction of mutation clone C12-279-GFPPAM-01 of C12-279 | |
|---|---|
| Primer name | Primer sequences |
| ChkCas12-PF1 | CCAAGCTGGCTAGCGTTTAAACTTAAG (SEQ ID NO: 731) |
| ChkCas12-PR1 | ATGATCTCCGAGCCGTTTTTGGTACC (SEQ ID NO: 732) |
| C279-D352R-PF1 | GCTGAAGAGACACAGCagaATCGCCGCCGCT (SEQ ID NO: 733) (underlined being introduced amino acid mutations) |
| C279-D352R-PR1 | GGGAAGCGGCGGCGATtctGCTGTGTCTCT (SEQ ID NO: 734) (underlined being introduced amino acid mutations) |

Primers were designed for the mutation position D352R (as shown in Table 13), and the mutation position was introduced by primers C279-D352R-PF1 and C279-D352R-PR1. Using pXC12-279-GFPPAM-DR5 (SEQ NO: 1) as a template, ChkCas12-PF1+C279-D352R-PRI was subjected to PCR amplification (Yijin Bio, PC019, UltraHiPF™ DNA Polymerase Kit) to obtain fragment C12-279-D352R-F1, ChkCas12-PR1+C279-D352R-PF1 was subjected to PCR amplification to obtain fragment C12-279-D352R-F2, plasmid pXC12-279-GFPPAM-DR5 (SEQ ID NO: 697) was digested using HindIII+KpnI, and 5646 bp vector fragment was gel recovered (Guangzhou Meiji Biotechnology Co., Ltd., D2110, HiPure Gel Pure Micro Kit), and was recombined in vitro with fragments C12-279-D352R-F1 and C12-279-D352R-F2 (NEB™, E2611L, Gibson Assembly® Master Mix), and the mutation clone plasmid C12-279-GFPPAM-01 was obtained by heat-shock transformation of *Escherichia coli.* c. Detection of the Editing Efficiency of Mutants in NAAN Reporter System

Plating: cells were plated when a confluence of the NAAN cell line reached 70-80%, and a number of cells seeded in a 24-well plate was 5*10^5 cells/well.

Transfection: transfection was performed 12-14 h after plating. 1.5 μL PEI (Yeasen Biotechnology™, 40815ES03, Polyethylenimine Linear (PEI) MW25000) and 500 ng mutation clone plasmid were added to 100 μL Opti-MEM™ reduced serum medium (Gibco, Thermo Fisher Scientific) per well of the 24-well plate, mixed, and added to the NAAN cell line for cell transfection after placing at room temperature for 20 min. After overnight transfection, a fresh culture medium was replaced, and the culture was continued for 72 h, followed by flow cytometry. Editing efficiencies of different mutant clones were characterized by the proportion of GFP-positive cells.

The results are shown in Table 16 and FIG. 16. The editing efficiency of different C12-279 mutants in NAAN cells is expressed as a multiple of the editing efficiency of C12-279. Multiple mutants improve the editing efficiency.

d. According to the results of a first round of mutation, a portion of mutation positions that significantly improved the editing efficiency were combined, and multiple mutation position combinations were tried to further improve the editing efficiency. The designed mutants were shown in Table 14.

TABLE 14

| Editing efficiency of different mutation position combinations of C12-279 in NAAN cell line | | |
|---|---|---|
| Mutation position 1 | Mutation position 2 | Vector name of the mutant |
| D352R | Q186R | C12-279-GFPPAM-28 |
| D352R | L260R | C12-279-GFPPAM-29 |
| D352R | A355R | C12-279-GFPPAM-30 |
| A355R | L260R | C12-279-GFPPAM-31 |
| P386R | C385R | C12-279-GFPPAM-32 |
| E485R | Q462R | C12-279-GFPPAM-33 |

The vector was constructed using essentially the same manner as described above, and the editing efficiency was tested in the NAAN cell line. The results are shown in FIG. 17.

e. Construction of Mutant Plasmid Targeting Fixed PAM Combination

As the PAM of the NAAN cell line was a mixed library, it may theoretically have a certain impact on an actual editing efficiency. To more intuitively and efficiently demonstrate the effect of mutation on the editing efficiency, based on a sequence between a start codon of the Reporter3 cell line and a GFP reading frame, a target site with a PAM sequence of TTG and a target sequence of CTCACCTCGCGACGCAATGATG (SEQ ID NO: 735) was selected for subsequent editing efficiency test.

Construction of Mutation Clones Targeting Reporter3 Cell Line

Based on C12-279-GFPPAM-DR5, the sgRNA was changed to target CTCACCTCGCGACGCAATGATG (SEQ ID NO: 735), the synthesized primers pCDH-PF1: GTACCGAAAAACATCATTGCGTCGCGAGGT-GAGGCGTC (SEQ ID NO: 754) and pCDH-PR1: CATGACGCCTCACCTCGCGACGCAAT-GATGTTTTTCG (SEQ ID NO: 755) were annealed. The plasmid C12-279-GFPPAM-DR5 was digested with Acc65I (Thermo Scientific™) and BsmBI (Thermo Scientific™) to recover the vector and then connected with an annealing product to obtain the mutation clone C12-279-pCDH targeting the Reporter3 cell line. The construction manner of the mutation clones targeting Reporter3 cell lines was the same as the manner described in this example, except that the vector plasmid needed to be changed from C12-279-GFPPAM-DR5 to C12-279-pCDH, and the primer Chk-Cas12-PRI needed to be replaced by ChkCas12-PR2: GCGACGCAATGATGTTTTTCGGTACC (SEQ ID NO: 736).

Editing efficiency of some selected mutants was tested in Reporter3 cell line using the same manner as described for the NAAN reporter system, except that the cell line was changed from NAAN cell line to Reporter3 cell line.

According to the results of the first round of mutation, the entire 3D structure was corrected and marked, and data of the first round was placed in a new model for predictive analysis. Finally, possible second round mutation positions were analyzed and predicted, and mutations and detections were performed. By analogy, the best mutation combination of C12-279 was determined through a plurality of rounds of mutations, selections, and iterations. Table 15 shows the editing efficiency of C12-279 mutants in the Reporter3 cell line. An absolute value (average) of the editing efficiency of the C12-279-pCDH group, i.e., the C12-279 protein, is 8.55%.

TABLE 15

Editing efficiency of C12-279 mutants in Reporter3 cell line (Expressed as multiple of editing efficiency of C12-279)

| Mutation position 1 | Mutation position 2 | Mutation position 3 | Group | Multiple of editing efficiency of C12-279 |
|---|---|---|---|---|
| N/A | N/A | N/A | PEI-control | 0.02 ± 0.01 |
| N/A | N/A | N/A | Reporter3 cell line | 0.03 ± 0.02 |
| N/A | N/A | N/A | C12-279-pCDH | 1.00 ± 0.18 |
| D352R | N/A | N/A | C12-279-pCDH-01 | 1.18 ± 0.22 |
| G989R | N/A | N/A | C12-279-pCDH-04 | 1.27 ± 0.2 |
| Q186R | N/A | N/A | C12-279-pCDH-05 | 1.60 ± 0.32 |

TABLE 15-continued

Editing efficiency of C12-279 mutants in Reporter3 cell line (Expressed as multiple of editing efficiency of C12-279)

| Mutation position 1 | Mutation position 2 | Mutation position 3 | Group | Multiple of editing efficiency of C12-279 |
|---|---|---|---|---|
| L260R | N/A | N/A | C12-279-pCDH-11 | 0.66 ± 0.14 |
| A355R | N/A | N/A | C12-279-pCDH-12 | 0.96 ± 0.14 |
| E485R | N/A | N/A | C12-279-pCDH-22 | 1.15 ± 0.32 |
| D352R | Q186R | N/A | C12-279-pCDH-28 | 1.39 ± 0.25 |
| A355R | L260R | N/A | C12-279-pCDH-31 | 0.95 ± 0.22 |
| D352R | Q186R | 133R | C12-279-pCDH-34 | 1.51 ± 0.31 |
| D352R | Q186R | G184R | C12-279-pCDH-35 | 2.28 |
| D352R | Q186R | S185R | C12-279-pCDH-36 | 1.91 |
| D352R | Q186R | G256R | C12-279-pCDH-37 | 0.06 ± 0.01 |
| D352R | Q186R | Y278R | C12-279-pCDH-38 | 1.86 ± 0.06 |
| D352R | Q186R | S285R | C12-279-pCDH-39 | 1.87 ± 0.06 |
| D352R | Q186R | Y316R | C12-279-pCDH-40 | 1.12 ± 0.2 |
| D352R | Q186R | H350R | C12-279-pCDH-41 | 2.11 |
| D352R | Q186R | A356R | C12-279-pCDH-42 | 2.01 ± 0.18 |
| D352R | Q186R | Q469R | C12-279-pCDH-43 | 1.61 ± 0.22 |
| D352R | Q186R | S491R | C12-279-pCDH-44 | 1.41 ± 0.48 |
| D352R | Q186R | K521R | C12-279-pCDH-45 | 1.73 ± 0.07 |
| D352R | Q186R | P525R | C12-279-pCDH-46 | 1.40 ± 0.09 |
| D352R | Q186R | K629R | C12-279-pCDH-47 | 1.74 ± 0.09 |
| D352R | Q186R | N633R | C12-279-pCDH-48 | 1.84 ± 0.06 |
| D352R | Q186R | D841R | C12-279-pCDH-49 | 1.83 ± 0.00 |
| D352R | Q186R | N898R | C12-279-pCDH-50 | 1.69 ± 0.05 |
| D352R | Q186R | K987R | C12-279-pCDH-51 | 1.76 ± 0.07 |
| D352R | Q186R | T991R | C12-279-pCDH-52 | 1.32 |
| D352R | Q186R | D1010R | C12-279-pCDH-53 | 1.58 ± 0.29 |
| D352R | Q186R | E1013R | C12-279-pCDH-54 | 2.00 ± 0.04 |

Example 11. Design of C12-101-07 Protein Mutants and Detection of Editing Efficiency Mutants shown in Table 16 were designed for the C12-101-07 protein.

The vector plasmid of mutant was constructed using a manner basically the same as that in Example 10, and the editing efficiency was detected.

a. Detection of the editing efficiency of single point mutation based on NAAN reporter system.

For selected mutation positions, C12-101-07-GFPPAM (SEQ ID NO: 737) was used as a cloning template plasmid and a control plasmid for transfection test, and the mutation clone was constructed by molecular cloning point mutation, and the editing efficiency was detected. The results are shown in Table 16. The editing efficiency of different C12-101-07 mutants in NAAN cell line is expressed as a multiple of the editing efficiency of C12-101-07. An absolute value (average) of the editing efficiencies of the C12-101-07-GFPPAM group, i.e., the C12-101-07 protein, is 0.23%.

TABLE 16

Different mutants of C12-101-07

| Mutation position | Mutation vector | Editing efficiency in NAAN cell line, expressed as multiple of the editing efficiency of C12-101-07 |
|---|---|---|
| Q172R | C12-101-07-GFPPAM-01 | 2.08 ± 1.05 |
| G182R | C12-101-07-GFPPAM-02 | 0.01 ± 0.02 |
| E183R | C12-101-07-GFPPAM-03 | 0.95 ± 0.56 |
| G184R | C12-101-07-GFPPAM-04 | 0.02 ± 0.04 |

TABLE 16-continued

| Different mutants of C12-101-07 | | |
|---|---|---|
| Mutation position | Mutation vector | Editing efficiency in NAAN cell line, expressed as multiple of the editing efficiency of C12-101-07 |
| K185R | C12-101-07-GFPPAM-05 | 1.01 ± 0.47 |
| K186R | C12-101-07-GFPPAM-06 | 0.02 ± 0.02 |
| V243R | C12-101-07-GFPPAM-07 | 0.71 ± 0.27 |
| L297R | C12-101-07-GFPPAM-08 | 0.04 ± 0.00 |
| N317R | C12-101-07-GFPPAM-09 | 0.52 ± 0.12 |
| E363R | C12-101-07-GFPPAM-10 | 0.19 ± 0.12 |
| H366R | C12-101-07-GFPPAM-11 | 0.02 ± 0.02 |
| V426R | C12-101-07-GFPPAM-12 | 1.15 ± 0.59 |
| K429R | C12-101-07-GFPPAM-13 | 0.80 ± 0.36 |
| L433R | C12-101-07-GFPPAM-14 | 0.57 ± 0.28 |
| S452R | C12-101-07-GFPPAM-15 | 1.09 ± 0.26 |
| S455R | C12-101-07-GFPPAM-16 | 0.07 ± 0.02 |
| K918R | C12-101-07-GFPPAM-17 | 0.50 ± 0.11 |
| T919R | C12-101-07-GFPPAM-18 | 0.29 ± 0.15 |
| T920R | C12-101-07-GFPPAM-19 | 1.21 ± 0.70 |
| A922R | C12-101-07-GFPPAM-20 | 1.18 ± 0.41 |
| N/A | C12-101-07-GFPPAM | 1.00 ± 0.67 |

b. The mutation positions that significantly improved the editing efficiency in the first round of mutations were combined to try two-point mutations. The mutants shown in Table 17 were designed.

Mutation clones were constructed using a point mutation molecular cloning method and the editing efficiency was determined based on the NAAN cell line.

The results are shown in Table 17. The editing efficiency of different C12-101-07 mutants in the NAAN cell line is expressed as the multiple of the editing efficiency of C12-101-07.

TABLE 17

| C12-101-07 mutants | | | |
|---|---|---|---|
| Mutation position 1 | Mutation position 2 | Mutation vector | Editing efficiency in NAAN cell line, expressed as multiple of the editing efficiency of C12-101-07 |
| Q172R | V426R | pXC12-101-07-TwoMut-01 | 2.15 ± 1.05 |
| Q172R | S452R | pXC12-101-07-TwoMut-02 | 1.89 ± 0.68 |
| Q172R | T920R | pXC12-101-07-TwoMut-03 | 4.04 ± 1.00 |
| V426R | S452R | pXC12-101-07-TwoMut-04 | 1.56 ± 0.52 |
| V426R | T920R | pXC12-101-07-TwoMut-05 | 2.11 ± 0.79 |
| S452R | T920R | pXC12-101-07-TwoMut-06 | 1.19 ± 0.21 |
| N/A | N/A | pXC12-101-07-GFPPAM | 1.00 ± 0.37 |

c. Construction of Mutation Clones Targeting Reporter3 Cell Lines and Detection of the Editing Efficiency Using a manner basically the same as that of Example 10, the target sequence on the original C12-101-07-GFPPAM vector was replaced. The sgRNA target site for the NAAN cell line was replaced with a site targeting the Reporter3 cell line, resulting in the control plasmid 101-07-sgRNA02. Then, the mutant vector was constructed, and the editing efficiency was tested in the Reporter3 cell line.

The results are shown in Table 18. The editing efficiency of different C12-101-07 mutations in the Reporter3 cell line is expressed as a multiple of the editing efficiency of C12-101-07. The absolute value (average) of the editing efficiency of the 101-07-sgRNA02 control group, i.e., the C12-101-07 protein, is 10.32%.

TABLE 18

| Editing efficiency of different mutants of C12-101-07 in Reporter3 cell lines (Expressed as multiple of editing efficiency of C12-101-07) | | | |
|---|---|---|---|
| Mutation position 1 | Mutation position 2 | Vector | Editing efficiency, expressed as multiple of the editing efficiency of C12-101-07 |
| V15R | N/A | pXC12-101-07-21 | 1.67 ± 0.04 |
| A173W | N/A | pXC12-101-07-22 | 0.1 ± 0.01 |
| G239R | N/A | pXC12-101-07-23 | 0.04 ± 0.00 |
| D264R | N/A | pXC12-101-07-24 | 1.28 ± 0.16 |
| E271R | N/A | pXC12-101-07-25 | 0.96 ± 0.1 |
| Y295R | N/A | pXC12-101-07-26 | 0.53 ± 0.03 |
| T329R | N/A | pXC12-101-07-27 | 1.3 ± 0.17 |
| E331R | N/A | pXC12-101-07-28 | 1.06 ± 0.01 |
| I335R | N/A | pXC12-101-07-29 | 1.52 ± 0.16 |
| S430R | N/A | pXC12-101-07-30 | 0.79 ± 0.15 |
| S465R | N/A | pXC12-101-07-31 | 1.18 ± 0.37 |
| E493R | N/A | pXC12-101-07-32 | 1.61 ± 0.02 |
| P497R | N/A | pXC12-101-07-33 | 0.15 ± 0.04 |
| K587R | N/A | pXC12-101-07-34 | 0.3 ± 0.01 |
| E768R | N/A | pXC12-101-07-35 | 1.4 ± 0.07 |
| T825R | N/A | pXC12-101-07-36 | 0.95 ± 0.04 |
| A911R | N/A | pXC12-101-07-37 | 1.33 ± 0.21 |
| G914R | N/A | pXC12-101-07-38 | 0.26 ± 0.05 |
| K915R | N/A | pXC12-101-07-39 | 1.03 ± 0.26 |
| I916R | N/A | pXC12-101-07-40 | 0.51 ± 0.12 |
| E940R | N/A | pXC12-101-07-42 | 1.13 ± 0.11 |
| N347E | N/A | pXC12-101-07-43 | 0.99 ± 0.13 |
| K339R | N/A | pXC12-101-07-44 | 1.13 ± 0.01 |
| N347E | K339R | pXC12-101-07-45 | 1.16 ± 0.08 |
| Q172R | V426R | pXC12-101-07-TwoMut-01 | 2.020.06 |
| Q172R | S452R | pXC12-101-07-TwoMut-02 | 1.72 ± 0.09 |
| Q172R | T920R | pXC12-101-07-TwoMut-03 | 2.15 ± 0.12 |
| V426R | S452R | pXC12-101-07-TwoMut-04 | 1.56 ± 0.12 |
| V426R | T920R | pXC12-101-07-TwoMut-05 | Not detected |
| S452R | T920R | pXC12-101-07-TwoMut-06 | Not detected |
| N/A | N/A | 101-07-sgRNA02 control | 1.00 ± 0.11 |

Example 12. Construction of Different Mutants by Site-Directed Mutagenesis of C12-279 Protein The amino acid sequence of C12-279 protein was SEQ ID NO: 696. Two mutation primers F/R were designed at the mutation position, and the required mutation sequence was introduced through the primers. Combined with the universal primers at both ends of the vector, PCR amplification was performed to obtain two mutation fragments F1 and F2. The mutation fragments F1 and F2 were homologously recombined with the linearized vector to obtain a mutation plasmid. In this example, single-point mutation (D426R, L860R) mutants and multi-point mutation (D426R&L860R) mutants were constructed using the two amino acid positions 426 and 860. The specific steps were as follows.

The primers for site-directed mutagenesis at positions 426 and 860 are shown in Table 19.

TABLE 19

| Primers | |
|---|---|
| Primer name | Primer sequences |
| ChkCas12-PF1 | CCAAGCTGGCTAGCGTTTAAACTTAAG (SEQ ID NO: 731) |
| ChkCas12-PR2 | GCGACGCAATGATGTTTTTCGGTACC (SEQ ID NO: 736) |
| 279_426_F | gagttcaagAGAggcttcgacagagagc (underlined being introduced amino acid mutation) (SEQ ID NO: 756) |
| 279_426_R | tcgaagccTCTcttgaactcggcgcagtag (underlined being introduced amino acid mutation) (SEQ ID NO: 757) |
| 279_860_F | aaccAGGagacagaacaagggcgagg (underlined being introduced amino acid mutation) (SEQ ID NO: 758) |
| 279_860_R | ccttgttctgtctCCTggtttccagcttgttcag (underlined being introduced amino acid mutation) (SEQ ID NO: 759) |

Construction of Single Point Mutation Clones at Positions 426 and 860

Using C12-279-pCDH plasmid as a template, ChkCas12-PF1+279_426_R was subjected to PCR amplification (Yijin Bio, PC019, UltraHiPF™ DNA Polymerase Kit) to obtain mutation fragment D426R-F1, and ChkCas12-PR2+279_426_F was subjected to PCR amplification to obtain mutation fragment D426R-F2. Plasmid C12-279-pCDH was digested with HindIII+KpnI, and 5647 bp vector fragment was gel recovered (Guangzhou Meiji Biotechnology Co., Ltd., D2110, HiPure Gel Pure Micro Kit). The 5647 bp vector fragment was recombined in vitro with fragments D426R-F1 and D426R-F2 (NEB™, E2611L, Gibson Assembly® Master Mix), and the plasmid C12-279-pCDH-426 with position 426 mutation was obtained by heat shock transformation of *Escherichia coli.*

The same steps and methods were used, except that primer 279_426_F was replaced with 279_860_F and primer 279_426_R was replaced with 279_860_R, and the same amplification and recombination were performed. The plasmid C12-279-pCDH-860 of the position 860 mutation was obtained by heat shock transformation of *Escherichia coli.* The construction method of the Cas protein mutation plasmids of other different positions was consistent with the method for the positions 426 and 860, except that the mutation primers for each different position needed to be designed.

Verification of Editing Activity of Cas Protein Mutants

The test was conducted based on the Reporter3 cell line constructed in the above examples. The sequence between the start codon and the GFP reading frame was 32 bases, which was not an integer multiple of 3, resulting in abnormal reading frame of GFP and no expression of GFP. The Reporter3 cell line was edited using a target site whose PAM recognized by the Cas protein mutant was TTG and target sequence was CTCACCTCGCGACGCAATGATG (SEQ ID NO: 735), indels were generated, and a normal reading frame of GFP was restored. A flow cytometry was used to detect the proportion of cells that restored GFP expression to characterize the editing efficiency of different mutants. The specific operations were as follows.

Cell culture and plating: when the cell line was cultured to 70-80% confluence, the plating was performed, and the count of cells seeded in a 24-well plate was 5*10^5 cells/well.

Transfection: the transfection was performed 12-14 h after plating. 1.5 μL PEI (Yeasen Biotechnology™ and 500 ng mutation plasmid were added to 100 μL Opti-MEM™ reduced serum medium (Gibco, Thermo Fisher Scientific) per well of the 24-well plate, mixed, and added to the Reporter3 cell line for cell transfection after placing at room temperature for 20 min. Fresh culture medium was replaced after overnight transfection and continued to be cultured for 72 h, the flow cytometry was used for detection. The editing efficiency of different mutation clones were characterized according to a GFP-positive cell proportion, and the average of a plurality of batches of data was taken. The specific results are shown in Table 20 and FIG. 18. An average absolute value of the editing efficiency of a wild-type C12-279 group is 9.0%

TABLE 20

Editing efficiency of each mutant of C12-279 in Reporter3 cell line (Expressed as multiple of editing efficiency of C12-279)

| Group | Editing efficiency (expressed as multiple of the editing efficiency of C12-279) |
|---|---|
| Wild-type C12-279 | 1.00 |
| Mut-01 (Q186R) | 1.58 |
| Mut-02 (Q186 & D352R) | 1.62 |
| Mut-03 (G184R & Q186R & D352R) | 1.87 |
| Cell Line NC negative control | 0.05 |
| PEI NC negative control | 0.08 |
| 1R | 2.07 |
| 2R | 1.79 |
| 3R | 2.05 |
| 4R | 1.53 |
| 5R | 2.00 |
| 6R | 0.98 |
| 7R | 1.91 |
| 8R | 0.81 |
| 9R | 0.82 |
| 10R | 1.60 |
| 12R | 0.10 |
| 13R | 0.91 |
| 14R | 1.13 |
| 15R | 1.32 |
| 16R | 1.37 |
| 19R | 1.26 |
| 21R | 1.29 |
| 22R | 1.19 |
| 23R | 1.07 |
| 24R | 1.56 |

TABLE 20-continued

Editing efficiency of each mutant of C12-279 in Reporter3 cell line (Expressed as multiple of editing efficiency of C12-279)

| Group | Editing efficiency (expressed as multiple of the editing efficiency of C12-279) |
|---|---|
| 25R | 1.05 |
| 26R | 1.18 |
| 27R | 1.33 |
| 28R | 0.51 |
| 29R | 0.08 |
| 30R | 1.59 |
| 32R | 1.30 |
| 33R | 0.80 |
| 34R | 1.08 |
| 35R | 0.03 |
| 36R | 0.07 |
| 37R | 0.94 |
| 38R | 0.17 |
| 39R | 1.23 |
| 40R | 0.08 |
| 41R | 0.52 |
| 42R | 0.45 |
| 43R | 1.14 |
| 44R | 0.93 |
| 46R | 1.10 |
| 47R | 1.34 |
| 48R | 1.43 |
| 49R | 1.17 |
| 50R | 0.20 |
| 51R | 1.46 |
| 53R | 0.05 |
| 54R | 0.42 |
| 55R | 1.40 |
| 56R | 0.28 |
| 57R | 0.07 |
| 58R | 1.42 |
| 59R | 1.51 |
| 60R | 0.05 |
| 61R | 0.84 |
| 62R | 0.71 |
| 64R | 0.06 |
| 65R | 0.19 |
| 66R | 1.42 |
| 67R | 0.47 |
| 68R | 0.12 |
| 69R | 0.65 |
| 70R | 0.98 |
| 71R | 0.06 |
| 72R | 0.08 |
| 73R | 0.03 |
| 74R | 0.44 |
| 75R | 0.05 |
| 76R | 1.12 |
| 77R | 0.72 |
| 78R | 1.28 |
| 79R | 0.64 |
| 80R | 0.20 |
| 81R | 1.19 |
| 82R | 0.99 |
| 83R | 0.89 |
| 84R | 0.97 |
| 85R | 1.35 |
| 86R | 1.01 |
| 88R | 0.13 |
| 89R | 1.34 |
| 90R | 1.30 |
| 91R | 0.84 |
| 92R | 0.81 |
| 93R | 0.27 |
| 94R | 0.07 |
| 95R | 0.10 |
| 96R | 0.05 |
| 97R | 0.09 |
| 98R | 0.12 |
| 99R | 0.07 |
| 101R | 0.39 |
| 102R | 0.98 |
| 103R | 1.25 |

TABLE 20-continued

Editing efficiency of each mutant of C12-279 in Reporter3 cell line (Expressed as multiple of editing efficiency of C12-279)

| Group | Editing efficiency (expressed as multiple of the editing efficiency of C12-279) |
|---|---|
| 104R | 1.00 |
| 105R | 1.13 |
| 106R | 0.33 |
| 108R | 1.41 |
| 109R | 0.81 |
| 110R | 1.03 |
| 111R | 0.61 |
| 112R | 0.78 |
| 114R | 1.25 |
| 115R | 1.06 |
| 116R | 0.95 |
| 117R | 0.98 |
| 118R | 1.41 |
| 119R | 0.80 |
| 120R | 0.29 |
| 121R | 1.35 |
| 123R | 1.34 |
| 124R | 1.29 |
| 125R | 1.33 |
| 126R | 0.93 |
| 127R | 1.20 |
| 128R | 1.31 |
| 129R | 1.30 |
| 130R | 0.97 |
| 131R | 1.00 |
| 132R | 0.43 |
| 133R | 0.92 |
| 134R | 0.98 |
| 135R | 0.12 |
| 136R | 0.39 |
| 137R | 0.09 |
| 138R | 1.43 |
| 139R | 1.37 |
| 140R | 1.26 |
| 141R | 1.60 |
| 142R | 1.02 |
| 143R | 1.20 |
| 144R | 1.11 |
| 145R | 0.95 |
| 146R | 1.16 |
| 147R | 0.92 |
| 148R | 0.10 |
| 149R | 0.10 |
| 151R | 1.06 |
| 152R | 1.20 |
| 153R | 0.08 |
| 154R | 0.97 |
| 155R | 1.20 |
| 156R | 0.16 |
| 157R | 0.99 |
| 158R | 0.85 |
| 159R | 1.09 |
| 160R | 0.12 |
| 161R | 1.23 |
| 162R | 0.57 |
| 163R | 0.31 |
| 164R | 0.09 |
| 165R | 0.92 |
| 166R | 0.95 |
| 167R | 0.08 |
| 169R | 1.15 |
| 170R | 0.47 |
| 171R | 0.07 |
| 172R | 0.10 |
| 174R | 0.09 |
| 175R | 1.40 |
| 176R | 0.16 |
| 177R | 0.10 |
| 178R | 1.60 |
| 179R | 0.19 |
| 180R | 0.34 |
| 182R | 1.09 |
| 183R | 1.08 |

TABLE 20-continued

Editing efficiency of each mutant of C12-279 in Reporter3 cell line (Expressed as multiple of editing efficiency of C12-279)

| Group | Editing efficiency (expressed as multiple of the editing efficiency of C12-279) |
| --- | --- |
| 184R | 1.22 |
| 185R | 1.41 |
| 186R | 1.23 |
| 187R | 0.30 |
| 188R | 0.39 |
| 189R | 0.11 |
| 190R | 0.08 |
| 191R | 1.01 |
| 192R | 0.04 |
| 194R | 0.10 |
| 195R | 1.22 |
| 196R | 0.40 |
| 197R | 1.34 |
| 198R | 0.19 |
| 199R | 0.07 |
| 200R | 1.06 |
| 202R | 0.19 |
| 203R | 1.31 |
| 204R | 0.03 |
| 205R | 0.60 |
| 206R | 1.07 |
| 207R | 0.06 |
| 208R | 0.04 |
| 209R | 0.89 |
| 210R | 0.91 |
| 211R | 0.05 |
| 212R | 0.49 |
| 213R | 1.24 |
| 214R | 1.02 |
| 215R | 0.06 |
| 216R | 1.08 |
| 217R | 1.10 |
| 218R | 0.94 |
| 219R | 0.97 |
| 220R | 1.07 |
| 221R | 0.95 |
| 222R | 0.67 |
| 223R | 1.27 |
| 224R | 1.06 |
| 225R | 0.72 |
| 227R | 0.45 |
| 228R | 0.06 |
| 229R | 0.70 |
| 230R | 0.47 |
| 231R | 0.39 |
| 232R | 0.05 |
| 233R | 0.59 |
| 234R | 1.38 |
| 235R | 0.51 |
| 236R | 0.06 |
| 237R | 0.99 |
| 238R | 0.05 |
| 239R | 1.10 |
| 240R | 0.36 |
| 242R | 0.59 |
| 243R | 0.45 |
| 244R | 0.05 |
| 245R | 0.41 |
| 247R | 0.70 |
| 248R | 0.04 |
| 249R | 0.12 |
| 250R | 1.29 |
| 251R | 0.86 |
| 252R | 1.18 |
| 253R | 0.06 |
| 255R | 0.30 |
| 256R | 0.05 |
| 257R | 1.41 |
| 258R | 0.06 |
| 259R | 0.36 |
| 260R | 0.99 |
| 261R | 0.07 |
| 262R | 0.09 |

TABLE 20-continued

Editing efficiency of each mutant of C12-279 in Reporter3 cell line (Expressed as multiple of editing efficiency of C12-279)

| Group | Editing efficiency (expressed as multiple of the editing efficiency of C12-279) |
| --- | --- |
| 263R | 0.69 |
| 265R | 0.87 |
| 266R | 0.96 |
| 267R | 0.80 |
| 268R | 1.18 |
| 269R | 1.32 |
| 270R | 0.11 |
| 271R | 0.93 |
| 272R | 0.76 |
| 273R | 0.77 |
| 274R | 1.14 |
| 275R | 0.10 |
| 276R | 1.20 |
| 278R | 0.60 |
| 279R | 0.12 |
| 281R | 1.03 |
| 282R | 0.09 |
| 283R | 0.13 |
| 284R | 0.93 |
| 285R | 0.93 |
| 286R | 0.05 |
| 287R | 1.08 |
| 288R | 0.87 |
| 289R | 0.68 |
| 290R | 0.76 |
| 291R | 0.83 |
| 292R | 0.09 |
| 293R | 0.95 |
| 294R | 0.11 |
| 295R | 1.18 |
| 296R | 1.12 |
| 297R | 1.07 |
| 298R | 0.04 |
| 299R | 1.26 |
| 300R | 0.04 |
| 301R | 0.43 |
| 302R | 0.05 |
| 303R | 1.21 |
| 305R | 1.07 |
| 306R | 0.21 |
| 308R | 1.22 |
| 309R | 1.26 |
| 310R | 0.80 |
| 313R | 0.94 |
| 315R | 1.15 |
| 316R | 0.49 |
| 317R | 0.38 |
| 318R | 1.06 |
| 319R | 0.54 |
| 320R | 0.05 |
| 321R | 0.23 |
| 322R | 1.29 |
| 323R | 0.55 |
| 324R | 0.07 |
| 325R | 0.44 |
| 327R | 1.19 |
| 328R | 0.08 |
| 329R | 1.04 |
| 330R | 0.29 |
| 331R | 0.21 |
| 332R | 0.04 |
| 333R | 1.67 |
| 334R | 0.68 |
| 335R | 0.77 |
| 336R | 0.04 |
| 337R | 0.88 |
| 339R | 0.06 |
| 340R | 0.91 |
| 341R | 0.99 |
| 342R | 0.60 |
| 343R | 0.12 |
| 344R | 0.78 |
| 345R | 0.70 |

TABLE 20-continued

Editing efficiency of each mutant of C12-279 in Reporter3 cell line (Expressed as multiple of editing efficiency of C12-279)

| Group | Editing efficiency (expressed as multiple of the editing efficiency of C12-279) |
|---|---|
| 346R | 0.92 |
| 347R | 1.37 |
| 348R | 1.28 |
| 350R | 1.19 |
| 351R | 0.97 |
| 352R | 1.15 |
| 353R | 1.15 |
| 354R | 1.15 |
| 355R | 1.13 |
| 356R | 1.56 |
| 357R | 1.03 |
| 358R | 1.00 |
| 359R | 1.03 |
| 360R | 1.12 |
| 361R | 1.25 |
| 362R | 0.96 |
| 363R | 1.13 |
| 364R | 0.81 |
| 365R | 0.84 |
| 366R | 0.03 |
| 367R | 0.18 |
| 368R | 1.00 |
| 369R | 1.29 |
| 370R | 0.42 |
| 371R | 1.18 |
| 372R | 1.06 |
| 373R | 0.04 |
| 374R | 0.02 |
| 375R | 1.40 |
| 376R | 1.60 |
| 377R | 1.20 |
| 378R | 1.41 |
| 379R | 1.57 |
| 380R | 1.07 |
| 381R | 1.05 |
| 382R | 1.01 |
| 383R | 1.51 |
| 384R | 0.04 |
| 385R | 1.20 |
| 386R | 1.09 |
| 387R | 1.14 |
| 388R | 0.99 |
| 389R | 0.06 |
| 390R | 0.26 |
| 391R | 1.05 |
| 392R | 1.15 |
| 393R | 0.04 |
| 394R | 0.87 |
| 395R | 0.10 |
| 396R | 1.28 |
| 397R | 1.40 |
| 398R | 0.99 |
| 399R | 1.01 |
| 400R | 1.62 |
| 401R | 1.03 |
| 402R | 1.21 |
| 403R | 1.20 |
| 404R | 1.02 |
| 405R | 1.33 |
| 406R | 1.13 |
| 407R | 1.07 |
| 408R | 1.38 |
| 409R | 1.09 |
| 410R | 0.81 |
| 411R | 1.20 |
| 412R | 1.21 |
| 413R | 1.01 |
| 414R | 0.91 |
| 415R | 0.03 |
| 416R | 1.48 |
| 417R | 0.92 |
| 418R | 1.30 |
| 419R | 0.87 |

TABLE 20-continued

Editing efficiency of each mutant of C12-279 in Reporter3 cell line (Expressed as multiple of editing efficiency of C12-279)

| Group | Editing efficiency (expressed as multiple of the editing efficiency of C12-279) |
|---|---|
| 420R | 1.10 |
| 421R | 1.17 |
| 422R | 1.19 |
| 423R | 0.79 |
| 424R | 1.12 |
| 425R | 1.24 |
| 426R | 2.22 |
| 427R | 0.68 |
| 428R | 0.44 |
| 429R | 0.74 |
| 431R | 1.15 |
| 432R | 0.05 |
| 433R | 0.91 |
| 435R | 1.29 |
| 436R | 0.04 |
| 437R | 0.29 |
| 439R | 0.50 |
| 440R | 0.04 |
| 441R | 1.18 |
| 442R | 1.06 |
| 443R | 1.44 |
| 444R | 1.10 |
| 446R | 1.24 |
| 447R | 1.23 |
| 448R | 1.12 |
| 449R | 1.46 |
| 450R | 1.27 |
| 451R | 0.97 |
| 452R | 1.04 |
| 453R | 0.04 |
| 454R | 1.29 |
| 455R | 1.04 |
| 456R | 1.45 |
| 457R | 0.11 |
| 458R | 0.03 |
| 459R | 1.53 |
| 460R | 0.03 |
| 461R | 1.11 |
| 462R | 1.58 |
| 463R | 1.05 |
| 464R | 0.81 |
| 467R | 1.22 |
| 469R | 1.46 |
| 470R | 1.03 |
| 471R | 0.10 |
| 472R | 0.10 |
| 473R | 1.19 |
| 474R | 0.03 |
| 475R | 1.28 |
| 476R | 0.99 |
| 477R | 0.20 |
| 478R | 1.13 |
| 479R | 0.48 |
| 480R | 1.03 |
| 481R | 0.46 |
| 482R | 1.30 |
| 483R | 0.41 |
| 484R | 1.68 |
| 485R | 1.52 |
| 486R | 0.47 |
| 487R | 0.22 |
| 488R | 0.91 |
| 489R | 1.16 |
| 490R | 0.77 |
| 491R | 1.12 |
| 492R | 1.04 |
| 493R | 0.82 |
| 494R | 1.31 |
| 496R | 1.18 |
| 497R | 0.75 |
| 499R | 1.07 |
| 500R | 0.94 |
| 501R | 1.33 |

TABLE 20-continued

Editing efficiency of each mutant of C12-279 in Reporter3 cell line (Expressed as multiple of editing efficiency of C12-279)

| Group | Editing efficiency (expressed as multiple of the editing efficiency of C12-279) |
|---|---|
| 502R | 1.02 |
| 503R | 0.61 |
| 504R | 0.56 |
| 506R | 0.10 |
| 507R | 0.93 |
| 508R | 0.05 |
| 509R | 1.47 |
| 510R | 0.07 |
| 511R | 0.85 |
| 512R | 0.60 |
| 513R | 0.22 |
| 514R | 1.10 |
| 515R | 1.36 |
| 516R | 0.85 |
| 517R | 0.62 |
| 518R | 1.11 |
| 519R | 0.09 |
| 520R | 0.86 |
| 521R | 0.90 |
| 522R | 1.17 |
| 523R | 0.10 |
| 524R | 0.33 |
| 525R | 0.89 |
| 526R | 0.08 |
| 527R | 1.00 |
| 528R | 0.04 |
| 529R | 0.38 |
| 531R | 0.07 |
| 532R | 0.42 |
| 533R | 1.07 |
| 534R | 0.09 |
| 535R | 0.31 |
| 536R | 0.39 |
| 537R | 0.62 |
| 538R | 1.02 |
| 539R | 0.83 |
| 540R | 1.04 |
| 541R | 0.91 |
| 542R | 1.21 |
| 543R | 0.12 |
| 544R | 0.05 |
| 545R | 0.81 |
| 546R | 1.11 |
| 547R | 0.72 |
| 548R | 1.02 |
| 549R | 1.21 |
| 550R | 0.08 |
| 552R | 0.68 |
| 553R | 1.23 |
| 555R | 0.35 |
| 556R | 1.17 |
| 557R | 0.79 |
| 558R | 1.37 |
| 559R | 1.17 |
| 560R | 0.92 |
| 561R | 1.41 |
| 562R | 1.08 |
| 563R | 1.12 |
| 564R | 1.08 |
| 565R | 1.23 |
| 566R | 1.07 |
| 567R | 1.25 |
| 568R | 1.34 |
| 569R | 0.67 |
| 570R | 0.07 |
| 571R | 0.07 |
| 572R | 1.29 |
| 573R | 0.10 |
| 574R | 1.16 |
| 575R | 0.85 |
| 576R | 0.67 |
| 577R | 1.28 |
| 578R | 1.15 |

TABLE 20-continued

Editing efficiency of each mutant of C12-279 in Reporter3 cell line (Expressed as multiple of editing efficiency of C12-279)

| Group | Editing efficiency (expressed as multiple of the editing efficiency of C12-279) |
|---|---|
| 579R | 0.96 |
| 580R | 1.38 |
| 581R | 1.19 |
| 582R | 1.16 |
| 583R | 0.72 |
| 584R | 1.18 |
| 585R | 1.31 |
| 586R | 1.12 |
| 587R | 0.73 |
| 589R | 1.01 |
| 590R | 1.13 |
| 592R | 0.10 |
| 593R | 1.20 |
| 594R | 0.09 |
| 595R | 1.16 |
| 596R | 0.07 |
| 597R | 1.45 |
| 598R | 1.22 |
| 599R | 1.23 |
| 601R | 0.25 |
| 602R | 0.74 |
| 603R | 1.01 |
| 604R | 0.79 |
| 605R | 1.26 |
| 606R | 1.13 |
| 607R | 1.52 |
| 608R | 0.82 |
| 609R | 1.45 |
| 610R | 1.15 |
| 611R | 0.68 |
| 612R | 1.20 |
| 613R | 0.07 |
| 614R | 0.79 |
| 615R | 0.04 |
| 616R | 0.06 |
| 618R | 1.35 |
| 619R | 0.09 |
| 620R | 0.77 |
| 621R | 1.28 |
| 622R | 0.05 |
| 623R | 1.44 |
| 624R | 0.05 |
| 625R | 1.00 |
| 626R | 0.07 |
| 627R | 0.24 |
| 628R | 0.47 |
| 630R | 0.55 |
| 631R | 1.17 |
| 632R | 1.05 |
| 633R | 1.19 |
| 634R | 1.26 |
| 635R | 1.18 |
| 636R | 1.38 |
| 637R | 1.17 |
| 638R | 1.69 |
| 639R | 1.55 |
| 640R | 1.55 |
| 641R | 0.95 |
| 642R | 1.30 |
| 643R | 1.14 |
| 644R | 0.69 |
| 645R | 0.44 |
| 646R | 1.24 |
| 647R | 0.53 |
| 648R | 0.04 |
| 649R | 0.12 |
| 650R | 0.04 |
| 651R | 0.04 |
| 652R | 0.04 |
| 653R | 0.37 |
| 654R | 0.56 |
| 655R | 0.69 |
| 656R | 0.83 |

TABLE 20-continued

Editing efficiency of each mutant of C12-279 in Reporter3 cell line (Expressed as multiple of editing efficiency of C12-279)

| Group | Editing efficiency (expressed as multiple of the editing efficiency of C12-279) |
|---|---|
| 657R | 1.10 |
| 658R | 0.07 |
| 659R | 0.14 |
| 660R | 0.54 |
| 661R | 0.10 |
| 662R | 0.75 |
| 663R | 0.09 |
| 664R | 1.06 |
| 665R | 1.17 |
| 666R | 1.04 |
| 667R | 1.06 |
| 668R | 1.10 |
| 669R | 1.09 |
| 670R | 1.25 |
| 671R | 1.06 |
| 672R | 1.16 |
| 673R | 1.20 |
| 674R | 1.22 |
| 675R | 1.21 |
| 676R | 0.21 |
| 678R | 1.19 |
| 679R | 1.20 |
| 680R | 1.01 |
| 681R | 0.12 |
| 683R | 0.46 |
| 684R | 0.10 |
| 685R | 1.02 |
| 686R | 0.05 |
| 688R | 0.39 |
| 689R | 0.04 |
| 691R | 0.13 |
| 692R | 0.86 |
| 693R | 0.10 |
| 694R | 1.20 |
| 695R | 0.54 |
| 696R | 1.32 |
| 697R | 1.70 |
| 698R | 0.90 |
| 699R | 1.37 |
| 700R | 0.84 |
| 701R | 0.70 |
| 702R | 0.11 |
| 703R | 0.12 |
| 704R | 0.08 |
| 705R | 0.53 |
| 706R | 0.35 |
| 707R | 0.49 |
| 708R | 0.12 |
| 709R | 0.51 |
| 710R | 1.14 |
| 711R | 0.77 |
| 712R | 1.35 |
| 713R | 0.90 |
| 715R | 1.17 |
| 716R | 1.19 |
| 717R | 0.69 |
| 719R | 1.23 |
| 720R | 0.86 |
| 721R | 1.24 |
| 722R | 1.42 |
| 723R | 1.08 |
| 724R | 1.14 |
| 725R | 1.24 |
| 727R | 1.32 |
| 728R | 1.26 |
| 729R | 1.21 |
| 730R | 1.20 |
| 731R | 1.44 |
| 732R | 1.39 |
| 733R | 1.49 |
| 734R | 1.34 |
| 736R | 0.92 |
| 737R | 1.22 |

TABLE 20-continued

Editing efficiency of each mutant of C12-279 in Reporter3 cell line (Expressed as multiple of editing efficiency of C12-279)

| Group | Editing efficiency (expressed as multiple of the editing efficiency of C12-279) |
|---|---|
| 738R | 1.05 |
| 739R | 1.08 |
| 740R | 1.17 |
| 741R | 1.16 |
| 742R | 1.27 |
| 743R | 0.99 |
| 744R | 0.08 |
| 745R | 1.33 |
| 746R | 1.16 |
| 747R | 1.03 |
| 748R | 1.19 |
| 749R | 1.01 |
| 751R | 1.39 |
| 752R | 0.95 |
| 753R | 1.01 |
| 754R | 1.24 |
| 755R | 1.42 |
| 756R | 1.18 |
| 758R | 1.41 |
| 759R | 1.13 |
| 760R | 1.39 |
| 761R | 0.19 |
| 762R | 0.25 |
| 764R | 0.64 |
| 765R | 0.91 |
| 766R | 1.18 |
| 767R | 1.34 |
| 768R | 1.36 |
| 769R | 0.24 |
| 771R | 1.63 |
| 772R | 0.11 |
| 773R | 1.56 |
| 774R | 1.19 |
| 775R | 1.09 |
| 776R | 1.19 |
| 779R | 1.55 |
| 780R | 1.18 |
| 781R | 1.66 |
| 782R | 1.24 |
| 783R | 0.06 |
| 784R | 1.51 |
| 785R | 1.77 |
| 786R | 1.54 |
| 787R | 0.06 |
| 789R | 1.41 |
| 790R | 1.06 |
| 791R | 0.11 |
| 792R | 1.84 |
| 794R | 1.49 |
| 795R | 0.30 |
| 797R | 1.08 |
| 798R | 1.40 |
| 800R | 0.09 |
| 801R | 0.23 |
| 802R | 1.33 |
| 804R | 0.61 |
| 805R | 0.22 |
| 806R | 0.13 |
| 807R | 0.11 |
| 808R | 0.90 |
| 809R | 0.62 |
| 810R | 1.11 |
| 811R | 0.22 |
| 812R | 0.94 |
| 813R | 0.99 |
| 814R | 0.42 |
| 815R | 0.47 |
| 817R | 1.16 |
| 818R | 0.23 |
| 819R | 1.14 |
| 821R | 0.91 |
| 822R | 1.48 |
| 823R | 1.76 |

TABLE 20-continued

Editing efficiency of each mutant of C12-279 in Reporter3 cell line (Expressed as multiple of editing efficiency of C12-279)

| Group | Editing efficiency (expressed as multiple of the editing efficiency of C12-279) |
|---|---|
| 824R | 0.32 |
| 825R | 1.46 |
| 826R | 1.60 |
| 827R | 0.34 |
| 828R | 1.19 |
| 829R | 1.73 |
| 830R | 1.79 |
| 831R | 0.76 |
| 832R | 1.25 |
| 833R | 1.51 |
| 834R | 1.40 |
| 835R | 1.32 |
| 836R | 1.53 |
| 837R | 1.32 |
| 838R | 1.21 |
| 839R | 1.30 |
| 840R | 1.36 |
| 841R | 0.11 |
| 842R | 1.58 |
| 844R | 1.14 |
| 845R | 1.72 |
| 846R | 1.91 |
| 847R | 1.61 |
| 848R | 1.38 |
| 849R | 0.07 |
| 850R | 1.74 |
| 851R | 1.59 |
| 852R | 1.22 |
| 853R | 1.67 |
| 854R | 0.08 |
| 855R | 1.48 |
| 856R | 1.45 |
| 857R | 1.19 |
| 858R | 1.87 |
| 859R | 1.40 |
| 860R | 1.84 |
| 862R | 1.14 |
| 863R | 1.27 |
| 864R | 0.80 |
| 865R | 1.07 |
| 866R | 1.58 |
| 867R | 0.19 |
| 868R | 0.54 |
| 870R | 0.90 |
| 872R | 0.14 |
| 873R | 1.11 |
| 874R | 0.49 |
| 875R | 1.03 |
| 876R | 0.05 |
| 877R | 0.96 |
| 879R | 1.23 |
| 880R | 0.85 |
| 881R | 1.39 |
| 882R | 0.93 |
| 883R | 1.13 |
| 884R | 1.43 |
| 885R | 0.13 |
| 886R | 1.25 |
| 887R | 1.12 |
| 888R | 0.05 |
| 890R | 0.05 |
| 891R | 0.06 |
| 892R | 1.42 |
| 893R | 1.64 |
| 894R | 0.04 |
| 895R | 0.31 |
| 896R | 0.74 |
| 897R | 0.53 |
| 898R | 1.07 |
| 899R | 1.33 |
| 900R | 1.44 |
| 901R | 1.30 |
| 902R | 0.30 |

TABLE 20-continued

Editing efficiency of each mutant of C12-279 in Reporter3 cell line (Expressed as multiple of editing efficiency of C12-279)

| Group | Editing efficiency (expressed as multiple of the editing efficiency of C12-279) |
|---|---|
| 903R | 1.27 |
| 904R | 1.62 |
| 905R | 1.36 |
| 906R | 0.15 |
| 909R | 1.05 |
| 910R | 1.18 |
| 911R | 0.17 |
| 912R | 0.06 |
| 913R | 1.32 |
| 914R | 0.26 |
| 916R | 1.29 |
| 917R | 0.31 |
| 918R | 0.40 |
| 919R | 1.04 |
| 920R | 0.47 |
| 921R | 0.38 |
| 922R | 1.36 |
| 923R | 0.43 |
| 924R | 1.25 |
| 925R | 0.11 |
| 926R | 1.49 |
| 927R | 0.19 |
| 928R | 0.59 |
| 930R | 0.83 |
| 931R | 1.10 |
| 932R | 1.21 |
| 933R | 0.87 |
| 934R | 0.94 |
| 935R | 0.13 |
| 936R | 0.45 |
| 937R | 0.19 |
| 938R | 0.90 |
| 939R | 0.49 |
| 940R | 0.04 |
| 941R | 0.05 |
| 942R | 0.10 |
| 943R | 0.11 |
| 944R | 0.11 |
| 945R | 0.08 |
| 946R | 0.05 |
| 947R | 0.94 |
| 948R | 0.10 |
| 949R | 1.05 |
| 950R | 0.95 |
| 951R | 0.88 |
| 952R | 0.85 |
| 953R | 1.02 |
| 954R | 1.11 |
| 955R | 0.42 |
| 956R | 1.44 |
| 957R | 0.85 |
| 958R | 1.20 |
| 959R | 0.46 |
| 960R | 1.20 |
| 961R | 0.07 |
| 963R | 0.11 |
| 964R | 1.10 |
| 965R | 1.06 |
| 966R | 0.95 |
| 967R | 1.17 |
| 968R | 0.19 |
| 969R | 0.84 |
| 970R | 0.57 |
| 971R | 0.09 |
| 972R | 0.84 |
| 973R | 0.46 |
| 974R | 0.96 |
| 975R | 0.36 |
| 976R | 0.53 |
| 977R | 0.76 |
| 979R | 0.07 |
| 980R | 0.55 |
| 981R | 1.20 |

TABLE 20-continued

Editing efficiency of each mutant of C12-279 in Reporter3 cell line (Expressed as multiple of editing efficiency of C12-279)

| Group | Editing efficiency (expressed as multiple of the editing efficiency of C12-279) |
|---|---|
| 982R | 0.67 |
| 983R | 0.15 |
| 985R | 1.81 |
| 986R | 0.89 |
| 987R | 0.08 |
| 988R | 1.60 |
| 989R | 1.55 |
| 990R | 1.06 |
| 991R | 0.84 |
| 992R | 1.56 |
| 993R | 1.43 |
| 994R | 0.80 |
| 995R | 0.26 |
| 996R | 1.51 |
| 997R | 1.32 |
| 998R | 0.10 |
| 999R | 0.12 |
| 1000R | 0.08 |
| 1001R | 0.97 |
| 1002R | 0.07 |
| 1003R | 0.17 |
| 1004R | 0.13 |
| 1005R | 0.45 |
| 1006R | 0.09 |
| 1007R | 0.91 |
| 1008R | 0.13 |
| 1009R | 1.39 |
| 1010R | 0.67 |
| 1011R | 0.99 |
| 1012R | 1.06 |
| 1013R | 0.10 |
| 1014R | 1.04 |
| 1015R | 0.09 |
| 1016R | 1.42 |
| 1017R | 1.06 |
| 1018R | 0.77 |
| 1021R | 0.89 |
| 1023R | 1.00 |
| 1024R | 1.12 |
| 1025R | 0.86 |
| 1026R | 0.56 |
| 1027R | 0.98 |
| 1028R | 0.78 |
| 1029R | 1.00 |
| 1030R | 0.90 |
| 1031R | 0.11 |
| 1032R | 1.17 |
| 1033R | 1.40 |
| 1035R | 0.09 |
| 1036R | 1.33 |
| 1037R | 1.17 |
| 1038R | 1.31 |
| 1039R | 1.17 |
| 1040R | 1.10 |
| 1041R | 1.18 |
| 1042R | 0.06 |
| 1043R | 1.09 |
| 1044R | 1.29 |
| 1045R | 1.42 |
| 1046R | 0.11 |
| 1047R | 0.83 |
| 1048R | 0.05 |
| 1049R | 0.05 |
| 1050R | 1.50 |
| 1052R | 0.07 |
| 1053R | 0.05 |
| 1055R | 1.19 |
| 1056R | 0.12 |
| 1057R | 0.08 |
| 1058R | 0.06 |
| 1059R | 1.05 |
| 1060R | 0.84 |
| 1061R | 1.29 |
| 1062R | 0.11 |
| 1063R | 0.07 |
| 1064R | 0.69 |
| 1065R | 1.05 |
| 1066R | 0.43 |
| 1067R | 1.33 |
| 1068R | 1.11 |
| 1069R | 0.84 |
| 1070R | 1.07 |
| 1071R | 1.10 |
| 1072R | 1.10 |
| 1073R | 1.44 |
| 1074R | 1.50 |
| 1075R | 1.16 |
| 1076R | 0.62 |
| 1077R | 0.34 |
| 1078R | 1.05 |
| 1079R | 0.07 |
| 1080R | 0.23 |
| 1081R | 0.09 |
| 1082R | 0.08 |
| 1083R | 0.06 |
| 1084R | 0.06 |
| 1085R | 0.10 |
| 1086R | 0.06 |
| 1087R | 0.06 |
| 1088R | 0.05 |
| 1089R | 0.06 |
| 1090R | 0.03 |
| 1091R | 0.10 |
| 1092R | 0.20 |
| 1093R | 0.27 |
| 1094R | 0.23 |
| 1095R | 1.41 |
| 1096R | 1.16 |
| 1097R | 1.15 |
| 1098R | 1.15 |
| 1100R | 1.59 |
| 1101R | 1.38 |
| 1102R | 1.29 |
| 1103R | 1.32 |
| 1104R | 1.35 |
| 1105R | 1.34 |
| 1107R | 1.39 |
| 1108R | 1.22 |
| 1109R | 0.20 |
| 1110R | 0.44 |
| 1111R | 1.20 |
| 1112R | 1.20 |
| 1113R | 1.02 |
| 1115R | 1.21 |
| 1116R | 1.28 |
| 1117R | 1.06 |
| 1120R | 1.26 |
| 1122R | 1.21 |
| 1123R | 1.22 |
| 1124R | 1.40 |
| 1125R | 1.30 |
| 1128R | 0.78 |
| 1129R | 1.40 |
| 1130R | 1.05 |
| 1131R | 1.34 |
| 1132R | 1.92 |
| 1133R | 1.32 |
| 1134R | 1.29 |
| 1135R | 1.37 |

In the table, nR (n is an integer) denotes that the amino acid residue at position n is mutated to R.

Construction of clones with different mutation position combinations of Cas mutant proteins and verification of editing activity According to the editing efficiency results of different mutation positions mentioned above, different mutation positions were selected for multiple mutation combinations, and the construction of plasmid of the Cas mutant with double-position 426 and 860 was introduced as an example.

Using C12-279-pCDH plasmid as the template, Chk-Cas12-PF1+279_426_R was subjected to PCR amplification to obtain the mutation fragment D426R-F1, 279_426_F+279_860_R was subjected to PCR amplification to obtain the mutation fragment D426R-L860R-F1, and ChkCas12-PR2+279_860_F was subjected to PCR amplification to obtain the mutation fragment L860R-F2. The plasmid C12-279-pCDH was digested with HindIII+KpnI, and the 5647 bp vector fragment was recovered by gel extraction, and was recombined in vitro with fragments D426R-F1, D426R-L860R-F1, and L860R-F2, and the mutant plasmid C12-279-pCDH-426-860 was obtained by heat shock transformation of *Escherichia coli*. The construction manner of other plasmids with multiple mutations was consistent with that of C12-279-pCDH-426-860.

The amino acid sequence of the Mut-02-1-426-846-858-860 mutation is:

```
                                        (SEQ ID NO: 760)
RFVVLSVNQFRCNPNAFRQASMKTDDEKKDTAIKSYTSWLLPNDRKEKDM

VRSFLALDQGSRFFFDLMQAWYGGLTPDIIKSVTKERDLVDLWCAIYWFR

PMKKELASHPIDRVDLAKTFQRYYGGPASDVVQEYLSASIGEDCCWNDCR

QKYQEFCKNLGVDFTPDLKTLVREKLIAVALNDGSRAAISNLFGNGGKED

RNVKVNICKKILIALEKAGKSVKYVRDVQSIILKCANAKDREDFNRIYAD

KNGRPGTLLLLLDRKGENTYDAEVLKRYLRKTIKSKNAPLVWNYNQKLFE
```

-continued

```
YIERGIRNLLRRTINYDAWAWGEMWRVGHTPLQTKATRNYHFAQEQLKRH

SRIAAASQSSHAIAVALNEFFESPFFDGENPFTICPHHLGKNLEKLFKAW

ADEKNQTDEEDAGETAITDYCAEFKRGFDREPIRNLLRYVYASLRSKYSA

KELIQAAKYNQQFERYQRQKAHPVTPDNQGYTWPEAVIKPSKAERKNREN

SLDTRIWVSVKLLQKDGTWEKHHIPFYNLRFFEEVYAAASIAEDMPSPTF

RNSRFGFKLPKLLNTHAKINKKKDGKKDKKAVNAAKREARIYLAAKEGR

LPAPSVPLDKLSAVIARVNGKFQVTVPVKFKVNKQPKYPLPQLGQIILGY

DQNLTANHAWALFEVVTEDTPGAHFCRNQYLRVLKTGQVRSITKTKDGQE

IDQLSYDGLEYKEYGEWRKQAKKFASQWYITTKVRKGKETTLLSQPALER

FESIEKYKPALYRENKEYARLLLAVIRRKTLNELEEIRPEIFRLVEQGFG

ICRFGSLSLSSFEAIRAAKAVIYGYFSTALKHDHNTPITDDERQARDPEL

FGLLNKLRTRRQNKGEEKINRAANALIRIALENKADFIRGEGDLPTTNKS

VKKGQNSRSMDWLARGLFNKICQLAVMHNIIPTAANPHSTSHQDPFEHNK

DFDDPQPAMKCRYAEFKIEDIGDSVLERLGTSLRNAKAGQTGAYYYKGAQ

DFLAHYGLQDIEEELKKCRRGRKANMPCWELQKRLIQKLGSKDAVVYIPM

RGGRIYLATHSVTTGAKPIIFNGEEVWVSNADEIAAVNIGLTIIPTSKKD

EEHPDRENDDKAIRKSVRRPRKSGERRSGDKMPATARKT.
```

The editing activity of multi-point mutations was verified using the same manner as described above in this example.

The results indicate that the editing efficiency of most multi-point mutants are improved compared with the wild-type, and specific results are shown in Table 21 and FIG. 19. The absolute value of the editing efficiency of the wild type C12-279 group is 8.7%.

TABLE 21

Editing efficiency of each mutant of C12-279 in Reporter3 cell line (expressed as multiple of editing efficiency of C12-279)

| Group | Editing efficiency (expressed as multiple of the editing efficiency of C12-279) | Group | Editing efficiency (expressed as multiple of the editing efficiency of C12-279) |
|---|---|---|---|
| Wt wild type | 1.00 | 858 + 988 + 1132 | 1.97 |
| 3 | 1.71 | 988 + 1132 | 1.53 |
| 5 | 1.66 | Mut-01 | 1.58 |
| 7 | 1.48 | Mut-01 + 376 | 1.99 |
| 333 | 1.57 | Mut-01 + 485 | 1.59 |
| 376 | 1.59 | Mut-02 | 1.72 |
| 426 | 1.85 | Mut-02 + 1 + 3 + 426 + 858 + 860 | 3.70 |
| 485 | 1.48 | Mut-02 + 1 + 3 + 426 + 860 | 3.35 |
| 846 | 1.61 | Mut-02 + 1 + 333 + 426 + 858 + 860 | 3.68 |
| 858 | 1.57 | Mut-02 + 1 + 333 + 426 + 860 | 2.84 |
| 860 | 1.78 | Mut-02 + 1 + 426 + 485 + 858 + 860 | 3.67 |
| 988 | 1.66 | Mut-02 + 1 + 426 + 485 + 860 | 3.25 |
| 1132 | 1.70 | Mut-02 + 1 + 426 + 846 + 858 + 860 | 3.88 |
| 2 + 5 + 846 + 858 | 2.68 | Mut-02 + 1 + 426 + 846 + 860 | 3.83 |
| 3 + 1132 | 0.66 | Mut-02 + 1 + 5 + 426 + 858 + 860 | 3.77 |
| 3 + 333 + 426 | 2.29 | Mut-02 + 1 + 5 + 426 + 860 | 3.62 |
| 3 + 426 + 858 | 2.51 | Mut-02 + 1132 | 2.10 |
| 3 + 426 + 860 | 2.42 | Mut-02 + 3 | 0.13 |
| 3 + 5 | 2.06 | Mut-02 + 3 + 376 + 426 | 2.57 |
| 3 + 7 | 1.38 | Mut-02 + 3 + 426 | 2.66 |
| 3 + 846 | 1.71 | Mut-02 + 3 + 426 + 858 + 860 | 3.58 |
| 3 + 846 + 1132 | 1.92 | Mut-02 + 3 + 426 + 860 | 3.68 |
| 3 + 846 + 858 | 2.50 | Mut-02 + 333 | 2.03 |
| 3 + 846 + 860 | 2.53 | Mut-02 + 333 + 336 + 352 + 376 + 426 | 0.13 |
| 3 + 846 + 988 | 2.32 | Mut-02 + 333 + 352 + 376 + 426 | 2.24 |
| 3 + 858 | 2.15 | Mut-02 + 333 + 426 | 2.40 |

TABLE 21-continued

Editing efficiency of each mutant of C12-279 in Reporter3 cell line (expressed as multiple of editing efficiency of C12-279)

| Group | Editing efficiency (expressed as multiple of the editing efficiency of C12-279) | Group | Editing efficiency (expressed as multiple of the editing efficiency of C12-279) |
|---|---|---|---|
| 3 + 858 + 860 | 2.48 | Mut-02 + 333 + 426 + 858 + 860 | 3.54 |
| 3 + 858 + 988 | 2.18 | Mut-02 + 333 + 426 + 860 | 3.49 |
| 3 + 860 | 2.41 | Mut-02 + 376 | 0.14 |
| 333 + 376 | 1.94 | Mut-02 + 376 + 426 | 2.54 |
| 333 + 376 + 426 | 2.75 | Mut-02 + 376 + 426 + 485 + 860 | 2.21 |
| 333 + 376 + 485 | 1.83 | Mut-02 + 376 + 426 + 860 + 865 | 2.57 |
| 333 + 426 | 2.47 | Mut-02 + 426 | 2.36 |
| 333 + 426 + 1132 | 2.27 | Mut-02 + 426 + 1132 | 1.87 |
| 333 + 426 + 485 | 2.33 | Mut-02 + 426 + 485 | 2.28 |
| 333 + 426 + 846 | 2.34 | Mut-02 + 426 + 485 + 858 + 860 | 3.06 |
| 333 + 426 + 858 | 2.28 | Mut-02 + 426 + 485 + 860 | 2.04 |
| 333 + 426 + 860 | 1.77 | Mut-02 + 426 + 485 + 860 | 3.04 |
| 333 + 485 | 1.79 | Mut-02 + 426 + 846 | 2.65 |
| 352 + 426 | 1.79 | Mut-02 + 426 + 846 + 858 + 860 | 3.29 |
| 376 + 426 | 1.94 | Mut-02 + 426 + 846 + 860 | 3.48 |
| 376 + 426 + 485 + 660 | 1.86 | Mut-02 + 426 + 860 | 3.06 |
| 376 + 485 | 1.51 | Mut-02 + 485 | 1.31 |
| 426 + 649 | 2.05 | Mut-02 + 5 | 2.69 |
| 426 + 846 + 858 + 860 | 3.02 | Mut-02 + 5 + 426 | 2.77 |
| 426 + 858 + 860 | 3.15 | Mut-02 + 5 + 426 + 858 + 860 | 3.58 |
| 426 + 858 + 988 | 0.62 | Mut-02 + 5 + 426 + 860 | 3.38 |
| 428 + 485 | 2.26 | Mut-02 + 639 | 2.18 |
| 5 + 1132 | 1.45 | Mut-02 + 7 | 2.60 |
| 5 + 333 + 426 | 2.97 | Mut-02 + 858 | 2.48 |
| 5 + 426 + 858 | 2.87 | Mut-02 + 860 | 3.00 |
| 5 + 426 + 860 | 3.30 | Mut-02 + 988 | 1.75 |
| 5 + 846 | 1.84 | Mut-03 | 2.01 |
| 5 + 846 + 1132 | 1.90 | Mut-03 + 1132 | 1.61 |
| 5 + 846 + 858 | 2.65 | Mut-03 + 3 | 1.94 |
| 5 + 846 + 860 | 2.32 | Mut-03 + 3 + 107 + 426 | 2.81 |
| 5 + 858 | 2.15 | Mut-03 + 3 + 376 | 2.44 |
| 5 + 858 + 988 | 2.18 | Mut-03 + 3 + 639 | 2.40 |
| 5 + 860 | 1.73 | Mut-03 + 333 | 1.78 |
| 7 + 426 + 846 | 3.02 | Mut-03 + 333 + 336 | 0.87 |
| 7 + 426 + 858 | 3.09 | Mut-03 + 376 | 2.30 |
| 846 + 1132 | 1.66 | Mut-03 + 376 + 1132 | 2.99 |
| 846 + 585 + 860 | 2.36 | Mut-03 + 426 | 2.20 |
| 846 + 858 | 1.96 | Mut-03 + 426 + 1132 | 2.11 |
| 846 + 858 + 1132 | 1.77 | Mut-03 + 485 | 1.51 |
| 846 + 858 + 988 | 2.51 | Mut-03 + 5 | 2.08 |
| 846 + 860 | 1.99 | Mut-03 + 639 | 2.13 |
| 846 + 860 + 1132 | 1.84 | Mut-03 + 639 + 1132 | 1.82 |
| 846 + 860 + 988 | 2.42 | Mut-03 + 7 | 1.19 |
| 846 + 988 | 1.72 | Mut-03 + 846 | 2.13 |
| 858 + 860 | 2.23 | Mut-03 + 858 | 2.06 |
| 858 + 860 + 1132 | 2.06 | Mut-03 + 860 | 2.47 |
| 858 + 988 | 2.11 | | |

In the table, the integer n indicates that the amino acid residue at position n is mutated to R. Mut-01 is a Q186R mutant, Mut-02 is a Q186R & D352R double-point mutant, and Mut-03 is a G184R+Q186R+D352R triple-point mutant; 5+426+860 indicates that the amino acid residues at positions 5, 426, and 860 are mutated to R, simultaneously; Mut-02+860 indicates a multi-point mutant obtained by introducing an additional mutation at position 860 (mutated to R) based on the Mut-02 mutant; and other multi-point mutants are similar (mutated to R).

Example 13. Detection of Editing Efficiency of Different Mutants for Different Target Sites of TTR and HBG In this example, for the TTR gene (GenBank® database accession number: NG_009490.1) and the HBG gene (GenBank® database accession number: NC_000011.10), the PAM sequence was selected as the target site of TTN, and sgRNAs targeting different positions were designed and constructed (as shown in Table 22) for combination with different mutants to detect the editing efficiency.

TABLE 22

| sgRNA targeting TTR and HBG | | | |
|---|---|---|---|
| sgRNA name | PAM | Target site | sgRNA sequence |
| C12-279-TTR01 | TTC | catgagcatgcagaggtgagt at (SEQ ID NO: 722) | gtaatgcgtctcccattgacgccatgagcatgcagaggtg agtat (SEQ ID NO: 783) |
| C12-279-TTR02 | TTT | tcctataaggtgtgaaagtctg g (SEQ ID NO: 761) | gtaatgcgtctcccattgacgctcctataaggtgtgaaagt ctgg (SEQ ID NO: 784) |
| C12-279-TTR03 | TTC | cagtaagatttggtgtctat (SEQ ID NO: 762) | gtaatgcgtctcccattgacgccagtaagatttggtgtctat (SEQ ID NO: 785) |
| C12-279-TTR04 | TTG | tatatcccttctacaaattcctc (SEQ ID NO: 763) | gtaatgcgtctcccattgacgctatatcccttctacaaattcc tc (SEQ ID NO: 786) |
| C12-279-TTR05 | TTT | GTGTCTGAGGCTG GCCCTACGGTG (SEQ ID NO: 764) | gtaatgcgtctcccattgacgcGTGTCTGAGGC TGGCCCTACGGTG (SEQ ID NO: 787) |
| C12-279-TTR06 | TTC | AGAAAGGCTGCTG ATGACACCTG (SEQ ID NO: 765) | gtaatgcgtctcccattgacgcAGAAAGGCTGC TGATGACACCTG (SEQ ID NO: 788) |
| C12-279-TTR07 | TTG | GCATCTCCCCATTC CATGAGCATG (SEQ ID NO: 766) | gtaatgcgtctcccattgacgcGCATCTCCCCAT TCCATGAGCATG (SEQ ID NO: 789) |
| C12-279-TTR08 | TTC | ACAGCCAACGACT CCGGCCCCG (SEQ ID NO: 767) | gtaatgcgtctcccattgacgcACAGCCAACGA CTCCGGCCCCG (SEQ ID NO: 790) |
| C12-279-TTR09 | TTG | TAGAAGGGATATA CAAAGTGGAA (SEQ ID NO: 768) | gtaatgcgtctcccattgacgcTAGAAGGGATA TACAAAGTGGAA (SEQ ID NO: 791) |
| C12-279-TTR10 | TTC | TAGATGCTGTCCG AG GCAGTCCTG (SEQ ID NO: 769) | gtaatgcgtctcccattgacgcTAGATGCTGTC CGAGGCAGTCCTG (SEQ ID NO: 792) |
| C12-279-TTR11 | TTT | GGTGTCTATTTCCA CTTTGTATA (SEQ ID NO: 770) | gtaatgcgtctcccattgacgcGGTGTCTATTTC CACTTTGTATA (SEQ ID NO: 793) |
| C12-279-TTR12 | TTT | CTGAACACATGCA CGGCCACATTG (SEQ ID NO: 771) | gtaatgcgtctcccattgacgcCTGAACACATG CACGGCCACATTG (SEQ ID NO: 794) |
| C12-279-TTR13 | TTA | CCCAGAGGCAAAT GGCTCCCAGG (SEQ ID NO: 772) | gtaatgcgtctcccattgacgcCCCAGAGGCAA ATGGCTCCCAGG (SEQ ID NO: 795) |
| C12-279-TTR14 | TTC | CTCCTCAGTTGTG AGCCCATGCA (SEQ ID NO: 773) | gtaatgcgtctcccattgacgcCTCCTCAGTIGT GAGCCCATGCA (SEQ ID NO: 796) |
| C12-279-HBG01 | TTG | GCCAGCCTTGCCT TGACCAATAG (SEQ ID NO: 774) | gtaatgcgtctcccattgacgcGCCAGCCTTGC CTTGACCAATAG (SEQ ID NO: 797) |
| C12-279-HBG02 | TTG | ACCAATAGTCTTA GAGTATCCAG (SEQ ID NO: 775) | gtaatgcgtctcccattgacgcACCAATAGTCT TAGAGTATCCAG (SEQ ID NO: 798) |
| C12-279-HBG03 | TTG | CCTTGTCAAGGCT ATTGGTCAAG (SEQ ID NO: 776) | gtaatgcgtctcccattgacgcCCTTGTCAAGG CTATTGGTCAAG (SEQ ID NO: 799) |
| C12-279-HBG04 | TTG | CCTTGACCAATAG CCTTGACAAG (SEQ ID NO: 777) | gtaatgcgtctcccattgacgcCCTTGACCAAT AGCCTTGACAAG (SEQ ID NO: 800) |
| C12-279-HBG05 | TTG | ACCAATAGCCTTG ACAAGGCAAA (SEQ ID NO: 778) | gtaatgcgtctcccattgacgcACCAATAGCCT TGACAAGGCAAA (SEQ ID NO: 801) |
| C12-279-HBG06 | TTG | GTCAAGGCAAGGC TGGCCAACCC (SEQ ID NO: 779) | gtaatgcgtctcccattgacgcGTCAAGGCAAG GCTGGCCAACCC (SEQ ID NO: 802) |

TABLE 22-continued sgRNA targeting TTR and HBG

| sgRNA name | PAM | Target site | sgRNA sequence |
|---|---|---|---|
| C12-279-HBG07 | TTG | GTCAAGTTTGCCT GTCAAGGC (SEQ ID NO: 780) | gtaatgcgtctcccattgacgcGTCAAGTTTGC CTTGTCAAGGC (SEQ ID NO: 803) |
| C12-279-HBG08 | TTG | TCAAGGCTATTGG TCAAGGCAAG (SEQ ID NO: 781) | gtaatgcgtctcccattgacgcTCAAGGCTATT GGTCAAGGCAAG (SEQ ID NO: 804) |
| C12-279-HBG09 | TTG | ACAAGGCAAACTT GACCAATAGTC (SEQ ID NO: 782) | gtaatgcgtctcccattgacgcACAAGGCAAAC TTGACCAATAGTC (SEQ ID NO: 805) |

The sgRNA plasmids were constructed according to the sgRNA sequences in the above table: the vector plasmid SpCas9-gRNA-pUC57Kan was linearized using BbsI (Thermo Fisher Scientific™) and XhoI (Thermo Fisher Scientific™), the primers were synthesized for different sgRNA sequences, annealed and connected to the linearized vector, and *Escherichia coli* was transformed to obtain the final sgRNA expression vector plasmid.

Different mutant plasmids were combined with different sgRNA plasmids, and HEK293T cells were transfected with PEI. After 48 h, the cells were collected and lysed using DirectPCR® Lysis Reagent (cell lysis reagent) (Viagen™: 302-C). Different primers were selected according to different target sites for PCR amplification and Sanger sequencing. The editing efficiency was analyzed using TIDE.

Specific amplification and sequencing primers were shown in Table 23. The experiment was repeated for three times, and the editing efficiency results are shown in FIGS. 20A and 20B. Each sgRNA group in each batch of experiments generates effective editing, and the editing efficiency at many target sites is better than that of wild-type C12-297.

TABLE 23

Primers for amplification and sequencing of different target sites

| Amplification primer name | Primer sequence | Corresponding sgRNA | Sequencing primer |
|---|---|---|---|
| ChkTTR-PF1 | GAACGAATGTTCCGATGCTCTAAT C (SEQ ID NO: 806) | C12-279-TTR05 | ChkTTR-PF1 |
| ChkTTR-PR1 | AATGAGGTAGAATGCTCAGAGTTCA AGT (SEQ ID NO: 807) | | |
| ChkTTR-PF2 | CAACTGTTCTCAGGGGGACCTATTTT C (SEQ ID NO: 808) | C12-279-TTR06, C12-279-TTR10, | ChkTTR-PF2 |
| ChkTTR-PR2 | CTCTACTGTCTGCCCCTAAATGATGC (SEQ ID NO: 809) | C12-279-TTR12, C12-279-TTR13 | |
| ChkTTR-PF3 | TGCCATTTAATTTCAGTTAGGAGTTTT C (SEQ ID NO: 810) | C12-279-TTR01, C12-279-TTR02, C12-279-TTR03, C12-279-TTR04, | ChkTTR-PF3 |
| ChkTTR-PR3 | CAGACCTCCGAGAAGCCAGATGT (SEQ ID NO: 811) | C12-279-TTR07, C12-279-TTR09, C12-279-TTR11 C12-279-TTR14 | |
| ChkTTR-PF4 | CAAGACCTGACTCTGTACTCCTGCTC T (SEQ ID NO: 812) | C12-279-TTR08 | ChkTTR-PR4 |
| ChkTTR-PR4 | ATTTGGATCTCTCCTAGCGTTCTGC (SEQ ID NO: 813) | | |
| ChkHBG01-PF1 | ACGGCTGACAAAAGAAGTCCTGG (SEQ ID NO: 814) | C12-279-HBG01 to | ChkHBG01-PR1 |
| ChkHBG01-PR1 | CATGGGTAGACAACCAGGAGCC (SEQ ID NO: 815) | C12-279-HBG09 | |

Example 14. Preparation and Activity Detection of Inactivated C12-279 Mutant

On the basis of the multi-point mutants designed in the previous examples, any one or more of the D651A, E891A, and D1082A mutations were further introduced, and the mutation clone plasmid was constructed using the same manner as in the previous example 10. Editing was performed in the Reporter3 cell line, and an analysis was performed on the proportion of cells that restored GFP expression after editing by flow cytometry to determine the editing efficiency of the mutant. Specific results are shown in FIG. 21. As long as each mutation in the figure contains at least one of D651A, E891A, and D1082A mutations, the editing efficiency is reduced to less than 1.3%. DeadCas12 (dCas12) may be obtained by introducing any of D651A, E891A, and D1082A.

The amino acid sequence of the dCas mutant Mut-02-1-426-846-858-860-D651A-E891A-D1082A is:

(SEQ ID NO: 816)

RFVVLSVNQFRCNPNAFRQASMKTDDEKKDTAIKSYTSWLLPNDRKEKDM
VRSFLALDQGSRFFFDLMQAWYGGLTPDIIKSVTKERDLVDLWCAIYWFR
PMKKELASHPIDRVDLAKTFQRYYGGPASDVVQEYLSASIGEDCCWNDCR
QKYQEFCKNLGVDFTPDLKTLVREKLIAVALNDGSRAAISNLFGNGGKED
RNVKVNICKKILIALEKAGKSVKYVRDVQSIILKCANAKDREDFNRIYAD
KNGRPGTLLLLLDRKGENTYDAEVLKRYLRKTIKSKNAPLVWNYNQKLFE
YIERGIRNLLRRTINYDAWAWGEMWRVGHTPLQTKATRNYHFAQEQLKRH
SRIAAASQSSHAIAVALNEFFESPFFDGENPFTICPHHLGKNLEKLFKAW
ADEKNQTDEEDAGETAITDYCAEFKRGFDREPIRNLLRYVYASLRSKYSA
KELIQAAKYNQQFERYQRQKAHPVTPDNQGYTWPEAVIKPSKAERKNREN
SLDTRIWVSVKLLQKDGTWEKHHIPFYNLRFFEEVYAAASIAEDMPSPTF

-continued

RNSRFGFKLPKLLNTHAKINKKKKDGKKDKKAVNAAKREARIYLAAKEGR
LPAPSVPLDKLSAVIARVNGKFQVTVPVKFKVNKQPKYPLPQLGQIILGY
AQNLTANHAWALFEVVTEDTPGAHFCRNQYLRVLKTGQVRSITKTKDGQE
IDQLSYDGLEYKEYGEWRKQAKKFASQWYITTKVRKGKETTLLSQPALER
FESIEKYKPALYRFNKEYARLLLAVIRRKTLNELEEIRPEIFRLVEQGFG
ICRFGSLSLSSFEAIRAAKAVIYGYFSTALKHDHNTPITDDERQARDPEL
FGLLNKLRTRRQNKGEEKINRAANALIRIALENKADFIRGAGDLPTTNKS
VKKGQNSRSMDWLARGLFNKICQLAVMHNIIPTAANPHSTSHQDPFEHNK
DFDDPQPAMKCRYAEFKIEDIGDSVLERLGTSLRNAKAGQTGAYYYKGAQ
DFLAHYGLQDIEEELKKCRRGRKANMPCWELQKRLIQKLGSKDAVVYIPM
RGGRIYLATHSVTTGAKPIIFNGEEVWVSNAAEIAAVNIGLTIIPTSKKD
EEHPDRENDDKAIRKSVRRPRKSGERRSGDKMPATARKT.

Example 15. mRNA+gRNA Delivery

The TTR gene was edited using the encoding mRNA of the Mut-02-3-426-860 mutant (obtained by in vitro transcription) together with the modified gRNA (as shown in Table 24).

TABLE 24

| Modified gRNA | | | |
|---|---|---|---|
| gRNA name | gRNA sequence (including modifications) | Modification | Editing efficiency determined by Sanger sequencing |
| C279-dmTTR01-01 | dAdTdGdTdGdTdTdTdTdGdT dCdAdAdAdAdGdAdCdCdTdTd TdTrGrUrArArUrGrCrGrUrCrUr CrCrArUrUrGrArCrGrCrCrArUr GrArGrCrArUrGrCrArGrArGrGr UrGrArGrUrA*mU (SEQ ID NO: 817) | adding a 25-nt DNA sequence to the 5' end and modifying the last nucleotide at the 3' end with phosphorothioate and 2'-oxymethylation. | 52.0% |
| C279-mTTR01-01 | mG*mU*mA*rArUrGrCrGrUrCr UrCrCrArUrUrGrArCrGrCrArUr GrArGrCrArUrGrCrArGrArGrGr UrGrArG*mU*mA*mU (SEQ ID NO: 818) | modifying three nucleotides at the 5' and 3' ends with phosphorothioate and 2'-oxymethyl | 29.5% |
| C279-dmTTR01-02 | dGdTdTdGdCdAdAdTdCdCdCd AdAdGrGrUrArArUrGrCrGrUrCr UrCrCrArUrGrArCrGrCrCrArUr GrArGrCrArUrGrCrArGrArGrGr UrGrArGrUrA*mU (SEQ ID NO: 819) | adding a 14-nt DNA sequence to the 5' end and modifying the last nucleotide at the 3' end with phosphorothioate and 2'-oxymethyl. | 47.5% |
| C279-mTTR01-02 | mG*rUrArArUrGrCrGrUrCrUrCr CrArUrUrGrArCrGrCrArUrGrAr GrCrArUrGrCrArGrArGrGrUrGr ArGrUrA*mU (SEQ ID NO: 820) | modifying a base at the 5' and 3' ends with phosphorothioate and 2'-oxymethyl | 26.8% |

In the table, "r" indicates a natural base, "d" indicates a deoxy modification, "m" indicates a methylation modification, and "*" indicates a phosphorothioate modification.

HEK293 cells were transformed with mRNA and gRNA by electroporation. After 48 h, cells were collected and lysed using DirectPCR® Lysis Reagent (cell lysis reagent) (Viagen™: 302-C). After that, a Sanger sequencing was performed on the lysed cells, and the editing efficiency was analyzed using TIDE. The results are shown in Table 24.

After adding DNA nucleotide sequence at the 3' end, the editing activity is significantly improved. For example, the added sequence is as follows.

dAdTdGdTdGdTdTdTdTdTdGdTdCdAdAdAdA-dGdAdCdCdTdTdTdT (SEQ ID NO: 821) or dGdTdTdGdCdAdAdTdCdCdCdAdAdG (SEQ ID NO: 822).

In addition, primers TTR-NGS-PF2 (GCGTAACTTAATCCAGACTTTCACACCTT, SEQ ID NO: 823) and TTR-NGS-PR2 (GGTCATTCATCACCTTCCTTAGGACA, SEQ ID NO: 824) were used for PCR amplification and library construction, and an NGS sequencing was performed to detect the editing efficiency. The electroporation editing efficiency of a combination of the mutants Mut-02-3-426-860 and C279-dmTTR01-01 reaches 79.64%.

Subsequently, C279-dmTTR01-02 was tested in combination with different mutants. The specific NGS sequencing results are shown in Table 25 and FIG. 22.

TABLE 25

Editing efficiency of modified gRNA (C279-dmTTR01-02) combined with different mutants (NGS assay)

| Mutant | sgRNA | Editing efficiency determined by NGS |
|---|---|---|
| Mut-02-426-860 | C279-dmTTR01-02 | 24.63% |
| Mut-02-5-426-860 | C279-dmTTR01-02 | 63.48% |
| Mut-02-1-5-426-858-860 | C279-dmTTR01-02 | 92.18% |
| Mut-02-1-426-846-858-860 | C279-dmTTR01-02 | 88.05% |
| Mut-02-1-3-426-858-860 | C279-dmTTR01-02 | 89.67% |
| Mut-02-3-426-860 | C279-dmTTR01-02 | 79.99% |

Example 16. Verification of Editing Efficiency of Different Endogenous Target Genes Different gRNA target sites were designed according to different disease-related target sites (Table 26), and the mutant Mut-02-1-426-846-858-860 protein was edited in combination with the gRNA in Table 26. The same manner as in example 13 was used, including the plasmid construction, the transfection, and the editing efficiency detection. The results are shown in Table 26.

TABLE 26

Editing efficiency of targeting different endogenous genes

| Name | Target gene | Sequence of PAM position | gRNA guide sequence | Editing efficiency |
|---|---|---|---|---|
| sgRNA-BCL11A-01-CTX-001-PAM-TTC | BCL11A | TTC | ctggagcctgtgataaaagcaac (SEQ ID NO: 825) | 27.40% |
| sgRNA-BCL11A-02-CTX-001-PAM-TGC | BCL11A | TGC | aagctaacagttgcttttatcac (SEQ ID NO: 826) | 1% |
| sgRNA-HBG-01-ZBTB7A-binding-site-PAM-TTG | HBG | TTG | cattgagatagtgtggggaaggg (SEQ ID NO: 827) | 10.40% |
| sgRNA-HBG-02-ZBTB7A-binding-site-PAM-TTT | HBG | TTT | gcattgagatagtgtggggaagg (SEQ ID NO: 828) | 10.90% |
| sgRNA-HBG-03-ZBTB7A-binding-site-PAM-TTG | HBG | TTG | agatagtgtggggaaggggcccc (SEQ ID NO: 829) | 23.20% |
| sgRNA-HBG-04-ZBTB7A-binding-site-PAM-TTG | HBG | TTG | ggggccccttccccacactatct (SEQ ID NO: 830) | 18.80% |
| sgRNA-HBG-05-ZBTB7A-binding-site-PAM-TAT | HBG | TAT | cctcttggggggccccttccccac (SEQ ID NO: 831) | 1% |
| sgRNA-HBG-06-ZBTB7A-binding-site-PAM-GTA | HBG | GTA | tcctcttggggccccttcccca (SEQ ID NO: 832) | 1.20% |
| sgRNA-HBG-07-ZBTB7A-binding-site-PAM-TTA | HBG | TTA | gcagtatcctcttgggggcccct (SEQ ID NO: 833) | 1.60% |
| sgRNA-HBG-08-(-175)-PAM-TTC | HBG | TTC | cccacactatctcaatgcaaata (SEQ ID NO: 834) | 43.10% |
| sgRNA-HBG-09-(-175)-PAM-TTT | HBG | TTT | cagacagatatttgcattgagat (SEQ ID NO: 835) | 39.40% |
| sgRNA-HBG-10-(-175)-PAM-TTT | HBG | TTT | agccagggaccgtttcagacaga (SEQ ID NO: 836) | 34.20% |
| sgRNA-HBG-11-(-88)-PAM-TTG | HBG | TTG | acaaggcaaacttgaccaatagt (SEQ ID NO: 837) | 33.20% |
| sgRNA-HBG-12-(-73)-PAM-TTG | HBG | TTG | accaatagtcttagagtatccag (SEQ ID NO: 775) | 14.80% |

TABLE 26-continued

| Name | Target gene | Sequence of PAM position | gRNA guide sequence | Editing efficiency |
|---|---|---|---|---|
| Editing efficiency of targeting different endogenous genes | | | | |
| sgRNA-HBG-13-(-56)-PAM-TTC | HBG | TTC | atccctagccagccgccggcccc (SEQ ID NO: 838) | 14.70% |
| sgRNA-BACH2-01-PAM-TTG | BACH2 | TTG | tagggtaccctcgtgcacccggg (SEQ ID NO: 839) | 9.60% |
| sgRNA-BACH2-02-PAM-TTC | BACH2 | TTC | cgcggcagccactcgctggtatc (SEQ ID NO: 840) | 29.70% |
| sgRNA-BACH2-03-PAM-TTG | BACH2 | TTG | gtccttgaggacagacaccactg (SEQ ID NO: 841) | 7.10% |
| sgRNA-BACH2-04-PAM-TTC | BACH2 | TTC | atccttgttttccagtggtgtct (SEQ ID NO: 842) | 17% |
| sgRNA-BACH2-05-PAM-TTG | BACH2 | TTG | gaagagttgaccatcagttatgg (SEQ ID NO: 843) | 28.70% |
| KLKB1-sgRNA01 | KLKB1 | TTC | CTCTACTCCTCAAGAA ACACCA (SEQ ID NO: 844) | 19% |
| KLKB1-sgRNA02 | KLKB1 | TTG | ACACAGAACCCTGCC ATTCTAAA (SEQ ID NO: 845) | 27.20% |
| KLKB1-sgRNA03 | KLKB1 | TTC | AGTCTGCACAACAAA AACAAGCA (SEQ ID NO: 846) | 24.30% |
| KLKB1-sgRNA04 | KLKB1 | TTG | GGGTGATAGGTGCAGA TGGTCCG (SEQ ID NO: 847) | 21.20% |
| KLKB1-sgRNA05 | KLKB1 | TTA | CCCAACAGTTGGTATA AATTGTG (SEQ ID NO: 848) | Not detected |
| KLKB1-sgRNA06 | KLKB1 | TTT | CAGTTCTGCACAACA AAAACAAGC (SEQ ID NO: 849) | 25.50% |
| KLKB1-sgRNA07 | KLKB1 | TTC | AGGTGGTCCCTTAGTT TGCAAAC (SEQ ID NO: 850) | 14.60% |
| KLKB1-sgRNA08 | KLKB1 | TTT | GGGGTGTACATGGAA GCTACATC (SEQ ID NO: 851) | 23.40% |
| KLKB1-sgRNA09 | KLKB1 | TTG | CCTATTAAAGTACAGT CC CGGAG (SEQ ID NO: 852) | 1% |
| KLKB1-sgRNA10 | KLKB1 | TTA | TAGCGGTAGGGTTCCT CCGGGA (SEQ ID NO: 853) | 9.40% |
| PCSK9-sgRNA01 | PCSK9 | TTC | CGTGCTCGGGTGCTTC GGCCAGG (SEQ ID NO: 854) | 10% |
| PCSK9-sgRNA02 | PCSK9 | TTA | CCCCTCCACGGTACCG GGCGGAT (SEQ ID NO: 855) | 20.40% |
| PCSK9-sgRNA03 | PCSK9 | TTC | ATCCGCCCGGTACCGT GGAGGGG (SEQ ID NO: 856) | 17.60% |
| PCSK9-sgRNA04 | PCSK9 | TTG | GCAGTTGAGCACGCG CAGGCTGC (SEQ ID NO: 857) | 21% |

TABLE 26-continued

Editing efficiency of targeting different endogenous genes

| Name | Target gene | Sequence of PAM position | gRNA guide sequence | Editing efficiency |
|---|---|---|---|---|
| PCSK9-sgRNA05 | PCSK9 | TTG | GCCACGCCGGCATCCC GCCCGCT (SEQ ID NO: 858) | 4.90% |
| PCSK9-sgRNA06 | PCSK9 | TTG | AGGACGCGGCTGTAC CCACCCGC (SEQ ID NO: 859) | 8.20% |
| PCSK9-sgRNA07 | PCSK9 | TTT | GGCCGCTGTGTGGAC CTCTTTGC (SEQ ID NO: 860) | 7.80% |
| PCSK9-sgRNA08 | PCSK9 | TTG | TCTACGGCGTAGGCCC CCAGGAC (SEQ ID NO: 861) | 29.00% |
| SOD1-sgRNA01 | SOD1 | TTG | CCCAAGTCTCCAACAT GCCTAAT (SEQ ID NO: 862) | 35.60% |
| SOD1-sgRNA02 | SOD1 | TTC | CCCACAACCTTCACTG GTCCATTA (SEQ ID NO: 863) | 32.10% |
| SOD1-sgRNA03 | SOD1 | TTA | ATGCTTCCCCACACCT TCACTGG (SEQ ID NO: 864) | 34.30% |
| SOD1-sgRNA04 | SOD1 | TTA | AGCATCTTGTTACCTC TCTTCAT (SEQ ID NO: 865) | Not detected |
| SOD1-sgRNA05 | SOD1 | TTG | GGCAATGTGACTGCTG ACAAAGA (SEQ ID NO: 866) | 38.20% |
| SOD1-sgRNA06 | SOD1 | TTC | AGCACGCACACGGCC TTCGTCGC (SEQ ID NO: 867) | 21.50% |
| SOD1-sgRNA07 | SOD1 | TTA | AAGGACTGACTGAAG GCCTGCAT (SEQ ID NO: 868) | 33.20% |
| BACE1-sgRNA01 | BACE1 | TTG | AGGGGGAAGCCAGCA CCACAAAG (SEQ ID NO: 869) | 28.90% |
| BACE1-sgRNA02 | BACE1 | TTC | CCTCTTAGTACAACTA TGACAAG (SEQ ID NO: 870) | Not detected |
| BACE1-sgRNA03 | BACE1 | TTC | CCAGTCATCTCACTCT ACCTAAT (SEQ ID NO: 871) | 24.50% |
| BACE1-sgRNA04 | BACE1 | TTG | CCCTCTCCCCAGTGCA CGATGAG (SEQ ID NO: 872) | 18.90% |
| BACE1-sgRNA05 | BACE1 | TTC | AGCAGGGAGATGTCAT CAGCAAA (SEQ ID NO: 873) | 27.90% |
| BACE1-sgRNA06 | BACE1 | TTA | GGTAGAGTGAGATGA CTGGGAAA (SEQ ID NO: 874) | 10.80% |
| BACE1-sgRNA07 | BACE1 | TTC | CCCCTCAACCAGTCTG AAGTGCT (SEQ ID NO: 875) | 35.30% |
| BACE1-sgRNA08 | BACE1 | TTC | AGATCCTGTCCATTGA TCTCCAC (SEQ ID NO: 876) | 5.70% |

TABLE 26-continued

| Editing efficiency of targeting different endogenous genes | | | | |
|---|---|---|---|---|
| Name | Target gene | Sequence of PAM position | gRNA guide sequence | Editing efficiency |
| BACE1-sgRNA09 | BACE1 | TTG | GCACGCACAGTGACG TTGGGGCC (SEQ ID NO: 877) | 4.30% |

Example 17. PAM Recognition of C12-279 Mutant Mut-02-1-426-846-858-860

Using the same manner as in the previous examples, the PAM recognized by the mutant Mut-02-1-426-846-858-860 was 5'-WTN-3' (W is A or T) by performing bacterial editing experiments in vivo and NGS sequencing, as shown in FIG. 23.

Although the specific examples of the present disclosure are described above, those skilled in the art should understand that these are only examples, and that various changes or modifications may be made to these examples without departing from the principles and essence of the present disclosure. Therefore, the scope of protection of the present disclosure is limited by the attached claims.

Example 18. Verification of Base Editing Activity

Based on the Mut-02-1-3-426-846-858-860 mutant, D651A, E891A and D1082A mutations were introduced to obtain dCas12 (SEQ ID NO: 975), a mutant version that lost the cutting ability. The deaminase domain was then fused to obtain a base editor. The editor fused with adenine deaminase was named ABE-dCas279-pCDNA3.1-01 (SEQ ID NO: 976). The base editing efficiency was tested for different targets, The experimental methods such as sgRNA construction, transfection, and editing efficiency detection are basically the same as those in Example 13. The final results are shown in Table 28.

TABLE 28

| Single base editing efficiency | | | | |
|---|---|---|---|---|
| Target Gene | PAM | Spacer Sequence | Spacer (SEQ ID NO) | Base editing efficiency |
| TTR | TTC | CATGAGCATGCAGAGGTGAGTAT | 722 | A8 base 14%<br>A12 base 11%<br>A22 base 10% |
| TTR | TTG | GCATCTCCCCATTCCATGAGCATG | 766 | A11 base 23% |
| TTR | TTG | TAGAAGGGATATACAAAGTGGAA | 768 | A11 base 23%<br>A13 base 9% |
| HBG | TTG | CCTTGACCAATAGCCTTGACAAG | 777 | A12 base 2% |

Example 19. CrRNA Backbone Sequence Modification

The crRNA (guide sequence SEQ ID NO: 735) with mutation of DR sequence (skeleton sequence) was tested in combination with Mut-02-1-426-846-858-860 (named C12-279-V4). The editing system was transfected into the Reporter 3 cell line using a method substantially the same as that in Example 10 above, and the gene editing activity before and after the crRNA mutation was characterized by GFP fluorescence intensity by flow cytometry. As shown in Table 29.

TABLE 29

| Designed mutants of DR sequences | | |
|---|---|---|
| Grouping | DR sequence | DR sequence (SEQ ID NO) |
| wt DR | gtaatgcgTctcccattg Acgc | 704 |
| DR-01 | gtaatgcgGctcccattgCcgc | 977 |
| DR-02 | gtaatgcgCctcccattgGcgc | 978 |
| DR-04 | gtaatgcgTctcccaGtgAcgc | 979 |
| DR-05 | gtaatgcgTctcccatGgAcgc | 980 |

The results show that the proportion of GFP-positive cells in each group is between 30% and 36%. The editing efficiency of DR-01 and DR-04 is slightly higher than that of wild-type DR. The editing efficiency of DR-02 and DR-05 is higher than that of DR-01 and DR-04.

Example 20. Testing Editing Efficiency after Fusion with Different Domains

Theoretically, in some cases, the fusion of a nuclease binding domain to a specific protein may enhance the binding ability of the original protein to DNA or RNA, and the fusion of a nuclease cleavage domain can enhance or expand the cleavage ability of the original protein.

Therefore, in this example, the mutant version of C12-279, Mut-02-1-426-846-858-860 (C12-279-V4), was fused with each domain in Table 30, and the editing efficiency was tested in the Reporter 3 cell line.

TABLE 30

| Fusion domains | |
|---|---|
| Domain name | SEQ ID NO |
| CHD2 | 981 |
| GSTM3 | 982 |
| OTUB1 | 983 |
| PHYHD1 | 984 |
| SCGN | 985 |
| SNCB | 986 |
| SSBP1 | 987 |
| SSO7d | 988 |
| TBCB | 989 |
| TIGER | 990 |
| topA | 991 |
| UCHL1 | 992 |
| YWHAQ | 993 |
| dRusA | 994 |
| albA | 995 |
| Cas2 | 996 |
| DBPJ | 997 |
| DDB1(S78E) | 998 |
| DG5P | 999 |
| hup | 1000 |
| SSDBP | 1001 |
| T5 | 1002 |

Take CHD2 as an example to illustrate: to construct a fusion protein expression plasmid, CHD2 was first codon optimized, a linker was added, and then gene synthesis was performed. The synthetic sequence is as follows:

```
>CHD2-Syn
                                        (SEQ ID NO: 1003)
GGTGGAGGAGGTGGGTCTGGCGTGGAGGACGACAGCCGCCTGCTGCTGG
GCATCTACGAGCACGGCTACGGCAACTGGGAGCTGATCAAGACCGACCC
CGAGCTGAAGCTGACCGACAAGCTG.
```

The bold black sequence is the inserted linker, and the underlined sequence is the base sequence after CHD2 codon optimization.

Using the synthetic fragment CHD2-Syn as a template, CHD2-PF (SEQ ID NO: 1004) and CHD2-PR (SEQ ID NO: 1005) as amplification primer sequences, we obtained fragment CHD2-F by PCR amplification. The plasmid C12-279-V4 was digested with XhoI, and the 8945 bp vector fragment was recovered by gel. It was recombined with fragment CHD2-F in vitro (NEB™, Gibson Assembly® Master Mix) and transformed into *Escherichia coli* by heat shock to obtain the fusion protein expression plasmid C12-279-V4-CDH2 (SEQ ID NO: 1006). The construction of other domain fusion proteins is exactly the same as CDH2 domain except that the fusion protein sequence is changed. The insertion position, insertion method and linker sequence are exactly the same. The Reporter 3 cell line was transfected and flow cytometry was performed in the same way. The editing efficiency was characterized by the ratio of the number of GFP-positive cells detected by flow cytometry. The results show that all fusion proteins have editing activity.

What is claimed is:

1. A non-naturally occurring Cas12 protein, wherein the Cas12 protein comprises an amino acid sequence having at least 70% sequence identity to the amino acid sequence shown in SEQ ID NO: 696, wherein the Cas12 protein has one or more mutations at amino acid residues with corresponding positions in the sequence shown in SEQ ID NO: 696;

the Cas12 protein forms a complex with a guide polynucleotide, the guide polynucleotide comprises a guide sequence that is reverse complementary to a target nucleic acid, and the guide polynucleotide comprises a scaffold sequence that interacts with the Cas12 protein.

2. The Cas12 protein of claim 1, wherein the Cas12 protein has at least one mutation in at least one of the amino acid residues corresponding to positions 1, 2, 3, 4, 5, 7, 10, 24, 30, 48, 51, 55, 58, 59, 66, 108, 118, 138, 141, 175, 178, 185, 186, 257, 333, 352, 356, 375, 376, 378, 379, 383, 397, 400, 416, 426, 443, 449, 456, 459, 462, 469, 484, 485, 509, 561, 597 607, 609, 623, 638, 639, 640, 697, 722, 731, 733, 755, 758, 771, 773, 779, 781, 784, 785, 786, 789, 792, 794, 798, 822, 823, 825, 826, 829, 830, 833, 834, 836, 842, 845, 846, 847, 850, 851, 853, 855, 856, 858, 859, 860, 866, 884, 892, 893, 900, 904, 926, 956, 985, 988, 989, 992, 993, 996, 1016, 1033, 1045, 1050, 1073, 1074, 1095, 1100, 1124, 1129, or 1132 of the amino acid sequence shown in SEQ ID NO: 696.

3. The Cas12 protein of claim 1, wherein the Cas12 protein has a mutation at an amino acid residue corresponding to any position selected from I33, G184, S185, Q186, G194, N195, G196, G197, N245, G256, L260, Y278, S285, Y316, H350, D352, A355, A356, C385, P386, H387, G390, K391, N392, D429, Q461, Q462, Q469, E485, S491, K521, P525, L611, K629, K631, N633, D841, N898, K987, A988, G989, Q990, T991, D1010, E1013, A1136, K1138, or T1139, in the amino acid sequence shown in SEQ ID NO: 696.

4. The Cas12 protein of claim 1, wherein the Cas12 protein has any mutation combination of the amino acid sequence shown in SEQ ID NO: 696 at positions corresponding to the amino acid sequence shown in SEQ ID NO: 696, and the mutation combination is selected from 186+352+1+426+846+858+860, 186+352+1+426+846+860, 186+352+1+5+426+858+860, 186+352+1+3+426+858+860, 186+352+3+426+860, 186+352+1+333+426+858+860, 186+352+1+426+485+858+860, 186+352+1+5+426+860, 186+352+3+426+858+860, 186+352+5+426+858+860, 186+352+333+426+858+860, 186+352+333+426+860, 186+352+426+846+860, 186+352+5+426+860, 186+352+1+3+426+860, 5+426+860, 186+352+426+846+85+860, 186+352+1+426+485+860, 426+858+860, 7+426+858, 186+352+426+860, 186+352+426+485+858+860, 186+352+426+485+860, 426+846+858+860, 7+426+846, 186+352+860, 184+186+352+376+1132, 5+333+426, 5+426+858, 186+352+1+333+426+860, 184+186+352+3+107+426, 186+352+5+426, 333+376+426, 186+352+5, 2+5+846+858, 186+352+3+426, 5+846+858, 186+352+426+846, 186+352+7, 186+352+3+376+426, 186+352+376+426+860+865, 186+352+376+426, 3+846+860, 846+858+988, 3+426+858, 3+846+858+860, 3+858+860, 186+352+858, 184+186+352+860, 333+426, 184+186+352+3+376, 3+426+860, 846+860+988, 3+860, 184+186+352+3+639, 186+352+333+426, 846+585+860, 186+352+426, 333+426+846, 333+426+485, 5+846+860, 3+846+988, 184+186+352+376, 3+333+426, 186+352+426+485, 333+426+858, 333+426+1132, 428+485, 186+352+333+352+376+426, 858+860, 186+352+376+426+485+860, 184+186+352+426, 186+352+639, 5+858+988, 3+858+988, 5+858, 3+858, 184+186+352+846, 184+186+352+639, 858+988, 184+186+352+426+1132, 186+352+1132, 184+186+352+5, 184+186+352+858, 858+860+1132, 3+5, 426+649, 186+352+426+485+860, 186+352+333, 184+186+352, 186+376, 846+860, 858+988+1132, 846+858, 333+376, 376+426, 184+186+352+3, 3+846+1132, 5+846+1132, 186+352+426+1132, 376+426+485+660, 426, 5+846, 846+860+1132, 333+376+485, 184+186+352+639+1132, 352+426, 333+485, 184+186+352+333, 846+858+1132, 333+426+860, 186+352+988, 5+860, 846+988, 186+352, 3+846, 846+1132, 184+186+352+1132, 186+485, 988+1132, 184+186+352+485, 376+485, 5+1132, 3+7, 186+352+485, 184+186+352+7, 184+186+352+333+336, 3+1132, 426+858+988, 186+352+376, 186+352+3, and 186+352+333+336+352+376+426.

5. A nuclease-inactivated mutant of the Cas12 protein of claim 1, wherein an inactivating mutation of the nuclease-inactivated mutant is selected from one or more of D651A, E891A, and D1082A corresponding to the amino acid sequence shown in SEQ ID NO: 696.

6. A fusion protein or conjugate, comprising:

(1) a Cas12 protein, wherein the Cas12 protein comprises an amino acid sequence having at least 70% sequence identity to the amino acid sequence shown in SEQ ID NO: 696; and (2) a homologous or heterologous functional domain.

7. The fusion protein or conjugate of claim 6, wherein the homologous or heterologous functional domain is selected from any one, two, three, four, or more of the following: a subcellular positioning signal, a DNA binding domain, a protease domain, a transcriptional activation domain, a transcriptional repression domain, a nuclease domain, a deaminase domain, a uracil DNA glycosylase domain (UDG), a uracil DNA glycosylase inhibitory domain (UGI), a DNA methyltransferase, a DNA demethylase, a histone methyltransferase, a histone demethylase, a transcription release factor, a histone acetylase domain, a histone deacetylase domain, a DNA ligase, an affinity tag, a reporter tag, an affinity domain, and a reporter domain.

8. The fusion protein or conjugate of claim 7, wherein the subcellular positioning signal is selected from a nuclear localization signal, a nuclear export signal, a mitochondrial localization signal, and a chloroplast localization signal.

9. An isolated nucleic acid, wherein the isolated nucleic acid encodes the Cas12 protein of claim 1.

10. A kit, comprising the Cas12 protein of claim 1.

* * * * *